US008765688B2

(12) United States Patent
Liebmann et al.

(10) Patent No.: US 8,765,688 B2
(45) Date of Patent: Jul. 1, 2014

(54) ANTI-DANDRUFF COMPOSITIONS CONTAINING PEPTIDES

(75) Inventors: Burghard Liebmann, Bensheim (DE); Heike Brüser, Speyer (DE); Heiko Barg, Speyer (DE); Daniel Hümmerich, Frankenthal (DE); Hubertus Peter Bell, Mannheim (DE)

(73) Assignee: BASF SE, Ludwigshafen (DE)

( * ) Notice: Subject to any disclaimer, the term of this patent is extended or adjusted under 35 U.S.C. 154(b) by 87 days.

(21) Appl. No.: 12/809,102

(22) PCT Filed: Dec. 19, 2008

(86) PCT No.: PCT/EP2008/010912
§ 371 (c)(1),
(2), (4) Date: Jun. 18, 2010

(87) PCT Pub. No.: WO2009/080306
PCT Pub. Date: Jul. 2, 2009

(65) Prior Publication Data
US 2010/0310644 A1      Dec. 9, 2010

Related U.S. Application Data

(60) Provisional application No. 61/080,705, filed on Jul. 15, 2008.

(30) Foreign Application Priority Data

Dec. 21, 2007 (EP) .................................... 07024988
Jul. 7, 2008 (EP) .................................... 08159834

(51) Int. Cl.
*A61K 38/10* (2006.01)
*A61K 38/00* (2006.01)
*C07K 7/00* (2006.01)
*C07K 14/00* (2006.01)
*A61K 9/127* (2006.01)

(52) U.S. Cl.
USPC .......... 514/21.4; 530/324; 530/325; 530/326; 530/327; 424/450

(58) Field of Classification Search
USPC ................. 530/324, 325, 326, 327; 424/450; 514/21.4; 536/23.1, 24.5
See application file for complete search history.

(56) References Cited

U.S. PATENT DOCUMENTS

| 6,255,279 | B1 | 7/2001 | Christophers et al. |
| 6,800,727 | B2 | 10/2004 | Hahm et al. |
| 2003/0096745 | A1 | 5/2003 | Hahm et al. |
| 2010/0310644 | A1 * | 12/2010 | Liebmann et al. ............ 424/450 |

FOREIGN PATENT DOCUMENTS

| CN | 1511843 A | 7/2004 |
| CN | 1896107 A | 1/2007 |
| CN | 101302249 A | 11/2008 |
| EP | 0 866 804 B1 | 9/1998 |
| WO | WO-00/32220 A1 | 6/2000 |
| WO | WO-03/014146 A1 | 2/2003 |
| WO | WO-2005/007758 A2 | 1/2005 |
| WO | WO-2009/080306 A8 | 7/2009 |

OTHER PUBLICATIONS

Cutsem, J.V., et al., "The In Vitro Antifungal Activity of Ketoconazole, Zinc Pyrithione, and Selenium Sulfide Against Pityrosporum and Their Efficicy as a Shampoo in the Treatment of Experimental Pityrosporosis in Guinea Pigs", Journal of the American Academy of Dermatology, vol. 22, No. 6, (1990), pp. 993-998.
Darbre, P.D., et al., "Concentrations of Parabens in Human Breast Tumours", Journal of Applied Toxicology, vol. 24, (2004), pp. 5-13.
Hancock, R. E. W., et al., "Antimicrobial and Host-Defense Peptides as New Anti-Infective Therapeutic Strategies", Nature Biotechnology, vol. 24, No. 12, (2006), pp. 1551-1557.
Hancock, R.E.W., et al., "Cationic Peptides: A New Source of Antibiotics", Trends in Biotechnology, vol. 16, (1998), pp. 82-88.
Hanson, L.H., et al., "Evaluation of Cilofungin, a Lipopeptide Antifungal Agent, In Vitro Against Fungi Isolated from Clinical Specimens", Antimicrobial Agents and Chemotherapy, vol. 33, No. 8, (1989), pp. 1391-1392.
Kim, H., et al., "Osteoclast differentiation-inhibiting peptide P1", Database EBI Accession No. ABR40065, Jun. 20, 2003. (X002519483).
McDaniel, S.C., "Sequence 140 from Patent WO2005007758", Database EBI Accession No. CS015658, Feb. 10, 2005. (XP002519484).
Hahm, K., et al., "Cecropin A-magainin 2 (CA-MA) peptide derived from insect peptides", Database EBI Accession No. ABU10349, Sep. 9, 2003. (XP002519485).
"Antibiotic-related peptide amino acid sequence—SEQ ID 6", Database EBI Accession No. ADV69545, Feb. 24, 2005.
Lee, D.G., et al., "Structure and Fungicidal Activity of a Synthetic Antimicrobial Peptide, P18, and Its Truncated Peptides", Biotechnology Letters, vol. 26, (2004), pp. 337-341.
López-García, B., et al., "Expression and Potential Function of Cathelicidin Antimicrobial Peptides in Dermatophytosis and Tinea Versicolor" Journal of Antimicrobial Chemotherapy, vol. 57, (2006), pp. 877-882.
Nenoff, P., et al., "In vitro Activity of Phytosphingosines Against *Malassezia furfur* and *Candida albicans*", Acta Derm Venerol, vol. 82, (2002), pp. 170-173.

(Continued)

*Primary Examiner* — Chih-Min Kam
(74) *Attorney, Agent, or Firm* — Drinker Biddle & Reath LLP

(57) ABSTRACT

The present invention relates to the use of special peptides in composition which can be used in particular in hair and skin cosmetics, and to such peptide-containing compositions. In particular, the present invention relates to the use of such peptides as active ingredient for inhibition or treatment of dandruff which does not accumulate in the body or in the environment. Furthermore, the invention relates to the production of such compositions, to the peptides used themselves, to their production and to coding nucleotide sequences for such peptides, to dispensing systems for such peptides and to screening methods for identifying suitable further peptides.

12 Claims, No Drawings

(56) References Cited

OTHER PUBLICATIONS

Nenoff, P., et al., "Spezies-Abhängige In-vitro-Empfindlichkeit van *Malassezia* gegenüber Antimykotika", Aktuelle Dermatologie, vol. 33, (2007), pp. 26-32.

Shin, S.Y., et al., "Cecropin A—Magainin 2 Hybrid Peptides Having Potent Antimicrobial Activity with Low Hemolytic Effect", Biochemistry and Molecular Biology International, vol. 44, No. 6, (1998), pp. 1119-1126.

Shin, S.Y., "Salt Resistance and Synergistic Effect with Vancomycin of ∝-Helical Antimicrobial Peptide P18", Biochemical and Biophysical Research Communications, vol. 290, (2002), pp. 558-562.

Shin, S.Y., et al., "Structure-Antibacterial, Antitumor and Hemolytic Activity Relationships of Cecropin A-Magainin 2 and Cecropin A-Melittin Hybrid Peptides", Journal of Peptide Research, vol. 53, (1999), pp. 82-90.

Shin, S.Y., et al., "Antibacterial, Antitumor and Hemolytic Activities of ∝-Helical Antibiotic Peptide, P18 and Its Analogs", Journal of Peptide Research, vol. 58, (2001), pp. 504-514.

Wade, D., et al., "Antibacterial Peptides Designed as Analogs or Hybrids of Cecropins and Melittin", International Journal of Peptide and Protein Research, vol. 40, (1992), pp. 429-436.

"Cecropin A; Magainin; genetic engineering; protein production; fusion protein; Vaccine, general; Antimicrobial", Database EBI Accession No. ARA28054, Apr. 17, 2008.

"Self-assembly short peptide R418, SEQ ID 1", Database EBI Accession No. AUO71580, XP002519487, Feb. 19, 2009.

* cited by examiner

ANTI-DANDRUFF COMPOSITIONS CONTAINING PEPTIDES

RELATED APPLICATIONS

This application is a national stage application (under 35 U.S.C. §371) of PCT/EP2008/010912, filed Dec. 19, 2008, which claims benefit of European application 07024988.3, filed Dec. 21, 2007, European Application 08159834.4, filed Jul. 7, 2008, and U.S. Provisional Application 61/080,705, filed Jul. 15, 2008.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Revised_ Sequence_List_13111_00148_US. The size of the text file is 1,257 kilobytes, and the text file was created on Jun. 21, 2012.

The present invention relates to the use of special peptides in compositions which can be used in particular in hair and skin cosmetics, and to such peptide-containing compositions. In particular, the present invention relates to the use of such peptides as preservative or as prevention, active ingredient for inhibition or treatment of dandruff which does not accumulate in the body or in the environment. Furthermore, the invention relates to the production of such compositions, to the peptides used themselves, to their production and to coding nucleotide sequences for such peptides, to dispensing systems for such peptides and to screening methods for identifying suitable further peptides.

BACKGROUND OF THE INVENTION

In the cosmetics field, microbial activity can lead to undesired changes, such as body odor, dandruff formation or open inflammations and spots. The prior art discloses the use of antimicrobial and/or antifungal substances in preparations, e.g. in cosmetics or in medicine. However, the development of new antimicrobial and/or antifungal compositions is constantly necessary due to the development of bacterial or fungal strains that are resistant to active ingredients. Of particular interest is the development of novel antimicrobial and antifungal compounds, respectively, which do not show negative effects on the human health and which show a good activity spectrum against harmful germs.

Diverse antimicrobial peptides are already described in the literature and summarized in reviews (Hancock, R. E. W. and Lehrer, R. 1998 in Trends in Biotechnology, 16: 82-88; Hancock, R. E. W. and Sahl, H. G. 2006 in Nature Biotechnology, 24: 1551-1557).

Fusion peptides, which combine two effective peptides, are likewise described in the literature. Wade et al. report on the antibacterial effect of various fusions of cecropin A from *Hyalophora cecropia* and bee toxin melittin (Wade, D. et al., 1992, International Journal of Peptide and Protein Research, 40: 429-436). Shin et al. describe the antibacterial effect of a fusion peptide of cecropin A from *Hyalophora cecropia* and magainin 2 from *Xenopus laevis*, consisting of 20 amino acids. Cecropin A consists of 37 amino acids and exhibits activity toward Gram-negative bacteria, but lower activity toward Gram-positive bacteria. Magainin 2 consists of 23 amino acids and is active against bacteria but also tumor cell lines. Compared to the fusion of cecropin A and melittin, this fusion exhibits considerably lower hemolytic activity for comparable antibacterial effect (Shin, S. Y. Kang, J. H., Lee, M. K., Kim, S. Y., Kim, Y., Hahm, K. S., 1998, Biochemistry and Molecular Biology International, 44: 1119-1126).

US 2003/0096745 A1 and U.S. Pat. No. 6,800,727 B2 claim these fusion peptides consisting of 20 amino acids and variants of this fusion which, as a result of the exchange of amino acids, in particular of positively charged amino acids and hydrophobic amino acids, are more positively charged and more hydrophobic.

Further developments of this cecropin-A-magainin-2 fusion peptide are described by Shin et al. 1999. It is found here that the construct P18 (HT2, SEQ ID NO:3) had lower hemolytic activity compared to the starting fusion, although the antibacterial activity toward *Escherichia coli* and *Bacillus subtilis* was not impaired (Shin et al. 1999 Journal of Peptide Research, 53: 82-90).

Furthermore, Shin et al. 2001 investigated the activity of the construct P18 and analogous constructs for their antibacterial activity also on other target bacteria such as *Pseudomonas aeruginosa* or *Proteus vulgaris* (Shin et al., 2001, Journal of Peptide Research, 58: 504-514).

First experiments on the effectiveness of P18 against fungi was published in January 2002 by Shin et al. Here, better effectiveness of the peptide P18 towards *Candida albicans* compared to magainin 2 was established (Shin et al., 2002, Biochemical and Biophysical Research Communications, 290: 558-562).

In addition to *Candida albicans*, the Ascomycetes *Aspergillus flavus, Fusarium oxysporum* and the Basidiomycete *Trichosporon beigelii* were inhibited with P18 and variants of the peptide. However, the most effective inhibition was achieved with P18 (Lee et al., 2004, Biotechnology Letters, 26: 337-341). An inhibition of lipophilic fungi, in particular of the genus *Malassezia* is not taught. Furthermore, no experiments are described which demonstrate a more effective effect of cecropin-magainin fusions compared to known, commercial antifungal substances.

The genus *Malassezia* are lipophilic fungi which in part belong to the normal resident flora on human skin. Many representatives are obligatorily lipophilic, only *M. pachydermatis* is described as optionally lipophilic. Nevertheless disorders which are associated with *Malassezia* ssp. are described. These include pityriasis versicolor, atopic dermatitis, pityriasis capitis, seborrhea and *pityrosporum* folliculitis or malassezia folliculitis, for which *Malassezia* ssp. are pathogens. (Cutsem et al., 1990, Journal of the American Academy of Dermatology, 22: 993-998, Nenoff et al., 2007, Aktuelle Dermatologie, 33: 26-32). For treatment, antimycotic, fungicidal agents are usually used. Examples thereof are ketoconazole, climbazole, zinc pyrithiones, piroctone olamine, selenium sulfides or some natural extracts (e.g. like juniper oil, rosemary oil), which are often added in the single-digit %, (w/w) range, for example, in antidandruff shampoo formulations.

However, some of the described substances for inhibiting, treating or preventing dandruff are either toxicologically unacceptable, or the cosmetic preparations are not effective enough (Kosmetische Medizin 5+6/2006).

The species *Malassezia furfur* is less sensitive toward several antimycotics compared to other *Malassezia* species (Nenoff et al., 2007, Aktuelle Dermatologie, 33: 26-32). It is likewise described that substances which considerably inhibit the growth of *Candida albicans* even at low concentrations, only prevent the growth of *Malassezia furfur* at high concentrations, if at all. Thus, Nenoff et al. describe the inhibition of *Candida albicans* by phytosphingosines at concentrations of about 152-269 µg/ml whereas an inhibition of *M. furfur* only took place at approximately 25-fold higher concentrations (6250 µg/ml) for basic phytosphingosines, or *M. furfur* appeared to be resistant to phytosphingosine salts (Nenoff et al., 2002, Acta Derm Venerol, 82:170-173).

Similar observations were made for the peptide cilofungin by Hanson et al. 1989. While 76% of the *C. albicans* strains did not grow at a cilofungin concentration of 0.62 µg/ml, the obligatorily lipophilic *M. furfur* was not inhibited at these concentrations. The minimum inhibitory concentration of cilofungin for *M. furfur* was not stated. It was evidently not within the investigated range between 0.31 µg/ml and 40 µg/ml (Hanson et al., 1989, Antimicrobial agents and chemotherapy, 33:1391-1392).

In 2006, Lopez-Garcia et al. describe the growth inhibition of *M. furfur* with Cecropin P1 and magainin 2. Here, a moderate antifungal effect of cecropin P1 and a comparably better effect of magainin 2 at a concentration of 25 µM were found (Lopez-Garcia et al., 2006, Journal of Antimicrobial Chemotherapy, 57:877-882).

EP-A-0 866 804 describes the use of beta-defensins from human skin as active ingredient in cosmetic or pharmaceutical formulations. However, an internal comparison with antifungal active ingredients of the prior art is not made.

WO-A-00/032220 describes the use of a fungal polypeptide as antifungal active ingredient for the treatment of dandruff. However, an internal comparison with antifungal active ingredients of the prior art is not made here either.

US 2003/0096745 describes a polypeptide of the sequence KWKKLLKKPPPLLKKLLKKL (SEQ ID NO: 4739) with antibacterial and antifungal activity toward certain microorganisms. Antifungal activity was shown toward *Candida albicans* and *Tricosphoron beigelii*. Cosmetic applications, in particular for the treatment of dandruff, are not proposed.

However, the use of antimicrobial substances, particularly regular use, can lead to intolerance in people, or even to health damage. Intolerances may be skin reddening, irritations or sensitizations. Systemic absorption into the human body can lead to impairment of body functions. Particularly regular use of some antimicrobial substances can lead to an increase in their concentration. One known example is parabens (Dabre et al., 2004, Journal of Applied Toxicology, 24: 5-13). Depending on the application, an accumulation in the human body or in the environment may thus result.

In addition, excessive and inappropriate use of antimicrobial substances result time and again in resistance of the target organisms.

There is therefore a need to provide novel cosmetic antimicrobial compositions which firstly have antifungal effectiveness and are suitable for avoiding or treating dandruff. In particular, these should not accumulate in the body since they can be degraded in the natural surroundings.

There is in particular a need to provide antifungal active ingredients which are more effective against dandruff than the customary antidandruff agents known hitherto and in particular are effective against the dandruff fungus *Malassezia furfur* and other *Malassezia* ssp. Preferably, the natural skin flora should not be impaired, and the active ingredients should also not accumulate in the body or in the environment, but be degraded in the natural surroundings.

It was therefore an object of the present invention to provide a novel, effective but biodegradable active ingredient for avoiding, inhibiting and/or treating dandruff, in particular scurf. Advantageously, active ingredient compounds are to be identified which are suitable for producing cosmetic and/or dermatocosmetic formulations or preparations. Furthermore, systemic absorption of the active ingredient should be avoided. Additionally, it should be ensured that the preparations have low or no cytoxicity. In particular, the active ingredient should be effective against the yeast fungus *Malassezia furfur*, and also against other *Malassezia* ssp., in particular, obligatorily lipophilic species.

SUMMARY OF THE INVENTION

This object was achieved by cosmetic compositions according to the definition in the attached patent claims.

Surprisingly, it has been found that the composition comprising at least one peptide with a claimed structure or a structure motif has adequate effectiveness against lipophilic fungal species, in particular *Malassezia furfur*, associated with good skin compatibility. Furthermore, a biodegradability was found which progresses more rapidly compared to customary antidandruff active ingredients such as zinc pyrithiones. Furthermore, it has surprisingly been found that the effect is better than the effect which is achieved with the peptides cecropin A or magainin II on their own.

DETAILED DESCRIPTION OF THE INVENTION

1. General Definitions

A "helix breaker" means a section within a peptide according to the invention which, in the region of this section of the peptide chain, inhibits the formation of a helical secondary structure. The formation of a helix structure further away from the helix breaker, however, is not suppressed. Typical helix breakers are known to the person skilled in the art. In particular, the amino acid proline is a peptide building block with the property of a helix breaker. The same is true for proline-containing peptide fragments.

Within the context of the invention, "hydrophobic amino acids" are alanine, valine, leucine, isoleucine, phenylalanine, methionine and tryptophan.

Within the context of the invention, "hydrophilic amino acids" are in particular amino acids with polar side chains, such as serine, threonine, cysteine, tyrosine, asparagine and glutamine; acidic amino acids, such as aspartic acid and glutamic acid; and in particular basic amino acids, such as lysine, arginine and histidine.

"Capable of forming an alpha-helix arms" is a sequence which promotes the formation of a helical structure under suitable conditions. Artificial suitable conditions for forming helix structures are, for example, the solvent systems based on trifluoroacetic acid that promote alpha-helix formation, and also SDS.

"Percentage alpha-helicity" is understood as meaning a measurement value determined with the help of circular dichroism (CD) analysis, where the sample to be measured is obtained under standard conditions, such as, in particular, 50% (v/v) trifluoroacetic acid in 10 mM sodium phosphate buffer, pH 7.0, or 30 mM SDS in 10 mM sodium phosphate buffer, pH 7.0, using a measurement cell with 1 mm path length and at peptide concentration of 100 µg/ml. The calculation is made according to the following formula:

% helicity=$100([\Theta]-[\Theta]^0)/[\Theta]^{100}$ in which
[$\Theta$] is the experimentally determined ellipticity at 222 nm;
[$\Theta$]$^0$ is the ellipticity at 222 nm and 0% helicity and
[$\Theta$]$^{100}$ is the ellipticity at 222 nm and 100% helicity.

Suitable measurement conditions are described, for example, by Shin et al., 1999, Journal of Peptide Research, 53:82-90, to which reference is hereby expressly made.

A "repetitive sequence motif" is understood as meaning the linear arrangement of preferably identical peptide sequences which are linked together directly or indirectly, i.e. via "linker groups", as defined herein.

The terms "mutants" and "variants" are used synonymously. These are understood as meaning in particular "functional" or "functionally equivalent" modifications, as described in more detail later, which still demonstrate the desired activity and thus applicability as antidandruff peptide.

The terms "cosmetic", dermatocosmetic" or "dermatological" are likewise used synonymously.

A "fusion product" is understood as meaning the covalent or noncovalent linking of peptides and proteins ("fusion peptides") and the covalent or noncovalent linking of peptides and polymers ("fusion polymers"). The linked constituents are cleavably joined together either irreversibly or reversibly, i.e. biologically, in particular enzymatically.

2. Preferred Embodiments

The invention firstly provides a cosmetic composition comprising, in a cosmetic carrier, a peptide which comprises at least one sequence motif of the following general formula I Hel1-HB-Hel2  (I)

in which
"HB" comprises 1 to 5, in particular 1, 2 or 3, continuous amino acid residues and is a part sequence motif with the function of a helix breaker, and
"Hel1" and "Hel2" are identical or different part sequence motifs which each comprise 5 to 15, such as, for example, 6 to 12, in particular 8, 9 or 10, continuous amino acid residues which are essentially selected from hydrophilic residues and hydrophobic, in particular, basic, residues different from proline, and are in each case capable of forming an alpha-helix arm where at least one of the helix arms has, in its axial projection, i.e. in the top view corresponding to a "helical wheel" diagram, an incomplete separation into a hydrophobic, in particular basic, and hydrophilic helix half. Here, for example 1, 2, 3 or 4 positions one half of the type (hydrophobic or hydrophilic) can be occupied by amino acid residues of the other type (hydrophilic or hydrophobic, respectively).

By contrast, completely separated hydrophobic and hydrophilic helix halves would consist exclusively of hydrophobic or hydrophilic amino acid residues according to the above definition. One example of a completely hydrophilically/hydrophobically separated helix to be mentioned is the sequence motif KLKKLLKK (SEQ ID NO: 4740).

A "helix half" is not necessarily to be understood here as meaning the numerical half, i.e. half the total number of amino acids of a helix. The numerical size of two halves can differ, for example, by 1 to 3 amino acids.

The invention secondly provides a cosmetic composition comprising, in a cosmetic carrier, a peptide which comprises at least one sequence motif of the following general formula I Hel1-HB-Hel2  (I)

in which
"HB" comprises 1 to 5, in particular 1, 2 or 3, continuous amino acid residues and is a part sequence motif with the function of a helix breaker, and
"Hel1" and "Hel2" are identical or different part sequence motifs which each comprise 5 to 15, such as, for example, 6 to 12, in particular 8, 9 or 10, continuous amino acid residues which are essentially selected from hydrophilic residues and hydrophobic, in particular, basic, residues different from proline, and are in each case capable of forming an alpha-helix arm, where the peptide has a percentage alpha-helicity (% helicity) of from about 25 to 98%, such as, for example, 30 to 80% or 30 to 60%, in 50% (v/v) trifluoroacetic acid, pH 7.0; or a % helicity value of from about 10 to 70%, or 12 to 55% or 12 to 40%, in 30 mM SDS, pH 7.0, in each case determined by CD spectrometry.

The invention thirdly provides a cosmetic composition comprising, in a cosmetic carrier, at least one peptide with a sequence or a repetitive sequence motif according to SEQ ID NO: 1:

(SEQ ID NO: 1)
$X_1\ X_2K\ X_3\ X_4\ X_5KIP\ X_{10}\ KFX_6X_7\ X_8\ AX_9KF$ in which
$X_{10}$ is a peptide bond or one or two arbitrary basic or hydrophobic amino acid residues or one or two proline residues and
$X_1$ to $X_9$ are arbitrary basic amino acid residues or hydrophobic amino acid residues different from proline;
where the repetitive sequence motifs may be identical or different;
and/or mutants or derivatives thereof.

In particular, the invention provides compositions according to the above definition comprising at least one peptide with a sequence or a repetitive sequence motif according to SEQ ID NO: 2:

(SEQ ID NO: 2)
$X_1\ X_2K\ X_3\ X_4\ X_5KIP\ X_{11}\ X_{12}\ KFX_6X_7\ X_8\ AX_9KF$ in which
$X_1$ is lysine, arginine or phenylalanine,
$X_2$ is lysine or tryptophan,
$X_3$ is leucine or lysine,
$X_4$ is phenylalanine or leucine,
$X_5$ is leucine or lysine,
$X_6$ is leucine or lysine,
$X_7$ is histidine or lysine,
$X_8$ is alanine, leucine, valine or serine,
$X_9$ is leucine or lysine,
$X_{11}$ is proline or a chemical bond, and
$X_{12}$ is proline or a chemical bond,
where the repetitive sequence motifs are identical or different;
and/or mutants or derivatives thereof.

Nonlimiting examples of the above sequences or repetitive sequence motifs according to SEQ ID NO: 3 are:

| P18 | KWKLFKKIPKFLHLAKKF-NH$_2$ | (SEQ ID NO: 3) |
| RP18 | RWKLFKKIPKFLHLAKKF | (SEQ ID NO: 4) |
| KKFP18 | FKKLFKKIPKFLHAAKKF | (SEQ ID NO: 5) |
| KKLP18 | KWKLLKKIPKFKKLALKF | (SEQ ID NO: 6) |
| AP18 | KWKLFKKIPKFLHAAKKF | (SEQ ID NO: 7) |
| KFLP18 | KWKKFLKIPKFLHAAKKF | (SEQ ID NO: 8) |
| KLLP18 | KWKKLLKIPKFLHAAKKF | (SEQ ID NO: 9) | and/or a mutant or derivative thereof.

Compositions according to the invention can in particular comprise peptides with a repetitive sequence motif, where a plurality, such as, in particular, 2 to 10 or 3 to 5, of peptides of the general formula I or according to SEQ ID NO: 1 to 9 or mutants or derivatives thereof are peptidically linked together via linker groups.

Here, the "linker groups" can comprise continuous, identical or different amino acid residues, preferably selected from alanine, glycine, threonine and serine, such as, for example, GGSGGT (SEQ ID NO: 4741), GGSGGS (SEQ ID NO: 4742), or poly-alanine linkers and poly-glycine linkers, where "poly" is 2 to 10; or selected from Asp, Pro, Asn and Gly, for example Asp-Pro and Asn-Gly.

Furthermore, peptides whose C-terminal carboxyl group is amidated can be used.

The invention also provides compositions comprising an, if appropriate, cleavable fusion polypeptide of at least one cosmetic, preferably peptidic auxiliary or active ingredient and at least one peptide according to the above definition. Examples of such active ingredients are: hydrophobins, keratin binding domains, albumin, lactoferrin, avidin, antibodies, preferably, keratin-binding antibodies, binding peptides for surfaces, preferably keratin-binding peptides, silk proteins, spider silk proteins, preferably C16, collagen, fibronectin, keratin, elastin, other structural proteins, preferably hair and skin structure proteins, binding proteins for skin and hair structure proteins, enamel-building proteins, amelogenin, binding proteins of the enamel-building proteins, binding proteins of amelogenin; where these fusions may be permanent or else cleavable.

The invention also provides fusion polymers of at least one cosmetic polymer and at least one peptide according to the above definition. Examples of such polymers are: polyhydroxyalkanoates, hyaluronic acid, glucan, spheroglucan, cellulose, xanthan, polyethylene glycol, polyglycerol, polylysine and silicones, which are present as covalent or noncovalent linkages.

Furthermore, it is conceivable that the abovementioned peptides can also be present in the compositions as covalent linkage to cosmetically/pharmaceutically active ingredients, such as panthenol, bisabolol, retinol, carotenoids, protein hydrolysates.

The invention also provides compositions according to the above definition, additionally comprising at least one further cosmetic or pharmaceutical active ingredient, such as, for example, at least one antiinflammatory active ingredient, an antimicrobial active ingredient for inhibiting the growth and/or the pathophysiological activity of undesired germs, such as, in particular, *Malasezzia furfur*, and/or a sebum-regulating active ingredient.

Examples of antiinflammatory active ingredients are: corticoids (e.g. cortisone), azathioprin, bisabolol, cyclosporin A, acetylsalicylic acid, ibuprofen, panthenol, camomile extract or aloe extracts, etc.

Examples of antimicrobial agents are: customary preservatives known to the person skilled in the art, such as alcohols, p-hydroxybenzoic acid esters, imidazolinylurea, formaldehyde, sorbic acid, benzoic acid, salicylic acid, etc. Such deodorizing substances are, for example, zinc ricinoleate, triclosan, undecylenic acid alkylolamides, triethyl citrate, chlorhexidine, etc. (cf. also section 3.5 below). They also include azoles (Ketoconazole, climbazole), zinc pyrithione, selenium sulfides, etc.

Examples of sebum-regulating active ingredients are: azelaic acid, sebacic acid, potassiumalezaoyldiglycinate, 10-hydroxydecanoic acid, 1,10-decanediol, aluminium salts, like aluminiumchlorohydrate, etc.

The peptide is present in the compositions according to the invention in a fraction of from 0.0001 to 50% by weight, in particular 0.001 to 10% by weight, and especially 0.005 to 0.1% by weight, in each case based on the total weight of the finished composition.

A further aspect of the present invention relates to compositions containing at least one peptide as defined above which shows for *Malassezia furfur* a minimal inhibitory concentration of about 1500 to 0.1 µM, as for example 500 to 1 µM, 100 to 5 µM or 50 to 10 µM, as determined under standard conditions. Standard conditions in this context relate to a *Malassezia furfur* culture, which shows an initial optical density of 0.1 at 600 nm, and which, after a 24 hour incubation with said peptide, which is contained at said minimum concentration in said culture medium, contains less than one colony-forming unit (CFU) of said microorganism per µl culture medium.

The invention further provides the use of a peptide according to the above definition or of a fusion polypeptide according to the above definition, optionally in combination with at least one further conventional, as for example low-molecular weight, antifungal agent, as for example Ketoconazole, Climbazole, Zincpyrithione or selenosulfides, for producing a cosmetic composition for the treatment or prevention of dandruff, in particular scurf, where the peptide is used in particular for suppressing the growth and/or the pathophysiological activity of lipophilic fungi, in particular *Malassezia furfur* and other species of the genus *Malassezia*, or for producing cosmetic compositions in which the peptide is present as preservative.

In this connection, various natural skin organisms are essentially not or only slightly inhibited in their growth and/or activity during the dandruff treatment.

The invention further provides a method of producing a cosmetic composition according to the above definition, where a peptide according to the above definition is formulated together with at least one customary cosmetic auxiliary and, if appropriate, further cosmetic or pharmaceutical active ingredients to give the desired administration form.

The invention further provides peptides according to the above definition and also nucleic acids coding for such peptides, and also complementary nucleic acids which hybridize with such coding nucleic acids under stringent conditions.

Furthermore, the invention relates to screening methods for antidandruff peptides, where, using a complementary nucleic acid according to the above definition as probe, a nucleic-acid-containing sample is screened for hybridizing sequences using the probe under stringent conditions.

Finally, the invention provides a dispensing system for releasing a peptide according to the above definition, where the peptide and, if appropriate, further ingredients present are associated with liposomes, zeolites, cyclodextrins, polyethyleneimine-based vector systems, which are, for example, present (dissolved, suspended, dispersed) therein.

P18 (SEQ ID NO: 3) is a peptide with a chain length of 18 amino acids which is derived from a fusion peptide from fragments of cecropin A from *Hyalaphora cecropia* and magainin from *Xenopus laevis*. Fungicidal activity was found for *Candida albicans, Trichosporon beigelii, Aspergillus flavus* and *Fusarium oxysporum* in experiments (Lee et al., (2004) Biotechnology Letters, 26:337-341.). However, the person skilled in the art is aware that the effect of fungicidal substances on different organisms can be very different. Particularly the effect on the lipophilic fungus *Malassezia furfur* and the lipophilic species of the genus *Malassezia* can differ for example significantly from the effect on *Candida albicans* (Hanson et al., (1989) Antimicrobial Agents and Chemotherapy, 33:1391-1392; Nenhoff et al., (2002) Acta Derm Venereol., 82:170-173). The effect of P18 observed according to the invention and structurally and functionally related peptides of the species described herein is therefore completely surprising to the person skilled in the art.

In a further particular embodiment, the secondary structure of the peptides according to the invention is a helix which is divided in the middle into two helices by a helix-breaking amino acid. In a depiction as "helical wheel", hydrophobic amino acids, in particular leucine residues, predominate on one side (or half of the helix), and positively charged amino acids, in particular lysine residues, predominate on the other side.

The peptides according to the invention are composed in particular of D- and/or L-amino acids, in particular L-amino acids.

The peptides described herein and/or derivatives thereof can be produced in a manner known per se, such as through chemical solid-phase synthesis, liquid synthesis or biotechnologically using recombinant production strains or cell cultures.

3. Further Embodiments of the Invention

3.1 Examples of Further Suitable Sequence Motifs

```
3.1.1 Sequence motif
X1 X2K X3 X4 X5KIP X11 X12 KFX6X7 X8 AX9KF
(SEQ ID NO: 2)
variant_0      KKKLFLKIPPPKFLHAALKF    seqid_11
variant_1      RKKLFLKIPPPKFLHAALKF    seqid_12
variant_2      FKKLFLKIPPPKFLHAALKF    seqid_13
variant_3      KWKLFLKIPPPKFLHAALKF    seqid_14
variant_4      RWKLFLKIPPPKFLHAALKF    seqid_15
variant_5      FWKLFLKIPPPKFLHAALKF    seqid_16
variant_6      KKKKFLKIPPPKFLHAALKF    seqid_17
variant_7      RKKKFLKIPPPKFLHAALKF    seqid_18
variant_8      FKKKFLKIPPPKFLHAALKF    seqid_19
variant_9      KWKKFLKIPPPKFLHAALKF    seqid_20
variant_10     RWKKFLKIPPPKFLHAALKF    seqid_21
variant_11     FWKKFLKIPPPKFLHAALKF    seqid_22
variant_12     KKKLLLKIPPPKFLHAALKF    seqid_23
variant_13     RKKLLLKIPPPKFLHAALKF    seqid_24
variant_14     FKKLLLKIPPPKFLHAALKF    seqid_25
variant_15     KWKLLLKIPPPKFLHAALKF    seqid_26
variant_16     RWKLLLKIPPPKFLHAALKF    seqid_27
variant_17     FWKLLLKIPPPKFLHAALKF    seqid_28
variant_18     KKKKLLKIPPPKFLHAALKF    seqid_29
variant_19     RKKKLLKIPPPKFLHAALKF    seqid_30
variant_20     FKKKLLKIPPPKFLHAALKF    seqid_31
variant_21     KWKKLLKIPPPKFLHAALKF    seqid_32
variant_22     RWKKLLKIPPPKFLHAALKF    seqid_33
variant_23     FWKKLLKIPPPKFLHAALKF    seqid_34
variant_24     KKKLFKKIPPPKFLHAALKF    seqid_35
variant_25     RKKLFKKIPPPKFLHAALKF    seqid_36
variant_26     FKKLFKKIPPPKFLHAALKF    seqid_37
variant_27     KWKLFKKIPPPKFLHAALKF    seqid_38
variant_28     RWKLFKKIPPPKFLHAALKF    seqid_39
variant_29     FWKLFKKIPPPKFLHAALKF    seqid_40
variant_30     KKKKFKKIPPPKFLHAALKF    seqid_41
variant_31     RKKKFKKIPPPKFLHAALKF    seqid_42
variant_32     FKKKFKKIPPPKFLHAALKF    seqid_43
variant_33     KWKKFKKIPPPKFLHAALKF    seqid_44
variant_34     RWKKFKKIPPPKFLHAALKF    seqid_45
variant_35     FWKKFKKIPPPKFLHAALKF    seqid_46
variant_36     KKKLLKKIPPPKFLHAALKF    seqid_47
variant_37     RKKLLKKIPPPKFLHAALKF    seqid_48
variant_38     FKKLLKKIPPPKFLHAALKF    seqid_49
variant_39     KWKLLKKIPPPKFLHAALKF    seqid_50
variant_40     RWKLLKKIPPPKFLHAALKF    seqid_51
variant_41     FWKLLKKIPPPKFLHAALKF    seqid_52
variant_42     KKKKLKKIPPPKFLHAALKF    seqid_53
variant_43     RKKKLKKIPPPKFLHAALKF    seqid_54
variant_44     FKKKLKKIPPPKFLHAALKF    seqid_55
variant_45     KWKKLKKIPPPKFLHAALKF    seqid_56
variant_46     RWKKLKKIPPPKFLHAALKF    seqid_57
variant_47     FWKKLKKIPPPKFLHAALKF    seqid_58
variant_48     KKKLFLKIPPKFLHAALKF     seqid_59
variant_49     RKKLFLKIPPKFLHAALKF     seqid_60
variant_50     FKKLFLKIPPKFLHAALKF     seqid_61
variant_51     KWKLFLKIPPKFLHAALKF     seqid_62
variant_52     RWKLFLKIPPKFLHAALKF     seqid_63
variant_53     FWKLFLKIPPKFLHAALKF     seqid_64
variant_54     KKKKFLKIPPKFLHAALKF     seqid_65
variant_55     RKKKFLKIPPKFLHAALKF     seqid_66
variant_56     FKKKFLKIPPKFLHAALKF     seqid_67
variant_57     KWKKFLKIPPKFLHAALKF     seqid_68
variant_58     RWKKFLKIPPKFLHAALKF     seqid_69
variant_59     FWKKFLKIPPKFLHAALKF     seqid_70
variant_60     KKKLLLKIPPKFLHAALKF     seqid_71
variant_61     RKKLLLKIPPKFLHAALKF     seqid_72
variant_62     FKKLLLKIPPKFLHAALKF     seqid_73
variant_63     KWKLLLKIPPKFLHAALKF     seqid_74
variant_64     RWKLLLKIPPKFLHAALKF     seqid_75
```

-continued

| | | |
|---|---|---|
| variant_65 | FWKLLLKIPPKFLHAALKF | seqid_76 |
| variant_66 | KKKKLLKIPPKFLHAALKF | seqid_77 |
| variant_67 | RKKKLLKIPPKFLHAALKF | seqid_78 |
| variant_68 | FKKKLLKIPPKFLHAALKF | seqid_79 |
| variant_69 | KWKKLLKIPPKFLHAALKF | seqid_80 |
| variant_70 | RWKKLLKIPPKFLHAALKF | seqid_81 |
| variant_71 | FWKKLLKIPPKFLHAALKF | seqid_82 |
| variant_72 | KKKLFKKIPPKFLHAALKF | seqid_83 |
| variant_73 | RKKLFKKIPPKFLHAALKF | seqid_84 |
| variant_74 | FKKLFKKIPPKFLHAALKF | seqid_85 |
| variant_75 | KWKLFKKIPPKFLHAALKF | seqid_86 |
| variant_76 | RWKLFKKIPPKFLHAALKF | seqid_87 |
| variant_77 | FWKLFKKIPPKFLHAALKF | seqid_88 |
| variant_78 | KKKKFKKIPPKFLHAALKF | seqid_89 |
| variant_79 | RKKKFKKIPPKFLHAALKF | seqid_90 |
| variant_80 | FKKKFKKIPPKFLHAALKF | seqid_91 |
| variant_81 | KWKKFKKIPPKFLHAALKF | seqid_92 |
| variant_82 | RWKKFKKIPPKFLHAALKF | seqid_93 |
| variant_83 | FWKKFKKIPPKFLHAALKF | seqid_94 |
| variant_84 | KKKLLKKIPPKFLHAALKF | seqid_95 |
| variant_85 | RKKLLKKIPPKFLHAALKF | seqid_96 |
| variant_86 | FKKLLKKIPPKFLHAALKF | seqid_97 |
| variant_87 | KWKLLKKIPPKFLHAALKF | seqid_98 |
| variant_88 | RWKLLKKIPPKFLHAALKF | seqid_99 |
| variant_89 | FWKLLKKIPPKFLHAALKF | seqid_100 |
| variant_90 | KKKKLKKIPPKFLHAALKF | seqid_101 |
| variant_91 | RKKKLKKIPPKFLHAALKF | seqid_102 |
| variant_92 | FKKKLKKIPPKFLHAALKF | seqid_103 |
| variant_93 | KWKKLKKIPPKFLHAALKF | seqid_104 |
| variant_94 | RWKKLKKIPPKFLHAALKF | seqid_105 |
| variant_95 | FWKKLKKIPPKFLHAALKF | seqid_106 |
| variant_144 | KKKLFLKIPKFLHAALKF | seqid_107 |
| variant_145 | RKKLFLKIPKFLHAALKF | seqid_108 |
| variant_146 | FKKLFLKIPKFLHAALKF | seqid_109 |
| variant_147 | KWKLFLKIPKFLHAALKF | seqid_110 |
| variant_148 | RWKLFLKIPKFLHAALKF | seqid_111 |
| variant_149 | FWKLFLKIPKFLHAALKF | seqid_112 |
| variant_150 | KKKKFLKIPKFLHAALKF | seqid_113 |
| variant_151 | RKKKFLKIPKFLHAALKF | seqid_114 |
| variant_152 | FKKKFLKIPKFLHAALKF | seqid_115 |
| variant_153 | KWKKFLKIPKFLHAALKF | seqid_116 |
| variant_154 | RWKKFLKIPKFLHAALKF | seqid_117 |
| variant_155 | FWKKFLKIPKFLHAALKF | seqid_118 |
| variant_156 | KKKLLLKIPKFLHAALKF | seqid_119 |
| variant_157 | RKKLLLKIPKFLHAALKF | seqid_120 |
| variant_158 | FKKLLLKIPKFLHAALKF | seqid_121 |
| variant_159 | KWKLLLKIPKFLHAALKF | seqid_122 |
| variant_160 | RWKLLLKIPKFLHAALKF | seqid_123 |
| variant_161 | FWKLLLKIPKFLHAALKF | seqid_124 |
| variant_162 | KKKKLLKIPKFLHAALKF | seqid_125 |
| variant_163 | RKKKLLKIPKFLHAALKF | seqid_126 |
| variant_164 | FKKKLLKIPKFLHAALKF | seqid_127 |
| variant_165 | KWKKLLKIPKFLHAALKF | seqid_128 |
| variant_166 | RWKKLLKIPKFLHAALKF | seqid_129 |
| variant_167 | FWKKLLKIPKFLHAALKF | seqid_130 |
| variant_168 | KKKLFKKIPKFLHAALKF | seqid_131 |
| variant_169 | RKKLFKKIPKFLHAALKF | seqid_132 |
| variant_170 | FKKLFKKIPKFLHAALKF | seqid_133 |
| variant_171 | KWKLFKKIPKFLHAALKF | seqid_134 |
| variant_172 | RWKLFKKIPKFLHAALKF | seqid_135 |
| variant_173 | FWKLFKKIPKFLHAALKF | seqid_136 |
| variant_174 | KKKKFKKIPKFLHAALKF | seqid_137 |
| variant_175 | RKKKFKKIPKFLHAALKF | seqid_138 |
| variant_176 | FKKKFKKIPKFLHAALKF | seqid_139 |
| variant_177 | KWKKFKKIPKFLHAALKF | seqid_140 |
| variant_178 | RWKKFKKIPKFLHAALKF | seqid_141 |
| variant_179 | FWKKFKKIPKFLHAALKF | seqid_142 |
| variant_180 | KKKLLKKIPKFLHAALKF | seqid_143 |
| variant_181 | RKKLLKKIPKFLHAALKF | seqid_144 |
| variant_182 | FKKLLKKIPKFLHAALKF | seqid_145 |
| variant_183 | KWKLLKKIPKFLHAALKF | seqid_146 |
| variant_184 | RWKLLKKIPKFLHAALKF | seqid_147 |
| variant_185 | FWKLLKKIPKFLHAALKF | seqid_148 |
| variant_186 | KKKKLKKIPKFLHAALKF | seqid_149 |
| variant_187 | RKKKLKKIPKFLHAALKF | seqid_150 |
| variant_188 | FKKKLKKIPKFLHAALKF | seqid_151 |
| variant_189 | KWKKLKKIPKFLHAALKF | seqid_152 |
| variant_190 | RWKKLKKIPKFLHAALKF | seqid_153 |
| variant_191 | FWKKLKKIPKFLHAALKF | seqid_154 |
| variant_192 | KKKLFLKIPPPKFKHAALKF | seqid_155 |
| variant_193 | RKKLFLKIPPPKFKHAALKF | seqid_156 |

| | | |
|---|---|---|
| variant_194 | FKKLFLKIPPPKFKHAALKF | seqid_157 |
| variant_195 | KWKLFLKIPPPKFKHAALKF | seqid_158 |
| variant_196 | RWKLFLKIPPPKFKHAALKF | seqid_159 |
| variant_197 | FWKLFLKIPPPKFKHAALKF | seqid_160 |
| variant_198 | KKKKFLKIPPPKFKHAALKF | seqid_161 |
| variant_199 | RKKKFLKIPPPKFKHAALKF | seqid_162 |
| variant_200 | FKKKFLKIPPPKFKHAALKF | seqid_163 |
| variant_201 | KWKKFLKIPPPKFKHAALKF | seqid_164 |
| variant_202 | RWKKFLKIPPPKFKHAALKF | seqid_165 |
| variant_203 | FWKKFLKIPPPKFKHAALKF | seqid_166 |
| variant_204 | KKKLLLKIPPPKFKHAALKF | seqid_167 |
| variant_205 | RKKLLLKIPPPKFKHAALKF | seqid_168 |
| variant_206 | FKKLLLKIPPPKFKHAALKF | seqid_169 |
| variant_207 | KWKLLLKIPPPKFKHAALKF | seqid_170 |
| variant_208 | RWKLLLKIPPPKFKHAALKF | seqid_171 |
| variant_209 | FWKLLLKIPPPKFKHAALKF | seqid_172 |
| variant_210 | KKKKLLKIPPPKFKHAALKF | seqid_173 |
| variant_211 | RKKKLLKIPPPKFKHAALKF | seqid_174 |
| variant_212 | FKKKLLKIPPPKFKHAALKF | seqid_175 |
| variant_213 | KWKKLLKIPPPKFKHAALKF | seqid_176 |
| variant_214 | RWKKLLKIPPPKFKHAALKF | seqid_177 |
| variant_215 | FWKKLLKIPPPKFKHAALKF | seqid_178 |
| variant_216 | KKKLFKKIPPPKFKHAALKF | seqid_179 |
| variant_217 | RKKLFKKIPPPKFKHAALKF | seqid_180 |
| variant_218 | FKKLFKKIPPPKFKHAALKF | seqid_181 |
| variant_219 | KWKLFKKIPPPKFKHAALKF | seqid_182 |
| variant_220 | RWKLFKKIPPPKFKHAALKF | seqid_183 |
| variant_221 | FWKLFKKIPPPKFKHAALKF | seqid_184 |
| variant_222 | KKKKFKKIPPPKFKHAALKF | seqid_185 |
| variant_223 | RKKKFKKIPPPKFKHAALKF | seqid_186 |
| variant_224 | FKKKFKKIPPPKFKHAALKF | seqid_187 |
| variant_225 | KWKKFKKIPPPKFKHAALKF | seqid_188 |
| variant_226 | RWKKFKKIPPPKFKHAALKF | seqid_189 |
| variant_227 | FWKKFKKIPPPKFKHAALKF | seqid_190 |
| variant_228 | KKKLLKKIPPPKFKHAALKF | seqid_191 |
| variant_229 | RKKLLKKIPPPKFKHAALKF | seqid_192 |
| variant_230 | FKKLLKKIPPPKFKHAALKF | seqid_193 |
| variant_231 | KWKLLKKIPPPKFKHAALKF | seqid_194 |
| variant_232 | RWKLLKKIPPPKFKHAALKF | seqid_195 |
| variant_233 | FWKLLKKIPPPKFKHAALKF | seqid_196 |
| variant_234 | KKKKLKKIPPPKFKHAALKF | seqid_197 |
| variant_235 | RKKKLKKIPPPKFKHAALKF | seqid_198 |
| variant_236 | FKKKLKKIPPPKFKHAALKF | seqid_199 |
| variant_237 | KWKKLKKIPPPKFKHAALKF | seqid_200 |
| variant_238 | RWKKLKKIPPPKFKHAALKF | seqid_201 |
| variant_239 | FWKKLKKIPPPKFKHAALKF | seqid_202 |
| variant_240 | KKKLFLKIPPKFKHAALKF | seqid_203 |
| variant_241 | RKKLFLKIPPKFKHAALKF | seqid_204 |
| variant_242 | FKKLFLKIPPKFKHAALKF | seqid_205 |
| variant_243 | KWKLFLKIPPKFKHAALKF | seqid_206 |
| variant_244 | RWKLFLKIPPKFKHAALKF | seqid_207 |
| variant_245 | FWKLFLKIPPKFKHAALKF | seqid_208 |
| variant_246 | KKKKFLKIPPKFKHAALKF | seqid_209 |
| variant_247 | RKKKFLKIPPKFKHAALKF | seqid_210 |
| variant_248 | FKKKFLKIPPKFKHAALKF | seqid_211 |
| variant_249 | KWKKFLKIPPKFKHAALKF | seqid_212 |
| variant_250 | RWKKFLKIPPKFKHAALKF | seqid_213 |
| variant_251 | FWKKFLKIPPKFKHAALKF | seqid_214 |
| variant_252 | KKKLLLKIPPKFKHAALKF | seqid_215 |
| variant_253 | RKKLLLKIPPKFKHAALKF | seqid_216 |
| variant_254 | FKKLLLKIPPKFKHAALKF | seqid_217 |
| variant_255 | KWKLLLKIPPKFKHAALKF | seqid_218 |
| variant_256 | RWKLLLKIPPKFKHAALKF | seqid_219 |
| variant_257 | FWKLLLKIPPKFKHAALKF | seqid_220 |
| variant_258 | KKKKLLKIPPKFKHAALKF | seqid_221 |
| variant_259 | RKKKLLKIPPKFKHAALKF | seqid_222 |
| variant_260 | FKKKLLKIPPKFKHAALKF | seqid_223 |
| variant_261 | KWKKLLKIPPKFKHAALKF | seqid_224 |
| variant_262 | RWKKLLKIPPKFKHAALKF | seqid_225 |
| variant_263 | FWKKLLKIPPKFKHAALKF | seqid_226 |
| variant_264 | KKKLFKKIPPKFKHAALKF | seqid_227 |
| variant_265 | RKKLFKKIPPKFKHAALKF | seqid_228 |
| variant_266 | FKKLFKKIPPKFKHAALKF | seqid_229 |
| variant_267 | KWKLFKKIPPKFKHAALKF | seqid_230 |
| variant_268 | RWKLFKKIPPKFKHAALKF | seqid_231 |
| variant_269 | FWKLFKKIPPKFKHAALKF | seqid_232 |
| variant_270 | KKKKFKKIPPKFKHAALKF | seqid_233 |
| variant_271 | RKKKFKKIPPKFKHAALKF | seqid_234 |
| variant_272 | FKKKFKKIPPKFKHAALKF | seqid_235 |
| variant_273 | KWKKFKKIPPKFKHAALKF | seqid_236 |
| variant_274 | RWKKFKKIPPKFKHAALKF | seqid_237 |

| | | |
|---|---|---|
| variant_275 | FWKKFKKIPPKFKHAALKF | seqid_238 |
| variant_276 | KKKLLKKIPPKFKHAALKF | seqid_239 |
| variant_277 | RKKLLKKIPPKFKHAALKF | seqid_240 |
| variant_278 | FKKLLKKIPPKFKHAALKF | seqid_241 |
| variant_279 | KWKLLKKIPPKFKHAALKF | seqid_242 |
| variant_280 | RWKLLKKIPPKFKHAALKF | seqid_243 |
| variant_281 | FWKLLKKIPPKFKHAALKF | seqid_244 |
| variant_282 | KKKKLKKIPPKFKHAALKF | seqid_245 |
| variant_283 | RKKKLKKIPPKFKHAALKF | seqid_246 |
| variant_284 | FKKKLKKIPPKFKHAALKF | seqid_247 |
| variant_285 | KWKKLKKIPPKFKHAALKF | seqid_248 |
| variant_286 | RWKKLKKIPPKFKHAALKF | seqid_249 |
| variant_287 | FWKKLKKIPPKFKHAALKF | seqid_250 |
| variant_336 | KKKLFLKIPKFKHAALKF | seqid_251 |
| variant_337 | RKKLFLKIPKFKHAALKF | seqid_252 |
| variant_338 | FKKLFLKIPKFKHAALKF | seqid_253 |
| variant_339 | KWKLFLKIPKFKHAALKF | seqid_254 |
| variant_340 | RWKLFLKIPKFKHAALKF | seqid_255 |
| variant_341 | FWKLFLKIPKFKHAALKF | seqid_256 |
| variant_342 | KKKKFLKIPKFKHAALKF | seqid_257 |
| variant_343 | RKKKFLKIPKFKHAALKF | seqid_258 |
| variant_344 | FKKKFLKIPKFKHAALKF | seqid_259 |
| variant_345 | KWKKFLKIPKFKHAALKF | seqid_260 |
| variant_346 | RWKKFLKIPKFKHAALKF | seqid_261 |
| variant_347 | FWKKFLKIPKFKHAALKF | seqid_262 |
| variant_348 | KKKLLLKIPKFKHAALKF | seqid_263 |
| variant_349 | RKKLLLKIPKFKHAALKF | seqid_264 |
| variant_350 | FKKLLLKIPKFKHAALKF | seqid_265 |
| variant_351 | KWKLLLKIPKFKHAALKF | seqid_266 |
| variant_352 | RWKLLLKIPKFKHAALKF | seqid_267 |
| variant_353 | FWKLLLKIPKFKHAALKF | seqid_268 |
| variant_354 | KKKKLLKIPKFKHAALKF | seqid_269 |
| variant_355 | RKKKLLKIPKFKHAALKF | seqid_270 |
| variant_356 | FKKKLLKIPKFKHAALKF | seqid_271 |
| variant_357 | KWKKLLKIPKFKHAALKF | seqid_272 |
| variant_358 | RWKKLLKIPKFKHAALKF | seqid_273 |
| variant_359 | FWKKLLKIPKFKHAALKF | seqid_274 |
| variant_360 | KKKLFKKIPKFKHAALKF | seqid_275 |
| variant_361 | RKKLFKKIPKFKHAALKF | seqid_276 |
| variant_362 | FKKLFKKIPKFKHAALKF | seqid_277 |
| variant_363 | KWKLFKKIPKFKHAALKF | seqid_278 |
| variant_364 | RWKLFKKIPKFKHAALKF | seqid_279 |
| variant_365 | FWKLFKKIPKFKHAALKF | seqid_280 |
| variant_366 | KKKKFKKIPKFKHAALKF | seqid_281 |
| variant_367 | RKKKFKKIPKFKHAALKF | seqid_282 |
| variant_368 | FKKKFKKIPKFKHAALKF | seqid_283 |
| variant_369 | KWKKFKKIPKFKHAALKF | seqid_284 |
| variant_370 | RWKKFKKIPKFKHAALKF | seqid_285 |
| variant_371 | FWKKFKKIPKFKHAALKF | seqid_286 |
| variant_372 | KKKLLKKIPKFKHAALKF | seqid_287 |
| variant_373 | RKKLLKKIPKFKHAALKF | seqid_288 |
| variant_374 | FKKLLKKIPKFKHAALKF | seqid_289 |
| variant_375 | KWKLLKKIPKFKHAALKF | seqid_290 |
| variant_376 | RWKLLKKIPKFKHAALKF | seqid_291 |
| variant_377 | FWKLLKKIPKFKHAALKF | seqid_292 |
| variant_378 | KKKKLKKIPKFKHAALKF | seqid_293 |
| variant_379 | RKKKLKKIPKFKHAALKF | seqid_294 |
| variant_380 | FKKKLKKIPKFKHAALKF | seqid_295 |
| variant_381 | KWKKLKKIPKFKHAALKF | seqid_296 |
| variant_382 | RWKKLKKIPKFKHAALKF | seqid_297 |
| variant_383 | FWKKLKKIPKFKHAALKF | seqid_298 |
| variant_384 | KKKLFLKIPPPKFLKAALKF | seqid_299 |
| variant_385 | RKKLFLKIPPPKFLKAALKF | seqid_300 |
| variant_386 | FKKLFLKIPPPKFLKAALKF | seqid_301 |
| variant_387 | KWKLFLKIPPPKFLKAALKF | seqid_302 |
| variant_388 | RWKLFLKIPPPKFLKAALKF | seqid_303 |
| variant_389 | FWKLFLKIPPPKFLKAALKF | seqid_304 |
| variant_390 | KKKKFLKIPPPKFLKAALKF | seqid_305 |
| variant_391 | RKKKFLKIPPPKFLKAALKF | seqid_306 |
| variant_392 | FKKKFLKIPPPKFLKAALKF | seqid_307 |
| variant_393 | KWKKFLKIPPPKFLKAALKF | seqid_308 |
| variant_394 | RWKKFLKIPPPKFLKAALKF | seqid_309 |
| variant_395 | FWKKFLKIPPPKFLKAALKF | seqid_310 |
| variant_396 | KKKLLLKIPPPKFLKAALKF | seqid_311 |
| variant_397 | RKKLLLKIPPPKFLKAALKF | seqid_312 |
| variant_398 | FKKLLLKIPPPKFLKAALKF | seqid_313 |
| variant_399 | KWKLLLKIPPPKFLKAALKF | seqid_314 |
| variant_400 | RWKLLLKIPPPKFLKAALKF | seqid_315 |
| variant_401 | FWKLLLKIPPPKFLKAALKF | seqid_316 |
| variant_402 | KKKKLLKIPPPKFLKAALKF | seqid_317 |
| variant_403 | RKKKLLKIPPPKFLKAALKF | seqid_318 |

| | | |
|---|---|---|
| variant_404 | FKKKLLLKIPPPKFLKAALKF | seqid_319 |
| variant_405 | KWKKLLLKIPPPKFLKAALKF | seqid_320 |
| variant_406 | RWKKLLLKIPPPKFLKAALKF | seqid_321 |
| variant_407 | FWKKLLLKIPPPKFLKAALKF | seqid_322 |
| variant_408 | KKKLFKKIPPPKFLKAALKF | seqid_323 |
| variant_409 | RKKLFKKIPPPKFLKAALKF | seqid_324 |
| variant_410 | FKKLFKKIPPPKFLKAALKF | seqid_325 |
| variant_411 | KWKLFKKIPPPKFLKAALKF | seqid_326 |
| variant_412 | RWKLFKKIPPPKFLKAALKF | seqid_327 |
| variant_413 | FWKLFKKIPPPKFLKAALKF | seqid_328 |
| variant_414 | KKKKFKKIPPPKFLKAALKF | seqid_329 |
| variant_415 | RKKKFKKIPPPKFLKAALKF | seqid_330 |
| variant_416 | FKKKFKKIPPPKFLKAALKF | seqid_331 |
| variant_417 | KWKKFKKIPPPKFLKAALKF | seqid_332 |
| variant_418 | RWKKFKKIPPPKFLKAALKF | seqid_333 |
| variant_419 | FWKKFKKIPPPKFLKAALKF | seqid_334 |
| variant_420 | KKKLLKKIPPPKFLKAALKF | seqid_335 |
| variant_421 | RKKLLKKIPPPKFLKAALKF | seqid_336 |
| variant_422 | FKKLLKKIPPPKFLKAALKF | seqid_337 |
| variant_423 | KWKLLKKIPPPKFLKAALKF | seqid_338 |
| variant_424 | RWKLLKKIPPPKFLKAALKF | seqid_339 |
| variant_425 | FWKLLKKIPPPKFLKAALKF | seqid_340 |
| variant_426 | KKKKLKKIPPPKFLKAALKF | seqid_341 |
| variant_427 | RKKKLKKIPPPKFLKAALKF | seqid_342 |
| variant_428 | FKKKLKKIPPPKFLKAALKF | seqid_343 |
| variant_429 | KWKKLKKIPPPKFLKAALKF | seqid_344 |
| variant_430 | RWKKLKKIPPPKFLKAALKF | seqid_345 |
| variant_431 | FWKKLKKIPPPKFLKAALKF | seqid_346 |
| variant_432 | KKKLFLKIPPKFLKAALKF | seqid_347 |
| variant_433 | RKKLFLKIPPKFLKAALKF | seqid_348 |
| variant_434 | FKKLFLKIPPKFLKAALKF | seqid_349 |
| variant_435 | KWKLFLKIPPKFLKAALKF | seqid_350 |
| variant_436 | RWKLFLKIPPKFLKAALKF | seqid_351 |
| variant_437 | FWKLFLKIPPKFLKAALKF | seqid_352 |
| variant_438 | KKKKFLKIPPKFLKAALKF | seqid_353 |
| variant_439 | RKKKFLKIPPKFLKAALKF | seqid_354 |
| variant_440 | FKKKFLKIPPKFLKAALKF | seqid_355 |
| variant_441 | KWKKFLKIPPKFLKAALKF | seqid_356 |
| variant_442 | RWKKFLKIPPKFLKAALKF | seqid_357 |
| variant_443 | FWKKFLKIPPKFLKAALKF | seqid_358 |
| variant_444 | KKKLLLKIPPKFLKAALKF | seqid_359 |
| variant_445 | RKKLLLKIPPKFLKAALKF | seqid_360 |
| variant_446 | FKKLLLKIPPKFLKAALKF | seqid_361 |
| variant_447 | KWKLLLKIPPKFLKAALKF | seqid_362 |
| variant_448 | RWKLLLKIPPKFLKAALKF | seqid_363 |
| variant_449 | FWKLLLKIPPKFLKAALKF | seqid_364 |
| variant_450 | KKKKLLKIPPKFLKAALKF | seqid_365 |
| variant_451 | RKKKLLKIPPKFLKAALKF | seqid_366 |
| variant_452 | FKKKLLKIPPKFLKAALKF | seqid_367 |
| variant_453 | KWKKLLKIPPKFLKAALKF | seqid_368 |
| variant_454 | RWKKLLKIPPKFLKAALKF | seqid_369 |
| variant_455 | FWKKLLKIPPKFLKAALKF | seqid_370 |
| variant_456 | KKKLFKKIPPKFLKAALKF | seqid_371 |
| variant_457 | RKKLFKKIPPKFLKAALKF | seqid_372 |
| variant_458 | FKKLFKKIPPKFLKAALKF | seqid_373 |
| variant_459 | KWKLFKKIPPKFLKAALKF | seqid_374 |
| variant_460 | RWKLFKKIPPKFLKAALKF | seqid_375 |
| variant_461 | FWKLFKKIPPKFLKAALKF | seqid_376 |
| variant_462 | KKKKFKKIPPKFLKAALKF | seqid_377 |
| variant_463 | RKKKFKKIPPKFLKAALKF | seqid_378 |
| variant_464 | FKKKFKKIPPKFLKAALKF | seqid_379 |
| variant_465 | KWKKFKKIPPKFLKAALKF | seqid_380 |
| variant_466 | RWKKFKKIPPKFLKAALKF | seqid_381 |
| variant_467 | FWKKFKKIPPKFLKAALKF | seqid_382 |
| variant_468 | KKKLLKKIPPKFLKAALKF | seqid_383 |
| variant_469 | RKKLLKKIPPKFLKAALKF | seqid_384 |
| variant_470 | FKKLLKKIPPKFLKAALKF | seqid_385 |
| variant_471 | KWKLLKKIPPKFLKAALKF | seqid_386 |
| variant_472 | RWKLLKKIPPKFLKAALKF | seqid_387 |
| variant_473 | FWKLLKKIPPKFLKAALKF | seqid_388 |
| variant_474 | KKKKLKKIPPKFLKAALKF | seqid_389 |
| variant_475 | RKKKLKKIPPKFLKAALKF | seqid_390 |
| variant_476 | FKKKLKKIPPKFLKAALKF | seqid_391 |
| variant_477 | KWKKLKKIPPKFLKAALKF | seqid_392 |
| variant_478 | RWKKLKKIPPKFLKAALKF | seqid_393 |
| variant_479 | FWKKLKKIPPKFLKAALKF | seqid_394 |
| variant_528 | KKKLFLKIPKFLKAALKF | seqid_395 |
| variant_529 | RKKLFLKIPKFLKAALKF | seqid_396 |
| variant_530 | FKKLFLKIPKFLKAALKF | seqid_397 |
| variant_531 | KWKLFLKIPKFLKAALKF | seqid_398 |
| variant_532 | RWKLFLKIPKFLKAALKF | seqid_399 |

| variant_533 | FWKLFLKIPKFLKAALKF | seqid_400 |
| variant_534 | KKKKFLKIPKFLKAALKF | seqid_401 |
| variant_535 | RKKKFLKIPKFLKAALKF | seqid_402 |
| variant_536 | FKKKFLKIPKFLKAALKF | seqid_403 |
| variant_537 | KWKKFLKIPKFLKAALKF | seqid_404 |
| variant_538 | RWKKFLKIPKFLKAALKF | seqid_405 |
| variant_539 | FWKKFLKIPKFLKAALKF | seqid_406 |
| variant_540 | KKKLLLKIPKFLKAALKF | seqid_407 |
| variant_541 | RKKLLLKIPKFLKAALKF | seqid_408 |
| variant_542 | FKKLLLKIPKFLKAALKF | seqid_409 |
| variant_543 | KWKLLLKIPKFLKAALKF | seqid_410 |
| variant_544 | RWKLLLKIPKFLKAALKF | seqid_411 |
| variant_545 | FWKLLLKIPKFLKAALKF | seqid_412 |
| variant_546 | KKKKLLKIPKFLKAALKF | seqid_413 |
| variant_547 | RKKKLLKIPKFLKAALKF | seqid_414 |
| variant_548 | FKKKLLKIPKFLKAALKF | seqid_415 |
| variant_549 | KWKKLLKIPKFLKAALKF | seqid_416 |
| variant_550 | RWKKLLKIPKFLKAALKF | seqid_417 |
| variant_551 | FWKKLLKIPKFLKAALKF | seqid_418 |
| variant_552 | KKKLFKKIPKFLKAALKF | seqid_419 |
| variant_553 | RKKLFKKIPKFLKAALKF | seqid_420 |
| variant_554 | FKKLFKKIPKFLKAALKF | seqid_421 |
| variant_555 | KWKLFKKIPKFLKAALKF | seqid_422 |
| variant_556 | RWKLFKKIPKFLKAALKF | seqid_423 |
| variant_557 | FWKLFKKIPKFLKAALKF | seqid_424 |
| variant_558 | KKKKFKKIPKFLKAALKF | seqid_425 |
| variant_559 | RKKKFKKIPKFLKAALKF | seqid_426 |
| variant_560 | FKKKFKKIPKFLKAALKF | seqid_427 |
| variant_561 | KWKKFKKIPKFLKAALKF | seqid_428 |
| variant_562 | RWKKFKKIPKFLKAALKF | seqid_429 |
| variant_563 | FWKKFKKIPKFLKAALKF | seqid_430 |
| variant_564 | KKKLLKKIPKFLKAALKF | seqid_431 |
| variant_565 | RKKLLKKIPKFLKAALKF | seqid_432 |
| variant_566 | FKKLLKKIPKFLKAALKF | seqid_433 |
| variant_567 | KWKLLKKIPKFLKAALKF | seqid_434 |
| variant_568 | RWKLLKKIPKFLKAALKF | seqid_435 |
| variant_569 | FWKLLKKIPKFLKAALKF | seqid_436 |
| variant_570 | KKKKLKKIPKFLKAALKF | seqid_437 |
| variant_571 | RKKKLKKIPKFLKAALKF | seqid_438 |
| variant_572 | FKKKLKKIPKFLKAALKF | seqid_439 |
| variant_573 | KWKKLKKIPKFLKAALKF | seqid_440 |
| variant_574 | RWKKLKKIPKFLKAALKF | seqid_441 |
| variant_575 | FWKKLKKIPKFLKAALKF | seqid_442 |
| variant_576 | KKKLFLKIPPPKFKKAALKF | seqid_443 |
| variant_577 | RKKLFLKIPPPKFKKAALKF | seqid_444 |
| variant_578 | FKKLFLKIPPPKFKKAALKF | seqid_445 |
| variant_579 | KWKLFLKIPPPKFKKAALKF | seqid_446 |
| variant_580 | RWKLFLKIPPPKFKKAALKF | seqid_447 |
| variant_581 | FWKLFLKIPPPKFKKAALKF | seqid_448 |
| variant_582 | KKKKFLKIPPPKFKKAALKF | seqid_449 |
| variant_583 | RKKKFLKIPPPKFKKAALKF | seqid_450 |
| variant_584 | FKKKFLKIPPPKFKKAALKF | seqid_451 |
| variant_585 | KWKKFLKIPPPKFKKAALKF | seqid_452 |
| variant_586 | RWKKFLKIPPPKFKKAALKF | seqid_453 |
| variant_587 | FWKKFLKIPPPKFKKAALKF | seqid_454 |
| variant_588 | KKKLLLKIPPPKFKKAALKF | seqid_455 |
| variant_589 | RKKLLLKIPPPKFKKAALKF | seqid_456 |
| variant_590 | FKKLLLKIPPPKFKKAALKF | seqid_457 |
| variant_591 | KWKLLLKIPPPKFKKAALKF | seqid_458 |
| variant_592 | RWKLLLKIPPPKFKKAALKF | seqid_459 |
| variant_593 | FWKLLLKIPPPKFKKAALKF | seqid_460 |
| variant_594 | KKKKLLKIPPPKFKKAALKF | seqid_461 |
| variant_595 | RKKKLLKIPPPKFKKAALKF | seqid_462 |
| variant_596 | FKKKLLKIPPPKFKKAALKF | seqid_463 |
| variant_597 | KWKKLLKIPPPKFKKAALKF | seqid_464 |
| variant_598 | RWKKLLKIPPPKFKKAALKF | seqid_465 |
| variant_599 | FWKKLLKIPPPKFKKAALKF | seqid_466 |
| variant_600 | KKKLFKKIPPPKFKKAALKF | seqid_467 |
| variant_601 | RKKLFKKIPPPKFKKAALKF | seqid_468 |
| variant_602 | FKKLFKKIPPPKFKKAALKF | seqid_469 |
| variant_603 | KWKLFKKIPPPKFKKAALKF | seqid_470 |
| variant_604 | RWKLFKKIPPPKFKKAALKF | seqid_471 |
| variant_605 | FWKLFKKIPPPKFKKAALKF | seqid_472 |
| variant_606 | KKKKFKKIPPPKFKKAALKF | seqid_473 |
| variant_607 | RKKKFKKIPPPKFKKAALKF | seqid_474 |
| variant_608 | FKKKFKKIPPPKFKKAALKF | seqid_475 |
| variant_609 | KWKKFKKIPPPKFKKAALKF | seqid_476 |
| variant_610 | RWKKFKKIPPPKFKKAALKF | seqid_477 |
| variant_611 | FWKKFKKIPPPKFKKAALKF | seqid_478 |
| variant_612 | KKKLLKKIPPPKFKKAALKF | seqid_479 |
| variant_613 | RKKLLKKIPPPKFKKAALKF | seqid_480 |

-continued

| variant_614 | FKKLLKKIPPPKFKKAALKF | seqid_481 |
| variant_615 | KWKLLKKIPPPKFKKAALKF | seqid_482 |
| variant_616 | RWKLLKKIPPPKFKKAALKF | seqid_483 |
| variant_617 | FWKLLKKIPPPKFKKAALKF | seqid_484 |
| variant_618 | KKKKLKKIPPPKFKKAALKF | seqid_485 |
| variant_619 | RKKKLKKIPPPKFKKAALKF | seqid_486 |
| variant_620 | FKKKLKKIPPPKFKKAALKF | seqid_487 |
| variant_621 | KWKKLKKIPPPKFKKAALKF | seqid_488 |
| variant_622 | RWKKLKKIPPPKFKKAALKF | seqid_489 |
| variant_623 | FWKKLKKIPPPKFKKAALKF | seqid_490 |
| variant_624 | KKKLFLKIPPKFKKAALKF | seqid_491 |
| variant_625 | RKKLFLKIPPKFKKAALKF | seqid_492 |
| variant_626 | FKKLFLKIPPKFKKAALKF | seqid_493 |
| variant_627 | KWKLFLKIPPKFKKAALKF | seqid_494 |
| variant_628 | RWKLFLKIPPKFKKAALKF | seqid_495 |
| variant_629 | FWKLFLKIPPKFKKAALKF | seqid_496 |
| variant_630 | KKKKFLKIPPKFKKAALKF | seqid_497 |
| variant_631 | RKKKFLKIPPKFKKAALKF | seqid_498 |
| variant_632 | FKKKFLKIPPKFKKAALKF | seqid_499 |
| variant_633 | KWKKFLKIPPKFKKAALKF | seqid_500 |
| variant_634 | RWKKFLKIPPKFKKAALKF | seqid_501 |
| variant_635 | FWKKFLKIPPKFKKAALKF | seqid_502 |
| variant_636 | KKKLLLKIPPKFKKAALKF | seqid_503 |
| variant_637 | RKKLLLKIPPKFKKAALKF | seqid_504 |
| variant_638 | FKKLLLKIPPKFKKAALKF | seqid_505 |
| variant_639 | KWKLLLKIPPKFKKAALKF | seqid_506 |
| variant_640 | RWKLLLKIPPKFKKAALKF | seqid_507 |
| variant_641 | FWKLLLKIPPKFKKAALKF | seqid_508 |
| variant_642 | KKKKLLKIPPKFKKAALKF | seqid_509 |
| variant_643 | RKKKLLKIPPKFKKAALKF | seqid_510 |
| variant_644 | FKKKLLKIPPKFKKAALKF | seqid_511 |
| variant_645 | KWKKLLKIPPKFKKAALKF | seqid_512 |
| variant_646 | RWKKLLKIPPKFKKAALKF | seqid_513 |
| variant_647 | FWKKLLKIPPKFKKAALKF | seqid_514 |
| variant_648 | KKKLFKKIPPKFKKAALKF | seqid_515 |
| variant_649 | RKKLFKKIPPKFKKAALKF | seqid_516 |
| variant_650 | FKKLFKKIPPKFKKAALKF | seqid_517 |
| variant_651 | KWKLFKKIPPKFKKAALKF | seqid_518 |
| variant_652 | RWKLFKKIPPKFKKAALKF | seqid_519 |
| variant_653 | FWKLFKKIPPKFKKAALKF | seqid_520 |

-continued

| variant_654 | KKKKFKKIPPKFKKAALKF | seqid_521 |
| variant_655 | RKKKFKKIPPKFKKAALKF | seqid_522 |
| variant_656 | FKKKFKKIPPKFKKAALKF | seqid_523 |
| variant_657 | KWKKFKKIPPKFKKAALKF | seqid_524 |
| variant_658 | RWKKFKKIPPKFKKAALKF | seqid_525 |
| variant_659 | FWKKFKKIPPKFKKAALKF | seqid_526 |
| variant_660 | KKKLLKKIPPKFKKAALKF | seqid_527 |
| variant_661 | RKKLLKKIPPKFKKAALKF | seqid_528 |
| variant_662 | FKKLLKKIPPKFKKAALKF | seqid_529 |
| variant_663 | KWKLLKKIPPKFKKAALKF | seqid_530 |
| variant_664 | RWKLLKKIPPKFKKAALKF | seqid_531 |
| variant_665 | FWKLLKKIPPKFKKAALKF | seqid_532 |
| variant_666 | KKKKLKKIPPKFKKAALKF | seqid_533 |
| variant_667 | RKKKLKKIPPKFKKAALKF | seqid_534 |
| variant_668 | FKKKLKKIPPKFKKAALKF | seqid_535 |
| variant_669 | KWKKLKKIPPKFKKAALKF | seqid_536 |
| variant_670 | RWKKLKKIPPKFKKAALKF | seqid_537 |
| variant_671 | FWKKLKKIPPKFKKAALKF | seqid_538 |
| variant_720 | KKKLFLKIPKFKKAALKF | seqid_539 |
| variant_721 | RKKLFLKIPKFKKAALKF | seqid_540 |
| variant_722 | FKKLFLKIPKFKKAALKF | seqid_541 |
| variant_723 | KWKLFLKIPKFKKAALKF | seqid_542 |
| variant_724 | RWKLFLKIPKFKKAALKF | seqid_543 |
| variant_725 | FWKLFLKIPKFKKAALKF | seqid_544 |
| variant_726 | KKKKFLKIPKFKKAALKF | seqid_545 |
| variant_727 | RKKKFLKIPKFKKAALKF | seqid_546 |
| variant_728 | FKKKFLKIPKFKKAALKF | seqid_547 |
| variant_729 | KWKKFLKIPKFKKAALKF | seqid_548 |
| variant_730 | RWKKFLKIPKFKKAALKF | seqid_549 |
| variant_731 | FWKKFLKIPKFKKAALKF | seqid_550 |
| variant_732 | KKKLLLKIPKFKKAALKF | seqid_551 |
| variant_733 | RKKLLLKIPKFKKAALKF | seqid_552 |
| variant_734 | FKKLLLKIPKFKKAALKF | seqid_553 |
| variant_735 | KWKLLLKIPKFKKAALKF | seqid_554 |
| variant_736 | RWKLLLKIPKFKKAALKF | seqid_555 |
| variant_737 | FWKLLLKIPKFKKAALKF | seqid_556 |
| variant_738 | KKKKLLKIPKFKKAALKF | seqid_557 |
| variant_739 | RKKKLLKIPKFKKAALKF | seqid_558 |
| variant_740 | FKKKLLKIPKFKKAALKF | seqid_559 |
| variant_741 | KWKKLLKIPKFKKAALKF | seqid_560 |
| variant_742 | RWKKLLKIPKFKKAALKF | seqid_561 |

-continued

| | | |
|---|---|---|
| variant_743 | FWKKLLKIPKFKKAALKF | seqid_562 |
| variant_744 | KKKLFKKIPKFKKAALKF | seqid_563 |
| variant_745 | RKKLFKKIPKFKKAALKF | seqid_564 |
| variant_746 | FKKLFKKIPKFKKAALKF | seqid_565 |
| variant_747 | KWKLFKKIPKFKKAALKF | seqid_566 |
| variant_748 | RWKLFKKIPKFKKAALKF | seqid_567 |
| variant_749 | FWKLFKKIPKFKKAALKF | seqid_568 |
| variant_750 | KKKKFKKIPKFKKAALKF | seqid_569 |
| variant_751 | RKKKFKKIPKFKKAALKF | seqid_570 |
| variant_752 | FKKKFKKIPKFKKAALKF | seqid_571 |
| variant_753 | KWKKFKKIPKFKKAALKF | seqid_572 |
| variant_754 | RWKKFKKIPKFKKAALKF | seqid_573 |
| variant_755 | FWKKFKKIPKFKKAALKF | seqid_574 |
| variant_756 | KKKLLKKIPKFKKAALKF | seqid_575 |
| variant_757 | RKKLLKKIPKFKKAALKF | seqid_576 |
| variant_758 | FKKLLKKIPKFKKAALKF | seqid_577 |
| variant_759 | KWKLLKKIPKFKKAALKF | seqid_578 |
| variant_760 | RWKLLKKIPKFKKAALKF | seqid_579 |
| variant_761 | FWKLLKKIPKFKKAALKF | seqid_580 |
| variant_762 | KKKKLKKIPKFKKAALKF | seqid_581 |
| variant_763 | RKKKLKKIPKFKKAALKF | seqid_582 |
| variant_764 | FKKKLKKIPKFKKAALKF | seqid_583 |
| variant_765 | KWKKLKKIPKFKKAALKF | seqid_584 |
| variant_766 | RWKKLKKIPKFKKAALKF | seqid_585 |
| variant_767 | FWKKLKKIPKFKKAALKF | seqid_586 |
| variant_768 | KKKLFLKIPPPKFLHLALKF | seqid_587 |
| variant_769 | RKKLFLKIPPPKFLHLALKF | seqid_588 |
| variant_770 | FKKLFLKIPPPKFLHLALKF | seqid_589 |
| variant_771 | KWKLFLKIPPPKFLHLALKF | seqid_590 |
| variant_772 | RWKLFLKIPPPKFLHLALKF | seqid_591 |
| variant_773 | FWKLFLKIPPPKFLHLALKF | seqid_592 |
| variant_774 | KKKKFLKIPPPKFLHLALKF | seqid_593 |
| variant_775 | RKKKFLKIPPPKFLHLALKF | seqid_594 |
| variant_776 | FKKKFLKIPPPKFLHLALKF | seqid_595 |
| variant_777 | KWKKFLKIPPPKFLHLALKF | seqid_596 |
| variant_778 | RWKKFLKIPPPKFLHLALKF | seqid_597 |
| variant_779 | FWKKFLKIPPPKFLHLALKF | seqid_598 |
| variant_780 | KKKLLLKIPPPKFLHLALKF | seqid_599 |
| variant_781 | RKKLLLKIPPPKFLHLALKF | seqid_600 |
| variant_782 | FKKLLLKIPPPKFLHLALKF | seqid_601 |
| variant_783 | KWKLLLKIPPPKFLHLALKF | seqid_602 |
| variant_784 | RWKLLLKIPPPKFLHLALKF | seqid_603 |
| variant_785 | FWKLLLKIPPPKFLHLALKF | seqid_604 |
| variant_786 | KKKKLLKIPPPKFLHLALKF | seqid_605 |
| variant_787 | RKKKLLKIPPPKFLHLALKF | seqid_606 |
| variant_788 | FKKKLLKIPPPKFLHLALKF | seqid_607 |
| variant_789 | KWKKLLKIPPPKFLHLALKF | seqid_608 |
| variant_790 | RWKKLLKIPPPKFLHLALKF | seqid_609 |
| variant_791 | FWKKLLKIPPPKFLHLALKF | seqid_610 |
| variant_792 | KKKLFKKIPPPKFLHLALKF | seqid_611 |
| variant_793 | RKKLFKKIPPPKFLHLALKF | seqid_612 |
| variant_794 | FKKLFKKIPPPKFLHLALKF | seqid_613 |
| variant_795 | KWKLFKKIPPPKFLHLALKF | seqid_614 |
| variant_796 | RWKLFKKIPPPKFLHLALKF | seqid_615 |
| variant_797 | FWKLFKKIPPPKFLHLALKF | seqid_616 |
| variant_798 | KKKKFKKIPPPKFLHLALKF | seqid_617 |
| variant_799 | RKKKFKKIPPPKFLHLALKF | seqid_618 |
| variant_800 | FKKKFKKIPPPKFLHLALKF | seqid_619 |
| variant_801 | KWKKFKKIPPPKFLHLALKF | seqid_620 |
| variant_802 | RWKKFKKIPPPKFLHLALKF | seqid_621 |
| variant_803 | FWKKFKKIPPPKFLHLALKF | seqid_622 |
| variant_804 | KKKLLKKIPPPKFLHLALKF | seqid_623 |
| variant_805 | RKKLLKKIPPPKFLHLALKF | seqid_624 |
| variant_806 | FKKLLKKIPPPKFLHLALKF | seqid_625 |
| variant_807 | KWKLLKKIPPPKFLHLALKF | seqid_626 |
| variant_808 | RWKLLKKIPPPKFLHLALKF | seqid_627 |
| variant_809 | FWKLLKKIPPPKFLHLALKF | seqid_628 |
| variant_810 | KKKKLKKIPPPKFLHLALKF | seqid_629 |
| variant_811 | RKKKLKKIPPPKFLHLALKF | seqid_630 |
| variant_812 | FKKKLKKIPPPKFLHLALKF | seqid_631 |
| variant_813 | KWKKLKKIPPPKFLHLALKF | seqid_632 |
| variant_814 | RWKKLKKIPPPKFLHLALKF | seqid_633 |
| variant_815 | FWKKLKKIPPPKFLHLALKF | seqid_634 |
| variant_816 | KKKLFLKIPPKFLHLALKF | seqid_635 |
| variant_817 | RKKLFLKIPPKFLHLALKF | seqid_636 |
| variant_818 | FKKLFLKIPPKFLHLALKF | seqid_637 |
| variant_819 | KWKLFLKIPPKFLHLALKF | seqid_638 |
| variant_820 | RWKLFLKIPPKFLHLALKF | seqid_639 |
| variant_821 | FWKLFLKIPPKFLHLALKF | seqid_640 |
| variant_822 | KKKKFLKIPPKFLHLALKF | seqid_641 |
| variant_823 | RKKKFLKIPPKFLHLALKF | seqid_642 |

| | | |
|---|---|---|
| variant_824 | FKKKFLKIPPKFLHLALKF | seqid_643 |
| variant_825 | KWKKFLKIPPKFLHLALKF | seqid_644 |
| variant_826 | RWKKFLKIPPKFLHLALKF | seqid_645 |
| variant_827 | FWKKFLKIPPKFLHLALKF | seqid_646 |
| variant_828 | KKKLLLKIPPKFLHLALKF | seqid_647 |
| variant_829 | RKKLLLKIPPKFLHLALKF | seqid_648 |
| variant_830 | FKKLLLKIPPKFLHLALKF | seqid_649 |
| variant_831 | KWKLLLKIPPKFLHLALKF | seqid_650 |
| variant_832 | RWKLLLKIPPKFLHLALKF | seqid_651 |
| variant_833 | FWKLLLKIPPKFLHLALKF | seqid_652 |
| variant_834 | KKKKLLKIPPKFLHLALKF | seqid_653 |
| variant_835 | RKKKLLKIPPKFLHLALKF | seqid_654 |
| variant_836 | FKKKLLKIPPKFLHLALKF | seqid_655 |
| variant_837 | KWKKLLKIPPKFLHLALKF | seqid_656 |
| variant_838 | RWKKLLKIPPKFLHLALKF | seqid_657 |
| variant_839 | FWKKLLKIPPKFLHLALKF | seqid_658 |
| variant_840 | KKKLFKKIPPKFLHLALKF | seqid_659 |
| variant_841 | RKKLFKKIPPKFLHLALKF | seqid_660 |
| variant_842 | FKKLFKKIPPKFLHLALKF | seqid_661 |
| variant_843 | KWKLFKKIPPKFLHLALKF | seqid_662 |
| variant_844 | RWKLFKKIPPKFLHLALKF | seqid_663 |
| variant_845 | FWKLFKKIPPKFLHLALKF | seqid_664 |
| variant_846 | KKKKFKKIPPKFLHLALKF | seqid_665 |
| variant_847 | RKKKFKKIPPKFLHLALKF | seqid_666 |
| variant_848 | FKKKFKKIPPKFLHLALKF | seqid_667 |
| variant_849 | KWKKFKKIPPKFLHLALKF | seqid_668 |
| variant_850 | RWKKFKKIPPKFLHLALKF | seqid_669 |
| variant_851 | FWKKFKKIPPKFLHLALKF | seqid_670 |
| variant_852 | KKKLLKKIPPKFLHLALKF | seqid_671 |
| variant_853 | RKKLLKKIPPKFLHLALKF | seqid_672 |
| variant_854 | FKKLLKKIPPKFLHLALKF | seqid_673 |
| variant_855 | KWKLLKKIPPKFLHLALKF | seqid_674 |
| variant_856 | RWKLLKKIPPKFLHLALKF | seqid_675 |
| variant_857 | FWKLLKKIPPKFLHLALKF | seqid_676 |
| variant_858 | KKKKLKKIPPKFLHLALKF | seqid_677 |
| variant_859 | RKKKLKKIPPKFLHLALKF | seqid_678 |
| variant_860 | FKKKLKKIPPKFLHLALKF | seqid_679 |
| variant_861 | KWKKLKKIPPKFLHLALKF | seqid_680 |
| variant_862 | RWKKLKKIPPKFLHLALKF | seqid_681 |
| variant_863 | FWKKLKKIPPKFLHLALKF | seqid_682 |
| variant_912 | KKKLFLKIPKFLHLALKF | seqid_683 |
| variant_913 | RKKLFLKIPKFLHLALKF | seqid_684 |
| variant_914 | FKKLFLKIPKFLHLALKF | seqid_685 |
| variant_915 | KWKLFLKIPKFLHLALKF | seqid_686 |
| variant_916 | RWKLFLKIPKFLHLALKF | seqid_687 |
| variant_917 | FWKLFLKIPKFLHLALKF | seqid_688 |
| variant_918 | KKKKFLKIPKFLHLALKF | seqid_689 |
| variant_919 | RKKKFLKIPKFLHLALKF | seqid_690 |
| variant_920 | FKKKFLKIPKFLHLALKF | seqid_691 |
| variant_921 | KWKKFLKIPKFLHLALKF | seqid_692 |
| variant_922 | RWKKFLKIPKFLHLALKF | seqid_693 |
| variant_923 | FWKKFLKIPKFLHLALKF | seqid_694 |
| variant_924 | KKKLLLKIPKFLHLALKF | seqid_695 |
| variant_925 | RKKLLLKIPKFLHLALKF | seqid_696 |
| variant_926 | FKKLLLKIPKFLHLALKF | seqid_697 |
| variant_927 | KWKLLLKIPKFLHLALKF | seqid_698 |
| variant_928 | RWKLLLKIPKFLHLALKF | seqid_699 |
| variant_929 | FWKLLLKIPKFLHLALKF | seqid_700 |
| variant_930 | KKKKLLKIPKFLHLALKF | seqid_701 |
| variant_931 | RKKKLLKIPKFLHLALKF | seqid_702 |
| variant_932 | FKKKLLKIPKFLHLALKF | seqid_703 |
| variant_933 | KWKKLLKIPKFLHLALKF | seqid_704 |
| variant_934 | RWKKLLKIPKFLHLALKF | seqid_705 |
| variant_935 | FWKKLLKIPKFLHLALKF | seqid_706 |
| variant_936 | KKKLFKKIPKFLHLALKF | seqid_707 |
| variant_937 | RKKLFKKIPKFLHLALKF | seqid_708 |
| variant_938 | FKKLFKKIPKFLHLALKF | seqid_709 |
| variant_939 | KWKLFKKIPKFLHLALKF | seqid_710 |
| variant_940 | RWKLFKKIPKFLHLALKF | seqid_711 |
| variant_941 | FWKLFKKIPKFLHLALKF | seqid_712 |
| variant_942 | KKKKFKKIPKFLHLALKF | seqid_713 |
| variant_943 | RKKKFKKIPKFLHLALKF | seqid_714 |
| variant_944 | FKKKFKKIPKFLHLALKF | seqid_715 |
| variant_945 | KWKKFKKIPKFLHLALKF | seqid_716 |
| variant_946 | RWKKFKKIPKFLHLALKF | seqid_717 |
| variant_947 | FWKKFKKIPKFLHLALKF | seqid_718 |
| variant_948 | KKKLLKKIPKFLHLALKF | seqid_719 |
| variant_949 | RKKLLKKIPKFLHLALKF | seqid_720 |
| variant_950 | FKKLLKKIPKFLHLALKF | seqid_721 |
| variant_951 | KWKLLKKIPKFLHLALKF | seqid_722 |
| variant_952 | RWKLLKKIPKFLHLALKF | seqid_723 |

| | | |
|---|---|---|
| variant_953 | FWKLLKKIPKFLHLALKF | seqid_724 |
| variant_954 | KKKKLKKIPKFLHLALKF | seqid_725 |
| variant_955 | RKKKLKKIPKFLHLALKF | seqid_726 |
| variant_956 | FKKKLKKIPKFLHLALKF | seqid_727 |
| variant_957 | KWKKLKKIPKFLHLALKF | seqid_728 |
| variant_958 | RWKKLKKIPKFLHLALKF | seqid_729 |
| variant_959 | FWKKLKKIPKFLHLALKF | seqid_730 |
| variant_960 | KKKLFLKIPPPKFKHLALKF | seqid_731 |
| variant_961 | RKKLFLKIPPPKFKHLALKF | seqid_732 |
| variant_962 | FKKLFLKIPPPKFKHLALKF | seqid_733 |
| variant_963 | KWKLFLKIPPPKFKHLALKF | seqid_734 |
| variant_964 | RWKLFLKIPPPKFKHLALKF | seqid_735 |
| variant_965 | FWKLFLKIPPPKFKHLALKF | seqid_736 |
| variant_966 | KKKKFLKIPPPKFKHLALKF | seqid_737 |
| variant_967 | RKKKFLKIPPPKFKHLALKF | seqid_738 |
| variant_968 | FKKKFLKIPPPKFKHLALKF | seqid_739 |
| variant_969 | KWKKFLKIPPPKFKHLALKF | seqid_740 |
| variant_970 | RWKKFLKIPPPKFKHLALKF | seqid_741 |
| variant_971 | FWKKFLKIPPPKFKHLALKF | seqid_742 |
| variant_972 | KKKLLLKIPPPKFKHLALKF | seqid_743 |
| variant_973 | RKKLLLKIPPPKFKHLALKF | seqid_744 |
| variant_974 | FKKLLLKIPPPKFKHLALKF | seqid_745 |
| variant_975 | KWKLLLKIPPPKFKHLALKF | seqid_746 |
| variant_976 | RWKLLLKIPPPKFKHLALKF | seqid_747 |
| variant_977 | FWKLLLKIPPPKFKHLALKF | seqid_748 |
| variant_978 | KKKKLLKIPPPKFKHLALKF | seqid_749 |
| variant_979 | RKKKLLKIPPPKFKHLALKF | seqid_750 |
| variant_980 | FKKKLLKIPPPKFKHLALKF | seqid_751 |
| variant_981 | KWKKLLKIPPPKFKHLALKF | seqid_752 |
| variant_982 | RWKKLLKIPPPKFKHLALKF | seqid_753 |
| variant_983 | FWKKLLKIPPPKFKHLALKF | seqid_754 |
| variant_984 | KKKLFKKIPPPKFKHLALKF | seqid_755 |
| variant_985 | RKKLFKKIPPPKFKHLALKF | seqid_756 |
| variant_986 | FKKLFKKIPPPKFKHLALKF | seqid_757 |
| variant_987 | KWKLFKKIPPPKFKHLALKF | seqid_758 |
| variant_988 | RWKLFKKIPPPKFKHLALKF | seqid_759 |
| variant_989 | FWKLFKKIPPPKFKHLALKF | seqid_760 |
| variant_990 | KKKKFKKIPPPKFKHLALKF | seqid_761 |
| variant_991 | RKKKFKKIPPPKFKHLALKF | seqid_762 |
| variant_992 | FKKKFKKIPPPKFKHLALKF | seqid_763 |
| variant_993 | KWKKFKKIPPPKFKHLALKF | seqid_764 |
| variant_994 | RWKKFKKIPPPKFKHLALKF | seqid_765 |
| variant_995 | FWKKFKKIPPPKFKHLALKF | seqid_766 |
| variant_996 | KKKLLKKIPPPKFKHLALKF | seqid_767 |
| variant_997 | RKKLLKKIPPPKFKHLALKF | seqid_768 |
| variant_998 | FKKLLKKIPPPKFKHLALKF | seqid_769 |
| variant_999 | KWKLLKKIPPPKFKHLALKF | seqid_770 |
| variant_1000 | RWKLLKKIPPPKFKHLALKF | seqid_771 |
| variant_1001 | FWKLLKKIPPPKFKHLALKF | seqid_772 |
| variant_1002 | KKKKLKKIPPPKFKHLALKF | seqid_773 |
| variant_1003 | RKKKLKKIPPPKFKHLALKF | seqid_774 |
| variant_1004 | FKKKLKKIPPPKFKHLALKF | seqid_775 |
| variant_1005 | KWKKLKKIPPPKFKHLALKF | seqid_776 |
| variant_1006 | RWKKLKKIPPPKFKHLALKF | seqid_777 |
| variant_1007 | FWKKLKKIPPPKFKHLALKF | seqid_778 |
| variant_1008 | KKKLFLKIPPKFKHLALKF | seqid_779 |
| variant_1009 | RKKLFLKIPPKFKHLALKF | seqid_780 |
| variant_1010 | FKKLFLKIPPKFKHLALKF | seqid_781 |
| variant_1011 | KWKLFLKIPPKFKHLALKF | seqid_782 |
| variant_1012 | RWKLFLKIPPKFKHLALKF | seqid_783 |
| variant_1013 | FWKLFLKIPPKFKHLALKF | seqid_784 |
| variant_1014 | KKKKFLKIPPKFKHLALKF | seqid_785 |
| variant_1015 | RKKKFLKIPPKFKHLALKF | seqid_786 |
| variant_1016 | FKKKFLKIPPKFKHLALKF | seqid_787 |
| variant_1017 | KWKKFLKIPPKFKHLALKF | seqid_788 |
| variant_1018 | RWKKFLKIPPKFKHLALKF | seqid_789 |
| variant_1019 | FWKKFLKIPPKFKHLALKF | seqid_790 |
| variant_1020 | KKKLLLKIPPKFKHLALKF | seqid_791 |
| variant_1021 | RKKLLLKIPPKFKHLALKF | seqid_792 |
| variant_1022 | FKKLLLKIPPKFKHLALKF | seqid_793 |
| variant_1023 | KWKLLLKIPPKFKHLALKF | seqid_794 |
| variant_1024 | RWKLLLKIPPKFKHLALKF | seqid_795 |
| variant_1025 | FWKLLLKIPPKFKHLALKF | seqid_796 |
| variant_1026 | KKKKLLKIPPKFKHLALKF | seqid_797 |
| variant_1027 | RKKKLLKIPPKFKHLALKF | seqid_798 |
| variant_1028 | FKKKLLKIPPKFKHLALKF | seqid_799 |
| variant_1029 | KWKKLLKIPPKFKHLALKF | seqid_800 |
| variant_1030 | RWKKLLKIPPKFKHLALKF | seqid_801 |
| variant_1031 | FWKKLLKIPPKFKHLALKF | seqid_802 |
| variant_1032 | KKKLFKKIPPKFKHLALKF | seqid_803 |
| variant_1033 | RKKLFKKIPPKFKHLALKF | seqid_804 |

-continued

| | | |
|---|---|---|
| variant_1034 | FKKLFKKIPPKFKHLALKF | seqid_805 |
| variant_1035 | KWKLFKKIPPKFKHLALKF | seqid_806 |
| variant_1036 | RWKLFKKIPPKFKHLALKF | seqid_807 |
| variant_1037 | FWKLFKKIPPKFKHLALKF | seqid_808 |
| variant_1038 | KKKKFKKIPPKFKHLALKF | seqid_809 |
| variant_1039 | RKKKFKKIPPKFKHLALKF | seqid_810 |
| variant_1040 | FKKKFKKIPPKFKHLALKF | seqid_811 |
| variant_1041 | KWKKFKKIPPKFKHLALKF | seqid_812 |
| variant_1042 | RWKKFKKIPPKFKHLALKF | seqid_813 |
| variant_1043 | FWKKFKKIPPKFKHLALKF | seqid_814 |
| variant_1044 | KKKLLKKIPPKFKHLALKF | seqid_815 |
| variant_1045 | RKKLLKKIPPKFKHLALKF | seqid_816 |
| variant_1046 | FKKLLKKIPPKFKHLALKF | seqid_817 |
| variant_1047 | KWKLLKKIPPKFKHLALKF | seqid_818 |
| variant_1048 | RWKLLKKIPPKFKHLALKF | seqid_819 |
| variant_1049 | FWKLLKKIPPKFKHLALKF | seqid_820 |
| variant_1050 | KKKKLKKIPPKFKHLALKF | seqid_821 |
| variant_1051 | RKKKLKKIPPKFKHLALKF | seqid_822 |
| variant_1052 | FKKKLKKIPPKFKHLALKF | seqid_823 |
| variant_1053 | KWKKLKKIPPKFKHLALKF | seqid_824 |
| variant_1054 | RWKKLKKIPPKFKHLALKF | seqid_825 |
| variant_1055 | FWKKLKKIPPKFKHLALKF | seqid_826 |
| variant_1104 | KKKLFLKIPKFKHLALKF | seqid_827 |
| variant_1105 | RKKLFLKIPKFKHLALKF | seqid_828 |
| variant_1106 | FKKLFLKIPKFKHLALKF | seqid_829 |
| variant_1107 | KWKLFLKIPKFKHLALKF | seqid_830 |
| variant_1108 | RWKLFLKIPKFKHLALKF | seqid_831 |
| variant_1109 | FWKLFLKIPKFKHLALKF | seqid_832 |
| variant_1110 | KKKKFLKIPKFKHLALKF | seqid_833 |
| variant_1111 | RKKKFLKIPKFKHLALKF | seqid_834 |
| variant_1112 | FKKKFLKIPKFKHLALKF | seqid_835 |
| variant_1113 | KWKKFLKIPKFKHLALKF | seqid_836 |
| variant_1114 | RWKKFLKIPKFKHLALKF | seqid_837 |
| variant_1115 | FWKKFLKIPKFKHLALKF | seqid_838 |
| variant_1116 | KKKLLLKIPKFKHLALKF | seqid_839 |
| variant_1117 | RKKLLLKIPKFKHLALKF | seqid_840 |
| variant_1118 | FKKLLLKIPKFKHLALKF | seqid_841 |
| variant_1119 | KWKLLLKIPKFKHLALKF | seqid_842 |
| variant_1120 | RWKLLLKIPKFKHLALKF | seqid_843 |
| variant_1121 | FWKLLLKIPKFKHLALKF | seqid_844 |
| variant_1122 | KKKKLLKIPKFKHLALKF | seqid_845 |
| variant_1123 | RKKKLLKIPKFKHLALKF | seqid_846 |
| variant_1124 | FKKKLLKIPKFKHLALKF | seqid_847 |
| variant_1125 | KWKKLLKIPKFKHLALKF | seqid_848 |
| variant_1126 | RWKKLLKIPKFKHLALKF | seqid_849 |
| variant_1127 | FWKKLLKIPKFKHLALKF | seqid_850 |
| variant_1128 | KKKLFKKIPKFKHLALKF | seqid_851 |
| variant_1129 | RKKLFKKIPKFKHLALKF | seqid_852 |
| variant_1130 | FKKLFKKIPKFKHLALKF | seqid_853 |
| variant_1131 | KWKLFKKIPKFKHLALKF | seqid_854 |
| variant_1132 | RWKLFKKIPKFKHLALKF | seqid_855 |
| variant_1133 | FWKLFKKIPKFKHLALKF | seqid_856 |
| variant_1134 | KKKKFKKIPKFKHLALKF | seqid_857 |
| variant_1135 | RKKKFKKIPKFKHLALKF | seqid_858 |
| variant_1136 | FKKKFKKIPKFKHLALKF | seqid_859 |
| variant_1137 | KWKKFKKIPKFKHLALKF | seqid_860 |
| variant_1138 | RWKKFKKIPKFKHLALKF | seqid_861 |
| variant_1139 | FWKKFKKIPKFKHLALKF | seqid_862 |
| variant_1140 | KKKLLKKIPKFKHLALKF | seqid_863 |
| variant_1141 | RKKLLKKIPKFKHLALKF | seqid_864 |
| variant_1142 | FKKLLKKIPKFKHLALKF | seqid_865 |
| variant_1143 | KWKLLKKIPKFKHLALKF | seqid_866 |
| variant_1144 | RWKLLKKIPKFKHLALKF | seqid_867 |
| variant_1145 | FWKLLKKIPKFKHLALKF | seqid_868 |
| variant_1146 | KKKKLKKIPKFKHLALKF | seqid_869 |
| variant_1147 | RKKKLKKIPKFKHLALKF | seqid_870 |
| variant_1148 | FKKKLKKIPKFKHLALKF | seqid_871 |
| variant_1149 | KWKKLKKIPKFKHLALKF | seqid_872 |
| variant_1150 | RWKKLKKIPKFKHLALKF | seqid_873 |
| variant_1151 | FWKKLKKIPKFKHLALKF | seqid_874 |
| variant_1152 | KKKLFLKIPPPKFLKLALKF | seqid_875 |
| variant_1153 | RKKLFLKIPPPKFLKLALKF | seqid_876 |
| variant_1154 | FKKLFLKIPPPKFLKLALKF | seqid_877 |
| variant_1155 | KWKLFLKIPPPKFLKLALKF | seqid_878 |
| variant_1156 | RWKLFLKIPPPKFLKLALKF | seqid_879 |
| variant_1157 | FWKLFLKIPPPKFLKLALKF | seqid_880 |
| variant_1158 | KKKKFLKIPPPKFLKLALKF | seqid_881 |
| variant_1159 | RKKKFLKIPPPKFLKLALKF | seqid_882 |
| variant_1160 | FKKKFLKIPPPKFLKLALKF | seqid_883 |
| variant_1161 | KWKKFLKIPPPKFLKLALKF | seqid_884 |
| variant_1162 | RWKKFLKIPPPKFLKLALKF | seqid_885 |

-continued

| | | |
|---|---|---|
| variant_1163 | FWKKFLKIPPPKFLKLALKF | seqid_886 |
| variant_1164 | KKKLLLKIPPPKFLKLALKF | seqid_887 |
| variant_1165 | RKKLLLKIPPPKFLKLALKF | seqid_888 |
| variant_1166 | FKKLLLKIPPPKFLKLALKF | seqid_889 |
| variant_1167 | KWKLLLKIPPPKFLKLALKF | seqid_890 |
| variant_1168 | RWKLLLKIPPPKFLKLALKF | seqid_891 |
| variant_1169 | FWKLLLKIPPPKFLKLALKF | seqid_892 |
| variant_1170 | KKKKLLKIPPPKFLKLALKF | seqid_893 |
| variant_1171 | RKKKLLKIPPPKFLKLALKF | seqid_894 |
| variant_1172 | FKKKLLKIPPPKFLKLALKF | seqid_895 |
| variant_1173 | KWKKLLKIPPPKFLKLALKF | seqid_896 |
| variant_1174 | RWKKLLKIPPPKFLKLALKF | seqid_897 |
| variant_1175 | FWKKLLKIPPPKFLKLALKF | seqid_898 |
| variant_1176 | KKKLFKKIPPPKFLKLALKF | seqid_899 |
| variant_1177 | RKKLFKKIPPPKFLKLALKF | seqid_900 |
| variant_1178 | FKKLFKKIPPPKFLKLALKF | seqid_901 |
| variant_1179 | KWKLFKKIPPPKFLKLALKF | seqid_902 |
| variant_1180 | RWKLFKKIPPPKFLKLALKF | seqid_903 |
| variant_1181 | FWKLFKKIPPPKFLKLALKF | seqid_904 |
| variant_1182 | KKKKFKKIPPPKFLKLALKF | seqid_905 |
| variant_1183 | RKKKFKKIPPPKFLKLALKF | seqid_906 |
| variant_1184 | FKKKFKKIPPPKFLKLALKF | seqid_907 |
| variant_1185 | KWKKFKKIPPPKFLKLALKF | seqid_908 |
| variant_1186 | RWKKFKKIPPPKFLKLALKF | seqid_909 |
| variant_1187 | FWKKFKKIPPPKFLKLALKF | seqid_910 |
| variant_1188 | KKKLLKKIPPPKFLKLALKF | seqid_911 |
| variant_1189 | RKKLLKKIPPPKFLKLALKF | seqid_912 |
| variant_1190 | FKKLLKKIPPPKFLKLALKF | seqid_913 |
| variant_1191 | KWKLLKKIPPPKFLKLALKF | seqid_914 |
| variant_1192 | RWKLLKKIPPPKFLKLALKF | seqid_915 |
| variant_1193 | FWKLLKKIPPPKFLKLALKF | seqid_916 |
| variant_1194 | KKKKLKKIPPPKFLKLALKF | seqid_917 |
| variant_1195 | RKKKLKKIPPPKFLKLALKF | seqid_918 |
| variant_1196 | FKKKLKKIPPPKFLKLALKF | seqid_919 |
| variant_1197 | KWKKLKKIPPPKFLKLALKF | seqid_920 |
| variant_1198 | RWKKLKKIPPPKFLKLALKF | seqid_921 |
| variant_1199 | FWKKLKKIPPPKFLKLALKF | seqid_922 |
| variant_1200 | KKKLFLKIPPPKFLKLALKF | seqid_923 |
| variant_1201 | RKKLFLKIPPPKFLKLALKF | seqid_924 |
| variant_1202 | FKKLFLKIPPPKFLKLALKF | seqid_925 |
| variant_1203 | KWKLFLKIPPPKFLKLALKF | seqid_926 |
| variant_1204 | RWKLFLKIPPPKFLKLALKF | seqid_927 |
| variant_1205 | FWKLFLKIPPPKFLKLALKF | seqid_928 |
| variant_1206 | KKKKFLKIPPPKFLKLALKF | seqid_929 |
| variant_1207 | RKKKFLKIPPPKFLKLALKF | seqid_930 |
| variant_1208 | FKKKFLKIPPPKFLKLALKF | seqid_931 |
| variant_1209 | KWKKFLKIPPPKFLKLALKF | seqid_932 |
| variant_1210 | RWKKFLKIPPPKFLKLALKF | seqid_933 |
| variant_1211 | FWKKFLKIPPPKFLKLALKF | seqid_934 |
| variant_1212 | KKKLLLKIPPPKFLKLALKF | seqid_935 |
| variant_1213 | RKKLLLKIPPPKFLKLALKF | seqid_936 |
| variant_1214 | FKKLLLKIPPPKFLKLALKF | seqid_937 |
| variant_1215 | KWKLLLKIPPPKFLKLALKF | seqid_938 |
| variant_1216 | RWKLLLKIPPPKFLKLALKF | seqid_939 |
| variant_1217 | FWKLLLKIPPPKFLKLALKF | seqid_940 |
| variant_1218 | KKKKLLKIPPPKFLKLALKF | seqid_941 |
| variant_1219 | RKKKLLKIPPPKFLKLALKF | seqid_942 |
| variant_1220 | FKKKLLKIPPPKFLKLALKF | seqid_943 |
| variant_1221 | KWKKLLKIPPPKFLKLALKF | seqid_944 |
| variant_1222 | RWKKLLKIPPPKFLKLALKF | seqid_945 |
| variant_1223 | FWKKLLKIPPPKFLKLALKF | seqid_946 |
| variant_1224 | KKKLFKKIPPPKFLKLALKF | seqid_947 |
| variant_1225 | RKKLFKKIPPPKFLKLALKF | seqid_948 |
| variant_1226 | FKKLFKKIPPPKFLKLALKF | seqid_949 |
| variant_1227 | KWKLFKKIPPPKFLKLALKF | seqid_950 |
| variant_1228 | RWKLFKKIPPPKFLKLALKF | seqid_951 |
| variant_1229 | FWKLFKKIPPPKFLKLALKF | seqid_952 |
| variant_1230 | KKKKFKKIPPPKFLKLALKF | seqid_953 |
| variant_1231 | RKKKFKKIPPPKFLKLALKF | seqid_954 |
| variant_1232 | FKKKFKKIPPPKFLKLALKF | seqid_955 |
| variant_1233 | KWKKFKKIPPPKFLKLALKF | seqid_956 |
| variant_1234 | RWKKFKKIPPPKFLKLALKF | seqid_957 |
| variant_1235 | FWKKFKKIPPPKFLKLALKF | seqid_958 |
| variant_1236 | KKKLLKKIPPPKFLKLALKF | seqid_959 |
| variant_1237 | RKKLLKKIPPPKFLKLALKF | seqid_960 |
| variant_1238 | FKKLLKKIPPPKFLKLALKF | seqid_961 |
| variant_1239 | KWKLLKKIPPPKFLKLALKF | seqid_962 |
| variant_1240 | RWKLLKKIPPPKFLKLALKF | seqid_963 |
| variant_1241 | FWKLLKKIPPPKFLKLALKF | seqid_964 |
| variant_1242 | KKKKLKKIPPPKFLKLALKF | seqid_965 |
| variant_1243 | RKKKLKKIPPPKFLKLALKF | seqid_966 |

-continued

| | | |
|---|---|---|
| variant_1244 | FKKKLKKIPPKFLKLALKF | seqid_967 |
| variant_1245 | KWKKLKKIPPKFLKLALKF | seqid_968 |
| variant_1246 | RWKKLKKIPPKFLKLALKF | seqid_969 |
| variant_1247 | FWKKLKKIPPKFLKLALKF | seqid_970 |
| variant_1296 | KKKLFLKIPKFLKLALKF | seqid_971 |
| variant_1297 | RKKLFLKIPKFLKLALKF | seqid_972 |
| variant_1298 | FKKLFLKIPKFLKLALKF | seqid_973 |
| variant_1299 | KWKLFLKIPKFLKLALKF | seqid_974 |
| variant_1300 | RWKLFLKIPKFLKLALKF | seqid_975 |
| variant_1301 | FWKLFLKIPKFLKLALKF | seqid_976 |
| variant_1302 | KKKKFLKIPKFLKLALKF | seqid_977 |
| variant_1303 | RKKKFLKIPKFLKLALKF | seqid_978 |
| variant_1304 | FKKKFLKIPKFLKLALKF | seqid_979 |
| variant_1305 | KWKKFLKIPKFLKLALKF | seqid_980 |
| variant_1306 | RWKKFLKIPKFLKLALKF | seqid_981 |
| variant_1307 | FWKKFLKIPKFLKLALKF | seqid_982 |
| variant_1308 | KKKLLLKIPKFLKLALKF | seqid_983 |
| variant_1309 | RKKLLLKIPKFLKLALKF | seqid_984 |
| variant_1310 | FKKLLLKIPKFLKLALKF | seqid_985 |
| variant_1311 | KWKLLLKIPKFLKLALKF | seqid_986 |
| variant_1312 | RWKLLLKIPKFLKLALKF | seqid_987 |
| variant_1313 | FWKLLLKIPKFLKLALKF | seqid_988 |
| variant_1314 | KKKKLLKIPKFLKLALKF | seqid_989 |
| variant_1315 | RKKKLLKIPKFLKLALKF | seqid_990 |
| variant_1316 | FKKKLLKIPKFLKLALKF | seqid_991 |
| variant_1317 | KWKKLLKIPKFLKLALKF | seqid_992 |
| variant_1318 | RWKKLLKIPKFLKLALKF | seqid_993 |
| variant_1319 | FWKKLLKIPKFLKLALKF | seqid_994 |
| variant_1320 | KKKLFKKIPKFLKLALKF | seqid_995 |
| variant_1321 | RKKLFKKIPKFLKLALKF | seqid_996 |
| variant_1322 | FKKLFKKIPKFLKLALKF | seqid_997 |
| variant_1323 | KWKLFKKIPKFLKLALKF | seqid_998 |
| variant_1324 | RWKLFKKIPKFLKLALKF | seqid_999 |
| variant_1325 | FWKLFKKIPKFLKLALKF | seqid_1000 |
| variant_1326 | KKKKFKKIPKFLKLALKF | seqid_1001 |
| variant_1327 | RKKKFKKIPKFLKLALKF | seqid_1002 |
| variant_1328 | FKKKFKKIPKFLKLALKF | seqid_1003 |
| variant_1329 | KWKKFKKIPKFLKLALKF | seqid_1004 |
| variant_1330 | RWKKFKKIPKFLKLALKF | seqid_1005 |
| variant_1331 | FWKKFKKIPKFLKLALKF | seqid_1006 |
| variant_1332 | KKKLLKKIPKFLKLALKF | seqid_1007 |
| variant_1333 | RKKLLKKIPKFLKLALKF | seqid_1008 |
| variant_1334 | FKKLLKKIPKFLKLALKF | seqid_1009 |
| variant_1335 | KWKLLKKIPKFLKLALKF | seqid_1010 |
| variant_1336 | RWKLLKKIPKFLKLALKF | seqid_1011 |
| variant_1337 | FWKLLKKIPKFLKLALKF | seqid_1012 |
| variant_1338 | KKKKLKKIPKFLKLALKF | seqid_1013 |
| variant_1339 | RKKKLKKIPKFLKLALKF | seqid_1014 |
| variant_1340 | FKKKLKKIPKFLKLALKF | seqid_1015 |
| variant_1341 | KWKKLKKIPKFLKLALKF | seqid_1016 |
| variant_1342 | RWKKLKKIPKFLKLALKF | seqid_1017 |
| variant_1343 | FWKKLKKIPKFLKLALKF | seqid_1018 |
| variant_1344 | KKKLFLKIPPPKFKKLALKF | seqid_1019 |
| variant_1345 | RKKLFLKIPPPKFKKLALKF | seqid_1020 |
| variant_1346 | FKKLFLKIPPPKFKKLALKF | seqid_1021 |
| variant_1347 | KWKLFLKIPPPKFKKLALKF | seqid_1022 |
| variant_1348 | RWKLFLKIPPPKFKKLALKF | seqid_1023 |
| variant_1349 | FWKLFLKIPPPKFKKLALKF | seqid_1024 |
| variant_1350 | KKKKFLKIPPPKFKKLALKF | seqid_1025 |
| variant_1351 | RKKKFLKIPPPKFKKLALKF | seqid_1026 |
| variant_1352 | FKKKFLKIPPPKFKKLALKF | seqid_1027 |
| variant_1353 | KWKKFLKIPPPKFKKLALKF | seqid_1028 |
| variant_1354 | RWKKFLKIPPPKFKKLALKF | seqid_1029 |
| variant_1355 | FWKKFLKIPPPKFKKLALKF | seqid_1030 |
| variant_1356 | KKKLLLKIPPPKFKKLALKF | seqid_1031 |
| variant_1357 | RKKLLLKIPPPKFKKLALKF | seqid_1032 |
| variant_1358 | FKKLLLKIPPPKFKKLALKF | seqid_1033 |
| variant_1359 | KWKLLLKIPPPKFKKLALKF | seqid_1034 |
| variant_1360 | RWKLLLKIPPPKFKKLALKF | seqid_1035 |
| variant_1361 | FWKLLLKIPPPKFKKLALKF | seqid_1036 |
| variant_1362 | KKKKLLKIPPPKFKKLALKF | seqid_1037 |
| variant_1363 | RKKKLLKIPPPKFKKLALKF | seqid_1038 |
| variant_1364 | FKKKLLKIPPPKFKKLALKF | seqid_1039 |
| variant_1365 | KWKKLLKIPPPKFKKLALKF | seqid_1040 |
| variant_1366 | RWKKLLKIPPPKFKKLALKF | seqid_1041 |
| variant_1367 | FWKKLLKIPPPKFKKLALKF | seqid_1042 |
| variant_1368 | KKKLFKKIPPPKFKKLALKF | seqid_1043 |
| variant_1369 | RKKLFKKIPPPKFKKLALKF | seqid_1044 |
| variant_1370 | FKKLFKKIPPPKFKKLALKF | seqid_1045 |
| variant_1371 | KWKLFKKIPPPKFKKLALKF | seqid_1046 |
| variant_1372 | RWKLFKKIPPPKFKKLALKF | seqid_1047 |

| | | |
|---|---|---|
| variant_1373 | FWKLFKKIPPPKFKKLALKF | seqid_1048 |
| variant_1374 | KKKKFKKIPPPKFKKLALKF | seqid_1049 |
| variant_1375 | RKKKFKKIPPPKFKKLALKF | seqid_1050 |
| variant_1376 | FKKKFKKIPPPKFKKLALKF | seqid_1051 |
| variant_1377 | KWKKFKKIPPPKFKKLALKF | seqid_1052 |
| variant_1378 | RWKKFKKIPPPKFKKLALKF | seqid_1053 |
| variant_1379 | FWKKFKKIPPPKFKKLALKF | seqid_1054 |
| variant_1380 | KKKLLKKIPPPKFKKLALKF | seqid_1055 |
| variant_1381 | RKKLLKKIPPPKFKKLALKF | seqid_1056 |
| variant_1382 | FKKLLKKIPPPKFKKLALKF | seqid_1057 |
| variant_1383 | KWKLLKKIPPPKFKKLALKF | seqid_1058 |
| variant_1384 | RWKLLKKIPPPKFKKLALKF | seqid_1059 |
| variant_1385 | FWKLLKKIPPPKFKKLALKF | seqid_1060 |
| variant_1386 | KKKKLKKIPPPKFKKLALKF | seqid_1061 |
| variant_1387 | RKKKLKKIPPPKFKKLALKF | seqid_1062 |
| variant_1388 | FKKKLKKIPPPKFKKLALKF | seqid_1063 |
| variant_1389 | KWKKLKKIPPPKFKKLALKF | seqid_1064 |
| variant_1390 | RWKKLKKIPPPKFKKLALKF | seqid_1065 |
| variant_1391 | FWKKLKKIPPPKFKKLALKF | seqid_1066 |
| variant_1392 | KKKLFLKIPPKFKKLALKF | seqid_1067 |
| variant_1393 | RKKLFLKIPPKFKKLALKF | seqid_1068 |
| variant_1394 | FKKLFLKIPPKFKKLALKF | seqid_1069 |
| variant_1395 | KWKLFLKIPPKFKKLALKF | seqid_1070 |
| variant_1396 | RWKLFLKIPPKFKKLALKF | seqid_1071 |
| variant_1397 | FWKLFLKIPPKFKKLALKF | seqid_1072 |
| variant_1398 | KKKKFLKIPPKFKKLALKF | seqid_1073 |
| variant_1399 | RKKKFLKIPPKFKKLALKF | seqid_1074 |
| variant_1400 | FKKKFLKIPPKFKKLALKF | seqid_1075 |
| variant_1401 | KWKKFLKIPPKFKKLALKF | seqid_1076 |
| variant_1402 | RWKKFLKIPPKFKKLALKF | seqid_1077 |
| variant_1403 | FWKKFLKIPPKFKKLALKF | seqid_1078 |
| variant_1404 | KKKLLLKIPPKFKKLALKF | seqid_1079 |
| variant_1405 | RKKLLLKIPPKFKKLALKF | seqid_1080 |
| variant_1406 | FKKLLLKIPPKFKKLALKF | seqid_1081 |
| variant_1407 | KWKLLLKIPPKFKKLALKF | seqid_1082 |
| variant_1408 | RWKLLLKIPPKFKKLALKF | seqid_1083 |
| variant_1409 | FWKLLLKIPPKFKKLALKF | seqid_1084 |
| variant_1410 | KKKKLLKIPPKFKKLALKF | seqid_1085 |
| variant_1411 | RKKKLLKIPPKFKKLALKF | seqid_1086 |
| variant_1412 | FKKKLLKIPPKFKKLALKF | seqid_1087 |
| variant_1413 | KWKKLLKIPPKFKKLALKF | seqid_1088 |
| variant_1414 | RWKKLLKIPPKFKKLALKF | seqid_1089 |
| variant_1415 | FWKKLLKIPPKFKKLALKF | seqid_1090 |
| variant_1416 | KKKLFKKIPPKFKKLALKF | seqid_1091 |
| variant_1417 | RKKLFKKIPPKFKKLALKF | seqid_1092 |
| variant_1418 | FKKLFKKIPPKFKKLALKF | seqid_1093 |
| variant_1419 | KWKLFKKIPPKFKKLALKF | seqid_1094 |
| variant_1420 | RWKLFKKIPPKFKKLALKF | seqid_1095 |
| variant_1421 | FWKLFKKIPPKFKKLALKF | seqid_1096 |
| variant_1422 | KKKKFKKIPPKFKKLALKF | seqid_1097 |
| variant_1423 | RKKKFKKIPPKFKKLALKF | seqid_1098 |
| variant_1424 | FKKKFKKIPPKFKKLALKF | seqid_1099 |
| variant_1425 | KWKKFKKIPPKFKKLALKF | seqid_1100 |
| variant_1426 | RWKKFKKIPPKFKKLALKF | seqid_1101 |
| variant_1427 | FWKKFKKIPPKFKKLALKF | seqid_1102 |
| variant_1428 | KKKLLKKIPPKFKKLALKF | seqid_1103 |
| variant_1429 | RKKLLKKIPPKFKKLALKF | seqid_1104 |
| variant_1430 | FKKLLKKIPPKFKKLALKF | seqid_1105 |
| variant_1431 | KWKLLKKIPPKFKKLALKF | seqid_1106 |
| variant_1432 | RWKLLKKIPPKFKKLALKF | seqid_1107 |
| variant_1433 | FWKLLKKIPPKFKKLALKF | seqid_1108 |
| variant_1434 | KKKKLKKIPPKFKKLALKF | seqid_1109 |
| variant_1435 | RKKKLKKIPPKFKKLALKF | seqid_1110 |
| variant_1436 | FKKKLKKIPPKFKKLALKF | seqid_1111 |
| variant_1437 | KWKKLKKIPPKFKKLALKF | seqid_1112 |
| variant_1438 | RWKKLKKIPPKFKKLALKF | seqid_1113 |
| variant_1439 | FWKKLKKIPPKFKKLALKF | seqid_1114 |
| variant_1488 | KKKLFLKIPKFKKLALKF | seqid_1115 |
| variant_1489 | RKKLFLKIPKFKKLALKF | seqid_1116 |
| variant_1490 | FKKLFLKIPKFKKLALKF | seqid_1117 |
| variant_1491 | KWKLFLKIPKFKKLALKF | seqid_1118 |
| variant_1492 | RWKLFLKIPKFKKLALKF | seqid_1119 |
| variant_1493 | FWKLFLKIPKFKKLALKF | seqid_1120 |
| variant_1494 | KKKKFLKIPKFKKLALKF | seqid_1121 |
| variant_1495 | RKKKFLKIPKFKKLALKF | seqid_1122 |
| variant_1496 | FKKKFLKIPKFKKLALKF | seqid_1123 |
| variant_1497 | KWKKFLKIPKFKKLALKF | seqid_1124 |
| variant_1498 | RWKKFLKIPKFKKLALKF | seqid_1125 |
| variant_1499 | FWKKFLKIPKFKKLALKF | seqid_1126 |
| variant_1500 | KKKLLLKIPKFKKLALKF | seqid_1127 |
| variant_1501 | RKKLLLKIPKFKKLALKF | seqid_1128 |

-continued

| | | |
|---|---|---|
| variant_1502 | FKKLLLKIPKFKKLALKF | seqid_1129 |
| variant_1503 | KWKLLLKIPKFKKLALKF | seqid_1130 |
| variant_1504 | RWKLLLKIPKFKKLALKF | seqid_1131 |
| variant_1505 | FWKLLLKIPKFKKLALKF | seqid_1132 |
| variant_1506 | KKKKLLKIPKFKKLALKF | seqid_1133 |
| variant_1507 | RKKKLLKIPKFKKLALKF | seqid_1134 |
| variant_1508 | FKKKLLKIPKFKKLALKF | seqid_1135 |
| variant_1509 | KWKKLLKIPKFKKLALKF | seqid_1136 |
| variant_1510 | RWKKLLKIPKFKKLALKF | seqid_1137 |
| variant_1511 | FWKKLLKIPKFKKLALKF | seqid_1138 |
| variant_1512 | KKKLFKKIPKFKKLALKF | seqid_1139 |
| variant_1513 | RKKLFKKIPKFKKLALKF | seqid_1140 |
| variant_1514 | FKKLFKKIPKFKKLALKF | seqid_1141 |
| variant_1515 | KWKLFKKIPKFKKLALKF | seqid_1142 |
| variant_1516 | RWKLFKKIPKFKKLALKF | seqid_1143 |
| variant_1517 | FWKLFKKIPKFKKLALKF | seqid_1144 |
| variant_1518 | KKKKFKKIPKFKKLALKF | seqid_1145 |
| variant_1519 | RKKKFKKIPKFKKLALKF | seqid_1146 |
| variant_1520 | FKKKFKKIPKFKKLALKF | seqid_1147 |
| variant_1521 | KWKKFKKIPKFKKLALKF | seqid_1148 |
| variant_1522 | RWKKFKKIPKFKKLALKF | seqid_1149 |
| variant_1523 | FWKKFKKIPKFKKLALKF | seqid_1150 |
| variant_1524 | KKKLLKKIPKFKKLALKF | seqid_1151 |
| variant_1525 | RKKLLKKIPKFKKLALKF | seqid_1152 |
| variant_1526 | FKKLLKKIPKFKKLALKF | seqid_1153 |
| variant_1527 | KWKLLKKIPKFKKLALKF | seqid_6 |
| variant_1528 | RWKLLKKIPKFKKLALKF | seqid_1154 |
| variant_1529 | FWKLLKKIPKFKKLALKF | seqid_1155 |
| variant_1530 | KKKKLKKIPKFKKLALKF | seqid_1156 |
| variant_1531 | RKKKLKKIPKFKKLALKF | seqid_1157 |
| variant_1532 | FKKKLKKIPKFKKLALKF | seqid_1158 |
| variant_1533 | KWKKLKKIPKFKKLALKF | seqid_1159 |
| variant_1534 | RWKKLKKIPKFKKLALKF | seqid_1160 |
| variant_1535 | FWKKLKKIPKFKKLALKF | seqid_1161 |
| variant_1536 | KKKLFLKIPPPKFLHVALKF | seqid_1162 |
| variant_1537 | RKKLFLKIPPPKFLHVALKF | seqid_1163 |
| variant_1538 | FKKLFLKIPPPKFLHVALKF | seqid_1164 |
| variant_1539 | KWKLFLKIPPPKFLHVALKF | seqid_1165 |
| variant_1540 | RWKLFLKIPPPKFLHVALKF | seqid_1166 |
| variant_1541 | FWKLFLKIPPPKFLHVALKF | seqid_1167 |
| variant_1542 | KKKKFLKIPPPKFLHVALKF | seqid_1168 |
| variant_1543 | RKKKFLKIPPPKFLHVALKF | seqid_1169 |
| variant_1544 | FKKKFLKIPPPKFLHVALKF | seqid_1170 |
| variant_1545 | KWKKFLKIPPPKFLHVALKF | seqid_1171 |
| variant_1546 | RWKKFLKIPPPKFLHVALKF | seqid_1172 |
| variant_1547 | FWKKFLKIPPPKFLHVALKF | seqid_1173 |
| variant_1548 | KKKLLLKIPPPKFLHVALKF | seqid_1174 |
| variant_1549 | RKKLLLKIPPPKFLHVALKF | seqid_1175 |
| variant_1550 | FKKLLLKIPPPKFLHVALKF | seqid_1176 |
| variant_1551 | KWKLLLKIPPPKFLHVALKF | seqid_1177 |
| variant_1552 | RWKLLLKIPPPKFLHVALKF | seqid_1178 |
| variant_1553 | FWKLLLKIPPPKFLHVALKF | seqid_1179 |
| variant_1554 | KKKKLLKIPPPKFLHVALKF | seqid_1180 |
| variant_1555 | RKKKLLKIPPPKFLHVALKF | seqid_1181 |
| variant_1556 | FKKKLLKIPPPKFLHVALKF | seqid_1182 |
| variant_1557 | KWKKLLKIPPPKFLHVALKF | seqid_1183 |
| variant_1558 | RWKKLLKIPPPKFLHVALKF | seqid_1184 |
| variant_1559 | FWKKLLKIPPPKFLHVALKF | seqid_1185 |
| variant_1560 | KKKLFKKIPPPKFLHVALKF | seqid_1186 |
| variant_1561 | RKKLFKKIPPPKFLHVALKF | seqid_1187 |
| variant_1562 | FKKLFKKIPPPKFLHVALKF | seqid_1188 |
| variant_1563 | KWKLFKKIPPPKFLHVALKF | seqid_1189 |
| variant_1564 | RWKLFKKIPPPKFLHVALKF | seqid_1190 |
| variant_1565 | FWKLFKKIPPPKFLHVALKF | seqid_1191 |
| variant_1566 | KKKKFKKIPPPKFLHVALKF | seqid_1192 |
| variant_1567 | RKKKFKKIPPPKFLHVALKF | seqid_1193 |
| variant_1568 | FKKKFKKIPPPKFLHVALKF | seqid_1194 |
| variant_1569 | KWKKFKKIPPPKFLHVALKF | seqid_1195 |
| variant_1570 | RWKKFKKIPPPKFLHVALKF | seqid_1196 |
| variant_1571 | FWKKFKKIPPPKFLHVALKF | seqid_1197 |
| variant_1572 | KKKLLKKIPPPKFLHVALKF | seqid_1198 |
| variant_1573 | RKKLLKKIPPPKFLHVALKF | seqid_1199 |
| variant_1574 | FKKLLKKIPPPKFLHVALKF | seqid_1200 |
| variant_1575 | KWKLLKKIPPPKFLHVALKF | seqid_1201 |
| variant_1576 | RWKLLKKIPPPKFLHVALKF | seqid_1202 |
| variant_1577 | FWKLLKKIPPPKFLHVALKF | seqid_1203 |
| variant_1578 | KKKKLKKIPPPKFLHVALKF | seqid_1204 |
| variant_1579 | RKKKLKKIPPPKFLHVALKF | seqid_1205 |
| variant_1580 | FKKKLKKIPPPKFLHVALKF | seqid_1206 |
| variant_1581 | KWKKLKKIPPPKFLHVALKF | seqid_1207 |
| variant_1582 | RWKKLKKIPPPKFLHVALKF | seqid_1208 |

| | | |
|---|---|---|
| variant_1583 | FWKKLKKIPPPKFLHVALKF | seqid_1209 |
| variant_1584 | KKKLFLKIPPKFLHVALKF | seqid_1210 |
| variant_1585 | RKKLFLKIPPKFLHVALKF | seqid_1211 |
| variant_1586 | FKKLFLKIPPKFLHVALKF | seqid_1212 |
| variant_1587 | KWKLFLKIPPKFLHVALKF | seqid_1213 |
| variant_1588 | RWKLFLKIPPKFLHVALKF | seqid_1214 |
| variant_1589 | FWKLFLKIPPKFLHVALKF | seqid_1215 |
| variant_1590 | KKKKFLKIPPKFLHVALKF | seqid_1216 |
| variant_1591 | RKKKFLKIPPKFLHVALKF | seqid_1217 |
| variant_1592 | FKKKFLKIPPKFLHVALKF | seqid_1218 |
| variant_1593 | KWKKFLKIPPKFLHVALKF | seqid_1219 |
| variant_1594 | RWKKFLKIPPKFLHVALKF | seqid_1220 |
| variant_1595 | FWKKFLKIPPKFLHVALKF | seqid_1221 |
| variant_1596 | KKKLLLKIPPKFLHVALKF | seqid_1222 |
| variant_1597 | RKKLLLKIPPKFLHVALKF | seqid_1223 |
| variant_1598 | FKKLLLKIPPKFLHVALKF | seqid_1224 |
| variant_1599 | KWKLLLKIPPKFLHVALKF | seqid_1225 |
| variant_1600 | RWKLLLKIPPKFLHVALKF | seqid_1226 |
| variant_1601 | FWKLLLKIPPKFLHVALKF | seqid_1227 |
| variant_1602 | KKKKLLKIPPKFLHVALKF | seqid_1228 |
| variant_1603 | RKKKLLKIPPKFLHVALKF | seqid_1229 |
| variant_1604 | FKKKLLKIPPKFLHVALKF | seqid_1230 |
| variant_1605 | KWKKLLKIPPKFLHVALKF | seqid_1231 |
| variant_1606 | RWKKLLKIPPKFLHVALKF | seqid_1232 |
| variant_1607 | FWKKLLKIPPKFLHVALKF | seqid_1233 |
| variant_1608 | KKKLFKKIPPKFLHVALKF | seqid_1234 |
| variant_1609 | RKKLFKKIPPKFLHVALKF | seqid_1235 |
| variant_1610 | FKKLFKKIPPKFLHVALKF | seqid_1236 |
| variant_1611 | KWKLFKKIPPKFLHVALKF | seqid_1237 |
| variant_1612 | RWKLFKKIPPKFLHVALKF | seqid_1238 |
| variant_1613 | FWKLFKKIPPKFLHVALKF | seqid_1239 |
| variant_1614 | KKKKFKKIPPKFLHVALKF | seqid_1240 |
| variant_1615 | RKKKFKKIPPKFLHVALKF | seqid_1241 |
| variant_1616 | FKKKFKKIPPKFLHVALKF | seqid_1242 |
| variant_1617 | KWKKFKKIPPKFLHVALKF | seqid_1243 |
| variant_1618 | RWKKFKKIPPKFLHVALKF | seqid_1244 |
| variant_1619 | FWKKFKKIPPKFLHVALKF | seqid_1245 |
| variant_1620 | KKKLLKKIPPKFLHVALKF | seqid_1246 |
| variant_1621 | RKKLLKKIPPKFLHVALKF | seqid_1247 |
| variant_1622 | FKKLLKKIPPKFLHVALKF | seqid_1248 |
| variant_1623 | KWKLLKKIPPKFLHVALKF | seqid_1249 |
| variant_1624 | RWKLLKKIPPKFLHVALKF | seqid_1250 |
| variant_1625 | FWKLLKKIPPKFLHVALKF | seqid_1251 |
| variant_1626 | KKKKLKKIPPKFLHVALKF | seqid_1252 |
| variant_1627 | RKKKLKKIPPKFLHVALKF | seqid_1253 |
| variant_1628 | FKKKLKKIPPKFLHVALKF | seqid_1254 |
| variant_1629 | KWKKLKKIPPKFLHVALKF | seqid_1255 |
| variant_1630 | RWKKLKKIPPKFLHVALKF | seqid_1256 |
| variant_1631 | FWKKLKKIPPKFLHVALKF | seqid_1257 |
| variant_1680 | KKKLFLKIPKFLHVALKF | seqid_1258 |
| variant_1681 | RKKLFLKIPKFLHVALKF | seqid_1259 |
| variant_1682 | FKKLFLKIPKFLHVALKF | seqid_1260 |
| variant_1683 | KWKLFLKIPKFLHVALKF | seqid_1261 |
| variant_1684 | RWKLFLKIPKFLHVALKF | seqid_1262 |
| variant_1685 | FWKLFLKIPKFLHVALKF | seqid_1263 |
| variant_1686 | KKKKFLKIPKFLHVALKF | seqid_1264 |
| variant_1687 | RKKKFLKIPKFLHVALKF | seqid_1265 |
| variant_1688 | FKKKFLKIPKFLHVALKF | seqid_1266 |
| variant_1689 | KWKKFLKIPKFLHVALKF | seqid_1267 |
| variant_1690 | RWKKFLKIPKFLHVALKF | seqid_1268 |
| variant_1691 | FWKKFLKIPKFLHVALKF | seqid_1269 |
| variant_1692 | KKKLLLKIPKFLHVALKF | seqid_1270 |
| variant_1693 | RKKLLLKIPKFLHVALKF | seqid_1271 |
| variant_1694 | FKKLLLKIPKFLHVALKF | seqid_1272 |
| variant_1695 | KWKLLLKIPKFLHVALKF | seqid_1273 |
| variant_1696 | RWKLLLKIPKFLHVALKF | seqid_1274 |
| variant_1697 | FWKLLLKIPKFLHVALKF | seqid_1275 |
| variant_1698 | KKKKLLKIPKFLHVALKF | seqid_1276 |
| variant_1699 | RKKKLLKIPKFLHVALKF | seqid_1277 |
| variant_1700 | FKKKLLKIPKFLHVALKF | seqid_1278 |
| variant_1701 | KWKKLLKIPKFLHVALKF | seqid_1279 |
| variant_1702 | RWKKLLKIPKFLHVALKF | seqid_1280 |
| variant_1703 | FWKKLLKIPKFLHVALKF | seqid_1281 |
| variant_1704 | KKKLFKKIPKFLHVALKF | seqid_1282 |
| variant_1705 | RKKLFKKIPKFLHVALKF | seqid_1283 |
| variant_1706 | FKKLFKKIPKFLHVALKF | seqid_1284 |
| variant_1707 | KWKLFKKIPKFLHVALKF | seqid_1285 |
| variant_1708 | RWKLFKKIPKFLHVALKF | seqid_1286 |
| variant_1709 | FWKLFKKIPKFLHVALKF | seqid_1287 |
| variant_1710 | KKKKFKKIPKFLHVALKF | seqid_1288 |
| variant_1711 | RKKKFKKIPKFLHVALKF | seqid_1289 |

| variant | sequence | seqid |
|---|---|---|
| variant_1712 | FKKKFKKIPKFLHVALKF | seqid_1290 |
| variant_1713 | KWKKFKKIPKFLHVALKF | seqid_1291 |
| variant_1714 | RWKKFKKIPKFLHVALKF | seqid_1292 |
| variant_1715 | FWKKFKKIPKFLHVALKF | seqid_1293 |
| variant_1716 | KKKLLKKIPKFLHVALKF | seqid_1294 |
| variant_1717 | RKKLLKKIPKFLHVALKF | seqid_1295 |
| variant_1718 | FKKLLKKIPKFLHVALKF | seqid_1296 |
| variant_1719 | KWKLLKKIPKFLHVALKF | seqid_1297 |
| variant_1720 | RWKLLKKIPKFLHVALKF | seqid_1298 |
| variant_1721 | FWKLLKKIPKFLHVALKF | seqid_1299 |
| variant_1722 | KKKKLKKIPKFLHVALKF | seqid_1300 |
| variant_1723 | RKKKLKKIPKFLHVALKF | seqid_1301 |
| variant_1724 | FKKKLKKIPKFLHVALKF | seqid_1302 |
| variant_1725 | KWKKLKKIPKFLHVALKF | seqid_1303 |
| variant_1726 | RWKKLKKIPKFLHVALKF | seqid_1304 |
| variant_1727 | FWKKLKKIPKFLHVALKF | seqid_1305 |
| variant_1728 | KKKLFLKIPPPKFKHVALKF | seqid_1306 |
| variant_1729 | RKKLFLKIPPPKFKHVALKF | seqid_1307 |
| variant_1730 | FKKLFLKIPPPKFKHVALKF | seqid_1308 |
| variant_1731 | KWKLFLKIPPPKFKHVALKF | seqid_1309 |
| variant_1732 | RWKLFLKIPPPKFKHVALKF | seqid_1310 |
| variant_1733 | FWKLFLKIPPPKFKHVALKF | seqid_1311 |
| variant_1734 | KKKKFLKIPPPKFKHVALKF | seqid_1312 |
| variant_1735 | RKKKFLKIPPPKFKHVALKF | seqid_1313 |
| variant_1736 | FKKKFLKIPPPKFKHVALKF | seqid_1314 |
| variant_1737 | KWKKFLKIPPPKFKHVALKF | seqid_1315 |
| variant_1738 | RWKKFLKIPPPKFKHVALKF | seqid_1316 |
| variant_1739 | FWKKFLKIPPPKFKHVALKF | seqid_1317 |
| variant_1740 | KKKLLLKIPPPKFKHVALKF | seqid_1318 |
| variant_1741 | RKKLLLKIPPPKFKHVALKF | seqid_1319 |
| variant_1742 | FKKLLLKIPPPKFKHVALKF | seqid_1320 |
| variant_1743 | KWKLLLKIPPPKFKHVALKF | seqid_1321 |
| variant_1744 | RWKLLLKIPPPKFKHVALKF | seqid_1322 |
| variant_1745 | FWKLLLKIPPPKFKHVALKF | seqid_1323 |
| variant_1746 | KKKKLLKIPPPKFKHVALKF | seqid_1324 |
| variant_1747 | RKKKLLKIPPPKFKHVALKF | seqid_1325 |
| variant_1748 | FKKKLLKIPPPKFKHVALKF | seqid_1326 |
| variant_1749 | KWKKLLKIPPPKFKHVALKF | seqid_1327 |
| variant_1750 | RWKKLLKIPPPKFKHVALKF | seqid_1328 |
| variant_1751 | FWKKLLKIPPPKFKHVALKF | seqid_1329 |
| variant_1752 | KKKLFKKIPPPKFKHVALKF | seqid_1330 |
| variant_1753 | RKKLFKKIPPPKFKHVALKF | seqid_1331 |
| variant_1754 | FKKLFKKIPPPKFKHVALKF | seqid_1332 |
| variant_1755 | KWKLFKKIPPPKFKHVALKF | seqid_1333 |
| variant_1756 | RWKLFKKIPPPKFKHVALKF | seqid_1334 |
| variant_1757 | FWKLFKKIPPPKFKHVALKF | seqid_1335 |
| variant_1758 | KKKKFKKIPPPKFKHVALKF | seqid_1336 |
| variant_1759 | RKKKFKKIPPPKFKHVALKF | seqid_1337 |
| variant_1760 | FKKKFKKIPPPKFKHVALKF | seqid_1338 |
| variant_1761 | KWKKFKKIPPPKFKHVALKF | seqid_1339 |
| variant_1762 | RWKKFKKIPPPKFKHVALKF | seqid_1340 |
| variant_1763 | FWKKFKKIPPPKFKHVALKF | seqid_1341 |
| variant_1764 | KKKLLKKIPPPKFKHVALKF | seqid_1342 |
| variant_1765 | RKKLLKKIPPPKFKHVALKF | seqid_1343 |
| variant_1766 | FKKLLKKIPPPKFKHVALKF | seqid_1344 |
| variant_1767 | KWKLLKKIPPPKFKHVALKF | seqid_1345 |
| variant_1768 | RWKLLKKIPPPKFKHVALKF | seqid_1346 |
| variant_1769 | FWKLLKKIPPPKFKHVALKF | seqid_1347 |
| variant_1770 | KKKKLKKIPPPKFKHVALKF | seqid_1348 |
| variant_1771 | RKKKLKKIPPPKFKHVALKF | seqid_1349 |
| variant_1772 | FKKKLKKIPPPKFKHVALKF | seqid_1350 |
| variant_1773 | KWKKLKKIPPPKFKHVALKF | seqid_1351 |
| variant_1774 | RWKKLKKIPPPKFKHVALKF | seqid_1352 |
| variant_1775 | FWKKLKKIPPPKFKHVALKF | seqid_1353 |
| variant_1776 | KKKLFLKIPPKFKHVALKF | seqid_1354 |
| variant_1777 | RKKLFLKIPPKFKHVALKF | seqid_1355 |
| variant_1778 | FKKLFLKIPPKFKHVALKF | seqid_1356 |
| variant_1779 | KWKLFLKIPPKFKHVALKF | seqid_1357 |
| variant_1780 | RWKLFLKIPPKFKHVALKF | seqid_1358 |
| variant_1781 | FWKLFLKIPPKFKHVALKF | seqid_1359 |
| variant_1782 | KKKKFLKIPPKFKHVALKF | seqid_1360 |
| variant_1783 | RKKKFLKIPPKFKHVALKF | seqid_1361 |
| variant_1784 | FKKKFLKIPPKFKHVALKF | seqid_1362 |
| variant_1785 | KWKKFLKIPPKFKHVALKF | seqid_1363 |
| variant_1786 | RWKKFLKIPPKFKHVALKF | seqid_1364 |
| variant_1787 | FWKKFLKIPPKFKHVALKF | seqid_1365 |
| variant_1788 | KKKLLLKIPPKFKHVALKF | seqid_1366 |
| variant_1789 | RKKLLLKIPPKFKHVALKF | seqid_1367 |
| variant_1790 | FKKLLLKIPPKFKHVALKF | seqid_1368 |
| variant_1791 | KWKLLLKIPPKFKHVALKF | seqid_1369 |
| variant_1792 | RWKLLLKIPPKFKHVALKF | seqid_1370 |

-continued

| | | |
|---|---|---|
| variant_1793 | FWKLLLKIPPKFKHVALKF | seqid_1371 |
| variant_1794 | KKKKLLKIPPKFKHVALKF | seqid_1372 |
| variant_1795 | RKKKLLKIPPKFKHVALKF | seqid_1373 |
| variant_1796 | FKKKLLKIPPKFKHVALKF | seqid_1374 |
| variant_1797 | KWKKLLKIPPKFKHVALKF | seqid_1375 |
| variant_1798 | RWKKLLKIPPKFKHVALKF | seqid_1376 |
| variant_1799 | FWKKLLKIPPKFKHVALKF | seqid_1377 |
| variant_1800 | KKKLFKKIPPKFKHVALKF | seqid_1378 |
| variant_1801 | RKKLFKKIPPKFKHVALKF | seqid_1379 |
| variant_1802 | FKKLFKKIPPKFKHVALKF | seqid_1380 |
| variant_1803 | KWKLFKKIPPKFKHVALKF | seqid_1381 |
| variant_1804 | RWKLFKKIPPKFKHVALKF | seqid_1382 |
| variant_1805 | FWKLFKKIPPKFKHVALKF | seqid_1383 |
| variant_1806 | KKKKFKKIPPKFKHVALKF | seqid_1384 |
| variant_1807 | RKKKFKKIPPKFKHVALKF | seqid_1385 |
| variant_1808 | FKKKFKKIPPKFKHVALKF | seqid_1386 |
| variant_1809 | KWKKFKKIPPKFKHVALKF | seqid_1387 |
| variant_1810 | RWKKFKKIPPKFKHVALKF | seqid_1388 |
| variant_1811 | FWKKFKKIPPKFKHVALKF | seqid_1389 |
| variant_1812 | KKKLLKKIPPKFKHVALKF | seqid_1390 |
| variant_1813 | RKKLLKKIPPKFKHVALKF | seqid_1391 |
| variant_1814 | FKKLLKKIPPKFKHVALKF | seqid_1392 |
| variant_1815 | KWKLLKKIPPKFKHVALKF | seqid_1393 |
| variant_1816 | RWKLLKKIPPKFKHVALKF | seqid_1394 |
| variant_1817 | FWKLLKKIPPKFKHVALKF | seqid_1395 |
| variant_1818 | KKKKLKKIPPKFKHVALKF | seqid_1396 |
| variant_1819 | RKKKLKKIPPKFKHVALKF | seqid_1397 |
| variant_1820 | FKKKLKKIPPKFKHVALKF | seqid_1398 |
| variant_1821 | KWKKLKKIPPKFKHVALKF | seqid_1399 |
| variant_1822 | RWKKLKKIPPKFKHVALKF | seqid_1400 |
| variant_1823 | FWKKLKKIPPKFKHVALKF | seqid_1401 |
| variant_1872 | KKKLFLKIPKFKHVALKF | seqid_1402 |
| variant_1873 | RKKLFLKIPKFKHVALKF | seqid_1403 |
| variant_1874 | FKKLFLKIPKFKHVALKF | seqid_1404 |
| variant_1875 | KWKLFLKIPKFKHVALKF | seqid_1405 |
| variant_1876 | RWKLFLKIPKFKHVALKF | seqid_1406 |
| variant_1877 | FWKLFLKIPKFKHVALKF | seqid_1407 |
| variant_1878 | KKKKFLKIPKFKHVALKF | seqid_1408 |
| variant_1879 | RKKKFLKIPKFKHVALKF | seqid_1409 |
| variant_1880 | FKKKFLKIPKFKHVALKF | seqid_1410 |
| variant_1881 | KWKKFLKIPKFKHVALKF | seqid_1411 |
| variant_1882 | RWKKFLKIPKFKHVALKF | seqid_1412 |
| variant_1883 | FWKKFLKIPKFKHVALKF | seqid_1413 |
| variant_1884 | KKKLLLKIPKFKHVALKF | seqid_1414 |
| variant_1885 | RKKLLLKIPKFKHVALKF | seqid_1415 |
| variant_1886 | FKKLLLKIPKFKHVALKF | seqid_1416 |
| variant_1887 | KWKLLLKIPKFKHVALKF | seqid_1417 |
| variant_1888 | RWKLLLKIPKFKHVALKF | seqid_1418 |
| variant_1889 | FWKLLLKIPKFKHVALKF | seqid_1419 |
| variant_1890 | KKKKLLKIPKFKHVALKF | seqid_1420 |
| variant_1891 | RKKKLLKIPKFKHVALKF | seqid_1421 |
| variant_1892 | FKKKLLKIPKFKHVALKF | seqid_1422 |
| variant_1893 | KWKKLLKIPKFKHVALKF | seqid_1423 |
| variant_1894 | RWKKLLKIPKFKHVALKF | seqid_1424 |
| variant_1895 | FWKKLLKIPKFKHVALKF | seqid_1425 |
| variant_1896 | KKKLFKKIPKFKHVALKF | seqid_1426 |
| variant_1897 | RKKLFKKIPKFKHVALKF | seqid_1427 |
| variant_1898 | FKKLFKKIPKFKHVALKF | seqid_1428 |
| variant_1899 | KWKLFKKIPKFKHVALKF | seqid_1429 |
| variant_1900 | RWKLFKKIPKFKHVALKF | seqid_1430 |
| variant_1901 | FWKLFKKIPKFKHVALKF | seqid_1431 |
| variant_1902 | KKKKFKKIPKFKHVALKF | seqid_1432 |
| variant_1903 | RKKKFKKIPKFKHVALKF | seqid_1433 |
| variant_1904 | FKKKFKKIPKFKHVALKF | seqid_1434 |
| variant_1905 | KWKKFKKIPKFKHVALKF | seqid_1435 |
| variant_1906 | RWKKFKKIPKFKHVALKF | seqid_1436 |
| variant_1907 | FWKKFKKIPKFKHVALKF | seqid_1437 |
| variant_1908 | KKKLLKKIPKFKHVALKF | seqid_1438 |
| variant_1909 | RKKLLKKIPKFKHVALKF | seqid_1439 |
| variant_1910 | FKKLLKKIPKFKHVALKF | seqid_1440 |
| variant_1911 | KWKLLKKIPKFKHVALKF | seqid_1441 |
| variant_1912 | RWKLLKKIPKFKHVALKF | seqid_1442 |
| variant_1913 | FWKLLKKIPKFKHVALKF | seqid_1443 |
| variant_1914 | KKKKLKKIPKFKHVALKF | seqid_1444 |
| variant_1915 | RKKKLKKIPKFKHVALKF | seqid_1445 |
| variant_1916 | FKKKLKKIPKFKHVALKF | seqid_1446 |
| variant_1917 | KWKKLKKIPKFKHVALKF | seqid_1447 |
| variant_1918 | RWKKLKKIPKFKHVALKF | seqid_1448 |
| variant_1919 | FWKKLKKIPKFKHVALKF | seqid_1449 |
| variant_1920 | KKKLFLKIPPPKFLKVALKF | seqid_1450 |
| variant_1921 | RKKLFLKIPPPKFLKVALKF | seqid_1451 |

| variant_1922 | FKKLFLKIPPPKFLKVALKF | seqid_1452 |
| variant_1923 | KWKLFLKIPPPKFLKVALKF | seqid_1453 |
| variant_1924 | RWKLFLKIPPPKFLKVALKF | seqid_1454 |
| variant_1925 | FWKLFLKIPPPKFLKVALKF | seqid_1455 |
| variant_1926 | KKKKFLKIPPPKFLKVALKF | seqid_1456 |
| variant_1927 | RKKKFLKIPPPKFLKVALKF | seqid_1457 |
| variant_1928 | FKKKFLKIPPPKFLKVALKF | seqid_1458 |
| variant_1929 | KWKKFLKIPPPKFLKVALKF | seqid_1459 |
| variant_1930 | RWKKFLKIPPPKFLKVALKF | seqid_1460 |
| variant_1931 | FWKKFLKIPPPKFLKVALKF | seqid_1461 |
| variant_1932 | KKKLLLKIPPPKFLKVALKF | seqid_1462 |
| variant_1933 | RKKLLLKIPPPKFLKVALKF | seqid_1463 |
| variant_1934 | FKKLLLKIPPPKFLKVALKF | seqid_1464 |
| variant_1935 | KWKLLLKIPPPKFLKVALKF | seqid_1465 |
| variant_1936 | RWKLLLKIPPPKFLKVALKF | seqid_1466 |
| variant_1937 | FWKLLLKIPPPKFLKVALKF | seqid_1467 |
| variant_1938 | KKKKLLKIPPPKFLKVALKF | seqid_1468 |
| variant_1939 | RKKKLLKIPPPKFLKVALKF | seqid_1469 |
| variant_1940 | FKKKLLKIPPPKFLKVALKF | seqid_1470 |
| variant_1941 | KWKKLLKIPPPKFLKVALKF | seqid_1471 |
| variant_1942 | RWKKLLKIPPPKFLKVALKF | seqid_1472 |
| variant_1943 | FWKKLLKIPPPKFLKVALKF | seqid_1473 |
| variant_1944 | KKKLFKKIPPPKFLKVALKF | seqid_1474 |
| variant_1945 | RKKLFKKIPPPKFLKVALKF | seqid_1475 |
| variant_1946 | FKKLFKKIPPPKFLKVALKF | seqid_1476 |
| variant_1947 | KWKLFKKIPPPKFLKVALKF | seqid_1477 |
| variant_1948 | RWKLFKKIPPPKFLKVALKF | seqid_1478 |
| variant_1949 | FWKLFKKIPPPKFLKVALKF | seqid_1479 |
| variant_1950 | KKKKFKKIPPPKFLKVALKF | seqid_1480 |
| variant_1951 | RKKKFKKIPPPKFLKVALKF | seqid_1481 |
| variant_1952 | FKKKFKKIPPPKFLKVALKF | seqid_1482 |
| variant_1953 | KWKKFKKIPPPKFLKVALKF | seqid_1483 |
| variant_1954 | RWKKFKKIPPPKFLKVALKF | seqid_1484 |
| variant_1955 | FWKKFKKIPPPKFLKVALKF | seqid_1485 |
| variant_1956 | KKKLLKKIPPPKFLKVALKF | seqid_1486 |
| variant_1957 | RKKLLKKIPPPKFLKVALKF | seqid_1487 |
| variant_1958 | FKKLLKKIPPPKFLKVALKF | seqid_1488 |
| variant_1959 | KWKLLKKIPPPKFLKVALKF | seqid_1489 |
| variant_1960 | RWKLLKKIPPPKFLKVALKF | seqid_1490 |
| variant_1961 | FWKLLKKIPPPKFLKVALKF | seqid_1491 |
| variant_1962 | KKKKLKKIPPPKFLKVALKF | seqid_1492 |
| variant_1963 | RKKKLKKIPPPKFLKVALKF | seqid_1493 |
| variant_1964 | FKKKLKKIPPPKFLKVALKF | seqid_1494 |
| variant_1965 | KWKKLKKIPPPKFLKVALKF | seqid_1495 |
| variant_1966 | RWKKLKKIPPPKFLKVALKF | seqid_1496 |
| variant_1967 | FWKKLKKIPPPKFLKVALKF | seqid_1497 |
| variant_1968 | KKKLFLKIPPKFLKVALKF | seqid_1498 |
| variant_1969 | RKKLFLKIPPKFLKVALKF | seqid_1499 |
| variant_1970 | FKKLFLKIPPKFLKVALKF | seqid_1500 |
| variant_1971 | KWKLFLKIPPKFLKVALKF | seqid_1501 |
| variant_1972 | RWKLFLKIPPKFLKVALKF | seqid_1502 |
| variant_1973 | FWKLFLKIPPKFLKVALKF | seqid_1503 |
| variant_1974 | KKKKFLKIPPKFLKVALKF | seqid_1504 |
| variant_1975 | RKKKFLKIPPKFLKVALKF | seqid_1505 |
| variant_1976 | FKKKFLKIPPKFLKVALKF | seqid_1506 |
| variant_1977 | KWKKFLKIPPKFLKVALKF | seqid_1507 |
| variant_1978 | RWKKFLKIPPKFLKVALKF | seqid_1508 |
| variant_1979 | FWKKFLKIPPKFLKVALKF | seqid_1509 |
| variant_1980 | KKKLLLKIPPKFLKVALKF | seqid_1510 |
| variant_1981 | RKKLLLKIPPKFLKVALKF | seqid_1511 |
| variant_1982 | FKKLLLKIPPKFLKVALKF | seqid_1512 |
| variant_1983 | KWKLLLKIPPKFLKVALKF | seqid_1513 |
| variant_1984 | RWKLLLKIPPKFLKVALKF | seqid_1514 |
| variant_1985 | FWKLLLKIPPKFLKVALKF | seqid_1515 |
| variant_1986 | KKKKLLKIPPKFLKVALKF | seqid_1516 |
| variant_1987 | RKKKLLKIPPKFLKVALKF | seqid_1517 |
| variant_1988 | FKKKLLKIPPKFLKVALKF | seqid_1518 |
| variant_1989 | KWKKLLKIPPKFLKVALKF | seqid_1519 |
| variant_1990 | RWKKLLKIPPKFLKVALKF | seqid_1520 |
| variant_1991 | FWKKLLKIPPKFLKVALKF | seqid_1521 |
| variant_1992 | KKKLFKKIPPKFLKVALKF | seqid_1522 |
| variant_1993 | RKKLFKKIPPKFLKVALKF | seqid_1523 |
| variant_1994 | FKKLFKKIPPKFLKVALKF | seqid_1524 |
| variant_1995 | KWKLFKKIPPKFLKVALKF | seqid_1525 |
| variant_1996 | RWKLFKKIPPKFLKVALKF | seqid_1526 |
| variant_1997 | FWKLFKKIPPKFLKVALKF | seqid_1527 |
| variant_1998 | KKKKFKKIPPKFLKVALKF | seqid_1528 |
| variant_1999 | RKKKFKKIPPKFLKVALKF | seqid_1529 |
| variant_2000 | FKKKFKKIPPKFLKVALKF | seqid_1530 |
| variant_2001 | KWKKFKKIPPKFLKVALKF | seqid_1531 |
| variant_2002 | RWKKFKKIPPKFLKVALKF | seqid_1532 |

-continued

| | | |
|---|---|---|
| variant_2003 | FWKKFKKIPPKFLKVALKF | seqid_1533 |
| variant_2004 | KKKLLKKIPPKFLKVALKF | seqid_1534 |
| variant_2005 | RKKLLKKIPPKFLKVALKF | seqid_1535 |
| variant_2006 | FKKLLKKIPPKFLKVALKF | seqid_1536 |
| variant_2007 | KWKLLKKIPPKFLKVALKF | seqid_1537 |
| variant_2008 | RWKLLKKIPPKFLKVALKF | seqid_1538 |
| variant_2009 | FWKLLKKIPPKFLKVALKF | seqid_1539 |
| variant_2010 | KKKKLKKIPPKFLKVALKF | seqid_1540 |
| variant_2011 | RKKKLKKIPPKFLKVALKF | seqid_1541 |
| variant_2012 | FKKKLKKIPPKFLKVALKF | seqid_1542 |
| variant_2013 | KWKKLKKIPPKFLKVALKF | seqid_1543 |
| variant_2014 | RWKKLKKIPPKFLKVALKF | seqid_1544 |
| variant_2015 | FWKKLKKIPPKFLKVALKF | seqid_1545 |
| variant_2064 | KKKLFLKIPKFLKVALKF | seqid_1546 |
| variant_2065 | RKKLFLKIPKFLKVALKF | seqid_1547 |
| variant_2066 | FKKLFLKIPKFLKVALKF | seqid_1548 |
| variant_2067 | KWKLFLKIPKFLKVALKF | seqid_1549 |
| variant_2068 | RWKLFLKIPKFLKVALKF | seqid_1550 |
| variant_2069 | FWKLFLKIPKFLKVALKF | seqid_1551 |
| variant_2070 | KKKKFLKIPKFLKVALKF | seqid_1552 |
| variant_2071 | RKKKFLKIPKFLKVALKF | seqid_1553 |
| variant_2072 | FKKKFLKIPKFLKVALKF | seqid_1554 |
| variant_2073 | KWKKFLKIPKFLKVALKF | seqid_1555 |
| variant_2074 | RWKKFLKIPKFLKVALKF | seqid_1556 |
| variant_2075 | FWKKFLKIPKFLKVALKF | seqid_1557 |
| variant_2076 | KKKLLLKIPKFLKVALKF | seqid_1558 |
| variant_2077 | RKKLLLKIPKFLKVALKF | seqid_1559 |
| variant_2078 | FKKLLLKIPKFLKVALKF | seqid_1560 |
| variant_2079 | KWKLLLKIPKFLKVALKF | seqid_1561 |
| variant_2080 | RWKLLLKIPKFLKVALKF | seqid_1562 |
| variant_2081 | FWKLLLKIPKFLKVALKF | seqid_1563 |
| variant_2082 | KKKKLLKIPKFLKVALKF | seqid_1564 |
| variant_2083 | RKKKLLKIPKFLKVALKF | seqid_1565 |
| variant_2084 | FKKKLLKIPKFLKVALKF | seqid_1566 |
| variant_2085 | KWKKLLKIPKFLKVALKF | seqid_1567 |
| variant_2086 | RWKKLLKIPKFLKVALKF | seqid_1568 |
| variant_2087 | FWKKLLKIPKFLKVALKF | seqid_1569 |
| variant_2088 | KKKLFKKIPKFLKVALKF | seqid_1570 |
| variant_2089 | RKKLFKKIPKFLKVALKF | seqid_1571 |
| variant_2090 | FKKLFKKIPKFLKVALKF | seqid_1572 |
| variant_2091 | KWKLFKKIPKFLKVALKF | seqid_1573 |
| variant_2092 | RWKLFKKIPKFLKVALKF | seqid_1574 |
| variant_2093 | FWKLFKKIPKFLKVALKF | seqid_1575 |
| variant_2094 | KKKKFKKIPKFLKVALKF | seqid_1576 |
| variant_2095 | RKKKFKKIPKFLKVALKF | seqid_1577 |
| variant_2096 | FKKKFKKIPKFLKVALKF | seqid_1578 |
| variant_2097 | KWKKFKKIPKFLKVALKF | seqid_1579 |
| variant_2098 | RWKKFKKIPKFLKVALKF | seqid_1580 |
| variant_2099 | FWKKFKKIPKFLKVALKF | seqid_1581 |
| variant_2100 | KKKLLKKIPKFLKVALKF | seqid_1582 |
| variant_2101 | RKKLLKKIPKFLKVALKF | seqid_1583 |
| variant_2102 | FKKLLKKIPKFLKVALKF | seqid_1584 |
| variant_2103 | KWKLLKKIPKFLKVALKF | seqid_1585 |
| variant_2104 | RWKLLKKIPKFLKVALKF | seqid_1586 |
| variant_2105 | FWKLLKKIPKFLKVALKF | seqid_1587 |
| variant_2106 | KKKKLKKIPKFLKVALKF | seqid_1588 |
| variant_2107 | RKKKLKKIPKFLKVALKF | seqid_1589 |
| variant_2108 | FKKKLKKIPKFLKVALKF | seqid_1590 |
| variant_2109 | KWKKLKKIPKFLKVALKF | seqid_1591 |
| variant_2110 | RWKKLKKIPKFLKVALKF | seqid_1592 |
| variant_2111 | FWKKLKKIPKFLKVALKF | seqid_1593 |
| variant_2112 | KKKLFLKIPPPKFKKVALKF | seqid_1594 |
| variant_2113 | RKKLFLKIPPPKFKKVALKF | seqid_1595 |
| variant_2114 | FKKLFLKIPPPKFKKVALKF | seqid_1596 |
| variant_2115 | KWKLFLKIPPPKFKKVALKF | seqid_1597 |
| variant_2116 | RWKLFLKIPPPKFKKVALKF | seqid_1598 |
| variant_2117 | FWKLFLKIPPPKFKKVALKF | seqid_1599 |
| variant_2118 | KKKKFLKIPPPKFKKVALKF | seqid_1600 |
| variant_2119 | RKKKFLKIPPPKFKKVALKF | seqid_1601 |
| variant_2120 | FKKKFLKIPPPKFKKVALKF | seqid_1602 |
| variant_2121 | KWKKFLKIPPPKFKKVALKF | seqid_1603 |
| variant_2122 | RWKKFLKIPPPKFKKVALKF | seqid_1604 |
| variant_2123 | FWKKFLKIPPPKFKKVALKF | seqid_1605 |
| variant_2124 | KKKLLLKIPPPKFKKVALKF | seqid_1606 |
| variant_2125 | RKKLLLKIPPPKFKKVALKF | seqid_1607 |
| variant_2126 | FKKLLLKIPPPKFKKVALKF | seqid_1608 |
| variant_2127 | KWKLLLKIPPPKFKKVALKF | seqid_1609 |
| variant_2128 | RWKLLLKIPPPKFKKVALKF | seqid_1610 |
| variant_2129 | FWKLLLKIPPPKFKKVALKF | seqid_1611 |
| variant_2130 | KKKKLLKIPPPKFKKVALKF | seqid_1612 |
| variant_2131 | RKKKLLKIPPPKFKKVALKF | seqid_1613 |

| | | |
|---|---|---|
| variant_2132 | FKKKLLKIPPPKFKKVALKF | seqid_1614 |
| variant_2133 | KWKKLLKIPPPKFKKVALKF | seqid_1615 |
| variant_2134 | RWKKLLKIPPPKFKKVALKF | seqid_1616 |
| variant_2135 | FWKKLLKIPPPKFKKVALKF | seqid_1617 |
| variant_2136 | KKKLFKKIPPPKFKKVALKF | seqid_1618 |
| variant_2137 | RKKLFKKIPPPKFKKVALKF | seqid_1619 |
| variant_2138 | FKKLFKKIPPPKFKKVALKF | seqid_1620 |
| variant_2139 | KWKLFKKIPPPKFKKVALKF | seqid_1621 |
| variant_2140 | RWKLFKKIPPPKFKKVALKF | seqid_1622 |
| variant_2141 | FWKLFKKIPPPKFKKVALKF | seqid_1623 |
| variant_2142 | KKKKFKKIPPPKFKKVALKF | seqid_1624 |
| variant_2143 | RKKKFKKIPPPKFKKVALKF | seqid_1625 |
| variant_2144 | FKKKFKKIPPPKFKKVALKF | seqid_1626 |
| variant_2145 | KWKKFKKIPPPKFKKVALKF | seqid_1627 |
| variant_2146 | RWKKFKKIPPPKFKKVALKF | seqid_1628 |
| variant_2147 | FWKKFKKIPPPKFKKVALKF | seqid_1629 |
| variant_2148 | KKKLLKKIPPPKFKKVALKF | seqid_1630 |
| variant_2149 | RKKLLKKIPPPKFKKVALKF | seqid_1631 |
| variant_2150 | FKKLLKKIPPPKFKKVALKF | seqid_1632 |
| variant_2151 | KWKLLKKIPPPKFKKVALKF | seqid_1633 |
| variant_2152 | RWKLLKKIPPPKFKKVALKF | seqid_1634 |
| variant_2153 | FWKLLKKIPPPKFKKVALKF | seqid_1635 |
| variant_2154 | KKKKLKKIPPPKFKKVALKF | seqid_1636 |
| variant_2155 | RKKKLKKIPPPKFKKVALKF | seqid_1637 |
| variant_2156 | FKKKLKKIPPPKFKKVALKF | seqid_1638 |
| variant_2157 | KWKKLKKIPPPKFKKVALKF | seqid_1639 |
| variant_2158 | RWKKLKKIPPPKFKKVALKF | seqid_1640 |
| variant_2159 | FWKKLKKIPPPKFKKVALKF | seqid_1641 |
| variant_2160 | KKKLFLKIPPKFKKVALKF | seqid_1642 |
| variant_2161 | RKKLFLKIPPKFKKVALKF | seqid_1643 |
| variant_2162 | FKKLFLKIPPKFKKVALKF | seqid_1644 |
| variant_2163 | KWKLFLKIPPKFKKVALKF | seqid_1645 |
| variant_2164 | RWKLFLKIPPKFKKVALKF | seqid_1646 |
| variant_2165 | FWKLFLKIPPKFKKVALKF | seqid_1647 |
| variant_2166 | KKKKFLKIPPKFKKVALKF | seqid_1648 |
| variant_2167 | RKKKFLKIPPKFKKVALKF | seqid_1649 |
| variant_2168 | FKKKFLKIPPKFKKVALKF | seqid_1650 |
| variant_2169 | KWKKFLKIPPKFKKVALKF | seqid_1651 |
| variant_2170 | RWKKFLKIPPKFKKVALKF | seqid_1652 |
| variant_2171 | FWKKFLKIPPKFKKVALKF | seqid_1653 |
| variant_2172 | KKKLLLKIPPKFKKVALKF | seqid_1654 |
| variant_2173 | RKKLLLKIPPKFKKVALKF | seqid_1655 |
| variant_2174 | FKKLLLKIPPKFKKVALKF | seqid_1656 |
| variant_2175 | KWKLLLKIPPKFKKVALKF | seqid_1657 |
| variant_2176 | RWKLLLKIPPKFKKVALKF | seqid_1658 |
| variant_2177 | FWKLLLKIPPKFKKVALKF | seqid_1659 |
| variant_2178 | KKKKLLKIPPKFKKVALKF | seqid_1660 |
| variant_2179 | RKKKLLKIPPKFKKVALKF | seqid_1661 |
| variant_2180 | FKKKLLKIPPKFKKVALKF | seqid_1662 |
| variant_2181 | KWKKLLKIPPKFKKVALKF | seqid_1663 |
| variant_2182 | RWKKLLKIPPKFKKVALKF | seqid_1664 |
| variant_2183 | FWKKLLKIPPKFKKVALKF | seqid_1665 |
| variant_2184 | KKKLFKKIPPKFKKVALKF | seqid_1666 |
| variant_2185 | RKKLFKKIPPKFKKVALKF | seqid_1667 |
| variant_2186 | FKKLFKKIPPKFKKVALKF | seqid_1668 |
| variant_2187 | KWKLFKKIPPKFKKVALKF | seqid_1669 |
| variant_2188 | RWKLFKKIPPKFKKVALKF | seqid_1670 |
| variant_2189 | FWKLFKKIPPKFKKVALKF | seqid_1671 |
| variant_2190 | KKKKFKKIPPKFKKVALKF | seqid_1672 |
| variant_2191 | RKKKFKKIPPKFKKVALKF | seqid_1673 |
| variant_2192 | FKKKFKKIPPKFKKVALKF | seqid_1674 |
| variant_2193 | KWKKFKKIPPKFKKVALKF | seqid_1675 |
| variant_2194 | RWKKFKKIPPKFKKVALKF | seqid_1676 |
| variant_2195 | FWKKFKKIPPKFKKVALKF | seqid_1677 |
| variant_2196 | KKKLLKKIPPKFKKVALKF | seqid_1678 |
| variant_2197 | RKKLLKKIPPKFKKVALKF | seqid_1679 |
| variant_2198 | FKKLLKKIPPKFKKVALKF | seqid_1680 |
| variant_2199 | KWKLLKKIPPKFKKVALKF | seqid_1681 |
| variant_2200 | RWKLLKKIPPKFKKVALKF | seqid_1682 |
| variant_2201 | FWKLLKKIPPKFKKVALKF | seqid_1683 |
| variant_2202 | KKKKLKKIPPKFKKVALKF | seqid_1684 |
| variant_2203 | RKKKLKKIPPKFKKVALKF | seqid_1685 |
| variant_2204 | FKKKLKKIPPKFKKVALKF | seqid_1686 |
| variant_2205 | KWKKLKKIPPKFKKVALKF | seqid_1687 |
| variant_2206 | RWKKLKKIPPKFKKVALKF | seqid_1688 |
| variant_2207 | FWKKLKKIPPKFKKVALKF | seqid_1689 |
| variant_2256 | KKKLFLKIPKFKKVALKF | seqid_1690 |
| variant_2257 | RKKLFLKIPKFKKVALKF | seqid_1691 |
| variant_2258 | FKKLFLKIPKFKKVALKF | seqid_1692 |
| variant_2259 | KWKLFLKIPKFKKVALKF | seqid_1693 |
| variant_2260 | RWKLFLKIPKFKKVALKF | seqid_1694 |

-continued

| variant_2261 | FWKLFLKIPKFKKVALKF | seqid_1695 |
| variant_2262 | KKKKFLKIPKFKKVALKF | seqid_1696 |
| variant_2263 | RKKKFLKIPKFKKVALKF | seqid_1697 |
| variant_2264 | FKKKFLKIPKFKKVALKF | seqid_1698 |
| variant_2265 | KWKKFLKIPKFKKVALKF | seqid_1699 |
| variant_2266 | RWKKFLKIPKFKKVALKF | seqid_1700 |
| variant_2267 | FWKKFLKIPKFKKVALKF | seqid_1701 |
| variant_2268 | KKKLLLKIPKFKKVALKF | seqid_1702 |
| variant_2269 | RKKLLLKIPKFKKVALKF | seqid_1703 |
| variant_2270 | FKKLLLKIPKFKKVALKF | seqid_1704 |
| variant_2271 | KWKLLLKIPKFKKVALKF | seqid_1705 |
| variant_2272 | RWKLLLKIPKFKKVALKF | seqid_1706 |
| variant_2273 | FWKLLLKIPKFKKVALKF | seqid_1707 |
| variant_2274 | KKKKLLKIPKFKKVALKF | seqid_1708 |
| variant_2275 | RKKKLLKIPKFKKVALKF | seqid_1709 |
| variant_2276 | FKKKLLKIPKFKKVALKF | seqid_1710 |
| variant_2277 | KWKKLLKIPKFKKVALKF | seqid_1711 |
| variant_2278 | RWKKLLKIPKFKKVALKF | seqid_1712 |
| variant_2279 | FWKKLLKIPKFKKVALKF | seqid_1713 |
| variant_2280 | KKKLFKKIPKFKKVALKF | seqid_1714 |
| variant_2281 | RKKLFKKIPKFKKVALKF | seqid_1715 |
| variant_2282 | FKKLFKKIPKFKKVALKF | seqid_1716 |
| variant_2283 | KWKLFKKIPKFKKVALKF | seqid_1717 |
| variant_2284 | RWKLFKKIPKFKKVALKF | seqid_1718 |
| variant_2285 | FWKLFKKIPKFKKVALKF | seqid_1719 |
| variant_2286 | KKKKFKKIPKFKKVALKF | seqid_1720 |
| variant_2287 | RKKKFKKIPKFKKVALKF | seqid_1721 |
| variant_2288 | FKKKFKKIPKFKKVALKF | seqid_1722 |
| variant_2289 | KWKKFKKIPKFKKVALKF | seqid_1723 |
| variant_2290 | RWKKFKKIPKFKKVALKF | seqid_1724 |
| variant_2291 | FWKKFKKIPKFKKVALKF | seqid_1725 |
| variant_2292 | KKKLLKKIPKFKKVALKF | seqid_1726 |
| variant_2293 | RKKLLKKIPKFKKVALKF | seqid_1727 |
| variant_2294 | FKKLLKKIPKFKKVALKF | seqid_1728 |
| variant_2295 | KWKLLKKIPKFKKVALKF | seqid_1729 |
| variant_2296 | RWKLLKKIPKFKKVALKF | seqid_1730 |
| variant_2297 | FWKLLKKIPKFKKVALKF | seqid_1731 |
| variant_2298 | KKKKLKKIPKFKKVALKF | seqid_1732 |
| variant_2299 | RKKKLKKIPKFKKVALKF | seqid_1733 |
| variant_2300 | FKKKLKKIPKFKKVALKF | seqid_1734 |
| variant_2301 | KWKKLKKIPKFKKVALKF | seqid_1735 |
| variant_2302 | RWKKLKKIPKFKKVALKF | seqid_1736 |
| variant_2303 | FWKKLKKIPKFKKVALKF | seqid_1737 |
| variant_2304 | KKKLFLKIPPPKFLHSALKF | seqid_1738 |
| variant_2305 | RKKLFLKIPPPKFLHSALKF | seqid_1739 |
| variant_2306 | FKKLFLKIPPPKFLHSALKF | seqid_1740 |
| variant_2307 | KWKLFLKIPPPKFLHSALKF | seqid_1741 |
| variant_2308 | RWKLFLKIPPPKFLHSALKF | seqid_1742 |
| variant_2309 | FWKLFLKIPPPKFLHSALKF | seqid_1743 |
| variant_2310 | KKKKFLKIPPPKFLHSALKF | seqid_1744 |
| variant_2311 | RKKKFLKIPPPKFLHSALKF | seqid_1745 |
| variant_2312 | FKKKFLKIPPPKFLHSALKF | seqid_1746 |
| variant_2313 | KWKKFLKIPPPKFLHSALKF | seqid_1747 |
| variant_2314 | RWKKFLKIPPPKFLHSALKF | seqid_1748 |
| variant_2315 | FWKKFLKIPPPKFLHSALKF | seqid_1749 |
| variant_2316 | KKKLLLKIPPPKFLHSALKF | seqid_1750 |
| variant_2317 | RKKLLLKIPPPKFLHSALKF | seqid_1751 |
| variant_2318 | FKKLLLKIPPPKFLHSALKF | seqid_1752 |
| variant_2319 | KWKLLLKIPPPKFLHSALKF | seqid_1753 |
| variant_2320 | RWKLLLKIPPPKFLHSALKF | seqid_1754 |
| variant_2321 | FWKLLLKIPPPKFLHSALKF | seqid_1755 |
| variant_2322 | KKKKLLKIPPPKFLHSALKF | seqid_1756 |
| variant_2323 | RKKKLLKIPPPKFLHSALKF | seqid_1757 |
| variant_2324 | FKKKLLKIPPPKFLHSALKF | seqid_1758 |
| variant_2325 | KWKKLLKIPPPKFLHSALKF | seqid_1759 |
| variant_2326 | RWKKLLKIPPPKFLHSALKF | seqid_1760 |
| variant_2327 | FWKKLLKIPPPKFLHSALKF | seqid_1761 |
| variant_2328 | KKKLFKKIPPPKFLHSALKF | seqid_1762 |
| variant_2329 | RKKLFKKIPPPKFLHSALKF | seqid_1763 |
| variant_2330 | FKKLFKKIPPPKFLHSALKF | seqid_1764 |
| variant_2331 | KWKLFKKIPPPKFLHSALKF | seqid_1765 |
| variant_2332 | RWKLFKKIPPPKFLHSALKF | seqid_1766 |
| variant_2333 | FWKLFKKIPPPKFLHSALKF | seqid_1767 |
| variant_2334 | KKKKFKKIPPPKFLHSALKF | seqid_1768 |
| variant_2335 | RKKKFKKIPPPKFLHSALKF | seqid_1769 |
| variant_2336 | FKKKFKKIPPPKFLHSALKF | seqid_1770 |
| variant_2337 | KWKKFKKIPPPKFLHSALKF | seqid_1771 |
| variant_2338 | RWKKFKKIPPPKFLHSALKF | seqid_1772 |
| variant_2339 | FWKKFKKIPPPKFLHSALKF | seqid_1773 |
| variant_2340 | KKKLLKKIPPPKFLHSALKF | seqid_1774 |
| variant_2341 | RKKLLKKIPPPKFLHSALKF | seqid_1775 |

| | | |
|---|---|---|
| variant_2342 | FKKLLKKIPPPKFLHSALKF | seqid_1776 |
| variant_2343 | KWKLLKKIPPPKFLHSALKF | seqid_1777 |
| variant_2344 | RWKLLKKIPPPKFLHSALKF | seqid_1778 |
| variant_2345 | FWKLLKKIPPPKFLHSALKF | seqid_1779 |
| variant_2346 | KKKKLKKIPPPKFLHSALKF | seqid_1780 |
| variant_2347 | RKKKLKKIPPPKFLHSALKF | seqid_1781 |
| variant_2348 | FKKKLKKIPPPKFLHSALKF | seqid_1782 |
| variant_2349 | KWKKLKKIPPPKFLHSALKF | seqid_1783 |
| variant_2350 | RWKKLKKIPPPKFLHSALKF | seqid_1784 |
| variant_2351 | FWKKLKKIPPPKFLHSALKF | seqid_1785 |
| variant_2352 | KKKLFLKIPPKFLHSALKF | seqid_1786 |
| variant_2353 | RKKLFLKIPPKFLHSALKF | seqid_1787 |
| variant_2354 | FKKLFLKIPPKFLHSALKF | seqid_1788 |
| variant_2355 | KWKLFLKIPPKFLHSALKF | seqid_1789 |
| variant_2356 | RWKLFLKIPPKFLHSALKF | seqid_1790 |
| variant_2357 | FWKLFLKIPPKFLHSALKF | seqid_1791 |
| variant_2358 | KKKKFLKIPPKFLHSALKF | seqid_1792 |
| variant_2359 | RKKKFLKIPPKFLHSALKF | seqid_1793 |
| variant_2360 | FKKKFLKIPPKFLHSALKF | seqid_1794 |
| variant_2361 | KWKKFLKIPPKFLHSALKF | seqid_1795 |
| variant_2362 | RWKKFLKIPPKFLHSALKF | seqid_1796 |
| variant_2363 | FWKKFLKIPPKFLHSALKF | seqid_1797 |
| variant_2364 | KKKLLLKIPPKFLHSALKF | seqid_1798 |
| variant_2365 | RKKLLLKIPPKFLHSALKF | seqid_1799 |
| variant_2366 | FKKLLLKIPPKFLHSALKF | seqid_1800 |
| variant_2367 | KWKLLLKIPPKFLHSALKF | seqid_1801 |
| variant_2368 | RWKLLLKIPPKFLHSALKF | seqid_1802 |
| variant_2369 | FWKLLLKIPPKFLHSALKF | seqid_1803 |
| variant_2370 | KKKKLLKIPPKFLHSALKF | seqid_1804 |
| variant_2371 | RKKKLLKIPPKFLHSALKF | seqid_1805 |
| variant_2372 | FKKKLLKIPPKFLHSALKF | seqid_1806 |
| variant_2373 | KWKKLLKIPPKFLHSALKF | seqid_1807 |
| variant_2374 | RWKKLLKIPPKFLHSALKF | seqid_1808 |
| variant_2375 | FWKKLLKIPPKFLHSALKF | seqid_1809 |
| variant_2376 | KKKLFKKIPPKFLHSALKF | seqid_1810 |
| variant_2377 | RKKLFKKIPPKFLHSALKF | seqid_1811 |
| variant_2378 | FKKLFKKIPPKFLHSALKF | seqid_1812 |
| variant_2379 | KWKLFKKIPPKFLHSALKF | seqid_1813 |
| variant_2380 | RWKLFKKIPPKFLHSALKF | seqid_1814 |
| variant_2381 | FWKLFKKIPPKFLHSALKF | seqid_1815 |
| variant_2382 | KKKKFKKIPPKFLHSALKF | seqid_1816 |
| variant_2383 | RKKKFKKIPPKFLHSALKF | seqid_1817 |
| variant_2384 | FKKKFKKIPPKFLHSALKF | seqid_1818 |
| variant_2385 | KWKKFKKIPPKFLHSALKF | seqid_1819 |
| variant_2386 | RWKKFKKIPPKFLHSALKF | seqid_1820 |
| variant_2387 | FWKKFKKIPPKFLHSALKF | seqid_1821 |
| variant_2388 | KKKLLKKIPPKFLHSALKF | seqid_1822 |
| variant_2389 | RKKLLKKIPPKFLHSALKF | seqid_1823 |
| variant_2390 | FKKLLKKIPPKFLHSALKF | seqid_1824 |
| variant_2391 | KWKLLKKIPPKFLHSALKF | seqid_1825 |
| variant_2392 | RWKLLKKIPPKFLHSALKF | seqid_1826 |
| variant_2393 | FWKLLKKIPPKFLHSALKF | seqid_1827 |
| variant_2394 | KKKKLKKIPPKFLHSALKF | seqid_1828 |
| variant_2395 | RKKKLKKIPPKFLHSALKF | seqid_1829 |
| variant_2396 | FKKKLKKIPPKFLHSALKF | seqid_1830 |
| variant_2397 | KWKKLKKIPPKFLHSALKF | seqid_1831 |
| variant_2398 | RWKKLKKIPPKFLHSALKF | seqid_1832 |
| variant_2399 | FWKKLKKIPPKFLHSALKF | seqid_1833 |
| variant_2448 | KKKLFLKIPKFLHSALKF | seqid_1834 |
| variant_2449 | RKKLFLKIPKFLHSALKF | seqid_1835 |
| variant_2450 | FKKLFLKIPKFLHSALKF | seqid_1836 |
| variant_2451 | KWKLFLKIPKFLHSALKF | seqid_1837 |
| variant_2452 | RWKLFLKIPKFLHSALKF | seqid_1838 |
| variant_2453 | FWKLFLKIPKFLHSALKF | seqid_1839 |
| variant_2454 | KKKKFLKIPKFLHSALKF | seqid_1840 |
| variant_2455 | RKKKFLKIPKFLHSALKF | seqid_1841 |
| variant_2456 | FKKKFLKIPKFLHSALKF | seqid_1842 |
| variant_2457 | KWKKFLKIPKFLHSALKF | seqid_1843 |
| variant_2458 | RWKKFLKIPKFLHSALKF | seqid_1844 |
| variant_2459 | FWKKFLKIPKFLHSALKF | seqid_1845 |
| variant_2460 | KKKLLLKIPKFLHSALKF | seqid_1846 |
| variant_2461 | RKKLLLKIPKFLHSALKF | seqid_1847 |
| variant_2462 | FKKLLLKIPKFLHSALKF | seqid_1848 |
| variant_2463 | KWKLLLKIPKFLHSALKF | seqid_1849 |
| variant_2464 | RWKLLLKIPKFLHSALKF | seqid_1850 |
| variant_2465 | FWKLLLKIPKFLHSALKF | seqid_1851 |
| variant_2466 | KKKKLLKIPKFLHSALKF | seqid_1852 |
| variant_2467 | RKKKLLKIPKFLHSALKF | seqid_1853 |
| variant_2468 | FKKKLLKIPKFLHSALKF | seqid_1854 |
| variant_2469 | KWKKLLKIPKFLHSALKF | seqid_1855 |
| variant_2470 | RWKKLLKIPKFLHSALKF | seqid_1856 |

-continued

| | | |
|---|---|---|
| variant_2471 | FWKKLLKIPKFLHSALKF | seqid_1857 |
| variant_2472 | KKKLFKKIPKFLHSALKF | seqid_1858 |
| variant_2473 | RKKLFKKIPKFLHSALKF | seqid_1859 |
| variant_2474 | FKKLFKKIPKFLHSALKF | seqid_1860 |
| variant_2475 | KWKLFKKIPKFLHSALKF | seqid_1861 |
| variant_2476 | RWKLFKKIPKFLHSALKF | seqid_1862 |
| variant_2477 | FWKLFKKIPKFLHSALKF | seqid_1863 |
| variant_2478 | KKKKFKKIPKFLHSALKF | seqid_1864 |
| variant_2479 | RKKKFKKIPKFLHSALKF | seqid_1865 |
| variant_2480 | FKKKFKKIPKFLHSALKF | seqid_1866 |
| variant_2481 | KWKKFKKIPKFLHSALKF | seqid_1867 |
| variant_2482 | RWKKFKKIPKFLHSALKF | seqid_1868 |
| variant_2483 | FWKKFKKIPKFLHSALKF | seqid_1869 |
| variant_2484 | KKKLLKKIPKFLHSALKF | seqid_1870 |
| variant_2485 | RKKLLKKIPKFLHSALKF | seqid_1871 |
| variant_2486 | FKKLLKKIPKFLHSALKF | seqid_1872 |
| variant_2487 | KWKLLKKIPKFLHSALKF | seqid_1873 |
| variant_2488 | RWKLLKKIPKFLHSALKF | seqid_1874 |
| variant_2489 | FWKLLKKIPKFLHSALKF | seqid_1875 |
| variant_2490 | KKKKLKKIPKFLHSALKF | seqid_1876 |
| variant_2491 | RKKKLKKIPKFLHSALKF | seqid_1877 |
| variant_2492 | FKKKLKKIPKFLHSALKF | seqid_1878 |
| variant_2493 | KWKKLKKIPKFLHSALKF | seqid_1879 |
| variant_2494 | RWKKLKKIPKFLHSALKF | seqid_1880 |
| variant_2495 | FWKKLKKIPKFLHSALKF | seqid_1881 |
| variant_2496 | KKKLFLKIPPPKFKHSALKF | seqid_1882 |
| variant_2497 | RKKLFLKIPPPKFKHSALKF | seqid_1883 |
| variant_2498 | FKKLFLKIPPPKFKHSALKF | seqid_1884 |
| variant_2499 | KWKLFLKIPPPKFKHSALKF | seqid_1885 |
| variant_2500 | RWKLFLKIPPPKFKHSALKF | seqid_1886 |
| variant_2501 | FWKLFLKIPPPKFKHSALKF | seqid_1887 |
| variant_2502 | KKKKFLKIPPPKFKHSALKF | seqid_1888 |
| variant_2503 | RKKKFLKIPPPKFKHSALKF | seqid_1889 |
| variant_2504 | FKKKFLKIPPPKFKHSALKF | seqid_1890 |
| variant_2505 | KWKKFLKIPPPKFKHSALKF | seqid_1891 |
| variant_2506 | RWKKFLKIPPPKFKHSALKF | seqid_1892 |
| variant_2507 | FWKKFLKIPPPKFKHSALKF | seqid_1893 |
| variant_2508 | KKKLLLKIPPPKFKHSALKF | seqid_1894 |
| variant_2509 | RKKLLLKIPPPKFKHSALKF | seqid_1895 |
| variant_2510 | FKKLLLKIPPPKFKHSALKF | seqid_1896 |
| variant_2511 | KWKLLLKIPPPKFKHSALKF | seqid_1897 |
| variant_2512 | RWKLLLKIPPPKFKHSALKF | seqid_1898 |
| variant_2513 | FWKLLLKIPPPKFKHSALKF | seqid_1899 |
| variant_2514 | KKKKLLKIPPPKFKHSALKF | seqid_1900 |
| variant_2515 | RKKKLLKIPPPKFKHSALKF | seqid_1901 |
| variant_2516 | FKKKLLKIPPPKFKHSALKF | seqid_1902 |
| variant_2517 | KWKKLLKIPPPKFKHSALKF | seqid_1903 |
| variant_2518 | RWKKLLKIPPPKFKHSALKF | seqid_1904 |
| variant_2519 | FWKKLLKIPPPKFKHSALKF | seqid_1905 |
| variant_2520 | KKKLFKKIPPPKFKHSALKF | seqid_1906 |
| variant_2521 | RKKLFKKIPPPKFKHSALKF | seqid_1907 |
| variant_2522 | FKKLFKKIPPPKFKHSALKF | seqid_1908 |
| variant_2523 | KWKLFKKIPPPKFKHSALKF | seqid_1909 |
| variant_2524 | RWKLFKKIPPPKFKHSALKF | seqid_1910 |
| variant_2525 | FWKLFKKIPPPKFKHSALKF | seqid_1911 |
| variant_2526 | KKKKFKKIPPPKFKHSALKF | seqid_1912 |
| variant_2527 | RKKKFKKIPPPKFKHSALKF | seqid_1913 |
| variant_2528 | FKKKFKKIPPPKFKHSALKF | seqid_1914 |
| variant_2529 | KWKKFKKIPPPKFKHSALKF | seqid_1915 |
| variant_2530 | RWKKFKKIPPPKFKHSALKF | seqid_1916 |
| variant_2531 | FWKKFKKIPPPKFKHSALKF | seqid_1917 |
| variant_2532 | KKKLLKKIPPPKFKHSALKF | seqid_1918 |
| variant_2533 | RKKLLKKIPPPKFKHSALKF | seqid_1919 |
| variant_2534 | FKKLLKKIPPPKFKHSALKF | seqid_1920 |
| variant_2535 | KWKLLKKIPPPKFKHSALKF | seqid_1921 |
| variant_2536 | RWKLLKKIPPPKFKHSALKF | seqid_1922 |
| variant_2537 | FWKLLKKIPPPKFKHSALKF | seqid_1923 |
| variant_2538 | KKKKLKKIPPPKFKHSALKF | seqid_1924 |
| variant_2539 | RKKKLKKIPPPKFKHSALKF | seqid_1925 |
| variant_2540 | FKKKLKKIPPPKFKHSALKF | seqid_1926 |
| variant_2541 | KWKKLKKIPPPKFKHSALKF | seqid_1927 |
| variant_2542 | RWKKLKKIPPPKFKHSALKF | seqid_1928 |
| variant_2543 | FWKKLKKIPPPKFKHSALKF | seqid_1929 |
| variant_2544 | KKKLFLKIPPKFKHSALKF | seqid_1930 |
| variant_2545 | RKKLFLKIPPKFKHSALKF | seqid_1931 |
| variant_2546 | FKKLFLKIPPKFKHSALKF | seqid_1932 |
| variant_2547 | KWKLFLKIPPKFKHSALKF | seqid_1933 |
| variant_2548 | RWKLFLKIPPKFKHSALKF | seqid_1934 |
| variant_2549 | FWKLFLKIPPKFKHSALKF | seqid_1935 |
| variant_2550 | KKKKFLKIPPKFKHSALKF | seqid_1936 |
| variant_2551 | RKKKFLKIPPKFKHSALKF | seqid_1937 |

| | | |
|---|---|---|
| variant_2552 | FKKKFLKIPPKFKHSALKF | seqid_1938 |
| variant_2553 | KWKKFLKIPPKFKHSALKF | seqid_1939 |
| variant_2554 | RWKKFLKIPPKFKHSALKF | seqid_1940 |
| variant_2555 | FWKKFLKIPPKFKHSALKF | seqid_1941 |
| variant_2556 | KKKLLLKIPPKFKHSALKF | seqid_1942 |
| variant_2557 | RKKLLLKIPPKFKHSALKF | seqid_1943 |
| variant_2558 | FKKLLLKIPPKFKHSALKF | seqid_1944 |
| variant_2559 | KWKLLLKIPPKFKHSALKF | seqid_1945 |
| variant_2560 | RWKLLLKIPPKFKHSALKF | seqid_1946 |
| variant_2561 | FWKLLLKIPPKFKHSALKF | seqid_1947 |
| variant_2562 | KKKKLLKIPPKFKHSALKF | seqid_1948 |
| variant_2563 | RKKKLLKIPPKFKHSALKF | seqid_1949 |
| variant_2564 | FKKKLLKIPPKFKHSALKF | seqid_1950 |
| variant_2565 | KWKKLLKIPPKFKHSALKF | seqid_1951 |
| variant_2566 | RWKKLLKIPPKFKHSALKF | seqid_1952 |
| variant_2567 | FWKKLLKIPPKFKHSALKF | seqid_1953 |
| variant_2568 | KKKLFKKIPPKFKHSALKF | seqid_1954 |
| variant_2569 | RKKLFKKIPPKFKHSALKF | seqid_1955 |
| variant_2570 | FKKLFKKIPPKFKHSALKF | seqid_1956 |
| variant_2571 | KWKLFKKIPPKFKHSALKF | seqid_1957 |
| variant_2572 | RWKLFKKIPPKFKHSALKF | seqid_1958 |
| variant_2573 | FWKLFKKIPPKFKHSALKF | seqid_1959 |
| variant_2574 | KKKKFKKIPPKFKHSALKF | seqid_1960 |
| variant_2575 | RKKKFKKIPPKFKHSALKF | seqid_1961 |
| variant_2576 | FKKKFKKIPPKFKHSALKF | seqid_1962 |
| variant_2577 | KWKKFKKIPPKFKHSALKF | seqid_1963 |
| variant_2578 | RWKKFKKIPPKFKHSALKF | seqid_1964 |
| variant_2579 | FWKKFKKIPPKFKHSALKF | seqid_1965 |
| variant_2580 | KKKLLKKIPPKFKHSALKF | seqid_1966 |
| variant_2581 | RKKLLKKIPPKFKHSALKF | seqid_1967 |
| variant_2582 | FKKLLKKIPPKFKHSALKF | seqid_1968 |
| variant_2583 | KWKLLKKIPPKFKHSALKF | seqid_1969 |
| variant_2584 | RWKLLKKIPPKFKHSALKF | seqid_1970 |
| variant_2585 | FWKLLKKIPPKFKHSALKF | seqid_1971 |
| variant_2586 | KKKKLKKIPPKFKHSALKF | seqid_1972 |
| variant_2587 | RKKKLKKIPPKFKHSALKF | seqid_1973 |
| variant_2588 | FKKKLKKIPPKFKHSALKF | seqid_1974 |
| variant_2589 | KWKKLKKIPPKFKHSALKF | seqid_1975 |
| variant_2590 | RWKKLKKIPPKFKHSALKF | seqid_1976 |
| variant_2591 | FWKKLKKIPPKFKHSALKF | seqid_1977 |
| variant_2640 | KKKLFLKIPKFKHSALKF | seqid_1978 |
| variant_2641 | RKKLFLKIPKFKHSALKF | seqid_1979 |
| variant_2642 | FKKLFLKIPKFKHSALKF | seqid_1980 |
| variant_2643 | KWKLFLKIPKFKHSALKF | seqid_1981 |
| variant_2644 | RWKLFLKIPKFKHSALKF | seqid_1982 |
| variant_2645 | FWKLFLKIPKFKHSALKF | seqid_1983 |
| variant_2646 | KKKKFLKIPKFKHSALKF | seqid_1984 |
| variant_2647 | RKKKFLKIPKFKHSALKF | seqid_1985 |
| variant_2648 | FKKKFLKIPKFKHSALKF | seqid_1986 |
| variant_2649 | KWKKFLKIPKFKHSALKF | seqid_1987 |
| variant_2650 | RWKKFLKIPKFKHSALKF | seqid_1988 |
| variant_2651 | FWKKFLKIPKFKHSALKF | seqid_1989 |
| variant_2652 | KKKLLLKIPKFKHSALKF | seqid_1990 |
| variant_2653 | RKKLLLKIPKFKHSALKF | seqid_1991 |
| variant_2654 | FKKLLLKIPKFKHSALKF | seqid_1992 |
| variant_2655 | KWKLLLKIPKFKHSALKF | seqid_1993 |
| variant_2656 | RWKLLLKIPKFKHSALKF | seqid_1994 |
| variant_2657 | FWKLLLKIPKFKHSALKF | seqid_1995 |
| variant_2658 | KKKKLLKIPKFKHSALKF | seqid_1996 |
| variant_2659 | RKKKLLKIPKFKHSALKF | seqid_1997 |
| variant_2660 | FKKKLLKIPKFKHSALKF | seqid_1998 |
| variant_2661 | KWKKLLKIPKFKHSALKF | seqid_1999 |
| variant_2662 | RWKKLLKIPKFKHSALKF | seqid_2000 |
| variant_2663 | FWKKLLKIPKFKHSALKF | seqid_2001 |
| variant_2664 | KKKLFKKIPKFKHSALKF | seqid_2002 |
| variant_2665 | RKKLFKKIPKFKHSALKF | seqid_2003 |
| variant_2666 | FKKLFKKIPKFKHSALKF | seqid_2004 |
| variant_2667 | KWKLFKKIPKFKHSALKF | seqid_2005 |
| variant_2668 | RWKLFKKIPKFKHSALKF | seqid_2006 |
| variant_2669 | FWKLFKKIPKFKHSALKF | seqid_2007 |
| variant_2670 | KKKKFKKIPKFKHSALKF | seqid_2008 |
| variant_2671 | RKKKFKKIPKFKHSALKF | seqid_2009 |
| variant_2672 | FKKKFKKIPKFKHSALKF | seqid_2010 |
| variant_2673 | KWKKFKKIPKFKHSALKF | seqid_2011 |
| variant_2674 | RWKKFKKIPKFKHSALKF | seqid_2012 |
| variant_2675 | FWKKFKKIPKFKHSALKF | seqid_2013 |
| variant_2676 | KKKLLKKIPKFKHSALKF | seqid_2014 |
| variant_2677 | RKKLLKKIPKFKHSALKF | seqid_2015 |
| variant_2678 | FKKLLKKIPKFKHSALKF | seqid_2016 |
| variant_2679 | KWKLLKKIPKFKHSALKF | seqid_2017 |
| variant_2680 | RWKLLKKIPKFKHSALKF | seqid_2018 |

-continued

| | | |
|---|---|---|
| variant_2681 | FWKLLKKIPKFKHSALKF | seqid_2019 |
| variant_2682 | KKKKLKKIPKFKHSALKF | seqid_2020 |
| variant_2683 | RKKKLKKIPKFKHSALKF | seqid_2021 |
| variant_2684 | FKKKLKKIPKFKHSALKF | seqid_2022 |
| variant_2685 | KWKKLKKIPKFKHSALKF | seqid_2023 |
| variant_2686 | RWKKLKKIPKFKHSALKF | seqid_2024 |
| variant_2687 | FWKKLKKIPKFKHSALKF | seqid_2025 |
| variant_2688 | KKKLFLKIPPPKFLKSALKF | seqid_2026 |
| variant_2689 | RKKLFLKIPPPKFLKSALKF | seqid_2027 |
| variant_2690 | FKKLFLKIPPPKFLKSALKF | seqid_2028 |
| variant_2691 | KWKLFLKIPPPKFLKSALKF | seqid_2029 |
| variant_2692 | RWKLFLKIPPPKFLKSALKF | seqid_2030 |
| variant_2693 | FWKLFLKIPPPKFLKSALKF | seqid_2031 |
| variant_2694 | KKKKFLKIPPPKFLKSALKF | seqid_2032 |
| variant_2695 | RKKKFLKIPPPKFLKSALKF | seqid_2033 |
| variant_2696 | FKKKFLKIPPPKFLKSALKF | seqid_2034 |
| variant_2697 | KWKKFLKIPPPKFLKSALKF | seqid_2035 |
| variant_2698 | RWKKFLKIPPPKFLKSALKF | seqid_2036 |
| variant_2699 | FWKKFLKIPPPKFLKSALKF | seqid_2037 |
| variant_2700 | KKKLLLKIPPPKFLKSALKF | seqid_2038 |
| variant_2701 | RKKLLLKIPPPKFLKSALKF | seqid_2039 |
| variant_2702 | FKKLLLKIPPPKFLKSALKF | seqid_2040 |
| variant_2703 | KWKLLLKIPPPKFLKSALKF | seqid_2041 |
| variant_2704 | RWKLLLKIPPPKFLKSALKF | seqid_2042 |
| variant_2705 | FWKLLLKIPPPKFLKSALKF | seqid_2043 |
| variant_2706 | KKKKLLKIPPPKFLKSALKF | seqid_2044 |
| variant_2707 | RKKKLLKIPPPKFLKSALKF | seqid_2045 |
| variant_2708 | FKKKLLKIPPPKFLKSALKF | seqid_2046 |
| variant_2709 | KWKKLLKIPPPKFLKSALKF | seqid_2047 |
| variant_2710 | RWKKLLKIPPPKFLKSALKF | seqid_2048 |
| variant_2711 | FWKKLLKIPPPKFLKSALKF | seqid_2049 |
| variant_2712 | KKKLFKKIPPPKFLKSALKF | seqid_2050 |
| variant_2713 | RKKLFKKIPPPKFLKSALKF | seqid_2051 |
| variant_2714 | FKKLFKKIPPPKFLKSALKF | seqid_2052 |
| variant_2715 | KWKLFKKIPPPKFLKSALKF | seqid_2053 |
| variant_2716 | RWKLFKKIPPPKFLKSALKF | seqid_2054 |
| variant_2717 | FWKLFKKIPPPKFLKSALKF | seqid_2055 |
| variant_2718 | KKKKFKKIPPPKFLKSALKF | seqid_2056 |
| variant_2719 | RKKKFKKIPPPKFLKSALKF | seqid_2057 |
| variant_2720 | FKKKFKKIPPPKFLKSALKF | seqid_2058 |
| variant_2721 | KWKKFKKIPPPKFLKSALKF | seqid_2059 |
| variant_2722 | RWKKFKKIPPPKFLKSALKF | seqid_2060 |
| variant_2723 | FWKKFKKIPPPKFLKSALKF | seqid_2061 |
| variant_2724 | KKKLLKKIPPPKFLKSALKF | seqid_2062 |
| variant_2725 | RKKLLKKIPPPKFLKSALKF | seqid_2063 |
| variant_2726 | FKKLLKKIPPPKFLKSALKF | seqid_2064 |
| variant_2727 | KWKLLKKIPPPKFLKSALKF | seqid_2065 |
| variant_2728 | RWKLLKKIPPPKFLKSALKF | seqid_2066 |
| variant_2729 | FWKLLKKIPPPKFLKSALKF | seqid_2067 |
| variant_2730 | KKKKLKKIPPPKFLKSALKF | seqid_2068 |
| variant_2731 | RKKKLKKIPPPKFLKSALKF | seqid_2069 |
| variant_2732 | FKKKLKKIPPPKFLKSALKF | seqid_2070 |
| variant_2733 | KWKKLKKIPPPKFLKSALKF | seqid_2071 |
| variant_2734 | RWKKLKKIPPPKFLKSALKF | seqid_2072 |
| variant_2735 | FWKKLKKIPPPKFLKSALKF | seqid_2073 |
| variant_2736 | KKKLFLKIPPKFLKSALKF | seqid_2074 |
| variant_2737 | RKKLFLKIPPKFLKSALKF | seqid_2075 |
| variant_2738 | FKKLFLKIPPPKFLKSALKF | seqid_2076 |
| variant_2739 | KWKLFLKIPPKFLKSALKF | seqid_2077 |
| variant_2740 | RWKLFLKIPPKFLKSALKF | seqid_2078 |
| variant_2741 | FWKLFLKIPPKFLKSALKF | seqid_2079 |
| variant_2742 | KKKKFLKIPPKFLKSALKF | seqid_2080 |
| variant_2743 | RKKKFLKIPPKFLKSALKF | seqid_2081 |
| variant_2744 | FKKKFLKIPPKFLKSALKF | seqid_2082 |
| variant_2745 | KWKKFLKIPPKFLKSALKF | seqid_2083 |
| variant_2746 | RWKKFLKIPPKFLKSALKF | seqid_2084 |
| variant_2747 | FWKKFLKIPPKFLKSALKF | seqid_2085 |
| variant_2748 | KKKLLLKIPPKFLKSALKF | seqid_2086 |
| variant_2749 | RKKLLLKIPPKFLKSALKF | seqid_2087 |
| variant_2750 | FKKLLLKIPPKFLKSALKF | seqid_2088 |
| variant_2751 | KWKLLLKIPPKFLKSALKF | seqid_2089 |
| variant_2752 | RWKLLLKIPPKFLKSALKF | seqid_2090 |
| variant_2753 | FWKLLLKIPPKFLKSALKF | seqid_2091 |
| variant_2754 | KKKKLLKIPPKFLKSALKF | seqid_2092 |
| variant_2755 | RKKKLLKIPPKFLKSALKF | seqid_2093 |
| variant_2756 | FKKKLLKIPPKFLKSALKF | seqid_2094 |
| variant_2757 | KWKKLLKIPPKFLKSALKF | seqid_2095 |
| variant_2758 | RWKKLLKIPPKFLKSALKF | seqid_2096 |
| variant_2759 | FWKKLLKIPPKFLKSALKF | seqid_2097 |
| variant_2760 | KKKLFKKIPPKFLKSALKF | seqid_2098 |
| variant_2761 | RKKLFKKIPPKFLKSALKF | seqid_2099 |

| | | |
|---|---|---|
| variant_2762 | FKKLFKKIPPKFLKSALKF | seqid_2100 |
| variant_2763 | KWKLFKKIPPKFLKSALKF | seqid_2101 |
| variant_2764 | RWKLFKKIPPKFLKSALKF | seqid_2102 |
| variant_2765 | FWKLFKKIPPKFLKSALKF | seqid_2103 |
| variant_2766 | KKKKFKKIPPKFLKSALKF | seqid_2104 |
| variant_2767 | RKKKFKKIPPKFLKSALKF | seqid_2105 |
| variant_2768 | FKKKFKKIPPKFLKSALKF | seqid_2106 |
| variant_2769 | KWKKFKKIPPKFLKSALKF | seqid_2107 |
| variant_2770 | RWKKFKKIPPKFLKSALKF | seqid_2108 |
| variant_2771 | FWKKFKKIPPKFLKSALKF | seqid_2109 |
| variant_2772 | KKKLLKKIPPKFLKSALKF | seqid_2110 |
| variant_2773 | RKKLLKKIPPKFLKSALKF | seqid_2111 |
| variant_2774 | FKKLLKKIPPKFLKSALKF | seqid_2112 |
| variant_2775 | KWKLLKKIPPKFLKSALKF | seqid_2113 |
| variant_2776 | RWKLLKKIPPKFLKSALKF | seqid_2114 |
| variant_2777 | FWKLLKKIPPKFLKSALKF | seqid_2115 |
| variant_2778 | KKKKLKKIPPKFLKSALKF | seqid_2116 |
| variant_2779 | RKKKLKKIPPKFLKSALKF | seqid_2117 |
| variant_2780 | FKKKLKKIPPKFLKSALKF | seqid_2118 |
| variant_2781 | KWKKLKKIPPKFLKSALKF | seqid_2119 |
| variant_2782 | RWKKLKKIPPKFLKSALKF | seqid_2120 |
| variant_2783 | FWKKLKKIPPKFLKSALKF | seqid_2121 |
| variant_2832 | KKKLFLKIPKFLKSALKF | seqid_2122 |
| variant_2833 | RKKLFLKIPKFLKSALKF | seqid_2123 |
| variant_2834 | FKKLFLKIPKFLKSALKF | seqid_2124 |
| variant_2835 | KWKLFLKIPKFLKSALKF | seqid_2125 |
| variant_2836 | RWKLFLKIPKFLKSALKF | seqid_2126 |
| variant_2837 | FWKLFLKIPKFLKSALKF | seqid_2127 |
| variant_2838 | KKKKFLKIPKFLKSALKF | seqid_2128 |
| variant_2839 | RKKKFLKIPKFLKSALKF | seqid_2129 |
| variant_2840 | FKKKFLKIPKFLKSALKF | seqid_2130 |
| variant_2841 | KWKKFLKIPKFLKSALKF | seqid_2131 |
| variant_2842 | RWKKFLKIPKFLKSALKF | seqid_2132 |
| variant_2843 | FWKKFLKIPKFLKSALKF | seqid_2133 |
| variant_2844 | KKKLLLKIPKFLKSALKF | seqid_2134 |
| variant_2845 | RKKLLLKIPKFLKSALKF | seqid_2135 |
| variant_2846 | FKKLLLKIPKFLKSALKF | seqid_2136 |
| variant_2847 | KWKLLLKIPKFLKSALKF | seqid_2137 |
| variant_2848 | RWKLLLKIPKFLKSALKF | seqid_2138 |
| variant_2849 | FWKLLLKIPKFLKSALKF | seqid_2139 |
| variant_2850 | KKKKLLKIPKFLKSALKF | seqid_2140 |
| variant_2851 | RKKKLLKIPKFLKSALKF | seqid_2141 |
| variant_2852 | FKKKLLKIPKFLKSALKF | seqid_2142 |
| variant_2853 | KWKKLLKIPKFLKSALKF | seqid_2143 |
| variant_2854 | RWKKLLKIPKFLKSALKF | seqid_2144 |
| variant_2855 | FWKKLLKIPKFLKSALKF | seqid_2145 |
| variant_2856 | KKKLFKKIPKFLKSALKF | seqid_2146 |
| variant_2857 | RKKLFKKIPKFLKSALKF | seqid_2147 |
| variant_2858 | FKKLFKKIPKFLKSALKF | seqid_2148 |
| variant_2859 | KWKLFKKIPKFLKSALKF | seqid_2149 |
| variant_2860 | RWKLFKKIPKFLKSALKF | seqid_2150 |
| variant_2861 | FWKLFKKIPKFLKSALKF | seqid_2151 |
| variant_2862 | KKKKFKKIPKFLKSALKF | seqid_2152 |
| variant_2863 | RKKKFKKIPKFLKSALKF | seqid_2153 |
| variant_2864 | FKKKFKKIPKFLKSALKF | seqid_2154 |
| variant_2865 | KWKKFKKIPKFLKSALKF | seqid_2155 |
| variant_2866 | RWKKFKKIPKFLKSALKF | seqid_2156 |
| variant_2867 | FWKKFKKIPKFLKSALKF | seqid_2157 |
| variant_2868 | KKKLLKKIPKFLKSALKF | seqid_2158 |
| variant_2869 | RKKLLKKIPKFLKSALKF | seqid_2159 |
| variant_2870 | FKKLLKKIPKFLKSALKF | seqid_2160 |
| variant_2871 | KWKLLKKIPKFLKSALKF | seqid_2161 |
| variant_2872 | RWKLLKKIPKFLKSALKF | seqid_2162 |
| variant_2873 | FWKLLKKIPKFLKSALKF | seqid_2163 |
| variant_2874 | KKKKLKKIPKFLKSALKF | seqid_2164 |
| variant_2875 | RKKKLKKIPKFLKSALKF | seqid_2165 |
| variant_2876 | FKKKLKKIPKFLKSALKF | seqid_2166 |
| variant_2877 | KWKKLKKIPKFLKSALKF | seqid_2167 |
| variant_2878 | RWKKLKKIPKFLKSALKF | seqid_2168 |
| variant_2879 | FWKKLKKIPKFLKSALKF | seqid_2169 |
| variant_2880 | KKKLFLKIPPPKFKKSALKF | seqid_2170 |
| variant_2881 | RKKLFLKIPPPKFKKSALKF | seqid_2171 |
| variant_2882 | FKKLFLKIPPPKFKKSALKF | seqid_2172 |
| variant_2883 | KWKLFLKIPPPKFKKSALKF | seqid_2173 |
| variant_2884 | RWKLFLKIPPPKFKKSALKF | seqid_2174 |
| variant_2885 | FWKLFLKIPPPKFKKSALKF | seqid_2175 |
| variant_2886 | KKKKFLKIPPPKFKKSALKF | seqid_2176 |
| variant_2887 | RKKKFLKIPPPKFKKSALKF | seqid_2177 |
| variant_2888 | FKKKFLKIPPPKFKKSALKF | seqid_2178 |
| variant_2889 | KWKKFLKIPPPKFKKSALKF | seqid_2179 |
| variant_2890 | RWKKFLKIPPPKFKKSALKF | seqid_2180 |

| | | |
|---|---|---|
| variant_2891 | FWKKFLKIPPPKFKKSALKF | seqid_2181 |
| variant_2892 | KKKLLLKIPPPKFKKSALKF | seqid_2182 |
| variant_2893 | RKKLLLKIPPPKFKKSALKF | seqid_2183 |
| variant_2894 | FKKLLLKIPPPKFKKSALKF | seqid_2184 |
| variant_2895 | KWKLLLKIPPPKFKKSALKF | seqid_2185 |
| variant_2896 | RWKLLLKIPPPKFKKSALKF | seqid_2186 |
| variant_2897 | FWKLLLKIPPPKFKKSALKF | seqid_2187 |
| variant_2898 | KKKKLLKIPPPKFKKSALKF | seqid_2188 |
| variant_2899 | RKKKLLKIPPPKFKKSALKF | seqid_2189 |
| variant_2900 | FKKKLLKIPPPKFKKSALKF | seqid_2190 |
| variant_2901 | KWKKLLKIPPPKFKKSALKF | seqid_2191 |
| variant_2902 | RWKKLLKIPPPKFKKSALKF | seqid_2192 |
| variant_2903 | FWKKLLKIPPPKFKKSALKF | seqid_2193 |
| variant_2904 | KKKLFKKIPPPKFKKSALKF | seqid_2194 |
| variant_2905 | RKKLFKKIPPPKFKKSALKF | seqid_2195 |
| variant_2906 | FKKLFKKIPPPKFKKSALKF | seqid_2196 |
| variant_2907 | KWKLFKKIPPPKFKKSALKF | seqid_2197 |
| variant_2908 | RWKLFKKIPPPKFKKSALKF | seqid_2198 |
| variant_2909 | FWKLFKKIPPPKFKKSALKF | seqid_2199 |
| variant_2910 | KKKKFKKIPPPKFKKSALKF | seqid_2200 |
| variant_2911 | RKKKFKKIPPPKFKKSALKF | seqid_2201 |
| variant_2912 | FKKKFKKIPPPKFKKSALKF | seqid_2202 |
| variant_2913 | KWKKFKKIPPPKFKKSALKF | seqid_2203 |
| variant_2914 | RWKKFKKIPPPKFKKSALKF | seqid_2204 |
| variant_2915 | FWKKFKKIPPPKFKKSALKF | seqid_2205 |
| variant_2916 | KKKLLKKIPPPKFKKSALKF | seqid_2206 |
| variant_2917 | RKKLLKKIPPPKFKKSALKF | seqid_2207 |
| variant_2918 | FKKLLKKIPPPKFKKSALKF | seqid_2208 |
| variant_2919 | KWKLLKKIPPPKFKKSALKF | seqid_2209 |
| variant_2920 | RWKLLKKIPPPKFKKSALKF | seqid_2210 |
| variant_2921 | FWKLLKKIPPPKFKKSALKF | seqid_2211 |
| variant_2922 | KKKKLKKIPPPKFKKSALKF | seqid_2212 |
| variant_2923 | RKKKLKKIPPPKFKKSALKF | seqid_2213 |
| variant_2924 | FKKKLKKIPPPKFKKSALKF | seqid_2214 |
| variant_2925 | KWKKLKKIPPPKFKKSALKF | seqid_2215 |
| variant_2926 | RWKKLKKIPPPKFKKSALKF | seqid_2216 |
| variant_2927 | FWKKLKKIPPPKFKKSALKF | seqid_2217 |
| variant_2928 | KKKLFLKIPPPKFKKSALKF | seqid_2218 |
| variant_2929 | RKKLFLKIPPPKFKKSALKF | seqid_2219 |
| variant_2930 | FKKLFLKIPPPKFKKSALKF | seqid_2220 |
| variant_2931 | KWKLFLKIPPPKFKKSALKF | seqid_2221 |
| variant_2932 | RWKLFLKIPPPKFKKSALKF | seqid_2222 |
| variant_2933 | FWKLFLKIPPPKFKKSALKF | seqid_2223 |
| variant_2934 | KKKKFLKIPPPKFKKSALKF | seqid_2224 |
| variant_2935 | RKKKFLKIPPPKFKKSALKF | seqid_2225 |
| variant_2936 | FKKKFLKIPPPKFKKSALKF | seqid_2226 |
| variant_2937 | KWKKFLKIPPPKFKKSALKF | seqid_2227 |
| variant_2938 | RWKKFLKIPPPKFKKSALKF | seqid_2228 |
| variant_2939 | FWKKFLKIPPPKFKKSALKF | seqid_2229 |
| variant_2940 | KKKLLLKIPPKFKKSALKF | seqid_2230 |
| variant_2941 | RKKLLLKIPPKFKKSALKF | seqid_2231 |
| variant_2942 | FKKLLLKIPPKFKKSALKF | seqid_2232 |
| variant_2943 | KWKLLLKIPPKFKKSALKF | seqid_2233 |
| variant_2944 | RWKLLLKIPPKFKKSALKF | seqid_2234 |
| variant_2945 | FWKLLLKIPPKFKKSALKF | seqid_2235 |
| variant_2946 | KKKKLLKIPPKFKKSALKF | seqid_2236 |
| variant_2947 | RKKKLLKIPPKFKKSALKF | seqid_2237 |
| variant_2948 | FKKKLLKIPPKFKKSALKF | seqid_2238 |
| variant_2949 | KWKKLLKIPPKFKKSALKF | seqid_2239 |
| variant_2950 | RWKKLLKIPPKFKKSALKF | seqid_2240 |
| variant_2951 | FWKKLLKIPPKFKKSALKF | seqid_2241 |
| variant_2952 | KKKLFKKIPPKFKKSALKF | seqid_2242 |
| variant_2953 | RKKLFKKIPPKFKKSALKF | seqid_2243 |
| variant_2954 | FKKLFKKIPPKFKKSALKF | seqid_2244 |
| variant_2955 | KWKLFKKIPPKFKKSALKF | seqid_2245 |
| variant_2956 | RWKLFKKIPPKFKKSALKF | seqid_2246 |
| variant_2957 | FWKLFKKIPPKFKKSALKF | seqid_2247 |
| variant_2958 | KKKKFKKIPPKFKKSALKF | seqid_2248 |
| variant_2959 | RKKKFKKIPPKFKKSALKF | seqid_2249 |
| variant_2960 | FKKKFKKIPPKFKKSALKF | seqid_2250 |
| variant_2961 | KWKKFKKIPPKFKKSALKF | seqid_2251 |
| variant_2962 | RWKKFKKIPPKFKKSALKF | seqid_2252 |
| variant_2963 | FWKKFKKIPPKFKKSALKF | seqid_2253 |
| variant_2964 | KKKLLKKIPPKFKKSALKF | seqid_2254 |
| variant_2965 | RKKLLKKIPPKFKKSALKF | seqid_2255 |
| variant_2966 | FKKLLKKIPPKFKKSALKF | seqid_2256 |
| variant_2967 | KWKLLKKIPPKFKKSALKF | seqid_2257 |
| variant_2968 | RWKLLKKIPPKFKKSALKF | seqid_2258 |
| variant_2969 | FWKLLKKIPPKFKKSALKF | seqid_2259 |
| variant_2970 | KKKKLKKIPPKFKKSALKF | seqid_2260 |
| variant_2971 | RKKKLKKIPPKFKKSALKF | seqid_2261 |

| | | |
|---|---|---|
| variant_2972 | FKKKLKKIPPKFKKSALKF | seqid_2262 |
| variant_2973 | KWKKLKKIPPKFKKSALKF | seqid_2263 |
| variant_2974 | RWKKLKKIPPKFKKSALKF | seqid_2264 |
| variant_2975 | FWKKLKKIPPKFKKSALKF | seqid_2265 |
| variant_3024 | KKKLFLKIPKFKKSALKF | seqid_2266 |
| variant_3025 | RKKLFLKIPKFKKSALKF | seqid_2267 |
| variant_3026 | FKKLFLKIPKFKKSALKF | seqid_2268 |
| variant_3027 | KWKLFLKIPKFKKSALKF | seqid_2269 |
| variant_3028 | RWKLFLKIPKFKKSALKF | seqid_2270 |
| variant_3029 | FWKLFLKIPKFKKSALKF | seqid_2271 |
| variant_3030 | KKKKFLKIPKFKKSALKF | seqid_2272 |
| variant_3031 | RKKKFLKIPKFKKSALKF | seqid_2273 |
| variant_3032 | FKKKFLKIPKFKKSALKF | seqid_2274 |
| variant_3033 | KWKKFLKIPKFKKSALKF | seqid_2275 |
| variant_3034 | RWKKFLKIPKFKKSALKF | seqid_2276 |
| variant_3035 | FWKKFLKIPKFKKSALKF | seqid_2277 |
| variant_3036 | KKKLLLKIPKFKKSALKF | seqid_2278 |
| variant_3037 | RKKLLLKIPKFKKSALKF | seqid_2279 |
| variant_3038 | FKKLLLKIPKFKKSALKF | seqid_2280 |
| variant_3039 | KWKLLLKIPKFKKSALKF | seqid_2281 |
| variant_3040 | RWKLLLKIPKFKKSALKF | seqid_2282 |
| variant_3041 | FWKLLLKIPKFKKSALKF | seqid_2283 |
| variant_3042 | KKKKLLKIPKFKKSALKF | seqid_2284 |
| variant_3043 | RKKKLLKIPKFKKSALKF | seqid_2285 |
| variant_3044 | FKKKLLKIPKFKKSALKF | seqid_2286 |
| variant_3045 | KWKKLLKIPKFKKSALKF | seqid_2287 |
| variant_3046 | RWKKLLKIPKFKKSALKF | seqid_2288 |
| variant_3047 | FWKKLLKIPKFKKSALKF | seqid_2289 |
| variant_3048 | KKKLFKKIPKFKKSALKF | seqid_2290 |
| variant_3049 | RKKLFKKIPKFKKSALKF | seqid_2291 |
| variant_3050 | FKKLFKKIPKFKKSALKF | seqid_2292 |
| variant_3051 | KWKLFKKIPKFKKSALKF | seqid_2293 |
| variant_3052 | RWKLFKKIPKFKKSALKF | seqid_2294 |
| variant_3053 | FWKLFKKIPKFKKSALKF | seqid_2295 |
| variant_3054 | KKKKFKKIPKFKKSALKF | seqid_2296 |
| variant_3055 | RKKKFKKIPKFKKSALKF | seqid_2297 |
| variant_3056 | FKKKFKKIPKFKKSALKF | seqid_2298 |
| variant_3057 | KWKKFKKIPKFKKSALKF | seqid_2299 |
| variant_3058 | RWKKFKKIPKFKKSALKF | seqid_2300 |
| variant_3059 | FWKKFKKIPKFKKSALKF | seqid_2301 |
| variant_3060 | KKKLLKKIPKFKKSALKF | seqid_2302 |
| variant_3061 | RKKLLKKIPKFKKSALKF | seqid_2303 |
| variant_3062 | FKKLLKKIPKFKKSALKF | seqid_2304 |
| variant_3063 | KWKLLKKIPKFKKSALKF | seqid_2305 |
| variant_3064 | RWKLLKKIPKFKKSALKF | seqid_2306 |
| variant_3065 | FWKLLKKIPKFKKSALKF | seqid_2307 |
| variant_3066 | KKKKLKKIPKFKKSALKF | seqid_2308 |
| variant_3067 | RKKKLKKIPKFKKSALKF | seqid_2309 |
| variant_3068 | FKKKLKKIPKFKKSALKF | seqid_2310 |
| variant_3069 | KWKKLKKIPKFKKSALKF | seqid_2311 |
| variant_3070 | RWKKLKKIPKFKKSALKF | seqid_2312 |
| variant_3071 | FWKKLKKIPKFKKSALKF | seqid_2313 |
| variant_3072 | KKKLFLKIPPPKFLHAAKKF | seqid_2314 |
| variant_3073 | RKKLFLKIPPPKFLHAAKKF | seqid_2315 |
| variant_3074 | FKKLFLKIPPPKFLHAAKKF | seqid_2316 |
| variant_3075 | KWKLFLKIPPPKFLHAAKKF | seqid_2317 |
| variant_3076 | RWKLFLKIPPPKFLHAAKKF | seqid_2318 |
| variant_3077 | FWKLFLKIPPPKFLHAAKKF | seqid_2319 |
| variant_3078 | KKKKFLKIPPPKFLHAAKKF | seqid_2320 |
| variant_3079 | RKKKFLKIPPPKFLHAAKKF | seqid_2321 |
| variant_3080 | FKKKFLKIPPPKFLHAAKKF | seqid_2322 |
| variant_3081 | KWKKFLKIPPPKFLHAAKKF | seqid_2323 |
| variant_3082 | RWKKFLKIPPPKFLHAAKKF | seqid_2324 |
| variant_3083 | FWKKFLKIPPPKFLHAAKKF | seqid_2325 |
| variant_3084 | KKKLLLKIPPPKFLHAAKKF | seqid_2326 |
| variant_3085 | RKKLLLKIPPPKFLHAAKKF | seqid_2327 |
| variant_3086 | FKKLLLKIPPPKFLHAAKKF | seqid_2328 |
| variant_3087 | KWKLLLKIPPPKFLHAAKKF | seqid_2329 |
| variant_3088 | RWKLLLKIPPPKFLHAAKKF | seqid_2330 |
| variant_3089 | FWKLLLKIPPPKFLHAAKKF | seqid_2331 |
| variant_3090 | KKKKLLKIPPPKFLHAAKKF | seqid_2332 |
| variant_3091 | RKKKLLKIPPPKFLHAAKKF | seqid_2333 |
| variant_3092 | FKKKLLKIPPPKFLHAAKKF | seqid_2334 |
| variant_3093 | KWKKLLKIPPPKFLHAAKKF | seqid_2335 |
| variant_3094 | RWKKLLKIPPPKFLHAAKKF | seqid_2336 |
| variant_3095 | FWKKLLKIPPPKFLHAAKKF | seqid_2337 |
| variant_3096 | KKKLFKKIPPPKFLHAAKKF | seqid_2338 |
| variant_3097 | RKKLFKKIPPPKFLHAAKKF | seqid_2339 |
| variant_3098 | FKKLFKKIPPPKFLHAAKKF | seqid_2340 |
| variant_3099 | KWKLFKKIPPPKFLHAAKKF | seqid_2341 |
| variant_3100 | RWKLFKKIPPPKFLHAAKKF | seqid_2342 |

-continued

| | | |
|---|---|---|
| variant_3101 | FWKLFKKIPPPKFLHAAKKF | seqid_2343 |
| variant_3102 | KKKKFKKIPPPKFLHAAKKF | seqid_2344 |
| variant_3103 | RKKKFKKIPPPKFLHAAKKF | seqid_2345 |
| variant_3104 | FKKKFKKIPPPKFLHAAKKF | seqid_2346 |
| variant_3105 | KWKKFKKIPPPKFLHAAKKF | seqid_2347 |
| variant_3106 | RWKKFKKIPPPKFLHAAKKF | seqid_2348 |
| variant_3107 | FWKKFKKIPPPKFLHAAKKF | seqid_2349 |
| variant_3108 | KKKLLKKIPPPKFLHAAKKF | seqid_2350 |
| variant_3109 | RKKLLKKIPPPKFLHAAKKF | seqid_2351 |
| variant_3110 | FKKLLKKIPPPKFLHAAKKF | seqid_2352 |
| variant_3111 | KWKLLKKIPPPKFLHAAKKF | seqid_2353 |
| variant_3112 | RWKLLKKIPPPKFLHAAKKF | seqid_2354 |
| variant_3113 | FWKLLKKIPPPKFLHAAKKF | seqid_2355 |
| variant_3114 | KKKKLKKIPPPKFLHAAKKF | seqid_2356 |
| variant_3115 | RKKKLKKIPPPKFLHAAKKF | seqid_2357 |
| variant_3116 | FKKKLKKIPPPKFLHAAKKF | seqid_2358 |
| variant_3117 | KWKKLKKIPPPKFLHAAKKF | seqid_2359 |
| variant_3118 | RWKKLKKIPPPKFLHAAKKF | seqid_2360 |
| variant_3119 | FWKKLKKIPPPKFLHAAKKF | seqid_2361 |
| variant_3120 | KKKLFLKIPPKFLHAAKKF | seqid_2362 |
| variant_3121 | RKKLFLKIPPKFLHAAKKF | seqid_2363 |
| variant_3122 | FKKLFLKIPPKFLHAAKKF | seqid_2364 |
| variant_3123 | KWKLFLKIPPKFLHAAKKF | seqid_2365 |
| variant_3124 | RWKLFLKIPPKFLHAAKKF | seqid_2366 |
| variant_3125 | FWKLFLKIPPKFLHAAKKF | seqid_2367 |
| variant_3126 | KKKKFLKIPPKFLHAAKKF | seqid_2368 |
| variant_3127 | RKKKFLKIPPKFLHAAKKF | seqid_2369 |
| variant_3128 | FKKKFLKIPPKFLHAAKKF | seqid_2370 |
| variant_3129 | KWKKFLKIPPKFLHAAKKF | seqid_2371 |
| variant_3130 | RWKKFLKIPPKFLHAAKKF | seqid_2372 |
| variant_3131 | FWKKFLKIPPKFLHAAKKF | seqid_2373 |
| variant_3132 | KKKLLLKIPPKFLHAAKKF | seqid_2374 |
| variant_3133 | RKKLLLKIPPKFLHAAKKF | seqid_2375 |
| variant_3134 | FKKLLLKIPPKFLHAAKKF | seqid_2376 |
| variant_3135 | KWKLLLKIPPKFLHAAKKF | seqid_2377 |
| variant_3136 | RWKLLLKIPPKFLHAAKKF | seqid_2378 |
| variant_3137 | FWKLLLKIPPKFLHAAKKF | seqid_2379 |
| variant_3138 | KKKKLLKIPPKFLHAAKKF | seqid_2380 |
| variant_3139 | RKKKLLKIPPKFLHAAKKF | seqid_2381 |
| variant_3140 | FKKKLLKIPPKFLHAAKKF | seqid_2382 |
| variant_3141 | KWKKLLKIPPKFLHAAKKF | seqid_2383 |
| variant_3142 | RWKKLLKIPPKFLHAAKKF | seqid_2384 |
| variant_3143 | FWKKLLKIPPKFLHAAKKF | seqid_2385 |
| variant_3144 | KKKLFKKIPPKFLHAAKKF | seqid_2386 |
| variant_3145 | RKKLFKKIPPKFLHAAKKF | seqid_2387 |
| variant_3146 | FKKLFKKIPPKFLHAAKKF | seqid_2388 |
| variant_3147 | KWKLFKKIPPKFLHAAKKF | seqid_2389 |
| variant_3148 | RWKLFKKIPPKFLHAAKKF | seqid_2390 |
| variant_3149 | FWKLFKKIPPKFLHAAKKF | seqid_2391 |
| variant_3150 | KKKKFKKIPPKFLHAAKKF | seqid_2392 |
| variant_3151 | RKKKFKKIPPKFLHAAKKF | seqid_2393 |
| variant_3152 | FKKKFKKIPPKFLHAAKKF | seqid_2394 |
| variant_3153 | KWKKFKKIPPKFLHAAKKF | seqid_2395 |
| variant_3154 | RWKKFKKIPPKFLHAAKKF | seqid_2396 |
| variant_3155 | FWKKFKKIPPKFLHAAKKF | seqid_2397 |
| variant_3156 | KKKLLKKIPPKFLHAAKKF | seqid_2398 |
| variant_3157 | RKKLLKKIPPKFLHAAKKF | seqid_2399 |
| variant_3158 | FKKLLKKIPPKFLHAAKKF | seqid_2400 |
| variant_3159 | KWKLLKKIPPKFLHAAKKF | seqid_2401 |
| variant_3160 | RWKLLKKIPPKFLHAAKKF | seqid_2402 |
| variant_3161 | FWKLLKKIPPKFLHAAKKF | seqid_2403 |
| variant_3162 | KKKKLKKIPPKFLHAAKKF | seqid_2404 |
| variant_3163 | RKKKLKKIPPKFLHAAKKF | seqid_2405 |
| variant_3164 | FKKKLKKIPPKFLHAAKKF | seqid_2406 |
| variant_3165 | KWKKLKKIPPKFLHAAKKF | seqid_2407 |
| variant_3166 | RWKKLKKIPPKFLHAAKKF | seqid_2408 |
| variant_3167 | FWKKLKKIPPKFLHAAKKF | seqid_2409 |
| variant_3216 | KKKLFLKIPKFLHAAKKF | seqid_2410 |
| variant_3217 | RKKLFLKIPKFLHAAKKF | seqid_2411 |
| variant_3218 | FKKLFLKIPKFLHAAKKF | seqid_2412 |
| variant_3219 | KWKLFLKIPKFLHAAKKF | seqid_2413 |
| variant_3220 | RWKLFLKIPKFLHAAKKF | seqid_2414 |
| variant_3221 | FWKLFLKIPKFLHAAKKF | seqid_2415 |
| variant_3222 | KKKKFLKIPKFLHAAKKF | seqid_2416 |
| variant_3223 | RKKKFLKIPKFLHAAKKF | seqid_2417 |
| variant_3224 | FKKKFLKIPKFLHAAKKF | seqid_2418 |
| variant_3225 | KWKKFLKIPKFLHAAKKF | seqid_8 |
| variant_3226 | RWKKFLKIPKFLHAAKKF | seqid_2419 |
| variant_3227 | FWKKFLKIPKFLHAAKKF | seqid_2420 |
| variant_3228 | KKKLLLKIPKFLHAAKKF | seqid_2421 |
| variant_3229 | RKKLLLKIPKFLHAAKKF | seqid_2422 |

| | | |
|---|---|---|
| variant_3230 | FKKLLLKIPKFLHAAKKF | seqid_2423 |
| variant_3231 | KWKLLLKIPKFLHAAKKF | seqid_2424 |
| variant_3232 | RWKLLLKIPKFLHAAKKF | seqid_2425 |
| variant_3233 | FWKLLLKIPKFLHAAKKF | seqid_2426 |
| variant_3234 | KKKKLLKIPKFLHAAKKF | seqid_2427 |
| variant_3235 | RKKKLLKIPKFLHAAKKF | seqid_2428 |
| variant_3236 | FKKKLLKIPKFLHAAKKF | seqid_2429 |
| variant_3237 | KWKKLLKIPKFLHAAKKF | seqid_9 |
| variant_3238 | RWKKLLKIPKFLHAAKKF | seqid_2430 |
| variant_3239 | FWKKLLKIPKFLHAAKKF | seqid_2431 |
| variant_3240 | KKKLFKKIPKFLHAAKKF | seqid_2432 |
| variant_3241 | RKKLFKKIPKFLHAAKKF | seqid_2433 |
| variant_3242 | FKKLFKKIPKFLHAAKKF | seqid_5 |
| variant_3243 | KWKLFKKIPKFLHAAKKF | seqid_7 |
| variant_3244 | RWKLFKKIPKFLHAAKKF | seqid_2434 |
| variant_3245 | FWKLFKKIPKFLHAAKKF | seqid_2435 |
| variant_3246 | KKKKFKKIPKFLHAAKKF | seqid_2436 |
| variant_3247 | RKKKFKKIPKFLHAAKKF | seqid_2437 |
| variant_3248 | FKKKFKKIPKFLHAAKKF | seqid_2438 |
| variant_3249 | KWKKFKKIPKFLHAAKKF | seqid_2439 |
| variant_3250 | RWKKFKKIPKFLHAAKKF | seqid_2440 |
| variant_3251 | FWKKFKKIPKFLHAAKKF | seqid_2441 |
| variant_3252 | KKKLLKKIPKFLHAAKKF | seqid_2442 |
| variant_3253 | RKKLLKKIPKFLHAAKKF | seqid_2443 |
| variant_3254 | FKKLLKKIPKFLHAAKKF | seqid_2444 |
| variant_3255 | KWKLLKKIPKFLHAAKKF | seqid_2445 |
| variant_3256 | RWKLLKKIPKFLHAAKKF | seqid_2446 |
| variant_3257 | FWKLLKKIPKFLHAAKKF | seqid_2447 |
| variant_3258 | KKKKLKKIPKFLHAAKKF | seqid_2448 |
| variant_3259 | RKKKLKKIPKFLHAAKKF | seqid_2449 |
| variant_3260 | FKKKLKKIPKFLHAAKKF | seqid_2450 |
| variant_3261 | KWKKLKKIPKFLHAAKKF | seqid_2451 |
| variant_3262 | RWKKLKKIPKFLHAAKKF | seqid_2452 |
| variant_3263 | FWKKLKKIPKFLHAAKKF | seqid_2453 |
| variant_3264 | KKKLFLKIPPPKFKHAAKKF | seqid_2454 |
| variant_3265 | RKKLFLKIPPPKFKHAAKKF | seqid_2455 |
| variant_3266 | FKKLFLKIPPPKFKHAAKKF | seqid_2456 |
| variant_3267 | KWKLFLKIPPPKFKHAAKKF | seqid_2457 |
| variant_3268 | RWKLFLKIPPPKFKHAAKKF | seqid_2458 |
| variant_3269 | FWKLFLKIPPPKFKHAAKKF | seqid_2459 |
| variant_3270 | KKKKFLKIPPPKFKHAAKKF | seqid_2460 |
| variant_3271 | RKKKFLKIPPPKFKHAAKKF | seqid_2461 |
| variant_3272 | FKKKFLKIPPPKFKHAAKKF | seqid_2462 |
| variant_3273 | KWKKFLKIPPPKFKHAAKKF | seqid_2463 |
| variant_3274 | RWKKFLKIPPPKFKHAAKKF | seqid_2464 |
| variant_3275 | FWKKFLKIPPPKFKHAAKKF | seqid_2465 |
| variant_3276 | KKKLLLKIPPPKFKHAAKKF | seqid_2466 |
| variant_3277 | RKKLLLKIPPPKFKHAAKKF | seqid_2467 |
| variant_3278 | FKKLLLKIPPPKFKHAAKKF | seqid_2468 |
| variant_3279 | KWKLLLKIPPPKFKHAAKKF | seqid_2469 |
| variant_3280 | RWKLLLKIPPPKFKHAAKKF | seqid_2470 |
| variant_3281 | FWKLLLKIPPPKFKHAAKKF | seqid_2471 |
| variant_3282 | KKKKLLKIPPPKFKHAAKKF | seqid_2472 |
| variant_3283 | RKKKLLKIPPPKFKHAAKKF | seqid_2473 |
| variant_3284 | FKKKLLKIPPPKFKHAAKKF | seqid_2474 |
| variant_3285 | KWKKLLKIPPPKFKHAAKKF | seqid_2475 |
| variant_3286 | RWKKLLKIPPPKFKHAAKKF | seqid_2476 |
| variant_3287 | FWKKLLKIPPPKFKHAAKKF | seqid_2477 |
| variant_3288 | KKKLFKKIPPPKFKHAAKKF | seqid_2478 |
| variant_3289 | RKKLFKKIPPPKFKHAAKKF | seqid_2479 |
| variant_3290 | FKKLFKKIPPPKFKHAAKKF | seqid_2480 |
| variant_3291 | KWKLFKKIPPPKFKHAAKKF | seqid_2481 |
| variant_3292 | RWKLFKKIPPPKFKHAAKKF | seqid_2482 |
| variant_3293 | FWKLFKKIPPPKFKHAAKKF | seqid_2483 |
| variant_3294 | KKKKFKKIPPPKFKHAAKKF | seqid_2484 |
| variant_3295 | RKKKFKKIPPPKFKHAAKKF | seqid_2485 |
| variant_3296 | FKKKFKKIPPPKFKHAAKKF | seqid_2486 |
| variant_3297 | KWKKFKKIPPPKFKHAAKKF | seqid_2487 |
| variant_3298 | RWKKFKKIPPPKFKHAAKKF | seqid_2488 |
| variant_3299 | FWKKFKKIPPPKFKHAAKKF | seqid_2489 |
| variant_3300 | KKKLLKKIPPPKFKHAAKKF | seqid_2490 |
| variant_3301 | RKKLLKKIPPPKFKHAAKKF | seqid_2491 |
| variant_3302 | FKKLLKKIPPPKFKHAAKKF | seqid_2492 |
| variant_3303 | KWKLLKKIPPPKFKHAAKKF | seqid_2493 |
| variant_3304 | RWKLLKKIPPPKFKHAAKKF | seqid_2494 |
| variant_3305 | FWKLLKKIPPPKFKHAAKKF | seqid_2495 |
| variant_3306 | KKKKLKKIPPPKFKHAAKKF | seqid_2496 |
| variant_3307 | RKKKLKKIPPPKFKHAAKKF | seqid_2497 |
| variant_3308 | FKKKLKKIPPPKFKHAAKKF | seqid_2498 |
| variant_3309 | KWKKLKKIPPPKFKHAAKKF | seqid_2499 |
| variant_3310 | RWKKLKKIPPPKFKHAAKKF | seqid_2500 |

| variant_3311 | FWKKLKKIPPPKFKHAAKKF | seqid_2501 |
| variant_3312 | KKKLFLKIPPKFKHAAKKF | seqid_2502 |
| variant_3313 | RKKLFLKIPPKFKHAAKKF | seqid_2503 |
| variant_3314 | FKKLFLKIPPKFKHAAKKF | seqid_2504 |
| variant_3315 | KWKLFLKIPPKFKHAAKKF | seqid_2505 |
| variant_3316 | RWKLFLKIPPKFKHAAKKF | seqid_2506 |
| variant_3317 | FWKLFLKIPPKFKHAAKKF | seqid_2507 |
| variant_3318 | KKKKFLKIPPKFKHAAKKF | seqid_2508 |
| variant_3319 | RKKKFLKIPPKFKHAAKKF | seqid_2509 |
| variant_3320 | FKKKFLKIPPKFKHAAKKF | seqid_2510 |
| variant_3321 | KWKKFLKIPPKFKHAAKKF | seqid_2511 |
| variant_3322 | RWKKFLKIPPKFKHAAKKF | seqid_2512 |
| variant_3323 | FWKKFLKIPPKFKHAAKKF | seqid_2513 |
| variant_3324 | KKKLLLKIPPKFKHAAKKF | seqid_2514 |
| variant_3325 | RKKLLLKIPPKFKHAAKKF | seqid_2515 |
| variant_3326 | FKKLLLKIPPKFKHAAKKF | seqid_2516 |
| variant_3327 | KWKLLLKIPPKFKHAAKKF | seqid_2517 |
| variant_3328 | RWKLLLKIPPKFKHAAKKF | seqid_2518 |
| variant_3329 | FWKLLLKIPPKFKHAAKKF | seqid_2519 |
| variant_3330 | KKKKLLKIPPKFKHAAKKF | seqid_2520 |
| variant_3331 | RKKKLLKIPPKFKHAAKKF | seqid_2521 |
| variant_3332 | FKKKLLKIPPKFKHAAKKF | seqid_2522 |
| variant_3333 | KWKKLLKIPPKFKHAAKKF | seqid_2523 |
| variant_3334 | RWKKLLKIPPKFKHAAKKF | seqid_2524 |
| variant_3335 | FWKKLLKIPPKFKHAAKKF | seqid_2525 |
| variant_3336 | KKKLFKKIPPKFKHAAKKF | seqid_2526 |
| variant_3337 | RKKLFKKIPPKFKHAAKKF | seqid_2527 |
| variant_3338 | FKKLFKKIPPKFKHAAKKF | seqid_2528 |
| variant_3339 | KWKLFKKIPPKFKHAAKKF | seqid_2529 |
| variant_3340 | RWKLFKKIPPKFKHAAKKF | seqid_2530 |
| variant_3341 | FWKLFKKIPPKFKHAAKKF | seqid_2531 |
| variant_3342 | KKKKFKKIPPKFKHAAKKF | seqid_2532 |
| variant_3343 | RKKKFKKIPPKFKHAAKKF | seqid_2533 |
| variant_3344 | FKKKFKKIPPKFKHAAKKF | seqid_2534 |
| variant_3345 | KWKKFKKIPPKFKHAAKKF | seqid_2535 |
| variant_3346 | RWKKFKKIPPKFKHAAKKF | seqid_2536 |
| variant_3347 | FWKKFKKIPPKFKHAAKKF | seqid_2537 |
| variant_3348 | KKKLLKKIPPKFKHAAKKF | seqid_2538 |
| variant_3349 | RKKLLKKIPPKFKHAAKKF | seqid_2539 |
| variant_3350 | FKKLLKKIPPKFKHAAKKF | seqid_2540 |
| variant_3351 | KWKLLKKIPPKFKHAAKKF | seqid_2541 |
| variant_3352 | RWKLLKKIPPKFKHAAKKF | seqid_2542 |
| variant_3353 | FWKLLKKIPPKFKHAAKKF | seqid_2543 |
| variant_3354 | KKKKLKKIPPKFKHAAKKF | seqid_2544 |
| variant_3355 | RKKKLKKIPPKFKHAAKKF | seqid_2545 |
| variant_3356 | FKKKLKKIPPKFKHAAKKF | seqid_2546 |
| variant_3357 | KWKKLKKIPPKFKHAAKKF | seqid_2547 |
| variant_3358 | RWKKLKKIPPKFKHAAKKF | seqid_2548 |
| variant_3359 | FWKKLKKIPPKFKHAAKKF | seqid_2549 |
| variant_3408 | KKKLFLKIPKFKHAAKKF | seqid_2550 |
| variant_3409 | RKKLFLKIPKFKHAAKKF | seqid_2551 |
| variant_3410 | FKKLFLKIPKFKHAAKKF | seqid_2552 |
| variant_3411 | KWKLFLKIPKFKHAAKKF | seqid_2553 |
| variant_3412 | RWKLFLKIPKFKHAAKKF | seqid_2554 |
| variant_3413 | FWKLFLKIPKFKHAAKKF | seqid_2555 |
| variant_3414 | KKKKFLKIPKFKHAAKKF | seqid_2556 |
| variant_3415 | RKKKFLKIPKFKHAAKKF | seqid_2557 |
| variant_3416 | FKKKFLKIPKFKHAAKKF | seqid_2558 |
| variant_3417 | KWKKFLKIPKFKHAAKKF | seqid_2559 |
| variant_3418 | RWKKFLKIPKFKHAAKKF | seqid_2560 |
| variant_3419 | FWKKFLKIPKFKHAAKKF | seqid_2561 |
| variant_3420 | KKKLLLKIPKFKHAAKKF | seqid_2562 |
| variant_3421 | RKKLLLKIPKFKHAAKKF | seqid_2563 |
| variant_3422 | FKKLLLKIPKFKHAAKKF | seqid_2564 |
| variant_3423 | KWKLLLKIPKFKHAAKKF | seqid_2565 |
| variant_3424 | RWKLLLKIPKFKHAAKKF | seqid_2566 |
| variant_3425 | FWKLLLKIPKFKHAAKKF | seqid_2567 |
| variant_3426 | KKKKLLKIPKFKHAAKKF | seqid_2568 |
| variant_3427 | RKKKLLKIPKFKHAAKKF | seqid_2569 |
| variant_3428 | FKKKLLKIPKFKHAAKKF | seqid_2570 |
| variant_3429 | KWKKLLKIPKFKHAAKKF | seqid_2571 |
| variant_3430 | RWKKLLKIPKFKHAAKKF | seqid_2572 |
| variant_3431 | FWKKLLKIPKFKHAAKKF | seqid_2573 |
| variant_3432 | KKKLFKKIPKFKHAAKKF | seqid_2574 |
| variant_3433 | RKKLFKKIPKFKHAAKKF | seqid_2575 |
| variant_3434 | FKKLFKKIPKFKHAAKKF | seqid_2576 |
| variant_3435 | KWKLFKKIPKFKHAAKKF | seqid_2577 |
| variant_3436 | RWKLFKKIPKFKHAAKKF | seqid_2578 |
| variant_3437 | FWKLFKKIPKFKHAAKKF | seqid_2579 |
| variant_3438 | KKKKFKKIPKFKHAAKKF | seqid_2580 |
| variant_3439 | RKKKFKKIPKFKHAAKKF | seqid_2581 |

| | | |
|---|---|---|
| variant_3440 | FKKKFKKIPKFKHAAKKF | seqid_2582 |
| variant_3441 | KWKKFKKIPKFKHAAKKF | seqid_2583 |
| variant_3442 | RWKKFKKIPKFKHAAKKF | seqid_2584 |
| variant_3443 | FWKKFKKIPKFKHAAKKF | seqid_2585 |
| variant_3444 | KKKLLKKIPKFKHAAKKF | seqid_2586 |
| variant_3445 | RKKLLKKIPKFKHAAKKF | seqid_2587 |
| variant_3446 | FKKLLKKIPKFKHAAKKF | seqid_2588 |
| variant_3447 | KWKLLKKIPKFKHAAKKF | seqid_2589 |
| variant_3448 | RWKLLKKIPKFKHAAKKF | seqid_2590 |
| variant_3449 | FWKLLKKIPKFKHAAKKF | seqid_2591 |
| variant_3450 | KKKKLKKIPKFKHAAKKF | seqid_2592 |
| variant_3451 | RKKKLKKIPKFKHAAKKF | seqid_2593 |
| variant_3452 | FKKKLKKIPKFKHAAKKF | seqid_2594 |
| variant_3453 | KWKKLKKIPKFKHAAKKF | seqid_2595 |
| variant_3454 | RWKKLKKIPKFKHAAKKF | seqid_2596 |
| variant_3455 | FWKKLKKIPKFKHAAKKF | seqid_2597 |
| variant_3456 | KKKLFLKIPPPKFLKAAKKF | seqid_2598 |
| variant_3457 | RKKLFLKIPPPKFLKAAKKF | seqid_2599 |
| variant_3458 | FKKLFLKIPPPKFLKAAKKF | seqid_2600 |
| variant_3459 | KWKLFLKIPPPKFLKAAKKF | seqid_2601 |
| variant_3460 | RWKLFLKIPPPKFLKAAKKF | seqid_2602 |
| variant_3461 | FWKLFLKIPPPKFLKAAKKF | seqid_2603 |
| variant_3462 | KKKKFLKIPPPKFLKAAKKF | seqid_2604 |
| variant_3463 | RKKKFLKIPPPKFLKAAKKF | seqid_2605 |
| variant_3464 | FKKKFLKIPPPKFLKAAKKF | seqid_2606 |
| variant_3465 | KWKKFLKIPPPKFLKAAKKF | seqid_2607 |
| variant_3466 | RWKKFLKIPPPKFLKAAKKF | seqid_2608 |
| variant_3467 | FWKKFLKIPPPKFLKAAKKF | seqid_2609 |
| variant_3468 | KKKLLLKIPPPKFLKAAKKF | seqid_2610 |
| variant_3469 | RKKLLLKIPPPKFLKAAKKF | seqid_2611 |
| variant_3470 | FKKLLLKIPPPKFLKAAKKF | seqid_2612 |
| variant_3471 | KWKLLLKIPPPKFLKAAKKF | seqid_2613 |
| variant_3472 | RWKLLLKIPPPKFLKAAKKF | seqid_2614 |
| variant_3473 | FWKLLLKIPPPKFLKAAKKF | seqid_2615 |
| variant_3474 | KKKKLLKIPPPKFLKAAKKF | seqid_2616 |
| variant_3475 | RKKKLLKIPPPKFLKAAKKF | seqid_2617 |
| variant_3476 | FKKKLLKIPPPKFLKAAKKF | seqid_2618 |
| variant_3477 | KWKKLLKIPPPKFLKAAKKF | seqid_2619 |
| variant_3478 | RWKKLLKIPPPKFLKAAKKF | seqid_2620 |
| variant_3479 | FWKKLLKIPPPKFLKAAKKF | seqid_2621 |
| variant_3480 | KKKLFKKIPPPKFLKAAKKF | seqid_2622 |
| variant_3481 | RKKLFKKIPPPKFLKAAKKF | seqid_2623 |
| variant_3482 | FKKLFKKIPPPKFLKAAKKF | seqid_2624 |
| variant_3483 | KWKLFKKIPPPKFLKAAKKF | seqid_2625 |
| variant_3484 | RWKLFKKIPPPKFLKAAKKF | seqid_2626 |
| variant_3485 | FWKLFKKIPPPKFLKAAKKF | seqid_2627 |
| variant_3486 | KKKKFKKIPPPKFLKAAKKF | seqid_2628 |
| variant_3487 | RKKKFKKIPPPKFLKAAKKF | seqid_2629 |
| variant_3488 | FKKKFKKIPPPKFLKAAKKF | seqid_2630 |
| variant_3489 | KWKKFKKIPPPKFLKAAKKF | seqid_2631 |
| variant_3490 | RWKKFKKIPPPKFLKAAKKF | seqid_2632 |
| variant_3491 | FWKKFKKIPPPKFLKAAKKF | seqid_2633 |
| variant_3492 | KKKLLKKIPPPKFLKAAKKF | seqid_2634 |
| variant_3493 | RKKLLKKIPPPKFLKAAKKF | seqid_2635 |
| variant_3494 | FKKLLKKIPPPKFLKAAKKF | seqid_2636 |
| variant_3495 | KWKLLKKIPPPKFLKAAKKF | seqid_2637 |
| variant_3496 | RWKLLKKIPPPKFLKAAKKF | seqid_2638 |
| variant_3497 | FWKLLKKIPPPKFLKAAKKF | seqid_2639 |
| variant_3498 | KKKKLKKIPPPKFLKAAKKF | seqid_2640 |
| variant_3499 | RKKKLKKIPPPKFLKAAKKF | seqid_2641 |
| variant_3500 | FKKKLKKIPPPKFLKAAKKF | seqid_2642 |
| variant_3501 | KWKKLKKIPPPKFLKAAKKF | seqid_2643 |
| variant_3502 | RWKKLKKIPPPKFLKAAKKF | seqid_2644 |
| variant_3503 | FWKKLKKIPPPKFLKAAKKF | seqid_2645 |
| variant_3504 | KKKLFLKIPPKFLKAAKKF | seqid_2646 |
| variant_3505 | RKKLFLKIPPKFLKAAKKF | seqid_2647 |
| variant_3506 | FKKLFLKIPPKFLKAAKKF | seqid_2648 |
| variant_3507 | KWKLFLKIPPKFLKAAKKF | seqid_2649 |
| variant_3508 | RWKLFLKIPPKFLKAAKKF | seqid_2650 |
| variant_3509 | FWKLFLKIPPKFLKAAKKF | seqid_2651 |
| variant_3510 | KKKKFLKIPPKFLKAAKKF | seqid_2652 |
| variant_3511 | RKKKFLKIPPKFLKAAKKF | seqid_2653 |
| variant_3512 | FKKKFLKIPPKFLKAAKKF | seqid_2654 |
| variant_3513 | KWKKFLKIPPKFLKAAKKF | seqid_2655 |
| variant_3514 | RWKKFLKIPPKFLKAAKKF | seqid_2656 |
| variant_3515 | FWKKFLKIPPKFLKAAKKF | seqid_2657 |
| variant_3516 | KKKLLLKIPPKFLKAAKKF | seqid_2658 |
| variant_3517 | RKKLLLKIPPKFLKAAKKF | seqid_2659 |
| variant_3518 | FKKLLLKIPPKFLKAAKKF | seqid_2660 |
| variant_3519 | KWKLLLKIPPKFLKAAKKF | seqid_2661 |
| variant_3520 | RWKLLLKIPPKFLKAAKKF | seqid_2662 |

| | | |
|---|---|---|
| variant_3521 | FWKLLLKIPPKFLKAAKKF | seqid_2663 |
| variant_3522 | KKKKLLKIPPKFLKAAKKF | seqid_2664 |
| variant_3523 | RKKKLLKIPPKFLKAAKKF | seqid_2665 |
| variant_3524 | FKKKLLKIPPKFLKAAKKF | seqid_2666 |
| variant_3525 | KWKKLLKIPPKFLKAAKKF | seqid_2667 |
| variant_3526 | RWKKLLKIPPKFLKAAKKF | seqid_2668 |
| variant_3527 | FWKKLLKIPPKFLKAAKKF | seqid_2669 |
| variant_3528 | KKKLFKKIPPKFLKAAKKF | seqid_2670 |
| variant_3529 | RKKLFKKIPPKFLKAAKKF | seqid_2671 |
| variant_3530 | FKKLFKKIPPKFLKAAKKF | seqid_2672 |
| variant_3531 | KWKLFKKIPPKFLKAAKKF | seqid_2673 |
| variant_3532 | RWKLFKKIPPKFLKAAKKF | seqid_2674 |
| variant_3533 | FWKLFKKIPPKFLKAAKKF | seqid_2675 |
| variant_3534 | KKKKFKKIPPKFLKAAKKF | seqid_2676 |
| variant_3535 | RKKKFKKIPPKFLKAAKKF | seqid_2677 |
| variant_3536 | FKKKFKKIPPKFLKAAKKF | seqid_2678 |
| variant_3537 | KWKKFKKIPPKFLKAAKKF | seqid_2679 |
| variant_3538 | RWKKFKKIPPKFLKAAKKF | seqid_2680 |
| variant_3539 | FWKKFKKIPPKFLKAAKKF | seqid_2681 |
| variant_3540 | KKKLLKKIPPKFLKAAKKF | seqid_2682 |
| variant_3541 | RKKLLKKIPPKFLKAAKKF | seqid_2683 |
| variant_3542 | FKKLLKKIPPKFLKAAKKF | seqid_2684 |
| variant_3543 | KWKLLKKIPPKFLKAAKKF | seqid_2685 |
| variant_3544 | RWKLLKKIPPKFLKAAKKF | seqid_2686 |
| variant_3545 | FWKLLKKIPPKFLKAAKKF | seqid_2687 |
| variant_3546 | KKKKLKKIPPKFLKAAKKF | seqid_2688 |
| variant_3547 | RKKKLKKIPPKFLKAAKKF | seqid_2689 |
| variant_3548 | FKKKLKKIPPKFLKAAKKF | seqid_2690 |
| variant_3549 | KWKKLKKIPPKFLKAAKKF | seqid_2691 |
| variant_3550 | RWKKLKKIPPKFLKAAKKF | seqid_2692 |
| variant_3551 | FWKKLKKIPPKFLKAAKKF | seqid_2693 |
| variant_3600 | KKKLFLKIPKFLKAAKKF | seqid_2694 |
| variant_3601 | RKKLFLKIPKFLKAAKKF | seqid_2695 |
| variant_3602 | FKKLFLKIPKFLKAAKKF | seqid_2696 |
| variant_3603 | KWKLFLKIPKFLKAAKKF | seqid_2697 |
| variant_3604 | RWKLFLKIPKFLKAAKKF | seqid_2698 |
| variant_3605 | FWKLFLKIPKFLKAAKKF | seqid_2699 |
| variant_3606 | KKKKFLKIPKFLKAAKKF | seqid_2700 |
| variant_3607 | RKKKFLKIPKFLKAAKKF | seqid_2701 |
| variant_3608 | FKKKFLKIPKFLKAAKKF | seqid_2702 |
| variant_3609 | KWKKFLKIPKFLKAAKKF | seqid_2703 |
| variant_3610 | RWKKFLKIPKFLKAAKKF | seqid_2704 |
| variant_3611 | FWKKFLKIPKFLKAAKKF | seqid_2705 |
| variant_3612 | KKKLLLKIPKFLKAAKKF | seqid_2706 |
| variant_3613 | RKKLLLKIPKFLKAAKKF | seqid_2707 |
| variant_3614 | FKKLLLKIPKFLKAAKKF | seqid_2708 |
| variant_3615 | KWKLLLKIPKFLKAAKKF | seqid_2709 |
| variant_3616 | RWKLLLKIPKFLKAAKKF | seqid_2710 |
| variant_3617 | FWKLLLKIPKFLKAAKKF | seqid_2711 |
| variant_3618 | KKKKLLKIPKFLKAAKKF | seqid_2712 |
| variant_3619 | RKKKLLKIPKFLKAAKKF | seqid_2713 |
| variant_3620 | FKKKLLKIPKFLKAAKKF | seqid_2714 |
| variant_3621 | KWKKLLKIPKFLKAAKKF | seqid_2715 |
| variant_3622 | RWKKLLKIPKFLKAAKKF | seqid_2716 |
| variant_3623 | FWKKLLKIPKFLKAAKKF | seqid_2717 |
| variant_3624 | KKKLFKKIPKFLKAAKKF | seqid_2718 |
| variant_3625 | RKKLFKKIPKFLKAAKKF | seqid_2719 |
| variant_3626 | FKKLFKKIPKFLKAAKKF | seqid_2720 |
| variant_3627 | KWKLFKKIPKFLKAAKKF | seqid_2721 |
| variant_3628 | RWKLFKKIPKFLKAAKKF | seqid_2722 |
| variant_3629 | FWKLFKKIPKFLKAAKKF | seqid_2723 |
| variant_3630 | KKKKFKKIPKFLKAAKKF | seqid_2724 |
| variant_3631 | RKKKFKKIPKFLKAAKKF | seqid_2725 |
| variant_3632 | FKKKFKKIPKFLKAAKKF | seqid_2726 |
| variant_3633 | KWKKFKKIPKFLKAAKKF | seqid_2727 |
| variant_3634 | RWKKFKKIPKFLKAAKKF | seqid_2728 |
| variant_3635 | FWKKFKKIPKFLKAAKKF | seqid_2729 |
| variant_3636 | KKKLLKKIPKFLKAAKKF | seqid_2730 |
| variant_3637 | RKKLLKKIPKFLKAAKKF | seqid_2731 |
| variant_3638 | FKKLLKKIPKFLKAAKKF | seqid_2732 |
| variant_3639 | KWKLLKKIPKFLKAAKKF | seqid_2733 |
| variant_3640 | RWKLLKKIPKFLKAAKKF | seqid_2734 |
| variant_3641 | FWKLLKKIPKFLKAAKKF | seqid_2735 |
| variant_3642 | KKKKLKKIPKFLKAAKKF | seqid_2736 |
| variant_3643 | RKKKLKKIPKFLKAAKKF | seqid_2737 |
| variant_3644 | FKKKLKKIPKFLKAAKKF | seqid_2738 |
| variant_3645 | KWKKLKKIPKFLKAAKKF | seqid_2739 |
| variant_3646 | RWKKLKKIPKFLKAAKKF | seqid_2740 |
| variant_3647 | FWKKLKKIPKFLKAAKKF | seqid_2741 |
| variant_3648 | KKKLFLKIPPPKFKKAAKKF | seqid_2742 |
| variant_3649 | RKKLFLKIPPPKFKKAAKKF | seqid_2743 |

| | | |
|---|---|---|
| variant_3650 | FKKLFLKIPPPKFKKAAKKF | seqid_2744 |
| variant_3651 | KWKLFLKIPPPKFKKAAKKF | seqid_2745 |
| variant_3652 | RWKLFLKIPPPKFKKAAKKF | seqid_2746 |
| variant_3653 | FWKLFLKIPPPKFKKAAKKF | seqid_2747 |
| variant_3654 | KKKKFLKIPPPKFKKAAKKF | seqid_2748 |
| variant_3655 | RKKKFLKIPPPKFKKAAKKF | seqid_2749 |
| variant_3656 | FKKKFLKIPPPKFKKAAKKF | seqid_2750 |
| variant_3657 | KWKKFLKIPPPKFKKAAKKF | seqid_2751 |
| variant_3658 | RWKKFLKIPPPKFKKAAKKF | seqid_2752 |
| variant_3659 | FWKKFLKIPPPKFKKAAKKF | seqid_2753 |
| variant_3660 | KKKLLLKIPPPKFKKAAKKF | seqid_2754 |
| variant_3661 | RKKLLLKIPPPKFKKAAKKF | seqid_2755 |
| variant_3662 | FKKLLLKIPPPKFKKAAKKF | seqid_2756 |
| variant_3663 | KWKLLLKIPPPKFKKAAKKF | seqid_2757 |
| variant_3664 | RWKLLLKIPPPKFKKAAKKF | seqid_2758 |
| variant_3665 | FWKLLLKIPPPKFKKAAKKF | seqid_2759 |
| variant_3666 | KKKKLLKIPPPKFKKAAKKF | seqid_2760 |
| variant_3667 | RKKKLLKIPPPKFKKAAKKF | seqid_2761 |
| variant_3668 | FKKKLLKIPPPKFKKAAKKF | seqid_2762 |
| variant_3669 | KWKKLLKIPPPKFKKAAKKF | seqid_2763 |
| variant_3670 | RWKKLLKIPPPKFKKAAKKF | seqid_2764 |
| variant_3671 | FWKKLLKIPPPKFKKAAKKF | seqid_2765 |
| variant_3672 | KKKLFKKIPPPKFKKAAKKF | seqid_2766 |
| variant_3673 | RKKLFKKIPPPKFKKAAKKF | seqid_2767 |
| variant_3674 | FKKLFKKIPPPKFKKAAKKF | seqid_2768 |
| variant_3675 | KWKLFKKIPPPKFKKAAKKF | seqid_2769 |
| variant_3676 | RWKLFKKIPPPKFKKAAKKF | seqid_2770 |
| variant_3677 | FWKLFKKIPPPKFKKAAKKF | seqid_2771 |
| variant_3678 | KKKKFKKIPPPKFKKAAKKF | seqid_2772 |
| variant_3679 | RKKKFKKIPPPKFKKAAKKF | seqid_2773 |
| variant_3680 | FKKKFKKIPPPKFKKAAKKF | seqid_2774 |
| variant_3681 | KWKKFKKIPPPKFKKAAKKF | seqid_2775 |
| variant_3682 | RWKKFKKIPPPKFKKAAKKF | seqid_2776 |
| variant_3683 | FWKKFKKIPPPKFKKAAKKF | seqid_2777 |
| variant_3684 | KKKLLKKIPPPKFKKAAKKF | seqid_2778 |
| variant_3685 | RKKLLKKIPPPKFKKAAKKF | seqid_2779 |
| variant_3686 | FKKLLKKIPPPKFKKAAKKF | seqid_2780 |
| variant_3687 | KWKLLKKIPPPKFKKAAKKF | seqid_2781 |
| variant_3688 | RWKLLKKIPPPKFKKAAKKF | seqid_2782 |
| variant_3689 | FWKLLKKIPPPKFKKAAKKF | seqid_2783 |
| variant_3690 | KKKKLKKIPPPKFKKAAKKF | seqid_2784 |
| variant_3691 | RKKKLKKIPPPKFKKAAKKF | seqid_2785 |
| variant_3692 | FKKKLKKIPPPKFKKAAKKF | seqid_2786 |
| variant_3693 | KWKKLKKIPPPKFKKAAKKF | seqid_2787 |
| variant_3694 | RWKKLKKIPPPKFKKAAKKF | seqid_2788 |
| variant_3695 | FWKKLKKIPPPKFKKAAKKF | seqid_2789 |
| variant_3696 | KKKLFLKIPPKFKKAAKKF | seqid_2790 |
| variant_3697 | RKKLFLKIPPKFKKAAKKF | seqid_2791 |
| variant_3698 | FKKLFLKIPPKFKKAAKKF | seqid_2792 |
| variant_3699 | KWKLFLKIPPKFKKAAKKF | seqid_2793 |
| variant_3700 | RWKLFLKIPPKFKKAAKKF | seqid_2794 |
| variant_3701 | FWKLFLKIPPKFKKAAKKF | seqid_2795 |
| variant_3702 | KKKKFLKIPPKFKKAAKKF | seqid_2796 |
| variant_3703 | RKKKFLKIPPKFKKAAKKF | seqid_2797 |
| variant_3704 | FKKKFLKIPPKFKKAAKKF | seqid_2798 |
| variant_3705 | KWKKFLKIPPKFKKAAKKF | seqid_2799 |
| variant_3706 | RWKKFLKIPPKFKKAAKKF | seqid_2800 |
| variant_3707 | FWKKFLKIPPKFKKAAKKF | seqid_2801 |
| variant_3708 | KKKLLLKIPPKFKKAAKKF | seqid_2802 |
| variant_3709 | RKKLLLKIPPKFKKAAKKF | seqid_2803 |
| variant_3710 | FKKLLLKIPPKFKKAAKKF | seqid_2804 |
| variant_3711 | KWKLLLKIPPKFKKAAKKF | seqid_2805 |
| variant_3712 | RWKLLLKIPPKFKKAAKKF | seqid_2806 |
| variant_3713 | FWKLLLKIPPKFKKAAKKF | seqid_2807 |
| variant_3714 | KKKKLLKIPPKFKKAAKKF | seqid_2808 |
| variant_3715 | RKKKLLKIPPKFKKAAKKF | seqid_2809 |
| variant_3716 | FKKKLLKIPPKFKKAAKKF | seqid_2810 |
| variant_3717 | KWKKLLKIPPKFKKAAKKF | seqid_2811 |
| variant_3718 | RWKKLLKIPPKFKKAAKKF | seqid_2812 |
| variant_3719 | FWKKLLKIPPKFKKAAKKF | seqid_2813 |
| variant_3720 | KKKLFKKIPPKFKKAAKKF | seqid_2814 |
| variant_3721 | RKKLFKKIPPKFKKAAKKF | seqid_2815 |
| variant_3722 | FKKLFKKIPPKFKKAAKKF | seqid_2816 |
| variant_3723 | KWKLFKKIPPKFKKAAKKF | seqid_2817 |
| variant_3724 | RWKLFKKIPPKFKKAAKKF | seqid_2818 |
| variant_3725 | FWKLFKKIPPKFKKAAKKF | seqid_2819 |
| variant_3726 | KKKKFKKIPPKFKKAAKKF | seqid_2820 |
| variant_3727 | RKKKFKKIPPKFKKAAKKF | seqid_2821 |
| variant_3728 | FKKKFKKIPPKFKKAAKKF | seqid_2822 |
| variant_3729 | KWKKFKKIPPKFKKAAKKF | seqid_2823 |
| variant_3730 | RWKKFKKIPPKFKKAAKKF | seqid_2824 |

| | | |
|---|---|---|
| variant_3731 | FWKKFKKIPPKFKKAAKKF | seqid_2825 |
| variant_3732 | KKKLLKKIPPKFKKAAKKF | seqid_2826 |
| variant_3733 | RKKLLKKIPPKFKKAAKKF | seqid_2827 |
| variant_3734 | FKKLLKKIPPKFKKAAKKF | seqid_2828 |
| variant_3735 | KWKLLKKIPPKFKKAAKKF | seqid_2829 |
| variant_3736 | RWKLLKKIPPKFKKAAKKF | seqid_2830 |
| variant_3737 | FWKLLKKIPPKFKKAAKKF | seqid_2831 |
| variant_3738 | KKKKLKKIPPKFKKAAKKF | seqid_2832 |
| variant_3739 | RKKKLKKIPPKFKKAAKKF | seqid_2833 |
| variant_3740 | FKKKLKKIPPKFKKAAKKF | seqid_2834 |
| variant_3741 | KWKKLKKIPPKFKKAAKKF | seqid_2835 |
| variant_3742 | RWKKLKKIPPKFKKAAKKF | seqid_2836 |
| variant_3743 | FWKKLKKIPPKFKKAAKKF | seqid_2837 |
| variant_3792 | KKKLFLKIPKFKKAAKKF | seqid_2838 |
| variant_3793 | RKKLFLKIPKFKKAAKKF | seqid_2839 |
| variant_3794 | FKKLFLKIPKFKKAAKKF | seqid_2840 |
| variant_3795 | KWKLFLKIPKFKKAAKKF | seqid_2841 |
| variant_3796 | RWKLFLKIPKFKKAAKKF | seqid_2842 |
| variant_3797 | FWKLFLKIPKFKKAAKKF | seqid_2843 |
| variant_3798 | KKKKFLKIPKFKKAAKKF | seqid_2844 |
| variant_3799 | RKKKFLKIPKFKKAAKKF | seqid_2845 |
| variant_3800 | FKKKFLKIPKFKKAAKKF | seqid_2846 |
| variant_3801 | KWKKFLKIPKFKKAAKKF | seqid_2847 |
| variant_3802 | RWKKFLKIPKFKKAAKKF | seqid_2848 |
| variant_3803 | FWKKFLKIPKFKKAAKKF | seqid_2849 |
| variant_3804 | KKKLLLKIPKFKKAAKKF | seqid_2850 |
| variant_3805 | RKKLLLKIPKFKKAAKKF | seqid_2851 |
| variant_3806 | FKKLLLKIPKFKKAAKKF | seqid_2852 |
| variant_3807 | KWKLLLKIPKFKKAAKKF | seqid_2853 |
| variant_3808 | RWKLLLKIPKFKKAAKKF | seqid_2854 |
| variant_3809 | FWKLLLKIPKFKKAAKKF | seqid_2855 |
| variant_3810 | KKKKLLKIPKFKKAAKKF | seqid_2856 |
| variant_3811 | RKKKLLKIPKFKKAAKKF | seqid_2857 |
| variant_3812 | FKKKLLKIPKFKKAAKKF | seqid_2858 |
| variant_3813 | KWKKLLKIPKFKKAAKKF | seqid_2859 |
| variant_3814 | RWKKLLKIPKFKKAAKKF | seqid_2860 |
| variant_3815 | FWKKLLKIPKFKKAAKKF | seqid_2861 |
| variant_3816 | KKKLFKKIPKFKKAAKKF | seqid_2862 |
| variant_3817 | RKKLFKKIPKFKKAAKKF | seqid_2863 |
| variant_3818 | FKKLFKKIPKFKKAAKKF | seqid_2864 |
| variant_3819 | KWKLFKKIPKFKKAAKKF | seqid_2865 |
| variant_3820 | RWKLFKKIPKFKKAAKKF | seqid_2866 |
| variant_3821 | FWKLFKKIPKFKKAAKKF | seqid_2867 |
| variant_3822 | KKKKFKKIPKFKKAAKKF | seqid_2868 |
| variant_3823 | RKKKFKKIPKFKKAAKKF | seqid_2869 |
| variant_3824 | FKKKFKKIPKFKKAAKKF | seqid_2870 |
| variant_3825 | KWKKFKKIPKFKKAAKKF | seqid_2871 |
| variant_3826 | RWKKFKKIPKFKKAAKKF | seqid_2872 |
| variant_3827 | FWKKFKKIPKFKKAAKKF | seqid_2873 |
| variant_3828 | KKKLLKKIPKFKKAAKKF | seqid_2874 |
| variant_3829 | RKKLLKKIPKFKKAAKKF | seqid_2875 |
| variant_3830 | FKKLLKKIPKFKKAAKKF | seqid_2876 |
| variant_3831 | KWKLLKKIPKFKKAAKKF | seqid_2877 |
| variant_3832 | RWKLLKKIPKFKKAAKKF | seqid_2878 |
| variant_3833 | FWKLLKKIPKFKKAAKKF | seqid_2879 |
| variant_3834 | KKKKLKKIPKFKKAAKKF | seqid_2880 |
| variant_3835 | RKKKLKKIPKFKKAAKKF | seqid_2881 |
| variant_3836 | FKKKLKKIPKFKKAAKKF | seqid_2882 |
| variant_3837 | KWKKLKKIPKFKKAAKKF | seqid_2883 |
| variant_3838 | RWKKLKKIPKFKKAAKKF | seqid_2884 |
| variant_3839 | FWKKLKKIPKFKKAAKKF | seqid_2885 |
| variant_3840 | KKKLFLKIPPPKFLHLAKKF | seqid_2886 |
| variant_3841 | RKKLFLKIPPPKFLHLAKKF | seqid_2887 |
| variant_3842 | FKKLFLKIPPPKFLHLAKKF | seqid_2888 |
| variant_3843 | KWKLFLKIPPPKFLHLAKKF | seqid_2889 |
| variant_3844 | RWKLFLKIPPPKFLHLAKKF | seqid_2890 |
| variant_3845 | FWKLFLKIPPPKFLHLAKKF | seqid_2891 |
| variant_3846 | KKKKFLKIPPPKFLHLAKKF | seqid_2892 |
| variant_3847 | RKKKFLKIPPPKFLHLAKKF | seqid_2893 |
| variant_3848 | FKKKFLKIPPPKFLHLAKKF | seqid_2894 |
| variant_3849 | KWKKFLKIPPPKFLHLAKKF | seqid_2895 |
| variant_3850 | RWKKFLKIPPPKFLHLAKKF | seqid_2896 |
| variant_3851 | FWKKFLKIPPPKFLHLAKKF | seqid_2897 |
| variant_3852 | KKKLLLKIPPPKFLHLAKKF | seqid_2898 |
| variant_3853 | RKKLLLKIPPPKFLHLAKKF | seqid_2899 |
| variant_3854 | FKKLLLKIPPPKFLHLAKKF | seqid_2900 |
| variant_3855 | KWKLLLKIPPPKFLHLAKKF | seqid_2901 |
| variant_3856 | RWKLLLKIPPPKFLHLAKKF | seqid_2902 |
| variant_3857 | FWKLLLKIPPPKFLHLAKKF | seqid_2903 |
| variant_3858 | KKKKLLKIPPPKFLHLAKKF | seqid_2904 |
| variant_3859 | RKKKLLKIPPPKFLHLAKKF | seqid_2905 |

| | | |
|---|---|---|
| variant_3860 | FKKKLLKIPPPKFLHLAKKF | seqid_2906 |
| variant_3861 | KWKKLLKIPPPKFLHLAKKF | seqid_2907 |
| variant_3862 | RWKKLLKIPPPKFLHLAKKF | seqid_2908 |
| variant_3863 | FWKKLLKIPPPKFLHLAKKF | seqid_2909 |
| variant_3864 | KKKLFKKIPPPKFLHLAKKF | seqid_2910 |
| variant_3865 | RKKLFKKIPPPKFLHLAKKF | seqid_2911 |
| variant_3866 | FKKLFKKIPPPKFLHLAKKF | seqid_2912 |
| variant_3867 | KWKLFKKIPPPKFLHLAKKF | seqid_2913 |
| variant_3868 | RWKLFKKIPPPKFLHLAKKF | seqid_2914 |
| variant_3869 | FWKLFKKIPPPKFLHLAKKF | seqid_2915 |
| variant_3870 | KKKKFKKIPPPKFLHLAKKF | seqid_2916 |
| variant_3871 | RKKKFKKIPPPKFLHLAKKF | seqid_2917 |
| variant_3872 | FKKKFKKIPPPKFLHLAKKF | seqid_2918 |
| variant_3873 | KWKKFKKIPPPKFLHLAKKF | seqid_2919 |
| variant_3874 | RWKKFKKIPPPKFLHLAKKF | seqid_2920 |
| variant_3875 | FWKKFKKIPPPKFLHLAKKF | seqid_2921 |
| variant_3876 | KKKLLKKIPPPKFLHLAKKF | seqid_2922 |
| variant_3877 | RKKLLKKIPPPKFLHLAKKF | seqid_2923 |
| variant_3878 | FKKLLKKIPPPKFLHLAKKF | seqid_2924 |
| variant_3879 | KWKLLKKIPPPKFLHLAKKF | seqid_2925 |
| variant_3880 | RWKLLKKIPPPKFLHLAKKF | seqid_2926 |
| variant_3881 | FWKLLKKIPPPKFLHLAKKF | seqid_2927 |
| variant_3882 | KKKKLKKIPPPKFLHLAKKF | seqid_2928 |
| variant_3883 | RKKKLKKIPPPKFLHLAKKF | seqid_2929 |
| variant_3884 | FKKKLKKIPPPKFLHLAKKF | seqid_2930 |
| variant_3885 | KWKKLKKIPPPKFLHLAKKF | seqid_2931 |
| variant_3886 | RWKKLKKIPPPKFLHLAKKF | seqid_2932 |
| variant_3887 | FWKKLKKIPPPKFLHLAKKF | seqid_2933 |
| variant_3888 | KKKLFLKIPPPKFLHLAKKF | seqid_2934 |
| variant_3889 | RKKLFLKIPPPKFLHLAKKF | seqid_2935 |
| variant_3890 | FKKLFLKIPPPKFLHLAKKF | seqid_2936 |
| variant_3891 | KWKLFLKIPPPKFLHLAKKF | seqid_2937 |
| variant_3892 | RWKLFLKIPPPKFLHLAKKF | seqid_2938 |
| variant_3893 | FWKLFLKIPPPKFLHLAKKF | seqid_2939 |
| variant_3894 | KKKKFLKIPPPKFLHLAKKF | seqid_2940 |
| variant_3895 | RKKKFLKIPPPKFLHLAKKF | seqid_2941 |
| variant_3896 | FKKKFLKIPPPKFLHLAKKF | seqid_2942 |
| variant_3897 | KWKKFLKIPPPKFLHLAKKF | seqid_2943 |
| variant_3898 | RWKKFLKIPPPKFLHLAKKF | seqid_2944 |
| variant_3899 | FWKKFLKIPPPKFLHLAKKF | seqid_2945 |
| variant_3900 | KKKLLLKIPPKFLHLAKKF | seqid_2946 |
| variant_3901 | RKKLLLKIPPKFLHLAKKF | seqid_2947 |
| variant_3902 | FKKLLLKIPPKFLHLAKKF | seqid_2948 |
| variant_3903 | KWKLLLKIPPKFLHLAKKF | seqid_2949 |
| variant_3904 | RWKLLLKIPPKFLHLAKKF | seqid_2950 |
| variant_3905 | FWKLLLKIPPKFLHLAKKF | seqid_2951 |
| variant_3906 | KKKKLLKIPPKFLHLAKKF | seqid_2952 |
| variant_3907 | RKKKLLKIPPKFLHLAKKF | seqid_2953 |
| variant_3908 | FKKKLLKIPPKFLHLAKKF | seqid_2954 |
| variant_3909 | KWKKLLKIPPKFLHLAKKF | seqid_2955 |
| variant_3910 | RWKKLLKIPPKFLHLAKKF | seqid_2956 |
| variant_3911 | FWKKLLKIPPKFLHLAKKF | seqid_2957 |
| variant_3912 | KKKLFKKIPPKFLHLAKKF | seqid_2958 |
| variant_3913 | RKKLFKKIPPKFLHLAKKF | seqid_2959 |
| variant_3914 | FKKLFKKIPPKFLHLAKKF | seqid_2960 |
| variant_3915 | KWKLFKKIPPKFLHLAKKF | seqid_2961 |
| variant_3916 | RWKLFKKIPPKFLHLAKKF | seqid_2962 |
| variant_3917 | FWKLFKKIPPKFLHLAKKF | seqid_2963 |
| variant_3918 | KKKKFKKIPPKFLHLAKKF | seqid_2964 |
| variant_3919 | RKKKFKKIPPKFLHLAKKF | seqid_2965 |
| variant_3920 | FKKKFKKIPPKFLHLAKKF | seqid_2966 |
| variant_3921 | KWKKFKKIPPKFLHLAKKF | seqid_2967 |
| variant_3922 | RWKKFKKIPPKFLHLAKKF | seqid_2968 |
| variant_3923 | FWKKFKKIPPKFLHLAKKF | seqid_2969 |
| variant_3924 | KKKLLKKIPPKFLHLAKKF | seqid_2970 |
| variant_3925 | RKKLLKKIPPKFLHLAKKF | seqid_2971 |
| variant_3926 | FKKLLKKIPPKFLHLAKKF | seqid_2972 |
| variant_3927 | KWKLLKKIPPKFLHLAKKF | seqid_2973 |
| variant_3928 | RWKLLKKIPPKFLHLAKKF | seqid_2974 |
| variant_3929 | FWKLLKKIPPKFLHLAKKF | seqid_2975 |
| variant_3930 | KKKKLKKIPPKFLHLAKKF | seqid_2976 |
| variant_3931 | RKKKLKKIPPKFLHLAKKF | seqid_2977 |
| variant_3932 | FKKKLKKIPPKFLHLAKKF | seqid_2978 |
| variant_3933 | KWKKLKKIPPKFLHLAKKF | seqid_2979 |
| variant_3934 | RWKKLKKIPPKFLHLAKKF | seqid_2980 |
| variant_3935 | FWKKLKKIPPKFLHLAKKF | seqid_2981 |
| variant_3984 | KKKLFLKIPKFLHLAKKF | seqid_2982 |
| variant_3985 | RKKLFLKIPKFLHLAKKF | seqid_2983 |
| variant_3986 | FKKLFLKIPKFLHLAKKF | seqid_2984 |
| variant_3987 | KWKLFLKIPKFLHLAKKF | seqid_2985 |
| variant_3988 | RWKLFLKIPKFLHLAKKF | seqid_2986 |

-continued

| | | |
|---|---|---|
| variant_3989 | FWKLFLKIPKFLHLAKKF | seqid_2987 |
| variant_3990 | KKKKFLKIPKFLHLAKKF | seqid_2988 |
| variant_3991 | RKKKFLKIPKFLHLAKKF | seqid_2989 |
| variant_3992 | FKKKFLKIPKFLHLAKKF | seqid_2990 |
| variant_3993 | KWKKFLKIPKFLHLAKKF | seqid_2991 |
| variant_3994 | RWKKFLKIPKFLHLAKKF | seqid_2992 |
| variant_3995 | FWKKFLKIPKFLHLAKKF | seqid_2993 |
| variant_3996 | KKKLLLKIPKFLHLAKKF | seqid_2994 |
| variant_3997 | RKKLLLKIPKFLHLAKKF | seqid_2995 |
| variant_3998 | FKKLLLKIPKFLHLAKKF | seqid_2996 |
| variant_3999 | KWKLLLKIPKFLHLAKKF | seqid_2997 |
| variant_4000 | RWKLLLKIPKFLHLAKKF | seqid_2998 |
| variant_4001 | FWKLLLKIPKFLHLAKKF | seqid_2999 |
| variant_4002 | KKKKLLKIPKFLHLAKKF | seqid_3000 |
| variant_4003 | RKKKLLKIPKFLHLAKKF | seqid_3001 |
| variant_4004 | FKKKLLKIPKFLHLAKKF | seqid_3002 |
| variant_4005 | KWKKLLKIPKFLHLAKKF | seqid_3003 |
| variant_4006 | RWKKLLKIPKFLHLAKKF | seqid_3004 |
| variant_4007 | FWKKLLKIPKFLHLAKKF | seqid_3005 |
| variant_4008 | KKKLFKKIPKFLHLAKKF | seqid_3006 |
| variant_4009 | RKKLFKKIPKFLHLAKKF | seqid_3007 |
| variant_4010 | FKKLFKKIPKFLHLAKKF | seqid_3008 |
| variant_4011 | KWKLFKKIPKFLHLAKKF | seqid_3 |
| variant_4012 | RWKLFKKIPKFLHLAKKF | seqid_4 |
| variant_4013 | FWKLFKKIPKFLHLAKKF | seqid_3009 |
| variant_4014 | KKKKFKKIPKFLHLAKKF | seqid_3010 |
| variant_4015 | RKKKFKKIPKFLHLAKKF | seqid_3011 |
| variant_4016 | FKKKFKKIPKFLHLAKKF | seqid_3012 |
| variant_4017 | KWKKFKKIPKFLHLAKKF | seqid_3013 |
| variant_4018 | RWKKFKKIPKFLHLAKKF | seqid_3014 |
| variant_4019 | FWKKFKKIPKFLHLAKKF | seqid_3015 |
| variant_4020 | KKKLLKKIPKFLHLAKKF | seqid_3016 |
| variant_4021 | RKKLLKKIPKFLHLAKKF | seqid_3017 |
| variant_4022 | FKKLLKKIPKFLHLAKKF | seqid_3018 |
| variant_4023 | KWKLLKKIPKFLHLAKKF | seqid_3019 |
| variant_4024 | RWKLLKKIPKFLHLAKKF | seqid_3020 |
| variant_4025 | FWKLLKKIPKFLHLAKKF | seqid_3021 |
| variant_4026 | KKKKLKKIPKFLHLAKKF | seqid_3022 |
| variant_4027 | RKKKLKKIPKFLHLAKKF | seqid_3023 |
| variant_4028 | FKKKLKKIPKFLHLAKKF | seqid_3024 |
| variant_4029 | KWKKLKKIPKFLHLAKKF | seqid_3025 |
| variant_4030 | RWKKLKKIPKFLHLAKKF | seqid_3026 |
| variant_4031 | FWKKLKKIPKFLHLAKKF | seqid_3027 |
| variant_4032 | KKKLFLKIPPPKFKHLAKKF | seqid_3028 |
| variant_4033 | RKKLFLKIPPPKFKHLAKKF | seqid_3029 |
| variant_4034 | FKKLFLKIPPPKFKHLAKKF | seqid_3030 |
| variant_4035 | KWKLFLKIPPPKFKHLAKKF | seqid_3031 |
| variant_4036 | RWKLFLKIPPPKFKHLAKKF | seqid_3032 |
| variant_4037 | FWKLFLKIPPPKFKHLAKKF | seqid_3033 |
| variant_4038 | KKKKFLKIPPPKFKHLAKKF | seqid_3034 |
| variant_4039 | RKKKFLKIPPPKFKHLAKKF | seqid_3035 |
| variant_4040 | FKKKFLKIPPPKFKHLAKKF | seqid_3036 |
| variant_4041 | KWKKFLKIPPPKFKHLAKKF | seqid_3037 |
| variant_4042 | RWKKFLKIPPPKFKHLAKKF | seqid_3038 |
| variant_4043 | FWKKFLKIPPPKFKHLAKKF | seqid_3039 |
| variant_4044 | KKKLLLKIPPPKFKHLAKKF | seqid_3040 |
| variant_4045 | RKKLLLKIPPPKFKHLAKKF | seqid_3041 |
| variant_4046 | FKKLLLKIPPPKFKHLAKKF | seqid_3042 |
| variant_4047 | KWKLLLKIPPPKFKHLAKKF | seqid_3043 |
| variant_4048 | RWKLLLKIPPPKFKHLAKKF | seqid_3044 |
| variant_4049 | FWKLLLKIPPPKFKHLAKKF | seqid_3045 |
| variant_4050 | KKKKLLKIPPPKFKHLAKKF | seqid_3046 |
| variant_4051 | RKKKLLKIPPPKFKHLAKKF | seqid_3047 |
| variant_4052 | FKKKLLKIPPPKFKHLAKKF | seqid_3048 |
| variant_4053 | KWKKLLKIPPPKFKHLAKKF | seqid_3049 |
| variant_4054 | RWKKLLKIPPPKFKHLAKKF | seqid_3050 |
| variant_4055 | FWKKLLKIPPPKFKHLAKKF | seqid_3051 |
| variant_4056 | KKKLFKKIPPPKFKHLAKKF | seqid_3052 |
| variant_4057 | RKKLFKKIPPPKFKHLAKKF | seqid_3053 |
| variant_4058 | FKKLFKKIPPPKFKHLAKKF | seqid_3054 |
| variant_4059 | KWKLFKKIPPPKFKHLAKKF | seqid_3055 |
| variant_4060 | RWKLFKKIPPPKFKHLAKKF | seqid_3056 |
| variant_4061 | FWKLFKKIPPPKFKHLAKKF | seqid_3057 |
| variant_4062 | KKKKFKKIPPPKFKHLAKKF | seqid_3058 |
| variant_4063 | RKKKFKKIPPPKFKHLAKKF | seqid_3059 |
| variant_4064 | FKKKFKKIPPPKFKHLAKKF | seqid_3060 |
| variant_4065 | KWKKFKKIPPPKFKHLAKKF | seqid_3061 |
| variant_4066 | RWKKFKKIPPPKFKHLAKKF | seqid_3062 |
| variant_4067 | FWKKFKKIPPPKFKHLAKKF | seqid_3063 |
| variant_4068 | KKKLLKKIPPPKFKHLAKKF | seqid_3064 |
| variant_4069 | RKKLLKKIPPPKFKHLAKKF | seqid_3065 |

| | | |
|---|---|---|
| variant_4070 | FKKLLKKIPPPKFKHLAKKF | seqid_3066 |
| variant_4071 | KWKLLKKIPPPKFKHLAKKF | seqid_3067 |
| variant_4072 | RWKLLKKIPPPKFKHLAKKF | seqid_3068 |
| variant_4073 | FWKLLKKIPPPKFKHLAKKF | seqid_3069 |
| variant_4074 | KKKKLKKIPPPKFKHLAKKF | seqid_3070 |
| variant_4075 | RKKKLKKIPPPKFKHLAKKF | seqid_3071 |
| variant_4076 | FKKKLKKIPPPKFKHLAKKF | seqid_3072 |
| variant_4077 | KWKKLKKIPPPKFKHLAKKF | seqid_3073 |
| variant_4078 | RWKKLKKPPPKFKHLAKKF | seqid_3074 |
| variant_4079 | FWKKLKKIPPPKFKHLAKKF | seqid_3075 |
| variant_4080 | KKKLFLKIPPKFKHLAKKF | seqid_3076 |
| variant_4081 | RKKLFLKIPPKFKHLAKKF | seqid_3077 |
| variant_4082 | FKKLFLKIPPKFKHLAKKF | seqid_3078 |
| variant_4083 | KWKLFLKIPPKFKHLAKKF | seqid_3079 |
| variant_4084 | RWKLFLKIPPKFKHLAKKF | seqid_3080 |
| variant_4085 | FWKLFLKIPPKFKHLAKKF | seqid_3081 |
| variant_4086 | KKKKFLKIPPKFKHLAKKF | seqid_3082 |
| variant_4087 | RKKKFLKIPPKFKHLAKKF | seqid_3083 |
| variant_4088 | FKKKFLKIPPKFKHLAKKF | seqid_3084 |
| variant_4089 | KWKKFLKIPPKFKHLAKKF | seqid_3085 |
| variant_4090 | RWKKFLKIPPKFKHLAKKF | seqid_3086 |
| variant_4091 | FWKKFLKIPPKFKHLAKKF | seqid_3087 |
| variant_4092 | KKKLLLKIPPKFKHLAKKF | seqid_3088 |
| variant_4093 | RKKLLLKIPPKFKHLAKKF | seqid_3089 |
| variant_4094 | FKKLLLKIPPKFKHLAKKF | seqid_3090 |
| variant_4095 | KWKLLLKIPPKFKHLAKKF | seqid_3091 |
| variant_4096 | RWKLLLKIPPKFKHLAKKF | seqid_3092 |
| variant_4097 | FWKLLLKIPPKFKHLAKKF | seqid_3093 |
| variant_4098 | KKKKLLKIPPKFKHLAKKF | seqid_3094 |
| variant_4099 | RKKKLLKIPPKFKHLAKKF | seqid_3095 |
| variant_4100 | FKKKLLKIPPKFKHLAKKF | seqid_3096 |
| variant_4101 | KWKKLLKIPPKFKHLAKKF | seqid_3097 |
| variant_4102 | RWKKLLKIPPKFKHLAKKF | seqid_3098 |
| variant_4103 | FWKKLLKIPPKFKHLAKKF | seqid_3099 |
| variant_4104 | KKKLFKKIPPKFKHLAKKF | seqid_3100 |
| variant_4105 | RKKLFKKIPPKFKHLAKKF | seqid_3101 |
| variant_4106 | FKKLFKKIPPKFKHLAKKF | seqid_3102 |
| variant_4107 | KWKLFKKIPPKFKHLAKKF | seqid_3103 |
| variant_4108 | RWKLFKKIPPKFKHLAKKF | seqid_3104 |
| variant_4109 | FWKLFKKIPPKFKHLAKKF | seqid_3105 |
| variant_4110 | KKKKFKKIPPKFKHLAKKF | seqid_3106 |
| variant_4111 | RKKKFKKIPPKFKHLAKKF | seqid_3107 |
| variant_4112 | FKKKFKKIPPKFKHLAKKF | seqid_3108 |
| variant_4113 | KWKKFKKIPPKFKHLAKKF | seqid_3109 |
| variant_4114 | RWKKFKKIPPKFKHLAKKF | seqid_3110 |
| variant_4115 | FWKKFKKIPPKFKHLAKKF | seqid_3111 |
| variant_4116 | KKKLLKKIPPKFKHLAKKF | seqid_3112 |
| variant_4117 | RKKLLKKIPPKFKHLAKKF | seqid_3113 |
| variant_4118 | FKKLLKKIPPKFKHLAKKF | seqid_3114 |
| variant_4119 | KWKLLKKIPPKFKHLAKKF | seqid_3115 |
| variant_4120 | RWKLLKKIPPKFKHLAKKF | seqid_3116 |
| variant_4121 | FWKLLKKIPPKFKHLAKKF | seqid_3117 |
| variant_4122 | KKKKLKKIPPKFKHLAKKF | seqid_3118 |
| variant_4123 | RKKKLKKIPPKFKHLAKKF | seqid_3119 |
| variant_4124 | FKKKLKKIPPKFKHLAKKF | seqid_3120 |
| variant_4125 | KWKKLKKIPPKFKHLAKKF | seqid_3121 |
| variant_4126 | RWKKLKKIPPKFKHLAKKF | seqid_3122 |
| variant_4127 | FWKKLKKIPPKFKHLAKKF | seqid_3123 |
| variant_4176 | KKKLFLKIPKFKHLAKKF | seqid_3124 |
| variant_4177 | RKKLFLKIPKFKHLAKKF | seqid_3125 |
| variant_4178 | FKKLFLKIPKFKHLAKKF | seqid_3126 |
| variant_4179 | KWKLFLKIPKFKHLAKKF | seqid_3127 |
| variant_4180 | RWKLFLKIPKFKHLAKKF | seqid_3128 |
| variant_4181 | FWKLFLKIPKFKHLAKKF | seqid_3129 |
| variant_4182 | KKKKFLKIPKFKHLAKKF | seqid_3130 |
| variant_4183 | RKKKFLKIPKFKHLAKKF | seqid_3131 |
| variant_4184 | FKKKFLKIPKFKHLAKKF | seqid_3132 |
| variant_4185 | KWKKFLKIPKFKHLAKKF | seqid_3133 |
| variant_4186 | RWKKFLKIPKFKHLAKKF | seqid_3134 |
| variant_4187 | FWKKFLKIPKFKHLAKKF | seqid_3135 |
| variant_4188 | KKKLLLKIPKFKHLAKKF | seqid_3136 |
| variant_4189 | RKKLLLKIPKFKHLAKKF | seqid_3137 |
| variant_4190 | FKKLLLKIPKFKHLAKKF | seqid_3138 |
| variant_4191 | KWKLLLKIPKFKHLAKKF | seqid_3139 |
| variant_4192 | RWKLLLKIPKFKHLAKKF | seqid_3140 |
| variant_4193 | FWKLLLKIPKFKHLAKKF | seqid_3141 |
| variant_4194 | KKKKLLKIPKFKHLAKKF | seqid_3142 |
| variant_4195 | RKKKLLKIPKFKHLAKKF | seqid_3143 |
| variant_4196 | FKKKLLKIPKFKHLAKKF | seqid_3144 |
| variant_4197 | KWKKLLKIPKFKHLAKKF | seqid_3145 |
| variant_4198 | RWKKLLKIPKFKHLAKKF | seqid_3146 |

| | | |
|---|---|---|
| variant_4199 | FWKKLLKIPKFKHLAKKF | seqid_3147 |
| variant_4200 | KKKLFKKIPKFKHLAKKF | seqid_3148 |
| variant_4201 | RKKLFKKIPKFKHLAKKF | seqid_3149 |
| variant_4202 | FKKLFKKIPKFKHLAKKF | seqid_3150 |
| variant_4203 | KWKLFKKIPKFKHLAKKF | seqid_3151 |
| variant_4204 | RWKLFKKIPKFKHLAKKF | seqid_3152 |
| variant_4205 | FWKLFKKIPKFKHLAKKF | seqid_3153 |
| variant_4206 | KKKKFKKIPKFKHLAKKF | seqid_3154 |
| variant_4207 | RKKKFKKIPKFKHLAKKF | seqid_3155 |
| variant_4208 | FKKKFKKIPKFKHLAKKF | seqid_3156 |
| variant_4209 | KWKKFKKIPKFKHLAKKF | seqid_3157 |
| variant_4210 | RWKKFKKIPKFKHLAKKF | seqid_3158 |
| variant_4211 | FWKKFKKIPKFKHLAKKF | seqid_3159 |
| variant_4212 | KKKLLKKIPKFKHLAKKF | seqid_3160 |
| variant_4213 | RKKLLKKIPKFKHLAKKF | seqid_3161 |
| variant_4214 | FKKLLKKIPKFKHLAKKF | seqid_3162 |
| variant_4215 | KWKLLKKIPKFKHLAKKF | seqid_3163 |
| variant_4216 | RWKLLKKIPKFKHLAKKF | seqid_3164 |
| variant_4217 | FWKLLKKIPKFKHLAKKF | seqid_3165 |
| variant_4218 | KKKKLKKIPKFKHLAKKF | seqid_3166 |
| variant_4219 | RKKKLKKIPKFKHLAKKF | seqid_3167 |
| variant_4220 | FKKKLKKIPKFKHLAKKF | seqid_3168 |
| variant_4221 | KWKKLKKIPKFKHLAKKF | seqid_3169 |
| variant_4222 | RWKKLKKIPKFKHLAKKF | seqid_3170 |
| variant_4223 | FWKKLKKIPKFKHLAKKF | seqid_3171 |
| variant_4224 | KKKLFLKIPPPKFLKLAKKF | seqid_3172 |
| variant_4225 | RKKLFLKIPPPKFLKLAKKF | seqid_3173 |
| variant_4226 | FKKLFLKIPPPKFLKLAKKF | seqid_3174 |
| variant_4227 | KWKLFLKIPPPKFLKLAKKF | seqid_3175 |
| variant_4228 | RWKLFLKIPPPKFLKLAKKF | seqid_3176 |
| variant_4229 | FWKLFLKIPPPKFLKLAKKF | seqid_3177 |
| variant_4230 | KKKKFLKIPPPKFLKLAKKF | seqid_3178 |
| variant_4231 | RKKKFLKIPPPKFLKLAKKF | seqid_3179 |
| variant_4232 | FKKKFLKIPPPKFLKLAKKF | seqid_3180 |
| variant_4233 | KWKKFLKIPPPKFLKLAKKF | seqid_3181 |
| variant_4234 | RWKKFLKIPPPKFLKLAKKF | seqid_3182 |
| variant_4235 | FWKKFLKIPPPKFLKLAKKF | seqid_3183 |
| variant_4236 | KKKLLLKIPPPKFLKLAKKF | seqid_3184 |
| variant_4237 | RKKLLLKIPPPKFLKLAKKF | seqid_3185 |
| variant_4238 | FKKLLLKIPPPKFLKLAKKF | seqid_3186 |
| variant_4239 | KWKLLLKIPPPKFLKLAKKF | seqid_3187 |
| variant_4240 | RWKLLLKIPPPKFLKLAKKF | seqid_3188 |
| variant_4241 | FWKLLLKIPPPKFLKLAKKF | seqid_3189 |
| variant_4242 | KKKKLLKIPPPKFLKLAKKF | seqid_3190 |
| variant_4243 | RKKKLLKIPPPKFLKLAKKF | seqid_3191 |
| variant_4244 | FKKKLLKIPPPKFLKLAKKF | seqid_3192 |
| variant_4245 | KWKKLLKIPPPKFLKLAKKF | seqid_3193 |
| variant_4246 | RWKKLLKIPPPKFLKLAKKF | seqid_3194 |
| variant_4247 | FWKKLLKIPPPKFLKLAKKF | seqid_3195 |
| variant_4248 | KKKLFKKIPPPKFLKLAKKF | seqid_3196 |
| variant_4249 | RKKLFKKIPPPKFLKLAKKF | seqid_3197 |
| variant_4250 | FKKLFKKIPPPKFLKLAKKF | seqid_3198 |
| variant_4251 | KWKLFKKIPPPKFLKLAKKF | seqid_3199 |
| variant_4252 | RWKLFKKIPPPKFLKLAKKF | seqid_3200 |
| variant_4253 | FWKLFKKIPPPKFLKLAKKF | seqid_3201 |
| variant_4254 | KKKKFKKIPPPKFLKLAKKF | seqid_3202 |
| variant_4255 | RKKKFKKIPPPKFLKLAKKF | seqid_3203 |
| variant_4256 | FKKKFKKIPPPKFLKLAKKF | seqid_3204 |
| variant_4257 | KWKKFKKIPPPKFLKLAKKF | seqid_3205 |
| variant_4258 | RWKKFKKIPPPKFLKLAKKF | seqid_3206 |
| variant_4259 | FWKKFKKIPPPKFLKLAKKF | seqid_3207 |
| variant_4260 | KKKLLKKIPPPKFLKLAKKF | seqid_3208 |
| variant_4261 | RKKLLKKIPPPKFLKLAKKF | seqid_3209 |
| variant_4262 | FKKLLKKIPPPKFLKLAKKF | seqid_3210 |
| variant_4263 | KWKLLKKIPPPKFLKLAKKF | seqid_3211 |
| variant_4264 | RWKLLKKIPPPKFLKLAKKF | seqid_3212 |
| variant_4265 | FWKLLKKIPPPKFLKLAKKF | seqid_3213 |
| variant_4266 | KKKKLKKIPPPKFLKLAKKF | seqid_3214 |
| variant_4267 | RKKKLKKIPPPKFLKLAKKF | seqid_3215 |
| variant_4268 | FKKKLKKIPPPKFLKLAKKF | seqid_3216 |
| variant_4269 | KWKKLKKIPPPKFLKLAKKF | seqid_3217 |
| variant_4270 | RWKKLKKIPPPKFLKLAKKF | seqid_3218 |
| variant_4271 | FWKKLKKIPPPKFLKLAKKF | seqid_3219 |
| variant_4272 | KKKLFLKIPPKFLKLAKKF | seqid_3220 |
| variant_4273 | RKKLFLKIPPKFLKLAKKF | seqid_3221 |
| variant_4274 | FKKLFLKIPPKFLKLAKKF | seqid_3222 |
| variant_4275 | KWKLFLKIPPKFLKLAKKF | seqid_3223 |
| variant_4276 | RWKLFLKIPPKFLKLAKKF | seqid_3224 |
| variant_4277 | FWKLFLKIPPKFLKLAKKF | seqid_3225 |
| variant_4278 | KKKKFLKIPPKFLKLAKKF | seqid_3226 |
| variant_4279 | RKKKFLKIPPKFLKLAKKF | seqid_3227 |

| | | |
|---|---|---|
| variant_4280 | FKKKFLKIPPKFLKLAKKF | seqid_3228 |
| variant_4281 | KWKKFLKIPPKFLKLAKKF | seqid_3229 |
| variant_4282 | RWKKFLKIPPKFLKLAKKF | seqid_3230 |
| variant_4283 | FWKKFLKIPPKFLKLAKKF | seqid_3231 |
| variant_4284 | KKKLLLKIPPKFLKLAKKF | seqid_3232 |
| variant_4285 | RKKLLLKIPPKFLKLAKKF | seqid_3233 |
| variant_4286 | FKKLLLKIPPKFLKLAKKF | seqid_3234 |
| variant_4287 | KWKLLLKIPPKFLKLAKKF | seqid_3235 |
| variant_4288 | RWKLLLKIPPKFLKLAKKF | seqid_3236 |
| variant_4289 | FWKLLLKIPPKFLKLAKKF | seqid_3237 |
| variant_4290 | KKKKLLKIPPKFLKLAKKF | seqid_3238 |
| variant_4291 | RKKKLLKIPPKFLKLAKKF | seqid_3239 |
| variant_4292 | FKKKLLKIPPKFLKLAKKF | seqid_3240 |
| variant_4293 | KWKKLLKIPPKFLKLAKKF | seqid_3241 |
| variant_4294 | RWKKLLKIPPKFLKLAKKF | seqid_3242 |
| variant_4295 | FWKKLLKIPPKFLKLAKKF | seqid_3243 |
| variant_4296 | KKKLFKKIPPKFLKLAKKF | seqid_3244 |
| variant_4297 | RKKLFKKIPPKFLKLAKKF | seqid_3245 |
| variant_4298 | FKKLFKKIPPKFLKLAKKF | seqid_3246 |
| variant_4299 | KWKLFKKIPPKFLKLAKKF | seqid_3247 |
| variant_4300 | RWKLFKKIPPKFLKLAKKF | seqid_3248 |
| variant_4301 | FWKLFKKIPPKFLKLAKKF | seqid_3249 |
| variant_4302 | KKKKFKKIPPKFLKLAKKF | seqid_3250 |
| variant_4303 | RKKKFKKIPPKFLKLAKKF | seqid_3251 |
| variant_4304 | FKKKFKKIPPKFLKLAKKF | seqid_3252 |
| variant_4305 | KWKKFKKIPPKFLKLAKKF | seqid_3253 |
| variant_4306 | RWKKFKKIPPKFLKLAKKF | seqid_3254 |
| variant_4307 | FWKKFKKIPPKFLKLAKKF | seqid_3255 |
| variant_4308 | KKKLLKKIPPKFLKLAKKF | seqid_3256 |
| variant_4309 | RKKLLKKIPPKFLKLAKKF | seqid_3257 |
| variant_4310 | FKKLLKKIPPKFLKLAKKF | seqid_3258 |
| variant_4311 | KWKLLKKIPPKFLKLAKKF | seqid_3259 |
| variant_4312 | RWKLLKKIPPKFLKLAKKF | seqid_3260 |
| variant_4313 | FWKLLKKIPPKFLKLAKKF | seqid_3261 |
| variant_4314 | KKKKLKKIPPKFLKLAKKF | seqid_3262 |
| variant_4315 | RKKKLKKIPPKFLKLAKKF | seqid_3263 |
| variant_4316 | FKKKLKKIPPKFLKLAKKF | seqid_3264 |
| variant_4317 | KWKKLKKIPPKFLKLAKKF | seqid_3265 |
| variant_4318 | RWKKLKKIPPKFLKLAKKF | seqid_3266 |
| variant_4319 | FWKKLKKIPPKFLKLAKKF | seqid_3267 |
| variant_4368 | KKKLFLKIPKFLKLAKKF | seqid_3268 |
| variant_4369 | RKKLFLKIPKFLKLAKKF | seqid_3269 |
| variant_4370 | FKKLFLKIPKFLKLAKKF | seqid_3270 |
| variant_4371 | KWKLFLKIPKFLKLAKKF | seqid_3271 |
| variant_4372 | RWKLFLKIPKFLKLAKKF | seqid_3272 |
| variant_4373 | FWKLFLKIPKFLKLAKKF | seqid_3273 |
| variant_4374 | KKKKFLKIPKFLKLAKKF | seqid_3274 |
| variant_4375 | RKKKFLKIPKFLKLAKKF | seqid_3275 |
| variant_4376 | FKKKFLKIPKFLKLAKKF | seqid_3276 |
| variant_4377 | KWKKFLKIPKFLKLAKKF | seqid_3277 |
| variant_4378 | RWKKFLKIPKFLKLAKKF | seqid_3278 |
| variant_4379 | FWKKFLKIPKFLKLAKKF | seqid_3279 |
| variant_4380 | KKKLLLKIPKFLKLAKKF | seqid_3280 |
| variant_4381 | RKKLLLKIPKFLKLAKKF | seqid_3281 |
| variant_4382 | FKKLLLKIPKFLKLAKKF | seqid_3282 |
| variant_4383 | KWKLLLKIPKFLKLAKKF | seqid_3283 |
| variant_4384 | RWKLLLKIPKFLKLAKKF | seqid_3284 |
| variant_4385 | FWKLLLKIPKFLKLAKKF | seqid_3285 |
| variant_4386 | KKKKLLKIPKFLKLAKKF | seqid_3286 |
| variant_4387 | RKKKLLKIPKFLKLAKKF | seqid_3287 |
| variant_4388 | FKKKLLKIPKFLKLAKKF | seqid_3288 |
| variant_4389 | KWKKLLKIPKFLKLAKKF | seqid_3289 |
| variant_4390 | RWKKLLKIPKFLKLAKKF | seqid_3290 |
| variant_4391 | FWKKLLKIPKFLKLAKKF | seqid_3291 |
| variant_4392 | KKKLFKKIPKFLKLAKKF | seqid_3292 |
| variant_4393 | RKKLFKKIPKFLKLAKKF | seqid_3293 |
| variant_4394 | FKKLFKKIPKFLKLAKKF | seqid_3294 |
| variant_4395 | KWKLFKKIPKFLKLAKKF | seqid_3295 |
| variant_4396 | RWKLFKKIPKFLKLAKKF | seqid_3296 |
| variant_4397 | FWKLFKKIPKFLKLAKKF | seqid_3297 |
| variant_4398 | KKKKFKKIPKFLKLAKKF | seqid_3298 |
| variant_4399 | RKKKFKKIPKFLKLAKKF | seqid_3299 |
| variant_4400 | FKKKFKKIPKFLKLAKKF | seqid_3300 |
| variant_4401 | KWKKFKKIPKFLKLAKKF | seqid_3301 |
| variant_4402 | RWKKFKKIPKFLKLAKKF | seqid_3302 |
| variant_4403 | FWKKFKKIPKFLKLAKKF | seqid_3303 |
| variant_4404 | KKKLLKKIPKFLKLAKKF | seqid_3304 |
| variant_4405 | RKKLLKKIPKFLKLAKKF | seqid_3305 |
| variant_4406 | FKKLLKKIPKFLKLAKKF | seqid_3306 |
| variant_4407 | KWKLLKKIPKFLKLAKKF | seqid_3307 |
| variant_4408 | RWKLLKKIPKFLKLAKKF | seqid_3308 |

| | | |
|---|---|---|
| variant_4409 | FWKLLKKIPKFLKLAKKF | seqid_3309 |
| variant_4410 | KKKKLKKIPKFLKLAKKF | seqid_3310 |
| variant_4411 | RKKKLKKIPKFLKLAKKF | seqid_3311 |
| variant_4412 | FKKKLKKIPKFLKLAKKF | seqid_3312 |
| variant_4413 | KWKKLKKIPKFLKLAKKF | seqid_3313 |
| variant_4414 | RWKKLKKIPKFLKLAKKF | seqid_3314 |
| variant_4415 | FWKKLKKIPKFLKLAKKF | seqid_3315 |
| variant_4416 | KKKLFLKIPPPKFKKLAKKF | seqid_3316 |
| variant_4417 | RKKLFLKIPPPKFKKLAKKF | seqid_3317 |
| variant_4418 | FKKLFLKIPPPKFKKLAKKF | seqid_3318 |
| variant_4419 | KWKLFLKIPPPKFKKLAKKF | seqid_3319 |
| variant_4420 | RWKLFLKIPPPKFKKLAKKF | seqid_3320 |
| variant_4421 | FWKLFLKIPPPKFKKLAKKF | seqid_3321 |
| variant_4422 | KKKKFLKIPPPKFKKLAKKF | seqid_3322 |
| variant_4423 | RKKKFLKIPPPKFKKLAKKF | seqid_3323 |
| variant_4424 | FKKKFLKIPPPKFKKLAKKF | seqid_3324 |
| variant_4425 | KWKKFLKIPPPKFKKLAKKF | seqid_3325 |
| variant_4426 | RWKKFLKIPPPKFKKLAKKF | seqid_3326 |
| variant_4427 | FWKKFLKIPPPKFKKLAKKF | seqid_3327 |
| variant_4428 | KKKLLLKIPPPKFKKLAKKF | seqid_3328 |
| variant_4429 | RKKLLLKIPPPKFKKLAKKF | seqid_3329 |
| variant_4430 | FKKLLLKIPPPKFKKLAKKF | seqid_3330 |
| variant_4431 | KWKLLLKIPPPKFKKLAKKF | seqid_3331 |
| variant_4432 | RWKLLLKIPPPKFKKLAKKF | seqid_3332 |
| variant_4433 | FWKLLLKIPPPKFKKLAKKF | seqid_3333 |
| variant_4434 | KKKKLLKIPPPKFKKLAKKF | seqid_3334 |
| variant_4435 | RKKKLLKIPPPKFKKLAKKF | seqid_3335 |
| variant_4436 | FKKKLLKIPPPKFKKLAKKF | seqid_3336 |
| variant_4437 | KWKKLLKIPPPKFKKLAKKF | seqid_3337 |
| variant_4438 | RWKKLLKIPPPKFKKLAKKF | seqid_3338 |
| variant_4439 | FWKKLLKIPPPKFKKLAKKF | seqid_3339 |
| variant_4440 | KKKLFKKIPPPKFKKLAKKF | seqid_3340 |
| variant_4441 | RKKLFKKIPPPKFKKLAKKF | seqid_3341 |
| variant_4442 | FKKLFKKIPPPKFKKLAKKF | seqid_3342 |
| variant_4443 | KWKLFKKIPPPKFKKLAKKF | seqid_3343 |
| variant_4444 | RWKLFKKIPPPKFKKLAKKF | seqid_3344 |
| variant_4445 | FWKLFKKIPPPKFKKLAKKF | seqid_3345 |
| variant_4446 | KKKKFKKIPPPKFKKLAKKF | seqid_3346 |
| variant_4447 | RKKKFKKIPPPKFKKLAKKF | seqid_3347 |
| variant_4448 | FKKKFKKIPPPKFKKLAKKF | seqid_3348 |
| variant_4449 | KWKKFKKIPPPKFKKLAKKF | seqid_3349 |
| variant_4450 | RWKKFKKIPPPKFKKLAKKF | seqid_3350 |
| variant_4451 | FWKKFKKIPPPKFKKLAKKF | seqid_3351 |
| variant_4452 | KKKLLKKIPPPKFKKLAKKF | seqid_3352 |
| variant_4453 | RKKLLKKIPPPKFKKLAKKF | seqid_3353 |
| variant_4454 | FKKLLKKIPPPKFKKLAKKF | seqid_3354 |
| variant_4455 | KWKLLKKIPPPKFKKLAKKF | seqid_3355 |
| variant_4456 | RWKLLKKIPPPKFKKLAKKF | seqid_3356 |
| variant_4457 | FWKLLKKIPPPKFKKLAKKF | seqid_3357 |
| variant_4458 | KKKKLKKIPPPKFKKLAKKF | seqid_3358 |
| variant_4459 | RKKKLKKIPPPKFKKLAKKF | seqid_3359 |
| variant_4460 | FKKKLKKIPPPKFKKLAKKF | seqid_3360 |
| variant_4461 | KWKKLKKIPPPKFKKLAKKF | seqid_3361 |
| variant_4462 | RWKKLKKIPPPKFKKLAKKF | seqid_3362 |
| variant_4463 | FWKKLKKIPPPKFKKLAKKF | seqid_3363 |
| variant_4464 | KKKLFLKIPPKFKKLAKKF | seqid_3364 |
| variant_4465 | RKKLFLKIPPKFKKLAKKF | seqid_3365 |
| variant_4466 | FKKLFLKIPPKFKKLAKKF | seqid_3366 |
| variant_4467 | KWKLFLKIPPKFKKLAKKF | seqid_3367 |
| variant_4468 | RWKLFLKIPPKFKKLAKKF | seqid_3368 |
| variant_4469 | FWKLFLKIPPKFKKLAKKF | seqid_3369 |
| variant_4470 | KKKKFLKIPPKFKKLAKKF | seqid_3370 |
| variant_4471 | RKKKFLKIPPKFKKLAKKF | seqid_3371 |
| variant_4472 | FKKKFLKIPPKFKKLAKKF | seqid_3372 |
| variant_4473 | KWKKFLKIPPKFKKLAKKF | seqid_3373 |
| variant_4474 | RWKKFLKIPPKFKKLAKKF | seqid_3374 |
| variant_4475 | FWKKFLKIPPKFKKLAKKF | seqid_3375 |
| variant_4476 | KKKLLLKIPPKFKKLAKKF | seqid_3376 |
| variant_4477 | RKKLLLKIPPKFKKLAKKF | seqid_3377 |
| variant_4478 | FKKLLLKIPPKFKKLAKKF | seqid_3378 |
| variant_4479 | KWKLLLKIPPKFKKLAKKF | seqid_3379 |
| variant_4480 | RWKLLLKIPPKFKKLAKKF | seqid_3380 |
| variant_4481 | FWKLLLKIPPKFKKLAKKF | seqid_3381 |
| variant_4482 | KKKKLLKIPPKFKKLAKKF | seqid_3382 |
| variant_4483 | RKKKLLKIPPKFKKLAKKF | seqid_3383 |
| variant_4484 | FKKKLLKIPPKFKKLAKKF | seqid_3384 |
| variant_4485 | KWKKLLKIPPKFKKLAKKF | seqid_3385 |
| variant_4486 | RWKKLLKIPPKFKKLAKKF | seqid_3386 |
| variant_4487 | FWKKLLKIPPKFKKLAKKF | seqid_3387 |
| variant_4488 | KKKLFKKIPPKFKKLAKKF | seqid_3388 |
| variant_4489 | RKKLFKKIPPKFKKLAKKF | seqid_3389 |

| | | |
|---|---|---|
| variant_4490 | FKKLFKKIPPKFKKLAKKF | seqid_3390 |
| variant_4491 | KWKLFKKIPPKFKKLAKKF | seqid_3391 |
| variant_4492 | RWKLFKKIPPKFKKLAKKF | seqid_3392 |
| variant_4493 | FWKLFKKIPPKFKKLAKKF | seqid_3393 |
| variant_4494 | KKKKFKKIPPKFKKLAKKF | seqid_3394 |
| variant_4495 | RKKKFKKIPPKFKKLAKKF | seqid_3395 |
| variant_4496 | FKKKFKKIPPKFKKLAKKF | seqid_3396 |
| variant_4497 | KWKKFKKIPPKFKKLAKKF | seqid_3397 |
| variant_4498 | RWKKFKKIPPKFKKLAKKF | seqid_3398 |
| variant_4499 | FWKKFKKIPPKFKKLAKKF | seqid_3399 |
| variant_4500 | KKKLLKKIPPKFKKLAKKF | seqid_3400 |
| variant_4501 | RKKLLKKIPPKFKKLAKKF | seqid_3401 |
| variant_4502 | FKKLLKKIPPKFKKLAKKF | seqid_3402 |
| variant_4503 | KWKLLKKIPPKFKKLAKKF | seqid_3403 |
| variant_4504 | RWKLLKKIPPKFKKLAKKF | seqid_3404 |
| variant_4505 | FWKLLKKIPPKFKKLAKKF | seqid_3405 |
| variant_4506 | KKKKLKKIPPKFKKLAKKF | seqid_3406 |
| variant_4507 | RKKKLKKIPPKFKKLAKKF | seqid_3407 |
| variant_4508 | FKKKLKKIPPKFKKLAKKF | seqid_3408 |
| variant_4509 | KWKKLKKIPPKFKKLAKKF | seqid_3409 |
| variant_4510 | RWKKLKKIPPKFKKLAKKF | seqid_3410 |
| variant_4511 | FWKKLKKIPPKFKKLAKKF | seqid_3411 |
| variant_4560 | KKKLFLKIPKFKKLAKKF | seqid_3412 |
| variant_4561 | RKKLFLKIPKFKKLAKKF | seqid_3413 |
| variant_4562 | FKKLFLKIPKFKKLAKKF | seqid_3414 |
| variant_4563 | KWKLFLKIPKFKKLAKKF | seqid_3415 |
| variant_4564 | RWKLFLKIPKFKKLAKKF | seqid_3416 |
| variant_4565 | FWKLFLKIPKFKKLAKKF | seqid_3417 |
| variant_4566 | KKKKFLKIPKFKKLAKKF | seqid_3418 |
| variant_4567 | RKKKFLKIPKFKKLAKKF | seqid_3419 |
| variant_4568 | FKKKFLKIPKFKKLAKKF | seqid_3420 |
| variant_4569 | KWKKFLKIPKFKKLAKKF | seqid_3421 |
| variant_4570 | RWKKFLKIPKFKKLAKKF | seqid_3422 |
| variant_4571 | FWKKFLKIPKFKKLAKKF | seqid_3423 |
| variant_4572 | KKKLLLKIPKFKKLAKKF | seqid_3424 |
| variant_4573 | RKKLLLKIPKFKKLAKKF | seqid_3425 |
| variant_4574 | FKKLLLKIPKFKKLAKKF | seqid_3426 |
| variant_4575 | KWKLLLKIPKFKKLAKKF | seqid_3427 |
| variant_4576 | RWKLLLKIPKFKKLAKKF | seqid_3428 |
| variant_4577 | FWKLLLKIPKFKKLAKKF | seqid_3429 |
| variant_4578 | KKKKLLKIPKFKKLAKKF | seqid_3430 |
| variant_4579 | RKKKLLKIPKFKKLAKKF | seqid_3431 |
| variant_4580 | FKKKLLKIPKFKKLAKKF | seqid_3432 |
| variant_4581 | KWKKLLKIPKFKKLAKKF | seqid_3433 |
| variant_4582 | RWKKLLKIPKFKKLAKKF | seqid_3434 |
| variant_4583 | FWKKLLKIPKFKKLAKKF | seqid_3435 |
| variant_4584 | KKKLFKKIPKFKKLAKKF | seqid_3436 |
| variant_4585 | RKKLFKKIPKFKKLAKKF | seqid_3437 |
| variant_4586 | FKKLFKKIPKFKKLAKKF | seqid_3438 |
| variant_4587 | KWKLFKKIPKFKKLAKKF | seqid_3439 |
| variant_4588 | RWKLFKKIPKFKKLAKKF | seqid_3440 |
| variant_4589 | FWKLFKKIPKFKKLAKKF | seqid_3441 |
| variant_4590 | KKKKFKKIPKFKKLAKKF | seqid_3442 |
| variant_4591 | RKKKFKKIPKFKKLAKKF | seqid_3443 |
| variant_4592 | FKKKFKKIPKFKKLAKKF | seqid_3444 |
| variant_4593 | KWKKFKKIPKFKKLAKKF | seqid_3445 |
| variant_4594 | RWKKFKKIPKFKKLAKKF | seqid_3446 |
| variant_4595 | FWKKFKKIPKFKKLAKKF | seqid_3447 |
| variant_4596 | KKKLLKKIPKFKKLAKKF | seqid_3448 |
| variant_4597 | RKKLLKKIPKFKKLAKKF | seqid_3449 |
| variant_4598 | FKKLLKKIPKFKKLAKKF | seqid_3450 |
| variant_4599 | KWKLLKKIPKFKKLAKKF | seqid_3451 |
| variant_4600 | RWKLLKKIPKFKKLAKKF | seqid_3452 |
| variant_4601 | FWKLLKKIPKFKKLAKKF | seqid_3453 |
| variant_4602 | KKKKLKKIPKFKKLAKKF | seqid_3454 |
| variant_4603 | RKKKLKKIPKFKKLAKKF | seqid_3455 |
| variant_4604 | FKKKLKKIPKFKKLAKKF | seqid_3456 |
| variant_4605 | KWKKLKKIPKFKKLAKKF | seqid_3457 |
| variant_4606 | RWKKLKKIPKFKKLAKKF | seqid_3458 |
| variant_4607 | FWKKLKKIPKFKKLAKKF | seqid_3459 |
| variant_4608 | KKKLFLKIPPPKFLHVAKKF | seqid_3460 |
| variant_4609 | RKKLFLKIPPPKFLHVAKKF | seqid_3461 |
| variant_4610 | FKKLFLKIPPPKFLHVAKKF | seqid_3462 |
| variant_4611 | KWKLFLKIPPPKFLHVAKKF | seqid_3463 |
| variant_4612 | RWKLFLKIPPPKFLHVAKKF | seqid_3464 |
| variant_4613 | FWKLFLKIPPPKFLHVAKKF | seqid_3465 |
| variant_4614 | KKKKFLKIPPPKFLHVAKKF | seqid_3466 |
| variant_4615 | RKKKFLKIPPPKFLHVAKKF | seqid_3467 |
| variant_4616 | FKKKFLKIPPPKFLHVAKKF | seqid_3468 |
| variant_4617 | KWKKFLKIPPPKFLHVAKKF | seqid_3469 |
| variant_4618 | RWKKFLKIPPPKFLHVAKKF | seqid_3470 |

| variant_4619 | FWKKFLKIPPPKFLHVAKKF | seqid_3471 |
| variant_4620 | KKKLLLKIPPPKFLHVAKKF | seqid_3472 |
| variant_4621 | RKKLLLKIPPPKFLHVAKKF | seqid_3473 |
| variant_4622 | FKKLLLKIPPPKFLHVAKKF | seqid_3474 |
| variant_4623 | KWKLLLKIPPPKFLHVAKKF | seqid_3475 |
| variant_4624 | RWKLLLKIPPPKFLHVAKKF | seqid_3476 |
| variant_4625 | FWKLLLKIPPPKFLHVAKKF | seqid_3477 |
| variant_4626 | KKKKLLKIPPPKFLHVAKKF | seqid_3478 |
| variant_4627 | RKKKLLKIPPPKFLHVAKKF | seqid_3479 |
| variant_4628 | FKKKLLKIPPPKFLHVAKKF | seqid_3480 |
| variant_4629 | KWKKLLKIPPPKFLHVAKKF | seqid_3481 |
| variant_4630 | RWKKLLKIPPPKFLHVAKKF | seqid_3482 |
| variant_4631 | FWKKLLKIPPPKFLHVAKKF | seqid_3483 |
| variant_4632 | KKKLFKKIPPPKFLHVAKKF | seqid_3484 |
| variant_4633 | RKKLFKKIPPPKFLHVAKKF | seqid_3485 |
| variant_4634 | FKKLFKKIPPPKFLHVAKKF | seqid_3486 |
| variant_4635 | KWKLFKKIPPPKFLHVAKKF | seqid_3487 |
| variant_4636 | RWKLFKKIPPPKFLHVAKKF | seqid_3488 |
| variant_4637 | FWKLFKKIPPPKFLHVAKKF | seqid_3489 |
| variant_4638 | KKKKFKKIPPPKFLHVAKKF | seqid_3490 |
| variant_4639 | RKKKFKKIPPPKFLHVAKKF | seqid_3491 |
| variant_4640 | FKKKFKKIPPPKFLHVAKKF | seqid_3492 |
| variant_4641 | KWKKFKKIPPPKFLHVAKKF | seqid_3493 |
| variant_4642 | RWKKFKKIPPPKFLHVAKKF | seqid_3494 |
| variant_4643 | FWKKFKKIPPPKFLHVAKKF | seqid_3495 |
| variant_4644 | KKKLLKKIPPPKFLHVAKKF | seqid_3496 |
| variant_4645 | RKKLLKKIPPPKFLHVAKKF | seqid_3497 |
| variant_4646 | FKKLLKKIPPPKFLHVAKKF | seqid_3498 |
| variant_4647 | KWKLLKKIPPPKFLHVAKKF | seqid_3499 |
| variant_4648 | RWKLLKKIPPPKFLHVAKKF | seqid_3500 |
| variant_4649 | FWKLLKKIPPPKFLHVAKKF | seqid_3501 |
| variant_4650 | KKKKLKKIPPPKFLHVAKKF | seqid_3502 |
| variant_4651 | RKKKLKKIPPPKFLHVAKKF | seqid_3503 |
| variant_4652 | FKKKLKKIPPPKFLHVAKKF | seqid_3504 |
| variant_4653 | KWKKLKKIPPPKFLHVAKKF | seqid_3505 |
| variant_4654 | RWKKLKKIPPPKFLHVAKKF | seqid_3506 |
| variant_4655 | FWKKLKKIPPPKFLHVAKKF | seqid_3507 |
| variant_4656 | KKKLFLKIPPKFLHVAKKF | seqid_3508 |
| variant_4657 | RKKLFLKIPPKFLHVAKKF | seqid_3509 |
| variant_4658 | FKKLFLKIPPKFLHVAKKF | seqid_3510 |
| variant_4659 | KWKLFLKIPPKFLHVAKKF | seqid_3511 |
| variant_4660 | RWKLFLKIPPKFLHVAKKF | seqid_3512 |
| variant_4661 | FWKLFLKIPPKFLHVAKKF | seqid_3513 |
| variant_4662 | KKKKFLKIPPKFLHVAKKF | seqid_3514 |
| variant_4663 | RKKKFLKIPPKFLHVAKKF | seqid_3515 |
| variant_4664 | FKKKFLKIPPKFLHVAKKF | seqid_3516 |
| variant_4665 | KWKKFLKIPPKFLHVAKKF | seqid_3517 |
| variant_4666 | RWKKFLKIPPKFLHVAKKF | seqid_3518 |
| variant_4667 | FWKKFLKIPPKFLHVAKKF | seqid_3519 |
| variant_4668 | KKKLLLKIPPKFLHVAKKF | seqid_3520 |
| variant_4669 | RKKLLLKIPPKFLHVAKKF | seqid_3521 |
| variant_4670 | FKKLLLKIPPKFLHVAKKF | seqid_3522 |
| variant_4671 | KWKLLLKIPPKFLHVAKKF | seqid_3523 |
| variant_4672 | RWKLLLKIPPKFLHVAKKF | seqid_3524 |
| variant_4673 | FWKLLLKIPPKFLHVAKKF | seqid_3525 |
| variant_4674 | KKKKLLKIPPKFLHVAKKF | seqid_3526 |
| variant_4675 | RKKKLLKIPPKFLHVAKKF | seqid_3527 |
| variant_4676 | FKKKLLKIPPKFLHVAKKF | seqid_3528 |
| variant_4677 | KWKKLLKIPPKFLHVAKKF | seqid_3529 |
| variant_4678 | RWKKLLKIPPKFLHVAKKF | seqid_3530 |
| variant_4679 | FWKKLLKIPPKFLHVAKKF | seqid_3531 |
| variant_4680 | KKKLFKKIPPKFLHVAKKF | seqid_3532 |
| variant_4681 | RKKLFKKIPPKFLHVAKKF | seqid_3533 |
| variant_4682 | FKKLFKKIPPKFLHVAKKF | seqid_3534 |
| variant_4683 | KWKLFKKIPPKFLHVAKKF | seqid_3535 |
| variant_4684 | RWKLFKKIPPKFLHVAKKF | seqid_3536 |
| variant_4685 | FWKLFKKIPPKFLHVAKKF | seqid_3537 |
| variant_4686 | KKKKFKKIPPKFLHVAKKF | seqid_3538 |
| variant_4687 | RKKKFKKIPPKFLHVAKKF | seqid_3539 |
| variant_4688 | FKKKFKKIPPKFLHVAKKF | seqid_3540 |
| variant_4689 | KWKKFKKIPPKFLHVAKKF | seqid_3541 |
| variant_4690 | RWKKFKKIPPKFLHVAKKF | seqid_3542 |
| variant_4691 | FWKKFKKIPPKFLHVAKKF | seqid_3543 |
| variant_4692 | KKKLLKKIPPKFLHVAKKF | seqid_3544 |
| variant_4693 | RKKLLKKIPPKFLHVAKKF | seqid_3545 |
| variant_4694 | FKKLLKKIPPKFLHVAKKF | seqid_3546 |
| variant_4695 | KWKLLKKIPPKFLHVAKKF | seqid_3547 |
| variant_4696 | RWKLLKKIPPKFLHVAKKF | seqid_3548 |
| variant_4697 | FWKLLKKIPPKFLHVAKKF | seqid_3549 |
| variant_4698 | KKKKLKKIPPKFLHVAKKF | seqid_3550 |
| variant_4699 | RKKKLKKIPPKFLHVAKKF | seqid_3551 |

| variant_4700 | FKKKLKKIPPKFLHVAKKF | seqid_3552 |
| variant_4701 | KWKKLKKIPPKFLHVAKKF | seqid_3553 |
| variant_4702 | RWKKLKKIPPKFLHVAKKF | seqid_3554 |
| variant_4703 | FWKKLKKIPPKFLHVAKKF | seqid_3555 |
| variant_4752 | KKKLFLKIPKFLHVAKKF | seqid_3556 |
| variant_4753 | RKKLFLKIPKFLHVAKKF | seqid_3557 |
| variant_4754 | FKKLFLKIPKFLHVAKKF | seqid_3558 |
| variant_4755 | KWKLFLKIPKFLHVAKKF | seqid_3559 |
| variant_4756 | RWKLFLKIPKFLHVAKKF | seqid_3560 |
| variant_4757 | FWKLFLKIPKFLHVAKKF | seqid_3561 |
| variant_4758 | KKKKFLKIPKFLHVAKKF | seqid_3562 |
| variant_4759 | RKKKFLKIPKFLHVAKKF | seqid_3563 |
| variant_4760 | FKKKFLKIPKFLHVAKKF | seqid_3564 |
| variant_4761 | KWKKFLKIPKFLHVAKKF | seqid_3565 |
| variant_4762 | RWKKFLKIPKFLHVAKKF | seqid_3566 |
| variant_4763 | FWKKFLKIPKFLHVAKKF | seqid_3567 |
| variant_4764 | KKKLLLKIPKFLHVAKKF | seqid_3568 |
| variant_4765 | RKKLLLKIPKFLHVAKKF | seqid_3569 |
| variant_4766 | FKKLLLKIPKFLHVAKKF | seqid_3570 |
| variant_4767 | KWKLLLKIPKFLHVAKKF | seqid_3571 |
| variant_4768 | RWKLLLKIPKFLHVAKKF | seqid_3572 |
| variant_4769 | FWKLLLKIPKFLHVAKKF | seqid_3573 |
| variant_4770 | KKKKLLKIPKFLHVAKKF | seqid_3574 |
| variant_4771 | RKKKLLKIPKFLHVAKKF | seqid_3575 |
| variant_4772 | FKKKLLKIPKFLHVAKKF | seqid_3576 |
| variant_4773 | KWKKLLKIPKFLHVAKKF | seqid_3577 |
| variant_4774 | RWKKLLKIPKFLHVAKKF | seqid_3578 |
| variant_4775 | FWKKLLKIPKFLHVAKKF | seqid_3579 |
| variant_4776 | KKKLFKKIPKFLHVAKKF | seqid_3580 |
| variant_4777 | RKKLFKKIPKFLHVAKKF | seqid_3581 |
| variant_4778 | FKKLFKKIPKFLHVAKKF | seqid_3582 |
| variant_4779 | KWKLFKKIPKFLHVAKKF | seqid_3583 |
| variant_4780 | RWKLFKKIPKFLHVAKKF | seqid_3584 |
| variant_4781 | FWKLFKKIPKFLHVAKKF | seqid_3585 |
| variant_4782 | KKKKFKKIPKFLHVAKKF | seqid_3586 |
| variant_4783 | RKKKFKKIPKFLHVAKKF | seqid_3587 |
| variant_4784 | FKKKFKKIPKFLHVAKKF | seqid_3588 |
| variant_4785 | KWKKFKKIPKFLHVAKKF | seqid_3589 |
| variant_4786 | RWKKFKKIPKFLHVAKKF | seqid_3590 |
| variant_4787 | FWKKFKKIPKFLHVAKKF | seqid_3591 |
| variant_4788 | KKKLLKKIPKFLHVAKKF | seqid_3592 |
| variant_4789 | RKKLLKKIPKFLHVAKKF | seqid_3593 |
| variant_4790 | FKKLLKKIPKFLHVAKKF | seqid_3594 |
| variant_4791 | KWKLLKKIPKFLHVAKKF | seqid_3595 |
| variant_4792 | RWKLLKKIPKFLHVAKKF | seqid_3596 |
| variant_4793 | FWKLLKKIPKFLHVAKKF | seqid_3597 |
| variant_4794 | KKKKLKKIPKFLHVAKKF | seqid_3598 |
| variant_4795 | RKKKLKKIPKFLHVAKKF | seqid_3599 |
| variant_4796 | FKKKLKKIPKFLHVAKKF | seqid_3600 |
| variant_4797 | KWKKLKKIPKFLHVAKKF | seqid_3601 |
| variant_4798 | RWKKLKKIPKFLHVAKKF | seqid_3602 |
| variant_4799 | FWKKLKKIPKFLHVAKKF | seqid_3603 |
| variant_4800 | KKKLFLKIPPPKFKHVAKKF | seqid_3604 |
| variant_4801 | RKKLFLKIPPPKFKHVAKKF | seqid_3605 |
| variant_4802 | FKKLFLKIPPPKFKHVAKKF | seqid_3606 |
| variant_4803 | KWKLFLKIPPPKFKHVAKKF | seqid_3607 |
| variant_4804 | RWKLFLKIPPPKFKHVAKKF | seqid_3608 |
| variant_4805 | FWKLFLKIPPPKFKHVAKKF | seqid_3609 |
| variant_4806 | KKKKFLKIPPPKFKHVAKKF | seqid_3610 |
| variant_4807 | RKKKFLKIPPPKFKHVAKKF | seqid_3611 |
| variant_4808 | FKKKFLKIPPPKFKHVAKKF | seqid_3612 |
| variant_4809 | KWKKFLKIPPPKFKHVAKKF | seqid_3613 |
| variant_4810 | RWKKFLKIPPPKFKHVAKKF | seqid_3614 |
| variant_4811 | FWKKFLKIPPPKFKHVAKKF | seqid_3615 |
| variant_4812 | KKKLLLKIPPPKFKHVAKKF | seqid_3616 |
| variant_4813 | RKKLLLKIPPPKFKHVAKKF | seqid_3617 |
| variant_4814 | FKKLLLKIPPPKFKHVAKKF | seqid_3618 |
| variant_4815 | KWKLLLKIPPPKFKHVAKKF | seqid_3619 |
| variant_4816 | RWKLLLKIPPPKFKHVAKKF | seqid_3620 |
| variant_4817 | FWKLLLKIPPPKFKHVAKKF | seqid_3621 |
| variant_4818 | KKKKLLKIPPPKFKHVAKKF | seqid_3622 |
| variant_4819 | RKKKLLKIPPPKFKHVAKKF | seqid_3623 |
| variant_4820 | FKKKLLKIPPPKFKHVAKKF | seqid_3624 |
| variant_4821 | KWKKLLKIPPPKFKHVAKKF | seqid_3625 |
| variant_4822 | RWKKLLKIPPPKFKHVAKKF | seqid_3626 |
| variant_4823 | FWKKLLKIPPPKFKHVAKKF | seqid_3627 |
| variant_4824 | KKKLFKKIPPPKFKHVAKKF | seqid_3628 |
| variant_4825 | RKKLFKKIPPPKFKHVAKKF | seqid_3629 |
| variant_4826 | FKKLFKKIPPPKFKHVAKKF | seqid_3630 |
| variant_4827 | KWKLFKKIPPPKFKHVAKKF | seqid_3631 |
| variant_4828 | RWKLFKKIPPPKFKHVAKKF | seqid_3632 |

| | | |
|---|---|---|
| variant_4829 | FWKLFKKIPPPKFKHVAKKF | seqid_3633 |
| variant_4830 | KKKKFKKIPPPKFKHVAKKF | seqid_3634 |
| variant_4831 | RKKKFKKIPPPKFKHVAKKF | seqid_3635 |
| variant_4832 | FKKKFKKIPPPKFKHVAKKF | seqid_3636 |
| variant_4833 | KWKKFKKIPPPKFKHVAKKF | seqid_3637 |
| variant_4834 | RWKKFKKIPPPKFKHVAKKF | seqid_3638 |
| variant_4835 | FWKKFKKIPPPKFKHVAKKF | seqid_3639 |
| variant_4836 | KKKLLKKIPPPKFKHVAKKF | seqid_3640 |
| variant_4837 | RKKLLKKIPPPKFKHVAKKF | seqid_3641 |
| variant_4838 | FKKLLKKIPPPKFKHVAKKF | seqid_3642 |
| variant_4839 | KWKLLKKIPPPKFKHVAKKF | seqid_3643 |
| variant_4840 | RWKLLKKIPPPKFKHVAKKF | seqid_3644 |
| variant_4841 | FWKLLKKIPPPKFKHVAKKF | seqid_3645 |
| variant_4842 | KKKKLKKIPPPKFKHVAKKF | seqid_3646 |
| variant_4843 | RKKKLKKIPPPKFKHVAKKF | seqid_3647 |
| variant_4844 | FKKKLKKIPPPKFKHVAKKF | seqid_3648 |
| variant_4845 | KWKKLKKIPPPKFKHVAKKF | seqid_3649 |
| variant_4846 | RWKKLKKIPPPKFKHVAKKF | seqid_3650 |
| variant_4847 | FWKKLKKIPPPKFKHVAKKF | seqid_3651 |
| variant_4848 | KKKLFLKIPPKFKHVAKKF | seqid_3652 |
| variant_4849 | RKKLFLKIPPKFKHVAKKF | seqid_3653 |
| variant_4850 | FKKLFLKIPPKFKHVAKKF | seqid_3654 |
| variant_4851 | KWKLFLKIPPKFKHVAKKF | seqid_3655 |
| variant_4852 | RWKLFLKIPPKFKHVAKKF | seqid_3656 |
| variant_4853 | FWKLFLKIPPKFKHVAKKF | seqid_3657 |
| variant_4854 | KKKKFLKIPPKFKHVAKKF | seqid_3658 |
| variant_4855 | RKKKFLKIPPKFKHVAKKF | seqid_3659 |
| variant_4856 | FKKKFLKIPPKFKHVAKKF | seqid_3660 |
| variant_4857 | KWKKFLKIPPKFKHVAKKF | seqid_3661 |
| variant_4858 | RWKKFLKIPPKFKHVAKKF | seqid_3662 |
| variant_4859 | FWKKFLKIPPKFKHVAKKF | seqid_3663 |
| variant_4860 | KKKLLLKIPPKFKHVAKKF | seqid_3664 |
| variant_4861 | RKKLLLKIPPKFKHVAKKF | seqid_3665 |
| variant_4862 | FKKLLLKIPPKFKHVAKKF | seqid_3666 |
| variant_4863 | KWKLLLKIPPKFKHVAKKF | seqid_3667 |
| variant_4864 | RWKLLLKIPPKFKHVAKKF | seqid_3668 |
| variant_4865 | FWKLLLKIPPKFKHVAKKF | seqid_3669 |
| variant_4866 | KKKKLLKIPPKFKHVAKKF | seqid_3670 |
| variant_4867 | RKKKLLKIPPKFKHVAKKF | seqid_3671 |
| variant_4868 | FKKKLLKIPPKFKHVAKKF | seqid_3672 |
| variant_4869 | KWKKLLKIPPKFKHVAKKF | seqid_3673 |
| variant_4870 | RWKKLLKIPPKFKHVAKKF | seqid_3674 |
| variant_4871 | FWKKLLKIPPKFKHVAKKF | seqid_3675 |
| variant_4872 | KKKLFKKIPPKFKHVAKKF | seqid_3676 |
| variant_4873 | RKKLFKKIPPKFKHVAKKF | seqid_3677 |
| variant_4874 | FKKLFKKIPPKFKHVAKKF | seqid_3678 |
| variant_4875 | KWKLFKKIPPKFKHVAKKF | seqid_3679 |
| variant_4876 | RWKLFKKIPPKFKHVAKKF | seqid_3680 |
| variant_4877 | FWKLFKKIPPKFKHVAKKF | seqid_3681 |
| variant_4878 | KKKKFKKIPPKFKHVAKKF | seqid_3682 |
| variant_4879 | RKKKFKKIPPKFKHVAKKF | seqid_3683 |
| variant_4880 | FKKKFKKIPPKFKHVAKKF | seqid_3684 |
| variant_4881 | KWKKFKKIPPKFKHVAKKF | seqid_3685 |
| variant_4882 | RWKKFKKIPPKFKHVAKKF | seqid_3686 |
| variant_4883 | FWKKFKKIPPKFKHVAKKF | seqid_3687 |
| variant_4884 | KKKLLKKIPPKFKHVAKKF | seqid_3688 |
| variant_4885 | RKKLLKKIPPKFKHVAKKF | seqid_3689 |
| variant_4886 | FKKLLKKIPPKFKHVAKKF | seqid_3690 |
| variant_4887 | KWKLLKKIPPKFKHVAKKF | seqid_3691 |
| variant_4888 | RWKLLKKIPPKFKHVAKKF | seqid_3692 |
| variant_4889 | FWKLLKKIPPKFKHVAKKF | seqid_3693 |
| variant_4890 | KKKKLKKIPPKFKHVAKKF | seqid_3694 |
| variant_4891 | RKKKLKKIPPKFKHVAKKF | seqid_3695 |
| variant_4892 | FKKKLKKIPPKFKHVAKKF | seqid_3696 |
| variant_4893 | KWKKLKKIPPKFKHVAKKF | seqid_3697 |
| variant_4894 | RWKKLKKIPPKFKHVAKKF | seqid_3698 |
| variant_4895 | FWKKLKKIPPKFKHVAKKF | seqid_3699 |
| variant_4944 | KKKLFLKIPKFKHVAKKF | seqid_3700 |
| variant_4945 | RKKLFLKIPKFKHVAKKF | seqid_3701 |
| variant_4946 | FKKLFLKIPKFKHVAKKF | seqid_3702 |
| variant_4947 | KWKLFLKIPKFKHVAKKF | seqid_3703 |
| variant_4948 | RWKLFLKIPKFKHVAKKF | seqid_3704 |
| variant_4949 | FWKLFLKIPKFKHVAKKF | seqid_3705 |
| variant_4950 | KKKKFLKIPKFKHVAKKF | seqid_3706 |
| variant_4951 | RKKKFLKIPKFKHVAKKF | seqid_3707 |
| variant_4952 | FKKKFLKIPKFKHVAKKF | seqid_3708 |
| variant_4953 | KWKKFLKIPKFKHVAKKF | seqid_3709 |
| variant_4954 | RWKKFLKIPKFKHVAKKF | seqid_3710 |
| variant_4955 | FWKKFLKIPKFKHVAKKF | seqid_3711 |
| variant_4956 | KKKLLLKIPKFKHVAKKF | seqid_3712 |
| variant_4957 | RKKLLLKIPKFKHVAKKF | seqid_3713 |

| | | |
|---|---|---|
| variant_4958 | FKKLLLKIPKFKHVAKKF | seqid_3714 |
| variant_4959 | KWKLLLKIPKFKHVAKKF | seqid_3715 |
| variant_4960 | RWKLLLKIPKFKHVAKKF | seqid_3716 |
| variant_4961 | FWKLLLKIPKFKHVAKKF | seqid_3717 |
| variant_4962 | KKKKLLKIPKFKHVAKKF | seqid_3718 |
| variant_4963 | RKKKLLKIPKFKHVAKKF | seqid_3719 |
| variant_4964 | FKKKLLKIPKFKHVAKKF | seqid_3720 |
| variant_4965 | KWKKLLKIPKFKHVAKKF | seqid_3721 |
| variant_4966 | RWKKLLKIPKFKHVAKKF | seqid_3722 |
| variant_4967 | FWKKLLKIPKFKHVAKKF | seqid_3723 |
| variant_4968 | KKKLFKKIPKFKHVAKKF | seqid_3724 |
| variant_4969 | RKKLFKKIPKFKHVAKKF | seqid_3725 |
| variant_4970 | FKKLFKKIPKFKHVAKKF | seqid_3726 |
| variant_4971 | KWKLFKKIPKFKHVAKKF | seqid_3727 |
| variant_4972 | RWKLFKKIPKFKHVAKKF | seqid_3728 |
| variant_4973 | FWKLFKKIPKFKHVAKKF | seqid_3729 |
| variant_4974 | KKKKFKKIPKFKHVAKKF | seqid_3730 |
| variant_4975 | RKKKFKKIPKFKHVAKKF | seqid_3731 |
| variant_4976 | FKKKFKKIPKFKHVAKKF | seqid_3732 |
| variant_4977 | KWKKFKKIPKFKHVAKKF | seqid_3733 |
| variant_4978 | RWKKFKKIPKFKHVAKKF | seqid_3734 |
| variant_4979 | FWKKFKKIPKFKHVAKKF | seqid_3735 |
| variant_4980 | KKKLLKKIPKFKHVAKKF | seqid_3736 |
| variant_4981 | RKKLLKKIPKFKHVAKKF | seqid_3737 |
| variant_4982 | FKKLLKKIPKFKHVAKKF | seqid_3738 |
| variant_4983 | KWKLLKKIPKFKHVAKKF | seqid_3739 |
| variant_4984 | RWKLLKKIPKFKHVAKKF | seqid_3740 |
| variant_4985 | FWKLLKKIPKFKHVAKKF | seqid_3741 |
| variant_4986 | KKKKLKKIPKFKHVAKKF | seqid_3742 |
| variant_4987 | RKKKLKKIPKFKHVAKKF | seqid_3743 |
| variant_4988 | FKKKLKKIPKFKHVAKKF | seqid_3744 |
| variant_4989 | KWKKLKKIPKFKHVAKKF | seqid_3745 |
| variant_4990 | RWKKLKKIPKFKHVAKKF | seqid_3746 |
| variant_4991 | FWKKLKKIPKFKHVAKKF | seqid_3747 |
| variant_4992 | KKKLFLKIPPPKFLKVAKKF | seqid_3748 |
| variant_4993 | RKKLFLKIPPPKFLKVAKKF | seqid_3749 |
| variant_4994 | FKKLFLKIPPPKFLKVAKKF | seqid_3750 |
| variant_4995 | KWKLFLKIPPPKFLKVAKKF | seqid_3751 |
| variant_4996 | RWKLFLKIPPPKFLKVAKKF | seqid_3752 |
| variant_4997 | FWKLFLKIPPPKFLKVAKKF | seqid_3753 |
| variant_4998 | KKKKFLKIPPPKFLKVAKKF | seqid_3754 |
| variant_4999 | RKKKFLKIPPPKFLKVAKKF | seqid_3755 |
| variant_5000 | FKKKFLKIPPPKFLKVAKKF | seqid_3756 |
| variant_5001 | KWKKFLKIPPPKFLKVAKKF | seqid_3757 |
| variant_5002 | RWKKFLKIPPPKFLKVAKKF | seqid_3758 |
| variant_5003 | FWKKFLKIPPPKFLKVAKKF | seqid_3759 |
| variant_5004 | KKKLLLKIPPPKFLKVAKKF | seqid_3760 |
| variant_5005 | RKKLLLKIPPPKFLKVAKKF | seqid_3761 |
| variant_5006 | FKKLLLKIPPPKFLKVAKKF | seqid_3762 |
| variant_5007 | KWKLLLKIPPPKFLKVAKKF | seqid_3763 |
| variant_5008 | RWKLLLKIPPPKFLKVAKKF | seqid_3764 |
| variant_5009 | FWKLLLKIPPPKFLKVAKKF | seqid_3765 |
| variant_5010 | KKKKLLKIPPPKFLKVAKKF | seqid_3766 |
| variant_5011 | RKKKLLKIPPPKFLKVAKKF | seqid_3767 |
| variant_5012 | FKKKLLKIPPPKFLKVAKKF | seqid_3768 |
| variant_5013 | KWKKLLKIPPPKFLKVAKKF | seqid_3769 |
| variant_5014 | RWKKLLKIPPPKFLKVAKKF | seqid_3770 |
| variant_5015 | FWKKLLKIPPPKFLKVAKKF | seqid_3771 |
| variant_5016 | KKKLFKKIPPPKFLKVAKKF | seqid_3772 |
| variant_5017 | RKKLFKKIPPPKFLKVAKKF | seqid_3773 |
| variant_5018 | FKKLFKKIPPPKFLKVAKKF | seqid_3774 |
| variant_5019 | KWKLFKKIPPPKFLKVAKKF | seqid_3775 |
| variant_5020 | RWKLFKKIPPPKFLKVAKKF | seqid_3776 |
| variant_5021 | FWKLFKKIPPPKFLKVAKKF | seqid_3777 |
| variant_5022 | KKKKFKKIPPPKFLKVAKKF | seqid_3778 |
| variant_5023 | RKKKFKKIPPPKFLKVAKKF | seqid_3779 |
| variant_5024 | FKKKFKKIPPPKFLKVAKKF | seqid_3780 |
| variant_5025 | KWKKFKKIPPPKFLKVAKKF | seqid_3781 |
| variant_5026 | RWKKFKKIPPPKFLKVAKKF | seqid_3782 |
| variant_5027 | FWKKFKKIPPPKFLKVAKKF | seqid_3783 |
| variant_5028 | KKKLLKKIPPPKFLKVAKKF | seqid_3784 |
| variant_5029 | RKKLLKKIPPPKFLKVAKKF | seqid_3785 |
| variant_5030 | FKKLLKKIPPPKFLKVAKKF | seqid_3786 |
| variant_5031 | KWKLLKKIPPPKFLKVAKKF | seqid_3787 |
| variant_5032 | RWKLLKKIPPPKFLKVAKKF | seqid_3788 |
| variant_5033 | FWKLLKKIPPPKFLKVAKKF | seqid_3789 |
| variant_5034 | KKKKLKKIPPPKFLKVAKKF | seqid_3790 |
| variant_5035 | RKKKLKKIPPPKFLKVAKKF | seqid_3791 |
| variant_5036 | FKKKLKKIPPPKFLKVAKKF | seqid_3792 |
| variant_5037 | KWKKLKKIPPPKFLKVAKKF | seqid_3793 |
| variant_5038 | RWKKLKKIPPPKFLKVAKKF | seqid_3794 |

| | | |
|---|---|---|
| variant_5039 | FWKKLKKIPPPKFLKVAKKF | seqid_3795 |
| variant_5040 | KKKLFLKIPPKFLKVAKKF | seqid_3796 |
| variant_5041 | RKKLFLKIPPKFLKVAKKF | seqid_3797 |
| variant_5042 | FKKLFLKIPPKFLKVAKKF | seqid_3798 |
| variant_5043 | KWKLFLKIPPKFLKVAKKF | seqid_3799 |
| variant_5044 | RWKLFLKIPPKFLKVAKKF | seqid_3800 |
| variant_5045 | FWKLFLKIPPKFLKVAKKF | seqid_3801 |
| variant_5046 | KKKKFLKIPPKFLKVAKKF | seqid_3802 |
| variant_5047 | RKKKFLKIPPKFLKVAKKF | seqid_3803 |
| variant_5048 | FKKKFLKIPPKFLKVAKKF | seqid_3804 |
| variant_5049 | KWKKFLKIPPKFLKVAKKF | seqid_3805 |
| variant_5050 | RWKKFLKIPPKFLKVAKKF | seqid_3806 |
| variant_5051 | FWKKFLKIPPKFLKVAKKF | seqid_3807 |
| variant_5052 | KKKLLLKIPPKFLKVAKKF | seqid_3808 |
| variant_5053 | RKKLLLKIPPKFLKVAKKF | seqid_3809 |
| variant_5054 | FKKLLLKIPPKFLKVAKKF | seqid_3810 |
| variant_5055 | KWKLLLKIPPKFLKVAKKF | seqid_3811 |
| variant_5056 | RWKLLLKIPPKFLKVAKKF | seqid_3812 |
| variant_5057 | FWKLLLKIPPKFLKVAKKF | seqid_3813 |
| variant_5058 | KKKKLLKIPPKFLKVAKKF | seqid_3814 |
| variant_5059 | RKKKLLKIPPKFLKVAKKF | seqid_3815 |
| variant_5060 | FKKKLLKIPPKFLKVAKKF | seqid_3816 |
| variant_5061 | KWKKLLKIPPKFLKVAKKF | seqid_3817 |
| variant_5062 | RWKKLLKIPPKFLKVAKKF | seqid_3818 |
| variant_5063 | FWKKLLKIPPKFLKVAKKF | seqid_3819 |
| variant_5064 | KKKLFKKIPPKFLKVAKKF | seqid_3820 |
| variant_5065 | RKKLFKKIPPKFLKVAKKF | seqid_3821 |
| variant_5066 | FKKLFKKIPPKFLKVAKKF | seqid_3822 |
| variant_5067 | KWKLFKKIPPKFLKVAKKF | seqid_3823 |
| variant_5068 | RWKLFKKIPPKFLKVAKKF | seqid_3824 |
| variant_5069 | FWKLFKKIPPKFLKVAKKF | seqid_3825 |
| variant_5070 | KKKKFKKIPPKFLKVAKKF | seqid_3826 |
| variant_5071 | RKKKFKKIPPKFLKVAKKF | seqid_3827 |
| variant_5072 | FKKKFKKIPPKFLKVAKKF | seqid_3828 |
| variant_5073 | KWKKFKKIPPKFLKVAKKF | seqid_3829 |
| variant_5074 | RWKKFKKIPPKFLKVAKKF | seqid_3830 |
| variant_5075 | FWKKFKKIPPKFLKVAKKF | seqid_3831 |
| variant_5076 | KKKLLKKIPPKFLKVAKKF | seqid_3832 |
| variant_5077 | RKKLLKKIPPKFLKVAKKF | seqid_3833 |
| variant_5078 | FKKLLKKIPPKFLKVAKKF | seqid_3834 |
| variant_5079 | KWKLLKKIPPKFLKVAKKF | seqid_3835 |
| variant_5080 | RWKLLKKIPPKFLKVAKKF | seqid_3836 |
| variant_5081 | FWKLLKKIPPKFLKVAKKF | seqid_3837 |
| variant_5082 | KKKKLKKIPPKFLKVAKKF | seqid_3838 |
| variant_5083 | RKKKLKKIPPKFLKVAKKF | seqid_3839 |
| variant_5084 | FKKKLKKIPPKFLKVAKKF | seqid_3840 |
| variant_5085 | KWKKLKKIPPKFLKVAKKF | seqid_3841 |
| variant_5086 | RWKKLKKIPPKFLKVAKKF | seqid_3842 |
| variant_5087 | FWKKLKKIPPKFLKVAKKF | seqid_3843 |
| variant_5136 | KKKLFLKIPKFLKVAKKF | seqid_3844 |
| variant_5137 | RKKLFLKIPKFLKVAKKF | seqid_3845 |
| variant_5138 | FKKLFLKIPKFLKVAKKF | seqid_3846 |
| variant_5139 | KWKLFLKIPKFLKVAKKF | seqid_3847 |
| variant_5140 | RWKLFLKIPKFLKVAKKF | seqid_3848 |
| variant_5141 | FWKLFLKIPKFLKVAKKF | seqid_3849 |
| variant_5142 | KKKKFLKIPKFLKVAKKF | seqid_3850 |
| variant_5143 | RKKKFLKIPKFLKVAKKF | seqid_3851 |
| variant_5144 | FKKKFLKIPKFLKVAKKF | seqid_3852 |
| variant_5145 | KWKKFLKIPKFLKVAKKF | seqid_3853 |
| variant_5146 | RWKKFLKIPKFLKVAKKF | seqid_3854 |
| variant_5147 | FWKKFLKIPKFLKVAKKF | seqid_3855 |
| variant_5148 | KKKLLLKIPKFLKVAKKF | seqid_3856 |
| variant_5149 | RKKLLLKIPKFLKVAKKF | seqid_3857 |
| variant_5150 | FKKLLLKIPKFLKVAKKF | seqid_3858 |
| variant_5151 | KWKLLLKIPKFLKVAKKF | seqid_3859 |
| variant_5152 | RWKLLLKIPKFLKVAKKF | seqid_3860 |
| variant_5153 | FWKLLLKIPKFLKVAKKF | seqid_3861 |
| variant_5154 | KKKKLLKIPKFLKVAKKF | seqid_3862 |
| variant_5155 | RKKKLLKIPKFLKVAKKF | seqid_3863 |
| variant_5156 | FKKKLLKIPKFLKVAKKF | seqid_3864 |
| variant_5157 | KWKKLLKIPKFLKVAKKF | seqid_3865 |
| variant_5158 | RWKKLLKIPKFLKVAKKF | seqid_3866 |
| variant_5159 | FWKKLLKIPKFLKVAKKF | seqid_3867 |
| variant_5160 | KKKLFKKIPKFLKVAKKF | seqid_3868 |
| variant_5161 | RKKLFKKIPKFLKVAKKF | seqid_3869 |
| variant_5162 | FKKLFKKIPKFLKVAKKF | seqid_3870 |
| variant_5163 | KWKLFKKIPKFLKVAKKF | seqid_3871 |
| variant_5164 | RWKLFKKIPKFLKVAKKF | seqid_3872 |
| variant_5165 | FWKLFKKIPKFLKVAKKF | seqid_3873 |
| variant_5166 | KKKKFKKIPKFLKVAKKF | seqid_3874 |
| variant_5167 | RKKKFKKIPKFLKVAKKF | seqid_3875 |

| variant | sequence | seqid |
|---|---|---|
| variant_5168 | FKKKFKKIPKFLKVAKKF | seqid_3876 |
| variant_5169 | KWKKFKKIPKFLKVAKKF | seqid_3877 |
| variant_5170 | RWKKFKKIPKFLKVAKKF | seqid_3878 |
| variant_5171 | FWKKFKKIPKFLKVAKKF | seqid_3879 |
| variant_5172 | KKKLLKKIPKFLKVAKKF | seqid_3880 |
| variant_5173 | RKKLLKKIPKFLKVAKKF | seqid_3881 |
| variant_5174 | FKKLLKKIPKFLKVAKKF | seqid_3882 |
| variant_5175 | KWKLLKKIPKFLKVAKKF | seqid_3883 |
| variant_5176 | RWKLLKKIPKFLKVAKKF | seqid_3884 |
| variant_5177 | FWKLLKKIPKFLKVAKKF | seqid_3885 |
| variant_5178 | KKKKLKKIPKFLKVAKKF | seqid_3886 |
| variant_5179 | RKKKLKKIPKFLKVAKKF | seqid_3887 |
| variant_5180 | FKKKLKKIPKFLKVAKKF | seqid_3888 |
| variant_5181 | KWKKLKKIPKFLKVAKKF | seqid_3889 |
| variant_5182 | RWKKLKKIPKFLKVAKKF | seqid_3890 |
| variant_5183 | FWKKLKKIPKFLKVAKKF | seqid_3891 |
| variant_5184 | KKKLFLKIPPPKFKKVAKKF | seqid_3892 |
| variant_5185 | RKKLFLKIPPPKFKKVAKKF | seqid_3893 |
| variant_5186 | FKKLFLKIPPPKFKKVAKKF | seqid_3894 |
| variant_5187 | KWKLFLKIPPPKFKKVAKKF | seqid_3895 |
| variant_5188 | RWKLFLKIPPPKFKKVAKKF | seqid_3896 |
| variant_5189 | FWKLFLKIPPPKFKKVAKKF | seqid_3897 |
| variant_5190 | KKKKFLKIPPPKFKKVAKKF | seqid_3898 |
| variant_5191 | RKKKFLKIPPPKFKKVAKKF | seqid_3899 |
| variant_5192 | FKKKFLKIPPPKFKKVAKKF | seqid_3900 |
| variant_5193 | KWKKFLKIPPPKFKKVAKKF | seqid_3901 |
| variant_5194 | RWKKFLKIPPPKFKKVAKKF | seqid_3902 |
| variant_5195 | FWKKFLKIPPPKFKKVAKKF | seqid_3903 |
| variant_5196 | KKKLLLKIPPPKFKKVAKKF | seqid_3904 |
| variant_5197 | RKKLLLKIPPPKFKKVAKKF | seqid_3905 |
| variant_5198 | FKKLLLKIPPPKFKKVAKKF | seqid_3906 |
| variant_5199 | KWKLLLKIPPPKFKKVAKKF | seqid_3907 |
| variant_5200 | RWKLLLKIPPPKFKKVAKKF | seqid_3908 |
| variant_5201 | FWKLLLKIPPPKFKKVAKKF | seqid_3909 |
| variant_5202 | KKKKLLKIPPPKFKKVAKKF | seqid_3910 |
| variant_5203 | RKKKLLKIPPPKFKKVAKKF | seqid_3911 |
| variant_5204 | FKKKLLKIPPPKFKKVAKKF | seqid_3912 |
| variant_5205 | KWKKLLKIPPPKFKKVAKKF | seqid_3913 |
| variant_5206 | RWKKLLKIPPPKFKKVAKKF | seqid_3914 |
| variant_5207 | FWKKLLKIPPPKFKKVAKKF | seqid_3915 |
| variant_5208 | KKKLFKKIPPPKFKKVAKKF | seqid_3916 |
| variant_5209 | RKKLFKKIPPPKFKKVAKKF | seqid_3917 |
| variant_5210 | FKKLFKKIPPPKFKKVAKKF | seqid_3918 |
| variant_5211 | KWKLFKKIPPPKFKKVAKKF | seqid_3919 |
| variant_5212 | RWKLFKKIPPPKFKKVAKKF | seqid_3920 |
| variant_5213 | FWKLFKKIPPPKFKKVAKKF | seqid_3921 |
| variant_5214 | KKKKFKKIPPPKFKKVAKKF | seqid_3922 |
| variant_5215 | RKKKFKKIPPPKFKKVAKKF | seqid_3923 |
| variant_5216 | FKKKFKKIPPPKFKKVAKKF | seqid_3924 |
| variant_5217 | KWKKFKKIPPPKFKKVAKKF | seqid_3925 |
| variant_5218 | RWKKFKKIPPPKFKKVAKKF | seqid_3926 |
| variant_5219 | FWKKFKKIPPPKFKKVAKKF | seqid_3927 |
| variant_5220 | KKKLLKKIPPPKFKKVAKKF | seqid_3928 |
| variant_5221 | RKKLLKKIPPPKFKKVAKKF | seqid_3929 |
| variant_5222 | FKKLLKKIPPPKFKKVAKKF | seqid_3930 |
| variant_5223 | KWKLLKKIPPPKFKKVAKKF | seqid_3931 |
| variant_5224 | RWKLLKKIPPPKFKKVAKKF | seqid_3932 |
| variant_5225 | FWKLLKKIPPPKFKKVAKKF | seqid_3933 |
| variant_5226 | KKKKLKKIPPPKFKKVAKKF | seqid_3934 |
| variant_5227 | RKKKLKKIPPPKFKKVAKKF | seqid_3935 |
| variant_5228 | FKKKLKKIPPPKFKKVAKKF | seqid_3936 |
| variant_5229 | KWKKLKKIPPPKFKKVAKKF | seqid_3937 |
| variant_5230 | RWKKLKKIPPPKFKKVAKKF | seqid_3938 |
| variant_5231 | FWKKLKKIPPPKFKKVAKKF | seqid_3939 |
| variant_5232 | KKKLFLKIPPKFKKVAKKF | seqid_3940 |
| variant_5233 | RKKLFLKIPPKFKKVAKKF | seqid_3941 |
| variant_5234 | FKKLFLKIPPKFKKVAKKF | seqid_3942 |
| variant_5235 | KWKLFLKIPPKFKKVAKKF | seqid_3943 |
| variant_5236 | RWKLFLKIPPKFKKVAKKF | seqid_3944 |
| variant_5237 | FWKLFLKIPPKFKKVAKKF | seqid_3945 |
| variant_5238 | KKKKFLKIPPKFKKVAKKF | seqid_3946 |
| variant_5239 | RKKKFLKIPPKFKKVAKKF | seqid_3947 |
| variant_5240 | FKKKFLKIPPKFKKVAKKF | seqid_3948 |
| variant_5241 | KWKKFLKIPPKFKKVAKKF | seqid_3949 |
| variant_5242 | RWKKFLKIPPKFKKVAKKF | seqid_3950 |
| variant_5243 | FWKKFLKIPPKFKKVAKKF | seqid_3951 |
| variant_5244 | KKKLLLKIPPKFKKVAKKF | seqid_3952 |
| variant_5245 | RKKLLLKIPPKFKKVAKKF | seqid_3953 |
| variant_5246 | FKKLLLKIPPKFKKVAKKF | seqid_3954 |
| variant_5247 | KWKLLLKIPPKFKKVAKKF | seqid_3955 |
| variant_5248 | RWKLLLKIPPKFKKVAKKF | seqid_3956 |

| | | |
|---|---|---|
| variant_5249 | FWKLLLKIPPKFKKVAKKF | seqid_3957 |
| variant_5250 | KKKKLLKIPPKFKKVAKKF | seqid_3958 |
| variant_5251 | RKKKLLKIPPKFKKVAKKF | seqid_3959 |
| variant_5252 | FKKKLLKIPPKFKKVAKKF | seqid_3960 |
| variant_5253 | KWKKLLKIPPKFKKVAKKF | seqid_3961 |
| variant_5254 | RWKKLLKIPPKFKKVAKKF | seqid_3962 |
| variant_5255 | FWKKLLKIPPKFKKVAKKF | seqid_3963 |
| variant_5256 | KKKLFKKIPPKFKKVAKKF | seqid_3964 |
| variant_5257 | RKKLFKKIPPKFKKVAKKF | seqid_3965 |
| variant_5258 | FKKLFKKIPPKFKKVAKKF | seqid_3966 |
| variant_5259 | KWKLFKKIPPKFKKVAKKF | seqid_3967 |
| variant_5260 | RWKLFKKIPPKFKKVAKKF | seqid_3968 |
| variant_5261 | FWKLFKKIPPKFKKVAKKF | seqid_3969 |
| variant_5262 | KKKKFKKIPPKFKKVAKKF | seqid_3970 |
| variant_5263 | RKKKFKKIPPKFKKVAKKF | seqid_3971 |
| variant_5264 | FKKKFKKIPPKFKKVAKKF | seqid_3972 |
| variant_5265 | KWKKFKKIPPKFKKVAKKF | seqid_3973 |
| variant_5266 | RWKKFKKIPPKFKKVAKKF | seqid_3974 |
| variant_5267 | FWKKFKKIPPKFKKVAKKF | seqid_3975 |
| variant_5268 | KKKLLKKIPPKFKKVAKKF | seqid_3976 |
| variant_5269 | RKKLLKKIPPKFKKVAKKF | seqid_3977 |
| variant_5270 | FKKLLKKIPPKFKKVAKKF | seqid_3978 |
| variant_5271 | KWKLLKKIPPKFKKVAKKF | seqid_3979 |
| variant_5272 | RWKLLKKIPPKFKKVAKKF | seqid_3980 |
| variant_5273 | FWKLLKKIPPKFKKVAKKF | seqid_3981 |
| variant_5274 | KKKKLKKIPPKFKKVAKKF | seqid_3982 |
| variant_5275 | RKKKLKKIPPKFKKVAKKF | seqid_3983 |
| variant_5276 | FKKKLKKIPPKFKKVAKKF | seqid_3984 |
| variant_5277 | KWKKLKKIPPKFKKVAKKF | seqid_3985 |
| variant_5278 | RWKKLKKIPPKFKKVAKKF | seqid_3986 |
| variant_5279 | FWKKLKKIPPKFKKVAKKF | seqid_3987 |
| variant_5328 | KKKLFLKIPKFKKVAKKF | seqid_3988 |
| variant_5329 | RKKLFLKIPKFKKVAKKF | seqid_3989 |
| variant_5330 | FKKLFLKIPKFKKVAKKF | seqid_3990 |
| variant_5331 | KWKLFLKIPKFKKVAKKF | seqid_3991 |
| variant_5332 | RWKLFLKIPKFKKVAKKF | seqid_3992 |
| variant_5333 | FWKLFLKIPKFKKVAKKF | seqid_3993 |
| variant_5334 | KKKKFLKIPKFKKVAKKF | seqid_3994 |
| variant_5335 | RKKKFLKIPKFKKVAKKF | seqid_3995 |
| variant_5336 | FKKKFLKIPKFKKVAKKF | seqid_3996 |
| variant_5337 | KWKKFLKIPKFKKVAKKF | seqid_3997 |
| variant_5338 | RWKKFLKIPKFKKVAKKF | seqid_3998 |
| variant_5339 | FWKKFLKIPKFKKVAKKF | seqid_3999 |
| variant_5340 | KKKLLLKIPKFKKVAKKF | seqid_4000 |
| variant_5341 | RKKLLLKIPKFKKVAKKF | seqid_4001 |
| variant_5342 | FKKLLLKIPKFKKVAKKF | seqid_4002 |
| variant_5343 | KWKLLLKIPKFKKVAKKF | seqid_4003 |
| variant_5344 | RWKLLLKIPKFKKVAKKF | seqid_4004 |
| variant_5345 | FWKLLLKIPKFKKVAKKF | seqid_4005 |
| variant_5346 | KKKKLLKIPKFKKVAKKF | seqid_4006 |
| variant_5347 | RKKKLLKIPKFKKVAKKF | seqid_4007 |
| variant_5348 | FKKKLLKIPKFKKVAKKF | seqid_4008 |
| variant_5349 | KWKKLLKIPKFKKVAKKF | seqid_4009 |
| variant_5350 | RWKKLLKIPKFKKVAKKF | seqid_4010 |
| variant_5351 | FWKKLLKIPKFKKVAKKF | seqid_4011 |
| variant_5352 | KKKLFKKIPKFKKVAKKF | seqid_4012 |
| variant_5353 | RKKLFKKIPKFKKVAKKF | seqid_4013 |
| variant_5354 | FKKLFKKIPKFKKVAKKF | seqid_4014 |
| variant_5355 | KWKLFKKIPKFKKVAKKF | seqid_4015 |
| variant_5356 | RWKLFKKIPKFKKVAKKF | seqid_4016 |
| variant_5357 | FWKLFKKIPKFKKVAKKF | seqid_4017 |
| variant_5358 | KKKKFKKIPKFKKVAKKF | seqid_4018 |
| variant_5359 | RKKKFKKIPKFKKVAKKF | seqid_4019 |
| variant_5360 | FKKKFKKIPKFKKVAKKF | seqid_4020 |
| variant_5361 | KWKKFKKIPKFKKVAKKF | seqid_4021 |
| variant_5362 | RWKKFKKIPKFKKVAKKF | seqid_4022 |
| variant_5363 | FWKKFKKIPKFKKVAKKF | seqid_4023 |
| variant_5364 | KKKLLKKIPKFKKVAKKF | seqid_4024 |
| variant_5365 | RKKLLKKIPKFKKVAKKF | seqid_4025 |
| variant_5366 | FKKLLKKIPKFKKVAKKF | seqid_4026 |
| variant_5367 | KWKLLKKIPKFKKVAKKF | seqid_4027 |
| variant_5368 | RWKLLKKIPKFKKVAKKF | seqid_4028 |
| variant_5369 | FWKLLKKIPKFKKVAKKF | seqid_4029 |
| variant_5370 | KKKKLKKIPKFKKVAKKF | seqid_4030 |
| variant_5371 | RKKKLKKIPKFKKVAKKF | seqid_4031 |
| variant_5372 | FKKKLKKIPKFKKVAKKF | seqid_4032 |
| variant_5373 | KWKKLKKIPKFKKVAKKF | seqid_4033 |
| variant_5374 | RWKKLKKIPKFKKVAKKF | seqid_4034 |
| variant_5375 | FWKKLKKIPKFKKVAKKF | seqid_4035 |
| variant_5376 | KKKLFLKIPPPKFLHSAKKF | seqid_4036 |
| variant_5377 | RKKLFLKIPPPKFLHSAKKF | seqid_4037 |

| variant_5378 | FKKLFLKIPPPKFLHSAKKF | seqid_4038 |
| variant_5379 | KWKLFLKIPPPKFLHSAKKF | seqid_4039 |
| variant_5380 | RWKLFLKIPPPKFLHSAKKF | seqid_4040 |
| variant_5381 | FWKLFLKIPPPKFLHSAKKF | seqid_4041 |
| variant_5382 | KKKKFLKIPPPKFLHSAKKF | seqid_4042 |
| variant_5383 | RKKKFLKIPPPKFLHSAKKF | seqid_4043 |
| variant_5384 | FKKKFLKIPPPKFLHSAKKF | seqid_4044 |
| variant_5385 | KWKKFLKIPPPKFLHSAKKF | seqid_4045 |
| variant_5386 | RWKKFLKIPPPKFLHSAKKF | seqid_4046 |
| variant_5387 | FWKKFLKIPPPKFLHSAKKF | seqid_4047 |
| variant_5388 | KKKLLLKIPPPKFLHSAKKF | seqid_4048 |
| variant_5389 | RKKLLLKIPPPKFLHSAKKF | seqid_4049 |
| variant_5390 | FKKLLLKIPPPKFLHSAKKF | seqid_4050 |
| variant_5391 | KWKLLLKIPPPKFLHSAKKF | seqid_4051 |
| variant_5392 | RWKLLLKIPPPKFLHSAKKF | seqid_4052 |
| variant_5393 | FWKLLLKIPPPKFLHSAKKF | seqid_4053 |
| variant_5394 | KKKKLLKIPPPKFLHSAKKF | seqid_4054 |
| variant_5395 | RKKKLLKIPPPKFLHSAKKF | seqid_4055 |
| variant_5396 | FKKKLLKIPPPKFLHSAKKF | seqid_4056 |
| variant_5397 | KWKKLLKIPPPKFLHSAKKF | seqid_4057 |
| variant_5398 | RWKKLLKIPPPKFLHSAKKF | seqid_4058 |
| variant_5399 | FWKKLLKIPPPKFLHSAKKF | seqid_4059 |
| variant_5400 | KKKLFKKIPPPKFLHSAKKF | seqid_4060 |
| variant_5401 | RKKLFKKIPPPKFLHSAKKF | seqid_4061 |
| variant_5402 | FKKLFKKIPPPKFLHSAKKF | seqid_4062 |
| variant_5403 | KWKLFKKIPPPKFLHSAKKF | seqid_4063 |
| variant_5404 | RWKLFKKIPPPKFLHSAKKF | seqid_4064 |
| variant_5405 | FWKLFKKIPPPKFLHSAKKF | seqid_4065 |
| variant_5406 | KKKKFKKIPPPKFLHSAKKF | seqid_4066 |
| variant_5407 | RKKKFKKIPPPKFLHSAKKF | seqid_4067 |
| variant_5408 | FKKKFKKIPPPKFLHSAKKF | seqid_4068 |
| variant_5409 | KWKKFKKIPPPKFLHSAKKF | seqid_4069 |
| variant_5410 | RWKKFKKIPPPKFLHSAKKF | seqid_4070 |
| variant_5411 | FWKKFKKIPPPKFLHSAKKF | seqid_4071 |
| variant_5412 | KKKLLKKIPPPKFLHSAKKF | seqid_4072 |
| variant_5413 | RKKLLKKIPPPKFLHSAKKF | seqid_4073 |
| variant_5414 | FKKLLKKIPPPKFLHSAKKF | seqid_4074 |
| variant_5415 | KWKLLKKIPPPKFLHSAKKF | seqid_4075 |
| variant_5416 | RWKLLKKIPPPKFLHSAKKF | seqid_4076 |
| variant_5417 | FWKLLKKIPPPKFLHSAKKF | seqid_4077 |
| variant_5418 | KKKKLKKIPPPKFLHSAKKF | seqid_4078 |
| variant_5419 | RKKKLKKIPPPKFLHSAKKF | seqid_4079 |
| variant_5420 | FKKKLKKIPPPKFLHSAKKF | seqid_4080 |
| variant_5421 | KWKKLKKIPPPKFLHSAKKF | seqid_4081 |
| variant_5422 | RWKKLKKIPPPKFLHSAKKF | seqid_4082 |
| variant_5423 | FWKKLKKIPPPKFLHSAKKF | seqid_4083 |
| variant_5424 | KKKLFLKIPPKFLHSAKKF | seqid_4084 |
| variant_5425 | RKKLFLKIPPKFLHSAKKF | seqid_4085 |
| variant_5426 | FKKLFLKIPPKFLHSAKKF | seqid_4086 |
| variant_5427 | KWKLFLKIPPKFLHSAKKF | seqid_4087 |
| variant_5428 | RWKLFLKIPPKFLHSAKKF | seqid_4088 |
| variant_5429 | FWKLFLKIPPKFLHSAKKF | seqid_4089 |
| variant_5430 | KKKKFLKIPPKFLHSAKKF | seqid_4090 |
| variant_5431 | RKKKFLKIPPKFLHSAKKF | seqid_4091 |
| variant_5432 | FKKKFLKIPPKFLHSAKKF | seqid_4092 |
| variant_5433 | KWKKFLKIPPKFLHSAKKF | seqid_4093 |
| variant_5434 | RWKKFLKIPPKFLHSAKKF | seqid_4094 |
| variant_5435 | FWKKFLKIPPKFLHSAKKF | seqid_4095 |
| variant_5436 | KKKLLLKIPPKFLHSAKKF | seqid_4096 |
| variant_5437 | RKKLLLKIPPKFLHSAKKF | seqid_4097 |
| variant_5438 | FKKLLLKIPPKFLHSAKKF | seqid_4098 |
| variant_5439 | KWKLLLKIPPKFLHSAKKF | seqid_4099 |
| variant_5440 | RWKLLLKIPPKFLHSAKKF | seqid_4100 |
| variant_5441 | FWKLLLKIPPKFLHSAKKF | seqid_4101 |
| variant_5442 | KKKKLLKIPPKFLHSAKKF | seqid_4102 |
| variant_5443 | RKKKLLKIPPKFLHSAKKF | seqid_4103 |
| variant_5444 | FKKKLLKIPPKFLHSAKKF | seqid_4104 |
| variant_5445 | KWKKLLKIPPKFLHSAKKF | seqid_4105 |
| variant_5446 | RWKKLLKIPPKFLHSAKKF | seqid_4106 |
| variant_5447 | FWKKLLKIPPKFLHSAKKF | seqid_4107 |
| variant_5448 | KKKLFKKIPPKFLHSAKKF | seqid_4108 |
| variant_5449 | RKKLFKKIPPKFLHSAKKF | seqid_4109 |
| variant_5450 | FKKLFKKIPPKFLHSAKKF | seqid_4110 |
| variant_5451 | KWKLFKKIPPKFLHSAKKF | seqid_4111 |
| variant_5452 | RWKLFKKIPPKFLHSAKKF | seqid_4112 |
| variant_5453 | FWKLFKKIPPKFLHSAKKF | seqid_4113 |
| variant_5454 | KKKKFKKIPPKFLHSAKKF | seqid_4114 |
| variant_5455 | RKKKFKKIPPKFLHSAKKF | seqid_4115 |
| variant_5456 | FKKKFKKIPPKFLHSAKKF | seqid_4116 |
| variant_5457 | KWKKFKKIPPKFLHSAKKF | seqid_4117 |
| variant_5458 | RWKKFKKIPPKFLHSAKKF | seqid_4118 |

| variant_5459 | FWKKFKKIPPKFLHSAKKF | seqid_4119 |
| variant_5460 | KKKLLKKIPPKFLHSAKKF | seqid_4120 |
| variant_5461 | RKKLLKKIPPKFLHSAKKF | seqid_4121 |
| variant_5462 | FKKLLKKIPPKFLHSAKKF | seqid_4122 |
| variant_5463 | KWKLLKKIPPKFLHSAKKF | seqid_4123 |
| variant_5464 | RWKLLKKIPPKFLHSAKKF | seqid_4124 |
| variant_5465 | FWKLLKKIPPKFLHSAKKF | seqid_4125 |
| variant_5466 | KKKKLKKIPPKFLHSAKKF | seqid_4126 |
| variant_5467 | RKKKLKKIPPKFLHSAKKF | seqid_4127 |
| variant_5468 | FKKKLKKIPPKFLHSAKKF | seqid_4128 |
| variant_5469 | KWKKLKKIPPKFLHSAKKF | seqid_4129 |
| variant_5470 | RWKKLKKIPPKFLHSAKKF | seqid_4130 |
| variant_5471 | FWKKLKKIPPKFLHSAKKF | seqid_4131 |
| variant_5520 | KKKLFLKIPKFLHSAKKF | seqid_4132 |
| variant_5521 | RKKLFLKIPKFLHSAKKF | seqid_4133 |
| variant_5522 | FKKLFLKIPKFLHSAKKF | seqid_4134 |
| variant_5523 | KWKLFLKIPKFLHSAKKF | seqid_4135 |
| variant_5524 | RWKLFLKIPKFLHSAKKF | seqid_4136 |
| variant_5525 | FWKLFLKIPKFLHSAKKF | seqid_4137 |
| variant_5526 | KKKKFLKIPKFLHSAKKF | seqid_4138 |
| variant_5527 | RKKKFLKIPKFLHSAKKF | seqid_4139 |
| variant_5528 | FKKKFLKIPKFLHSAKKF | seqid_4140 |
| variant_5529 | KWKKFLKIPKFLHSAKKF | seqid_4141 |
| variant_5530 | RWKKFLKIPKFLHSAKKF | seqid_4142 |
| variant_5531 | FWKKFLKIPKFLHSAKKF | seqid_4143 |
| variant_5532 | KKKLLLKIPKFLHSAKKF | seqid_4144 |
| variant_5533 | RKKLLLKIPKFLHSAKKF | seqid_4145 |
| variant_5534 | FKKLLLKIPKFLHSAKKF | seqid_4146 |
| variant_5535 | KWKLLLKIPKFLHSAKKF | seqid_4147 |
| variant_5536 | RWKLLLKIPKFLHSAKKF | seqid_4148 |
| variant_5537 | FWKLLLKIPKFLHSAKKF | seqid_4149 |
| variant_5538 | KKKKLLKIPKFLHSAKKF | seqid_4150 |
| variant_5539 | RKKKLLKIPKFLHSAKKF | seqid_4151 |
| variant_5540 | FKKKLLKIPKFLHSAKKF | seqid_4152 |
| variant_5541 | KWKKLLKIPKFLHSAKKF | seqid_4153 |
| variant_5542 | RWKKLLKIPKFLHSAKKF | seqid_4154 |
| variant_5543 | FWKKLLKIPKFLHSAKKF | seqid_4155 |
| variant_5544 | KKKLFKKIPKFLHSAKKF | seqid_4156 |
| variant_5545 | RKKLFKKIPKFLHSAKKF | seqid_4157 |
| variant_5546 | FKKLFKKIPKFLHSAKKF | seqid_4158 |
| variant_5547 | KWKLFKKIPKFLHSAKKF | seqid_4159 |
| variant_5548 | RWKLFKKIPKFLHSAKKF | seqid_4160 |
| variant_5549 | FWKLFKKIPKFLHSAKKF | seqid_4161 |
| variant_5550 | KKKKFKKIPKFLHSAKKF | seqid_4162 |
| variant_5551 | RKKKFKKIPKFLHSAKKF | seqid_4163 |
| variant_5552 | FKKKFKKIPKFLHSAKKF | seqid_4164 |
| variant_5553 | KWKKFKKIPKFLHSAKKF | seqid_4165 |
| variant_5554 | RWKKFKKIPKFLHSAKKF | seqid_4166 |
| variant_5555 | FWKKFKKIPKFLHSAKKF | seqid_4167 |
| variant_5556 | KKKLLKKIPKFLHSAKKF | seqid_4168 |
| variant_5557 | RKKLLKKIPKFLHSAKKF | seqid_4169 |
| variant_5558 | FKKLLKKIPKFLHSAKKF | seqid_4170 |
| variant_5559 | KWKLLKKIPKFLHSAKKF | seqid_4171 |
| variant_5560 | RWKLLKKIPKFLHSAKKF | seqid_4172 |
| variant_5561 | FWKLLKKIPKFLHSAKKF | seqid_4173 |
| variant_5562 | KKKKLKKIPKFLHSAKKF | seqid_4174 |
| variant_5563 | RKKKLKKIPKFLHSAKKF | seqid_4175 |
| variant_5564 | FKKKLKKIPKFLHSAKKF | seqid_4176 |
| variant_5565 | KWKKLKKIPKFLHSAKKF | seqid_4177 |
| variant_5566 | RWKKLKKIPKFLHSAKKF | seqid_4178 |
| variant_5567 | FWKKLKKIPKFLHSAKKF | seqid_4179 |
| variant_5568 | KKKLFLKIPPPKFKHSAKKF | seqid_4180 |
| variant_5569 | RKKLFLKIPPPKFKHSAKKF | seqid_4181 |
| variant_5570 | FKKLFLKIPPPKFKHSAKKF | seqid_4182 |
| variant_5571 | KWKLFLKIPPPKFKHSAKKF | seqid_4183 |
| variant_5572 | RWKLFLKIPPPKFKHSAKKF | seqid_4184 |
| variant_5573 | FWKLFLKIPPPKFKHSAKKF | seqid_4185 |
| variant_5574 | KKKKFLKIPPPKFKHSAKKF | seqid_4186 |
| variant_5575 | RKKKFLKIPPPKFKHSAKKF | seqid_4187 |
| variant_5576 | FKKKFLKIPPPKFKHSAKKF | seqid_4188 |
| variant_5577 | KWKKFLKIPPPKFKHSAKKF | seqid_4189 |
| variant_5578 | RWKKFLKIPPPKFKHSAKKF | seqid_4190 |
| variant_5579 | FWKKFLKIPPPKFKHSAKKF | seqid_4191 |
| variant_5580 | KKKLLLKIPPPKFKHSAKKF | seqid_4192 |
| variant_5581 | RKKLLLKIPPPKFKHSAKKF | seqid_4193 |
| variant_5582 | FKKLLLKIPPPKFKHSAKKF | seqid_4194 |
| variant_5583 | KWKLLLKIPPPKFKHSAKKF | seqid_4195 |
| variant_5584 | RWKLLLKIPPPKFKHSAKKF | seqid_4196 |
| variant_5585 | FWKLLLKIPPPKFKHSAKKF | seqid_4197 |
| variant_5586 | KKKKLLKIPPPKFKHSAKKF | seqid_4198 |
| variant_5587 | RKKKLLKIPPPKFKHSAKKF | seqid_4199 |

| | | |
|---|---|---|
| variant_5588 | FKKKLLKIPPPKFKHSAKKF | seqid_4200 |
| variant_5589 | KWKKLLKIPPPKFKHSAKKF | seqid_4201 |
| variant_5590 | RWKKLLKIPPPKFKHSAKKF | seqid_4202 |
| variant_5591 | FWKKLLKIPPPKFKHSAKKF | seqid_4203 |
| variant_5592 | KKKLFKKIPPPKFKHSAKKF | seqid_4204 |
| variant_5593 | RKKLFKKIPPPKFKHSAKKF | seqid_4205 |
| variant_5594 | FKKLFKKIPPPKFKHSAKKF | seqid_4206 |
| variant_5595 | KWKLFKKIPPPKFKHSAKKF | seqid_4207 |
| variant_5596 | RWKLFKKIPPPKFKHSAKKF | seqid_4208 |
| variant_5597 | FWKLFKKIPPPKFKHSAKKF | seqid_4209 |
| variant_5598 | KKKKFKKIPPPKFKHSAKKF | seqid_4210 |
| variant_5599 | RKKKFKKIPPPKFKHSAKKF | seqid_4211 |
| variant_5600 | FKKKFKKIPPPKFKHSAKKF | seqid_4212 |
| variant_5601 | KWKKFKKIPPPKFKHSAKKF | seqid_4213 |
| variant_5602 | RWKKFKKIPPPKFKHSAKKF | seqid_4214 |
| variant_5603 | FWKKFKKIPPPKFKHSAKKF | seqid_4215 |
| variant_5604 | KKKLLKKIPPPKFKHSAKKF | seqid_4216 |
| variant_5605 | RKKLLKKIPPPKFKHSAKKF | seqid_4217 |
| variant_5606 | FKKLLKKIPPPKFKHSAKKF | seqid_4218 |
| variant_5607 | KWKLLKKIPPPKFKHSAKKF | seqid_4219 |
| variant_5608 | RWKLLKKIPPPKFKHSAKKF | seqid_4220 |
| variant_5609 | FWKLLKKIPPPKFKHSAKKF | seqid_4221 |
| variant_5610 | KKKKLKKIPPPKFKHSAKKF | seqid_4222 |
| variant_5611 | RKKKLKKIPPPKFKHSAKKF | seqid_4223 |
| variant_5612 | FKKKLKKIPPPKFKHSAKKF | seqid_4224 |
| variant_5613 | KWKKLKKIPPPKFKHSAKKF | seqid_4225 |
| variant_5614 | RWKKLKKIPPPKFKHSAKKF | seqid_4226 |
| variant_5615 | FWKKLKKIPPPKFKHSAKKF | seqid_4227 |
| variant_5616 | KKKLFLKIPPKFKHSAKKF | seqid_4228 |
| variant_5617 | RKKLFLKIPPKFKHSAKKF | seqid_4229 |
| variant_5618 | FKKLFLKIPPKFKHSAKKF | seqid_4230 |
| variant_5619 | KWKLFLKIPPKFKHSAKKF | seqid_4231 |
| variant_5620 | RWKLFLKIPPKFKHSAKKF | seqid_4232 |
| variant_5621 | FWKLFLKIPPKFKHSAKKF | seqid_4233 |
| variant_5622 | KKKKFLKIPPKFKHSAKKF | seqid_4234 |
| variant_5623 | RKKKFLKIPPKFKHSAKKF | seqid_4235 |
| variant_5624 | FKKKFLKIPPKFKHSAKKF | seqid_4236 |
| variant_5625 | KWKKFLKIPPKFKHSAKKF | seqid_4237 |
| variant_5626 | RWKKFLKIPPKFKHSAKKF | seqid_4238 |
| variant_5627 | FWKKFLKIPPKFKHSAKKF | seqid_4239 |
| variant_5628 | KKKLLLKIPPKFKHSAKKF | seqid_4240 |
| variant_5629 | RKKLLLKIPPKFKHSAKKF | seqid_4241 |
| variant_5630 | FKKLLLKIPPKFKHSAKKF | seqid_4242 |
| variant_5631 | KWKLLLKIPPKFKHSAKKF | seqid_4243 |
| variant_5632 | RWKLLLKIPPKFKHSAKKF | seqid_4244 |
| variant_5633 | FWKLLLKIPPKFKHSAKKF | seqid_4245 |
| variant_5634 | KKKKLLKIPPKFKHSAKKF | seqid_4246 |
| variant_5635 | RKKKLLKIPPKFKHSAKKF | seqid_4247 |
| variant_5636 | FKKKLLKIPPKFKHSAKKF | seqid_4248 |
| variant_5637 | KWKKLLKIPPKFKHSAKKF | seqid_4249 |
| variant_5638 | RWKKLLKIPPKFKHSAKKF | seqid_4250 |
| variant_5639 | FWKKLLKIPPKFKHSAKKF | seqid_4251 |
| variant_5640 | KKKLFKKIPPKFKHSAKKF | seqid_4252 |
| variant_5641 | RKKLFKKIPPKFKHSAKKF | seqid_4253 |
| variant_5642 | FKKLFKKIPPKFKHSAKKF | seqid_4254 |
| variant_5643 | KWKLFKKIPPKFKHSAKKF | seqid_4255 |
| variant_5644 | RWKLFKKIPPKFKHSAKKF | seqid_4256 |
| variant_5645 | FWKLFKKIPPKFKHSAKKF | seqid_4257 |
| variant_5646 | KKKKFKKIPPKFKHSAKKF | seqid_4258 |
| variant_5647 | RKKKFKKIPPKFKHSAKKF | seqid_4259 |
| variant_5648 | FKKKFKKIPPKFKHSAKKF | seqid_4260 |
| variant_5649 | KWKKFKKIPPKFKHSAKKF | seqid_4261 |
| variant_5650 | RWKKFKKIPPKFKHSAKKF | seqid_4262 |
| variant_5651 | FWKKFKKIPPKFKHSAKKF | seqid_4263 |
| variant_5652 | KKKLLKKIPPKFKHSAKKF | seqid_4264 |
| variant_5653 | RKKLLKKIPPKFKHSAKKF | seqid_4265 |
| variant_5654 | FKKLLKKIPPKFKHSAKKF | seqid_4266 |
| variant_5655 | KWKLLKKIPPKFKHSAKKF | seqid_4267 |
| variant_5656 | RWKLLKKIPPKFKHSAKKF | seqid_4268 |
| variant_5657 | FWKLLKKIPPKFKHSAKKF | seqid_4269 |
| variant_5658 | KKKKLKKIPPKFKHSAKKF | seqid_4270 |
| variant_5659 | RKKKLKKIPPKFKHSAKKF | seqid_4271 |
| variant_5660 | FKKKLKKIPPKFKHSAKKF | seqid_4272 |
| variant_5661 | KWKKLKKIPPKFKHSAKKF | seqid_4273 |
| variant_5662 | RWKKLKKIPPKFKHSAKKF | seqid_4274 |
| variant_5663 | FWKKLKKIPPKFKHSAKKF | seqid_4275 |
| variant_5712 | KKKLFLKIPKFKHSAKKF | seqid_4276 |
| variant_5713 | RKKLFLKIPKFKHSAKKF | seqid_4277 |
| variant_5714 | FKKLFLKIPKFKHSAKKF | seqid_4278 |
| variant_5715 | KWKLFLKIPKFKHSAKKF | seqid_4279 |
| variant_5716 | RWKLFLKIPKFKHSAKKF | seqid_4280 |

| variant | sequence | seqid |
|---|---|---|
| variant_5717 | FWKLFLKIPKFKHSAKKF | seqid_4281 |
| variant_5718 | KKKKFLKIPKFKHSAKKF | seqid_4282 |
| variant_5719 | RKKKFLKIPKFKHSAKKF | seqid_4283 |
| variant_5720 | FKKKFLKIPKFKHSAKKF | seqid_4284 |
| variant_5721 | KWKKFLKIPKFKHSAKKF | seqid_4285 |
| variant_5722 | RWKKFLKIPKFKHSAKKF | seqid_4286 |
| variant_5723 | FWKKFLKIPKFKHSAKKF | seqid_4287 |
| variant_5724 | KKKLLLKIPKFKHSAKKF | seqid_4288 |
| variant_5725 | RKKLLLKIPKFKHSAKKF | seqid_4289 |
| variant_5726 | FKKLLLKIPKFKHSAKKF | seqid_4290 |
| variant_5727 | KWKLLLKIPKFKHSAKKF | seqid_4291 |
| variant_5728 | RWKLLLKIPKFKHSAKKF | seqid_4292 |
| variant_5729 | FWKLLLKIPKFKHSAKKF | seqid_4293 |
| variant_5730 | KKKKLLKIPKFKHSAKKF | seqid_4294 |
| variant_5731 | RKKKLLKIPKFKHSAKKF | seqid_4295 |
| variant_5732 | FKKKLLKIPKFKHSAKKF | seqid_4296 |
| variant_5733 | KWKKLLKIPKFKHSAKKF | seqid_4297 |
| variant_5734 | RWKKLLKIPKFKHSAKKF | seqid_4298 |
| variant_5735 | FWKKLLKIPKFKHSAKKF | seqid_4299 |
| variant_5736 | KKKLFKKIPKFKHSAKKF | seqid_4300 |
| variant_5737 | RKKLFKKIPKFKHSAKKF | seqid_4301 |
| variant_5738 | FKKLFKKIPKFKHSAKKF | seqid_4302 |
| variant_5739 | KWKLFKKIPKFKHSAKKF | seqid_4303 |
| variant_5740 | RWKLFKKIPKFKHSAKKF | seqid_4304 |
| variant_5741 | FWKLFKKIPKFKHSAKKF | seqid_4305 |
| variant_5742 | KKKKFKKIPKFKHSAKKF | seqid_4306 |
| variant_5743 | RKKKFKKIPKFKHSAKKF | seqid_4307 |
| variant_5744 | FKKKFKKIPKFKHSAKKF | seqid_4308 |
| variant_5745 | KWKKFKKIPKFKHSAKKF | seqid_4309 |
| variant_5746 | RWKKFKKIPKFKHSAKKF | seqid_4310 |
| variant_5747 | FWKKFKKIPKFKHSAKKF | seqid_4311 |
| variant_5748 | KKKLLKKIPKFKHSAKKF | seqid_4312 |
| variant_5749 | RKKLLKKIPKFKHSAKKF | seqid_4313 |
| variant_5750 | FKKLLKKIPKFKHSAKKF | seqid_4314 |
| variant_5751 | KWKLLKKIPKFKHSAKKF | seqid_4315 |
| variant_5752 | RWKLLKKIPKFKHSAKKF | seqid_4316 |
| variant_5753 | FWKLLKKIPKFKHSAKKF | seqid_4317 |
| variant_5754 | KKKKLKKIPKFKHSAKKF | seqid_4318 |
| variant_5755 | RKKKLKKIPKFKHSAKKF | seqid_4319 |
| variant_5756 | FKKKLKKIPKFKHSAKKF | seqid_4320 |
| variant_5757 | KWKKLKKIPKFKHSAKKF | seqid_4321 |
| variant_5758 | RWKKLKKIPKFKHSAKKF | seqid_4322 |
| variant_5759 | FWKKLKKIPKFKHSAKKF | seqid_4323 |
| variant_5760 | KKKLFLKIPPPKFLKSAKKF | seqid_4324 |
| variant_5761 | RKKLFLKIPPPKFLKSAKKF | seqid_4325 |
| variant_5762 | FKKLFLKIPPPKFLKSAKKF | seqid_4326 |
| variant_5763 | KWKLFLKIPPPKFLKSAKKF | seqid_4327 |
| variant_5764 | RWKLFLKIPPPKFLKSAKKF | seqid_4328 |
| variant_5765 | FWKLFLKIPPPKFLKSAKKF | seqid_4329 |
| variant_5766 | KKKKFLKIPPPKFLKSAKKF | seqid_4330 |
| variant_5767 | RKKKFLKIPPPKFLKSAKKF | seqid_4331 |
| variant_5768 | FKKKFLKIPPPKFLKSAKKF | seqid_4332 |
| variant_5769 | KWKKFLKIPPPKFLKSAKKF | seqid_4333 |
| variant_5770 | RWKKFLKIPPPKFLKSAKKF | seqid_4334 |
| variant_5771 | FWKKFLKIPPPKFLKSAKKF | seqid_4335 |
| variant_5772 | KKKLLLKIPPPKFLKSAKKF | seqid_4336 |
| variant_5773 | RKKLLLKIPPPKFLKSAKKF | seqid_4337 |
| variant_5774 | FKKLLLKIPPPKFLKSAKKF | seqid_4338 |
| variant_5775 | KWKLLLKIPPPKFLKSAKKF | seqid_4339 |
| variant_5776 | RWKLLLKIPPPKFLKSAKKF | seqid_4340 |
| variant_5777 | FWKLLLKIPPPKFLKSAKKF | seqid_4341 |
| variant_5778 | KKKKLLKIPPPKFLKSAKKF | seqid_4342 |
| variant_5779 | RKKKLLKIPPPKFLKSAKKF | seqid_4343 |
| variant_5780 | FKKKLLKIPPPKFLKSAKKF | seqid_4344 |
| variant_5781 | KWKKLLKIPPPKFLKSAKKF | seqid_4345 |
| variant_5782 | RWKKLLKIPPPKFLKSAKKF | seqid_4346 |
| variant_5783 | FWKKLLKIPPPKFLKSAKKF | seqid_4347 |
| variant_5784 | KKKLFKKIPPPKFLKSAKKF | seqid_4348 |
| variant_5785 | RKKLFKKIPPPKFLKSAKKF | seqid_4349 |
| variant_5786 | FKKLFKKIPPPKFLKSAKKF | seqid_4350 |
| variant_5787 | KWKLFKKIPPPKFLKSAKKF | seqid_4351 |
| variant_5788 | RWKLFKKIPPPKFLKSAKKF | seqid_4352 |
| variant_5789 | FWKLFKKIPPPKFLKSAKKF | seqid_4353 |
| variant_5790 | KKKKFKKIPPPKFLKSAKKF | seqid_4354 |
| variant_5791 | RKKKFKKIPPPKFLKSAKKF | seqid_4355 |
| variant_5792 | FKKKFKKIPPPKFLKSAKKF | seqid_4356 |
| variant_5793 | KWKKFKKIPPPKFLKSAKKF | seqid_4357 |
| variant_5794 | RWKKFKKIPPPKFLKSAKKF | seqid_4358 |
| variant_5795 | FWKKFKKIPPPKFLKSAKKF | seqid_4359 |
| variant_5796 | KKKLLKKIPPPKFLKSAKKF | seqid_4360 |
| variant_5797 | RKKLLKKIPPPKFLKSAKKF | seqid_4361 |

-continued

| | | |
|---|---|---|
| variant_5798 | FKKLLKKIPPPKFLKSAKKF | seqid_4362 |
| variant_5799 | KWKLLKKIPPPKFLKSAKKF | seqid_4363 |
| variant_5800 | RWKLLKKIPPPKFLKSAKKF | seqid_4364 |
| variant_5801 | FWKLLKKIPPPKFLKSAKKF | seqid_4365 |
| variant_5802 | KKKKLKKIPPPKFLKSAKKF | seqid_4366 |
| variant_5803 | RKKKLKKIPPPKFLKSAKKF | seqid_4367 |
| variant_5804 | FKKKLKKIPPPKFLKSAKKF | seqid_4368 |
| variant_5805 | KWKKLKKIPPPKFLKSAKKF | seqid_4369 |
| variant_5806 | RWKKLKKIPPPKFLKSAKKF | seqid_4370 |
| variant_5807 | FWKKLKKIPPPKFLKSAKKF | seqid_4371 |
| variant_5808 | KKKLFLKIPPKFLKSAKKF | seqid_4372 |
| variant_5809 | RKKLFLKIPPKFLKSAKKF | seqid_4373 |
| variant_5810 | FKKLFLKIPPKFLKSAKKF | seqid_4374 |
| variant_5811 | KWKLFLKIPPKFLKSAKKF | seqid_4375 |
| variant_5812 | RWKLFLKIPPKFLKSAKKF | seqid_4376 |
| variant_5813 | FWKLFLKIPPKFLKSAKKF | seqid_4377 |
| variant_5814 | KKKKFLKIPPKFLKSAKKF | seqid_4378 |
| variant_5815 | RKKKFLKIPPKFLKSAKKF | seqid_4379 |
| variant_5816 | FKKKFLKIPPKFLKSAKKF | seqid_4380 |
| variant_5817 | KWKKFLKIPPKFLKSAKKF | seqid_4381 |
| variant_5818 | RWKKFLKIPPKFLKSAKKF | seqid_4382 |
| variant_5819 | FWKKFLKIPPKFLKSAKKF | seqid_4383 |
| variant_5820 | KKKLLLKIPPKFLKSAKKF | seqid_4384 |
| variant_5821 | RKKLLLKIPPKFLKSAKKF | seqid_4385 |
| variant_5822 | FKKLLLKIPPKFLKSAKKF | seqid_4386 |
| variant_5823 | KWKLLLKIPPKFLKSAKKF | seqid_4387 |
| variant_5824 | RWKLLLKIPPKFLKSAKKF | seqid_4388 |
| variant_5825 | FWKLLLKIPPKFLKSAKKF | seqid_4389 |
| variant_5826 | KKKKLLKIPPKFLKSAKKF | seqid_4390 |
| variant_5827 | RKKKLLKIPPKFLKSAKKF | seqid_4391 |
| variant_5828 | FKKKLLKIPPKFLKSAKKF | seqid_4392 |
| variant_5829 | KWKKLLKIPPKFLKSAKKF | seqid_4393 |
| variant_5830 | RWKKLLKIPPKFLKSAKKF | seqid_4394 |
| variant_5831 | FWKKLLKIPPKFLKSAKKF | seqid_4395 |
| variant_5832 | KKKLFKKIPPKFLKSAKKF | seqid_4396 |
| variant_5833 | RKKLFKKIPPKFLKSAKKF | seqid_4397 |
| variant_5834 | FKKLFKKIPPKFLKSAKKF | seqid_4398 |
| variant_5835 | KWKLFKKIPPKFLKSAKKF | seqid_4399 |
| variant_5836 | RWKLFKKIPPKFLKSAKKF | seqid_4400 |
| variant_5837 | FWKLFKKIPPKFLKSAKKF | seqid_4401 |
| variant_5838 | KKKKFKKIPPKFLKSAKKF | seqid_4402 |
| variant_5839 | RKKKFKKIPPKFLKSAKKF | seqid_4403 |
| variant_5840 | FKKKFKKIPPKFLKSAKKF | seqid_4404 |
| variant_5841 | KWKKFKKIPPKFLKSAKKF | seqid_4405 |
| variant_5842 | RWKKFKKIPPKFLKSAKKF | seqid_4406 |
| variant_5843 | FWKKFKKIPPKFLKSAKKF | seqid_4407 |
| variant_5844 | KKKLLKKIPPKFLKSAKKF | seqid_4408 |
| variant_5845 | RKKLLKKIPPKFLKSAKKF | seqid_4409 |
| variant_5846 | FKKLLKKIPPKFLKSAKKF | seqid_4410 |
| variant_5847 | KWKLLKKIPPKFLKSAKKF | seqid_4411 |
| variant_5848 | RWKLLKKIPPKFLKSAKKF | seqid_4412 |
| variant_5849 | FWKLLKKIPPKFLKSAKKF | seqid_4413 |
| variant_5850 | KKKKLKKIPPKFLKSAKKF | seqid_4414 |
| variant_5851 | RKKKLKKIPPKFLKSAKKF | seqid_4415 |
| variant_5852 | FKKKLKKIPPKFLKSAKKF | seqid_4416 |
| variant_5853 | KWKKLKKIPPKFLKSAKKF | seqid_4417 |
| variant_5854 | RWKKLKKIPPKFLKSAKKF | seqid_4418 |
| variant_5855 | FWKKLKKIPPKFLKSAKKF | seqid_4419 |
| variant_5904 | KKKLFLKIPKFLKSAKKF | seqid_4420 |
| variant_5905 | RKKLFLKIPKFLKSAKKF | seqid_4421 |
| variant_5906 | FKKLFLKIPKFLKSAKKF | seqid_4422 |
| variant_5907 | KWKLFLKIPKFLKSAKKF | seqid_4423 |
| variant_5908 | RWKLFLKIPKFLKSAKKF | seqid_4424 |
| variant_5909 | FWKLFLKIPKFLKSAKKF | seqid_4425 |
| variant_5910 | KKKKFLKIPKFLKSAKKF | seqid_4426 |
| variant_5911 | RKKKFLKIPKFLKSAKKF | seqid_4427 |
| variant_5912 | FKKKFLKIPKFLKSAKKF | seqid_4428 |
| variant_5913 | KWKKFLKIPKFLKSAKKF | seqid_4429 |
| variant_5914 | RWKKFLKIPKFLKSAKKF | seqid_4430 |
| variant_5915 | FWKKFLKIPKFLKSAKKF | seqid_4431 |
| variant_5916 | KKKLLLKIPKFLKSAKKF | seqid_4432 |
| variant_5917 | RKKLLLKIPKFLKSAKKF | seqid_4433 |
| variant_5918 | FKKLLLKIPKFLKSAKKF | seqid_4434 |
| variant_5919 | KWKLLLKIPKFLKSAKKF | seqid_4435 |
| variant_5920 | RWKLLLKIPKFLKSAKKF | seqid_4436 |
| variant_5921 | FWKLLLKIPKFLKSAKKF | seqid_4437 |
| variant_5922 | KKKKLLKIPKFLKSAKKF | seqid_4438 |
| variant_5923 | RKKKLLKIPKFLKSAKKF | seqid_4439 |
| variant_5924 | FKKKLLKIPKFLKSAKKF | seqid_4440 |
| variant_5925 | KWKKLLKIPKFLKSAKKF | seqid_4441 |
| variant_5926 | RWKKLLKIPKFLKSAKKF | seqid_4442 |

-continued

| | | |
|---|---|---|
| variant_5927 | FWKKLLKIPKFLKSAKKF | seqid_4443 |
| variant_5928 | KKKLFKKIPKFLKSAKKF | seqid_4444 |
| variant_5929 | RKKLFKKIPKFLKSAKKF | seqid_4445 |
| variant_5930 | FKKLFKKIPKFLKSAKKF | seqid_4446 |
| variant_5931 | KWKLFKKIPKFLKSAKKF | seqid_4447 |
| variant_5932 | RWKLFKKIPKFLKSAKKF | seqid_4448 |
| variant_5933 | FWKLFKKIPKFLKSAKKF | seqid_4449 |
| variant_5934 | KKKKFKKIPKFLKSAKKF | seqid_4450 |
| variant_5935 | RKKKFKKIPKFLKSAKKF | seqid_4451 |
| variant_5936 | FKKKFKKIPKFLKSAKKF | seqid_4452 |
| variant_5937 | KWKKFKKIPKFLKSAKKF | seqid_4453 |
| variant_5938 | RWKKFKKIPKFLKSAKKF | seqid_4454 |
| variant_5939 | FWKKFKKIPKFLKSAKKF | seqid_4455 |
| variant_5940 | KKKLLKKIPKFLKSAKKF | seqid_4456 |
| variant_5941 | RKKLLKKIPKFLKSAKKF | seqid_4457 |
| variant_5942 | FKKLLKKIPKFLKSAKKF | seqid_4458 |
| variant_5943 | KWKLLKKIPKFLKSAKKF | seqid_4459 |
| variant_5944 | RWKLLKKIPKFLKSAKKF | seqid_4460 |
| variant_5945 | FWKLLKKIPKFLKSAKKF | seqid_4461 |
| variant_5946 | KKKKLKKIPKFLKSAKKF | seqid_4462 |
| variant_5947 | RKKKLKKIPKFLKSAKKF | seqid_4463 |
| variant_5948 | FKKKLKKIPKFLKSAKKF | seqid_4464 |
| variant_5949 | KWKKLKKIPKFLKSAKKF | seqid_4465 |
| variant_5950 | RWKKLKKIPKFLKSAKKF | seqid_4466 |
| variant_5951 | FWKKLKKIPKFLKSAKKF | seqid_4467 |
| variant_5952 | KKKLFLKIPPPKFKKSAKKF | seqid_4468 |
| variant_5953 | RKKLFLKIPPPKFKKSAKKF | seqid_4469 |
| variant_5954 | FKKLFLKIPPPKFKKSAKKF | seqid_4470 |
| variant_5955 | KWKLFLKIPPPKFKKSAKKF | seqid_4471 |
| variant_5956 | RWKLFLKIPPPKFKKSAKKF | seqid_4472 |
| variant_5957 | FWKLFLKIPPPKFKKSAKKF | seqid_4473 |
| variant_5958 | KKKKFLKIPPPKFKKSAKKF | seqid_4474 |
| variant_5959 | RKKKFLKIPPPKFKKSAKKF | seqid_4475 |
| variant_5960 | FKKKFLKIPPPKFKKSAKKF | seqid_4476 |
| variant_5961 | KWKKFLKIPPPKFKKSAKKF | seqid_4477 |
| variant_5962 | RWKKFLKIPPPKFKKSAKKF | seqid_4478 |
| variant_5963 | FWKKFLKIPPPKFKKSAKKF | seqid_4479 |
| variant_5964 | KKKLLLKIPPPKFKKSAKKF | seqid_4480 |
| variant_5965 | RKKLLLKIPPPKFKKSAKKF | seqid_4481 |
| variant_5966 | FKKLLLKIPPPKFKKSAKKF | seqid_4482 |
| variant_5967 | KWKLLLKIPPPKFKKSAKKF | seqid_4483 |
| variant_5968 | RWKLLLKIPPPKFKKSAKKF | seqid_4484 |
| variant_5969 | FWKLLLKIPPPKFKKSAKKF | seqid_4485 |
| variant_5970 | KKKKLLKIPPPKFKKSAKKF | seqid_4486 |
| variant_5971 | RKKKLLKIPPPKFKKSAKKF | seqid_4487 |
| variant_5972 | FKKKLLKIPPPKFKKSAKKF | seqid_4488 |
| variant_5973 | KWKKLLKIPPPKFKKSAKKF | seqid_4489 |
| variant_5974 | RWKKLLKIPPPKFKKSAKKF | seqid_4490 |
| variant_5975 | FWKKLLKIPPPKFKKSAKKF | seqid_4491 |
| variant_5976 | KKKLFKKIPPPKFKKSAKKF | seqid_4492 |
| variant_5977 | RKKLFKKIPPPKFKKSAKKF | seqid_4493 |
| variant_5978 | FKKLFKKIPPPKFKKSAKKF | seqid_4494 |
| variant_5979 | KWKLFKKIPPPKFKKSAKKF | seqid_4495 |
| variant_5980 | RWKLFKKIPPPKFKKSAKKF | seqid_4496 |
| variant_5981 | FWKLFKKIPPPKFKKSAKKF | seqid_4497 |
| variant_5982 | KKKKFKKIPPPKFKKSAKKF | seqid_4498 |
| variant_5983 | RKKKFKKIPPPKFKKSAKKF | seqid_4499 |
| variant_5984 | FKKKFKKIPPPKFKKSAKKF | seqid_4500 |
| variant_5985 | KWKKFKKIPPPKFKKSAKKF | seqid_4501 |
| variant_5986 | RWKKFKKIPPPKFKKSAKKF | seqid_4502 |
| variant_5987 | FWKKFKKIPPPKFKKSAKKF | seqid_4503 |
| variant_5988 | KKKLLKKIPPPKFKKSAKKF | seqid_4504 |
| variant_5989 | RKKLLKKIPPPKFKKSAKKF | seqid_4505 |
| variant_5990 | FKKLLKKIPPPKFKKSAKKF | seqid_4506 |
| variant_5991 | KWKLLKKIPPPKFKKSAKKF | seqid_4507 |
| variant_5992 | RWKLLKKIPPPKFKKSAKKF | seqid_4508 |
| variant_5993 | FWKLLKKIPPPKFKKSAKKF | seqid_4509 |
| variant_5994 | KKKKLKKIPPPKFKKSAKKF | seqid_4510 |
| variant_5995 | RKKKLKKIPPPKFKKSAKKF | seqid_4511 |
| variant_5996 | FKKKLKKIPPPKFKKSAKKF | seqid_4512 |
| variant_5997 | KWKKLKKIPPPKFKKSAKKF | seqid_4513 |
| variant_5998 | RWKKLKKIPPPKFKKSAKKF | seqid_4514 |
| variant_5999 | FWKKLKKIPPPKFKKSAKKF | seqid_4515 |
| variant_6000 | KKKLFLKIPPKFKKSAKKF | seqid_4516 |
| variant_6001 | RKKLFLKIPPKFKKSAKKF | seqid_4517 |
| variant_6002 | FKKLFLKIPPKFKKSAKKF | seqid_4518 |
| variant_6003 | KWKLFLKIPPKFKKSAKKF | seqid_4519 |
| variant_6004 | RWKLFLKIPPKFKKSAKKF | seqid_4520 |
| variant_6005 | FWKLFLKIPPKFKKSAKKF | seqid_4521 |
| variant_6006 | KKKKFLKIPPKFKKSAKKF | seqid_4522 |
| variant_6007 | RKKKFLKIPPKFKKSAKKF | seqid_4523 |

-continued

| | | |
|---|---|---|
| variant_6008 | FKKKFLKIPPKFKKSAKKF | seqid_4524 |
| variant_6009 | KWKKFLKIPPKFKKSAKKF | seqid_4525 |
| variant_6010 | RWKKFLKIPPKFKKSAKKF | seqid_4526 |
| variant_6011 | FWKKFLKIPPKFKKSAKKF | seqid_4527 |
| variant_6012 | KKKLLLKIPPKFKKSAKKF | seqid_4528 |
| variant_6013 | RKKLLLKIPPKFKKSAKKF | seqid_4529 |
| variant_6014 | FKKLLLKIPPKFKKSAKKF | seqid_4530 |
| variant_6015 | KWKLLLKIPPKFKKSAKKF | seqid_4531 |
| variant_6016 | RWKLLLKIPPKFKKSAKKF | seqid_4532 |
| variant_6017 | FWKLLLKIPPKFKKSAKKF | seqid_4533 |
| variant_6018 | KKKKLLKIPPKFKKSAKKF | seqid_4534 |
| variant_6019 | RKKKLLKIPPKFKKSAKKF | seqid_4535 |
| variant_6020 | FKKKLLKIPPKFKKSAKKF | seqid_4536 |
| variant_6021 | KWKKLLKIPPKFKKSAKKF | seqid_4537 |
| variant_6022 | RWKKLLKIPPKFKKSAKKF | seqid_4538 |
| variant_6023 | FWKKLLKIPPKFKKSAKKF | seqid_4539 |
| variant_6024 | KKKLFKKIPPKFKKSAKKF | seqid_4540 |
| variant_6025 | RKKLFKKIPPKFKKSAKKF | seqid_4541 |
| variant_6026 | FKKLFKKIPPKFKKSAKKF | seqid_4542 |
| variant_6027 | KWKLFKKIPPKFKKSAKKF | seqid_4543 |
| variant_6028 | RWKLFKKIPPKFKKSAKKF | seqid_4544 |
| variant_6029 | FWKLFKKIPPKFKKSAKKF | seqid_4545 |
| variant_6030 | KKKKFKKIPPKFKKSAKKF | seqid_4546 |
| variant_6031 | RKKKFKKIPPKFKKSAKKF | seqid_4547 |
| variant_6032 | FKKKFKKIPPKFKKSAKKF | seqid_4548 |
| variant_6033 | KWKKFKKIPPKFKKSAKKF | seqid_4549 |
| variant_6034 | RWKKFKKIPPKFKKSAKKF | seqid_4550 |
| variant_6035 | FWKKFKKIPPKFKKSAKKF | seqid_4551 |
| variant_6036 | KKKLLKKIPPKFKKSAKKF | seqid_4552 |
| variant_6037 | RKKLLKKIPPKFKKSAKKF | seqid_4553 |
| variant_6038 | FKKLLKKIPPKFKKSAKKF | seqid_4554 |
| variant_6039 | KWKLLKKIPPKFKKSAKKF | seqid_4555 |
| variant_6040 | RWKLLKKIPPKFKKSAKKF | seqid_4556 |
| variant_6041 | FWKLLKKIPPKFKKSAKKF | seqid_4557 |
| variant_6042 | KKKKLKKIPPKFKKSAKKF | seqid_4558 |
| variant_6043 | RKKKLKKIPPKFKKSAKKF | seqid_4559 |
| variant_6044 | FKKKLKKIPPKFKKSAKKF | seqid_4560 |
| variant_6045 | KWKKLKKIPPKFKKSAKKF | seqid_4561 |
| variant_6046 | RWKKLKKIPPKFKKSAKKF | seqid_4562 |
| variant_6047 | FWKKLKKIPPKFKKSAKKF | seqid_4563 |
| variant_6096 | KKKLFLKIPKFKKSAKKF | seqid_4564 |
| variant_6097 | RKKLFLKIPKFKKSAKKF | seqid_4565 |
| variant_6098 | FKKLFLKIPKFKKSAKKF | seqid_4566 |
| variant_6099 | KWKLFLKIPKFKKSAKKF | seqid_4567 |
| variant_6100 | RWKLFLKIPKFKKSAKKF | seqid_4568 |
| variant_6101 | FWKLFLKIPKFKKSAKKF | seqid_4569 |
| variant_6102 | KKKKFLKIPKFKKSAKKF | seqid_4570 |
| variant_6103 | RKKKFLKIPKFKKSAKKF | seqid_4571 |
| variant_6104 | FKKKFLKIPKFKKSAKKF | seqid_4572 |
| variant_6105 | KWKKFLKIPKFKKSAKKF | seqid_4573 |
| variant_6106 | RWKKFLKIPKFKKSAKKF | seqid_4574 |
| variant_6107 | FWKKFLKIPKFKKSAKKF | seqid_4575 |
| variant_6108 | KKKLLLKIPKFKKSAKKF | seqid_4576 |
| variant_6109 | RKKLLLKIPKFKKSAKKF | seqid_4577 |
| variant_6110 | FKKLLLKIPKFKKSAKKF | seqid_4578 |
| variant_6111 | KWKLLLKIPKFKKSAKKF | seqid_4579 |
| variant_6112 | RWKLLLKIPKFKKSAKKF | seqid_4580 |
| variant_6113 | FWKLLLKIPKFKKSAKKF | seqid_4581 |
| variant_6114 | KKKKLLKIPKFKKSAKKF | seqid_4582 |
| variant_6115 | RKKKLLKIPKFKKSAKKF | seqid_4583 |
| variant_6116 | FKKKLLKIPKFKKSAKKF | seqid_4584 |
| variant_6117 | KWKKLLKIPKFKKSAKKF | seqid_4585 |
| variant_6118 | RWKKLLKIPKFKKSAKKF | seqid_4586 |
| variant_6119 | FWKKLLKIPKFKKSAKKF | seqid_4587 |
| variant_6120 | KKKLFKKIPKFKKSAKKF | seqid_4588 |
| variant_6121 | RKKLFKKIPKFKKSAKKF | seqid_4589 |
| variant_6122 | FKKLFKKIPKFKKSAKKF | seqid_4590 |
| variant_6123 | KWKLFKKIPKFKKSAKKF | seqid_4591 |
| variant_6124 | RWKLFKKIPKFKKSAKKF | seqid_4592 |
| variant_6125 | FWKLFKKIPKFKKSAKKF | seqid_4593 |
| variant_6126 | KKKKFKKIPKFKKSAKKF | seqid_4594 |
| variant_6127 | RKKKFKKIPKFKKSAKKF | seqid_4595 |
| variant_6128 | FKKKFKKIPKFKKSAKKF | seqid_4596 |
| variant_6129 | KWKKFKKIPKFKKSAKKF | seqid_4597 |
| variant_6130 | RWKKFKKIPKFKKSAKKF | seqid_4598 |
| variant_6131 | FWKKFKKIPKFKKSAKKF | seqid_4599 |
| variant_6132 | KKKLLKKIPKFKKSAKKF | seqid_4600 |
| variant_6133 | RKKLLKKIPKFKKSAKKF | seqid_4601 |
| variant_6134 | FKKLLKKIPKFKKSAKKF | seqid_4602 |
| variant_6135 | KWKLLKKIPKFKKSAKKF | seqid_4603 |
| variant_6136 | RWKLLKKIPKFKKSAKKF | seqid_4604 |

| variant_6137 | FWKLLKKIPKFKKSAKKF | seqid_4605 |
| variant_6138 | KKKKLKKIPKFKKSAKKF | seqid_4606 |
| variant_6139 | RKKKLKKIPKFKKSAKKF | seqid_4607 |
| variant_6140 | FKKKLKKIPKFKKSAKKF | seqid_4608 |
| variant_6141 | KWKKLKKIPKFKKSAKKF | seqid_4609 |
| variant_6142 | RWKKLKKIPKFKKSAKKF | seqid_4610 |
| variant_6143 | FWKKLKKIPKFKKSAKKF | seqid_4611 |

3.1.2 Sequence motif
$KX_2KX_3X_4X_5KIPX_{11}X_{12}KFLHX_8AKKF$
(SEQ ID NO: 10)

| variant_0 | KLKLLLKIPPPKFLHAAKKF | seqid_4612 |
| variant_1 | KWKLLLKIPPPKFLHAAKKF | seqid_2329 |
| variant_2 | KLKKLLKIPPPKFLHAAKKF | seqid_4613 |
| variant_3 | KWKKLLKIPPPKFLHAAKKF | seqid_2335 |
| variant_4 | KLKLFLKIPPPKFLHAAKKF | seqid_4614 |
| variant_5 | KWKLFLKIPPPKFLHAAKKF | seqid_2317 |
| variant_6 | KLKKFLKIPPPKFLHAAKKF | seqid_4615 |
| variant_7 | KWKKFLKIPPPKFLHAAKKF | seqid_2323 |
| variant_8 | KLKLLKKIPPPKFLHAAKKF | seqid_4616 |
| variant_9 | KWKLLKKIPPPKFLHAAKKF | seqid_2353 |
| variant_10 | KLKKLKKIPPPKFLHAAKKF | seqid_4617 |
| variant_11 | KWKKLKKIPPPKFLHAAKKF | seqid_2359 |
| variant_12 | KLKLFKKIPPPKFLHAAKKF | seqid_4618 |
| variant_13 | KWKLFKKIPPPKFLHAAKKF | seqid_2341 |
| variant_14 | KLKKFKKIPPPKFLHAAKKF | seqid_4619 |
| variant_15 | KWKKFKKIPPPKFLHAAKKF | seqid_2347 |
| variant_16 | KLKLLLKIPPKFLHAAKKF | seqid_4620 |
| variant_17 | KWKLLLKIPPKFLHAAKKF | seqid_2377 |
| variant_18 | KLKKLLKIPPKFLHAAKKF | seqid_4621 |
| variant_19 | KWKKLLKIPPKFLHAAKKF | seqid_2383 |
| variant_20 | KLKLFLKIPPKFLHAAKKF | seqid_4622 |
| variant_21 | KWKLFLKIPPKFLHAAKKF | seqid_2365 |
| variant_22 | KLKKFLKIPPKFLHAAKKF | seqid_4623 |
| variant_23 | KWKKFLKIPPKFLHAAKKF | seqid_2371 |
| variant_24 | KLKLLKKIPPKFLHAAKKF | seqid_4624 |
| variant_25 | KWKLLKKIPPKFLHAAKKF | seqid_2401 |
| variant_26 | KLKKLKKIPPKFLHAAKKF | seqid_4625 |
| variant_27 | KWKKLKKIPPKFLHAAKKF | seqid_2407 |
| variant_28 | KLKLFKKIPPKFLHAAKKF | seqid_4626 |
| variant_29 | KWKLFKKIPPKFLHAAKKF | seqid_2389 |
| variant_30 | KLKKFKKIPPKFLHAAKKF | seqid_4627 |
| variant_31 | KWKKFKKIPPKFLHAAKKF | seqid_2395 |
| variant_48 | KLKLLLKIPKFLHAAKKF | seqid_4628 |
| variant_49 | KWKLLLKIPKFLHAAKKF | seqid_2424 |
| variant_50 | KLKKLLKIPKFLHAAKKF | seqid_4629 |
| variant_51 | KWKKLLKIPKFLHAAKKF | seqid_9 |
| variant_52 | KLKLFLKIPKFLHAAKKF | seqid_4630 |
| variant_53 | KWKLFLKIPKFLHAAKKF | seqid_2413 |
| variant_54 | KLKKFLKIPKFLHAAKKF | seqid_4631 |
| variant_55 | KWKKFLKIPKFLHAAKKF | seqid_8 |
| variant_56 | KLKLLKKIPKFLHAAKKF | seqid_4632 |
| variant_57 | KWKLLKKIPKFLHAAKKF | seqid_2445 |
| variant_58 | KLKKLKKIPKFLHAAKKF | seqid_4633 |
| variant_59 | KWKKLKKIPKFLHAAKKF | seqid_2451 |
| variant_60 | KLKLFKKIPKFLHAAKKF | seqid_4634 |
| variant_61 | KWKLFKKIPKFLHAAKKF | seqid_7 |
| variant_62 | KLKKFKKIPKFLHAAKKF | seqid_4635 |
| variant_63 | KWKKFKKIPKFLHAAKKF | seqid_2439 |
| variant_64 | KLKLLLKIPPPKFLHVAKKF | seqid_4636 |
| variant_65 | KWKLLLKIPPPKFLHVAKKF | seqid_3475 |
| variant_66 | KLKKLLKIPPPKFLHVAKKF | seqid_4637 |
| variant_67 | KWKKLLKIPPPKFLHVAKKF | seqid_3481 |
| variant_68 | KLKLFLKIPPPKFLHVAKKF | seqid_4638 |
| variant_69 | KWKLFLKIPPPKFLHVAKKF | seqid_3463 |
| variant_70 | KLKKFLKIPPPKFLHVAKKF | seqid_4639 |
| variant_71 | KWKKFLKIPPPKFLHVAKKF | seqid_3469 |
| variant_72 | KLKLLKKIPPPKFLHVAKKF | seqid_4640 |
| variant_73 | KWKLLKKIPPPKFLHVAKKF | seqid_3499 |
| variant_74 | KLKKLKKIPPPKFLHVAKKF | seqid_4641 |
| variant_75 | KWKKLKKIPPPKFLHVAKKF | seqid_3505 |
| variant_76 | KLKLFKKIPPPKFLHVAKKF | seqid_4642 |
| variant_77 | KWKLFKKIPPPKFLHVAKKF | seqid_3487 |
| variant_78 | KLKKFKKIPPPKFLHVAKKF | seqid_4643 |
| variant_79 | KWKKFKKIPPPKFLHVAKKF | seqid_3493 |
| variant_80 | KLKLLLKIPPKFLHVAKKF | seqid_4644 |
| variant_81 | KWKLLLKIPPKFLHVAKKF | seqid_3523 |
| variant_82 | KLKKLLKIPPKFLHVAKKF | seqid_4645 |
| variant_83 | KWKKLLKIPPKFLHVAKKF | seqid_3529 |
| variant_84 | KLKLFLKIPPKFLHVAKKF | seqid_4646 |
| variant_85 | KWKLFLKIPPKFLHVAKKF | seqid_3511 |
| variant_86 | KLKKFLKIPPKFLHVAKKF | seqid_4647 |
| variant_87 | KWKKFLKIPPKFLHVAKKF | seqid_3517 |

| | | |
|---|---|---|
| variant_88 | KLKLLKKIPPKFLHVAKKF | seqid_4648 |
| variant_89 | KWKLLKKIPPKFLHVAKKF | seqid_3547 |
| variant_90 | KLKKLKKIPPKFLHVAKKF | seqid_4649 |
| variant_91 | KWKKLKKIPPKFLHVAKKF | seqid_3553 |
| variant_92 | KLKLFKKIPPKFLHVAKKF | seqid_4650 |
| variant_93 | KWKLFKKIPPKFLHVAKKF | seqid_3535 |
| variant_94 | KLKKFKKIPPKFLHVAKKF | seqid_4651 |
| variant_95 | KWKKFKKIPPKFLHVAKKF | seqid_3541 |
| variant_112 | KLKLLLKIPKFLHVAKKF | seqid_4652 |
| variant_113 | KWKLLLKIPKFLHVAKKF | seqid_3571 |
| variant_114 | KLKKLLKIPKFLHVAKKF | seqid_4653 |
| variant_115 | KWKKLLKIPKFLHVAKKF | seqid_3577 |
| variant_116 | KLKLFLKIPKFLHVAKKF | seqid_4654 |
| variant_117 | KWKLFLKIPKFLHVAKKF | seqid_3559 |
| variant_118 | KLKKFLKIPKFLHVAKKF | seqid_4655 |
| variant_119 | KWKKFLKIPKFLHVAKKF | seqid_3565 |
| variant_120 | KLKLLKKIPKFLHVAKKF | seqid_4656 |
| variant_121 | KWKLLKKIPKFLHVAKKF | seqid_3595 |
| variant_122 | KLKKLKKIPKFLHVAKKF | seqid_4657 |
| variant_123 | KWKKLKKIPKFLHVAKKF | seqid_3601 |
| variant_124 | KLKLFKKIPKFLHVAKKF | seqid_4658 |
| variant_125 | KWKLFKKIPKFLHVAKKF | seqid_3583 |
| variant_126 | KLKKFKKIPKFLHVAKKF | seqid_4659 |
| variant_127 | KWKKFKKIPKFLHVAKKF | seqid_3589 |
| variant_128 | KLKLLLKIPPPKFLHLAKKF | seqid_4660 |
| variant_129 | KWKLLLKIPPPKFLHLAKKF | seqid_2901 |
| variant_130 | KLKKLLKIPPPKFLHLAKKF | seqid_4661 |
| variant_131 | KWKKLLKIPPPKFLHLAKKF | seqid_2907 |
| variant_132 | KLKLFLKIPPPKFLHLAKKF | seqid_4662 |
| variant_133 | KWKLFLKIPPPKFLHLAKKF | seqid_2889 |
| variant_134 | KLKKFLKIPPPKFLHLAKKF | seqid_4663 |
| variant_135 | KWKKFLKIPPPKFLHLAKKF | seqid_2895 |
| variant_136 | KLKLLKKIPPPKFLHLAKKF | seqid_4664 |
| variant_137 | KWKLLKKIPPPKFLHLAKKF | seqid_2925 |
| variant_138 | KLKKLKKIPPPKFLHLAKKF | seqid_4665 |
| variant_139 | KWKKLKKIPPPKFLHLAKKF | seqid_2931 |
| variant_140 | KLKLFKKIPPPKFLHLAKKF | seqid_4666 |
| variant_141 | KWKLFKKIPPPKFLHLAKKF | seqid_2913 |
| variant_142 | KLKKFKKIPPPKFLHLAKKF | seqid_4667 |
| variant_143 | KWKKFKKIPPPKFLHLAKKF | seqid_2919 |
| variant_144 | KLKLLLKIPPKFLHLAKKF | seqid_4668 |
| variant_145 | KWKLLLKIPPKFLHLAKKF | seqid_2949 |
| variant_146 | KLKKLLKIPPKFLHLAKKF | seqid_4669 |
| variant_147 | KWKKLLKIPPKFLHLAKKF | seqid_2955 |
| variant_148 | KLKLFLKIPPKFLHLAKKF | seqid_4670 |
| variant_149 | KWKLFLKIPPKFLHLAKKF | seqid_2937 |
| variant_150 | KLKKFLKIPPKFLHLAKKF | seqid_4671 |
| variant_151 | KWKKFLKIPPKFLHLAKKF | seqid_2943 |
| variant_152 | KLKLLKKIPPKFLHLAKKF | seqid_4672 |
| variant_153 | KWKLLKKIPPKFLHLAKKF | seqid_2973 |
| variant_154 | KLKKLKKIPPKFLHLAKKF | seqid_4673 |
| variant_155 | KWKKLKKIPPKFLHLAKKF | seqid_2979 |
| variant_156 | KLKLFKKIPPKFLHLAKKF | seqid_4674 |
| variant_157 | KWKLFKKIPPKFLHLAKKF | seqid_2961 |
| variant_158 | KLKKFKKIPPKFLHLAKKF | seqid_4675 |
| variant_159 | KWKKFKKIPPKFLHLAKKF | seqid_2967 |
| variant_176 | KLKLLLKIPKFLHLAKKF | seqid_4676 |
| variant_177 | KWKLLLKIPKFLHLAKKF | seqid_2997 |
| variant_178 | KLKKLLKIPKFLHLAKKF | seqid_4677 |
| variant_179 | KWKKLLKIPKFLHLAKKF | seqid_3003 |
| variant_180 | KLKLFLKIPKFLHLAKKF | seqid_4678 |
| variant_181 | KWKLFLKIPKFLHLAKKF | seqid_2985 |
| variant_182 | KLKKFLKIPKFLHLAKKF | seqid_4679 |
| variant_183 | KWKKFLKIPKFLHLAKKF | seqid_2991 |
| variant_184 | KLKLLKKIPKFLHLAKKF | seqid_4680 |
| variant_185 | KWKLLKKIPKFLHLAKKF | seqid_3019 |
| variant_186 | KLKKLKKIPKFLHLAKKF | seqid_4681 |
| variant_187 | KWKKLKKIPKFLHLAKKF | seqid_3025 |
| variant_188 | KLKLFKKIPKFLHLAKKF | seqid_4682 |
| variant_189 | KWKLFKKIPKFLHLAKKF | seqid_3 |
| variant_190 | KLKKFKKIPKFLHLAKKF | seqid_4683 |
| variant_191 | KWKKFKKIPKFLHLAKKF | seqid_3013 |
| variant_192 | KLKLLLKIPPPKFLHSAKKF | seqid_4684 |
| variant_193 | KWKLLLKIPPPKFLHSAKKF | seqid_4051 |
| variant_194 | KLKKLLKIPPPKFLHSAKKF | seqid_4685 |
| variant_195 | KWKKLLKIPPPKFLHSAKKF | seqid_4057 |
| variant_196 | KLKLFLKIPPPKFLHSAKKF | seqid_4686 |
| variant_197 | KWKLFLKIPPPKFLHSAKKF | seqid_4039 |
| variant_198 | KLKKFLKIPPPKFLHSAKKF | seqid_4687 |
| variant_199 | KWKKFLKIPPPKFLHSAKKF | seqid_4045 |
| variant_200 | KLKLLKKIPPPKFLHSAKKF | seqid_4688 |

```
variant_201    KWKLLKKIPPPKFLHSAKKF    seqid_4075
variant_202    KLKKLKKIPPPKFLHSAKKF    seqid_4689
variant_203    KWKKLKKIPPPKFLHSAKKF    seqid_4081
variant_204    KLKLFKKIPPPKFLHSAKKF    seqid_4690
variant_205    KWKLFKKIPPPKFLHSAKKF    seqid_4063
variant_206    KLKKFKKIPPPKFLHSAKKF    seqid_4691
variant_207    KWKKFKKIPPPKFLHSAKKF    seqid_4069
variant_208    KLKLLLKIPPKFLHSAKKF     seqid_4692
variant_209    KWKLLLKIPPKFLHSAKKF     seqid_4099
variant_210    KLKKLLKIPPKFLHSAKKF     seqid_4693
variant_211    KWKKLLKIPPKFLHSAKKF     seqid_4105
variant_212    KLKLFLKIPPKFLHSAKKF     seqid_4694
variant_213    KWKLFLKIPPKFLHSAKKF     seqid_4087
variant_214    KLKKFLKIPPKFLHSAKKF     seqid_4695
variant_215    KWKKFLKIPPKFLHSAKKF     seqid_4093
variant_216    KLKLLKKIPPKFLHSAKKF     seqid_4696
variant_217    KWKLLKKIPPKFLHSAKKF     seqid_4123
variant_218    KLKKLKKIPPKFLHSAKKF     seqid_4697
variant_219    KWKKLKKIPPKFLHSAKKF     seqid_4129
variant_220    KLKLFKKIPPKFLHSAKKF     seqid_4698
variant_221    KWKLFKKIPPKFLHSAKKF     seqid_4111
variant_222    KLKKFKKIPPKFLHSAKKF     seqid_4699
variant_223    KWKKFKKIPPKFLHSAKKF     seqid_4117
variant_240    KLKLLLKIPKFLHSAKKF      seqid_4700
variant_241    KWKLLLKIPKFLHSAKKF      seqid_4147
variant_242    KLKKLLKIPKFLHSAKKF      seqid_4701
variant_243    KWKKLLKIPKFLHSAKKF      seqid_4153
variant_244    KLKLFLKIPKFLHSAKKF      seqid_4702
variant_245    KWKLFLKIPKFLHSAKKF      seqid_4135
variant_246    KLKKFLKIPKFLHSAKKF      seqid_4703
variant_247    KWKKFLKIPKFLHSAKKF      seqid_4141
variant_248    KLKLLKKIPKFLHSAKKF      seqid_4704
variant_249    KLNKLLKKIPKFLHSAKKF     seqid_4171
variant_250    KLKKLKKIPKFLHSAKKF      seqid_4705
variant_251    KWKKLKKIPKFLHSAKKF      seqid_4177
variant_252    KLKLFKKIPKFLHSAKKF      seqid_4706
variant_253    KWKLFKKIPKFLHSAKKF      seqid_4708
variant_254    KLKKFKKIPKFLHSAKKF      seqid_4707
variant_255    KWKKFKKIPKFLHSAKKF      seqid_4165
```

3.1.3 Sequence Motif HEL1-HB-HEL2

As further non-limiting examples there may be mentioned:

```
Variant_1     KWKLFKKIGPKFLHLAKKF-NH2         SEQ ID NO: 4709
Variant_2     KWKLFKKGPGKFLHSAKKF-NH2         SEQ ID NO: 4710
Variant_3     KWKLFKKIEKVGQGPGKFLHSAKKFG-NH2  SEQ ID NO: 4711
Variant_4     WKLFKKIPKFLHLAKKF-NH2           SEQ ID NO: 4712
Variant_5     FKLFLLIPKFLHLAKKF-NH2           SEQ ID NO: 4713
Variant_6     KWFKKIPKFLHLAKKF-NH2            SEQ ID NO: 4714
Variant_7     WFKKIPKFLHLAKKF-NH2             SEQ ID NO: 4715
Variant_8     KWKKIPKFLHLLKKF-NH2             SEQ ID NO: 4716
Variant_9     WFKKIPKFLHLLKKF-NH2             SEQ ID NO: 4717
Variant_10    KWKLFKKIPFLHLAKKF-NH2           SEQ ID NO: 4718
Variant_11    KWKLFKKIPKFLHLAKK-NH2           SEQ ID NO: 4719
Variant_12    KWKLFKKIPLHLAKKF-NH2            SEQ ID NO: 4720
Variant_13    KWKLFKKIPKFLHLAK-NH2            SEQ ID NO: 4721
Variant_14    KWKLFKKIPHLAKKF-NH2             SEQ ID NO: 4722
Variant_15    KWKLFKKIPKFLHLA-NH2             SEQ ID NO: 4723
Variant_16    KWKLFKKIPLAKKF-NH2              SEQ ID NO: 4724
```

-continued

| | | |
|---|---|---|
| Variant_17 | KWKLFKKIPKFLHL-NH₂ | SEQ ID NO: 4725 |
| Variant_18 | FKKALHLFKPIKKFLKWK-NH₂ | SEQ ID NO: 4726 |
| Variant_19 | KFLHLAKKFPKWKLFKKI-NH₂ | SEQ ID NO: 4727 |
| Variant_20 | KWKKLLKKPLLKKLLKKL-NH₂ | SEQ ID NO: 4728 |
| Variant_21 | KWKLKPLLKKLLKKL-NH₂ | SEQ ID NO: 4729 |
| Variant_22 | KWKKLLKKPLKLKL-NH₂ | SEQ ID NO: 4730 |
| Variant_23 | KLLKKPLKLKL-NH₂ | SEQ ID NO: 4731 |

Also comprised by the present invention are the above sequences, wherein, however, the C-terminal end is not amidated and, consequently, such sequences, terminated by a carboxy group (in the form of its salt or as free acid).

3.1.4 Modifications of SEQ ID NO:3

In these modifications the peptide according to SEQ ID NO:3 is elongated by any arbitrary amino acid residue on its N-terminal and/or C-terminal end. Non-limiting examples of additional residues comprise Asp, Pro, Asn and Gly. If the N- and the C-terminal end is elongated simultaneously the additional N-terminal residue preferably is Pro or Gly and the corresponding C-terminal residue is Asp and Asn, respectively.

As further non-limiting examples there may be mentioned:

| | |
|---|---|
| PKWKLFKKIPKFLHLAKKF-NH₂ | (SEQ ID NO: 4732) |
| KWKLFKKIPKFLHLAKKFD-NH₂ | (SEQ ID NO: 4733) |
| PKWKLFKKIPKFLHLAKKFD-NH₂ | (SEQ ID NO: 4734) |
| GKWKLFKKIPKFLHLAKKF-NH₂ | (SEQ ID NO: 4735) |
| KWKLFKKIPKFLHLAKKFN-NH₂ | (SEQ ID NO: 4736) |
| GKWKLFKKIPKFLHLAKKFN-NH₂ | (SEQ ID NO: 4737) |
| PKWKLFKKIPKFLHLAKKFN-NH₂ | (SEQ ID NO: 4738) |

Also comprised are the above sequences wherein the C-terminal end is not amidated, and, consequently, sequences which are terminated by a carboxy group (in the form of its salt or free acid).

3.2 Further Modifications of Peptides According to the Invention

Besides the peptide sequences depicted above, preference is also given to functional equivalents, functional derivatives and salts of this sequence.

According to the invention, "functional equivalents" is also understood in particular as meaning mutants which, in at least one sequence position of the abovementioned amino acid sequences, have an amino acid other than the one specifically specified, but nevertheless have the property of preventing, inhibiting and treating dandruff. "Functional equivalents" thus include the mutants obtainable by one or more amino acid additions, substitutions, deletions and/or inversions, where said changes can occur in any sequence position provided they lead to a mutant with the profile of properties according to the invention. Functional equivalence exists in particular also when the reactivity patterns between mutant and unmodified polypeptide are in qualitative agreement.

"Functional equivalents" in the above sense are also "precursors" of the polypeptides described and also "functional derivatives" and "salts" of the polypeptides.

"Precursors" here are natural or synthetic precursors of the polypeptides with or without the desired biological activity.

Examples of suitable amino acid substitutions are given in the table below:

| Original residue | Examples of substitution |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The expression "salts" is understood as meaning both salts of carboxyl groups and also acid addition salts of amino groups of the peptide molecules according to the invention. Salts of carboxyl groups can be produced in a manner known per se and comprise inorganic salts, such as, for example, sodium, calcium, ammonium, iron and zinc salts, and also salts with organic bases, such as, for example, amines, such as triethanolamine, arginine, lysine, piperidine and the like. Acid addition salts, such as, for example, salts with mineral acids, such as hydrochloric acid or sulfuric acid and salts with organic acids, such as acetic acid and oxalic acid, are likewise provided by the invention.

"Functional derivatives" (or "derivatives") of polypeptides according to the invention can likewise be produced on functional amino acid side groups or on their N or C terminal end using known techniques. Such derivatives comprise, for example, aliphatic esters of carboxylic acid groups, amides of carboxylic acid groups obtainable by reaction with ammonia or with a primary or secondary amine; N-acyl derivatives of free amino groups, prepared by reaction with acyl groups, or O-acyl derivatives of free hydroxy groups, prepared by reaction with acyl groups. Furthermore, 1 to 5, such as, for example, 2, 3 or 4, arbitrary D- or L-amino acid residues can additionally be covalently (peptidically) bonded at the N and/or C terminal end; or 1 to 5, as for example 1, 2, 3 or 4 residues may be missing at the N-terminal and/or C-terminal end.

Non-limiting examples of additional N-terminal and/or C-terminal residues comprise Asp, Pro, Asn, Gly. In case the N-terminal end and the C-terminal end are simultaneously elongated, the N-terminal residue may preferably be Pro or Gly and the corresponding C-terminal residue may preferably be Asp and Asn, respectively.

Through variation of the amino acid sequence of the described antimicrobial peptides and fusing with additional protein or peptide sequences, it is possible to generate structures which specifically recognize certain surfaces, e.g. skin, nails, hair, or are recognized and bonded by these surfaces or the receptors present therein.

Consequently, it is possible to more effectively bring the described antimicrobial peptides to the desired site of action, and/or to improve their absorption. Through coupling and/or fusion of binding proteins to the described antimicrobial peptides, protein-peptide fusion products resulting therefrom would be steered in a more targeted manner to appropriate sites of action, e.g. microorganism surfaces or body compartments, and/or reside longer at these sites, resulting in an extended and improved peptide effect. Furthermore, through variation of the amino acid sequence of the described antimicrobial peptides and/or fusion with additional protein or peptide sequences, it is possible to steer the peptides to desired sites of action in a targeted manner in order to thus achieve, for example, higher peptide specificity, lower peptide consumption or peptide dose, and also more rapid or greater peptide effect.

3.3 Nucleic Acids, Expression Constructs, Vectors and Microorganisms According to the Invention 3.3.1 Nucleic Acids:

The invention furthermore comprises the nucleic acid molecules coding for the peptides and fusion peptides used according to the invention.

All of the nucleic acid sequences mentioned herein (single- and double-strand DNA and RNA sequences, such as, for example, cDNA and mRNA) can be prepared in a manner known per se by chemical synthesis from the nucleotide building blocks, such as, for example, by fragment condensation of individual overlapping, complementary nucleic acid building blocks of the double helix. The chemical synthesis of oligonucleotides can take place, for example, in a known manner according to the phosphoamidite method (Voet, Voet, $2^{nd}$ edition, Wiley Press New York, pages 896-897). The annealing of synthetic oligonucleotides and filling in of gaps with the aid of the Klenow fragment of DNA polymerase, and ligation reactions and also general cloning methods are described in Sambrook et al. (1989), Molecular Cloning: A laboratory manual, Cold Spring Harbor Laboratory Press.

The invention provides both isolated nucleic acid molecules which code for polypeptides or proteins according to the invention, or biologically active sections thereof, and to nucleic acid fragments which can be used, for example, as hybridization probes or primers for the identification or amplification of coding nucleic acids according to the invention.

The nucleic acid molecules according to the invention can additionally comprise untranslated sequences of the 3' and/or 5' end of the coding region of the gene.

An "isolated" nucleic acid molecule is separated off from other nucleic acid molecules which are present in the natural source of the nucleic acid and can, moreover, be essentially free of other cellular material or culture medium if produced by recombinant techniques, or be free of chemical precursors or other chemicals if chemically synthesized.

A nucleic acid molecule according to the invention can be isolated by means of standard molecular biology techniques and the sequence information provided according to the invention. For example, cDNA can be isolated from a suitable cDNA library by using one of the specifically disclosed complete sequences or a section thereof as hybridization probe and standard hybridization techniques (as described, for example, in Sambrook, J., Fritsch, E. F. and Maniatis, T. Molecular Cloning: A Laboratory Manual. 2nd edition, Cold Spring Harbor Laboratory, Cold Spring Harbor Laboratory Press, Cold Spring Harbor, N.Y., 1989). Moreover, a nucleic acid molecule comprising one of the disclosed sequences or a section thereof can be isolated by polymerase chain reaction using the oligonucleotide primers generated on the basis of this sequence. The nucleic acid amplified in this way can be cloned into a suitable vector and characterized by DNA sequence analysis. The oligonucleotides according to the invention can also be prepared by standard synthesis methods, e.g. using an automatic DNA synthesizer.

The invention furthermore comprises the nucleic acid molecules complementary to the specifically described nucleotide sequences, or a section thereof.

The nucleotide sequences according to the invention allow the generation of probes and primers which can be used for the identification and/or cloning of homologous sequences in other cell types and organisms. Such probes and primers usually comprise a nucleotide sequence range which, under stringent conditions, hybridizes to at least about 12, preferably at least about 25, such as, for example, about 40, 50 or 75, consecutive nucleotides of a sense strand of a nucleic acid sequence according to the invention or of a corresponding antisense strand.

Also comprised according to the invention are those nucleic acid sequences which comprise so-called silent mutations or which are modified, compared to a specifically specified sequence, according to the codon usage of a specific source organism or host organism, as are naturally occurring variants, such as, for example, splice variants or allelic variants, thereof. Likewise provided are sequences obtainable by conservative nucleotide substitutions (i.e. the amino acid in question is replaced by an amino acid of identical charge, size, polarity and/or solubility).

The invention also provides the molecules derived from the specifically disclosed nucleic acids by sequence polymorphisms. These genetic polymorphisms can exist between individuals within a population, owing to natural variation. These natural variations usually bring about a variance of from 1 to 5% in the nucleotide sequence of a gene.

Furthermore, the invention also comprises nucleic acid sequences which hybridize with the abovementioned coding sequences or are complementary thereto. These polynucleotides can be found when screening genomic or cDNA libraries and, if appropriate, be replicated therefrom by means of PCR using suitable primers and then isolated using suitable probes, for example. A further possibility is the transformation of suitable microorganisms with polynucleotides or vectors according to the invention, replication of the microorganisms and thus of the polynucleotides and subsequent isolation thereof. Moreover, polynucleotides according to the invention can also be synthesized by a chemical method.

The property of being able to "hybridize" to polynucleotides is understood as meaning the ability of a poly- or oligonucleotide, to bind, under stringent conditions, to a virtually complementary sequence while nonspecific bonds between noncomplementary partners do not take place under these conditions. For this purpose, the sequences should be 70-100%, preferably 90-100%, complementary. The property of complementary sequences of being able to bind specifically to one another is utilized, for example, in the Northern or Southern blot technique or during primer binding in PCR or RT-PCR. Usually, for this purpose, oligonucleotides above a length of 30 base pairs are used. Stringent conditions are understood as meaning, for example in the Northern blot technique, the use of a 50-70° C., preferably 60-65° C. hot washing solution, for example 0.1×SSC buffer with 0.1% SDS (20×SSC: 3 M NaCl, 0.3 M Na citrate, pH 7.0) for the elution of nonspecific hybridized cDNA probes or oligonucleotides. As mentioned above, in this process, only highly complementary nucleic acids remain bound to one another. Establishing stringent conditions is known to the person skilled in the art and is described, for example, in Ausubel et al., Current Protocols in Molecular Biology, John Wiley & Sons, N.Y. (1989), 6.3.1-6.3.6.

3.3.2 Expression Constructs and Vectors:

The invention moreover provides expression constructs comprising, under the genetic control of regulatory nucleic acid sequences, a nucleic acid sequence coding for a polypeptide according to the invention, and also vectors comprising at least one of these expression constructs. Preferably, such constructs according to the invention comprise a promoter 5' upstream of the particular coding sequence and a terminator sequence 3' downstream and also, if appropriate, further customary regulatory elements, in each case operatively linked to the coding sequence. An "operative linkage" is understood as meaning the sequential arrangement of promoter, coding sequence, terminator and, if appropriate further regulatory elements such that each of the regulatory elements can perform its function during the expression of the coding sequence as intended. Examples of operatively linkable sequences are targeting sequences and also enhancers, polyadenylation signals and the like. Further regulatory elements comprise selectable markers, amplification signals, replication origins and the like. Suitable regulatory sequences are described, for example, in Goeddel, Gene Expression Technology: Methods in Enzymology 185, Academic Press, San Diego, Calif. (1990).

In addition to the artificial regulatory sequences, the natural regulatory sequence may still be present upstream of the actual structural gene. Through genetic modification, this natural regulation can, if appropriate, be switched off and the expression of the genes increased or decreased. However, the gene construct can also be simpler in design, i.e. no additional regulatory signals are inserted upstream of the structure gene and the natural promoter together with its regulation is not removed. Instead, the natural regulatory sequence is mutated such that regulation no longer takes place and gene expression is increased or reduced. The nucleic acid sequences may be present in one or more copies in the gene construct.

Examples of promoters that can be used are: cos, tac, trp, tet, trp-tet, lpp, lac, lpp-lac, lacIq, T7, T5, T3, gal, trc, ara, SP6, lambda-P$_R$ or in the lambda-P$_L$ promoter, which are advantageously used in Gram-negative bacteria; and also the Gram-positive promoters amy and SPO2, the yeast promoters ADC1, MFa, AC, P-60, CYC1, GAPDH or the plant promoters CaMV/35S, SSU, OCS, lib4, usp, STLS1, B33, not or the ubiquitin or phaseolin promoter. Particular preference is given to using inducible promoters, such as, for example, photo- and in particular temperature-inducible promoters, such as the P$_r$P$_l$ promoter. In principle, all natural promoters with their regulatory sequences can be used. Moreover, synthetic promoters can also be used advantageously.

The specified regulatory sequences are intended to permit the targeted expression of the nucleic acid sequences and protein expression. Depending on the host organism, this may mean, for example, that the gene is expressed or overexpressed only after induction, or that it is immediately expressed and/or overexpressed.

The regulatory sequences or factors can here preferably have a beneficial effect on, and thereby increase or decrease, the expression. Thus, the regulatory elements can advantageously be enhanced at the transcriptional level by using strong transcription signals such as promoters and/or "enhancers". However, in addition, it is also possible to enhance translation by, for example, improving the stability of the mRNA.

The expression cassette is prepared by fusing a suitable promoter with a suitable coding nucleotide sequence and a terminator signal or polyadenylation signal. For this purpose, customary recombinant and cloning techniques are used, as are described, for example, in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

For expression, the recombinant nucleic acid construct or gene construct is advantageously inserted, in a suitable host organism, into a host-specific vector which facilitates optimal expression of the genes in the host. Vectors are well known to the person skilled in the art and can be found, for example, in "Cloning Vectors" (Pouwels P. H. et al., ed., Elsevier, Amsterdam-New York-Oxford, 1985). Apart from plasmids, vectors are also to be understood as meaning all other vectors known to the person skilled in the art, such as, for example, phages, viruses, such as SV40, CMV, baculovirus and adenovirus, transposons, IS elements, phasmids, cosmids, and linear or circular DNA. These vectors can be replicated autonomously in the host organism or be replicated chromosomally.

3.3.3 Examples of Suitable Expression Vectors which May be Mentioned are:

Customary fusion expression vectors, such as pGEX (Pharmacia Biotech Inc; Smith, D. B. and Johnson, K. S. (1988) Gene 67:31-40), pMAL (New England Biolabs, Beverly, Mass.) and pRIT 5 (Pharmacia, Piscataway, N.J.), in which glutathione-5-transferase (GST), maltose E binding protein or protein A is fused to the recombinant target protein.

Non-fusion protein expression vectors such as pTrc (Amann et al., (1988) Gene 69:301-315) and pET 11d (Studier et al. Gene Expression Technology: Methods in Enzymology 185, Academic Press, San Diego, Calif. (1990) 60-89).

Yeast expression vectors for expression in the yeast *S. cerevisiae*, such as pYepSec1 (Baldari et al., (1987) Embo J. 6:229-234), pMFa (Kurjan and Herskowitz (1982) Cell 30:933-943), pJRY88 (Schultz et al., (1987) Gene 54:113-123) and pYES2 (Invitrogen Corporation, San Diego, Calif.). Vectors and methods for the construction of vectors which are suitable for use in other fungi, such as filamentous fungi, comprise those which are described in detail in: van den Hondel, C. A. M. J. J. & Punt, P. J. (1991) "Gene transfer systems and vector development for filamentous fungi, in: Applied Molecular Genetics of Fungi, J. F. Peberdy et al., eds., S. 1-28, Cambridge University Press: Cambridge.

Baculovirus vectors which are available for the expression of proteins in cultivated insect cells (for example Sf9 cells) comprise the pAc series (Smith et al., (1983) Mol. Cell. Biol. 3:2156-2165) and the pVL series (Lucklow and Summers, (1989) Virology 170:31-39).

Plant expression vectors, such as those described in detail in: Becker, D., Kemper, E., Schell, J. and Masterson, R. (1992) "New plant binary vectors with selectable markers located proximal to the left border", Plant Mol. Biol.

20:1195-1197; and Bevan, M. W. (1984) "Binary *Agrobacterium* vectors for plant transformation", Nucl. Acids Res. 12:8711-8721.

Mammal expression vectors, such as pCDM8 (Seed, B. (1987) Nature 329:840) and pMT2PC (Kaufman et al. (1987) EMBO J. 6:187-195).

Further suitable expression systems for prokaryotic and eukaryotic cells are described in chapter 16 and 17 by Sambrook, J., Fritsch, E. F. and Maniatis, T., Molecular cloning: A Laboratory Manual, 2nd edition, Cold Spring Harbor Laboratory, Cold Spring Harbor Laboratory Press, Cold Spring Harbor, N.Y., 1989.

3.3.4 Recombinant Microorganisms:

With the aid of the vectors according to the invention it is possible to prepare recombinant microorganisms which are transformed, for example, with at least one vector according to the invention and can be used for producing the polypeptides according to the invention. The abovedescribed recombinant constructs according to the invention are advantageously introduced into a suitable host system and expressed. In this context, preference is given to using customary cloning and transfection methods known to the person skilled in the art such as, for example, coprecipitation, protoplast fusion, electroporation, retroviral transfection and the like, in order to express said nucleic acids in the particular expression system. Suitable systems are described, for example, in Current Protocols in Molecular Biology, F. Ausubel et al., ed., Wiley Interscience, New York 1997, or Sambrook et al., Molecular Cloning: A Laboratory Manual. 2nd edition, Cold Spring Harbor Laboratory, Cold Spring Harbor Laboratory Press, Cold Spring Harbor, N.Y., 1989.

According to the invention, it is also possible to prepare homologously recombinant microorganisms. For this, a vector is prepared which comprises at least one section of a gene according to the invention or of a coding sequence, into which, if appropriate, at least one amino acid deletion, addition or substitution has been introduced in order to modify, for example to functionally disrupt, the sequence according to the invention ("knockout" vector). The introduced sequence may, for example, also be a homolog from a related microorganism or be derived from a mammalian, yeast or insect source. Alternatively, the vector used for homologous recombination may be designed such that the endogenous gene is mutated or otherwise modified upon homologous recombination, while still encoding the functional protein (for example the upstream regulatory region may be modified in such a way that, as a result, the expression of the endogenous protein is modified). The modified section of the gene according to the invention is in the homologous recombination vector. The construction of suitable vectors for homologous recombination is described, for example, in Thomas, K. R. and Capecchi, M. R. (1987) Cell 51:503.

Suitable host organisms are in principle all organisms which permit an expression of the nucleic acids according to the invention, their allelic variants, their functional equivalents or derivatives. Host organisms are to be understood as meaning, for example, bacteria, fungi, yeasts, plant or animal cells. Preferred organisms are bacteria, such as those of the genera *Escherichia*, such as, for example, *Escherichia coli*, *Streptomyces*, *Bacillus* or *Pseudomonas*, eukaryotic microorganisms, such as *Saccharomyces cerevisiae, Aspergillus*, higher eukaryotic cells from animals or plants, for example Sf9 or CHO cells.

The selection of successfully transformed organisms can take place by marker genes which are likewise present in the vector or in the expression cassette. Examples of such marker genes are genes for antibiotic resistance and for enzymes which catalyze a color-imparting reaction, which results in staining of the transformed cell. These can then be selected by automatic cell sorting. Microorganisms that have been successfully transformed with a vector and carry an appropriate antibiotic resistance gene (e.g. G418 or hygromycin) can be selected by appropriate antibiotic-comprising media or nutrient media. Marker proteins present on the cell surface can be used for selection by means of affinity chromatography.

As alternative preparation methods for sequences according to the invention, reference may be made to the chemical synthesis methods known per se, such as solid-phase synthesis or liquid-phase synthesis.

3.4 Recombinant Preparation of the Polypeptides:

The peptides used according to the invention can be prepared using recombinant techniques in a manner known per se, where a microorganism producing polypeptides is cultivated, if appropriate the expression of the polypeptides is induced and these are isolated from the culture. The polypeptides can also be produced on an industrial scale in this way if desired.

The recombinant microorganism can be cultured and fermented by known methods. Bacteria can be replicated, for example, in TB or LB medium and at a temperature of from 20 to 40° C. and a pH of from 6 to 9. Suitable culturing conditions are described in detail, for example, in T. Maniatis, E. F. Fritsch and J. Sambrook, Molecular Cloning: A Laboratory Manual, Cold Spring Harbor Laboratory, Cold Spring Harbor, N.Y. (1989).

If the polypeptides are not secreted into the culture medium, the cells are then disrupted and the product is obtained from the lysate by known protein isolation methods. The cells may alternatively be disrupted by high-frequency ultrasound, by high pressure, such as, for example, in a French pressure cell, by osmolysis, by the action of detergents, lytic enzymes or organic solvents, by homogenizers or by a combination of two or more of the methods listed.

The polypeptides can be purified by known chromatographic methods, such as molecular sieve chromatography (gel filtration), such as Q-Sepharose chromatography, ion exchange chromatography and hydrophobic chromatography, and by other customary methods, such as ultrafiltration, crystallization, salting out, dialysis and native gel electrophoresis. Suitable methods are described, for example, in Cooper, F. G., Biochemische Arbeitsmethoden, Verlag Walter de Gruyter, Berlin, New York or in Scopes, R., Protein Purification, Springer Verlag, New York, Heidelberg, Berlin.

It is particularly advantageous for isolation of the recombinant protein to use vector systems or oligonucleotides which extend the cDNA by specific nucleotide sequences and thus code for modified polypeptides or fusion proteins which serve, for example, for simpler purification. Suitable modifications of this type are, for example, so-called "tags" which act as anchors, such as, for example, the modification known as hexa-histidine anchor, or epitopes which can be recognized as antigens of antibodies (described, for example, in Harlow, E. and Lane, D., 1988, Antibodies: A Laboratory Manual. Cold Spring Harbor (N.Y.) Press). These anchors can be used to attach the proteins to a solid support, such as, for example, a polymer matrix which can, for example, be packed in a chromatography column, or can be used on a microtiter plate or another support.

These anchors can at the same time also be used for recognizing the proteins. Moreover, for recognizing the proteins, it is also possible to use customary markers, such as fluorescent dyes, enzyme markers which form a detectable reaction product following reaction with a substrate, or radioactive labels, alone or in combination with the anchors for derivatizing the proteins.

3.5 Embodiments of Compositions According to the Invention 3.5.1 General Fields of Application and Formulations The antimicrobial peptides according to the invention have a broad field of application in human cosmetics, in particular skincare and haircare, and also animal care, but can also be used pharmacologically.

The cosmetic compositions according to the invention are in particular skin cosmetic, nail cosmetic, hair cosmetic, dermatological, hygiene or pharmaceutical compositions. In particular, the antimicrobial peptides according to the invention are used for skin cosmetics, nail cosmetics and/or hair cosmetics or as oral care compositions. They permit the growth inhibition of undesired microorganisms which cause damage to hair and to skin, e.g. dandruff formation, to nails, e.g. increased nail brittleness, thickened nails, or which cause itching or burning.

According to a further embodiment, hair cosmetic or skin cosmetic preparations according to the invention serve in particular for the care or the protection of the skin or of the hair and are in the form of an emulsion, a dispersion, a suspension, an aqueous surfactant preparation, a milk, a lotion, a cream, a balsam, an ointment, a gel, granules, a powder, a stick preparation, such as, for example, a lipstick, a foam, an aerosol or a spray. Such formulations are highly suited to topical preparations. Suitable emulsions are oil-in-water emulsions and water-in-oil emulsions or microemulsions.

As a rule, the hair cosmetic or skin cosmetic preparation is used for application to the skin (topically) or to the hair. In this connection, "topical preparations" are to be understood as meaning those preparations which are suitable for applying the active ingredients to the skin in fine distribution. Of suitability for this purpose are, for example, aqueous and aqueous-alcoholic solutions, sprays, foams, foam aerosols, ointments, aqueous gels, emulsions of the O/W or W/O type, microemulsions or cosmetic stick preparations.

According to one embodiment of the cosmetic composition according to the invention, it comprises a carrier. Preferred carriers are water, a gas, a water-based liquid, an oil, a gel, an emulsion or microemulsion, a dispersion or a mixture thereof. Said carriers exhibit good skin compatibility. Aqueous gels, emulsions or microemulsions are particularly advantageous for topical preparations.

Besides customary additives and auxiliaries, the cosmetic compositions according to the invention can additionally comprise cosmetically and/or dermatologically active ingredients.

Examples of suitable further active ingredients are:

Suitable cosmetically and/or dermatologically active ingredients are, for example, coloring active ingredients, skin and hair pigmentation agents, tinting agents, tanning agents, bleaches, keratin-hardening substances, antimicrobial active ingredients, photofilter active ingredients, repellent active ingredients, hyperemic substances, keratolytically and keratoplastically effective substances, antidandruff active ingredients, antiphlogistics, keratinizing substances, antioxidative active ingredients and active ingredients that act as free-radical scavengers, substances which moisturize the skin or keep the skin moisturized, refatting active ingredients, antierythimatous or antiallergic active ingredients, branched fatty acids, such as 18-methyleicosanoic acid, and mixtures thereof.

Artificially skin-tanning active ingredients which are suitable for tanning the skin without natural or artificial irradiation with UV rays; these are, for example, dihydroxyacetone, alloxan and walnut shell extract. Suitable keratin-hardening substances are generally active ingredients which can also be used as antiperspirants, such as, for example, potassium aluminum sulfate, aluminum hydroxychloride, aluminum lactate, etc.

Antimicrobial active ingredients which are used in order to destroy microorganisms or to inhibit their growth. They thus serve both as preservatives and as deodorizing substance which reduces the formation or the intensity of body odor. These include, for example, customary preservatives known to the person skilled in the art, such as p-hydroxybenzoic acid esters, imidazolinylurea, formaldehyde, sorbic acid, benzoic acid, salicylic acid etc. Such deodorizing substances are, for example, zinc ricinoleate, triclosan, undecylenic acid alkylolamides, triethyl citrate, chlorhexidin etc.

Suitable auxiliaries and additives for the production of hair cosmetic, nail cosmetic or skin cosmetic preparations are familiar to the person skilled in the art and can be found in handbooks on cosmetics, for example Schrader, Grundlagen und Rezepturen der Kosmetika [Fundamentals and formulations of cosmetics], Hüthig Verlag, Heidelberg, 1989, ISBN 3-7785-1491-1. The auxiliaries and additives are preferably cosmetically and/or pharmaceutically acceptable auxiliaries. Of pharmaceutical acceptability are the auxiliaries known for use in the field of pharmacy, food technology and related fields, in particular those listed in the relevant pharmacopeia (e.g. DAB, Ph. Eur., BP, NF), and other auxiliaries whose properties do not preclude a physiological application.

Suitable auxiliaries may be: lubricants, wetting agents, emulsifying and suspending agents, preservatives, antioxidants, antiirritatives, chelating agents, emulsion stabilizers, film formers, gel formers, odor masking agents, hydrocolloids, solvents, solubility promoters, neutralizers, permeation accelerators, pigments, quaternary ammonium compounds, refatting and superfatting agents, ointment, cream or oil base substances, silicone derivatives, stabilizers, sterilants, propellants, drying agents, opacifiers, thickeners, waxes, softeners, white oil. An embodiment in this regard is based on technical knowledge, as presented, for example, in Fiedler, H. P. Lexikon der Hilfsstoffe für Pharmazie, Kosmetik and angrenzende Gebiete [Lexicon of auxiliaries for pharmacy, cosmetics and related fields], $4^{th}$ edition, Aulendorf: ECV-Editio-Kantor-Verlag, 1996.

Further suitable additives are selected from perfume oils, hair polymers, hair and skin conditioners, graft polymers, water-soluble or dispersible silicone-containing polymers, photoprotective agents, bleaches, care agents, colorants, tinting agents, tanning agents, dyes, consistency regulators, humectants, refatting agents, collagen, protein hydrolyzates, lipids, antioxidants, antifoams, antistatics, emollients, softeners, peroxide decomposers.

Specific examples of suitable auxiliaries and additives are (these may also be covalently or noncovalently bonded to the peptides according to the invention):

(1) Antioxidants selected from amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotinoids, carotenes (e.g. β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thiorodoxin, glutathione, cysteine, cystine, cystamine and the glycosyl, N-acetyl, methyl, ethyl, propyl, amyl, butyl, and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximines, buthionine sulfones, penta-, hexa-, heptathionine sulfoximine), in particular in very low tolerated doses (e.g. pmol to µmol/kg range), also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives thereof (e.g. sodium ascorbate, ascorbyl palmitate, Mg ascorbyl phosphate, ascorbyl acetate), tocopherol and derivatives (e.g. vitamin E acetate, tocotrienol), vitamin A and derivatives (vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide).

(2) Peroxide decomposers, i.e. compounds which are able to decompose peroxides, particularly preferably lipid peroxides. These are to be understood as including organic substances, such as, for example, pyridine-2-thiol-3-carboxylic acid, 2-methoxy-pyrimidinolcarboxylic acids, 2-methoxypyridinecarboxylic acids, 2-dimethylaminopyrimidinolcarboxylic acids, 2-dimethylaminopyridinecarboxylic acids.

(3) Thickeners, such as crosslinked polyacrylic acids and derivatives thereof, polysaccharides and derivatives thereof, such as xanthan gum, agar agar, alginates or tyloses, cellulose derivatives, e.g. carboxymethylcellulose or hydroxycarboxymethylcellulose, fatty alcohols, monoglycerides and fatty acids, polyvinyl alcohol and polyvinylpyrrolidone. Preference is given to using nonionic thickeners.

(4) Preservatives which are listed below with their E numbers

| | | |
|---|---|---|
| E 200 | Sorbic acid | |
| E 201 | Sodium sorbate | |
| E 202 | Potassium sorbate | |
| E 203 | Calcium sorbate | |
| E 210 | Benzoic acid | |
| E 211 | Sodium benzoate | |
| E 212 | Potassium benzoate | |
| E 213 | Calcium benzoate | |
| E 214 | Ethyl p-hydroxybenzoate | |
| E 215 | Ethyl p-hydroxybenzoate Na salt | |
| E 216 | n-Propyl p-hydroxybenzoate | |
| E 217 | n-Propyl p-hydroxybenzoate Na salt | |
| E 218 | Methyl p-hydroxybenzoate | |
| E 219 | Methyl p-hydroxybenzoate Na salt | |
| E 220 | Sulfur dioxide | |
| E 221 | Sodium sulfite | |
| E 222 | Sodium hydrogen sulfite | |
| E 223 | Sodium disulfite | |
| E 224 | Potassium disulfite | |
| E 226 | Calcium sulfite | |
| E 227 | Calcium hydrogensulfite | |
| E 228 | Potassium hydrogensulfite | |
| E 230 | Biphenyl (diphenyl) | |
| E 231 | Orthophenylphenol | |
| E 232 | Sodium orthophenylphenoxide | |
| E 233 | Thiabendazole | |
| E 235 | Natamycin | |
| E 236 | Formic acid | |
| E 237 | Sodium formate | |
| E 238 | Calcium formate | |
| E 239 | Hexamethylenetetramine | |
| E 249 | Potassium nitrite | |
| E 250 | Sodium nitrite | |
| E 251 | Sodium nitrate | |
| E 252 | Potassium nitrate | |
| E 280 | Propionic acid | |
| E 281 | Sodium propionate | |
| E 282 | Calcium propionate | |
| E 283 | Potassium propionate | |
| E 290 | Carbon dioxide | |

Also suitable according to the invention are preservatives or preservative auxiliaries customary in cosmetics, such as dibromodicyanobutane (2-bromo-2-bromomethyl-glutarodinitrile), 3-iodo-2-propynyl butylcarbamate, 2-bromo-2-nitropropane-1,3-diol, imidazolidinylurea, 5-chloro-2-methyl-4-isothiazolin-3-one, 2-chloroacetamide, benzalkonium chloride, benzyl alcohol, formaldehyde donors.

Also suitable as preservatives are phenyl hydroxyalkyl ethers, in particular the compound known under the name phenoxyethanol, on account of their bactericidal and fungicidal effects on a number of microorganisms.

Other antimicrobial agents are also likewise suitable for being incorporated into the preparations according to the invention. Advantageous substances are, for example, 2,4,4'-trichloro-2'-hydroxydiphenyl ether (irgasan), 1,6-di(4-chlorophenylbiguanido)-hexane (chlorhexidine), 3,4,4'-trichlorocarbanilide, quaternary ammonium compounds, oil of cloves, mint oil, thyme oil, triethyl citrate, farnesol (3,7,11-trimethyl-2,6,10-dodecatrien-14), and also the active ingredients and active ingredient combinations described in the patent laid-open specifications DE-37 40 186, DE-39 38 140, DE-42 04 321, DE-42 29 707, DE-43 09 372, DE-44 11 664, DE-195 41 967, DE-195 43 695, DE-195 43 696, DE-195 47 160, DE-196 02 108, DE-196 02 110, DE-196 02 111, DE-196 31 003, DE-196 31 004 and DE-196 34 019 and the patent specifications DE-42 29 737, DE-42 37 081, DE-43 24 219, DE-44 29 467, DE-44 23 410 and DE-195 16 705. Sodium hydrogencarbonate is also to be used advantageously. Antimicrobial polypeptides can likewise also be used.

(5) Photofilter active ingredients which absorbed UV rays in the UV-B and/or UV-A region. Suitable UV filters are, for example, 2,4,6-triaryl-1,3,5-triazines in which the aryl groups can in each case carry at least one substituent which is preferably selected from hydroxy, alkoxy, specifically methoxy, alkoxycarbonyl, specifically methoxycarbonyl and ethoxycarbonyl, and mixtures thereof. Also suitable are p-aminobenzoic acid esters, cinnamic acid esters, benzophenonones, camphor derivatives, and pigments that block UV rays, such as titanium dioxide, talc and zinc oxide.

Suitable UV filter substances are any desired UV-A and UV-B filter substances. Examples are:

| No. | Substance | CAS No. (=acid) |
|---|---|---|
| 1 | 4-Aminobenzoic acid | 150-13-0 |
| 2 | 3-(4'-Trimethylammonium)benzylidenebornan-2-one methylsulfate | 52793-97-2 |
| 3 | 3,3,5-Trimethylcyclohexyl salicylate (homosalate) | 118-56-9 |
| 4 | 2-Hydroxy-4-methoxybenzophenone (oxybenzone) | 131-57-7 |
| 5 | 2-Phenylbenzimidazole-5-sulfonic acid and its potassium, sodium and triethanolamine salts | 27503-81-7 |
| 6 | 3,3'-(1,4-Phenylenedimethine)bis(7,7-dimethyl-2-oxobicyclo[2.2.1]heptane-1-methanesulfonic acid) and its salts | 90457-82-2 |
| 7 | Polyethoxyethyl 4-bis(polyethoxy)aminobenzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | 2-Isoamyl 4-methoxycinnamate | 71617-10-2 |
| 11 | 2-Ethylhexyl 4-methoxycinnamate | 5466-77-3 |
| 12 | 2-Hydroxy-4-methoxybenzophenone-5-sulfonic acid (sulisobenzone) and the sodium salt | 4065-45-6 |
| 13 | 3-(4'-Sulfobenzylidene)bornan-2-one and salts | 58030-58-6 |
| 14 | 3-Benzylidenebornan-2-one | 16087-24-8 |
| 15 | 1-(4'-Isopropylphenyl)-3-phenylpropane-1,3-dione | 63260-25-9 |
| 16 | 4-Isopropylbenzylsalicylate | 94134-93-7 |
| 17 | 3-Imidazol-4-ylacrylic acid and its ethyl ester | 104-98-3 |
| 18 | Ethyl 2-cyano-3,3-diphenylacrylate | 5232-99-5 |
| 19 | 2'-Ethylhexyl 2-cyano-3,3-diphenylacrylate | 6197-30-4 |
| 20 | Menthyl o-aminobenzoate or: 5-methyl-2-(1-methylethyl)-2-aminobenzoate | 134-09-8 |
| 21 | Glyceryl p-aminobenzoate or: 1-glyceryl 4-aminobenzoate | 136-44-7 |
| 22 | 2,2'-Dihydroxy-4-methoxybenzophenone (dioxybenzone) | 131-53-3 |
| 23 | 2-Hydroxy-4-methoxy-4-methylbenzophenone (mexenone) | 1641-17-4 |
| 24 | Triethanolaminee salicylate | 2174-16-5 |
| 25 | Dimethoxyphenylglyoxalic acid or: sodium 3,4-dimethoxyphenylglyoxalate | 4732-70-1 |
| 26 | 3-(4'Sulfobenzylidene)bornan-2-one and its salts | 56039-58-8 |
| 27 | 4-tert-Butyl-4'-methoxy-dibenzoylmethane | 70356-09-1 |
| 28 | 2,2',4,4'-Tetrahydroxybenzophenone | 131-55-5 |
| 29 | 2,2'-Methylenebis[6-(2H-benzotriazol-2-yl)-4-(1,1,3,3,-tetramethylbutyl)phenol] | 103597-45-1 |
| 30 | 2,2'-(1,4-Phenylene)bis-1H-benzimidazole-4,6-disulfonic acid, Na salt | 180898-37-7 |
| 31 | 2,4-bis[4-(2-Ethylhexyloxy)-2-hydroxy]phenyl-6-(4-methoxyphenyl)(1,3,5)-triazine | 187393-00-6 |
| 32 | 3-(4-Methylbenzylidene)camphor | 36861-47-9 |
| 33 | Polyethoxyethyl 4-bis(polyethoxy)paraaminobenzoate | 113010-52-9 |
| 34 | 2,4-Dihydroxybenzophenone | 131-56-6 |
| 35 | 2,2'-Dihydroxy-4,4'-dimethoxybenzophenone-5,5'-disodium sulfonate | 3121-60-6 |
| 36 | 2-[4-(Diethylamino)-2-hydroxybenzoyl]hexyl benzoate | 302776-68-7 |
| 37 | 2-(2H-Benzotriazol-2-yl)-4-methyl-6-[2-methyl-3-[1,3,3,3-tetramethyl-1-[(trimethylsilyl)oxy]disiloxanyl]propyl]phenol | 155633-54-8 |
| 38 | 1,1-[(2,2'-Dimethylpropoxy)carbonyl]-4,4-diphenyl-1,3-butadiene | 363602-15-7 |

Furthermore, the cosmetic and dermatological preparations according to the invention can advantageously comprise inorganic pigments which block UV rays and are based on metal oxides and/or other metal compounds that are insoluble or sparingly soluble in water selected from the group of the oxides of zinc (ZnO), titanium ($TiO_2$), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals and mixtures of such oxides.

The inorganic pigments here may be present in coated form, i.e. be surface-treated. This surface treatment can, for example, consist in providing the pigments with a thin hydrophobic layer by the method known per se, as described in DE-A-33 14 742.

(6) Repellent active ingredients, i.e. compounds which are able to keep away or drive away certain animals, in particular insects, from people. These include, for example, 2-ethyl-1,3-hexanediol, N,N-diethyl-m-toluamide etc. Suitable hyperemic substances, which stimulate blood flow through the skin, are, for example, essential oils, such as dwarf-pine needle extract, lavender extract, rosemary extract, juniper berry extract, horse chestnut extract, birch leaf extract, hay flower extract, ethyl acetate, camphor, menthol, peppermint oil, rosemary extract, eucalyptus oil etc. Suitable keratolytic and keratoplastic substances are, for example, salicylic acid, calcium thioglycolate, thioglycolic acid and its salts, sulfur etc. Suitable antidandruff active ingredients are, for example, sulfur, sulfur polyethylene glycol sorbitan monooleate, sulfur ricinol polyethoxylate, zinc pyrithione, aluminum pyrithione etc. Suitable antiphlogistics, which counteract skin irritations, are, for example, allantoin, bisabolol, dragosantol, camomile extract, panthenol etc.

(7) Cosmetically or pharmaceutically acceptable polymers, such as cationic, amphoteric and neutral polymers.

Suitable polymers are, for example, cationic polymers with the INCI name Polyquaternium, e.g. copolymers of vinylpyrrolidone/N-vinylimidazolium salts (Luviquat FC, Luviquat HM, Luviquat MS, Luviquat, Care), copolymers of N-vinylpyrrolidone/dimethylaminoethyl methacrylate, quaternized with diethyl sulfate (Luviquat PQ 11), copolymers of N-vinylcaprolactam/N-vinylpyrrolidone/N-vinylimidazolium salts (Luviquat E Hold), cationic cellulose derivatives (Polyquaternium-4 and -10), acrylamido copolymers (Polyquaternium-7) and chitosan.

Suitable cationic (quaternized) polymers are also Merquat (polymer based on dimethyldiallylammonium chloride), Gafquat (quaternary polymers which are formed by the reaction of polyvinylpyrrolidone with quaternary ammonium compounds), polymer JR (hydroxyethylcellulose with cationic groups) and cationic polymers based on plants, e.g. guar polymers, such as the Jaguar grades from Rhodia.

Further suitable polymers are also neutral polymers, such as polyvinylpyrrolidones, copolymers of N-vinylpyrrolidone and vinyl acetate and/or vinyl propionate, polysiloxanes, polyvinylcaprolactam and other copolymers with N-vinylpyrrolidone, polyethyleneimines and salts thereof, polyvinylamines and salts thereof, cellulose derivatives, polyaspartic acid salts and derivatives thereof. These include, for example, Luviflex® Swing (partially saponified copolymer of polyvinyl acetate and polyethylene glycol, BASF).

Suitable polymers are also nonionic, water-soluble or water-dispersible polymers or oligomers, such as polyvinylcaprolactam, e.g. Luviskol® Plus (BASF), or polyvinylpyrrolidone and copolymers thereof, in particular with vinyl esters, such as vinyl acetate, e.g. Luviskol® VA 37 (BASF), polyamides, e.g. based on itaconic acid and aliphatic diamines, as are described, for example, in DE-A-43 33 238.

Suitable polymers are also amphoteric or zwitterionic polymers, such as the octylacrylamide/methyl methacrylate/tert-butylaminoethyl methacrylate-hydroxypropyl methacrylate copolymers obtainable under the names Amphomer (National Starch), and also zwitterionic polymers as are disclosed, for example, in the German patent applications DE 39 29 973, DE 21 50 557, DE 28 17 369 and DE 37 08 451. Acrylamidopropyltrimethylammonium chloride/acrylic acid or methacrylic acid copolymers and the alkali metal and ammonium salts thereof are preferred zwitterionic polymers. Furthermore, suitable zwitterionic polymers are methacryloylethyl-betaine/methacrylate copolymers, which are commercially available under the name Amersette (AMERCHOL), and copolymers of hydroxyethyl methacrylate, methyl methacrylate, N,N-dimethylaminoethyl methacrylate and acrylic acid (Jordapon (D)).

Suitable polymers are also nonionic, siloxane-containing, water-soluble or dispersible polymers, e.g. polyether siloxanes, such as Tegopren (Goldschmidt) and Besi (Wacker).

3.5.2 Particular Compositions According to the Invention

According to a preferred embodiment, the compositions according to the invention are a skin or hair cleaning composition.

Preferred skin or hair cleaning compositions are soaps of liquid to gel-like consistency, such as transparent soaps, luxury soaps, deodorant soaps, cream soaps, baby soaps, skin protection soaps, abrasive soaps and syndets, pasty soaps, soft soaps and washing pastes, peeling soaps, wet wipes, liquid washing, shower and bathing preparations, such as washing lotions, shower baths and shower gels, foam baths, oil baths and scrub preparations, shaving foams, shaving lotions and shaving creams.

According to a further preferred embodiment, the compositions according to the invention are a shower gel, a shampoo formulation or a bathing preparation. Such formulations comprise at least one antimicrobial peptide and usually anionic surfactants as base surfactants and amphoteric and/or nonionic surfactants as cosurfactants. Further suitable active ingredients and/or auxiliaries are generally selected from lipids, perfume oils, dyes, organic acids, preservatives and antioxidants, and also thickeners/gel formers, skin conditioners and humectants.

i) Specific Embodiments for Compositions for Applying to the Skin:

Suitable skin cosmetic compositions are, for example, face tonics, face masks, deodorants and other cosmetic lotions. Compositions for use in decorative cosmetics comprise, for example, concealing sticks, stage make-up, mascara and eye shadows, lipsticks, kohl pencils, eyeliners, blushers, powders and eyebrow pencils.

Furthermore, the dermatological agents according to the invention can be used in nose-strips for pore cleansing, in antiacne compositions, repellents, shaving compositions, aftershave and preshave care compositions, aftersun care compositions, hair removal compositions, hair colorants, intimate care compositions, foot care compositions and in babycare.

The skincare compositions according to the invention are in particular W/O or O/W skin creams, day and night creams, eye creams, face creams, antiwrinkle creams, sunscreen creams, moisturizing creams, bleaching creams, self-tanning creams, vitamin creams, skin lotions, care lotions and moisturizing lotions.

Skin cosmetic and dermatological compositions preferably comprise at least one peptide in an amount of from about 0.0001 to 50% by weight, preferably 0.001 to 10% by weight, very particularly preferably 0.0057 to 0.1% by weight, based on the total weight of the composition.

Depending on the field of application, the skin cosmetic compositions according to the invention can be applied in a form suitable for skincare, such as, for example, as cream, foam, gel, stick, mousse, milk, spray (pump spray or propellant-containing spray).

Besides the peptides according to the invention and suitable carriers, the skin cosmetic preparations can also comprise further active ingredients and auxiliaries customary in skin cosmetics, as described previously. These include, preferably, emulsifiers, preservatives, perfume oils, cosmetic active ingredients, such as phytantriol, vitamin A, E and C, retinol, bisabolol, panthenol, photoprotective agents, bleaches, colorants, tinting agents, tanning agents, collagen, enzymes, protein hydrolyzates, stabilizers, pH regulators, dyes, salts, thickeners, gel formers, consistency regulators, silicones, humectants, refatting agents and further customary additives.

Preferred oil and fat components of the skin cosmetic and dermatological compositions are the abovementioned mineral and synthetic oils, such as, for example, paraffins, silicone oils and aliphatic hydrocarbons with more than 8 carbon atoms, animal and vegetable oils, such as, for example, sunflower oil, coconut oil, avocado oil, olive oil, lanolin, or waxes, fatty acids, fatty acid esters, such as, for example, triglycerides of $C_6$-$C_{30}$-fatty acids, wax esters, such as, for example, jojoba oil, fatty alcohols, vaseline, hydrogenated lanolin and acetylated lanolin, and mixtures thereof.

To establish certain properties, such as, for example, improving the feel to the touch, the spreading behavior, the water resistance and/or the binding of active ingredients and auxiliaries, such as pigments, the skin cosmetic and dermatological preparations can additionally also comprise conditioning substances based on silicone compounds. Suitable silicone compounds are, for example, polyalkylsiloxanes, polyarylsiloxanes, polyarylalkylsiloxanes, polyether siloxanes or silicone resins.

The cosmetic or dermatological preparations are produced in accordance with customary methods known to the person skilled in the art.

To produce the dermatological compositions according to the invention, the active ingredients can be mixed or diluted with a suitable auxiliary (excipient). Excipients can be solid, semisolid or liquid materials which can serve as vehicles, carriers or medium for the active ingredient. The admixing of further auxiliaries takes place if desired in the manner known to the person skilled in the art. Furthermore, the polymers and dispersions are suitable as auxiliaries in pharmacy, preferably as or in (a) coating(s) or (a) binder(s) for solid drug forms. They can also be used in creams and as tablet coatings and tablet binders.

Preferably, the cosmetic and dermatological compositions are present in the form of emulsions, in particular as water-in-oil (W/O) or oil-in-water (O/W) emulsions. However, it is also possible to choose other types of formulation, for example gels, oils, oleogels, multiple emulsions, for example in the form of W/O/W or O/W/O emulsions, anhydrous ointments or ointment bases etc. Emulsifier-free formulations such as hydrodispersions, hydrogels or a Pickering emulsion are also advantageous embodiments.

The preparation of emulsions takes place by known methods. Besides at least one peptide according to the invention, the emulsions generally comprise customary constituents, such as fatty alcohols, fatty acid esters and in particular fatty acid triglycerides, fatty acids, lanolin and derivatives thereof, natural or synthetic oils or waxes and emulsifiers in the presence of water. The selection of additives specific to the type of emulsion and the preparation of suitable emulsions is described, for example, in Schrader, Grundlagen and Rezepturen der Kosmetika [Fundamentals and formulations of cosmetics], Hüthig Buch Verlag, Heidelberg, 2nd edition, 1989, third part, to which reference is hereby expressly made.

A suitable emulsion as W/O emulsion, e.g. for a skin cream etc., generally comprises an aqueous phase which is emulsified in an oil or fatty phase by means of a suitable emulsifier system. A polyelectrolyte complex can be used for producing the aqueous phase.

Preferred fatty components which may be present in the fatty phase of the emulsions are: hydrocarbon oils, such as paraffin oil, Purcellin oil, perhydrosqualene and solutions of microcrystalline waxes in these oils; animal or vegetable oils, such as sweet almond oil, avocado oil, calophylum oil, lanolin and derivatives thereof, castor oil, sesame oil, olive oil, jojoba oil, karite oil, hoplostethus oil, mineral oils whose distillation start under atmospheric pressure is at about 250° C. and whose distillation end point is at 410° C., such as, for example, vaselin oil, esters of saturated or unsaturated fatty acids, such as alkyl myristates, e.g. isopropyl, butyl or cetyl myristate, hexadecyl stearate, ethyl or isopropyl palmitate, octanoic acid or decanoic acid triglycerides and cetyl ricinoleate.

The fatty phase can also comprise silicone oils that are soluble in other oils, such as dimethylpolysiloxane, methylphenylpolysiloxane and the silicone glycol copolymer, fatty acids and fatty alcohols.

Besides the peptides according to the invention, it is also possible to use waxes, such as, for example, carnauba wax, candelilla wax, beeswax, microcrystalline wax, ozokerite wax and Ca, Mg and Al oleates, myristates, linoleates and stearates.

Furthermore, an emulsion according to the invention can be in the form of an O/W emulsion. Such a type of emulsion usually comprises an oil phase, emulsifiers which stabilize the oil phase in the water phase, and an aqueous phase, which is usually present in thickened form. Suitable emulsifiers are preferably O/W emulsifiers, such as polyglycerol esters, sorbitan esters or partially esterified glycerides.

According to a further preferred embodiment, the compositions according to the invention are a shower gel, a shampoo formulation or a bathing preparation.

Such formulations comprise at least one peptide according to the invention and usually anionic surfactants as base surfactants and amphoteric and/or nonionic surfactants as cosurfactants. Further suitable active ingredients and/or auxiliaries are generally selected from lipids, perfume oils, dyes, organic acids, preservatives and antioxidants, and thickeners/gel formers, skin conditioners and moisturizers.

These formulations comprise preferably 2 to 50% by weight, preferably 5 to 40% by weight, particularly preferably 8 to 30% by weight, of surfactants, based on the total weight of the formulation.

All anionic, neutral, amphoteric or cationic surfactants customarily used in body cleaning compositions can be used in the washing, showering and bathing preparations.

Suitable anionic surfactants are, for example, alkyl sulfates, alkyl ether sulfates, alkylsulfonates, alkylarylsulfonates, alkyl succinates, alkyl sulfosuccinates, N-alkoyl sarcosinates, acyl taurates, acyl isothionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and also ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

These include, for example, sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecylbenzenesulfonate, triethanolamine dodecylbenzenesulfonate.

Suitable amphoteric surfactants are, for example, alkylbetaines, alkylamidopropylbetaines, alkylsulfobetaines, alkyl glycinates, alkyl carboxyglycinates, alkyl amphoacetates or -propionates, alkyl amphodiacetates or -dipropionates.

For example, cocodimethylsulfopropylbetaine, laurylbetaine, cocamidopropylbetaine or sodium cocamphopropionate can be used.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 moles per mole of alcohol. Also suitable are alkylamine oxides, mono- or dialkylalkanolamines, fatty acid esters of polyethylene glycols, ethoxylated fatty acid amides, alkyl polyglycosides or sorbitan ether esters.

Furthermore, the washing, showering and bathing preparations can comprise customary cationic surfactants, such as, for example, quaternary ammonium compounds, for example cetyltrimethylammonium chloride.

Furthermore, the shower gel/shampoo formulations can comprise thickeners, such as, for example, sodium chloride PEG-55, propylene glycol oleate, PEG-120 methylglucose dioleate and others, and also preservatives, further active ingredients and auxiliaries and water.

ii) Specific Embodiments for Hair Treatment Compositions

According to a further preferred embodiment, the compositions according to the invention are a hair treatment composition.

Hair treatment compositions according to the invention comprise preferably at least one peptide according to the invention in an amount in the range from about 0.0001 to 50% by weight, preferably 0.001 to 10% by weight, particularly preferably 0.0057 to 0.1% by weight, based on the total weight of the composition.

Preferably, the hair treatment compositions according to the invention are in the form of a setting foam, hair mousse, hair gel, shampoo, hairspray, hair foam, end fluid, neutralizer for permanent waves, hair colorant and bleach or "hot-oil treatment". Depending on the field of use, the hair cosmetic preparations can be applied as (aerosol) spray, (aerosol) foam, gel, gel spray, cream, lotion or wax. Hairsprays here comprise both aerosol sprays and also pump sprays without propellant gas. Hair foams comprise both aerosol foams and also pump foams without propellant gas. Hairsprays and hair foams comprise preferably predominantly or exclusively water-soluble or water-dispersible components. If the compounds used in the hairsprays and hair foams according to the invention are water-dispersible, they can be applied in the form of aqueous microdispersions with particle diameters of usually 1 to 350 nm, preferably 1 to 250 nm. The solids contents of these preparations are usually in a range from about 0.5 to 20% by weight. These microdispersions generally require no emulsifiers or surfactants for their stabilization.

The hair cosmetic formulations according to the invention comprise, in a preferred embodiment, a) 0.0001 to 50% by weight of at least one peptide according to the invention, b) 20 to 99.95% by weight of water and/or alcohol, c) 0 to 50% by weight of at least one propellant gas, d) 0 to 5% by weight of at least one emulsifier, e) 0 to 3% by weight of at least one thickener, and also up to 25% by weight of further constituents.

Alcohol is to be understood as meaning all alcohols customary in cosmetics, for example ethanol, isopropanol, n-propanol.

Also included here are all styling and conditioner polymers known in cosmetics which can be used in combination with the peptides according to the invention if quite specific properties are to be set.

Suitable conventional hair cosmetics polymers are, for example, the aforementioned cationic, anionic, neutral, nonionic and amphoteric polymers, to which reference is hereby made.

To establish certain properties, the preparations can additionally also comprise conditioning substances based on silicone compounds. Suitable silicone compounds are, for example, polyalkylsiloxanes, polyarylsiloxanes, polyarylalkylsiloxanes, polyether siloxanes, silicone resins or dimethicone copolyols (CTFA) and aminofunctional silicone compounds, such as amodimethicones (CTFA).

The polymers according to the invention are suitable in particular as setting agents in hairstyling preparations, in particular hairsprays (aerosol sprays and pump sprays without propellant gas) and hair foams (aerosol foams and pump foams without propellant gas).

In a preferred embodiment, spray preparations comprise a) 0.0001 to 50% by weight of at least one polypeptide according to the invention, b) 20 to 99.9% by weight of water and/or alcohol, c) 0 to 70% by weight of at least one propellant, d) 0 to 20% by weight of further constituents.

Propellants are the propellants customarily used for hairsprays or aerosol foams. Preference is given to mixtures of propane/butane, pentane, dimethyl ether, 1,1-difluoroethane (HFC-152 a), carbon dioxide, nitrogen or compressed air.

A formulation for aerosol hair foams preferred according to the invention comprises a) 0.0001 to 50% by weight of at least one peptide according to the invention, b) 55 to 99.8% by weight of water and/or alcohol, c) 5 to 20% by weight of a propellant, d) 0.1 to 5% by weight of an emulsifier, e) 0 to 10% by weight of further constituents.

Emulsifiers that can be used are all emulsifiers customarily used in hair foams. Suitable emulsifiers may be nonionic, cationic or anionic or amphoteric.

Examples of nonionic emulsifiers (INCI nomenclature) are laureths, e.g. laureth-4; ceteths, e.g. ceteth-1, polyethylene glycol cetyl ether, ceteareths, e.g. ceteareth-25, polyglycol fatty acid glycerides, hydroxylated lecithin, lactyl esters of fatty acids, alkyl polyglycosides.

Examples of cationic emulsifiers are cetyldimethyl-2-hydroxyethylammonium dihydrogenphosphate, cetyltrimonium chloride, cetyltrimmonium bromide, cocotrimonium methyl sulfate, quaternium-1 to x (INCI).

Anionic emulsifiers can be selected, for example, from the group of alkyl sulfates, alkyl ether sulfates, alkylsulfonates, alkylarylsulfonates, alkyl succinates, alkyl sulfosuccinates, N-alkoyl sarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and also ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

A preparation suitable according to the invention for styling gels can, for example, have the following composition: a) 0.0001 to 50% by weight of at least one peptide according to the invention, b) 80 to 99.85% by weight of water and/or alcohol, c) 0 to 3% by weight, preferably 0.05 to 2% by weight, of a gel former, d) 0 to 20% by weight of further constituents.

The use of gel formers may be advantageous in order to set specific rheological or other application properties of the gels. Gel formers that can be used are all gel formers customary in cosmetics. These include lightly crosslinked polyacrylic acid, for example carbomer (INCI), cellulose derivatives, e.g. hydroxypropylcellulose, hydroxyethylcellulose, cationically modified celluloses, polysaccharides, e.g. xanthan gum, caprylic/capric triglyceride, sodium acrylate copolymers, polyquaternium-32 (and) paraffinum liquidum (INCI), sodium acrylate copolymers (and) paraffinum liquidum (and) PPG-1 trideceth-6, acrylamidopropyltrimonium chloride/acrylamide copolymers, steareth-10 allyl ether, acrylate copolymers, polyquaternium-37 (and) paraffinum liquidum (and) PPG-1 trideceth-6, polyquaternium 37 (and) propylene glycol dicaprate dicaprylate (and) PPG-1 trideceth-6, polyquaternium-7, polyquaternium-44.

A preparation comprising the peptides according to the invention can preferably be used in shampoo formulations as antidandruff agent. Preferred shampoo formulations comprise a) 0.0001 to 50% by weight of at least one peptide according to the invention, b) 25 to 94.95% by weight of water, c) 5 to 50% by weight of surfactants, c) 0 to 5% by weight of a further conditioner, d) 0 to 10% by weight of further cosmetic constituents.

All anionic, neutral, amphoteric or cationic surfactants customarily used in shampoos can be used in the shampoo formulations.

Suitable anionic surfactants are, for example, alkyl sulfates, alkyl ether sulfates, alkylsulfonates, alkylarylsulfonates, alkyl succinates, alkyl sulfosuccinates, N-alkoyl sarcosinates, acyl taurates, acyl isothionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

Of suitability are, for example, sodium lauryl sulfate, ammonium lauryl sulfate, sodium lauryl ether sulfate, ammonium lauryl ether sulfate, sodium lauroyl sarcosinate, sodium oleyl succinate, ammonium lauryl sulfosuccinate, sodium dodecylbenzenesulfonate, triethanolamine dodecylbenzenesulfonate.

Suitable amphoteric surfactants are, for example, alkylbetaines, alkylamidopropylbetaines, alkylsulfobetaines, alkyl glycinates, alkyl carboxyglycinates, alkyl amphoacetates or -propionates, alkyl amphodiacetates or -dipropionates.

For example, cocodimethylsulfopropylbetaine, laurylbetaine, cocamidopropylbetaine or sodium cocamphopropionate can be used.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 moles per mole of alcohol. Also suitable are alkylamine oxides, mono- or dialkylalkanolamides, fatty acid esters of polyethylene glycols, alkyl polyglycosides or sorbitan ether esters.

Furthermore, the shampoo formulations can comprise customary cationic surfactants, such as, for example, quaternary ammonium compounds, for example cetyltrimethylammonium chloride.

To achieve certain effects, customary conditioners can be used in combination with the peptides according to the invention in the shampoo formulations.

These include, for example, the abovementioned cationic polymers with the INCI name Polyquaternium, in particular copolymers of vinylpyrrolidone/N-vinylimidazolium salts (Luviquat FC, Luviquat HM, Luviquat MS, Luviquat Care), copolymers of N-vinylpyrrolidone/dimethylaminoethyl methacrylate, quaternized with diethyl sulfate (Luviquat D PQ 11), copolymers of N-vinylcaprolactam/N-vinylpyrrolidone/N-vinylimidazolium salts (Luviquat D Hold), cationic cellulose derivatives (Polyquaternium-4 and -10), acrylamide copolymers (Polyquaternium-7). In addition, protein hydrolyzates can be used, and also conditioning substances based on silicone compounds, for example polyalkylsiloxanes, polyarylsiloxanes, polyarylalkylsiloxanes, polyether siloxanes or silicone resins. Further suitable silicone compounds are dimethicone copolyols (CTFA) and aminofunctional silicone compounds such as amodimethicones (CTFA). In addition, cationic guar derivatives, such as guar hydroxypropyltrimonium chloride (INCI) can be used.

The invention will now be illustrated further by reference to the following nonlimiting examples.

EXPERIMENTAL SECTION

1. Test Examples A

Example 1

Inhibition of *Malassezia furfur* by P18

Growth medium: M472-Pitysporum medium according to DSMZ
40 g/l malt extract
20 g/l ox bile
10 g/l Tween 40

The components were sterilized at 121° C., 1 bar superatmospheric pressure for 20 minutes.

2 g/l of olive oil were sterilized by filtration and, after autoclaving, added to the other components.

Since it was a two-phase medium, the complete medium was treated with sonication in order to enlarge the phase boundary.

For agar plates, if appropriate, 150 g/l of agar agar were added to the medium.

The growth test was carried out as follows: A shake flask with M472-Pitysporum medium was inoculated with *M. furfur* and incubated with shaking overnight at 30° C. and 200 rpm.

A 96-well microtiter plate was filled with in each case 100 μl of M472-Pitysporum medium and inoculated with *M. furfur* suspension of the overnight culture. The *M. furfur* suspension was adjusted at the start of the experiment to an optical density, measured at 620 nm, of 0.02. The concentrates of the inhibitor solutions were 1 mM in water or DMSO.

The growth of the following batches was compared by measuring the optical density:

*M. furfur* suspension without the addition of an inhibitor.

*M. furfur* suspension without the addition of an inhibitor, but the addition of 2.5 μl of DMSO, which is comparable with the remaining experiments. This was to exclude that an inhibition is attributable merely to the effect of the DMSO, or a false positive result being observed.

*M. furfur* suspension and addition of an aqueous P18 solution with a final concentration of 25 μM.

*M. furfur* suspension and addition of a P18 solution in DMSO with a final concentration of 25 μM.

*M. furfur* suspension and addition of a zinc pyrithione (ZPT, Sigma-Aldrich) solution in DMSO with a final concentration of 25 μM.

*M. furfur* suspension and addition of a Ketoconazole (Sigma-Aldrich) solution in DMSO with a final concentration of 25 μM.

The microtiter plate was incubated with shaking at 30° C.

The growth was observed over 40 hours by measuring the optical density. The colony-forming units (CFU) were then determined by plating out 10 μl from each of the suspensions and, after incubation for 6 days, counting the colonies. The CFU was determined in order to exclude an influence of the two-phase medium and also the growth form of *M. furfur* on the optical density. However, in all of the experiments, the CFU correlated with the measured growth curves. The CFU measurement was helpful in order to detect weak growth compared to no measurable growth. The experiments were carried out at least in triple determinations and independently repeated. The results of one example experiment are summarized in Tables 1 and 2.

TABLE 1

Measurement of the optical density

| Incubation time [h] | without inhib. | without inhib. with DMSO | Addition of aqueous P18 solution [25 μM] | Addition of P18 solution in DMSO [25 μM] | Addition of ZPT solution in DMSO [25 μM] | Addition of Ketoconazole solution in DMSO [25 μM] |
|---|---|---|---|---|---|---|
| 0 | 0 | 0 | 0 | 0 | 0 | 0 |
| 16 | 0 | 0 | 0 | 0 | 0 | 0 |
| 24 | 0.21 | 0.12 | 0 | 0 | 0 | 0.004 |
| 40 | 0.42 | 0.25 | 0 | 0 | 0 | 0.013 |

TABLE 2

Counting the colony-forming units

| Incubation time [h] | without inhib. | without inhib. with DMSO | Addition of aqueous P18 solution [25 μM] | Addition of P18 solution in DMSO [25 μM] | Addition of ZPT solution in DMSO [25 μM] | Addition of Ketoconazole solution in DMSO [25 μM] |
|---|---|---|---|---|---|---|
| 16 | >10 000 | >10 000 | 62 | 8 | 42 | 80 |
| 24 | >10 000 | >10 000 | 41 | 0 | 22 | 22 |
| 40 | >10 000 | >10 000 | 120 | 0 | 28 | 90 |

The measurements for the optical density and the CFU show that the growth of *M. furfur* is effectively inhibited over the observed time period. Up to 40 hours, this inhibition was more effective compared to active ingredients such as zinc pyrithione (ZPT) or Ketoconazole.

Example 2

Inhibition of *Malassezia furfur* by P18 Compared to Magainin 2 and Cecropin A

The fusion peptide P18 is derived from magainin 2 and cecropin A. It was therefore investigated whether P18 more effectively inhibits the growth of *Malassezia furfur* than magainin 2 or cecropin A alone. For this, the procedure was as described in Example 1. 1 mM stock solutions of the fusion peptide P18, magainin 2 and cecropin A in DMSO were prepared. The final concentrations of the peptides in the growth experiments were 25 μM. The same amount of DMSO was likewise added to the suspension without inhibitor in order to exclude a growth-inhibiting effect of the DMSO.

The growth of the following mixtures was compared by measuring the optical density:

*M. furfur* suspension without the addition of an inhibitor, but with the addition of 2.5 μl of DMSO, which is comparable with the remaining experiments. This was to exclude that an inhibition is attributable merely to the effect of the DMSO.

*M. furfur* suspension and addition of a magainin 2 solution in DMSO with a final concentration of 25 μM.

*M. furfur* suspension and addition of a cecropin A solution in DMSO with a final concentration of 25 μM.

*M. furfur* suspension and addition of a peptide P18 (SEQ ID NO$_3$) solution in DMSO with a final concentration of 25 μM.

The experimental results of an example experiment are summarized in Table 3 below.

TABLE 3

CFU comparison of P18, magainin 2 and cecropin A

| Incubation time [h] | without inhib. with DMSO | Addition of magainin 2 solution in DMSO [25 μM] | Addition of Cecropin A solution in DMSO [25 μM] | Addition of P18 solution in DMSO [25 μM] |
|---|---|---|---|---|
| 64 | >10 000 | >10 000 | >5000 | 0 |
| 72 | >10 000 | >10 000 | >5000 | 23 |

It was found that the peptide P18 inhibits the growth of *M. furfur* more effectively than magainin 2 or cecropin A alone.

Example 3

Long-Term Stability of P18

The long-term stability of P18 was observed over a period of 2 weeks. For this, a 1 mM P18 solution in water was incubated at 37° C. over the entire period. At the start of the experiment and then on these two weeks, the antimicrobial activity was detected through inhibition of the growth of *Escherichia coli*. The growth medium used here was LB medium as complex medium. The medium comprised 10 g of trypton, 5 g of yeast extract and 10 g of NaCl per liter.

The growth test was carried out as follows: A shake flask of LB medium was inoculated with *Escherichia coli* and incubated overnight with shaking at 37° C. and 200 rpm. A 96-well microtiter plate was filled with in each case 100 μl of LB medium and inoculated with *E. coli* suspension of the overnight culture. The *E. coli* suspension was adjusted at the start of the experiment to an optical density, measured at 620 nm, of about 0.02. The concentrates of the P18 inhibitor solutions were 1 mM in water.

The growth of the following mixtures was compared by measuring the optical density:

*E. coli* suspension without the addition of an inhibitor.

*E. coli* suspension and addition of an aqueous P18 solution with a final concentration of 25 μM. The aqueous P18 solution had been freshly prepared.

E. coli suspension and addition of an aqueous P18 solution with a final concentration of 25 µM. The aqueous stock solution had been incubated for 2 weeks at 37° C.

The growth was observed over a period of 40 hours by measuring the optical density. It was found that the antimicrobial activity was unchanged even after incubation for 2 weeks at 37° C. and effectively inhibited the growth of *E. coli* over a period of 40 hours. The results are summarized in Table 4.

TABLE 4

Long-term stability, measured via the optical density at 620 nm

| Incubation time [h] | Sterile LB medium | E. coli suspension without inhib. | Addition of fresh aqueous P18 solution [25 µM] | Addition of stored aqueous P18 solution [25 µM] |
|---|---|---|---|---|
| 0 | 0 | 0.017 | 0.098 | 0.081 |
| 16 | 0 | 0.656 | 0 | 0 |
| 24 | 0 | 0.546 | 0 | 0 |
| 40 | 0 | 0.508 | 0 | 0 |

Example 4

Biodegradability of P18

Firstly, the peptide P18 was digested by adding chymotrypsin (from bovine pancreas, Sigma). For this, a 1 mM P18 solution was prepared and treated in accordance with the manufacturer's instructions. The samples were incubated for 16 hours at 37° C. The negative control used was a sample of a P18 solution without addition of chymotrypsin or a control solution which comprised only chymotrypsin, but no P18. The antimicrobial activity of P18 on *E. coli* cells was then investigated. The test was carried out as described in Example 3.

The growth of the following mixtures was compared by measuring the optical density:

*E. coli* suspension without the addition of an inhibitor.

*E. coli* suspension and addition of an aqueous P18 solution with a final concentration of 10 µM. The P18 solution had been stored beforehand for 16 hours at 37° C.

*E. coli* suspension and addition of an aqueous P18 solution with a final concentration of 10 µM. The P18 solution had been stored beforehand in accordance with the manufacturer's instructions for 16 hours at 37° C. and treated with chymotrypsin.

*E. coli* suspension and addition of an aqueous chymotrypsin solution which comprised, as control, the same amount of chymotrypsin as the P18 solution which was digested with chymotrypsin. This solution too had been stored beforehand for 16 hours at 37° C. This mixture was chosen in order to exclude an antimicrobial effect of the chymotrypsin.

The growth was observed over a period of 16 hours by measuring the optical density. It was found that the optical density of all samples developed similarly, i.e. microbial growth took place. Only the mixture to which undigested P18 solution had been added exhibited no or strongly inhibited microbial growth. These results show that a digestion of P18 with a serine protease, such as, for example, chymotrypsin, is possible, and demonstrate the biodegradability of the peptide. The results are summarized in Table 5.

TABLE 5

Biodegradability measured via the optical density at 620 nm in two independent experiments

| Incubation time [h] | E. coli suspension without inhib. | Addition of aqueous P18 solution [10 µM] | Addition of aqueous P18 solution [10 µM] digested with chymotrypsin | Addition of chymotrypsin control solution |
|---|---|---|---|---|
| 0 | 0.01-0.008 | 0-0 | 0.01-0 | 0.02-0.01 |
| 16 | 0.6-0.49 | 0.01-0.09 | 0.64-0.63 | 0.58-0.54 |

Example 5

Inhibition of Gram-Positive and Gram-Negative Bacteria

The growth inhibition by P18 was investigated on Gram-positive and Gram-negative bacteria. Shin et al. 1999 (loc.cit.) had already detected an inhibition on the model organisms *Escherichia coli* and *Bacillus subtilis* within a period up to 18 hours. However, growth experiments in this paper showed that an inhibition by P18 acts differently on Gram-positive and Gram-negative bacteria.

The growth medium used for this was LB medium as complex medium for the organisms *Escherichia coli*, *Bacillus subtilis* and *Brevibacterium epidermidis*. The medium comprised 10 g of trypton, 5 g of yeast extract and 10 g of NaCl per liter.

The growth test was carried out as follows: A shake flask with medium was inoculated with *Escherichia coli*, *Bacillus subtilis* or *Brevibacterium epidermidis* and incubated with shaking overnight at 30° C. and 200 rpm. A 96-well microtiter plate was filled with in each case 100 µl LB medium and inoculated with *E.-coli*, *B.-subtilis* or *B. epidermidis* suspensions of the overnight culture. The bacteria suspension was adjusted at the start of the experiment to an optical density, measured at 620 nm, of about 0.02. The concentrates of the P18 inhibitor solutions were 1 mM in water.

The growth of the following mixtures was compared by measuring the optical density:

bacteria suspension without the addition of an inhibitor;

bacteria suspension and addition of an aqueous P18 solution with a final concentration of 25 µM. The aqueous P18 solution had been freshly prepared.

The growth was observed over a period of 40 hours by measuring the optical density. It was found that P18 effectively inhibited the growth of the Gram-negative *E. coli* over this period. The growth of Gram-positive bacteria was inhibited initially. Within the experimental period of 40 hours, however, the model organisms *B. subtilis* and *B. epidermidis* inhibited with P18 achieved growth densities comparable with the noninhibited culture. These results suggest a different effect of P18 on Gram-positive and Gram-negative organisms. This property is advantageous since the human skin flora is preferably populated by Gram-positive bacteria and consequently an application of P18 does not disrupt this in the long term. The results are summarized in Table 6 below.

TABLE 6

Comparison of the growth of Gram-negative and Gram-positive model organisms, measured by the optical density at 620 nm (n.d. not measured).

| Incubation time [h] | E. coli suspension without inhib. | E. coli suspension with inhib. [25 µM P18 solution] | B. subtilis suspension without inhib. | B. subtilis suspension with inhib. [25 µM P18 solution] | B. epidermidis suspension without inhib. | B. epidermidis suspension with inhib. [25 µM P18 solution] |
|---|---|---|---|---|---|---|
| 16 | 0.5 | 0.09 | 0.77 | 0.25 | 0.85 | 0.29 |
| 24 | 0.68 | 0.06 | 0.71 | 0.96 | 1.11 | 0.56 |
| 40 | 0.84 | 0.07 | 0.76 | 0.67 | 1.39 | 1.24 |

The values given are mean values from 8 mixtures.

2. Formulation Examples A

Dermocosmetic preparations comprising the peptide P18 are described below. The peptide P18 is specified in the examples below by way of representation of all of the other peptides described above. It will be appreciated by the person skilled in the art that all of the other specified peptides according to the invention can also be used in the preparations given below.

AI=Active ingredient

Example 6

Use of P18 in an emulsion for day care—O/W type

AI 1%:

| | % | Ingredient (INCI) |
|---|---|---|
| A | 1.7 | Ceteareth-6, stearyl alcohol |
| | 0.7 | Ceteareth-25 |
| | 2.0 | Diethylaminohydroxybenzoylhexyl benzoate |
| | 2.0 | PEG-14 dimethicon |
| | 3.6 | Cetearyl alcohol |
| | 6.0 | Ethylhexyl methoxycinnamate |
| | 2.0 | Dibutyl adipate |
| B | 5.0 | Glycerol |
| | 0.2 | Disodium EDTA |
| | 1.0 | Panthenol |
| | q.s. | Preservative |
| | 67.8 | Aqua dem. |
| C | 4.0 | Caprylic/capric triglyceride, sodium acrylate copolymer |
| D | 0.2 | Sodium ascorbyl phosphate |
| | 1.0 | Tocopheryl acetate |
| | 0.2 | Bisabolol |
| | 1.0 | Caprylic/capric triglyceride, sodium ascorbate, tocopherol, retinol |
| | 1.0 | Aqueous solution with about 7% P18 |
| E | q.s. | Sodium hydroxide |

AI 5%:

| | % | Ingredient (INCI) |
|---|---|---|
| A | 1.7 | Ceteareth-6, stearyl alcohol |
| | 0.7 | Ceteareth-25 |
| | 2.0 | Diethylaminohydroxybenzoylhexyl benzoate |
| | 2.0 | PEG-14 dimethicone |
| | 3.6 | Cetearyl alcohol |
| | 6.0 | Ethylhexyl methoxycinnamate |
| | 2.0 | Dibutyl adipate |
| B | 5.0 | Glycerol |
| | 0.2 | Disodium EDTA |
| | 1.0 | Panthenol |
| | q.s. | Preservative |
| | 63.8 | Aqua dem. |
| C | 4.0 | Caprylic/capric triglyceride, sodium acrylate copolymer |
| D | 0.2 | Sodium ascorbyl phosphate |
| | 1.0 | Tocopheryl acetate |
| | 0.2 | Bisabolol |
| | 1.0 | Caprylic/capric triglyceride, sodium ascorbate, tocopherol, retinol |
| | 5.0 | Aqueous solution with about 7% P18 |
| E | q.s. | Sodium hydroxide |

Preparation: Heat phases A and B separately from one another to about 80° C. Stir phase B into phase A and homogenize. Stir phase C into the combined phases A and B and homogenize again. Cool, with stirring, to about 40° C., add phase D, adjust the pH to about 6.5 with phase E, homogenize and cool to room temperature with stirring.

The formulation is prepared without protective gas. Bottling must be into oxygen-impermeable packagings, e.g. aluminum tubes.

Example 7

Use of P18 in a protective day cream—O/W type

AI 1%:

| | % | Ingredient (INCI) |
|---|---|---|
| A | 1.7 | Ceteareth-6, stearyl alcohol |
| | 0.7 | Ceteareth-25 |
| | 2.0 | Diethylaminohydroxybenzoylhexyl benzoate |
| | 2.0 | PEG-14 dimethicone |
| | 3.6 | Cetearyl alcohol |
| | 6.0 | Ethylhexyl methoxycinnamate |
| | 2.0 | Dibutyl adipate |
| B | 5.0 | Glycerol |
| | 0.2 | Disodium EDTA |
| | 1.0 | Panthenol |
| | q.s. | Preservative |
| | 68.6 | Aqua dem. |
| C | 4.0 | Caprylic/capric triglyceride, sodium acrylate copolymer |
| D | 1.0 | Sodium ascorbyl phosphate |
| | 1.0 | Tocopheryl acetate |
| | 0.2 | Bisabolol |
| | 1.0 | Aqueous solution with about 7% P18 |
| E | q.s. | Sodium hydroxide |

AI 5%:

| | % | Ingredient (INCI) |
|---|---|---|
| A | 1.7 | Ceteareth-6, stearyl alcohol |
| | 0.7 | Ceteareth-25 |
| | 2.0 | Diethylaminohydroxybenzoylhexyl benzoate |

-continued

|   | % | Ingredient (INCI) |
|---|---|---|
|   | 2.0 | PEG-14 dimethicone |
|   | 3.6 | Cetearyl alcohol |
|   | 6.0 | Ethylhexyl methoxycinnamate |
|   | 2.0 | Dibutyl adipate |
| B | 5.0 | Glycerol |
|   | 0.2 | Disodium EDTA |
|   | 1.0 | Panthenol |
|   | q.s. | Preservative |
|   | 64.6 | Aqua dem. |
| C | 4.0 | Caprylic/capric triglyceride, sodium acrylate copolymer |
| D | 1.0 | Sodium ascorbyl phosphate |
|   | 1.0 | Tocopheryl acetate |
|   | 0.2 | Bisabolol |
|   | 5.0 | Aqueous solution with about 7% P18 |
| E | q.s. | Sodium hydroxide |

Preparation: Heat phases A and B separately from one another to about 80° C. Stir phase B into phase A and homogenize. Incorporate phase C into the combined phases A and B and homogenize. Cool, with stirring, to about 40° C. Add phase D, adjust the pH to about 6.5 with phase E and homogenize. Cool to room temperature with stirring.

Example 8

Use of P18 in a Face Cleansing Lotion—O/W type

AI 1%:

|   | % | Ingredient (INCI) |
|---|---|---|
| A | 10.0 | Cetearyl ethylhexanoate |
|   | 10.0 | Caprylic/capric triglyceride |
|   | 1.5 | Cyclopentasiloxane, cyclohexasiloxane |
|   | 2.0 | PEG-40-hydrogenated castor oil |
| B | 3.5 | Caprylic/capric triglyceride, sodium acrylate copolymer |
| C | 1.0 | Tocopheryl acetate |
|   | 0.2 | Bisabolol |
|   | q.s. | Preservative |
|   | q.s. | Perfume oil |
| D | 3.0 | Polyquaternium-44 |
|   | 0.5 | Cocotrimonium methosulfate |
|   | 0.5 | Ceteareth-25 |
|   | 2.0 | Panthenol, propylene glycol |
|   | 4.0 | Propylene glycol |
|   | 0.1 | Disodium EDTA |
|   | 1.0 | Aqueous solution with about 7% P18 |
|   | 60.7 | Aqua dem. |

AI 5%:

|   | % | Ingredient (INCI) |
|---|---|---|
| A | 10.0 | Cetearyl ethylhexanoate |
|   | 10.0 | Caprylic/capric triglyceride |
|   | 1.5 | Cyclopentasiloxane, cyclohexasiloxane |
|   | 2.0 | PEG-40-hydrogenated castor oil |
| B | 3.5 | Caprylic/capric triglyceride, sodium acrylate copolymer |
| C | 1.0 | Tocopheryl acetate |
|   | 0.2 | Bisabolol |
|   | q.s. | Preservative |
|   | q.s. | Perfume oil |
| D | 3.0 | Polyquaternium-44 |
|   | 0.5 | Cocotrimonium methosulfate |
|   | 0.5 | Ceteareth-25 |
|   | 2.0 | Panthenol, propylene glycol |
|   | 4.0 | Propylene glycol |
|   | 0.1 | Disodium EDTA |
|   | 5.0 | Aqueous solution with about 7% P18 |
|   | 56.7 | Aqua dem. |

Preparation: Dissolve phase A. Stir phase B into phase A, incorporate phase C into the combined phases A and B. Dissolve phase D, stir into the combined phases A, B and C and homogenize. Afterstir for 15 min.

Example 9

Use of P18 in a Daily Care Body Spray

AI 1%:

|   | % | Ingredient (INCI) |
|---|---|---|
| A | 3.0 | Ethylhexyl methoxycinnamate |
|   | 2.0 | Diethylaminohydroxybenzoylhexyl benzoate |
|   | 1.0 | Polyquaternium-44 |
|   | 3.0 | Propylene glycol |
|   | 2.0 | Panthenol, propylene glycol |
|   | 1.0 | Cyclopentasiloxane, cyclohexasiloxane |
|   | 10.0 | Octyldodecanol |
|   | 0.5 | PVP |
|   | 10.0 | Caprylic/capric triglyceride |
|   | 3.0 | $C_{12-15}$-Alkyl benzoate |
|   | 3.0 | Glycerol |
|   | 1.0 | Tocopheryl acetate |
|   | 0.3 | Bisabolol |
|   | 1.0 | Aqueous solution with about 7% P18 |
|   | 59.2 | Alcohol |

AI 5%:

|   | % | Ingredient (INCI) |
|---|---|---|
| A | 3.0 | Ethylhexyl methoxycinnamate |
|   | 2.0 | Diethylaminohydroxybenzoylhexyl benzoate |
|   | 1.0 | Polyquaternium-44 |
|   | 3.0 | Propylene glycol |
|   | 2.0 | Panthenol, propylene glycol |
|   | 1.0 | Cyclopentasiloxane, cyclohexasiloxane |
|   | 10.0 | Octyldodecanol |
|   | 0.5 | PVP |
|   | 10.0 | Caprylic/capric triglyceride |
|   | 3.0 | $C_{12-15}$-Alkyl benzoate |
|   | 3.0 | Glycerol |
|   | 1.0 | Tocopheryl acetate |
|   | 0.3 | Bisabolol |
|   | 5.0 | Aqueous solution with about 7% P18 |
|   | 55.2 | Alcohol |

Preparation: Weigh in the components of phase A and dissolve to give a clear solution.

Example 10

Use of P18 in a Skincare Gel

AI 1%:

|   | % | Ingredient (INCI) |
|---|---|---|
| A | 3.6 | PEG-40-hydrogenated castor oil |
|   | 15.0 | Alcohol |
|   | 0.1 | Bisabolol |
|   | 0.5 | Tocopheryl acetate |
|   | q.s. | Perfume oil |
| B | 3.0 | Panthenol |
|   | 0.6 | Carbomer |
|   | 1.0 | Aqueous solution with about 7% P18 |
|   | 75.4 | Aqua dem. |
| C | 0.8 | Triethanolamine |

AI 5%:

|   | %    | Ingredient (INCI)             |
|---|------|-------------------------------|
| A | 3.6  | PEG-40-hydrogenated castor oil |
|   | 15.0 | Alcohol                       |
|   | 0.1  | Bisabolol                     |
|   | 0.5  | Tocopheryl acetate            |
|   | q.s. | Perfume oil                   |
| B | 3.0  | Panthenol                     |
|   | 0.6  | Carbomer                      |
|   | 5.0  | Aqueous solution with about 7% P18 |
|   | 71.4 | Aqua dem.                     |
| C | 0.8  | Triethanolamine               |

Preparation: Dissolve phase A to give a clear solution. Allow phase B to swell and neutralize with phase C. Stir phase A into the homogenized phase B and homogenize.

Example 11

Use of P18 in an Aftershave Lotion

AI 1%:

|   | %    | Ingredient (INCI)             |
|---|------|-------------------------------|
| A | 10.0 | Cetearyl ethylhexanoate       |
|   | 5.0  | Tocopheryl acetate            |
|   | 1.0  | Bisabolol                     |
|   | 0.1  | Perfume oil                   |
|   | 0.3  | Acrylates/$C_{10-30}$ alkyl acrylate crosspolymer |
| B | 15.0 | Alcohol                       |
|   | 1.0  | Panthenol                     |
|   | 3.0  | Glycerol                      |
|   | 1.0  | Aqueous solution with about 7% P18 |
|   | 0.1  | Triethanolamine               |
|   | 63.5 | Aqua dem.                     |

AI 5%:

|   | %    | Ingredient (INCI)             |
|---|------|-------------------------------|
| A | 10.0 | Cetearyl ethylhexanoate       |
|   | 5.0  | Tocopheryl acetate            |
|   | 1.0  | Bisabolol                     |
|   | 0.1  | Perfume oil                   |
|   | 0.3  | Acrylates/$C_{10-30}$ alkyl acrylate crosspolymer |
| B | 15.0 | Alcohol                       |
|   | 1.0  | Panthenol                     |
|   | 3.0  | Glycerol                      |
|   | 5.0  | Aqueous solution with about 7% P18 |
|   | 0.1  | Triethanolamine               |
|   | 59.5 | Aqua dem.                     |

Preparation: Mix the components of phase A. Dissolve phase B, incorporate into phase A and homogenize.

Example 12

Use of P18 in an Aftersun Lotion

AI 1%:

|   | %    | Ingredient (INCI)             |
|---|------|-------------------------------|
| A | 0.4  | Acrylates/$C_{10-30}$-alkyl acrylate crosspolymer |
|   | 15.0 | Cetearyl ethylhexanoate       |
|   | 0.2  | Bisabolol                     |
|   | 1.0  | Tocopheryl acetate            |
|   | q.s. | Perfume oil                   |
| B | 1.0  | Panthenol                     |
|   | 15.0 | Alcohol                       |
|   | 3.0  | Glycerol                      |
|   | 1.0  | Aqueous solution with about 7% P18 |
|   | 63.2 | Aqua dem.                     |
| C | 0.2  | Triethanolamine               |

AI 5%:

|   | %    | Ingredient (INCI)             |
|---|------|-------------------------------|
| A | 0.4  | Acrylates/$C_{10-30}$ alkyl acrylate crosspolymer |
|   | 15.0 | Cetearyl ethylhexanoate       |
|   | 0.2  | Bisabolol                     |
|   | 1.0  | Tocopheryl acetate            |
|   | q.s. | Perfume oil                   |
| B | 1.0  | Panthenol                     |
|   | 15.0 | Alcohol                       |
|   | 3.0  | Glycerol                      |
|   | 5.0  | Aqueous solution with about 7% P18 |
|   | 59.2 | Aqua dem.                     |
| C | 0.2  | Triethanolamine               |

Preparation: Mix the components of phase A. Stir phase B into phase A with homogenization. Neutralize with phase C and homogenize again.

Example 13

Use of P18 in a Sunscreen Lotion

AI 1%:

|   | %    | Ingredient (INCI)             |
|---|------|-------------------------------|
| A | 4.5  | Ethylhexyl methoxycinnamate   |
|   | 2.0  | Diethylaminohydroxybenzoylhexyl benzoate |
|   | 3.0  | Octocrylene                   |
|   | 2.5  | Di-$C_{12-13}$-alkyl malate   |
|   | 0.5  | Tocopheryl acetate            |
|   | 4.0  | Polyglyceryl-3 methylglucose distearate |
| B | 3.5  | Cetearyl isononanoate         |
|   | 1.0  | VP/eicosene copolymer         |
|   | 5.0  | Isohexadecane                 |
|   | 2.5  | Di-$C_{12-13}$-alkyl malate   |
|   | 3.0  | Titanium dioxide, trimethoxycaprylylsilane |
| C | 5.0  | Glycerol                      |
|   | 1.0  | Sodium cetearyl sulfate       |
|   | 0.5  | Xanthan gum                   |
|   | 59.7 | Aqua dem.                     |
| D | 1.0  | Aqueous solution with about 7% P18 |
|   | 1.0  | Phenoxyethanol, methyl paraben, ethyl paraben, butyl paraben, propyl paraben, isobutyl paraben |
|   | 0.3  | Bisabolol                     |

AI 5%:

|   | %    | Ingredient (INCI)             |
|---|------|-------------------------------|
| A | 4.5  | Ethylhexyl methoxycinnamate   |
|   | 2.0  | Diethylaminohydroxybenzoylhexyl benzoate |
|   | 3.0  | Octocrylene                   |
|   | 2.5  | Di-$C_{12-13}$-alkyl malate   |
|   | 0.5  | Tocopheryl acetate            |
|   | 4.0  | Polyglyceryl-3 methylglucose distearate |
| B | 3.5  | Cetearyl isononanoate         |
|   | 1.0  | VP/eicosene copolymer         |
|   | 5.0  | Isohexadecane                 |
|   | 2.5  | Di-$C_{12-13}$-alkyl malate   |
|   | 3.0  | Titanium dioxide, trimethoxycaprylylsilane |

-continued

| | % | Ingredient (INCI) |
|---|---|---|
| C | 5.0 | Glycerol |
| | 1.0 | Sodium cetearyl sulfate |
| | 0.5 | Xanthan gum |
| | 55.7 | Aqua dem. |
| D | 5.0 | Aqueous solution with about 7% P18 |
| | 1.0 | Phenoxyethanol, methyl paraben, ethyl paraben, butyl paraben, propyl paraben, isobutyl paraben |
| | 0.3 | Bisabolol |

Preparation: Heat the components of phases A and B separately from one another to about 80° C. Stir phase B into phase A and homogenize. Heat phase C to about 80° C. and stir into the combined phases A and B with homogenization. Cool to about 40° C. with stirring, add phase D and homogenize again.

Example 14

Use of P18 in a Sunscreen Lotion—O/W Type

AI 1%

| | % | Ingredient (INCI) |
|---|---|---|
| A | 2.0 | Ceteareth-6, stearyl alcohol |
| | 2.0 | Ceteareth-25 |
| | 3.0 | Tribehenin |
| | 2.0 | Cetearyl alcohol |
| | 2.0 | Cetearyl ethylhexanoate |
| | 5.0 | Ethylhexyl methoxycinnamate |
| | 1.0 | Ethylhexyltriazone |
| | 1.0 | VP/eicosene copolymer |
| | 7.0 | Isopropyl myristate |
| B | 5.0 | Zinc oxide, triethoxycaprylylsilane |
| C | 0.2 | Xanthan gum |
| | 0.5 | Hydroxyethyl acrylate/sodium acryloyldimethyltaurate copolymer, squalane, polysorbate 60 |
| | 0.2 | Disodium EDTA |
| | 5.0 | Propylene glycol |
| | 0.5 | Panthenol |
| | 60.9 | Aqua dem. |
| D | 1.0 | Aqueous solution with about 7% P18 |
| | 0.5 | Phenoxyethanol, methyl paraben, ethyl paraben, butyl paraben, propyl paraben, isopropyl paraben |
| | 1.0 | Tocopheryl acetate |
| | 0.2 | Bisabolol |

AI 5%

| | % | Ingredient (INCI) |
|---|---|---|
| A | 2.0 | Ceteareth-6, Stearyl alcohol |
| | 2.0 | Ceteareth-25 |
| | 3.0 | Tribehenin |
| | 2.0 | Cetearyl alcohol |
| | 2.0 | Cetearyl ethylhexanoate |
| | 5.0 | Ethylhexyl methoxycinnamate |
| | 1.0 | Ethylhexyltriazone |
| | 1.0 | VP/eicosene copolymer |
| | 7.0 | Isopropyl myristate |
| B | 5.0 | Zinc oxide, triethoxycaprylylsilane |
| C | 0.2 | Xanthan gum |
| | 0.5 | Hydroxyethyl acrylate/sodium acryloyldimethyltaurate copolymer, squalane, polysorbate 60 |
| | 0.2 | Disodium EDTA |
| | 5.0 | Propylene glycol |
| | 0.5 | Panthenol |
| | 56.9 | Aqua dem. |

-continued

| | % | Ingredient (INCI) |
|---|---|---|
| D | 5.0 | Aqueous solution with about 7% P18 |
| | 0.5 | Phenoxyethanol, methyl paraben, ethyl paraben, butyl paraben, propyl paraben, isopropyl paraben |
| | 1.0 | Tocopheryl acetate |
| | 0.2 | Bisabolol |

Preparation: Heat phase A to about 80° C., stir in phase B and homogenize for 3 min. Likewise heat phase C to 80° C. and stir into the combined phases A and B with homogenization. Cool to about 40° C., stir in phase D and homogenize again.

Example 15

Use of P18 in a Sunscreen Lotion—O/W Type

AI 1%:

| | % | Ingredient (INCI) |
|---|---|---|
| A | 3.5 | Ceteareth-6, stearyl alcohol |
| | 1.5 | Ceteareth-25 |
| | 7.5 | Ethylhexyl methoxycinnamate |
| | 2.0 | Diethylaminohydroxybenzoylhexyl benzoate |
| | 2.0 | Cyclopentasiloxane, cyclohexasiloxane |
| | 0.5 | Beeswax |
| | 3.0 | Cetearyl alcohol |
| | 10.0 | Caprylic/capric triglyceride |
| B | 5.0 | Titanium dioxide, silicon dioxide, methicone, aluminum oxide |
| C | 3.0 | Glycerol |
| | 0.2 | Disodium EDTA |
| | 0.3 | Xanthan gum |
| | 1.0 | Decyl glucoside |
| | 2.0 | Panthenol, propylene glycol |
| | 56.3 | Aqua dem. |
| D | 1.0 | Aqueous solution with about 7% P18 |
| | 1.0 | Tocopheryl acetate |
| | 0.2 | Bisabolol |
| | q.s. | Perfume oil |
| | q.s. | Preservative |

AI 5%:

| | % | Ingredient (INCI) |
|---|---|---|
| A | 3.5 | Ceteareth-6, Stearyl alcohol |
| | 1.5 | Ceteareth-25 |
| | 7.5 | Ethylhexyl methoxycinnamate |
| | 2.0 | Diethylaminohydroxybenzoylhexyl benzoate |
| | 2.0 | Cyclopentasiloxane, cyclohexasiloxane |
| | 0.5 | Beeswax |
| | 3.0 | Cetearyl alcohol |
| | 10.0 | Caprylic/capric triglyceride |
| B | 5.0 | Titanium dioxide, silicon dioxide, methicone, aluminum oxide |
| C | 3.0 | Glycerol |
| | 0.2 | Disodium EDTA |
| | 0.3 | Xanthan gum |
| | 1.0 | Decyl glucoside |
| | 2.0 | Panthenol, propylene glycol |
| | 52.3 | Aqua dem. |
| D | 5.0 | Aqueous solution with about 7% P18 |
| | 1.0 | Tocopheryl acetate |
| | 0.2 | Bisabolol |
| | q.s. | Perfume oil |
| | q.s. | Preservative |

Preparation: Heat phase A to about 80° C., stir in phase B and homogenize for 3 min. Likewise heat phase C to 80° C.

and stir into the combined phases A and B with homogenization. Cool to about 40° C., stir in phase D and homogenize again.

Example 16

Use of P18 in a Foot Balm

AI 1%:

| | % | Ingredient (INCI) |
|---|---|---|
| A | 2.0 | Ceteareth-6, Stearyl alcohol |
| | 2.0 | Ceteareth-25 |
| | 5.0 | Cetearyl ethylhexanoate |
| | 4.0 | Cetyl alcohol |
| | 4.0 | Glyceryl stearate |
| | 5.0 | Mineral oil |
| | 0.2 | Menthol |
| | 0.5 | Camphor |
| B | 69.3 | Aqua dem. |
| | q.s. | Preservative |
| C | 1.0 | Bisabolol |
| | 1.0 | Tocopheryl acetate |
| D | 1.0 | Aqueous solution with about 7% P18 |
| | 5.0 | Witch hazel extract |

AI 5%:

| | % | Ingredient (INCI) |
|---|---|---|
| A | 2.0 | Ceteareth-6, Stearyl alcohol |
| | 2.0 | Ceteareth-25 |
| | 5.0 | Cetearyl ethylhexanoate |
| | 4.0 | Cetyl alcohol |
| | 4.0 | Glyceryl stearate |
| | 5.0 | Mineral oil |
| | 0.2 | Menthol |
| | 0.5 | Camphor |
| B | 65.3 | Aqua dem. |
| | q.s. | Preservative |
| C | 1.0 | Bisabolol |
| | 1.0 | Tocopheryl acetate |
| D | 5.0 | Aqueous solution with about 7% P18 |
| | 5.0 | Witch hazel extract |

Preparation: Heat the components of phases A and B separately from one another to about 80° C. Stir phase B into phase A with homogenization. With stirring, cool to about 40° C., add phases C and D and briefly afterhomogenize. With stirring, cool to room temperature.

Example 17

Use of P18 in a W/O Emulsion with Bisabolol

AI 1%:

| | % | Ingredient (INCI) |
|---|---|---|
| A | 6.0 | PEG-7-hydrogenated castor oil |
| | 8.0 | Cetearyl ethylhexanoate |
| | 5.0 | Isopropyl myristate |
| | 15.0 | Mineral oil |
| | 0.3 | Magnesium stearate |
| | 0.3 | Aluminum stearate |
| | 2.0 | PEG-45/dodecyl glycol copolymer |
| B | 5.0 | Glycerol |
| | 0.7 | Magnesium sulfate |
| | 55.6 | Aqua dem. |

-continued

| | % | Ingredient (INCI) |
|---|---|---|
| C | 1.0 | Aqueous solution with about 7% P18 |
| | 0.5 | Tocopheryl acetate |
| | 0.6 | Bisabolol |

AI 5%:

| | % | Ingredient (INCI) |
|---|---|---|
| A | 6.0 | PEG-7-hydrogenated castor oil |
| | 8.0 | Cetearyl ethylhexanoate |
| | 5.0 | Isopropyl myristate |
| | 15.0 | Mineral oil |
| | 0.3 | Magnesium stearate |
| | 0.3 | Aluminum stearate |
| | 2.0 | PEG-45/dodecyl glycol copolymer |
| B | 5.0 | Glycerol |
| | 0.7 | Magnesium sulfate |
| | 51.6 | Aqua dem. |
| C | 5.0 | Aqueous solution with about 7% P18 |
| | 0.5 | Tocopheryl acetate |

Preparation: Heat phases A and B separately from one another to about 85° C. Stir phase B into phase A and homogenize. With stirring, cool to about 40° C., add phase C and briefly homogenize again. With stirring, cool to room temperature.

Example 18

Foam Conditioner with Setting Agent

AI 1%:

| | % | Ingredient (INCI) |
|---|---|---|
| A | 10.0 | PVP/VA copolymer |
| | 0.2 | Hydroxyethylcetyldimonium phosphate |
| | 0.2 | Ceteareth-25 |
| | 0.5 | Dimethicone copolyol |
| | q.s. | Perfume oil |
| | 10.0 | Alcohol |
| | 1.0 | Aqueous solution with about 7% P18 |
| | 68.1 | Aqua dem. |
| | 10.0 | Propane/butane |

AI 5%:

| | % | Ingredient (INCI) |
|---|---|---|
| A | 10.0 | PVP/VA copolymer |
| | 0.2 | Hydroxyethylcetyldimonium phosphate |
| | 0.2 | Ceteareth-25 |
| | 0.5 | Dimethicone copolyol |
| | q.s. | Perfume oil |
| | 10.0 | Alcohol |
| | 5.0 | Aqueous solution with about 7% P18 |
| | 64.1 | Aqua dem. |
| | 10.0 | Propane/butane |

Preparation: Weigh the components of phase A together, stir until everything has dissolved, and bottle.

Example 19

Foam Conditioner

AI 1%:

|   | % | Ingredient (INCI) |
|---|---|---|
| A | 1.0 | Polyquaternium-4 |
|   | 0.5 | Hydroxyethylcetyldimonium phosphate |
|   | 1.0 | Aqueous solution with about 7% P18 |
|   | q.s. | Perfume oil |
|   | q.s. | Preservative |
|   | 91.5 | Aqua dem. |
|   | 6.0 | Propane/butane |

AI 5%:

|   | % | Ingredient (INCI) |
|---|---|---|
| A | 1.0 | Polyquaternium-4 |
|   | 0.5 | Hydroxyethylcetyldimonium phosphate |
|   | 5.0 | Aqueous solution with about 7% P18 |
|   | q.s. | Perfume oil |
|   | q.s. | Preservative |
|   | 87.5 | Aqua dem. |
|   | 6.0 | Propane/butane |

Preparation: Weigh the components of phase A together, stir until everything has dissolved to give a clear solution, and bottle.

Example 20

Foam Conditioner

AI 1%:

|   | % | Ingredient (INCI) |
|---|---|---|
| A | 1.0 | Polyquaternium-11 |
|   | 0.5 | Hydroxyethylcetyldimonium phosphate |
|   | 1.0 | Aqueous solution with about 7% P18 |
|   | q.s. | Perfume oil |
|   | q.s. | Preservative |
|   | 91.5 | Aqua dem. |
|   | 6.0 | Propane/butane |

AI 5%:

|   | % | Ingredient (INCI) |
|---|---|---|
| A | 1.0 | Polyquaternium-11 |
|   | 0.5 | Hydroxyethylcetyldimonium phosphate |
|   | 5.0 | Aqueous solution with about 7% P18 |
|   | q.s. | Perfume oil |
|   | q.s. | Preservative |
|   | 87.5 | Aqua dem. |
|   | 6.0 | Propane/butane |

Preparation: Weigh the components of phase A together, stir until everything has dissolved to give a clear solution, and bottle.

Example 21

Styling Foam

AI 1%:

|   | % | Ingredient (INCI) |
|---|---|---|
| A | 0.5 | Laureth-4 |
|   | q.s. | Perfume oil |
| B | 77.3 | Aqua dem. |
|   | 10.0 | Polyquaternium-28 |
|   | 1.0 | Aqueous solution with about 7% P18 |
|   | 0.5 | Dimethicone copolyol |
|   | 0.2 | Ceteareth-25 |
|   | 0.2 | Panthenol |
|   | 0.1 | PEG-25 PABA |
|   | 0.2 | Hydroxyethylcellulose |
| C | 10.0 | HFC 152 A |

AI 5%:

|   | % | Ingredient (INCI) |
|---|---|---|
| A | 0.5 | Laureth-4 |
|   | q.s. | Perfume oil |
| B | 73.3 | Aqua dem. |
|   | 10.0 | Polyquaternium-28 |
|   | 5.0 | Aqueous solution with about 7% P18 |
|   | 0.5 | Dimethicone copolyol |
|   | 0.2 | Ceteareth-25 |
|   | 0.2 | Panthenol |
|   | 0.1 | PEG-25 PABA |
|   | 0.2 | Hydroxyethylcellulose |
| C | 10.0 | HFC 152 A |

Preparation: Mix the components of phase A. Add the components of phase B one after the other and dissolve. Bottle with phase C.

Example 22

Styling Foam

AI 1%:

|   | % | Ingredient (INCI) |
|---|---|---|
| A | 2.0 | Cocotrimonium methosulfate |
|   | q.s. | Perfume oil |
| B | 78.5 | Aqua dem. |
|   | 6.7 | Acrylate copolymer |
|   | 0.6 | AMP |
|   | 1.0 | Aqueous solution with about 7% P18 |
|   | 0.5 | Dimethicone copolyol |
|   | 0.2 | Ceteareth-25 |
|   | 0.2 | Panthenol |
|   | 0.1 | PEG-25 PABA |
|   | 0.2 | Hydroxyethylcellulose |
| C | 10.0 | HFC 152 A |

AI 5%:

|   | % | Ingredient (INCI) |
|---|---|---|
| A | 2.0 | Cocotrimonium methosulfate |
|   | q.s. | Perfume oil |
| B | 74.5 | Aqua dem. |
|   | 6.7 | Acrylate copolymer |
|   | 0.6 | AMP |

-continued

|   | %    | Ingredient (INCI)                    |
|---|------|--------------------------------------|
|   | 5.0  | Aqueous solution with about 7% P18   |
|   | 0.5  | Dimethicone copolyol                 |
|   | 0.2  | Ceteareth-25                         |
|   | 0.2  | Panthenol                            |
|   | 0.1  | PEG-25 PABA                          |
|   | 0.2  | Hydroxyethylcellulose                |
| C | 10.0 | HFC 152 A                            |

Preparation: Mix the components of phase A. Add the components of phase B one after the other and dissolve. Bottle with phase C.

Example 23

Styling Foam

AI 1%:

|   | %     | Ingredient (INCI)                  |
|---|-------|------------------------------------|
| A | 2.0   | Cocotrimonium methosulfate         |
|   | q.s.  | Perfume oil                        |
| B | 7.70  | Polyquaternium-44                  |
|   | 1.0   | Aqueous solution with about 7% P18 |
|   | q.s.  | Preservative                       |
|   | 79.3  | Aqua dem.                          |
| C | 10.0  | Propane/butane                     |

AI 5%:

|   | %     | Ingredient (INCI)                  |
|---|-------|------------------------------------|
| A | 2.0   | Cocotrimonium methosulfate         |
|   | q.s.  | Perfume oil                        |
| B | 7.70  | Polyquaternium-44                  |
|   | 5.0   | Aqueous solution with about 7% P18 |
|   | q.s.  | Preservative                       |
|   | 75.3  | Aqua dem.                          |
| C | 10.0  | Propane/butane                     |

Preparation: Mix the components of phase A. Dissolve the components of phase B to give a clear solution, then stir phase B into phase A. Adjust the pH to 6-7, bottle with phase C.

Example 24

Styling Foam

AI 1%:

|   | %     | Ingredient (INCI)                                    |
|---|-------|------------------------------------------------------|
| A | 2.00  | Cocotrimonium methosulfate                           |
|   | q.s.  | Perfume oil                                          |
| B | 72.32 | Aqua dem.                                            |
|   | 2.00  | VP/acrylates/lauryl methacrylate copolymer           |
|   | 0.53  | AMP                                                  |
|   | 1.00  | Aqueous solution with about 7% P18                   |
|   | 0.20  | Ceteareth-25                                         |
|   | 0.50  | Panthenol                                            |
|   | 0.05  | Benzophenone-4                                       |
|   | 0.20  | Amodimethicone, cetrimonium chloride, trideceth-12   |
|   | 15.00 | Alcohol                                              |
| C | 0.20  | Hydroxyethylcellulose                                |
| D | 6.00  | Propane/butane                                       |

AI 5%:

|   | %     | Ingredient (INCI)                                    |
|---|-------|------------------------------------------------------|
| A | 2.00  | Cocotrimonium methosulfate                           |
|   | q.s.  | Perfume oil                                          |
| B | 68.32 | Aqua dem.                                            |
|   | 2.00  | VP/acrylates/lauryl methacrylate copolymer           |
|   | 0.53  | AMP                                                  |
|   | 5.00  | Aqueous solution with about 7% P18                   |
|   | 0.20  | Ceteareth-25                                         |
|   | 0.50  | Panthenol                                            |
|   | 0.05  | Benzophenone-4                                       |
|   | 0.20  | Amodimethicone, cetrimonium chloride, trideceth-12   |
|   | 15.00 | Alcohol                                              |
| C | 0.20  | Hydroxyethylcellulose                                |
| D | 6.00  | Propane/butane                                       |

Preparation: Mix the components of phase A. Add the components of phase B one after the other and dissolve. Dissolve phase C in the mixture of A and B, then adjust the pH to 6-7. Bottle with phase D.

Example 25

Styling Foam

AI 1%:

|   | %     | Ingredient (INCI)                                    |
|---|-------|------------------------------------------------------|
| A | 2.00  | Cetrimonium chloride                                 |
|   | q.s.  | Perfume oil                                          |
| B | 67.85 | Aqua dem.                                            |
|   | 7.00  | Polyquaternium-46                                    |
|   | 1.00  | Aqueous solution with about 7% P18                   |
|   | 0.20  | Ceteareth-25                                         |
|   | 0.50  | Panthenol                                            |
|   | 0.05  | Benzophenone-4                                       |
|   | 0.20  | Amodimethicone, cetrimonium chloride, trideceth-12   |
|   | 15.00 | Alcohol                                              |
| C | 0.20  | Hydroxyethylcellulose                                |
| D | 6.00  | Propane/butane                                       |

AI 5%:

|   | %     | Ingredient (INCI)                                    |
|---|-------|------------------------------------------------------|
| A | 2.00  | Cetrimonium chloride                                 |
|   | q.s.  | Perfume oil                                          |
| B | 63.85 | Aqua dem.                                            |
|   | 7.00  | Polyquaternium-46                                    |
|   | 5.00  | Aqueous solution with about 7% P18                   |
|   | 0.20  | Ceteareth-25                                         |
|   | 0.50  | Panthenol                                            |
|   | 0.05  | Benzophenone-4                                       |
|   | 0.20  | Amodimethicone, cetrimonium chloride, trideceth-12   |
|   | 15.00 | Alcohol                                              |
| C | 0.20  | Hydroxyethylcellulose                                |
| D | 6.00  | Propane/butane                                       |

Preparation: Mix the components of phase A. Add the components of phase B one after the other and dissolve. Dissolve phase C in the mixture of phase A and B, then adjust the pH to 6-7. Bottle with phase D.

Example 26

Styling Foam

AI 1%:

|   | %    | Ingredient (INCI)                  |
|---|------|------------------------------------|
| A | q.s. | PEG-40-hydrogenated castor oil     |
|   | q.s. | Perfume oil                        |
|   | 85.5 | Aqua dem.                          |
| B | 7.0  | Sodium polystyrenesulfonate        |
|   | 1.0  | Aqueous solution with about 7% P18 |
|   | 0.5  | Cetrimonium bromide                |
|   | q.s. | Preservative                       |
| C | 6.0  | Propane/butane                     |

AI 5%:

|   | %    | Ingredient (INCI)                  |
|---|------|------------------------------------|
| A | q.s. | PEG-40-hydrogenated castor oil     |
|   | q.s. | Perfume oil                        |
|   | 81.5 | Aqua dem.                          |
| B | 7.0  | Sodium polystyrenesulfonate        |
|   | 5.0  | Aqueous solution with about 7% P18 |
|   | 0.5  | Cetrimonium bromide                |
|   | q.s. | Preservative                       |
| C | 6.0  | Propane/butane                     |

Preparation: Solubilize phase A. Weigh phase B into phase A and dissolve to give a clear solution. Adjust the pH to 6-7, bottle with phase C.

Example 27

Styling Foam

AI 1%:

|   | %    | Ingredient (INCI)                  |
|---|------|------------------------------------|
| A | q.s. | PEG-40-hydrogenated castor oil     |
|   | q.s. | Perfume oil                        |
|   | 92.0 | Aqua dem.                          |
| B | 0.5  | Polyquaternium-10                  |
|   | 1.0  | Aqueous solution with about 7% P18 |
|   | 0.5  | Cetrimonium bromide                |
|   | q.s. | Preservative                       |
| C | 6.0  | Propane/butane                     |

AI 5%:

|   | %    | Ingredient (INCI)                  |
|---|------|------------------------------------|
| A | q.s. | PEG-40-hydrogenated castor oil     |
|   | q.s. | Perfume oil                        |
|   | 88.0 | Aqua dem.                          |
| B | 0.5  | Polyquaternium-10                  |
|   | 5.0  | Aqueous solution with about 7% P18 |
|   | 0.5  | Cetrimonium bromide                |
|   | q.s. | Preservative                       |
| C | 6.0  | Propane/butane                     |

Preparation: Solubilize phase A. Weigh phase B into phase A and dissolve to give a clear solution. Adjust the pH to 6-7, bottle with phase C.

Example 28

Styling Foam

AI 1%:

|   | %    | Ingredient (INCI)                  |
|---|------|------------------------------------|
| A | q.s. | PEG-40-hydrogenated castor oil     |
|   | q.s. | Perfume oil                        |
|   | 82.5 | Aqua dem.                          |
| B | 10.0 | Polyquaternium-16                  |
|   | 1.0  | Aqueous solution with about 7% P18 |
|   | 0.5  | Hydroxyethylcetyldimonium phosphate|
|   | q.s. | Preservative                       |
| C | 6.0  | Propane/butane                     |

AI 5%:

|   | %    | Ingredient (INCI)                  |
|---|------|------------------------------------|
| A | q.s. | PEG-40-hydrogenated castor oil     |
|   | q.s. | Perfume oil                        |
|   | 78.5 | Aqua dem.                          |
| B | 10.0 | Polyquaternium-16                  |
|   | 5.0  | Aqueous solution with about 7% P18 |
|   | 0.5  | Hydroxyethylcetyldimonium phosphate|
|   | q.s. | Preservative                       |
| C | 6.0  | Propane/butane                     |

Preparation: Solubilize phase A. Weigh phase B into phase A and dissolve to give a clear solution. Adjust the pH to 6-7, bottle with phase C.

Example 29

Styling Foam

AI 1%:

|   | %    | Ingredient (INCI)                  |
|---|------|------------------------------------|
| A | 2.0  | Cocotrimonium methosulfate         |
|   | q.s. | Perfume oil                        |
| B | 84.0 | Aqua dem.                          |
|   | 2.0  | Chitosan                           |
|   | 1.0  | Aqueous solution with about 7% P18 |
|   | 0.5  | Dimethicone copolyol               |
|   | 0.2  | Ceteareth-25                       |
|   | 0.2  | Panthenol                          |
|   | 0.1  | PEG-25 PABA                        |
|   | 10.0 | HFC 152 A                          |

AI 5%:

|   | %    | Ingredient (INCI)                  |
|---|------|------------------------------------|
| A | 2.0  | Cocotrimonium methosulfate         |
|   | q.s. | Perfume oil                        |
| B | 80.0 | Aqua dem.                          |
|   | 2.0  | Chitosan                           |
|   | 5.0  | Aqueous solution with about 7% P18 |
|   | 0.5  | Dimethicone copolyol               |
|   | 0.2  | Ceteareth-25                       |
|   | 0.2  | Panthenol                          |
|   | 0.1  | PEG-25 PABA                        |
|   | 10.0 | HFC 152 A                          |

Preparation: Mix the components of phase A. Add the components of phase B one after the other and dissolve. Bottle with phase C.

Example 30

Care Shampoo

AI 1%

|   | %    | Ingredient (INCI) |
|---|------|---|
| A | 30.0 | Sodium laureth sulfate |
|   | 6.0  | Sodium cocoamphoacetate |
|   | 6.0  | Cocamidopropylbetaine |
|   | 3.0  | Sodium laureth sulfate, glycol distearate, cocamide-MEA, laureth-10 |
|   | 1.0  | Aqueous solution with about 7% P18 |
|   | 7.7  | Polyquaternium-44 |
|   | 2.0  | Amodimethicone |
|   | q.s. | Perfume oil |
|   | q.s. | Preservative |
|   | 1.0  | Sodium chloride |
|   | 43.3 | Aqua dem. |
| B | q.s. | Citric acid |

AI 5%

|   | %    | Ingredient (INCI) |
|---|------|---|
| A | 30.0 | Sodium laureth sulfate |
|   | 6.0  | Sodium cocoamphoacetate |
|   | 6.0  | Cocamidopropylbetaine |
|   | 3.0  | Sodium laureth sulfate, glycol distearate, cocamide-MEA, laureth-10 |
|   | 5.0  | Aqueous solution with about 7% P18 |
|   | 7.7  | Polyquaternium-44 |
|   | 2.0  | Amodimethicone |
|   | q.s. | Perfume oil |
|   | q.s. | Preservative |
|   | 1.0  | Sodium chloride |
|   | 39.3 | Aqua dem. |
| B | q.s. | Citric acid |

Preparation: Mix the components of phase A and dissolve. Adjust the pH to 6-7 with citric acid.

Example 31

Shower Gel

AI 1%

|   | %    | Ingredient (INCI) |
|---|------|---|
| A | 40.0 | Sodium laureth sulfate |
|   | 5.0  | Decyl glucoside |
|   | 5.0  | Cocamidopropylbetaine |
|   | 1.0  | Aqueous solution with about 7% P18 |
|   | 1.0  | Panthenol |
|   | q.s. | Perfume oil |
|   | q.s. | Preservative |
|   | 2.0  | Sodium chloride |
|   | 46.0 | Aqua dem. |
| B | q.s. | Citric acid |

AI 5%

|   | %    | Ingredient (INCI) |
|---|------|---|
| A | 40.0 | Sodium laureth sulfate |
|   | 5.0  | Decyl glucoside |
|   | 5.0  | Cocamidopropylbetaine |
|   | 5.0  | Aqueous solution with about 7% P18 |
|   | 1.0  | Panthenol |
|   | q.s. | Perfume oil |
|   | q.s. | Preservative |
|   | 2.0  | Sodium chloride |
|   | 42.0 | Aqua dem. |
| B | q.s. | Citric acid |

Preparation: Mix the components of phase A and dissolve. Adjust the pH to 6-7 with citric acid.

Example 32

Shampoo

AI 1%

|   | %    | Ingredient (INCI) |
|---|------|---|
| A | 40.0 | Sodium laureth sulfate |
|   | 5.0  | Sodium $C_{12-15}$-pareth-15-sulfonate |
|   | 5.0  | Decyl glucoside |
|   | q.s. | Perfume oil |
|   | 0.1  | Phytantriol |
|   | 44.6 | Aqua dem. |
|   | 1.0  | Aqueous solution with about 7% P18 |
|   | 0.3  | Polyquaternium-10 |
|   | 1.0  | Panthenol |
|   | q.s. | Preservative |
|   | 1.0  | Laureth-3 |
|   | 2.0  | Sodium chloride |

AI 5%

|   | %    | Ingredient (INCI) |
|---|------|---|
| A | 40.0 | Sodium laureth sulfate |
|   | 5.0  | Sodium $C_{12-15}$-pareth-15-sulfonate |
|   | 5.0  | Decyl glucoside |
|   | q.s. | Perfume oil |
|   | 0.1  | Phytantriol |
|   | 40.6 | Aqua dem. |
|   | 5.0  | Aqueous solution with about 7% P18 |
|   | 0.3  | Polyquaternium-10 |
|   | 1.0  | Panthenol |
|   | q.s. | Preservative |
|   | 1.0  | Laureth-3 |
|   | 2.0  | Sodium chloride |

Preparation: Mix the components of phase A and dissolve. Adjust the pH to 6-7 with citric acid.

Example 33

Shampoo

AI 1%

|   | %    | Ingredient (INCI) |
|---|------|---|
| A | 15.0 | Cocamidopropylbetaine |
|   | 10.0 | Disodium cocoamphodiacetate |
|   | 5.0  | Polysorbate 20 |
|   | 5.0  | Decyl glucoside |
|   | q.s. | Perfume oil |

-continued

|   | % | Ingredient (INCI) |
|---|---|---|
|   | q.s. | Preservative |
|   | 1.0 | Aqueous solution with about 7% P18 |
|   | 0.15 | Guar hydroxypropyltrimonium chloride |
|   | 2.0 | Laureth-3 |
|   | 58.0 | Aqua dem. |
|   | q.s. | Citric acid |
| B | 3.0 | PEG-150 distearate |

AI 5%

|   | % | Ingredient (INCI) |
|---|---|---|
| A | 15.0 | Cocamidopropylbetaine |
|   | 10.0 | Disodium cocoamphodiacetate |
|   | 5.0 | Polysorbate 20 |
|   | 5.0 | Decyl glucoside |
|   | q.s. | Perfume oil |
|   | q.s. | Preservative |
|   | 5.0 | Aqueous solution with about 7% P18 |
|   | 0.15 | Guar hydroxypropyltrimonium chloride |
|   | 2.0 | Laureth-3 |
|   | 54.0 | Aqua dem. |
|   | q.s. | Citric acid |
| B | 3.0 | PEG-150 distearate |

Preparation: Weigh in the components of phase A and dissolve. Adjust the pH to 6-7. Add phase B and heat to about 50° C. With stirring, cool to room temperature.

Example 34

Moisturizing Bodycare Cream

AI 1%

|   | % | Ingredient (INCI) |
|---|---|---|
| A | 2.0 | Ceteareth-25 |
|   | 2.0 | Ceteareth-6, stearyl alcohol |
|   | 3.0 | Cetearyl ethylhexanoate |
|   | 1.0 | Dimethicone |
|   | 4.0 | Cetearyl alcohol |
|   | 3.0 | Glyceryl stearate SE |
|   | 5.0 | Mineral oil |
|   | 4.0 | *Simmondsia chinensis* (jojoba) seed oil |
|   | 3.0 | Mineral oil, lanolin alcohol |
| B | 5.0 | Propylene glycol |
|   | 1.0 | Aqueous solution with about 7% P18 |
|   | 1.0 | Panthenol |
|   | 0.5 | Magnesium aluminum silicate |
|   | q.s. | Preservative |
|   | 65.5 | Aqua dem. |
| C | q.s. | Perfume oil |
| D | q.s. | Citric acid |

AI 5%

|   | % | Ingredient (INCI) |
|---|---|---|
| A | 2.0 | Ceteareth-25 |
|   | 2.0 | Ceteareth-6, stearyl alcohol |
|   | 3.0 | Cetearyl ethylhexanoate |
|   | 1.0 | Dimethicone |
|   | 4.0 | Cetearyl alcohol |
|   | 3.0 | Glyceryl stearate SE |
|   | 5.0 | Mineral oil |
|   | 4.0 | *Simmondsia chinensis* (jojoba) seed oil |
|   | 3.0 | Mineral oil, lanolin alcohol |

-continued

|   | % | Ingredient (INCI) |
|---|---|---|
| B | 5.0 | Propylene glycol |
|   | 5.0 | Aqueous solution with about 7% P18 |
|   | 1.0 | Panthenol |
|   | 0.5 | Magnesium aluminum silicate |
|   | q.s. | Preservative |
|   | 61.5 | Aqua dem. |
| C | q.s. | Perfume oil |
| D | q.s. | Citric acid |

Preparation: Heat phases A and B separately to about 80° C. Briefly prehomogenize phase B, then stir phase B into phase A and homogenize again. Cool to about 40° C., add phase C and homogenize well again. Adjust the pH to 6-7 with citric acid.

Example 35

Moisturizing Bodycare Cream

AI 1%

|   | % | Ingredient (INCI) |
|---|---|---|
| A | 6.0 | PEG-7-hydrogenated castor oil |
|   | 10.0 | Cetearyl ethylhexanoate |
|   | 5.0 | Isopropyl myristate |
|   | 7.0 | Mineral oil |
|   | 0.5 | Shea butter (*Butyrospermum parkii*) |
|   | 0.5 | Aluminum stearate |
|   | 0.5 | Magnesium stearate |
|   | 0.2 | Bisabolol |
|   | 0.7 | Quaternium-18 hectorite |
| B | 5.0 | Dipropylene glycol |
|   | 0.7 | Magnesium sulfate |
|   | q.s. | Preservative |
|   | 62.9 | Aqua dem. |
|   | q.s. | Perfume oil |
| C | 1.0 | Aqueous solution with about 7% P18 |

AI 5%

|   | % | Ingredient (INCI) |
|---|---|---|
| A | 6.0 | PEG-7-hydrogenated castor oil |
|   | 10.0 | Cetearyl ethylhexanoate |
|   | 5.0 | Isopropyl myristate |
|   | 7.0 | Mineral oil |
|   | 0.5 | Shea butter (*Butyrospermum parkii*) |
|   | 0.5 | Aluminum stearate |
|   | 0.5 | Magnesium stearate |
|   | 0.2 | Bisabolol |
|   | 0.7 | Quaternium-18 hectorite |
| B | 5.0 | Dipropylene glycol |
|   | 0.7 | Magnesium sulfate |
|   | q.s. | Preservative |
|   | 58.9 | Aqua dem. |
|   | q.s. | Perfume oil |
| C | 5.0 | Aqueous solution with about 7% P18 |

Preparation: Heat phases A and B separately to about 80° C. Stir phase B into phase A and homogenize. With stirring, cool to about 40° C., add phase C and homogenize again. With stirring, allow to cool to room temperature.

Example 36

Liquid Make-Up—O/W Type

AI 1%

|   | % | Ingredient (INCI) |
|---|---|---|
| A | 2.0 | Ceteareth-6, stearyl alcohol |
|   | 2.0 | Ceteareth-25 |
|   | 6.0 | Glyceryl stearate |
|   | 1.0 | Cetyl alcohol |
|   | 8.0 | Mineral oil |
|   | 7.0 | Cetearyl ethylhexanoate |
|   | 0.2 | Dimethicone |
| B | 3.0 | Propylene glycol |
|   | 1.0 | Panthenol |
|   | q.s. | Preservative |
|   | 61.9 | Aqua dem. |
| C | 0.1 | Bisabolol |
|   | 1.0 | Aqueous solution with about 7% P18 |
|   | q.s. | Perfume oil |
| D | 5.7 | C.I. 77 891, titanium dioxide |
|   | 1.1 | Iron oxides |

AI 5%

|   | % | Ingredient (INCI) |
|---|---|---|
| A | 2.0 | Ceteareth-6, stearyl alcohol |
|   | 2.0 | Ceteareth-25 |
|   | 6.0 | Glyceryl stearate |
|   | 1.0 | Cetyl alcohol |
|   | 8.0 | Mineral oil |
|   | 7.0 | Cetearyl ethylhexanoate |
|   | 0.2 | Dimethicone |
| B | 3.0 | Propylene glycol |
|   | 1.0 | Panthenol |
|   | q.s. | Preservative |
|   | 57.9 | Aqua dem. |
| C | 0.1 | Bisabolol |
|   | 5.0 | Aqueous solution with about 7% P18 |
|   | q.s. | Perfume oil |
| D | 5.7 | C.I. 77 891, titanium dioxide |
|   | 1.1 | Iron oxides |

Preparation: Heat phases A and B separately to about 80° C. Stir phase B into phase A and homogenize. With stirring, cool to about 40° C., add phases C and D and thoroughly homogenize again. With stirring, allow to cool to room temperature.

Example 37

Dermocosmetic Preparations

Dermocosmetic preparations according to the invention comprising the peptide P18 according to the invention are described below. The concentrations can vary according to the invention.
The data below are parts by weight.
(1) Clear Shampoo

| Ingredients (INCI) | 1 | 2 | 3 | 4 | 5 |
|---|---|---|---|---|---|
| Sodium laureth sulfate | 13.00 | 15.00 | 10.50 | 12.50 | 10.00 |
| Cocamidopropylbetaine | 7.50 | 7.00 | 5.00 | 5.50 | 10.00 |
| PEG-7 glyceryl cocoate | 2.00 | 2.50 | 3.50 | 5.00 | 2.30 |
| Perfume oil | 0.10 | 0.10 | 0.10 | 0.10 | 0.10 |
| P18 | 1.0 | 5.0 | 0.1 | 0.5 | 10.0 |
| D-Panthenol USP | 1.00 | 1.50 | 1.80 | 1.70 | 1.40 |

-continued

| Ingredients (INCI) | 1 | 2 | 3 | 4 | 5 |
|---|---|---|---|---|---|
| Preservative | 0.10 | 0.10 | 0.10 | 0.10 | 0.10 |
| Citric acid | 0.10 | 0.10 | 0.10 | 0.10 | 0.10 |
| Luviquat ® Ultra Care | 1.50 | 1.00 | 1.50 | 1.20 | 1.10 |
| Sodium chloride | 1.50 | 1.40 | 1.40 | 1.30 | 1.50 |
| Aqua dem. | ad 100 | ad 100 | ad 100 | ad 100 | ad 100 |

(2) Shampoo

| Ingredients (INCI) | 1 | 2 | 3 | 4 | 5 |
|---|---|---|---|---|---|
| Sodium laureth sulfate | 35.00 | 40.00 | 30.00 | 45.00 | 27.00 |
| Decyl glucoside | 5.00 | 5.50 | 4.90 | 3.50 | 7.00 |
| Cocamidopropylbetaine | 10.00 | 5.00 | 12.50 | 7.50 | 15.00 |
| Perfume oil | 0.10 | 0.10 | 0.10 | 0.10 | 0.10 |
| P18 | 1.0 | 5.0 | 0.1 | 0.5 | 10.0 |
| D-Panthenol USP | 0.50 | 1.00 | 0.80 | 1.50 | 0.50 |
| Preservative | 0.10 | 0.10 | 0.10 | 0.10 | 0.10 |
| Citric acid | 0.10 | 0.10 | 0.10 | 0.10 | 0.10 |
| Laureth-3 | 0.50 | 2.00 | 0.50 | 0.50 | 2.00 |
| Sodium chloride | 1.50 | 1.50 | 1.50 | 1.50 | 1.50 |
| Aqua dem. | ad 100 | ad 100 | ad 100 | ad 100 | ad 100 |

(3) Clear Conditioner-Shampoo

| Ingredients (INCI) | 1 | 2 | 3 | 4 | 5 |
|---|---|---|---|---|---|
| ® Disodium Cocoamphodiacetate | 10.00 | 15.00 | 20.00 | 12.00 | 17.00 |
| ® Decyl Glucoside | 5.00 | 6.00 | 7.00 | 8.00 | 4.00 |
| ® Cocamidopropyl Betaine | 15.00 | 12.00 | 10.00 | 18.00 | 20.00 |
| Luviquat ® FC 550 | 0.30 | 0.20 | 0.20 | 0.20 | 0.30 |
| Perfume oil | 0.10 | 0.10 | 0.10 | 0.10 | 0.10 |
| P18 | 20.0 | 5.0 | 1.0 | 0.5 | 10.0 |
| Cremophor ® PS 20 | 5.00 | 1.00 | 1.00 | 7.00 | 5.00 |
| Preservative | 0.10 | 0.10 | 0.10 | 0.10 | 0.10 |
| ® Laureth-3 | 2.00 | 1.00 | 0.50 | 2.00 | 2.00 |
| Citric acid | 0.20 | 0.20 | 0.20 | 0.20 | 0.20 |
| PEG-12 distearate | 3.00 | 2.00 | 2.00 | 3.00 | 2.50 |
| Aqua dem. | ad 100 | ad 100 | ad 100 | ad 100 | ad 100 |

(4) Foam O/W Emulsions

|   | Emulsion 1 % by wt. | % by vol. | Emulsion 2 % by wt. | % by vol. |
|---|---|---|---|---|
| Stearic acid | 5.00 | | 1.00 | |
| Cetyl alcohol | 5.50 | | | |
| Cetearyl alcohol | | | 2.00 | |
| PEG-40 stearate | 8.50 | | | |
| PEG-20 stearate | | | 1.00 | |
| Caprylic/capric triglyceride | 4.00 | | 2.00 | |
| $C_{12-15}$-Alkyl benzoate | 10.00 | | 15.00 | |
| Cyclomethicone | 4.00 | | | |
| Dimethicone | | | 0.50 | |
| P18 | 5.0 | | 10.0 | |
| Ethylhexyl isostearate | | | 5.00 | |
| Myristyl myristate | | | 2.00 | |
| Ceresin | 1.50 | | | |
| Glycerol | | | 3.00 | |
| Hydroxypropyl starch phosphate | 1.00 | | 3.50 | |
| BHT | | | 0.02 | |
| Disodium EDTA | 0.50 | | 0.10 | |
| Perfume oil, preservative | q.s. | | q.s. | |
| Colorant | q.s. | | q.s. | |
| Potassium hydroxide | q.s. | | q.s. | |
| Aqua dem. | ad 100 | | ad 100 | |
|  | Adjust pH to 6.5-7.5 | | Adjust pH to 5.0-6.0 | |

-continued

|  | Emulsion 1 % by wt. | % by vol. | Emulsion 2 % by wt. | % by vol. |
|---|---|---|---|---|
| Emulsion 1 |  | 70 |  |  |
| Emulsion 2 |  |  |  | 35 |
| Nitrogen |  | 30 |  |  |
| Propane/butane |  |  |  | 65 |

(5) Conditioner-Shampoo with Pearlescence

|  | 1 | 2 | 3 |
|---|---|---|---|
| Polyquaternium-10 | 0.50 | 0.50 | 0.40 |
| Sodium laureth sulfate | 9.00 | 8.50 | 8.90 |
| Cocamidopropylbetaine | 2.50 | 2.60 | 3.00 |
| Uvinul ® MS 40 | 1.50 | 0.50 | 1.00 |
| P18 | 1.0 | 5.0 | 0.5 |
| Pearlescence solution | 2.00 | 2.50 |  |
| Disodium EDTA | 0.10 | 0.15 | 0.05 |
| Preservative, perfume oil, thickener | q.s. | q.s. | q.s. |
| Aqua dem. | ad 100 | ad 100 | ad 100 |

Adjust pH to 6.0

(6) Clear conditioner-shampoo

|  | 1 | 2 | 3 |
|---|---|---|---|
| Polyquaternium-10 | 0.50 | 0.50 | 0.50 |
| Sodium laureth sulfate | 9.00 | 8.50 | 9.50 |
| P18 | 5.0 | 0.1 | 3.0 |
| Uvinul M ® 40 | 1.00 | 1.50 | 0.50 |
| Preservative, perfume oil, thickener | q.s. | q.s. | q.s. |
| Aqua dem. | ad 100 | ad 100 | ad 100 |

Adjust pH to 6.0

(7) Clear Conditioner-Shampoo with Volume Effect

|  | 1 | 2 | 3 |
|---|---|---|---|
| Sodium laureth sulfate | 10.00 | 10.50 | 11.00 |
| Uvinul ® MC 80 | 2.00 | 1.50 | 2.30 |
| P18 | 10.0 | 0.1 | 0.5 |
| Cocamidopropylbetaine | 2.50 | 2.60 | 2.20 |
| Disodium EDTA | 0.01 | 0.10 | 0.01 |
| Preservative, perfume oil, thickener | q.s. | q.s. | q.s. |
| Aqua dem. | ad 100 | ad 100 | ad 100 |

Adjust pH to 6.0

(8) Gel Cream

|  | 1 | 2 | 3 | 4 |
|---|---|---|---|---|
| Acrylates/$C_{10-30}$-alkyl acrylate crosspolymer | 0.40 | 0.35 | 0.40 | 0.35 |
| Carbomer | 0.20 | 0.22 | 0.20 | 0.22 |
| Xanthan gum | 0.10 | 0.13 | 0.10 | 0.13 |
| Cetearyl alcohol | 3.00 | 2.50 | 3.00 | 2.50 |
| $C_{12-15}$-Alkyl benzoate | 4.00 | 4.50 | 4.00 | 4.50 |
| Caprylic/capric triglyceride | 3.00 | 3.50 | 3.00 | 3.50 |
| Uvinul ® A Plus ™ | 2.00 | 1.50 | 0.75 | 1.00 |
| UvaSorb ® k2A |  | 3.00 |  |  |
| Ethylhexylbis-isopentylbenzoxazolylphenylmelamine |  |  |  |  |
| Uvinul ® MC 80 | 3.00 |  | 1.00 |  |
| Bis-Ethylhexyloxyphenol methoxyphenyltriazine |  | 1.50 |  | 2.00 |
| Butylmethoxydibenzoylmethane |  |  | 2.00 |  |
| Disodium phenyldibenzimidazoletetrasulfonate | 2.50 |  | 0.50 | 2.00 |
| Uvinul ® T 150 | 4.00 |  | 3.00 | 4.00 |
| Octocrylene |  | 4.00 |  |  |
| Diethylhexylbutamidotriazone | 1.00 |  |  | 2.00 |
| Phenylbenzimidazolesulfonic acid | 0.50 |  | 3.00 |  |
| Methylenebis-benzotriazolyltetramethylbutylphenol | 2.00 |  | 0.50 | 1.50 |
| Ethylhexyl salicylate |  |  | 3.00 |  |
| Drometrizole trisiloxane |  |  | 0.50 |  |
| Terephthalidenedicamphorsulfonic acid |  | 1.50 |  | 1.00 |
| Diethylhexyl 2,6-naphthalate | 3.50 | 4.00 | 7.00 | 9.00 |
| Titanium dioxide-microfine | 1.00 |  | 3.00 |  |
| Zinc oxide-microfine |  |  |  | 0.25 |
| P18 | 0.1 | .5 | 1.0 | 0.02 |
| Cyclomethicone | 5.00 | 5.50 | 5.00 | 5.50 |
| Dimethicone | 1.00 | 0.60 | 1.00 | 0.60 |
| Glycerol | 1.00 | 1.20 | 1.00 | 1.20 |
| Sodium hydroxide | q.s. | q.s. | q.s. | q.s. |
| Preservative | 0.30 | 0.23 | 0.30 | 0.23 |
| Perfume oil | 0.20 |  | 0.20 |  |
| Aqua dem. | ad 100 | ad 100 | ad 100 | ad 100 |

Adjust pH to 6.0

(9) OW Sunscreen Formulation

|  | 1 | 2 | 3 | 4 | 5 | 6 | 7 |
|---|---|---|---|---|---|---|---|
| Glyceryl stearate SE | 0.50 | 1.00 | 3.00 |  |  | 1.50 |  |
| Glyceryl stearate citrate | 2.00 |  | 1.00 | 2.00 | 4.00 |  |  |
| Stearic acid |  | 3.00 |  | 2.00 |  |  |  |
| PEG-40 stearate | 0.50 |  |  |  |  | 2.00 |  |

-continued

|  | 1 | 2 | 3 | 4 | 5 | 6 | 7 |
|---|---|---|---|---|---|---|---|
| Cetyl phosphate |  |  |  |  |  | 1.00 |  |
| Sodium cetearyl sulfate |  |  |  |  |  |  | 0.75 |
| Stearyl alcohol |  |  | 3.00 |  |  | 2.00 | 0.60 |
| Cetyl alcohol | 2.50 | 1.10 |  | 1.50 | 0.60 |  | 2.00 |
| P18 | 10.0 | 0.5 | 3.0 | 5.0 | 0.1 | 0.02 | 7.5 |
| Uvinul ® A Plus ™ | 2.00 | 1.50 | 0.75 | 1.00 | 2.10 | 4.50 | 5.00 |
| UvaSorb ® k2A Ethylhexylbisisopentyl-benzoxazolylphenylmelamine |  |  |  |  |  |  |  |
| Ethylhexyl methoxycinnamate Uvinul ® MC 80 |  |  |  |  | 5.00 | 6.00 | 8.00 |
| Bisethylhexyloxyphenol methoxyphenyltriazine |  | 1.50 |  | 2.00 | 2.50 |  | 2.50 |
| Butylmethoxydibenzoylmethane |  |  | 2.00 |  | 2.00 | 1.50 |  |
| Disodium phenyldibenzimidazole-tetrasulfonate | 2.50 |  | 0.50 | 2.00 |  | 0.30 |  |
| Ethylhexyl Triazone Uvinul ® T 150 | 4.00 |  | 3.00 | 4.00 |  | 2.00 |  |
| Octocrylene |  | 4.00 |  |  |  |  | 7.50 |
| Diethylhexylbutamidotriazone | 1.00 |  |  | 2.00 | 1.00 |  | 1.00 |
| Phenylbenzimidazolesulfonic acid | 0.50 |  | 3.00 |  |  |  |  |
| Methylenebis-benzotriazolyltetramethylbutyl-phenol | 2.00 |  | 0.50 | 1.50 | 2.50 |  |  |
| Ethylhexyl salicylate |  |  | 3.00 |  |  |  | 5.00 |
| Drometrizole trisiloxane |  |  | 0.50 |  |  | 1.00 |  |
| Terephthalidenedicamphor-sulfonic acid |  | 1.50 |  | 1.00 | 1.00 |  | 0.50 |
| Diethylhexyl 2,6-naphthalate | 3.50 |  | 7.00 |  | 6.00 | 9.00 |  |
| Titanium dioxide-microfine | 1.00 |  | 3.00 |  | 3.50 |  | 1.50 |
| Zinc oxide-microfine |  |  |  | 0.25 |  | 2.00 |  |
| $C_{12-15}$-Alkyl benzoate |  | 0.25 |  |  | 4.00 | 7.00 |  |
| Dicapryl ether |  |  | 3.50 |  | 2.00 |  |  |
| Butylene glycol dicaprylate/dicaprate | 5.00 |  | 6.00 |  |  |  |  |
| Cocoglyceride |  |  | 6.00 |  | 2.00 |  |  |
| Dimethicone | 0.50 |  | 1.00 |  | 2.00 |  |  |
| Cyclomethicone | 2.00 |  | 0.50 |  | 0.50 |  |  |
| *Butyrospermum parkii* (shea butter) |  | 2.00 |  |  |  |  |  |
| VP/hexadecene copolymer | 0.20 |  |  | 0.50 |  | 1.00 |  |
| Glycerol | 3.00 | 7.50 |  | 7.50 | 5.00 |  | 2.50 |
| Xanthan gum | 0.15 |  | 0.05 |  |  | 0.30 |  |
| Sodium carbomer |  | 0.20 |  | 0.15 | 0.25 |  |  |
| Vitamin E acetate | 0.60 |  | 0.23 |  | 0.70 | 1.00 |  |
| Biosaccharide gum-1 |  | 3.00 | 10.00 |  |  |  |  |
| *Glycine soya* (soybean) oil |  |  |  | 0.50 |  | 1.50 | 1.00 |
| Ethylhexylglycerol | 0.30 |  |  |  |  |  |  |
| DMDM hydantoin |  | 0.60 | 0.40 | 0.20 |  |  |  |
| Iodopropynyl butylcarbamate |  |  |  | 0.18 | 0.20 |  |  |
| Methyl paraben | 0.15 |  | 0.25 |  | 0.50 |  |  |
| Phenoxyethanol | 1.00 | 0.40 |  |  | 0.40 | 0.50 | 0.40 |
| Trisodium EDTA | 0.02 |  | 0.05 |  |  |  |  |
| Tetrasodium iminodisuccinate |  |  |  | 0.25 | 1.00 |  |  |
| Ethanol | 2.00 | 1.50 |  | 3.00 |  | 1.20 | 5.00 |
| Perfume oil | 0.10 | 0.25 | 0.30 |  | 0.40 | 0.20 |  |
| Aqua dem. | ad 100 | ad 100 | ad 100 | ad 100 | ad 100 | ad 100 | ad 100 |

(10) Hydrodispersion

|  | 1 | 2 | 3 | 4 | 5 |
|---|---|---|---|---|---|
| Ceteareth-20 | 1.00 |  |  | 0.50 |  |
| Cetyl alcohol |  |  | 1.00 |  |  |
| Sodium carbomer |  | 0.20 |  | 0.30 |  |
| Acrylates/$C_{10-30}$-alkyl acrylate crosspolymer | 0.50 |  | 0.40 | 0.10 | 0.50 |
| Xanthan gum |  | 0.30 | 0.15 |  |  |
| P18 | 5.0 | 0.5 | 3.0 | 0.1 | 10.0 |
| Uvinul ® A Plus ™ | 2.00 | 1.50 | 0.75 | 1.00 | 2.10 |
| UvaSorb ® k2A ethylhexylbis-isopentylbenzoxazolylphenylmelamine |  | 3.50 |  |  |  |

|  | 1 | 2 | 3 | 4 | 5 |
|---|---|---|---|---|---|
| Ethylhexyl methoxycinnamate Uvinul ® MC 80 |  |  |  |  | 5.00 |
| Bisethylhexyloxyphenol methoxyphenyltriazine |  | 1.50 |  | 2.00 | 2.50 |
| Butylmethoxydibenzoylmethane |  |  | 2.00 |  | 2.00 |
| Disodium phenyldibenzimidazoletetrasulfonate | 2.50 |  | 0.50 | 2.00 |  |
| Ethylhexyltriazone Uvinul ® T 150 | 4.00 |  | 3.00 | 4.00 |  |
| Octocrylene |  | 4.00 |  |  |  |
| Diethylhexylbutamidotriazone | 1.00 |  |  | 2.00 | 1.00 |
| Phenylbenzimidazolesulfonic acid | 0.50 |  | 3.00 |  |  |
| Methylenebis-benzotriazolyltetramethylbutylphenol | 2.00 |  | 0.50 | 1.50 | 2.50 |
| Ethylhexyl salicylate |  |  | 3.00 |  |  |
| Drometrizole trisiloxane |  |  | 0.50 |  |  |
| Terephthalidenedicamphorsulfonic acid |  | 1.50 |  | 1.00 | 1.00 |
| Diethylhexyl 2,6-naphthalate |  |  | 7.00 |  | 9.00 |
| Titanium dioxide-microfine | 1.00 |  | 3.00 |  | 3.50 |
| Zinc oxide-microfine |  |  |  | 0.25 |  |
| $C_{12-15}$-Alkyl benzoate | 2.00 | 2.50 |  |  |  |
| Dicapryl ether |  | 4.00 |  |  |  |
| Butylene glycol dicaprylate/dicaprate | 4.00 |  | 2.00 | 6.00 |  |
| Dicapryl carbonate |  | 2.00 | 6.00 |  |  |
| Dimethicone |  | 0.50 | 1.00 |  |  |
| Phenyltrimethicone | 2.00 |  | 0.50 |  |  |
| *Butyrospermum parkii* (shea butter) |  | 2.00 |  | 5.00 |  |
| VP/hexadecene copolymer | 0.50 |  |  | 0.50 | 1.00 |
| Tricontanyl-PVP | 0.50 |  | 1.00 |  |  |
| Ethylhexylglycerol |  |  | 1.00 |  | 0.80 |
| Glycerol | 3.00 | 7.50 |  | 7.50 | 8.50 |
| *Glycine soya* (soybean) oil |  |  | 1.50 |  | 1.00 |
| Vitamin E acetate | 0.50 |  | 0.25 |  | 1.00 |
| Glucosylrutin | 0.60 |  |  | 0.25 |  |
| Biosaccharide gum-1 |  | 2.50 | 0.50 |  | 2.00 |
| DMDM hydantoin |  | 0.60 | 0.45 | 0.25 |  |
| Iodopropynyl butylcarbamate | 0.20 |  |  |  |  |
| Methyl paraben | 0.50 |  | 0.25 | 0.15 |  |
| Phenoxyethanol | 0.50 | 0.40 |  | 1.00 |  |
| Trisodium EDTA |  | 0.01 | 0.05 |  | 0.10 |
| Ethanol | 3.00 | 2.00 | 1.50 |  | 7.00 |
| Perfume oil | 0.20 |  | 0.05 | 0.40 |  |
| Aqua dem. | ad 100 | ad 100 | ad 100 | ad 100 | ad 100 |

(11) WO Sunscreen Emulsion

|  | 1 | 2 | 3 | 4 | 5 |
|---|---|---|---|---|---|
| Cetyldimethicone |  | 2.50 |  | 4.00 |  |
| Polyglyceryl-2 dipolyhydroxystearate | 5.00 |  |  |  | 4.50 |
| PEG-30 dipolyhydroxystearate |  |  | 5.00 |  |  |
| P18 | 5.0 | 1.0 | 10.0 | 0.5 | 0.1 |
| Uvinul ® A Plus ™ | 2.00 | 1.50 | 0.75 | 1.00 | 2.10 |
| UvaSorb ® k2A |  | 2.00 |  |  |  |
| Ethylhexylbis-isopentylbenzoxazolylphenylmelamine |  |  |  |  |  |
| Ethylhexyl methoxycinnamate Uvinul ® MC 80 |  |  |  |  | 5.00 |
| Bisethylhexyloxyphenol methoxyphenyl-triazine |  | 1.50 |  | 2.00 | 2.50 |
| Butylmethoxydibenzoylmethane |  |  | 2.00 |  | 2.00 |
| Disodium phenyldibenzimidazoletetrasulfonate | 2.50 |  | 0.50 | 2.00 |  |
| Ethylhexyltriazone Uvinul ® T 150 | 4.00 |  | 3.00 | 4.00 |  |
| Octocrylene |  | 4.00 |  |  |  |
| Diethylhexylbutamidotriazone | 1.00 |  |  | 2.00 | 1.00 |
| Phenylbenzimidazolesulfonic acid | 0.50 |  | 3.00 |  |  |
| Methylenebisbenzotriazolyltetra-methylbutylphenol | 2.00 |  | 0.50 | 1.50 | 2.50 |
| Ethylhexyl salicylate |  |  | 3.00 |  |  |
| Drometrizole trisiloxane |  |  | 0.50 |  |  |
| Terephthalidenedicamphorsulfonic acid |  | 1.50 |  | 1.00 | 1.00 |
| Diethylhexyl 2,6-naphthalate |  |  | 7.00 |  | 4.00 |
| Titanium dioxide-microfine | 1.00 |  | 3.00 |  | 3.50 |
| Zinc oxide-microfine |  |  |  | 0.25 |  |

-continued

|  | 1 | 2 | 3 | 4 | 5 |
|---|---|---|---|---|---|
| Mineral oil |  | 12.00 | 10.00 |  | 8.00 |
| $C_{12-15}$-Alkyl benzoate |  |  |  | 9.00 |  |
| Dicaprylyl ether | 10.00 |  |  |  | 7.00 |
| Butylene glycol dicaprylate/dicaprate |  |  | 2.00 | 8.00 | 4.00 |
| Dicaprylyl carbonate | 5.00 |  | 6.00 |  |  |
| Dimethicone |  | 4.00 | 1.00 | 5.00 |  |
| Cyclomethicone | 2.00 | 25.00 |  |  | 2.00 |
| *Butyrospermum parkii* (shea butter) |  |  | 3.00 |  |  |
| Petrolatum |  | 4.50 |  |  |  |
| VP/hexadecene copolymer | 0.50 |  |  | 0.50 | 1.00 |
| Ethylhexylglycerol |  | 0.30 | 1.00 |  | 0.50 |
| Glycerol | 3.00 | 7.50 |  | 7.50 | 8.50 |
| *Glycine soya* (soybean) oil |  | 1.00 | 1.50 |  | 1.00 |
| Magnesium sulfate $MgSO_4$ | 1.00 | 0.50 |  | 0.50 |  |
| Magnesium chloride $MgCl_2$ |  |  | 1.00 |  | 0.70 |
| Vitamin E acetate | 0.50 |  | 0.25 |  | 1.00 |
| Ascorbyl palmitate | 0.50 |  |  | 2.00 |  |
| Biosaccharide gum-1 |  |  |  | 3.50 | 1.00 |
| DMDM hydantoin |  | 0.60 | 0.40 | 0.20 |  |
| Methyl paraben | 0.50 |  | 0.25 | 0.15 |  |
| Phenoxyethanol | 0.50 | 0.40 |  | 1.00 |  |
| Trisodium EDTA | 0.12 | 0.05 |  | 0.30 |  |
| Ethanol | 3.00 |  | 1.50 |  | 5.00 |
| Perfume oil | 0.20 |  | 0.40 | 0.35 |  |
| Aqua dem. | ad 100 | ad 100 | ad 100 | ad 100 | ad 100 |

(12) Sticks

|  | 1 | 2 | 3 | 4 |
|---|---|---|---|---|
| Caprylic/capric triglyceride | 12.00 | 10.00 | 6.00 |  |
| Octyldodecanol | 7.00 | 14.00 | 8.00 | 3.00 |
| Butylene glycol dicaprylate/dicaprate |  |  |  | 12.00 |
| Pentaerythrityl tetraisostearate | 10.00 | 6.00 | 8.00 | 7.00 |
| Polyglyceryl-3 diisostearate | 2.50 |  |  |  |
| Bisdiglyceryl polyacyladipate-2 | 9.00 | 8.00 | 10.00 | 8.00 |
| Cetearyl alcohol | 8.00 | 11.00 | 9.00 | 7.00 |
| Myristyl myristate | 3.50 | 3.00 | 4.00 | 3.00 |
| Beeswax | 5.00 | 5.00 | 6.00 | 6.00 |
| *Copernicia cerifera* (carnauba) wax | 1.50 | 2.00 | 2.00 | 1.50 |
| Cera alba | 0.50 | 0.50 | 0.50 | 0.40 |
| $C_{16-40}$ Alkyl stearate |  | 1.50 | 1.50 | 1.50 |
| P18 | 0.5 | 3.0 | 1.0 | 5.0 |
| Uvinul ® A Plus ™ | 2.00 | 1.50 | 0.75 | 9.00 |
| UvaSorb ® k2A |  | 2.00 |  | 4.00 |
| Ethylhexylbis-isopentylbenzoxazolylphenyl-melamine |  |  |  |  |
| Ethylhexyl methoxycinnamate Uvinul ® MC 80 |  | 3.00 |  |  |
| Bis-Ethylhexyloxyphenol methoxyphenyltriazine |  | 1.50 |  | 2.00 |

-continued

|  | 1 | 2 | 3 | 4 |
|---|---|---|---|---|
| Butylmethoxydibenzoylmethane |  |  | 2.00 |  |
| Disodium phenyldibenzimidazole-tetrasulfonate | 2.50 |  | 0.50 | 2.00 |
| Ethylhexyltriazone Uvinul ® T 150 | 4.00 |  | 3.00 | 4.00 |
| Octocrylene |  | 4.00 |  |  |
| Diethylhexylbutamidotriazone | 1.00 |  |  | 2.00 |
| Phenylbenzimidazolesulfonic acid | 0.50 |  | 3.00 |  |
| Methylenebis-benzotriazolyltetramethyl-butylphenol | 2.00 |  | 0.50 | 1.50 |
| Ethylhexyl salicylate |  |  | 3.00 |  |
| Drometrizole trisiloxane |  |  | 0.50 |  |
| Terephthalidenedicamphorsulfonic acid |  | 1.50 |  | 1.00 |
| Diethylhexyl 2,6-naphthalate |  |  | 7.00 |  |
| Titanium dioxide-microfine | 1.00 |  | 3.00 |  |
| Zinc oxide-microfine |  |  |  | 0.25 |
| Vitamin E acetate | 0.50 | 1.00 |  |  |
| Ascorbyl palmitate | 0.05 |  | 0.05 |  |
| *Buxux chinensis* (jojoba) oil | 2.00 | 1.00 |  | 1.00 |
| Perfume oil, BHT | 0.10 | 0.25 |  | 0.35 |
| *Ricinus communis* (castor) oil | ad 100 | ad 100 | ad 100 | ad 100 |

(13) PIT Emulsion

|  | 1 | 2 | 3 | 4 | 5 | 6 | 7 | 8 |
|---|---|---|---|---|---|---|---|---|
| Glyceryl monostearate SE | 0.50 | 2.00 | 3.00 | 5.00 |  | 0.50 | 4.00 |  |
| Glyceryl isostearate |  |  |  |  | 3.50 | 4.00 | 2.00 |  |
| Isoceteth-20 |  |  | 0.50 |  | 2.00 |  |  |  |
| Ceteareth-12 |  |  | 5.00 | 1.00 |  |  | 3.50 | 5.00 |
| Ceteareth-20 |  |  | 5.00 | 1.00 |  |  |  | 3.50 |
| PEG-100 stearate |  |  |  | 2.80 |  | 2.30 | 3.30 |  |
| Cetyl alcohol | 5.20 |  | 1.20 | 1.00 | 1.30 |  | 0.50 | 0.30 |
| Cetyl palmitate | 2.50 | 1.20 |  | 1.50 |  | 0.50 |  | 1.50 |
| Cetyldimethicone copolyol |  |  |  | 0.50 |  | 1.00 |  |  |
| Polyglyceryl-2 dioleate |  |  |  | 0.75 | 0.30 |  |  |  |
| P18 | 0.1 | 5.0 | 0.01 | 0.5 | 3.0 | 0.25 | 10.0 | 3.0 |
| Uvinul ® A Plus ™ | 2.00 | 1.50 | 0.75 | 1.00 | 2.10 | 4.50 | 5.00 | 2.10 |

|  | 1 | 2 | 3 | 4 | 5 | 6 | 7 | 8 |
|---|---|---|---|---|---|---|---|---|
| UvaSorb ® k2A Ethylhexylbisisopentylbenzoxazolylphenylmelamine |  |  | 4.00 |  |  |  | 1.50 |  |
| Ethylhexyl methoxycinnamate Uvinul ® MC 80 |  |  |  |  | 5.00 | 6.00 | 8.00 | 5.00 |
| Bisethylhexyloxyphenol methoxyphenyltriazine |  | 1.50 |  | 2.00 | 2.50 |  | 2.50 | 2.50 |
| Butylmethoxydibenzoylmethane |  |  | 2.00 |  | 2.00 | 1.50 |  | 2.00 |
| Disodium phenyldibenzimidazoletetrasulfonate | 2.50 |  | 0.50 | 2.00 |  | 0.30 |  |  |
| Ethylhexyltriazone Uvinul ® T 150 | 4.00 |  |  | 3.00 | 4.00 |  | 2.00 |  |
| Octocrylene |  | 4.00 |  |  |  |  | 7.50 |  |
| Diethylhexylbutamidotriazone | 1.00 |  |  | 2.00 | 1.00 |  | 1.00 | 1.00 |
| Phenylbenzimidazole sulfonic acid | 0.50 |  | 3.00 |  |  |  |  |  |
| Methylenebis-benzotriazolyltetramethylbutylphenol | 2.00 |  | 0.50 | 1.50 | 2.50 |  |  | 2.50 |
| Ethylhexyl salicylate |  |  | 3.00 |  |  |  | 5.00 |  |
| Drometrizole trisiloxane |  |  | 0.50 |  |  | 1.00 |  |  |
| Terephthalidene-dicamphorsulfonic acid |  | 1.50 |  | 1.00 | 1.00 |  | 0.50 | 1.00 |
| Diethylhexyl 2,6-naphthalate |  |  | 7.00 |  | 10.00 | 7.50 |  | 8.00 |
| Titanium dioxide-microfine | 1.00 |  | 3.00 |  | 3.50 |  | 1.50 | 3.50 |
| Zinc oxide-microfine |  |  |  | 0.25 |  | 2.00 |  |  |
| $C_{12-15}$-Alkyl benzoate | 3.50 |  |  | 6.35 |  |  |  | 0.10 |
| Cocoglyceride |  | 3.00 |  | 3.00 |  |  |  | 1.00 |
| Dicapryl ether | 4.50 |  |  |  |  |  |  |  |
| Dicaprylyl carbonate |  | 4.30 |  | 3.00 |  |  |  | 7.00 |
| Dibutyl adipate |  |  |  | 0.50 |  |  |  | 0.30 |
| Phenyltrimethicone | 2.00 |  |  | 3.50 |  | 2.00 |  |  |
| Cyclomethicone |  | 3.00 |  |  |  |  |  |  |
| $C_{1-5}$ Alkylgalactomannan |  | 0.50 |  |  | 2.00 |  |  |  |
| Hydrogenated cocoglyceride |  |  |  |  | 3.00 | 4.00 |  |  |
| Behenoxy-dimethicone |  |  |  |  |  |  | 1.50 | 2.00 |
| VP/hexadecene copolymer |  |  |  | 1.00 | 1.20 |  |  |  |
| Glycerol | 4.00 | 6.00 | 5.00 |  | 8.00 | 10.00 |  |  |
| Vitamin E acetate | 0.20 | 0.30 | 0.40 |  | 0.30 |  |  |  |
| *Butyrospermum parkii* (shea butter) |  | 2.00 |  | 3.60 |  | 2.00 |  |  |
| Iodopropyl butylcarbamate | 0.12 |  |  |  | 0.20 |  |  |  |
| Biosaccharide gum-1 |  |  |  | 0.10 |  |  |  |  |
| DMDM hydantoin | 0.10 |  |  |  | 0.12 |  | 0.13 |  |
| Methyl paraben |  | 0.50 | 0.30 |  | 0.35 |  |  |  |
| Phenoxyethanol | 0.50 | 0.40 |  | 1.00 |  |  |  |  |
| Ethylhexylglycerol |  | 0.30 |  |  | 1.00 |  | 0.35 |  |
| Ethanol | 2.00 |  | 2.00 |  |  | 5.00 |  |  |
| Trisodium EDTA | 0.40 |  | 0.15 |  |  | 0.20 |  |  |
| Perfume oil | 0.20 |  | 0.20 |  | 0.24 | 0.16 | 0.10 | 0.10 |
| Aqua dem. | ad 100 | ad 100 | ad 100 | ad 100 | ad 100 | ad 100 | ad 100 | ad 100 |

(14) Gel Cream

|  | 1 | 2 | 3 | 4 |
|---|---|---|---|---|
| Acrylates/$C_{10-30}$-alkyl acrylate crosspolymer | 0.40 | 0.35 | 0.40 | 0.35 |
| Carbomer | 0.20 | 0.22 | 0.20 | 0.22 |
| Luvigel ® EM | 1.50 | 2.50 | 2.80 | 3.50 |
| Xanthan gum | 0.10 | 0.13 | 0.10 | 0.13 |
| Cetearyl alcohol | 3.00 | 2.50 | 3.00 | 2.50 |
| $C_{12-15}$-Alkyl benzoate | 4.00 | 4.50 | 4.00 | 4.50 |
| Caprylic/capric triglyceride | 3.00 | 3.50 | 3.00 | 3.50 |
| Titanium dioxide-microfine | 1.00 |  | 1.50 |  |

187 -continued

|                       | 1    | 2    | 3    | 4    |
|-----------------------|------|------|------|------|
| Zinc oxide-microfine  |      | 2.00 |      | 0.25 |
| P18                   | 0.5  | 10.0 | 3.0  | 5.0  |
| Dihydroxyacetone      |      |      | 3.00 | 5.00 |
| Cyclomethicone        | 5.00 | 5.50 | 5.00 | 5.50 |
| Dimethicone           | 1.00 | 0.60 | 1.00 | 0.60 |
| Glycerol              | 1.00 | 1.20 | 1.00 | 1.20 |
| Sodium hydroxide      | q.s. | q.s. | q.s. | q.s. |

188 -continued

|              | 1      | 2      | 3      | 4      |
|--------------|--------|--------|--------|--------|
| Preservative | 0.30   | 0.23   | 0.30   | 0.23   |
| Perfume oil  | 0.20   |        | 0.20   |        |
| Aqua dem.    | ad 100 | ad 100 | ad 100 | ad 100 |

Adjust pH to 6.0

(15) OW Self-Tanning Formulations

|                                      | 1      | 2      | 3      | 4      | 5      | 6      | 7      |
|--------------------------------------|--------|--------|--------|--------|--------|--------|--------|
| Glyceryl monostearate SE             | 0.50   | 1.00   | 3.00   |        |        | 1.50   |        |
| Glyceryl stearate citrate            | 2.00   |        | 1.00   | 2.00   | 4.00   |        |        |
| Stearic acid                         |        | 3.00   |        | 2.00   |        |        |        |
| PEG-40 stearate                      | 0.50   |        |        |        |        | 2.00   |        |
| Cetyl phosphate                      |        |        |        |        |        | 1.00   |        |
| Cetearyl sulfate                     |        |        |        |        |        |        | 0.75   |
| Stearyl alcohol                      |        |        | 3.00   |        |        | 2.00   | 0.60   |
| Cetyl alcohol                        | 2.50   | 1.10   |        | 1.50   | 0.60   |        | 2.00   |
| P18                                  | 0.1    | 0.5    | 0.025  | 5.0    | 3.0    | 10.0   | 1.0    |
| Dihydroxyacetone                     |        |        | 3.00   | 5.00   |        | 4      |        |
| Titanium dioxide-microfine           | 1.00   |        |        |        | 1.50   |        | 1.50   |
| Zinc oxide-microfine                 |        |        |        | 0.25   |        | 2.00   |        |
| $C_{12-15}$-Alkyl benzoate           |        | 0.25   |        |        | 4.00   | 7.00   |        |
| Dicapryl ether                       |        |        |        | 3.50   | 2.00   |        |        |
| Butylene glycol dicaprylate/dicaprate| 5.00   |        |        | 6.00   |        |        |        |
| Cocoglyceride                        |        |        | 6.00   |        | 2.00   |        |        |
| Dimethicone                          | 0.50   |        | 1.00   |        | 2.00   |        |        |
| Cyclomethicone                       | 2.00   |        | 0.50   |        | 0.50   |        |        |
| *Butyrospermum parkii* (shea butter) |        | 2.00   |        |        |        |        |        |
| VP/hexadecene copolymer              | 0.20   |        |        | 0.50   |        | 1.00   |        |
| Glycerol                             | 3.00   | 7.50   |        | 7.50   | 5.00   |        | 2.50   |
| Xanthan gum                          | 0.15   |        | 0.05   |        |        | 0.30   |        |
| Sodium carbomer                      |        | 0.20   |        | 0.15   | 0.25   |        |        |
| Vitamin E acetate                    | 0.60   |        | 0.23   |        | 0.70   | 1.00   |        |
| Biosaccharide gum-1                  |        | 3.00   | 10.00  |        |        |        |        |
| *Glycine soya* (soybean) oil         |        |        |        | 0.50   |        | 1.50   | 1.00   |
| Ethylhexylglycerol                   | 0.30   |        |        |        |        |        |        |
| DMDM hydantoin                       |        | 0.60   | 0.40   | 0.20   |        |        |        |
| Iodopropynyl butylcarbamate          |        |        |        | 0.18   | 0.20   |        |        |
| Methyl paraben                       | 0.15   |        | 0.25   |        | 0.50   |        |        |
| Phenoxyethanol                       | 1.00   | 0.40   |        |        | 0.40   | 0.50   | 0.40   |
| Trisodium EDTA                       | 0.02   |        | 0.05   |        |        |        |        |
| Tetrasodium iminodisuccinate         |        |        |        | 0.25   | 1.00   |        |        |
| Ethanol                              | 2.00   | 1.50   |        | 3.00   |        | 1.20   | 5.00   |
| Perfume oil                          | 0.10   | 0.25   | 0.30   |        | 0.40   | 0.20   |        |
| Aqua dem.                            | ad 100 | ad 100 | ad 100 | ad 100 | ad 100 | ad 100 | ad 100 |

(16) OW Make-Up

|                                      | 1      | 2      | 3      | 4      | 5      | 6      | 7      |
|--------------------------------------|--------|--------|--------|--------|--------|--------|--------|
| Glyceryl monostearate SE             | 0.50   | 1.00   | 3.00   |        |        | 1.50   |        |
| Glyceryl stearate citrate            | 2.00   |        | 1.00   | 2.00   | 4.00   |        |        |
| Stearic acid                         |        | 3.00   |        | 2.00   |        |        |        |
| PEG-40 stearate                      | 0.50   |        |        |        |        | 2.00   |        |
| Cetyl phosphate                      |        |        |        |        |        | 1.00   |        |
| Cetearyl sulfate                     |        |        |        |        |        |        | 0.75   |
| Stearyl alcohol                      |        |        | 3.00   |        |        | 2.00   | 0.60   |
| Cetyl alcohol                        | 2.50   | 1.10   |        | 1.50   | 0.60   |        | 2.00   |
| P18                                  | 3.0    | 5.0    | 2.0    | 0.5    | 1.0    | 5.0    | 10.0   |
| Titanium dioxide                     | 10.00  | 12.00  | 9.00   | 8.50   | 11.00  | 9.50   | 10.00  |
| Iron oxide                           | 2.00   | 4.00   | 3.00   | 5.00   | 3.40   | 6.00   | 4.40   |
| Zinc oxide                           |        | 4.00   |        | 2.00   |        | 3.00   |        |
| $C_{12-15}$-Alkyl benzoate           |        | 0.25   |        |        | 4.00   | 7.00   |        |
| Dicapryl ether                       |        |        |        | 3.50   | 2.00   |        |        |
| Butylene glycol dicaprylate/dicaprate| 5.00   |        |        | 6.00   |        |        |        |
| Cocoglyceride                        |        |        | 6.00   |        | 2.00   |        |        |

-continued

|  | 1 | 2 | 3 | 4 | 5 | 6 | 7 |
|---|---|---|---|---|---|---|---|
| Dimethicone | 0.50 |  | 1.00 |  | 2.00 |  |  |
| Cyclomethicone | 2.00 |  | 0.50 |  | 0.50 |  |  |
| *Butyrospermum parkii* (shea butter) |  | 2.00 |  |  |  |  |  |
| VP/hexadecene copolymer | 0.20 |  |  | 0.50 |  | 1.00 |  |
| Glycerol | 3.00 | 7.50 |  | 7.50 | 5.00 |  | 2.50 |
| Xanthan gum | 0.15 |  | 0.05 |  |  | 0.30 |  |
| Sodium carbomer |  | 0.20 |  | 0.15 | 0.25 |  |  |
| Vitamin E acetate | 0.60 |  | 0.23 |  | 0.70 | 1.00 |  |
| *Glycine soya* (soybean) oil |  |  |  | 0.50 |  | 1.50 | 1.00 |
| Ethylhexylglycerol | 0.30 |  |  |  |  |  |  |
| DMDM hydantoin |  | 0.60 | 0.40 | 0.20 |  |  |  |
| Iodopropynyl butylcarbamate |  |  |  | 0.18 | 0.20 |  |  |
| Methyl paraben | 0.15 |  | 0.25 |  | 0.50 |  |  |
| Phenoxyethanol | 1.00 | 0.40 |  |  | 0.40 | 0.50 | 0.40 |
| Trisodium EDTA | 0.02 |  | 0.05 |  |  |  |  |
| Tetrasodium iminodisuccinate |  |  |  | 0.25 | 1.00 |  |  |
| Ethanol | 2.00 | 1.50 |  | 3.00 |  | 1.20 | 5.00 |
| Perfume oil | 0.10 | 0.25 | 0.30 |  | 0.40 | 0.20 |  |
| Aqua dem. | ad 100 | ad 100 | ad 100 | ad 100 | ad 100 | ad 100 | ad 100 |

(17) Self-Tannins Hydrodispersion

|  | 1 | 2 | 3 | 4 | 5 |
|---|---|---|---|---|---|
| Ceteareth-20 | 1.00 |  |  | 0.50 |  |
| Cetyl alcohol |  | 1.00 |  |  |  |
| Luvigel ® EM |  | 2.00 |  | 2.50 | 2.00 |
| Acrylates/C$_{10-30}$-alkyl acrylate crosspolymer | 0.50 |  | 0.40 | 0.10 | 0.50 |
| Xanthan gum |  | 0.30 | 0.15 |  |  |
| P18 | 3.0 | 1.0 | 0.5 | 0.1 | 5.0 |
| Dihydroxyacetone |  |  | 3.00 | 5.00 |  |
| Uvinul ® A Plus ™ | 2.00 | 1.50 | 0.75 | 1.00 | 2.10 |
| Titanium dioxide-microfine | 1.00 |  | 1.00 |  | 1.00 |
| Zinc oxide-microfine |  | 1.90 |  | 0.25 |  |
| C$_{12-15}$-Alkyl benzoate | 2.00 | 2.50 |  |  |  |
| Dicapryl ether |  | 4.00 |  |  |  |
| Butylene glycol dicaprylate/dicaprate | 4.00 |  | 2.00 | 6.00 |  |
| Dicapryl carbonate |  | 2.00 | 6.00 |  |  |
| Dimethicone |  |  | 0.50 | 1.00 |  |
| Phenyltrimethicone | 2.00 |  | 0.50 |  |  |
| *Butyrospermum parkii* (shea butter) |  | 2.00 |  | 5.00 |  |
| VP/hexadecene copolymer | 0.50 |  |  | 0.50 | 1.00 |
| Tricontanyl-PVP | 0.50 |  | 1.00 |  |  |
| Ethylhexylglycerol |  |  | 1.00 |  | 0.80 |
| Glycerol | 3.00 | 7.50 |  | 7.50 | 8.50 |
| *Glycine soya* (soybean) oil |  |  | 1.50 |  | 1.00 |
| Vitamin E acetate | 0.50 |  | 0.25 |  | 1.00 |
| Glucosylrutin | 0.60 |  |  | 0.25 |  |
| DMDM hydantoin |  | 0.60 | 0.45 | 0.25 |  |
| Iodopropynyl butylcarbamate | 0.20 |  |  |  |  |
| Methyl paraben | 0.50 |  | 0.25 | 0.15 |  |
| Phenoxyethanol | 0.50 | 0.40 |  | 1.00 |  |
| Trisodium EDTA |  | 0.01 | 0.05 |  | 0.10 |
| Ethanol | 3.00 | 2.00 | 1.50 |  | 7.00 |
| Perfume oil | 0.20 |  | 0.05 | 0.40 |  |
| Aqua dem. | ad 100 | ad 100 | ad 100 | ad 100 | ad 100 |

(18) Aftersun Hydrodispersion

|  | 1 | 2 | 3 | 4 | 5 |
|---|---|---|---|---|---|
| Ceteareth-20 | 1.00 |  |  | 0.50 |  |
| Cetyl alcohol |  |  | 1.00 |  |  |
| Luvigel ® EM |  | 2.00 |  | 2.50 | 2.00 |
| Acrylates/C$_{10-30}$-alkyl acrylate crosspolymer | 0.50 | 0.30 | 0.40 | 0.10 | 0.50 |
| Xanthan gum |  | 0.30 | 0.15 |  |  |
| P18 | 0.1 | 5.0 | 0.5 | 3.0 | 1.0 |
| C$_{12-15}$-Alkyl benzoate | 2.00 | 2.50 |  |  |  |
| Dicapryl ether |  | 4.00 |  |  |  |
| Butylene glycol dicaprylate/dicaprate | 4.00 |  |  | 2.00 | 6.00 |
| Dicapryl carbonate |  | 2.00 | 6.00 |  |  |
| Dimethicone |  |  | 0.50 | 1.00 |  |

-continued

|  | 1 | 2 | 3 | 4 | 5 |
|---|---|---|---|---|---|
| Phenyltrimethicone | 2.00 |  | 0.50 |  |  |
| Tricontanyl-PVP | 0.50 |  | 1.00 |  |  |
| Ethylhexylglycerol |  |  | 1.00 |  | 0.80 |
| Glycerol | 3.00 | 7.50 |  | 7.50 | 8.50 |
| *Glycine soya* (soybean) oil |  |  | 1.50 |  | 1.00 |
| Vitamin E acetate | 0.50 |  | 0.25 |  | 1.00 |
| Glucosylrutin | 0.60 |  |  | 0.25 |  |
| Trisodium EDTA |  | 0.01 | 0.05 |  | 0.10 |
| Ethanol | 15.00 | 10.00 | 8.00 | 12.00 | 9.00 |
| Perfume oil | 0.20 |  | 0.05 | 0.40 |  |
| Aqua dem. | ad 100 | ad 100 | ad 100 | ad 100 | ad 100 |

(19) WO Emulsions

|  | 1 | 2 | 3 | 4 | 5 |
|---|---|---|---|---|---|
| Cetyldimethicone |  | 2.50 |  | 4.00 |  |
| Polyglyceryl-2 dipolyhydroxystearate | 5.00 |  |  |  | 4.50 |
| PEG-30 dipolyhydroxystearate |  |  | 5.00 |  |  |
| P18 | 5.0 | 10.0 | 0.1 | 0.5 | 1.0 |
| Uvinul ® A Plus ™ | 2.00 | 1.50 | 0.75 | 1.00 | 2.10 |
| Titanium dioxide-microfine | 1.00 |  | 3.00 |  | 3.50 |
| Zinc oxide-microfine |  | 0.90 |  | 0.25 |  |
| Mineral oil |  | 12.00 | 10.00 |  | 8.00 |

-continued

|  | 1 | 2 | 3 | 4 | 5 |
|---|---|---|---|---|---|
| $C_{12-15}$-Alkyl benzoate |  |  |  | 9.00 |  |
| Dicaprylyl ether | 10.00 |  |  |  | 7.00 |
| Butylene glycol dicaprylate/dicaprate |  |  | 2.00 | 8.00 | 4.00 |
| Dicaprylyl carbonate | 5.00 |  | 6.00 |  |  |
| Dimethicone |  | 4.00 | 1.00 | 5.00 |  |
| Cyclomethicone | 2.00 | 25.00 |  |  | 2.00 |
| *Butyrospermum parkii* (shea butter) |  |  | 3.00 |  |  |
| Vaseline |  | 4.50 |  |  |  |
| VP/hexadecene copolymer | 0.50 |  |  | 0.50 | 1.00 |
| Ethylhexylglycerol |  | 0.30 | 1.00 |  | 0.50 |
| Glycerol | 3.00 | 7.50 |  | 7.50 | 8.50 |
| *Glycine soya* (soybean) oil |  | 1.00 | 1.50 |  | 1.00 |
| Magnesium sulfate | 1.00 | 0.50 |  | 0.50 |  |
| Magnesium chloride |  |  | 1.00 |  | 0.70 |
| Vitamin E acetate | 0.50 |  | 0.25 |  | 1.00 |
| Ascorbyl palmitate | 0.50 |  |  | 2.00 |  |
| Biosaccharide gum-1 |  |  |  | 3.50 | 7.00 |
| DMDM hydantoin |  | 0.60 | 0.40 | 0.20 |  |
| Methyl paraben | 0.50 |  | 0.25 | 0.15 |  |
| Phenoxyethanol | 0.50 | 0.40 |  |  | 1.00 |
| Trisodium EDTA | 0.12 | 0.05 |  | 0.30 |  |
| Ethanol | 3.00 |  | 1.50 |  | 5.00 |
| Perfume oil | 0.20 |  | 0.40 | 0.35 |  |
| Aqua dem. | ad 100 | ad 100 | ad 100 | ad 100 | ad 100 |

(20) Solids-Stabilized Emulsion (Pickering Emulsions)

|  | 1 | 2 | 3 | 4 | 5 |
|---|---|---|---|---|---|
| Mineral oil |  |  | 16.00 | 16.00 |  |
| Octyldodecanol | 9.00 | 9.00 | 5.00 |  |  |
| Caprylic/capric triglyceride | 9.00 | 9.00 | 6.00 |  |  |
| $C_{12-15}$-Alkyl benzoate |  |  |  | 5.00 | 8.00 |
| Butylene glycol dicaprylate/dicaprate |  |  |  |  | 8.00 |
| Dicaprylyl ether | 9.00 |  |  | 4.00 |  |
| Dicaprylyl carbonate |  | 9.00 |  |  |  |
| Hydroxyoctacosanyl hydroxystearate | 2.00 | 2.00 | 2.20 | 2.50 | 1.50 |
| Disteardimonium hectorite | 1.00 | 0.75 |  | 0.50 | 0.25 |
| Cera microcristallina + paraffinum liquidum |  |  | 0.35 |  | 5.00 |
| Hydroxypropylmethylcellulose |  |  | 0.10 |  | 0.05 |
| Dimethicone |  |  |  |  | 3.00 |
| P18 | 1.0 | 0.5 | 0.1 | 3.0 | 5.0 |
| Titanium dioxide + aluminum oxide + simethicone + aqua |  | 3.00 |  |  |  |
| Titanium dioxide + trimethoxycaprylylsilane |  | 2.00 | 4.00 | 2.00 | 4.00 |
| Silicon dimethylsilylate | 2.50 |  |  | 6.00 | 2.50 |
| Boron nitride |  |  | 1.00 |  |  |
| Starch/sodium metaphosphate polymer | 2.00 |  |  |  |  |
| Manioc starch or tapioca |  | 0.50 |  |  |  |
| Sodium chloride | 5.00 | 7.00 | 8.50 | 3.00 | 4.50 |
| Glycerol |  |  |  | 1.00 |  |
| Trisodium EDTA | 1.00 | 1.00 | 1.00 | 1.00 | 1.00 |
| Vitamin E acetate | 5.00 | 10.00 | 3.00 | 6.00 | 10.00 |
| Ascorbyl palmitate | 1.00 | 1.00 |  | 1.00 |  |
| Methyl paraben |  | 0.60 |  |  | 0.20 |
| Propyl paraben |  |  |  |  | 0.20 |
| Phenoxyethanol |  |  | 0.20 |  |  |
| Hexamidine diisethionate |  |  | 0.40 | 0.50 | 0.40 |
| Diazolidinylurea |  |  |  |  | 0.08 |
| Ethanol |  |  | 0.23 | 0.20 |  |
| Perfume oil | 5.00 |  | 3.00 | 4.00 |  |
| Aqua dem. | 0.20 |  | 0.30 | 0.10 |  |
|  | ad 100 | ad 100 | ad 100 | ad 100 | ad 100 |

(21) Sticks

|  | 1 | 2 | 3 | 4 |
|---|---|---|---|---|
| Caprylic/capric triglyceride | 12.00 | 10.00 | 6.00 | |
| Octyldodecanol | 7.00 | 14.00 | 8.00 | 3.00 |
| Butylene glycol dicaprylate/dicaprate | | | | 12.00 |
| Pentaerythrityl tetraisostearate | 10.00 | 6.00 | 8.00 | 7.00 |
| Polyglyceryl-3 diisostearate | 2.50 | | | |
| Bisdiglyceryl polyacyladipate-2 | 9.00 | 8.00 | 10.00 | 8.00 |
| Cetearyl alcohol | 8.00 | 11.00 | 9.00 | 7.00 |
| Myristyl myristate | 3.50 | 3.00 | 4.00 | 3.00 |
| Beeswax | 5.00 | 5.00 | 6.00 | 6.00 |
| *Copernicia cerifera* (carnauba) wax | 1.50 | 2.00 | 2.00 | 1.50 |
| Cera Alba | 0.50 | 0.50 | 0.50 | 0.40 |
| $C_{16-40}$-Alkyl stearate | | 1.50 | 1.50 | 1.50 |
| P18 | 10.0 | 1.0 | 3.0 | 0.1 |
| Uvinul ® A Plus ™ | 2.00 | 1.50 | 0.75 | 9.00 |
| Titanium dioxide-microfine | 1.00 | | 3.00 | |
| Zinc oxide-microfine | | 1.00 | | 0.25 |
| Vitamin E acetate | 0.50 | 1.00 | | |
| Ascorbyl palmitate | 0.05 | | 0.05 | |
| *Buxux chinensis* (jojoba) oil | 2.00 | 1.00 | | 1.00 |
| Perfume oil, BHT | 0.10 | 0.25 | | 0.35 |
| *Ricinus communis* (castor) oil | ad 100 | ad 100 | ad 100 | ad 100 |

(22) Self-Tanning PIT Emulsions

|  | 1 | 2 | 3 | 4 | 5 | 6 | 7 | 8 |
|---|---|---|---|---|---|---|---|---|
| Glyceryl monostearate SE | 0.50 | 2.00 | 3.00 | 5.00 | | 0.50 | 4.00 | |
| Glyceryl isostearate | | | | | 3.50 | 4.00 | 2.00 | |
| Isoceteth-20 | | 0.50 | | | 2.00 | | | |
| Ceteareth-12 | | 5.00 | | 1.00 | | | 3.50 | 5.00 |
| Ceteareth-20 | | 5.00 | | 1.00 | | | | 3.50 |
| PEG-100 stearate | | | | 2.80 | | 2.30 | 3.30 | |
| Cetyl alcohol | 5.20 | | 1.20 | 1.00 | 1.30 | | 0.50 | 0.30 |
| Cetyl palmitate | 2.50 | 1.20 | | 1.50 | | 0.50 | | 1.50 |
| Cetyldimethicone copolyol | | | | 0.50 | | 1.00 | | |
| Polyglyceryl-2 | | | | 0.75 | 0.30 | | | |
| P18 | 0.1 | 0.5 | 0.01 | 5.0 | 0.5 | 3.0 | 0.025 | 10.0 |
| Dihydroxyacetone | | | 3.00 | 5.00 | | | 4.00 | |
| Uvinul ® A Plus ™ | 2.00 | 1.50 | 0.75 | 1.00 | 2.10 | 4.50 | 5.00 | 2.10 |
| Titanium dioxide-microfine | 1.00 | | 1.50 | | 3.50 | | 1.50 | 1.00 |
| Zinc oxide-microfine | | 1.00 | | 0.25 | | 2.00 | | 1.50 |
| $C_{12-15}$-Alkyl benzoate | 3.50 | | | 6.35 | | | | 0.10 |
| Cocoglyceride | | 3.00 | | 3.00 | | | | 1.00 |
| Dicapryl ether | 4.50 | | | | | | | |
| Dicaprylyl carbonate | | 4.30 | | 3.00 | | | 7.00 | |
| Dibutyl adipate | | | | 0.50 | | | | 0.30 |
| Phenyltrimethicone | 2.00 | | | 3.50 | | 2.00 | | |
| Cyclomethicone | | 3.00 | | | | | | |
| $C_{1-5}$-Alkylgalactomannan | | 0.50 | | | 2.00 | | | |
| Hydrogenated cocoglyceride | | | | | 3.00 | 4.00 | | |
| Behenoxydimethicone | | | | | | 1.50 | 2.00 | |
| VP/hexadecene copolymer | | | | 1.00 | 1.20 | | | |
| Glycerol | 4.00 | 6.00 | 5.00 | | 8.00 | 10.00 | | |
| Vitamin E acetate | 0.20 | 0.30 | 0.40 | | 0.30 | | | |
| *Butyrosperumu parkii* (shea butter) | | 2.00 | | 3.60 | | 2.00 | | |
| Iodopropyl butylcarbamate | 0.12 | | | | 0.20 | | | |
| DMDM hydantoin | 0.10 | | | | 0.12 | | 0.13 | |
| Methyl paraben | | 0.50 | 0.30 | | 0.35 | | | |
| Phenoxyethanol | 0.50 | 0.40 | | 1.00 | | | | |
| Ethylhexylglycerol | | 0.30 | | | 1.00 | | 0.35 | |
| Ethanol | 2.00 | | 2.00 | | | 5.00 | | |
| Trisodium EDTA | 0.40 | | 0.15 | | | 0.20 | | |
| Perfume oil | 0.20 | | 0.20 | | 0.24 | 0.16 | 0.10 | 0.10 |
| Aqua dem. | ad 100 | ad 100 | ad 100 | ad 100 | ad 100 | ad 100 | ad 100 | ad 100 |

(23) Oil Gel

|  | 1 | 2 | 3 | 4 |
|---|---|---|---|---|
| Caprylic/capric triglycerides | 12.00 | 10.00 | 6.00 | |
| Octyldodecanol | 7.00 | 14.00 | 8.00 | 3.00 |
| Butylene glycol dicaprylate/dicaprate | | | | 12.00 |
| Pentaerythrityl tetraisostearate | 10.00 | 6.00 | 8.00 | 7.00 |
| Polyglyceryl-3 diisostearate | 2.50 | | | |
| Bisdiglyceryl polyacyladipate-2 | 9.00 | 8.00 | 10.00 | 8.00 |
| Myristyl myristate | 3.50 | 3.00 | 4.00 | 3.00 |
| Quaternium-18 bentonite | 5.00 | 5.00 | 6.00 | 6.00 |
| Propylene carbonate | 15.00 | 20.00 | 18.00 | 19.50 |
| P18 | 1.0 | 0.5 | 3.0 | 5.0 |
| Vitamin acetate | 0.50 | 1.00 | | |
| Ascorbyl palmitate | 0.05 | | 0.05 | |
| *Buxus chinensis* (jojoba) oil | 2.00 | 1.00 | | 1.00 |
| Perfume oil, BHT | 0.10 | 0.25 | | 0.35 |
| *Ricinus communis* (castor) oil | ad 100 | ad 100 | ad 100 | ad 100 |

Example 38

Cosmetic Sunscreen Preparations

The formulations below describe cosmetic sunscreen preparations comprising a combination of at least one inorganic pigment, preferably zinc oxide and/or titanium dioxide, and organic UV-A and UV-B filters.

The formulations given below are prepared in a customary manner known to the person skilled in the art.

The content of P18 refers to 100% of active ingredient. The active ingredient according to the invention can either be used in pure form or in the form of an aqueous solution. In the case of the aqueous solution, the content of water dem. in the particular formulation has to be adjusted.

(1)

| | | | |
|---|---|---|---|
| A | 7.50 | Uvinul MC 80 | Ethylhexyl cinnamate |
| | 2.00 | Uvinul M 40 | Benzophenone-3 |
| | 0.80 | Rylo PG 11 | Polyglyceryl dimer soyate |
| | 1.00 | Span 60 | Sorbitan stearate |
| | 0.50 | Vitamin E acetate | Tocopheryl acetate |
| | 3.00 | Dracorin 100 SE | Glyceryl stearate, PEG-100 stearate |
| | 1.00 | Cremophor CO 410 | PEG-40-hydrogenated castor oil |
| B | 3.00 | T-Lite SF | Titanium dioxide, aluminum oxide hydrate, dimethicone/methicone copolymer |
| | 1.00 | Cetiol SB 45 | *Butyrospermum parkii* (shea butter) |
| | 6.50 | Finsolv TN | $C_{12-15}$-Alkyl benzoate |
| C | 5.00 | Butylene glycol | Butylene glycol |
| | 0.30 | Keltrol | Xanthan gum |
| | 0.10 | Edeta BD | Disodium EDTA |
| | 0.10 | Allantoin | Allantoin |
| | 66.20 | Water dem. | Aqua dem. |
| D | 1.00 | Sepigel 305 | Polyacrylamide, $C_{13-14}$-isoparaffin, laureth-7 |
| | 1% | P18 | |
| | q.s. | | Preservative |

(2)

| | | | |
|---|---|---|---|
| A | 7.50 | Uvinul MC 80 | Ethylhexyl cinnamate |
| | 2.00 | Uvinul M 40 | Benzophenone-3 |
| | 0.80 | Rylo PG 11 | Polyglyceryl dimer soyate |
| | 1.00 | Span 60 | Sorbitan stearate |
| | 0.50 | Vitamin E acetate | Tocopheryl acetate |
| | 3.00 | Dracorin 100 SE | Glyceryl stearate, PEG-100 stearate |
| | 1.00 | Cremophor CO 410 | PEG-40-hydrogenated castor oil |
| B | 3.00 | Z-COTE MAX | Zinc oxide (and) diphenylcaprylmethicone |
| | 1.00 | Cetiol SB 45 | *Butyrospermum parkii* (shea butter) |
| | 6.50 | Finsolv TN | $C_{12-15}$-Alkyl benzoate |
| C | 5.00 | Butylene glycol | Butylene glycol |
| | 0.30 | Keltrol | Xanthan gum |
| | 0.10 | Edeta BD | Disodium EDTA |
| | 0.10 | Allantoin | Allantoin |
| | 66.20 | Water dem. | Aqua dem. |
| D | 2.00 | Simulgel NS | Hydroxyethyl acrylate/sodium acryloyldimethyltaurate copolymer, squalane, polysorbate 60 |
| | 1% | P18 | |
| | q.s. | | Preservative |

(3)

| | | | |
|---|---|---|---|
| A | 7.50 | Uvinul MC 80 | Ethylhexyl cinnamate |
| | 2.00 | Uvinul A Plus | Diethylaminohydroxybenzoylhexyl benzoate |
| | 0.80 | Rylo PG 11 | Polyglyceryl dimer soyate |
| | 1.00 | Span 60 | Sorbitan stearate |
| | 0.50 | Vitamin E acetate | Tocopheryl acetate |
| | 3.00 | Dracorin 100 SE | Glyceryl stearate, PEG-100 stearate |
| | 1.00 | Cremophor CO 410 | PEG-40-hydrogenated castor oil |
| B | 3.00 | Z-COTE MAX | Zinc oxide (and) diphenylcaprylmethicone |
| | 1.00 | Cetiol SB 45 | *Butyrospermum parkii* (shea butter) |
| | 6.50 | Finsolv TN | $C_{12-15}$-Alkyl benzoate |
| C | 5.00 | Butylene glycol | Butylene glycol |
| | 0.30 | Keltrol | Xanthan gum |
| | 0.10 | Edeta BD | Disodium EDTA |
| | 0.10 | Allantoin | Allantoin |
| | 66.20 | Water dem. | Aqua dem. |
| D | 2.00 | Simulgel NS | Hydroxyethyl acrylate/sodium acryloyldimethyltaurate copolymer, squalane, polysorbate 60 |
| | 1% | P18 | |
| | q.s. | | Preservative |

(4)

| | | | |
|---|---|---|---|
| A | 4.00 | Uvinul MC 80 | Ethylhexyl cinnamate |
| | 2.00 | Uvinul T 150 | Ethylhexyltriazone |
| | 2.00 | Uvinul A Plus | Diethylaminohydroxybenzoylhexyl benzoate |
| | 0.80 | Rylo PG 11 | Polyglyceryl dimer soyate |
| | 1.00 | Span 60 | Sorbitan stearate |
| | 0.50 | Vitamin E acetate | Tocopheryl acetate |
| | 3.00 | Dracorin 100 SE | Glyceryl stearate, PEG-100 stearate |
| | 1.00 | Cremophor CO 410 | PEG-40-hydrogenated castor oil |
| B | 3.00 | Z-COTE MAX | Zinc oxide (and) diphenylcaprylmethicone |
| | 1.00 | Cetiol SB 45 | *Butyrospermum parkii* (shea butter) |
| | 6.50 | Finsolv TN | $C_{12-15}$-Alkyl benzoate |
| C | 5.00 | Butylene glycol | Butylene glycol |
| | 0.30 | Keltrol | Xanthan gum |
| | 0.10 | Edeta BD | Disodium EDTA |
| | 0.10 | Allantoin | Allantoin |
| | 66.20 | Water dem. | Aqua dem. |
| D | 2.00 | Simulgel NS | Hydroxyethyl acrylate/sodium acryloyldimethyltaurate copolymer, squalane, polysorbate 60 |
| | 1% | P18 | |
| | q.s. | | Preservative |

(5)

| | | | |
|---|---|---|---|
| A | 4.00 | Uvinul MC 80 | Ethylhexyl cinnamate |
| | 2.00 | Uvinul T 150 | Ethylhexyltriazone |
| | 2.00 | Uvinul A Plus | Diethylaminohydroxybenzoylhexyl benzoate |
| | 0.80 | Rylo PG 11 | Polyglyceryl dimer soyate |
| | 1.00 | Span 60 | Sorbitan stearate |
| | 0.50 | Vitamin E acetate | Tocopheryl acetate |
| | 3.00 | Dracorin 100 SE | Glyceryl stearate, PEG-100 stearate |
| | 1.00 | Cremophor CO 410 | PEG-40-hydrogenated castor oil |
| B | 3.00 | T-Lite SF | Titanium dioxide, aluminum hydrate, dimethicone/methicone copolymer |
| | 1.00 | Cetiol SB 45 | *Butyrospermum parkii* (shea butter) |
| | 6.50 | Finsolv TN | $C_{12-15}$-Alkyl benzoate |
| C | 5.00 | Butylene glycol | Butylene glycol |
| | 0.30 | Keltrol | Xanthan gum |
| | 0.10 | Edeta BD | Disodium EDTA |
| | 0.10 | Allantoin | Allantoin |
| | 66.20 | Water dem. | Aqua dem. |
| D | 2.00 | Simulgel NS | Hydroxyethyl acrylate/sodium acryloyldimethyltaurate copolymer, squalane, polysorbate 60 |
| | 1% | P18 | |
| | q.s. | | Preservative |

(6)

| | | | |
|---|---|---|---|
| A | 4.00 | Uvinul MC 80 | Ethylhexyl cinnamate |
| | 2.00 | Uvinul T 150 | Ethylhexyltriazone |
| | 2.00 | Uvinul A Plus | Diethylaminohydroxybenzoylhexyl benzoate |
| | 0.80 | Rylo PG 11 | Polyglyceryl dimer soyate |
| | 1.00 | Span 60 | Sorbitan stearate |
| | 0.50 | Vitamin E acetate | Tocopheryl acetate |
| | 3.00 | Dracorin 100 SE | Glyceryl stearate, PEG-100 stearate |
| | 1.00 | Cremophor CO 410 | PEG-40-hydrogenated castor oil |
| B | 3.00 | Z-COTE MAX | Zinc oxide (and) diphenylcaprylmethicone |

(7)

| | | | |
|---|---|---|---|
| C | 1.00 | Cetiol SB 45 | *Butyrospermum parkii* (shea butter) |
| | 6.50 | Finsolv TN | C$_{12-15}$-Alkyl benzoate |
| | 5.00 | Butylene glycol | Butylene glycol |
| | 0.30 | Keltrol | Xanthan gum |
| | 0.10 | Edeta BD | Disodium EDTA |
| | 0.10 | Allantoin | Allantoin |
| | 66.20 | Water dem. | Aqua dem. |
| D | 2.00 | Simulgel NS | Hydroxyethyl acrylate/sodium acryloyldimethyltaurate copolymer, squalane, polysorbate 60 |
| | 1% | P18 | |
| | q.s. | | Preservative |

(8)

| | | | |
|---|---|---|---|
| A | 4.00 | Uvinul MC 80 | Ethylhexyl cinnamate |
| | 1.00 | Uvinul T 150 | Ethylhexyltriazone |
| | 2.00 | Parsol 1789 | Butylmethoxydibenzoylmethane |
| | 0.80 | Rylo PG 11 | Polyglyceryl dimer soyate |
| | 1.00 | Span 60 | Sorbitan stearate |
| | 0.50 | Vitamin E acetate | Tocopheryl acetate |
| | 3.00 | Dracorin 100 SE | Glyceryl stearate, PEG-100 stearate |
| | 1.00 | Cremophor CO 410 | PEG-40-hydrogenated castor oil |
| B | 3.00 | T-Lite SF-S | Titanium dioxide, silicon hydrate, aluminum hydrate, methicone/dimethicone copolymer |
| | 1.00 | Cetiol SB 45 | *Butyrospermum parkii* (shea butter) |
| | 6.50 | Finsolv TN | C$_{12-15}$-Alkyl benzoate |
| C | 5.00 | Butylene glycol | Butylene glycol |
| | 0.30 | Keltrol | Xanthan gum |
| | 0.10 | Edeta BD | Disodium EDTA |
| | 0.10 | Allantoin | Allantoin |
| | 66.70 | Water dem. | Aqua dem. |
| D | 2.00 | Simulgel NS | Hydroxyethyl acrylate/sodium acryloyldimethyltaurate copolymer, squalane, polysorbate 60 |
| | 0.5% | P18 | |
| | q.s. | | Preservative |

(9)

| | | | |
|---|---|---|---|
| A | 4.00 | Uvinul MC 80 | Ethylhexyl cinnamate |
| | 1.00 | Uvinul T 150 | Ethylhexyltriazone |
| | 2.00 | Parsol 1789 | Butylmethoxydibenzoylmethane |
| | 0.80 | Rylo PG 11 | Polyglyceryl dimer soyate |
| | 1.00 | Span 60 | Sorbitan stearate |
| | 0.50 | Vitamin E acetate | Tocopheryl acetate |
| | 3.00 | Dracorin 100 SE | Glyceryl stearate, PEG-100 stearate |
| | 1.00 | Cremophor CO 410 | PEG-40-hydrogenated castor oil |
| B | 3.00 | Z-COTE MAX | Zinc oxide (and) diphenylcaprylmethicone |
| | 1.00 | Cetiol SB 45 | *Butyrospermum parkii* (shea butter) |
| | 6.50 | Finsolv TN | C$_{12-15}$-Alkyl benzoate |
| C | 5.00 | Butylene glycol | Butylene glycol |
| | 0.30 | Keltrol | Xanthan gum |
| | 0.10 | Edeta BD | Disodium EDTA |
| | 0.10 | Allantoin | Allantoin |
| | 67.10 | Water dem. | Aqua dem. |
| D | 2.00 | Simulgel NS | Hydroxyethyl acrylate/sodium acryloyldimethyltaurate copolymer, squalane, polysorbate 60 |
| | 0.1% | P18 | |
| | q.s. | | Preservative |

| | | | |
|---|---|---|---|
| A | 5.00 | Uvinul N 539 T | Octocrylene |
| | 2.00 | Parsol 1789 | Butylmethoxydibenzoylmethane |
| | 0.80 | Rylo PG 11 | Polyglyceryl dimer soyate |
| | 1.00 | Span 60 | Sorbitan stearate |
| | 0.50 | Vitamin E acetate | Tocopheryl acetate |
| | 3.00 | Dracorin 100 SE | Glyceryl stearate, PEG-100 stearate |
| | 1.00 | Cremophor CO 410 | PEG-40-hydrogenated castor oil |
| B | 3.00 | T-Lite SF-S | Titanium dioxide, silicon hydrate, aluminum hydrate, methicone/dimethicone copolymer |
| | 1.00 | Cetiol SB 45 | *Butyrospermum parkii* (shea butter) |
| | 6.50 | Finsolv TN | C$_{12-15}$-Alkyl benzoate |
| C | 5.00 | Butylene glycol | Butylene glycol |
| | 0.30 | Keltrol | Xanthan gum |
| | 0.10 | Edeta BD | Disodium EDTA |
| | 0.10 | Allantoin | Allantoin |
| | 66.20 | Water dem. | Aqua dem. |
| D | 2.00 | Simulgel NS | Hydroxyethyl acrylate/sodium acryloyldimethyltaurate copolymer, squalane, polysorbate 60 |
| | 1% | P18 | |
| | q.s. | | Preservative |

(10)

| | | | |
|---|---|---|---|
| A | 5.00 | Uvinul N 539 T | Octocrylene |
| | 2.00 | Uvinul A Plus | Diethylaminohydroxybenzoylhexyl benzoate |
| | 0.80 | Rylo PG 11 | Polyglyceryl dimer soyate |
| | 1.00 | Span 60 | Sorbitan stearate |
| | 0.50 | Vitamin E acetate | Tocopheryl acetate |
| | 3.00 | Dracorin 100 SE | Glyceryl stearate, PEG-100 stearate |
| | 1.00 | Cremophor CO 410 | PEG-40-hydrogenated castor oil |
| B | 3.00 | T-Lite SF | Titanium dioxide, aluminum hydrate, dimethicone/methicone copolymer |
| | 1.00 | Cetiol SB 45 | *Butyrospermum parkii* (shea butter) |
| | 6.50 | Finsolv TN | C$_{12-15}$-Alkyl benzoate |
| C | 5.00 | Butylene glycol | Butylene glycol |
| | 0.30 | Keltrol | Xanthan gum |
| | 0.10 | Edeta BD | Disodium EDTA |
| | 0.10 | Allantoin | Allantoin |
| | 65.20 | Water dem. | Aqua dem. |
| D | 2.00 | Simulgel NS | Hydroxyethyl acrylate/sodium acryloyldimethyltaurate copolymer, squalane, polysorbate 60 |
| | 2% | P18 | |
| | q.s. | | Preservative |

(11)

| | | | |
|---|---|---|---|
| A | 5.00 | Uvinul N 539 T | Octocrylene |
| | 2.00 | Uvinul A Plus | Diethylaminohydroxybenzoylhexyl benzoate |
| | 0.80 | Rylo PG 11 | Polyglyceryl dimer soyate |
| | 1.00 | Span 60 | Sorbitan stearate |
| | 0.50 | Vitamin E acetate | Tocopheryl acetate |
| | 3.00 | Dracorin 100 SE | Glyceryl stearate, PEG-100 stearate |
| | 1.00 | Cremophor CO 410 | PEG-40-hydrogenated castor oil |
| B | 3.00 | Z-COTE MAX | Zinc oxide (and) diphenylcaprylmethicone |
| | 1.00 | Cetiol SB 45 | *Butyrospermum parkii* (shea butter) |
| | 6.50 | Finsolv TN | C$_{12-15}$-Alkyl benzoate |
| C | 5.00 | Butylene glycol | Butylene glycol |
| | 0.30 | Keltrol | Xanthan gum |
| | 0.10 | Edeta BD | Disodium EDTA |
| | 0.10 | Allantoin | Allantoin |
| | 66.70 | Water dem. | Aqua dem. |
| D | 2.00 | Simulgel NS | Hydroxyethyl acrylate/sodium acryloyldimethyltaurate copolymer, squalane, polysorbate 60 |
| | 0.5% | P18 | |
| | q.s. | | Preservative |

(12)

| | | | |
|---|---|---|---|
| A | 5.00 | Uvinul N 539 T | Octocrylene |
| | 2.00 | Uvinul A Plus | Diethylaminohydroxybenzoylhexyl benzoate |

-continued

|   |       |                  |                                                                                 |
|---|-------|------------------|---------------------------------------------------------------------------------|
|   | 0.80  | Rylo PG 11       | Polyglyceryl dimer soyate                                                       |
|   | 1.00  | Span 60          | Sorbitan stearate                                                               |
|   | 0.50  | Vitamin E acetate| Tocopheryl acetate                                                              |
|   | 3.00  | Dracorin 100 SE  | Glyceryl stearate, PEG-100 stearate                                             |
|   | 1.00  | Cremophor CO 410 | PEG-40-hydrogenated castor oil                                                  |
| B | 3.00  | Z-COTE MAX       | Zinc oxide (and) diphenylcaprylmethicone                                        |
|   | 1.00  | Cetiol SB 45     | *Butyrospermum parkii* (shea butter)                                            |
|   | 6.50  | Finsolv TN       | $C_{12-15}$-Alkyl benzoate                                                      |
| C | 5.00  | Butylene glycol  | Butylene glycol                                                                 |
|   | 0.30  | Keltrol          | Xanthan gum                                                                     |
|   | 0.10  | Edeta BD         | Disodium EDTA                                                                   |
|   | 0.10  | Allantoin        | Allantoin                                                                       |
|   | 2.0   | Mexoryl SX       | Terephthalidenedicamphorsulfonic acid                                           |
|   | 66.20 | Water dem.       | Aqua dem.                                                                       |
| D | 2.00  | Simulgel NS      | Hydroxyethyl acrylate/sodium acryloyldimethyltaurate copolymer, squalane, polysorbate 60 |
|   | 1%    | P18              |                                                                                 |
|   | q.s.  |                  | Preservative                                                                    |

(13)

|   |       |                  |                                                                                 |
|---|-------|------------------|---------------------------------------------------------------------------------|
| A | 5.00  | Uvinul N 539 T   | Octocrylene                                                                     |
|   | 2.00  | Uvinul A Plus    | Diethylaminohydroxybenzoylhexyl benzoate                                        |
|   | 0.80  | Rylo PG 11       | Polyglyceryl dimer soyate                                                       |
|   | 1.00  | Span 60          | Sorbitan stearate                                                               |
|   | 0.50  | Vitamin E acetate| Tocopheryl acetate                                                              |
|   | 3.00  | Dracorin 100 SE  | Glyceryl stearate, PEG-100 stearate                                             |
|   | 1.00  | Cremophor CO 410 | PEG-40-hydrogenated castor oil                                                  |
| B | 3.00  | Z-COTE MAX       | Zinc oxide (and) diphenylcaprylmethicone                                        |
|   | 1.00  | Cetiol SB 45     | *Butyrospermum parkii* (shea butter)                                            |
|   | 6.50  | Finsolv TN       | $C_{12-15}$-Alkyl benzoate                                                      |
| C | 5.00  | Butylene glycol  | Butylene glycol                                                                 |
|   | 0.30  | Keltrol          | Xanthan gum                                                                     |
|   | 0.10  | Edeta BD         | Disodium EDTA                                                                   |
|   | 0.10  | Allantoin        | Allantoin                                                                       |
|   | 2.0   | Mexoryl SX       | Terephthalidenedicamphorsulfonic acid                                           |
|   | 65.20 | Water dem.       | Aqua dem.                                                                       |
| D | 2.00  | Simulgel NS      | Hydroxyethyl acrylate/sodium acryloyldimethyltaurate copolymer, squalane, polysorbate 60 |
|   | 2%    | P18              |                                                                                 |
|   | q.s.  |                  | Preservative                                                                    |

(14)

|   |       |                  |                                                                                 |
|---|-------|------------------|---------------------------------------------------------------------------------|
| A | 5.00  | Uvinul N 539 T   | Octocrylene                                                                     |
|   | 2.00  | Uvinul A Plus    | Diethylaminohydroxybenzoylhexyl benzoate                                        |
|   | 2.00  | Mexoryl XL       | Drometrizole trisiloxane                                                        |
|   | 0.80  | Rylo PG 11       | Polyglyceryl dimer soyate                                                       |
|   | 1.00  | Span 60          | Sorbitan stearate                                                               |
|   | 0.50  | Vitamin E acetate| Tocopheryl acetate                                                              |
|   | 3.00  | Dracorin 100 SE  | Glyceryl stearate, PEG-100 stearate                                             |
|   | 1.00  | Cremophor CO 410 | PEG-40-hydrogenated castor oil                                                  |
| B | 3.00  | Z-COTE MAX       | Zinc oxide (and) diphenylcaprylmethicone                                        |
|   | 1.00  | Cetiol SB 45     | *Butyrospermum parkii* (shea butter)                                            |
|   | 6.50  | Finsolv TN       | $C_{12-15}$-Alkyl benzoate                                                      |
| C | 5.00  | Butylene glycol  | Butylene glycol                                                                 |
|   | 0.30  | Keltrol          | Xanthan gum                                                                     |
|   | 0.10  | Edeta BD         | Disodium EDTA                                                                   |
|   | 0.10  | Allantoin        | Allantoin                                                                       |
|   | 67.10 | Water dem.       | Aqua dem.                                                                       |
| D | 2.00  | Simulgel NS      | Hydroxyethyl acrylate/sodium acryloyldimethyltaurate copolymer, squalane, polysorbate 60 |
|   | 0.1%  | P18              |                                                                                 |
|   | q.s.  |                  | Preservative                                                                    |

(15)

|   |       |                  |                                                                                 |
|---|-------|------------------|---------------------------------------------------------------------------------|
| A | 5.00  | Uvinul N 539 T   | Octocrylene                                                                     |
|   | 2.00  | Tinosorb S       | Bisethylhexyloxyphenol methoxyphenyltriazine                                    |
|   | 0.80  | Rylo PG 11       | Polyglyceryl dimer soyate                                                       |
|   | 1.00  | Span 60          | Sorbitan stearate                                                               |
|   | 0.50  | Vitamin E acetate| Tocopheryl acetate                                                              |
|   | 3.00  | Dracorin 100 SE  | Glyceryl stearate, PEG-100 stearate                                             |
|   | 1.00  | Cremophor CO 410 | PEG-40-hydrogenated castor oil                                                  |
| B | 3.00  | Z-COTE MAX       | Zinc oxide (and) diphenylcaprylmethicone                                        |
|   | 1.00  | Cetiol SB 45     | *Butyrospermum parkii* (shea butter)                                            |
|   | 6.50  | Finsolv TN       | $C_{12-15}$-Alkyl benzoate                                                      |
| C | 5.00  | Butylene glycol  | Butylene glycol                                                                 |
|   | 0.30  | Keltrol          | Xanthan gum                                                                     |
|   | 0.10  | Edeta BD         | Disodium EDTA                                                                   |
|   | 0.10  | Allantoin        | Allantoin                                                                       |
|   | 66.20 | Water dem.       | Aqua dem.                                                                       |
| D | 2.00  | Simulgel NS      | Hydroxyethyl acrylate/sodium acryloyldimethyltaurate copolymer, squalane, polysorbate 60 |
|   | 1%    | P18              |                                                                                 |
|   | q.s.  |                  | Preservative                                                                    |

(16)

|   |       |                  |                                                                                 |
|---|-------|------------------|---------------------------------------------------------------------------------|
| A | 7.50  | Uvinul MC 80     | Ethylhexyl methoxycinnamate                                                     |
|   | 5.00  | Uvinul N 539 T   | Octocrylene                                                                     |
|   | 3.00  | Emulgade PL 68/50| Cetearyl glucoside, cetearyl alcohol                                            |
|   | 2.00  | Dracorin 100 SE  | Glyceryl stearate, PEG-100 stearate                                             |
|   | 1.00  | Fitoderm         | Squalane                                                                        |
|   | 0.50  | Cremophor WO 7   | PEG-7-hydrogenated castor oil                                                   |
|   | 0.50  | Cremophor PS 20  | Polysorbate 20                                                                  |
|   | 2.00  | Dry Flo Pure     | Aluminum starch octenyl succinate                                               |
| B | 5.00  | Z-COTE MAX       | Zinc oxide (and) diphenylcaprylmethicone                                        |
| C | 4.00  | 1,2-Propylene glycol Care | Propylene glycol                                                       |
|   | 0.20  | Keltrol          | Xanthan gum                                                                     |
|   | 0.50  | Simulgel 600     | Acrylamide/sodium acryloyldimethyltaurate copolymer, isohexadecane, polysorbate 80 |
|   | ad 100| Water dem.       | Aqua dem.                                                                       |
|   | q.s.  |                  | Preservative                                                                    |
|   | 0.50  | Vitamin E acetate| Tocopheryl acetate                                                              |
|   | 2%    | P18              |                                                                                 |
|   | 1.00  | RetiSTAR         | Caprylic/capric triglyceride, sodium ascorbate, tocopherol, retinol             |

(17)

|   |       |                  |                                                                                 |
|---|-------|------------------|---------------------------------------------------------------------------------|
| A | 7.50  | Uvinul MC 80     | Ethylhexyl methoxycinnamate                                                     |
|   | 2.00  | Uvinul N 539 T   | Octocrylene                                                                     |
|   | 3.00  | Emulgade PL 68/50| Cetearyl glucoside, cetearyl alcohol                                            |
|   | 2.00  | Dracorin 100 SE  | Glyceryl stearate, PEG-100 stearate                                             |
|   | 1.00  | Fitoderm         | Squalane                                                                        |
|   | 0.50  | Cremophor WO 7   | PEG-7-hydrogenated castor oil                                                   |
|   | 0.50  | Cremophor PS 20  | Polysorbate 20                                                                  |
|   | 2.00  | Dry Flo Pure     | Aluminum starch octenyl succinate                                               |
| B | 5.00  | T-Lite SF-S      | Titanium dioxide, silicon hydrate, aluminum hydrate, methicone/dimethicone copolymer |
| C | 4.00  | 1,2-Propylene glycol Care | Propylene glycol                                                       |
|   | 0.20  | Keltrol          | Xanthan gum                                                                     |
|   | 0.50  | Simulgel 600     | Acrylamide/sodium acryloyldimethyltaurate copolymer, isohexadecane, polysorbate 80 |
|   | ad 100| Water dem.       | Aqua dem.                                                                       |
|   | q.s.  |                  | Preservative                                                                    |
|   | 0.50  | Vitamin E acetate| Tocopheryl acetate                                                              |
|   | 1%    | P18              |                                                                                 |
|   | 2.00  | RetiSTAR         | Caprylic/capric triglyceride, sodium ascorbate, tocopherol, retinol             |

(18)

| | | | |
|---|---|---|---|
| A | 7.50 | Uvinul MC 80 | Ethylhexyl methoxycinnamate |
| | 5.00 | Uvinul N 539 T | Octocrylene |
| | 3.00 | Emulgade PL 68/50 | Cetearyl glucoside, cetearyl alcohol |
| | 2.00 | Dracorin 100 SE | Glyceryl stearate, PEG-100 stearate |
| | 1.00 | Fitoderm | Squalane |
| | 0.50 | Cremophor WO 7 | PEG-7-hydrogenated castor oil |
| | 0.50 | Cremophor PS 20 | Polysorbate 20 |
| | 2.00 | Dry Flo Pure | Aluminum starch octenyl succinate |
| B | 5.00 | T-Lite SF | Titanium dioxide, aluminum hydrate, dimethicone/methicone copolymer |
| C | 4.00 | 1,2-Propylene glycol Care | Propylene glycol |
| | 1.00 | D-Panthenol 50 P | Panthenol, propylene glycol |
| | 0.20 | Keltrol | Xanthan gum |
| | 0.50 | Simulgel 600 | Acrylamide/sodium acryloyldimethyltaurate copolymer, isohexadecane, polysorbate 80 |
| | ad 100 | Water dem. | Aqua dem. |
| | q.s. | Preservative | |
| | 0.50 | Vitamin E acetate | Tocopheryl acetate |
| | 1% | P18 | |
| | 1.00 | RetiSTAR | Caprylic/capric triglyceride, sodium ascorbate, tocopherol, retinol |

(19)

| | | | |
|---|---|---|---|
| A | 5.50 | Uvinul MC 80 | Ethylhexyl methoxycinnamate |
| | 2.00 | Uvinul A Plus | Diethylaminohydroxybenzoylhexyl benzoate |
| | 3.00 | Uvinul N 539 T | Octocrylene |
| | 3.00 | Emulgade PL 68/50 | Cetearyl glucoside, cetearyl alcohol |
| | 2.00 | Dracorin 100 SE | Glyceryl stearate, PEG-100 stearate |
| | 1.00 | Fitoderm | Squalane |
| | 0.50 | Cremophor WO 7 | PEG-7-hydrogenated castor oil |
| | 0.50 | Cremophor PS 20 | Polysorbate 20 |
| | 2.00 | Dry Flo Pure | Aluminum starch octenyl succinate |
| B | 5.00 | T-Lite SF | Titanium dioxide, aluminum hydrate, dimethicone/methicone copolymer |
| C | 4.00 | 1,2-Propylene glycol Care | Propylene glycol |
| | 0.20 | Keltrol | Xanthan gum |
| | 0.50 | Simulgel 600 | Acrylamide/sodium acryloyldimethyltaurate copolymer, isohexadecane, polysorbate 80 |
| | ad 100 | Water dem. | Aqua dem. |
| | q.s. | Preservative | |
| | 0.50 | Vitamin E acetate | Tocopheryl acetate |
| | 2% | P18 | |
| | 1.00 | RetiSTAR | Caprylic/capric triglyceride, sodium ascorbate, tocopherol, retinol |

(20)

| | | | |
|---|---|---|---|
| A | 1.00 | Abil Care 85 | Bis-PEG-/PPG-16-/16 PEG-/PPG-16-/16-dimethicone, caprylic/capric triglyceride |
| | 3.00 | Cremophor CO 40 | PEG-40-hydrogenated castor oil |
| | 0.30 | Cremophor WO 7 | PEG-7-hydrogenated castor oil |
| | 2.00 | Parsol 1789 | Butylmethoxydibenzoylmethane |
| | 2.00 | Mexoryl XL | Drometrizoletrisiloxane |
| | 10.00 | Witconol APM | PPG-3 myristyl ether |
| | 1.00 | Uvinul T 150 | Ethylhexyltriazone |
| | 1.00 | Dow Corning 345 Fluid | Cyclopentasiloxane, cyclohexasiloxane |
| | 5.00 | Uvinul N 539 T | Octocrylene |
| B | 3.00 | Z-COTE MAX | Zinc oxide (and) diphenylcaprylmethicone |
| C | 5.00 | 1,2-Propylene glycol | Propylene glycol |
| | 1.00 | Mexoryl SX | Terephthalidenedicamphorsulfonic acid |
| | 0.20 | Keltrol | Xanthan gum |
| | 0.06 | Edeta BD | Disodium EDTA |
| | 0.04 | TEA | Triethanolamine |
| | 0.30 | Carbopol Ultrez 10P | Carbomer |
| | 63.50 | Water dem. | Aqua dem. |
| | 1% | P18 | |
| D | q.s. | Perfume oil | |
| | 0.50 | Glydant | DMDM hydantoin |

(21)

| | | | |
|---|---|---|---|
| A | 5.50 | Uvinul MC 80 | Ethylhexyl methoxycinnamate |
| | 2.00 | Uvinul A Plus | Diethylaminohydroxybenzoylhexyl benzoate |
| | 3.00 | Uvinul N 539 T | Octocrylene |
| | 3.00 | Emulgade PL 68/50 | Cetearyl glucoside, cetearyl alcohol |
| | 2.00 | Dracorin 100 SE | Glyceryl stearate, PEG-100 stearate |
| | 1.00 | Fitoderm | Squalane |
| | 0.50 | Cremophor WO 7 | PEG-7-hydrogenated castor oil |
| | 0.50 | Cremophor PS 20 | Polysorbate 20 |
| | 2.00 | Dry Flo Pure | Aluminum starch octenyl succinate |
| B | 5.00 | T-Lite SF-S | Titanium dioxide, silicon hydrate, aluminum hydrate, methicone/dimethicone copolymer |
| C | 4.00 | 1,2-Propylene glycol Care | Propylene glycol |
| | 0.20 | Keltrol | Xanthan gum |
| | 2.00 | Simulgel NS | Hydroxyethyl acrylate/sodium acryloyldimethyltaurate copolymer, squalane, polysorbate 60 |
| | 66.30 | Water dem. | Aqua dem. |
| | q.s. | Preservative | |
| | 0.50 | Vitamin E acetate | Tocopheryl acetate |
| | 0.5% | P18 | |
| | 1.00 | RetiSTAR | Caprylic/capric triglyceride, sodium ascorbate, tocopherol, retinol |

(22)

| | | | |
|---|---|---|---|
| A | 2.00 | Cremophor A 6 | Ceteareth-6, stearyl alcohol |
| | 2.00 | Cremophor A 25 | Ceteareth-25 |
| | 3.00 | Syncrowax HRC | Tribehenin |
| | 2.00 | Lanette O | Cetearyl alcohol |
| | 2.00 | Luvitol EHO | Cetearyl ethylhexanoate |
| | 5.00 | Uvinul MC 80 | Ethylhexyl methoxycinnamate |
| | 1.00 | Ganex V-220 | VP/eicosene copolymer |
| | 7.00 | Isopropyl palmitate | Isopropyl palmitate |
| B | 3.00 | Z-COTE MAX | Zinc oxide (and) diphenylcaprylmethicone |
| C | 0.20 | Keltrol | Xanthan gum |
| | 0.50 | Simulgel NS | Hydroxyethyl acrylate/sodium acryloyldimethyltaurate copolymer, squalane, polysorbate 60 |
| | 65.10 | Water dem. | Aqua dem. |
| | 0.20 | Edeta BD | Disodium EDTA |
| | 5.00 | 1,2-Propylene glycol Care | Propylene glycol |
| | 0.5% | P18 | |
| D | 1.00 | Vitamin E acetate | Tocopheryl acetate |
| | q.s. | Preservative | |

(23)

| | | | |
|---|---|---|---|
| A | 2.00 | Cremophor A 6 | Ceteareth-6, stearyl alcohol |
| | 2.00 | Cremophor A 25 | Ceteareth-25 |
| | 3.00 | Syncrowax HRC | Tribehenin |
| | 2.00 | Lanette O | Cetearyl alcohol |
| | 2.00 | Luvitol EHO | Cetearyl ethylhexanoate |
| | 5.00 | Uvinul MC 80 | Ethylhexyl methoxycinnamate |
| | 1.00 | Ganex V-220 | VP/eicosene copolymer |
| | 7.00 | Isopropyl palmitate | Isopropyl palmitate |
| B | 3.00 | T-Lite SF | Titanium dioxide, aluminum hydrate, dimethicone/methicone copolymer |
| C | 0.50 | Keltrol | Xanthan gum |
| | 0.50 | Simulgel NS | Hydroxyethyl acrylate/sodium acryloyldimethyltaurate copolymer, squalane, polysorbate 60 |

-continued

|   |       |                       |                      |
|---|-------|-----------------------|----------------------|
|   | 65.10 | Water dem.            | Aqua dem.            |
|   | 0.20  | Edeta BD              | Disodium EDTA        |
|   | 5.00  | 1,2-Propylene glycol Care | Propylene glycol |
|   | 0.5%  | P18                   |                      |
| D | 1.00  | Vitamin E acetate     | Tocopheryl acetate   |
|   | q.s.  | Preservative          |                      |

(24)

|   |       |                       |                      |
|---|-------|-----------------------|----------------------|
| A | 2.00  | Cremophor A 6         | Ceteareth-6, stearyl alcohol |
|   | 2.00  | Cremophor A 25        | Ceteareth-25         |
|   | 3.00  | Syncrowax HRC         | Tribehenin           |
|   | 2.00  | Lanette O             | Cetearyl alcohol     |
|   | 2.00  | Luvitol EHO           | Cetearyl ethylhexanoate |
|   | 5.00  | Uvinul MC 80          | Ethylhexyl methoxycinnamate |
|   | 1.00  | Ganex V-220           | VP/eicosene copolymer |
|   | 7.00  | Isopropyl palmitate   | Isopropyl palmitate  |
| B | 3.00  | T-Lite SF-S           | Titanium dioxide, silicon hydrate, aluminum hydrate, methicone/dimethicone copolymer |
| C | 0.50  | Keltrol               | Xanthan gum          |
|   | 0.50  | Simulgel NS           | Hydroxyethyl acrylate/sodium acryloyldimethyltaurate copolymer, squalane, polysorbate 60 |
|   | 64.60 | Water dem.            | Aqua dem.            |
|   | 0.20  | Edeta BD              | Disodium EDTA        |
|   | 5.00  | 1,2-Propylene glycol Care | Propylene glycol |
|   | 1%    | P18                   |                      |
| D | 1.00  | Vitamin E acetate     | Tocopheryl acetate   |
|   | q.s.  | Preservative          |                      |

(25)

|   |       |                       |                      |
|---|-------|-----------------------|----------------------|
| A | 2.00  | Cremophor A 6         | Ceteareth-6, stearyl alcohol |
|   | 2.00  | Cremophor A 25        | Ceteareth-25         |
|   | 3.00  | Syncrowax HRC         | Tribehenin           |
|   | 2.00  | Lanette O             | Cetearyl alcohol     |
|   | 2.00  | Luvitol EHO           | Cetearyl ethylhexanoate |
|   | 5.00  | Uvinul MC 80          | Ethylhexyl methoxycinnamate |
|   | 1.00  | Ganex V-220           | VP/eicosene copolymer |
|   | 7.00  | Isopropyl palmitate   | Isopropyl palmitate  |
| B | 3.00  | T-Lite SF-S           | Titanium dioxide, silicon hydrate, aluminum hydrate, methicone/dimethicone copolymer |
| C | 0.50  | Keltrol               | Xanthan gum          |
|   | 0.50  | Simulgel NS           | Hydroxyethyl acrylate/sodium acryloyldimethyltaurate copolymer, squalane, polysorbate 60 |
|   | 64.10 | Water dem.            | Aqua dem.            |
|   | 2.00  | Neoheliopan AP        | Disodium phenyldibenzimidazoletetrasulfonate |
|   | 0.20  | Edeta BD              | Disodium EDTA        |
|   | 5.00  | 1,2-Propylene glycol Care | Propylene glycol |
| D | 1.00  | Vitamin E acetate     | Tocopheryl acetate   |
|   | 1%    | P18                   |                      |
|   | q.s.  | Preservative          |                      |

(26)

|   |       |                       |                      |
|---|-------|-----------------------|----------------------|
| A | 2.00  | Cremophor A 6         | Ceteareth-6, stearyl alcohol |
|   | 2.00  | Cremophor A 25        | Ceteareth-25         |
|   | 3.00  | Syncrowax HRC         | Tribehenin           |
|   | 2.00  | Lanette O             | Cetearyl alcohol     |
|   | 2.00  | Luvitol EHO           | Cetearyl ethylhexanoate |
|   | 7.00  | Uvinul N 539 T        | Octocrylene          |
|   | 1.00  | Ganex V-220           | VP/eicosene copolymer |
|   | 7.00  | Isopropyl palmitate   | Isopropyl palmitate  |
| B | 3.00  | T-Lite SF-S           | Titanium dioxide, silicon hydrate, aluminum hydrate, methicone/dimethicone copolymer |
| C | 0.50  | Keltrol               | Xanthan gum          |
|   | 0.50  | Simulgel NS           | Hydroxyethyl acrylate/sodium acryloyldimethyltaurate copolymer, squalane, polysorbate 60 |
|   | 64.60 | Water dem.            | Aqua dem.            |
|   | 1.00  | Mexoryl SX            | Terephthalidenedicamphorsulfonic acid |
|   | 0.20  | Edeta BD              | Disodium EDTA        |
|   | 5.00  | 1,2-Propylene glycol Care | Propylene glycol |
| D | 1.00  | Vitamin E acetate     | Tocopheryl acetate   |
|   | 1%    | P18                   |                      |
|   | q.s.  | Preservative          |                      |

(27)

|   |       |                       |                      |
|---|-------|-----------------------|----------------------|
| A | 2.00  | Cremophor A 6         | Ceteareth-6, stearyl alcohol |
|   | 2.00  | Cremophor A 25        | Ceteareth-25         |
|   | 3.00  | Syncrowax HRC         | Tribehenin           |
|   | 2.00  | Lanette O             | Cetearyl alcohol     |
|   | 2.00  | Luvitol EHO           | Cetearyl ethylhexanoate |
|   | 2.00  | Mexoryl XL            | Drometrizole trisiloxane |
|   | 5.00  | Uvinul N 539 T        | Octocrylene          |
|   | 1.00  | Ganex V-220           | VP/eicosene copolymer |

-continued

|   | | | |
|---|---|---|---|
|   | 7.00 | Isopropyl palmitate | Isopropyl palmitate |
| B | 3.00 | T-Lite SF | Titanium dioxide, aluminum hydrate, dimethicone/methicone copolymer |
| C | 0.50 | Keltrol | Xanthan gum |
|   | 0.50 | Simulgel NS | Hydroxyethyl acrylate/sodium acryloyldimethyltaurate copolymer, squalane, polysorbate 60 |
|   | 65.10 | Water dem. | Aqua dem. |
|   | 0.20 | Edeta BD | Disodium EDTA |
|   | 5.00 | 1,2-Propylene glycol Care | Propylene glycol |
| D | 1.00 | Vitamin E acetate | Tocopheryl acetate |
|   | 0.5% | P18 | |
|   | q.s. | Preservative | |

(28)

|   | | |
|---|---|---|
| 1.00 | Urea | Urea |
| 2.00 | Neoheliopan AP | Disodium phenyldibenzimidazoletetrasulfonate |
| 2.00 | Glycerol 87% | Glycerol |
| 1.20 | Aristoflex AVC | Ammonium acryloyldimethyltaurate/VP copolymer |
| 71.30 | Water dem. | Aqua dem. |
| B 3.00 | Cremophor CO 40 | PEG-40-hydrogenated castor oil |
| q.s. | Perfume oil | |
| 5.00 | Miglyol 812 | Caprylic/capric triglyceride |
| 2.00 | Uvinul N 539 T | Octocrylene |
| 8.00 | Z-COTE MAX | Zinc oxide (and) diphenylcaprylmethicone |
| 0.1% | P18 | |
| q.s. | Preservative | |

(29)

|  |  |  |
|---|---|---|
| 5.00 | Z-COTE MAX | Zinc oxide (and) diphenylcaprylmethicone |
| 2.00 | Parsol 1789 | Butylmethoxydibenzoylmethane |
| 1.00 | Uvinul T150 | Ethylhexyltriazone |
| 5.00 | Uvinul MC 80 | Ethylhexyl methoxycinnamate |
| 2.00 | Uvinul T 539 N | Octocrylene |
| 0.50 | Abil 350 | Dimethicone |
| 2.75 | Carnico wax LT 20 | Carnauba (*Copernica cerifera*) wax, paraffins |
| 3.70 | Candelilla wax LT 281 LJ | Candelilla (*Euphorbia cerifera*) wax |
| 1.80 | Beeswax 3050 PH | Beeswax |
| 3.20 | TeCero-wax 30445 | Microcrystalline wax |
| 3.20 | TeCero-wax 1030 K | Microcrystalline wax |
| 1.34 | Cutina CP | Cetyl palmitate |
| 6.40 | Vaseline | Petrolatum |
| 7.30 | Softisan 100 | Hydrogenated cocoglycerides |
| 10.00 | Luvitol EHO | Cetearyl ethylhexanoate |
| 0.17 | Bisabolol nat. | Bisabolol |
| 1.84 | Vitamin E acetate | Tocopheryl acetate |
| 0.42 | D,L-Alpha-Tocopherol | Tocopherol |
| 1% | P18 | |
| 40.38 | Castor oil | Castor (*Ricinus communis*) oil |

(30)

|  |  |  |
|---|---|---|
| 5.00 | T-Lite SF | Titanium dioxide, aluminum hydrate, dimethicone/methicone copolymer |
| 2.00 | Parsol 1789 | Butylmethoxydibenzoylmethane |
| 1.00 | Uvinul T150 | Ethylhexyltriazone |
| 3.00 | Uvinul MC 80 | Ethylhexyl methoxycinnamate |
| 2.00 | Uvinul N 539 T | Octocrylene |
| 0.50 | Abil 350 | Dimethicone |
| 2.75 | Carnico wax LT 20 | Carnauba (*Copernica cerifera*) wax, paraffin |
| 3.70 | Candelilla wax LT 281 LJ | Candelilla (*Euphorbia cerifera*) wax |
| 1.80 | Beeswax 3050 PH | Beeswax |
| 3.20 | TeCero-wax 30445 | Microcrystalline wax |

-continued

|  |  |  |
|---|---|---|
| 3.20 | TeCero-wax 1030 K | Microcrystalline wax |
| 1.34 | Cutina CP | Cetyl palmitate |
| 6.40 | Vaseline | Petrolatum |
| 7.30 | Softisan 100 | Hydrogenated cocoglycerides |
| 10.00 | Luvitol EHO | Cetearyl ethylhexanoate |
| 0.17 | Bisabolol nat. | Bisabolol |
| 1.84 | Vitamin E acetate | Tocopheryl acetate |
| 0.42 | D,L-Alpha-Tocopherol | Tocopherol |
| 1% | P18 | |
| 40.38 | Castor oil | Castor (*Ricinus communis*) oil |

(31)

|  |  |  |
|---|---|---|
| 5.00 | T-Lite SF-S | Titanium dioxide, silicon hydrate, aluminum hydrate, methicone/dimethicone copolymer |
| 2.00 | Uvinul A Plus | Diethylaminohydroxybenzoylhexyl benzoate |
| 2.00 | Mexoryl XL | Drometrizole trisiloxane |
| 3.00 | Uvinul MC 80 | Ethylhexyl methoxycinnamate |
| 0.50 | Abil 350 | Dimethicone |
| 2.75 | Carnico wax LT 20 | Carnauba (*Copernica cerifera*) wax, paraffins |
| 3.70 | Candelilla wax LT 281 LJ | Candelilla (*Euphorbia cerifera*) wax |
| 1.80 | Beeswax 3050 PH | Beeswax |
| 3.20 | TeCero-wax 30445 | Microcrystalline wax |
| 3.20 | TeCero-wax 1030 K | Microcrystalline wax |
| 1.34 | Cutina CP | Cetyl palmitate |
| 6.40 | Vaseline | Petrolatum |
| 7.30 | Softisan 100 | Hydrogenated cocoglycerides |
| 10.00 | Luvitol EHO | Cetearyl ethylhexanoate |
| 0.17 | Bisabolol nat. | Bisabolol |
| 1.84 | Vitamin E acetate | Tocopheryl acetate |
| 0.42 | D,L-Alpha-Tocopherol | Tocopherol |
| 2% | P18 | |
| 39.38 | Castor oil | Castor (*Ricinus communis*) oil |

(32)

|   | | | |
|---|---|---|---|
| A | 6.00 | Cremophor WO 7 | PEG-7-hydrogenated castor oil |
|   | 2.00 | Elfacos ST 9 | PEG-45-/dodecyl glycol copolymer |
|   | 3.00 | Isopropyl myristate | Isopropylmyristate |
|   | 8.00 | Jojoba oil | *Simmondsia chinensis* (jojoba) seed oil |
|   | 4.00 | Uvinul MC 80 | Ethylhexyl methoxycinnamate |
|   | 2.00 | Uvinul A Plus | Diethylaminohydroxybenzoylhexyl benzoate |
|   | 1.00 | Abil 350 | Dimethicone |
| B | 5.00 | Z-COTE MAX | Zinc oxide (and) diphenylcaprylmethicone |
|   | 3.00 | T-Lite SF | Titanium dioxide, aluminum hydrate, dimethicone/methicone copolymer |
| C | 0.20 | Edeta BD | Disodium EDTA |
|   | 5.00 | Glycerol 87% | Glycerol |
|   | 0.30 | Chemag 2000 | Imidazolidinylurea |
|   | 59.00 | Water dem. | Aqua dem. |

(33)

|   |       |                      |                                                                                              |
|---|-------|----------------------|----------------------------------------------------------------------------------------------|
|   | 2.00  | Cremophor A 6        | Ceteareth-6, stearyl alcohol                                                                 |
|   | 2.00  | Cremophor A 25       | Ceteareth-25                                                                                 |
|   | 3.00  | Syncrowax HRC        | Tribehenin                                                                                   |
|   | 2.00  | Lanette O            | Cetearyl alcohol                                                                             |
|   | 2.00  | Luvitol EHO          | Cetearyl ethylhexanoate                                                                      |
|   | 5.00  | Uvinul MC 80         | Ethylhexyl methoxycinnamate                                                                  |
|   | 1.00  | Uvinul T 150         | Ethylhexyltriazone                                                                           |
|   | 1.00  | Ganex V-220          | VP/eicosene copolymer                                                                        |
|   | 7.00  | Isopropyl myristate  | Isopropyl myristate                                                                          |
| B | 5.00  | Z-COTE MAX           | Zinc oxide (and) diphenylcaprylmethicone                                                     |
| C | 0.20  | Keltrol              | Xanthan gum                                                                                  |
|   | 0.50  | Simulgel NS          | Hydroxyethyl acrylate/sodium acryloyldimethyltaurate copolymer, squalane, polysorbate 60     |
|   | 61.10 | Water dem.           | Aqua dem.                                                                                    |
|   | 0.20  | Edeta BD             | Disodium EDTA                                                                                |
|   | 5.00  | 1,2-Propylene glycol Care | Propylene glycol                                                                        |
| D | 1.00  | Vitamin E acetate    | Tocopheryl acetate                                                                           |
|   | 1.5%  | P18                  |                                                                                              |
|   | q.s.  | Preservative         |                                                                                              |

(34)

|   |      |                         |                                           |
|---|------|-------------------------|-------------------------------------------|
| A | 2.00 | Luvitol EHO             | Cetearyl ethylhexanoate                   |
|   | 5.00 | Paraffin oil            | Mineral oil                               |
|   | 5.00 | Z-COTE MAX              | Zinc oxide (and) diphenylcaprylmethicone  |
| B | 1.00 | Cremophor A 6           | Ceteareth-6, stearyl alcohol              |
|   | 2.00 | Cremophor A 25          | Ceteareth-25                              |
|   | 3.00 | Glycerol monostearate   | Glyceryl stearate                         |
|   | 4.00 | Cetylstearyl alcohol    | Cetearyl alcohol                          |
| C | 5.00 | 1,2-Propylene glycol Care | Propylene glycol                        |
|   | 7.50 | Luviquat Care           | Polyquaternium-44                         |
|   | q.s. | Preservative            |                                           |
|   | q.s. | Perfume oil             |                                           |

Continuation of previous formulation:

|   |      |             |           |
|---|------|-------------|-----------|
| D | q.s. | Perfume oil |           |
|   | 1%   | P18         |           |
|   | q.s. | Preservative |          |

|       |            |           |
|-------|------------|-----------|
| 1%    | P18        |           |
| 64.50 | Water dem. | Aqua dem. |

(35)

|       |                        |                                                                      |
|-------|------------------------|----------------------------------------------------------------------|
| 5.00  | T-Lite SF              | Titanium dioxide, aluminum hydrate, dimethicone/methicone copolymer  |
| 10.00 | Z-COTE MAX             | Zinc oxide (and) diphenylcaprylmethicone                             |
| 12.00 | Beeswax 3044 PH        | Beeswax                                                              |
| 8.00  | Candelilla wax LT 281 LJ | Candelilla (*Euphorbia cerifera*) wax                              |
| 5.00  | Tegin                  | Glyceryl stearate SE                                                 |
| 5.00  | Dow Corning 345 Fluid  | Cyclopentasiloxane, cyclohexasiloxane                                |
| 5.00  | Witconol APM           | PPG-3 myristyl ether                                                 |
| 5.00  | Softisan 154           | Hydrogenated palm oil                                                |
| 8.00  | Paraffin oil, thick-liquid | Mineral oil                                                      |
| 3.00  | Vaseline               | Petrolatum                                                           |
| 2%    | P18                    |                                                                      |
| 32.00 | Castor oil             | Castor (*Ricinus communis*) oil                                      |

(36)

|       |                          |                                                 |
|-------|--------------------------|-------------------------------------------------|
| 3.00  | Uvinul MC 80             | Ethylhexyl methoxycinnamate                     |
| 2.00  | Uvinul T 150             | Ethylhexyltriazone                              |
| 2.00  | Uvinul A Plus            | Diethylaminohydroxybenzoylhexyl benzoate        |
| 10.00 | Z-COTE MAX               | Zinc oxide (and) diphenylcaprylmethicone        |
| 12.00 | Beeswax 3044 PH          | Beeswax                                         |
| 3.00  | Vaseline                 | Petrolatum                                      |
| 8.00  | Candelilla wax LT 281 LJ | Candelilla (*Euphorbia cerifera*) wax           |
| 8.00  | Paraffin oil, thick-liquid | Mineral oil                                   |
| 5.00  | Tegin                    | Glyceryl stearate SE                            |
| 5.00  | Softisan 154             | Hydrogenated palm oil                           |
| 5.00  | Witconol APM             | PPG-3 myristyl ether                            |
| 5.00  | Dow Corning 345 Fluid    | Cyclopentasiloxane, cyclohexasiloxane           |
| 0.1%  | P18                      |                                                 |
| 28.90 | Castor oil               | Castor (*Ricinus communis*) oil                 |

(37)

|   |       |                           |                                                                       |
|---|-------|---------------------------|-----------------------------------------------------------------------|
|   | 5.00  | T-Lite SF                 | Titanium dioxide, aluminum hydrate, dimethicone/methicone copolymer   |
|   | 6.00  | Finsolv TN                | $C_{12-15}$-Alkyl benzoate                                            |
|   | 10.00 | Uvinul MC 80              | Ethylhexyl methoxycinnamate                                           |
|   | 6.00  | Miglyol 812               | Caprylic/capric triglyceride                                          |
|   | 5.00  | Arlacel P 135             | PEG-30 dipolyhydroxystearate                                          |
|   | 2.00  | Ganex V 216               | PVP/hexadecene copolymer                                              |
|   | 2.00  | Elfacos ST 9              | PEG-45/dodecyl glycol copolymer                                       |
| B | 3.00  | 1,2-Propylene glycol Care | Propylene glycol                                                      |
|   | 0.10  | Edeta BD                  | Disodium EDTA                                                         |
|   | 1.00  | Magnesium sulfate 7-hydrate | Magnesium sulfate                                                   |
|   | 59.40 | Water dem.                | Aqua dem.                                                             |
|   | 0.5%  | P18                       |                                                                       |
|   | q.s.  | Preservative              |                                                                       |

(38)

|   |      |               |                                                                                                                                                           |
|---|------|---------------|-----------------------------------------------------------------------------------------------------------------------------------------------------------|
| A | 4.00 | Dehymuls SBL  | Polyglyceryl-2 dipolyhydroxystearate, dicaprylyl ether, cocoglycerides, sorbitan sesquioleate, Cera alba, aluminum stearate, dicocoylpentaerythrityldistearyl citrate |
|   | 1.00 | Dehymuls PGPH | Polyglyceryl-2 dipolyhydroxystearate                                                                                                                      |
|   | 8.00 | Finsolv TN    | $C_{12-15}$-Alkyl benzoate                                                                                                                                |

-continued

|   |        |                            |                                                                 |
|---|--------|----------------------------|-----------------------------------------------------------------|
|   | 4.00   | Miglyol 812                | Caprylic/capric triglyceride                                    |
|   | 4.00   | Uvinul MC 80               | Ethylhexyl methoxycinnamate                                     |
|   | 2.00   | Uvinul N 539 T             | Octocrylene                                                     |
| B | 5.00   | Z-COTE MAX                 | Zinc oxide (and) diphenylcaprylmethicone                        |
| C | 3.00   | 1,2-Propylene glycol Care  | Propylene glycol                                                |
|   | 0.30   | Abiol                      | Imidazolidinylurea                                              |
|   | 1.00   | Magnesium sulfate 7-hydrate| Magnesium sulfate                                               |
|   | ad 100 | Water dem.                 | Aqua dem.                                                       |
|   | 1.5%   | P18                        |                                                                 |
| D | q.s.   | Preservative               |                                                                 |

(39)

|   |        |                            |                                                                 |
|---|--------|----------------------------|-----------------------------------------------------------------|
| A | 4.00   | Dehymuls SBL               | Polyglyceryl-2 dipolyhydroxystearate, dicaprylyl ether, cocoglycerides, sorbitan sesquioleate, Cera alba, aluminum stearate, dicocoylpentaerythrityldistearyl citrate |
|   | 1.00   | Dehymuls PGPH              | Polyglyceryl-2 dipolyhydroxystearate                            |
|   | 8.00   | Finsolv TN                 | $C_{12-15}$-Alkyl benzoate                                      |
|   | 4.00   | Miglyol 812                | Caprylic/capric triglyceride                                    |
|   | 4.00   | Uvinul MC 80               | Ethylhexyl methoxycinnamate                                     |
|   | 2.00   | Uvinul N 539 T             | Octocrylene                                                     |
| B | 5.00   | T-Lite SF-S                | Titanium dioxide, silicon hydrate, aluminum hydrate, methicone/dimethicone copolymer |
| C | 3.00   | 1,2-Propylene glycol Care  | Propylene glycol                                                |
|   | 0.30   | Abiol                      | Imidazolidinylurea                                              |
|   | 1.00   | Magnesium sulfate 7-hydrate| Magnesium sulfate                                               |
|   | 1.0%   | P18                        |                                                                 |
|   | ad 100 | Water dem.                 | Aqua dem.                                                       |
| D | q.s.   | Preservative               |                                                                 |

(40)

|   |        |                            |                                                                 |
|---|--------|----------------------------|-----------------------------------------------------------------|
| A | 4.00   | Dehymuls SBL               | Polyglyceryl-2 dipolyhydroxystearate, dicaprylyl ether, cocoglycerides, sorbitan sesquioleate, Cera alba, aluminum stearate, dicocoylpentaerythrityldistearyl citrate |
|   | 1.00   | Dehymuls PGPH              | Polyglyceryl-2 dipolyhydroxystearate                            |
|   | 8.00   | Finsolv TN                 | $C_{12-15}$-Alkyl benzoate                                      |
|   | 4.00   | Miglyol 812                | Caprylic/capric triglyceride                                    |
|   | 8.00   | Uvinul A Plus B            | Ethylhexyl methoxycinnamate and diethylaminohydroxybenzoylhexyl benzoate |
|   | 2.00   | Uvinul N 539 T             | Octocrylene                                                     |
| B | 5.00   | Z-COTE MAX                 | Zinc oxide (and) diphenylcaprylmethicone                        |
| C | 3.00   | 1,2-Propylene glycol Care  | Propylene glycol                                                |
|   | 0.30   | Abiol                      | Imidazolidinylurea                                              |
|   | 1.00   | Magnesium sulfate 7-hydrate| Magnesium sulfate                                               |
|   | 0.1%   | P18                        |                                                                 |
|   | ad 100 | Water dem.                 | Aqua dem.                                                       |
|   | q.s.   | Preservative               |                                                                 |

(41)

|   |      |                |                                                                 |
|---|------|----------------|-----------------------------------------------------------------|
| A | 4.00 | Dehymuls SBL   | Polyglyceryl-2 dipolyhydroxystearate, dicaprylyl ether, cocoglycerides, sorbitan sesquioleate, Cera alba, aluminum stearate, dicocoylpentaerythrityldistearyl citrate |
|   | 1.00 | Dehymuls PGPH  | Polyglyceryl-2 dipolyhydroxystearate                            |
|   | 8.00 | Finsolv TN     | $C_{12-15}$-Alkyl benzoate                                      |
|   | 4.00 | Miglyol 812    | Caprylic/capric triglyceride                                    |
|   | 8.00 | Uvinul A Plus B| Ethylhexyl methoxycinnamate and diethylaminohydroxybenzoylhexyl benzoate |

|   |       | Uvinul N 539 T | Octocrylene |
|---|-------|----------------|-------------|
|   | 2.00  |                |             |
| B | 5.00  | T-Lite SF      | Titanium dioxide, aluminum hydrate, dimethicone/methicone copolymer |
| C | 3.00  | 1,2-Propylene glycol Care | Propylene glycol |
|   | 0.30  | Abiol          | Imidazolidinylurea |
|   | 1.00  | Magnesium sulfate 7-hydrate | Magnesium sulfate |
|   | ad 100 | Water dem.    | Aqua dem. |
|   | 0.2%  | P18            |             |
|   | q.s.  | Preservative   |             |

(42)

| A | 4.00  | Dehymuls SBL   | Polyglyceryl-2 dipolyhydroxystearate, dicaprylyl ether, cocoglycerides, sorbitan sesquioleate, Cera alba, aluminum stearate, dicocoylpentaerythrityldistearyl citrate |
|---|-------|----------------|---|
|   | 1.00  | Dehymuls PGPH  | Polyglyceryl-2 dipolyhydroxystearate |
|   | 8.00  | Finsolv TN     | $C_{12-15}$-Alkyl benzoate |
|   | 4.00  | Miglyol 812    | Caprylic/capric triglyceride |
|   | 8.00  | Uvinul A Plus B | Ethylhexyl methoxycinnamate and diethylaminohydroxybenzoylhexyl benzoate |
|   | 2.00  | Uvinul N 539 T | Octocrylene |
| B | 5.00  | T-Lite SF-S    | Titanium dioxide, silicon hydrate, aluminum hydrate, methicone/dimethicone copolymer |
| C | 3.00  | 1,2-Propylene glycol Care | Propylene glycol |
|   | 0.30  | Abiol          | Imidazolidinylurea |
|   | 1.00  | Magnesium sulfate 7-hydrate | Magnesium sulfate |
|   | 0.5%  | P18            |   |
|   | ad 100 | Water dem.    | Aqua dem. |
|   | q.s.  | Preservative   |   |

(43)

| A | 4.00  | Dehymuls SBL   | Polyglyceryl-2 dipolyhydroxystearate, dicaprylyl ether, cocoglycerides, sorbitan sesquioleate, Cera alba, aluminum stearate, dicocoylpentaerythrityldistearyl citrate |
|---|-------|----------------|---|
|   | 1.00  | Dehymuls PGPH  | Polyglyceryl-2 dipolyhydroxystearate |
|   | 8.00  | Finsolv TN     | $C_{12-15}$-Alkyl benzoate |
|   | 4.00  | Miglyol 812    | Caprylic/capric triglyceride |
|   | 7.00  | Uvinul MC 80   | Ethylhexyl methoxycinnamate |
|   | 2.00  | Mexoryl XL     | Drometrizole trisiloxane |
| B | 5.00  | Z-COTE MAX     | Titanium dioxide, aluminum hydrate, dimethicone/methicone copolymer |
| C | 3.00  | 1,2-Propylene glycol Care | Propylene glycol |
|   | 0.30  | Abiol          | Imidazolidinylurea |
|   | 1.00  | Magnesium sulfate 7-hydrate | Magnesium sulfate |
|   | ad 100 | Water dem.    | Aqua dem. |
|   | 0.01% | P18            |   |
|   | q.s.  | Preservative   |   |

(44)

| A | 7.50  | Uvinul MC 80   | Ethylhexyl methoxycinnamate |
|---|-------|----------------|---|
|   | 3.00  | Uvinul N 539 T | Octocrylene |
|   | 2.00  | Uvinul A Plus  | Diethylaminohydroxybenzoylhexyl benzoate |
|   | 1.00  | Cremophor CO 40 | PEG-40 hydrogenated castor oil |
|   | 10.00 | Miglyol 812    | Caprylic/capric triglyceride |
|   | 1.50  | Dow Corning 345 Fluid | Cyclopentasiloxane, cyclohexasiloxane |
| B | 3.50  | Luvigel EM     | Caprylic/capric triglyceride, sodium acrylate copolymer |
| C | 46.00 | Water dem.     | Aqua dem. |
| D | 5.00  | 1,2-Propylene glycol Care | Propylene glycol |

-continued

|   | 0.50  | Cremophor A 25 | Ceteareth-25 |
|---|-------|----------------|---|
|   | 0.05% | P18            |   |
|   | 20.00 | Ethanol 96%    | Alcohol |

(45)

| A | 1.00  | Uvinul A Plus  | Diethylaminohydroxybenzoylhexyl benzoate |
|---|-------|----------------|---|
|   | 1.00  | Tinosorb S     | Bisethylhexyloxyphenol methoxyphenyltriazine |
|   | 3.00  | Uvinul MC 80   | Ethylhexyl methoxycinnamate |

-continued

|   |      |                    |                                                               |
|---|------|--------------------|---------------------------------------------------------------|
|   | 8.00 | Miglyol 812        | Caprylic/capric triglyceride                                  |
|   | 1.50 | Dow Corning 350 Fluid | Dimethicone                                                |
|   | 3.00 | Z-COTE MAX         | Titanium dioxide, aluminum hydrate, dimethicone/methicone copolymer |
|   | 3.00 | Finsolv TN         | C$_{12-15}$-Alkyl benzoate                                    |
|   | 1.00 | Cremophor CO 40    | PEG-40 hydrogenated castor oil                                |
| B | 2.00 | Luvigel EM         | Caprylic/capric triglyceride, sodium acrylate copolymer       |
| C | 54.80| Water dem.         | Aqua dem.                                                     |
| D | 15.00| Ethanol 96%        | Alcohol                                                       |
|   | 5.00 | 1,2-Propylene glycol Care | Propylene glycol                                       |
|   | 0.50 | Cremophor A 25     | Ceteareth-25                                                  |
|   | 1.0% | P18                |                                                               |
|   | 1.00 | Vitamin E acetate  | Tocopheryl acetate                                            |
|   | 0.20 | Bisabolol rac.     | Bisabolol                                                     |

(46)

|   |      |                  |                                                                                                                                                     |
|---|------|------------------|-----------------------------------------------------------------------------------------------------------------------------------------------------|
| A | 4.00 | Dehymuls SBL     | Polyglyceryl-2 dipolyhydroxystearate, dicaprylyl ether, cocoglycerides, sorbitan sesquioleate, Cera alba, aluminum stearate, dicocoylpentaerythrityldistearyl citrate |
|   | 1.00 | Dehymuls PGPH    | Polyglyceryl-2 dipolyhydroxystearate                                                                                                                |
|   | 6.00 | Finsolv TN       | C$_{12-15}$-Alkyl benzoate                                                                                                                          |
|   | 6.00 | Miglyol 812      | Caprylic/capric triglyceride                                                                                                                        |
|   | 5.00 | Uvinul MC 80     | Ethylhexyl methoxycinnamate                                                                                                                         |
|   | 3.00 | Neoheliopan HMS  | Homosalate                                                                                                                                          |
| B | 5.00 | Z-COTE MAX       | Zinc oxide (and) diphenylcaprylmethicone                                                                                                            |
| C | 3.00 | 1,2-Propylene glycol Care | Propylene glycol                                                                                                                           |
|   | 0.30 | Chemag 2000      | Imidazolidinylurea                                                                                                                                  |
|   | 1.00 | Magnesium sulfate 7-hydrate | Magnesium sulfate                                                                                                                         |
|   | 65.10| Water dem.       | Aqua dem.                                                                                                                                           |
|   | 0.1% | P18              |                                                                                                                                                     |
|   | q.s. | Preservative     |                                                                                                                                                     |

(47)

|   |       |                    |                                                                 |
|---|-------|--------------------|-----------------------------------------------------------------|
| A | 4.00  | Tego Care 450      | Polyglyceryl-3 methylglucose distearate                         |
|   | 4.50  | Uvinul MC 80       | Ethylhexyl methoxycinnamate                                     |
|   | 3.00  | Uvinul N 539 T     | Octocrylene                                                     |
|   | 2.00  | Uvinul T 150       | Ethylhexyltriazone                                              |
|   | 0.50  | Vitamin E acetate  | Tocopheryl acetate                                              |
| B | 5.00  | Isohexadecane      | Isohexadecane                                                   |
|   | 5.00  | Cosmacol EMI       | Di-C$_{12-13}$-alkyl malate                                     |
|   | 3.50  | Cetiol SN          | Cetearyl isononanoate                                           |
|   | 1.00  | Ganex V-220        | VP/eicosene copolymer                                           |
|   | 5.00  | T-Lite SF          | Titanium dioxide, aluminum hydrate, dimethicone/methicone copolymer |
| C | 60.00 | Water dem.         | Water                                                           |
|   | 5.00  | Glycerol 87%       | Glycerol                                                        |
|   | 1.00  | Lanette E          | Sodium cetearyl sulfate                                         |
|   | 0.30  | Keltrol            | Xanthan gum                                                     |
|   | 0.2%  | P18                |                                                                 |
| D | q.s.  | Preservative       |                                                                 |

(48)

|   |      |                    |                                         |
|---|------|--------------------|-----------------------------------------|
| A | 4.00 | Tego Care 450      | Polyglyceryl-3 methylglucose distearate |
|   | 4.50 | Uvinul MC 80       | Ethylhexyl methoxycinnamate             |
|   | 3.00 | Uvinul N 539 T     | Octocrylene                             |
|   | 2.00 | Neoheliopan HMS    | Homosalate                              |
|   | 0.50 | Vitamin E acetate  | Tocopheryl acetate                      |
| B | 5.00 | Isohexadecane      | Isohexadecane                           |
|   | 5.00 | Cosmacol EMI       | Di-C$_{12-13}$-alkyl malate             |
|   | 3.50 | Cetiol SN          | Cetearyl isononanoate                   |
|   | 1.00 | Ganex V-220        | VP/eicosene copolymer                   |
|   | 5.00 | T-Lite SF          | Titanium dioxide, aluminum hydrate, dimethicone/methicone copolymer |
| C | 59.20| Water dem.         | Aqua dem.                               |
|   | 5.00 | Glycerol 87%       | Glycerol                                |
|   | 1.00 | Lanette E          | Sodium cetearyl sulfate                 |
|   | 0.30 | Keltrol            | Xanthan gum                             |
|   | 1.0% | P18                |                                         |
| D | q.s. | Preservative       |                                         |

(49)

|   |      |                    |                                         |
|---|------|--------------------|-----------------------------------------|
| A | 4.00 | Tego Care 450      | Polyglyceryl-3 methylglucose distearate |
|   | 4.50 | Uvinul MC 80       | Ethylhexyl methoxycinnamate             |
|   | 3.00 | Neoheliopan OS     | Octisalate                              |
|   | 2.00 | Neoheliopan HMS    | Homosalate                              |
|   | 0.50 | Vitamin E acetate  | Tocopheryl acetate                      |
| B | 5.00 | Isohexadecane      | Isohexadecane                           |
|   | 5.00 | Cosmacol EMI       | Di-C$_{12-13}$-alkyl malate             |
|   | 3.50 | Cetiol SN          | Cetearyl isononanoate                   |
|   | 1.00 | Ganex V-220        | VP/eicosene copolymer                   |
|   | 5.00 | Z-COTE MAX         | Zinc oxide (and) diphenylcaprylmethicone|
| C | 60.15| Water dem.         | Aqua dem                                |
|   | 5.00 | Glycerol 87%       | Glycerol                                |
|   | 1.00 | Lanette E          | Sodium cetearyl sulfate                 |
|   | 0.30 | Keltrol            | Xanthan gum                             |
|   | 0.05%| P18                |                                         |
| D | q.s. | Preservative       |                                         |

(50)

|   |      |                    |                                         |
|---|------|--------------------|-----------------------------------------|
| A | 4.00 | Tego Care 450      | Polyglyceryl-3 methylglucose distearate |
|   | 4.50 | Uvinul N 539 T     | Octocrylene                             |
|   | 3.00 | Neoheliopan OS     | Octisalate                              |
|   | 2.00 | Neoheliopan HMS    | Homosalate                              |
|   | 0.50 | Vitamin E acetate  | Tocopheryl acetate                      |
| B | 5.00 | Isohexadecane      | Isohexadecane                           |
|   | 5.00 | Cosmacol EMI       | Di-C$_{12-13}$-alkyl malate             |
|   | 3.50 | Cetiol SN          | Cetearyl isononanoate                   |
|   | 1.00 | Ganex V-220        | VP/eicosene copolymer                   |
|   | 5.00 | Z-COTE MAX         | Zinc oxide (and) diphenylcaprylmethicone|
| C | 60.19| Water dem.         | Aqua dem.                               |
|   | 5.00 | Glycerol 87%       | Glycerol                                |
|   | 1.00 | Lanette E          | Sodium cetearyl sulfate                 |

|   |   |   |   |
|---|---|---|---|
|   | 0.30 | Keltrol | Xanthan gum |
|   | 0.01% | P18 |   |
| D | q.s. | Preservative |   |

(51)

|   |   |   |   |
|---|---|---|---|
| A | 4.00 | Tego Care 450 | Polyglyceryl-3 methylglucose distearate |
|   | 4.50 | Uvinul N 539 T | Octocrylene |
|   | 3.00 | Neoheliopan OS | Octisalate |
|   | 2.00 | Neoheliopan HMS | Homosalate |
|   | 0.50 | Vitamin E acetate | Tocopheryl acetate |
| B | 5.00 | Isohexadecane | Isohexadecane |
|   | 5.00 | Cosmacol EMI | Di-$C_{12-13}$-alkyl malate |
|   | 3.50 | Cetiol SN | Cetearyl isononanoate |
|   | 1.00 | Ganex V-220 | VP/eicosene copolymer |
|   | 5.00 | T-Lite SF-S | Titanium dioxide, silicon hydrate, aluminum hydrate, methicone/dimethicone copolymer |
| C | 59.20 | Water dem. | Aqua dem. |
|   | 5.00 | Glycerol 87% | Glycerol |
|   | 1.00 | Lanette E | Sodium cetearyl sulfate |
|   | 0.30 | Keltrol | Xanthan gum |
|   | 1.0% | P18 |   |
| D | q.s. | Preservative |   |

(52)

|   |   |   |   |
|---|---|---|---|
| A | 8.00 | Cetiol B | Dibutyl adipate |
|   | 8.00 | Finsolv TN | $C_{12-15}$-Alkyl benzoate |
|   | 12.00 | Myritol 331 | Cocoglycerides |
|   | 1.00 | Lanette E | Sodium cetearyl sulfate |
|   | 4.00 | Eumulgin VL 75 | Lauryl glucoside, polyglyceryl-2 dipolyhydroxystearate, glycerol |
|   | 2.00 | Lanette O | Cetearyl alcohol |
|   | 3.00 | Tinosorb S | Bisethylhexyloxyphenol methoxyphenyltriazine |
|   | 1.00 | Vitamin E acetate | Tocopheryl acetate |
| B | 4.00 | Z-COTE MAX | Zinc oxide (and) diphenylcaprylmethicone |
| C | 3.00 | Glycerol 87% | Glycerol |
|   | 0.05 | Edeta BD | Disodium EDTA |
|   | 0.20 | Allantoin | Allantoin |
|   | 0.30 | Keltrol | Xanthan gum |
|   | 1.50 | Veegum Ultra | Magnesium aluminum silicate |
|   | 49.45 | Water dem. | Aqua dem. |
|   | 1.0% | P18 |   |
| D | q.s. | Preservative |   |

(53)

|   |   |   |   |
|---|---|---|---|
| A | 8.00 | Cetiol B | Dibutyl adipate |
|   | 8.00 | Finsolv TN | $C_{12-15}$-Alkyl benzoate |
|   | 12.00 | Myritol 331 | Cocoglycerides |
|   | 1.00 | Lanette E | Sodium cetearyl sulfate |
|   | 4.00 | Eumulgin VL 75 | Laurylglucosid, polyglyceryl-2 dipolyhydroxystearate, glycerol |
|   | 2.00 | Lanette O | Cetearyl alcohol |
|   | 3.00 | Tinosorb S | Bisethylhexyloxyphenol methoxyphenyltriazine |
|   | 1.00 | Vitamin E acetate | Tocopheryl acetate |
| B | 4.00 | T-Lite SF | Titanium dioxide, aluminum hydrate, dimethicone/methicone copolymer |
| C | 3.00 | Glycerol 87% | Glycerol |
|   | 0.05 | Edeta BD | Disodium EDTA |
|   | 0.20 | Allantoin | Allantoin |
|   | 0.30 | Keltrol | Xanthan gum |
|   | 1.50 | Veegum Ultra | Magnesium aluminum silicate |
|   | 50.25 | Water dem. | Aqua dem. |
| D | 0.50 | Citric acid | Citric acid |
|   | q.s. | Perfume oil |   |
|   | 0.2% | P18 |   |
|   | q.s. | Preservative |   |

(54)

|   |   |   |   |
|---|---|---|---|
| A | 5.00 | Cosmacol EMI | Di-$C_{12-13}$-alkyl malate |
|   | 4.50 | Uvinul MC 80 | Ethylhexyl methoxycinnamate |
|   | 3.00 | Uvinul N 539 T | Octocrylene |
|   | 2.00 | Uvinul T 150 | Ethylhexyltriazone |
| B | 4.00 | Tego Care 450 | Polyglyceryl-3 methylglucose distearate |
|   | 5.00 | Isohexadecane | Isohexadecane |
|   | 3.50 | Cetiol SN | Cetearyl isononanoate |
|   | 0.50 | Vitamin E acetate | Tocopheryl acetate |
|   | 1.00 | Ganex V-220 | VP/eicosene copolymer |
|   | 2.50 | T-Lite SF | Titanium dioxide, aluminum hydrate, dimethicone/methicone copolymer |
| C | 5.00 | Glycerol 87% | Glycerol |
|   | 2.00 | Lanette E | Sodium cetearyl sulfate |
|   | 0.30 | Keltrol | Xanthan gum |
|   | 1.00 | Pationic 138 C | Sodium lauroyl lactylate |
|   | 1.00 | Pationic SSL | Sodium stearoyl lactylate |
|   | 42.00 | Water dem. | Aqua dem. |
| D | 5.00 | Eusolex 232 | Phenylbenzimidazolesulfonic acid |
|   | 10.00 | Water dem. | Aqua dem |
| E | 0.70 | Sodium hydroxide | Sodium hydroxide |
|   | 1.0% | P18 |   |
|   | q.s. | Preservative |   |

(55)

|   |   |   |   |
|---|---|---|---|
| A | 5.00 | Cosmacol EMI | Di-$C_{12-13}$Alkyl malate |
|   | 4.50 | Uvinul MC 80 | Ethylhexyl methoxycinnamate |
|   | 3.00 | Uvinul N 539 T | Octocrylene |
|   | 2.00 | Uvinul A Plus | Diethylaminohydroxybenzoylhexyl benzoate |
| B | 4.00 | Tego Care 450 | Polyglyceryl-3 methylglucose distearate |
|   | 5.00 | Isohexadecane | Isohexadecane |
|   | 3.50 | Cetiol SN | Cetearyl isononanoate |
|   | 0.50 | Vitamin E acetate | Tocopheryl acetate |
|   | 1.00 | Ganex V-220 | VP/eicosene copolymer |
|   | 2.50 | T-Lite SF | Titanium dioxide, aluminum hydrate, dimethicone/methicone copolymer |
| C | 5.00 | Glycerol 87% | Glycerol |
|   | 2.00 | Lanette E | Sodium cetearyl sulfate |
|   | 0.30 | Keltrol | Xanthan gum |
|   | 1.00 | Pationic 138 C | Sodium lauroyl lactylate |
|   | 1.00 | Pationic SSL | Sodium stearoyl lactylate |
|   | 41.00 | Water dem. | Aqua dem |
| D | 5.00 | Eusolex 232 | Phenylbenzimidazolesulfonic acid |
|   | 2.0% | P18 |   |
|   | 10.00 | Water dem. | Aqua dem |
| E | 0.70 | Sodium hydroxide | Sodium hydroxid |
|   | q.s. | Preservative |   |

(56)

|   |   |   |   |
|---|---|---|---|
| A | 5.00 | Cosmacol EMI | Di-$C_{12-13}$Alkyl malate |
|   | 4.50 | Uvinul MC 80 | Ethylhexyl methoxycinnamate |
|   | 3.00 | Uvinul N 539 T | Octocrylene |
|   | 2.00 | Uvinul A Plus | Diethylaminohydroxybenzoylhexyl benzoate |
| B | 4.00 | Tego Care 450 | Polyglyceryl-3 methylglucose distearate |
|   | 5.00 | Isohexadecane | Isohexadecane |
|   | 3.50 | Cetiol SN | Cetearyl isononanoate |
|   | 0.50 | Vitamin E acetate | Tocopheryl acetate |
|   | 1.00 | Ganex V-220 | VP/eicosene copolymer |
|   | 2.50 | Z-COTE MAX | Zinc oxide (and) diphenylcaprylmethicone |

-continued

| | | | |
|---|---|---|---|
| C | 5.00 | Glycerol 87% | Glycerol |
| | 2.00 | Lanette E | Sodium cetearyl sulfate |
| | 0.30 | Keltrol | Xanthan gum |
| | 1.00 | Pationic 138 C | Sodium lauroyl lactylate |
| | 1.00 | Pationic SSL | Sodium stearoyl lactylate |
| | 42.50 | Water dem. | Aqua dem |
| D | 5.00 | Eusolex 232 | Phenylbenzimidazolesulfonic acid |
| | 0.5% | P18 | |
| | 10.00 | Water dem. | Aqua dem |
| E | 0.70 | Sodium hydroxide | Sodium hydroxide |
| | q.s. | Preservative | |

(57)

| | | | |
|---|---|---|---|
| A | 5.00 | Cosmacol EMI | Di-$C_{12-13}$Alkyl malate |
| | 7.50 | Uvinul N 539 T | Octocrylene |
| | 2.00 | Mexoryl XL | Drometrizole trisiloxane |
| B | 4.00 | Tego Care 450 | Polyglyceryl-3 methylglucose distearate |
| | 5.00 | Isohexadecane | Isohexadecane |
| | 3.50 | Cetiol SN | Cetearyl isononanoate |
| | 0.50 | Vitamin E acetate | Tocopheryl acetate |
| | 1.00 | Ganex V-220 | VP/eicosene copolymer |
| | 5.00 | Z-COTE MAX | Zinc oxide (and) diphenylcaprylmethicone |
| C | 5.00 | Glycerol 87% | Glycerol |
| | 2.00 | Lanette E | Sodium cetearyl sulfate |
| | 0.30 | Keltrol | Xanthan gum |
| | 1.00 | Pationic 138 C | Sodium lauroyl lactylate |
| | 1.00 | Pationic SSL | Sodium stearoyl lactylate |
| | 40.50 | Water dem. | Aqua dem |
| D | 5.00 | Eusolex 232 | Phenylbenzimidazolesulfonic acid |
| | 1.0% | P18 | |
| | 10.00 | Water dem. | Aqua dem |
| E | 0.70 | Sodium hydroxide | Sodium hydroxide |
| | q.s. | Preservative | |

(58)

| | | | |
|---|---|---|---|
| A | 5.00 | Cosmacol EMI | Di-$C_{12-13}$Alkyl malate |
| | 5.50 | Uvinul N 539 T | Octocrylene |
| | 2.00 | Uvinul A Plus | Diethylaminohydrobenzoylhexyl benzoate |
| | 2.00 | Mexoryl XL | Drometrizole trisiloxane |
| B | 4.00 | Tego Care 450 | Polyglyceryl-3 methylglucose distearate |
| | 5.00 | Isohexadecane | Isohexadecane |
| | 3.50 | Cetiol SN | Cetearyl isononanoate |
| | 0.50 | Vitamin E acetate | Tocopheryl acetate |
| | 1.00 | Ganex V-220 | VP/eicosene copolymer |
| | 5.00 | Z-COTE MAX | Zinc oxide (and) diphenylcaprylmethicone |
| C | 5.00 | Glycerol 87% | Glycerol |
| | 2.00 | Lanette E | Sodium cetearyl sulfate |
| | 0.30 | Keltrol | Xanthan gum |
| | 1.00 | Pationic 138 C | Sodium lauroyl lactylate |
| | 1.00 | Pationic SSL | Sodium stearoyl lactylate |
| | 41.50 | Water dem. | Aqua dem |
| D | 5.00 | Eusolex 232 | Phenylbenzimidazolesulfonic acid |
| | 0.5% | P18 | |
| | 9.50 | Water dem. | Aqua dem |
| E | 0.70 | Sodium hydroxide | Sodium hydroxide |
| | q.s. | Preservative | |

(59)

| | | | |
|---|---|---|---|
| A | 5.00 | Cosmacol EMI | Di-$C_{12-13}$Alkyl malate |
| | 5.50 | Uvinul N 539 T | Octocrylene |
| | 2.00 | Uvinul A Plus | Diethylaminohydrobenzoylhexyl benzoate |
| | 2.00 | Mexoryl XL | Drometrizole trisiloxane |

-continued

| | | | |
|---|---|---|---|
| B | 4.00 | Tego Care 450 | Polyglyceryl-3 methylglucose distearate |
| | 5.00 | Isohexadecane | Isohexadecane |
| | 3.50 | Cetiol SN | Cetearyl isononanoate |
| | 0.50 | Vitamin E acetate | Tocopheryl acetate |
| | 1.00 | Ganex V-220 | VP/eicosene copolymer |
| | 5.00 | T-Lite SF-S | Titanium dioxide, silicon hydrate, aluminum hydrate, methicone/dimethicone copolymer |
| C | 5.00 | Glycerol 87% | Glycerol |
| | 2.00 | Lanette E | Sodium cetearyl sulfate |
| | 0.30 | Keltrol | Xanthan gum |
| | 1.00 | Pationic 138 C | Sodium lauroyl lactylate |
| | 1.00 | Pationic SSL | Sodium stearoyl lactylate |
| | 40.50 | Water dem. | Aqua dem |
| D | 5.00 | Eusolex 232 | Phenylbenzimidazolesulfonic acid |
| | 1.0% | P18 | |
| | 10.00 | Water dem. | Aqua dem |
| E | 0.70 | Sodium hydroxide | Sodium hydroxide |
| | q.s. | Preservative | |

(60)

| | | | |
|---|---|---|---|
| A | 8.00 | Cetiol B | Dibutyl adipate |
| | 8.00 | Finsolv TN | $C_{12-15}$-Alkyl benzoate |
| | 10.00 | Myritol 331 | Cocoglycerides |
| | 1.00 | Lanette E | Sodium cetearyl sulfate |
| | 4.00 | Eumulgin VL 75 | Lauryl glucoside, polyglyceryl-2 dipolyhydroxystearate, glycerol |
| | 2.00 | Lanette O | Cetearyl alcohol |
| | 1.00 | Tinosorb S | Bisethylhexyloxyphenol methoxyphenyltriazine |
| | 1.00 | Uvinul T 150 | Ethylhexyltriazone |
| | 1.00 | Vitamin E acetate | Tocopheryl acetate |
| B | 5.00 | T-Lite SF | Titanium dioxide, aluminum hydrate, dimethicone/methicone copolymer |
| C | 3.00 | Glycerol 87% | Glycerol |
| | 0.05 | Edeta BD | Disodium EDTA |
| | 0.20 | Allantoin | Allantoin |
| | 0.30 | Keltrol | Xanthan gum |
| | 2.0% | P18 | |
| | 1.50 | Veegum Ultra | Magnesium aluminum silicate |
| | ad 100 | Water dem. | Aqua dem |
| D | q.s. | Perfume oil | |
| | q.s. | Preservative | |

(61)

| | | | |
|---|---|---|---|
| A | 8.00 | Cetiol B | Dibutyl adipate |
| | 8.00 | Finsolv TN | $C_{12-15}$-Alkyl benzoate |
| | 10.00 | Myritol 331 | Cocoglycerides |
| | 1.00 | Lanette E | Sodium cetearyl sulfate |
| | 4.00 | Eumulgin VL 75 | Lauryl glucoside, polyglyceryl-2 dipolyhydroxystearate, glycerol |
| | 2.00 | Lanette O | Cetearyl alcohol |
| | 1.00 | Tinosorb S | Bisethylhexyloxyphenol methoxyphenyltriazine |
| | 1.00 | Uvinul T 150 | Ethylhexyltriazone |
| | 1.00 | Vitamin E acetate | Tocopheryl acetate |
| B | 5.00 | Z-COTE MAX | Zinc oxide (and) diphenylcaprylmethicone |
| C | 3.00 | Glycerol 87% | Glycerol |
| | 0.05 | Edeta BD | Disodium EDTA |
| | 0.20 | Allantoin | Allantoin |
| | 0.30 | Keltrol | Xanthan gum |
| | 1.0% | P18 | |
| | 1.50 | Veegum Ultra | Magnesium aluminum silicate |
| | ad 100 | Water dem. | Aqua dem |
| D | q.s. | Perfume oil | |
| | q.s. | Preservative | |

(62)

| | | | |
|---|---|---|---|
| A | 3.00 | Glycerol 87% | Glycerol |
| | 0.20 | Edeta BD | Disodium EDTA |
| | 0.30 | Abiol | Imidazolidinylurea |
| | 1.00 | Plantacare 2000 | Decyl glucoside |
| | 0.30 | Keltrol T | Xanthan gum |
| | 57.00 | Water dem. | Aqua dem. |
| B | 5.00 | T-Lite SF-S | Titanium dioxide, silicon hydrate, aluminum hydrate, methicone/dimethicone copolymer |
| C | 7.50 | Uvinul MC 80 | Ethylhexyl methoxycinnamate |
| | 2.00 | Uvinul A Plus | Diethylaminohydroxybenzoylhexyl benzoate |
| | 2.00 | Dow Corning 345 Fluid | Cyclopentasiloxane, cyclohexasiloxane |
| | 3.50 | Cremophor A 6 | Ceteareth-6, stearyl alcohol |
| | 1.50 | Cremophor A 25 | Ceteareth-25 |
| | 0.50 | Beeswax 3044 PH | Beeswax |
| | 3.00 | Lanette O | Cetearyl alcohol |
| | 10.00 | Miglyol 812 | Caprylic/capric triglyceride |
| D | 1.00 | Vitamin E acetate | Tocopheryl acetate |
| | 2.0% | P18 | |
| | 0.20 | Bisabolol rac. | Bisabolol |

(63)

| | | | |
|---|---|---|---|
| A | 3.00 | Glycerol 87% | Glycerol |
| | 0.20 | Edeta BD | Disodium EDTA |
| | 0.30 | Abiol | Imidazolidinylurea |
| | 1.00 | Plantacare 2000 | Decyl glucoside |
| | 0.30 | Keltrol T | Xanthan gum |
| | 58.00 | Water dem. | Aqua dem. |
| B | 5.00 | Z-COTE MAX | Zinc oxide (and) diphenylcaprylmethicone |
| C | 7.50 | Uvinul MC 80 | Ethylhexyl methoxycinnamate |
| | 2.00 | Uvinul A Plus | Diethylaminohydroxybenzoylhexyl benzoate |
| | 2.00 | Dow Corning 345 Fluid | Cyclopentasiloxane, cyclohexasiloxane |
| | 3.50 | Cremophor A 6 | Ceteareth-6, stearyl alcohol |
| | 1.50 | Cremophor A 25 | Ceteareth-25 |
| | 0.50 | Beeswax 3044 PH | Beeswax |
| | 3.00 | Lanette O | Cetearyl alcohol |
| | 10.00 | Miglyol 812 | Caprylic/capric triglyceride |
| D | 1.00 | Vitamin E acetate | Tocopheryl acetate |
| | 1.0% | P18 | |
| | 0.20 | Bisabolol rac. | Bisabolol |

(64)

| | | | |
|---|---|---|---|
| A | 3.00 | Glycerol 87% | Glycerol |
| | 0.20 | Edeta BD | Disodium EDTA |
| | 0.30 | Abiol | Imidazolidinylurea |
| | 1.00 | Plantacare 2000 | Decyl glucoside |
| | 0.30 | Keltrol T | Xanthan gum |
| | 58.50 | Water dem. | Aqua dem. |
| B | 5.00 | T-Lite SF-S | Titanium dioxide, silicon hydrate, aluminum hydrate, methicone/dimethicone copolymer |
| C | 7.50 | Uvinul MC 80 | Ethylhexyl methoxycinnamate |
| | 5.00 | Uvinul N 539 T | Octocrylene |
| | 2.00 | Parsol 1789 | Butylmethoxydibenzoylmethane |
| | 2.00 | Dow Corning 345 Fluid | Cyclopentasiloxane, cyclohexasiloxane |
| | 3.50 | Cremophor A 6 | Ceteareth-6, stearyl alcohol |
| | 1.50 | Cremophor A 25 | Ceteareth-25 |
| | 0.50 | Beeswax 3044 PH | Beeswax |
| | 3.00 | Lanette O | Cetearyl alcohol |
| | 10.00 | Miglyol 812 | Caprylic/capric triglyceride |
| D | 1.00 | Vitamin E acetate | Tocopheryl acetate |
| | 0.5% | P18 | |
| | 0.20 | Bisabolol rac. | Bisabolol |

(65)

| | | | |
|---|---|---|---|
| A | 3.00 | Glycerol 87% | Glycerol |
| | 0.20 | Edeta BD | Disodium EDTA |
| | 0.30 | Abiol | Imidazolidinylurea |
| | 1.00 | Plantacare 2000 | Decyl glucoside |
| | 0.30 | Keltrol T | Xanthan gum |
| | 2.00 | Mexoryl SL | Terephthalidenedicamphorsulfonic acid |
| | 58.40 | Water dem. | Aqua dem. |
| B | 6.00 | T-Lite SF-S | Titanium dioxide, silicon hydrate, aluminum hydrate, methicone/dimethicone copolymer |
| C | 6.00 | Uvinul N 539 T | Octocrylene |
| | 2.00 | Parsol 1789 | Butylmethoxydibenzoylmethane |
| | 2.00 | Dow Corning 345 Fluid | Cyclopentasiloxane, cyclohexasiloxane |
| | 3.50 | Cremophor A 6 | Ceteareth-6, stearyl alcohol |
| | 1.50 | Cremophor A 25 | Ceteareth-25 |
| | 0.50 | Beeswax 3044 PH | Beeswax |
| | 3.00 | Lanette O | Cetearyl alcohol |
| | 10.00 | Miglyol 812 | Caprylic/capric triglyceride |
| D | 1.00 | Vitamin E acetate | Tocopheryl acetate |
| | 0.1% | P18 | |
| | 0.20 | Bisabolol rac. | Bisabolol |

(66)

| | | | |
|---|---|---|---|
| A | 3.00 | Glycerol 87% | Glycerol |
| | 0.20 | Edeta BD | Disodium EDTA |
| | 0.30 | Abiol | Imidazolidinylurea |
| | 1.00 | Plantacare 2000 | Decyl glucoside |
| | 0.30 | Keltrol T | Xanthan gum |
| | 2.00 | Mexoryl SL | Terephthalidenedicamphorsulfonic acid |
| | 58.45 | Water dem. | Aqua dem. |
| B | 6.00 | Z-COTE MAX | Zinc oxide (and) diphenylcaprylmethicone |
| | 6.00 | Uvinul N 539 T | Octocrylene |
| | 2.00 | Parsol 1789 | Butylmethoxydibenzoylmethane |
| | 2.00 | Dow Corning 345 Fluid | Cyclopentasiloxane, cyclohexasiloxane |
| | 3.50 | Cremophor A 6 | Ceteareth-6, stearyl alcohol |
| | 1.50 | Cremophor A 25 | Ceteareth-25 |
| | 0.50 | Beeswax 3044 PH | Beeswax |
| | 3.00 | Lanette O | Cetearyl alcohol |
| | 10.00 | Miglyol 812 | Caprylic/capric triglyceride |
| D | 1.00 | Vitamin E acetate | Tocopheryl acetate |
| | 0.05% | P18 | |
| | 0.20 | Bisabolol rac. | Bisabolol |

(67)

| | | | |
|---|---|---|---|
| A | 3.00 | Glycerol 87% | Glycerol |
| | 0.20 | Edeta BD | Disodium EDTA |
| | 0.30 | Abiol | Imidazolidinylurea |
| | 1.00 | Plantacare 2000 | Decyl glucoside |
| | 0.30 | Keltrol T | Xanthan gum |
| | 2.00 | Neoheliopan AP | Disodium phenyldibenzimidazoletetrasulfonate |
| | 57.50 | Water dem. | Aqua dem. |
| B | 6.00 | Z-COTE MAX | Zinc oxide (and) diphenylcaprylmethicone |
| | 6.00 | Uvinul N 539 T | Octocrylene |
| | 2.00 | Parsol 1789 | Butylmethoxydibenzoylmethane |
| | 2.00 | Dow Corning 345 Fluid | Cyclopentasiloxane, cyclohexasiloxane |
| | 3.50 | Cremophor A 6 | Ceteareth-6, stearyl alcohol |
| | 1.50 | Cremophor A 25 | Ceteareth-25 |
| | 0.50 | Beeswax 3044 PH | Beeswax |
| | 3.00 | Lanette O | Cetearyl alcohol |
| | 10.00 | Miglyol 812 | Caprylic/capric triglyceride |
| D | 1.00 | Vitamin E acetate | Tocopheryl acetate |
| | 1.0% | P18 | |
| | 0.20 | Bisabolol rac. | Bisabolol |

(68)

|   |       |                     |                                                                        |
|---|-------|---------------------|------------------------------------------------------------------------|
| A | 25.00 | Dow Corning 345 Fluid | Cyclopentasiloxane, cyclohexasiloxane                                |
|   | 20.00 | Dow Corning 245 Fluid | Cyclopentasiloxane                                                   |
|   | 8.00  | Uvinul MC 80        | Ethylhexyl methoxycinnamate                                            |
|   | 4.00  | Abil EM 90          | Cetyl-PEG-/PPG-10-/1-dimethicone                                       |
|   | 7.00  | T-Lite SF           | Titanium dioxide, aluminum hydrate, dimethicone/methicone copolymer    |
| B | 17.00 | Ethanol 95%         | Alcohol                                                                |
|   | 10.00 | Z-COTE MAX          | Zinc oxide (and) diphenylcaprylmethicone                               |
|   | 4.50  | Water dem.          | Aqua dem.                                                              |
|   | 3.00  | Glycerol 87%        | Glycerol                                                               |
|   | 0.5%  | P18                 |                                                                        |
|   | 1.00  | Talc                | Talc                                                                   |

(69)

|   |       |                     |                                                                                               |
|---|-------|---------------------|-----------------------------------------------------------------------------------------------|
| A | 25.00 | Dow Corning 345 Fluid | Cyclopentasiloxane, cyclohexasiloxane                                                       |
|   | 20.00 | Dow Corning 245 Fluid | Cyclopentasiloxane                                                                          |
|   | 8.00  | Uvinul MC 80        | Ethylhexyl methoxycinnamate                                                                   |
|   | 4.00  | Abil EM 90          | Cetyl-PEG-/PPG-10-/1-dimethicone                                                              |
|   | 7.00  | T-Lite SF-S         | Titanium dioxide, silicon hydrate, aluminum hydrate, methicone/dimethicone copolymer          |
| B | 17.00 | Ethanol 95%         | Alcohol                                                                                       |
|   | 9.99  | Z-COTE MAX          | Zinc oxide (and) diphenylcaprylmethicone                                                      |
|   | 5.00  | Water dem.          | Aqua dem.                                                                                     |
|   | 3.00  | Glycerol 87%        | Glycerol                                                                                      |
|   | 0.01% | P18                 |                                                                                               |
|   | 1.00  | Talc                | Talc                                                                                          |

(70)

|   |       |                     |                                                                     |
|---|-------|---------------------|---------------------------------------------------------------------|
| A | 20.00 | Dow Corning 345 Fluid | Cyclopentasiloxane, cyclohexasiloxane                             |
|   | 10.00 | Dow Corning 245 Fluid | Cyclopentasiloxane                                                |
|   | 7.50  | Uvinul MC 80        | Ethylhexyl methoxycinnamate                                         |
|   | 2.00  | Uvinul T 150        | Ethylhexyltriazone                                                  |
|   | 12.00 | Cosmacol EMI        | Di-$C_{12-13}$-alkyl malate                                         |
|   | 4.00  | Abil EM 90          | Cetyl-PEG-/PPG-10-/1-dimethicone                                    |
| B | 7.00  | T-Lite SF           | Titanium dioxide, aluminum hydrate, dimethicone/methicone copolymer |
| C | 15.00 | Ethanol 95%         | Alcohol                                                             |
|   | 10.00 | Z-COTE MAX          | Zinc oxide (and) diphenylcaprylmethicone                            |
|   | 3.00  | Glycerol 87%        | Glycerol                                                            |
|   | 1.5%  | P18                 |                                                                     |
|   | 8.00  | Water dem.          | Aqua dem.                                                           |

(71)

|   |       |                     |                                                                     |
|---|-------|---------------------|---------------------------------------------------------------------|
| A | 20.00 | Dow Corning 345 Fluid | Cyclopentasiloxane, cyclohexasiloxane                             |
|   | 10.00 | Dow Corning 245 Fluid | Cyclopentasiloxane                                                  |
|   | 7.50  | Uvinul MC 80        | Ethylhexyl methoxycinnamate                                         |
|   | 2.00  | Tinosorb S          | Bisethylhexyloxyphenol methoxyphenyltriazine                        |
|   | 12.00 | Cosmacol EMI        | Di-$C_{12-13}$-alkyl malate                                         |
|   | 4.00  | Abil EM 90          | Cetyl-PEG-/PPG-10-/1-dimethicone                                    |
| B | 7.00  | T-Lite SF           | Titanium dioxide, aluminum hydrate, dimethicone/methicone copolymer |
| C | 15.00 | Ethanol 95%         | Alcohol                                                             |
|   | 10.00 | Z-COTE MAX          | Zinc oxide (and) diphenylcaprylmethicone                            |
|   | 3.00  | Glycerol 87%        | Glycerol                                                            |
|   | 0.5%  | P18                 |                                                                     |
|   | 9.00  | Water dem.          | Aqua dem.                                                           |

(72)

|   |       |                 |                                                                                            |
|---|-------|-----------------|--------------------------------------------------------------------------------------------|
| A | 2.00  | Cremophor WO 7  | PEG-7-hydrogenated castor oil                                                              |
|   | 6.00  | Abil B 8839     | Cyclopentasiloxane, cyclohexasiloxane                                                      |
|   | 3.00  | T-Lite SF       | Titanium dioxide, aluminum hydrate, dimethicone/methicone copolymer                        |
|   | 4.00  | Isopropyl palmitate | Isopropyl palmitate                                                                    |
|   | 1.00  | Abil 350        | Dimethicone                                                                                |
| B | 7.00  | Uvinul MC 80    | Ethylhexyl methoxycinnamate                                                                |
|   | 1.00  | Uvinul T 150    | Ethylhexyltriazone                                                                         |
|   | 7.00  | Finsolv TN      | $C_{12-15}$-Alkyl benzoate                                                                 |
|   | 4.00  | Abil WE 09      | Polyglyceryl-4 isostearate, cetyl-PEG-/PPG-10-/1-dimethicone, hexyl laurate                |
| C | 0.50  | Sodium chloride | Sodium chloride                                                                            |
|   | 0.20  | Edeta BD        | Disodium EDTA                                                                              |
|   | 61.30 | Water dem.      | Aqua dem                                                                                   |
| D | 1.00  | Vitamin E acetate | Tocopheryl acetate                                                                       |
|   | 1.0%  | P18             |                                                                                            |
|   | q.s.  | Preservative    |                                                                                            |

(73)

|   |       |                 |                                                                                            |
|---|-------|-----------------|--------------------------------------------------------------------------------------------|
| A | 2.00  | Cremophor WO 7  | PEG-7-hydrogenated castor oil                                                              |
|   | 6.00  | Abil B 8839     | Cyclopentasiloxane, cyclohexasiloxane                                                      |
|   | 3.00  | Z-COTE MAX      | Zinc oxide (and) diphenylcaprylmethicone                                                   |
|   | 4.00  | Isopropyl palmitate | Isopropyl palmitate                                                                    |
|   | 1.00  | Abil 350        | Dimethicone                                                                                |
| B | 7.00  | Uvinul MC 80    | Ethylhexyl methoxycinnamate                                                                |
|   | 1.00  | Uvinul T 150    | Ethylhexyltriazone                                                                         |
|   | 7.00  | Finsolv TN      | $C_{12-15}$-Alkyl benzoate                                                                 |
|   | 4.00  | Abil WE 09      | Polyglyceryl-4 isostearate, cetyl-PEG-/PPG-10-/1-dimethicone, hexyl laurate                |
| C | 0.50  | Sodium chloride | Sodium chloride                                                                            |
|   | 0.20  | Edeta BD        | Disodium EDTA                                                                              |
|   | 62.20 | Water dem.      | Aqua dem                                                                                   |
| D | 1.00  | Vitamin E acetate | Tocopheryl acetate                                                                       |
|   | 0.1%  | P18             |                                                                                            |
|   | q.s.  | Preservative    |                                                                                            |

(74)

|   |       |                 |                                                                                            |
|---|-------|-----------------|--------------------------------------------------------------------------------------------|
| A | 2.00  | Cremophor WO 7  | PEG-7-hydrogenated castor oil                                                              |
|   | 6.00  | Abil B 8839     | Cyclopentasiloxane, cyclohexasiloxane                                                      |
|   | 3.00  | Z-COTE MAX      | Zinc oxide (and) diphenylcaprylmethicone                                                   |
|   | 4.00  | Isopropyl palmitate | Isopropyl palmitate                                                                    |
|   | 1.00  | Abil 350        | Dimethicone                                                                                |
| B | 7.00  | Uvinul MC 80    | Ethylhexyl methoxycinnamate                                                                |
|   | 1.00  | Tinosorb S      | Bisethylhexyloxyphenol methoxyphenyltriazine                                               |
|   | 7.00  | Finsolv TN      | $C_{12-15}$-Alkyl benzoate                                                                 |
|   | 4.00  | Abil WE 09      | Polyglyceryl-4 isostearate, cetyl-PEG-/PPG-10-/1-dimethicone, hexyl laurate                |
| C | 0.50  | Sodium chloride | Sodium chloride                                                                            |
|   | 0.20  | Edeta BD        | Disodium EDTA                                                                              |
|   | 60.30 | Water dem.      | Aqua dem                                                                                   |
| D | 1.00  | Vitamin E acetate | Tocopheryl acetate                                                                       |
|   | 2.0%  | P18             |                                                                                            |
|   | q.s.  | Preservative    |                                                                                            |

(75)

| | | | |
|---|---|---|---|
| A | 2.00 | Cremophor WO 7 | PEG-7-hydrogenated castor oil |
| | 6.00 | Abil B 8839 | Cyclopentasiloxane, cyclohexasiloxane |
| | 6.00 | Z-COTE MAX | Zinc oxide (and) diphenylcaprylmethicone |
| | 4.00 | Isopropyl palmitate | Isopropyl palmitate |
| | 1.00 | Abil 350 | Dimethicone |
| B | 4.00 | Uvinul N 539 T | Octocrylene |
| | 1.00 | Tinosorb S | Bisethylhexyloxyphenol methoxyphenyltriazine |
| | 7.00 | Finsolv TN | $C_{12-15}$-Alkyl benzoate |
| | 4.00 | Abil WE 09 | Polyglyceryl-4 isostearate, cetyl-PEG-/PPG-10-/1-dimethicone, hexyl laurate |
| C | 0.50 | Sodium chloride | Sodium chloride |
| | 0.20 | Edeta BD | Disodium EDTA |
| | 62.10 | Water dem. | Aqua dem |
| D | 1.00 | Vitamin E acetate | Tocopheryl acetate |
| | 0.2% | P18 | |
| | q.s. | Preservative | |

(76)

| | | | |
|---|---|---|---|
| A | 2.00 | Cremophor WO 7 | PEG-7-hydrogenated castor oil |
| | 6.00 | Abil B 8839 | Cyclopentasiloxane, cyclohexasiloxane |
| | 6.00 | Z-COTE MAX | Zinc oxide (and) diphenylcaprylmethicone |
| | 4.00 | Isopropyl palmitate | Isopropyl palmitate |
| | 1.00 | Abil 350 | Dimethicone |
| B | 3.00 | Uvinul N 539 T | Octocrylene |
| | 1.00 | Mexoryl XL | Drometrizole trisiloxane |
| | 1.00 | Tinosorb S | Bisethylhexyloxyphenol methoxyphenyltriazine |
| | 7.00 | Finsolv TN | $C_{12-15}$-Alkyl benzoate |
| | 4.00 | Abil WE 09 | Polyglyceryl-4 isostearate, cetyl-PEG-/PPG-10-/1-dimethicone, hexyl laurate |
| C | 0.50 | Sodium chloride | Sodium chloride |
| | 0.20 | Edeta BD | Disodium EDTA |
| | 1.0% | P18 | |
| | 61.30 | Water dem. | Aqua dem |
| D | 1.00 | Vitamin E acetate | Tocopheryl acetate |
| | q.s. | Preservative | |

(77)

| | | | |
|---|---|---|---|
| A | 2.00 | Cremophor WO 7 | PEG-7-hydrogenated castor oil |
| | 6.00 | Abil B 8839 | Cyclopentasiloxane, cyclohexasiloxane |
| | 6.00 | T-Lite SF-S | Titanium dioxide, silicon hydrate, aluminum hydrate, methicone/dimethicone copolymer |
| | 4.00 | Isopropyl palmitate | Isopropyl palmitate |
| | 1.00 | Abil 350 | Dimethicone |
| B | 3.00 | Uvinul N 539 T | Octocrylene |
| | 1.00 | Mexoryl XL | Drometrizole trisiloxane |
| | 1.00 | Tinosorb S | Bisethylhexyloxyphenol methoxyphenyltriazine |
| | 7.00 | Finsolv TN | $C_{12-15}$-Alkyl benzoate |
| | 4.00 | Abil WE 09 | Polyglyceryl-4 isostearate, cetyl-PEG-/PPG-10-/1-dimethicone, hexyl laurate |
| C | 0.50 | Sodium chloride | Sodium chloride |
| | 0.20 | Edeta BD | Disodium EDTA |
| | 61.80 | Water dem. | Aqua dem |
| D | 1.00 | Vitamin E acetate | Tocopheryl acetate |
| | 0.5% | P18 | |
| | q.s. | Preservative | |

(78)

| | | | |
|---|---|---|---|
| A | 4.50 | Uvinul MC 80 | Ethylhexyl methoxycinnamate |
| | 3.00 | Uvinul N 539 T | Octocrylene |
| | 1.00 | Uvinul T 150 | Ethylhexyltriazone |
| | 2.50 | Cosmacol EMI | Di-$C_{12-13}$-alkyl malate |
| B | 0.50 | Vitamin E acetate | Tocopheryl acetate |
| | 4.00 | Tego Care 450 | Polyglyceryl-3 methylglucose distearate |
| C | 3.50 | Cetiol SN | Cetearyl isononanoate |
| | 1.00 | Ganex V-220 | VP/eicosene copolymer |
| | 5.00 | Isohexadecane | Isohexadecane |
| | 2.50 | Cosmacol EMI | Di-$C_{12-13}$-alkyl malate |
| | 5.00 | Z-COTE MAX | Zinc oxide (and) diphenylcaprylmethicone |
| D | 44.00 | Water dem. | Aqua dem. |
| | 5.00 | Glycerol 87% | Glycerol |
| | 1.00 | Lanette E | Sodium cetearyl sulfate |
| | 15.00 | Luviquat Care | Polyquaternium-44 |
| | 1.0% | P18 | |
| | 0.50 | Keltrol | Xanthan gum |
| E | 1.00 | Phenonip | |

(79)

| | | | |
|---|---|---|---|
| A | 4.50 | Uvinul MC 80 | Ethylhexyl methoxycinnamate |
| | 3.00 | Uvinul N 539 T | Octocrylene |
| | 1.00 | Tinosorb S | Bisethoxyhexyloxyphenol methoxyphenyltriazine |
| | 2.50 | Cosmacol EMI | Di-$C_{12-13}$-alkyl malate |
| B | 0.50 | Vitamin E acetate | Tocopheryl acetate |
| | 4.00 | Tego Care 450 | Polyglyceryl-3 methylglucose distearate |
| C | 3.50 | Cetiol SN | Cetearyl isononanoate |
| | 1.00 | Ganex V-220 | VP/eicosene copolymer |
| | 5.00 | Isohexadecane | Isohexadecane |
| | 2.50 | Cosmacol EMI | Di-$C_{12-13}$-alkyl malate |
| | 5.00 | Z-COTE MAX | Zinc oxide (and) diphenylcaprylmethicone |
| D | 44.90 | Water dem. | Aqua dem. |
| | 5.00 | Glycerol 87% | Glycerol |
| | 1.00 | Lanette E | Sodium cetearyl sulfate |
| | 15.00 | Luviquat Care | Polyquaternium-44 |
| | 0.1% | P18 | |
| | 0.50 | Keltrol | Xanthan gum |
| E | 1.00 | Phenonip | |

(80)

| | | | |
|---|---|---|---|
| A | 1.50 | Mexoryl XL | Drometrizole trisiloxane |
| | 5.00 | Uvinul N 539 T | Octocrylene |
| | 1.00 | Tinosorb S | Bisethylhexyloxyphenol methoxyphenyltriazine |
| | 2.50 | Cosmacol EMI | Di-$C_{12-13}$-alkyl malate |
| B | 0.50 | Vitamin E acetate | Tocopheryl acetate |
| | 4.00 | Tego Care 450 | Polyglyceryl-3 methylglucose distearate |
| C | 3.50 | Cetiol SN | Cetearyl isononanoate |
| | 1.00 | Ganex V-220 | VP/eicosene copolymer |
| | 5.00 | Isohexadecane | Isohexadecane |
| | 2.50 | Cosmacol EMI | Di-$C_{12-13}$-alkyl malate |
| | 5.00 | Z-COTE MAX | Zinc oxide (and) diphenylcaprylmethicone |
| D | 44.50 | Water dem. | Aqua dem. |
| | 5.00 | Glycerol 87% | Glycerol |
| | 1.00 | Lanette E | Sodium cetearyl sulfate |
| | 15.00 | Luviquat Care | Polyquaternium-44 |
| | 1.5% | P18 | |
| | 0.50 | Keltrol | Xanthan gum |
| E | 1.00 | Phenonip | |

(81)

| | | | |
|---|---|---|---|
| A | 1.50 | Mexoryl XL | Drometrizole trisiloxane |
| | 5.00 | Uvinul N 539 T | Octocrylene |
| | 1.00 | Tinosorb S | Bisethylhexyloxyphenol methoxyphenyltriazine |

(continued)

| | | | |
|---|---|---|---|
| | 2.50 | Cosmacol EMI | Di-C$_{12-13}$-alkyl malate |
| B | 0.50 | Vitamin E acetate | Tocopheryl acetate |
| | 4.00 | Tego Care 450 | Polyglyceryl-3 methylglucose distearate |
| C | 3.50 | Cetiol SN | Cetearyl isononanoate |
| | 1.00 | Ganex V-220 | VP/eicosene copolymer |
| | 5.00 | Isohexadecane | Isohexadecane |
| | 2.50 | Cosmacol EMI | Di-C$_{12-13}$-alkyl malate |
| | 5.00 | T-Lite SF | Titanium dioxide, aluminum hydrate, dimethicone/methicone copolymer |
| D | 45.00 | Water dem. | Aqua dem. |
| | 5.00 | Glycerol 87% | Glycerol |
| | 1.00 | Lanette E | Sodium cetearyl sulfate |
| | 15.00 | Luviquat Care | Polyquaternium-44 |
| | 1.0% | P18 | |
| | 0.50 | Keltrol | Xanthan gum |
| E | 1.00 | Phenonip | |

(82)

| | | | |
|---|---|---|---|
| A | 1.00 | Abil Care 85 | Bis-PEG-/PPG-16-/16-PEG-/PPG-16-/16-dimethicone, caprylic/capric triglyceride |
| | 3.00 | Cremophor CO 40 | PEG-40-hydrogenated castor oil |
| | 0.30 | Cremophor WO 7 | PEG-7-hydrogenated castor oil |
| | 5.00 | Uvinul MC 80 | Ethylhexyl methoxycinnamate |
| | 10.00 | Witconol APM | PPG-3 myristyl ether |
| | 2.00 | Uvinul T 150 | Ethylhexyltriazone |
| | 1.00 | Dow Corning 345 Fluid | Cyclopentasiloxane, cyclohexasiloxane |
| | 5.00 | Uvinul N 539 T | Octocrylene |
| B | 5.00 | Z-COTE MAX | Zinc oxide (and) diphenylcaprylmethicone |
| C | 5.00 | 1,2-Propylene glycol | Propylene glycol |
| | 0.20 | Keltrol | Xanthan gum |
| | 0.10 | Edeta BD | Disodium EDTA |
| | 2.0% | P18 | |
| | 1.50 | Simulgel 600 | Acrylamide/sodium acryloyldimethyltaurate copolymer, isohexadecane, polysorbate 80 |
| | 58.40 | Water dem. | Aqua dem. |
| D | q.s. | Perfume oil | |
| | 0.50 | Glydant | DMDM hydantoin |

(83)

| | | | |
|---|---|---|---|
| A | 2.00 | Abil Care 85 | Bis-PEG-/PPG-16-/16-PEG-/PPG-16-/16-dimethicone, caprylic/capric triglyceride |
| | 4.00 | Finsolv TN | C$_{12-15}$-Alkyl benzoate |
| | 1.50 | Miglyol 812 | Caprylic/capric triglyceride |
| | 0.50 | Vitamin E acetate | Tocopheryl acetate |
| | 7.50 | Uvinul MC 80 | Ethylhexyl methoxycinnamate |
| | 4.00 | Cetiol B | Dibutyl adipate |
| | 3.00 | Luvitol EHO | Cetearyl ethylhexanoate |
| | 1.00 | Cremophor CO 40 | PEG-40-hydrogenated castor oil |
| | 1.00 | Paraffin oil, thin-liquid | Mineral oil |
| | 3.00 | Plantacare 2000 | Decyl glucoside |
| | 0.50 | Phenonip | |
| | q.s. | Perfume oil | |
| B | 4.00 | Z-COTE MAX | Zinc oxide (and) diphenylcaprylmethicone |
| C | 2.00 | Simulgel NS | Hydroxyethyl acrylate/sodium acryloyldimethyltaurate copolymer, squalane, polysorbate 60 |
| | 0.20 | Keltrol | Xanthan gum |
| | 0.10 | Edeta BD | Disodium EDTA |
| | 1.0% | P18 | |
| | 64.20 | Water dem. | Aqua dem |

(84)

| | | | |
|---|---|---|---|
| A | 6.00 | Gilugel SIL 5 | Cyclomethicone (and) aluminum-/magnesium hydroxide stearate |
| | 5.00 | Uvinul MC 80 | Ethylhexyl methoxycinnamate |
| | 2.00 | Uvinul A Plus | Diethylaminohydroxybenzoylhexyl benzoate |
| | 1.00 | Uvinul T 150 | Ethylhexyltriazone |
| | 7.00 | Finsolv TN | C$_{12-15}$-Alkyl benzoate |
| | 4.00 | Abil WE 09 | Polyglyceryl-4 isostearate, cetyl-PEG-/PPG-10-/1-dimethicone, hexyl laurate |
| | 2.00 | Cosmacol EMI | Di-C$_{12-13}$-alkyl malate |
| | 3.00 | Isopropyl palmitate | Isopropyl palmitate |
| | 5.00 | Abil B 8839 | Cyclopentasiloxane, cyclohexasiloxane |
| | 0.50 | Abil 350 | Dimethicone |
| B | 0.50 | Sodium chloride | Sodium chloride |
| | 0.20 | Edeta BD | Disodium EDTA |
| | 0.2% | P18 | |
| | 62.10 | Water dem. | Aqua dem. |
| C | 1.00 | Vitamin E acetate | Tocopheryl acetate |
| | 0.50 | Phenonip | |

(85)

| | | | |
|---|---|---|---|
| A | 4.50 | Uvinul MC 80 | Ethylhexyl methoxycinnamate |
| | 2.00 | Tinosorb S | Bisethylhexyloxyphenol methoxyphenyltriazine |
| | 3.00 | Uvinul N 539 T | Octocrylene |
| | 2.50 | Cosmacol EMI | Di-C$_{12-13}$-alkyl malate |
| | 0.50 | Vitamin E acetate | Tocopheryl acetate |
| | 4.00 | Tego Care 450 | Polyglyceryl-3 methylglucose distearate |
| B | 3.50 | Cetiol SN | Cetearyl isononanoate |
| | 1.00 | Ganex V-220 | VP/eicosene copolymer |
| | 5.00 | Isohexadecane | Isohexadecane |
| | 2.50 | Cosmacol EMI | Di-C$_{12-13}$-alkyl malate |
| | 3.00 | T-Lite SF | Titanium dioxide, aluminum hydrate, dimethicone/methicone copolymer |
| C | 5.00 | Glycerol 87% | Glycerol |
| | 1.00 | Lanette E | Sodium cetearyl sulfate |
| | 0.50 | Keltrol | Xanthan gum |
| | 1.0% | P18 | |
| | 59.70 | Water dem. | Aqua dem. |
| D | 1.00 | Phenonip | |
| | 0.30 | Bisabolol rac. | Bisabolol |

(86)

| | | | |
|---|---|---|---|
| A | 2.00 | Abil Care 85 | Bis-PEG-/PPG-16-/16-PEG-/PPG-16-/16-dimethicone, caprylic/capric triglyceride |
| | 4.00 | Finsolv TN | C$_{12-15}$-Alkyl benzoate |
| | 1.50 | Miglyol 812 | Caprylic/capric triglyceride |
| | 0.50 | Vitamin E acetate | Tocopheryl acetate |
| | 7.50 | Uvinul MC 80 | Ethylhexyl methoxycinnamate |
| | 4.00 | Cetiol B | Dibutyl adipate |
| | 1.00 | Luvitol EHO | Cetearyl ethylhexanoate |
| | 1.00 | Cremophor CO 40 | PEG-40 hydrogenated castor oil |
| | 1.00 | Paraffin oil, thin-liquid | Mineral oil |
| | 3.00 | Plantacare 2000 | Decyl glucoside |
| | 1.00 | Uvinul A Plus | Diethylaminohydroxybenzoylhexyl benzoate |
| | 0.50 | Phenonip | |
| | 2.50 | Uvinul T 150 | Ethylhexyltriazone |
| | q.s. | Perfume oil | |
| B | 4.00 | Z-COTE MAX | Zinc oxide (and) diphenylcapryl-methicone |
| C | 2.00 | Simulgel NS | Hydroxyethyl acrylate/sodium acryloyldimethyltaurate copolymer, squalane, polysorbate 60 |

(87)

| | | | |
|---|---|---|---|
| A | 4.00 | Eumulgin VL 75 | Lauryl glucoside, polyglyceryl-2 dipolyhydroxystearate, glycerol |
| | 2.00 | Lanette O | Cetearyl alcohol |
| | 12.00 | Myritol 331 | Cocoglycerides |
| | 8.00 | Finsolv TN | $C_{12-15}$-Alkyl benzoate |
| | 8.00 | Cetiol B | Dibutyl adipate |
| B | 6.00 | T-Lite SF | Titanium dioxide, aluminum hydrate, dimethicone/methicone copolymer |
| | 5.00 | Z-COTE MAX | Zinc oxide (and) diphenylcapryl-methicone |
| C | 3.00 | Glycerol 87% | Glycerol |
| | 0.10 | Edeta BD | Disodium EDTA |
| | 1.50 | Veegum Ultra | Magnesium aluminum silicate |
| | 1.50 | Lanette E | Sodium cetearyl sulfate |
| | 2.0% | P18 | |
| | 0.30 | Keltrol | Xanthan gum |
| | 45.10 | Water dem. | Water |
| D | 1.00 | Phenonip | Phenoxyethanol, methyl paraben, ethyl paraben, butyl paraben, propyl paraben, isobutyl paraben |

(88)

| | | | |
|---|---|---|---|
| A | 4.00 | Eumulgin VL 75 | Lauryl glucoside, polyglyceryl-2 dipolyhydroxystearate, glycerol |
| | 2.00 | Lanette O | Cetearyl alcohol |
| | 12.00 | Myritol 331 | Cocoglycerides |
| | 8.00 | Finsolv TN | $C_{12-15}$-Alkyl benzoate |
| | 8.00 | Cetiol B | Dibutyl adipate |
| B | 6.00 | Uvinul N 539 T | Octocrylene |
| | 5.00 | Z-COTE MAX | Zinc oxide (and) diphenylcapryl-methicone |
| C | 3.00 | Glycerol 87% | Glycerol |
| | 0.10 | Edeta BD | Disodium EDTA |
| | 1.50 | Veegum Ultra | Magnesium aluminum silicate |
| | 1.50 | Lanette E | Sodium cetearyl sulfate |
| | 0.30 | Carbopol Ultrez 10 P | Carbomer |
| | 1.0% | P18 | |
| | 46.10 | Water dem. | Aqua dem. |
| D | 1.00 | Phenonip | Phenoxyethanol, methyl paraben, ethyl paraben, butyl paraben, propyl paraben, isobutyl paraben |

(89)

| | | | |
|---|---|---|---|
| A | 4.00 | Eumulgin VL 75 | Lauryl glucoside, polyglyceryl-2 dipolyhydroxystearate, glycerol |
| | 2.00 | Lanette O | Cetearyl alcohol |
| | 10.00 | Myritol 331 | Cocoglycerides |
| | 8.00 | Finsolv TN | $C_{12-15}$-Alkyl benzoate |
| | 8.00 | Cetiol B | Dibutyl adipate |
| B | 2.00 | Uvinul A Plus | Diethylaminohydroxybenzoylhexyl benzoate |
| | 5.00 | Z-COTE MAX | Zinc oxide (and) diphenylcapryl-methicone |
| C | 3.00 | Glycerol 87% | Glycerol |
| | 0.10 | Edeta BD | Disodium EDTA |
| | 1.50 | Veegum Ultra | Magnesium aluminum silicate |
| | 1.50 | Lanette E | Sodium cetearyl sulfate |
| | 5.0% | P18 | |
| | 0.30 | Carbopol Ultrez 10 P | Carbomer |
| | ad | Water dem. | Water |
| D | 1.00 | Phenonip | Phenoxyethanol, methyl paraben, ethyl paraben, butyl paraben, propyl paraben, isobutyl paraben |

(90)

| | | | |
|---|---|---|---|
| A | 3.50 | Cremophor A 6 | Ceteareth-6, stearyl alcohol |
| | 1.50 | Cremophor A 25 | Ceteareth-25 |
| | 7.50 | Uvinul MC 80 | Ethylhexyl methoxycinnamate |
| | 2.00 | Uvinul A Plus | Diethylaminohydroxybenzoylhexyl benzoate |
| | 2.00 | Dow Corning 345 | Cyclopentasiloxane, cyclohexasiloxane fluid |
| | 0.50 | Beeswax 3044 PH | Beeswax |
| | 3.00 | Lanette O | Cetearyl alcohol |
| | 10.00 | Miglyol 812 | Caprylic/capric triglyceride |
| B | 5.00 | T-Lite SF-S | Titanium dioxide, silicon hydrate, aluminum hydrate, methicone/dimethicone copolymer |
| C | 3.00 | Glycerol 87% | Glycerol |
| | 0.20 | Edeta BD | Disodium EDTA |
| | 0.30 | Keltrol T | Xanthan gum |
| | 1.00 | Plantacare 2000 | Decyl glucoside |
| | 2.0% | P18 | |
| | 57.30 | Water dem. | Aqua dem. |
| D | 1.00 | Vitamin E acetate | Tocopheryl acetate |
| | 0.20 | Bisabolol rac. | Bisabolol |

(91)

| | | | |
|---|---|---|---|
| A | 10.00 | Uvinul A Plus B | Ethylhexyl methoxycinnamate, diethylaminohydroxybenzoylhexyl benzoate |
| | 10.00 | Uvinul N 539 T | Octocrylene |
| | 4.00 | Eumulgin VL 75 | Lauryl glucoside, polyglyceryl-2 dipolyhydroxystearate, glycerol |
| | 8.00 | Cetiol B | Dibutyl adipate |
| | 8.00 | Finsolv TN | $C_{12-15}$-Alkyl benzoate |
| | 12.00 | Myritol 331 | Cocoglycerides |
| | 1.00 | Lanette E | Sodium cetearyl sulfate |
| | 2.00 | Lanette O | Cetearyl alcohol |
| B | 3.00 | Z-COTE MAX | Zinc oxide (and) diphenylcapryl-methicone |
| C | 35.08 | Water dem. | Aqua dem. |
| | 0.38 | Citric acid | Citric acid |
| | 2.9 | Glycerol 87% | Glycerol |
| | 0.05 | Edeta BD | Disodium EDTA |
| | 0.20 | Allantoin | Allantoin |
| | 0.30 | Keltrol | Xanthan gum |
| | 0.1% | P18 | |
| | 1.50 | Veegum Ultra | Magnesium aluminum silicate |
| D | 0.50 | Phenonip | |
| | 1.00 | Vitamin E acetate | Tocopheryl acetate |

(92)

| | | | |
|---|---|---|---|
| A | 0.70 | Cremophor A 25 | Ceteareth-25 |
| | 1.70 | Cremophor A 6 | Ceteareth-6, stearyl alcohol |
| | 2.00 | Uvinul A Plus | Diethylaminohydroxybenzoylhexyl benzoate |
| | 3.00 | Uvinul N 539 T | Octocrylene |
| | 3.00 | Z-COTE MAX | Zinc oxide (and) diphenylcapryl-methicone |
| | 2.00 | Abil B 8843 | PEG-14 dimethicone |
| | 3.60 | Lanette O | Cetearyl alcohol |
| | 4.00 | Uvinul MC 80 | Ethylhexyl methoxycinnamate |
| | 2.00 | Cetiol B | Dibutyl adipate |
| B | 4.00 | Glycerol 87% | Glycerol |
| | 0.20 | Edeta BD | Disodium EDTA |
| | 71.00 | Water dem. | Panthenol |
| C | 4.00 | Luvigel EM | Caprylic/capric triglyceride, sodium acrylate copolymer |
| D | 1.00 | Vitamin E acetate | Tocopheryl acetate |
| | 1.0% | P18 | |
| | 0.20 | Bisabolol rac. | Bisabolol |
| | q.s. | Preservative | |

(93)

| | | | |
|---|---|---|---|
| A | 7.50 | Uvinul MC 80 | Ethylhexyl methoxycinnamate |
| | 5.00 | Uvinul N 539 T | Octocrylene |
| | 3.00 | Emulgade PL 68/50 | Cetearyl glucoside, cetearyl alcohol |
| | 2.00 | Dracorin 100 SE | Glyceryl stearate, PEG-100 stearates |
| | 1.00 | Fitoderm | Squalane |
| | 0.50 | Cremophor WO 7 | PEG-7 hydrogenated castor oil |
| | 0.50 | Cremophor PS 20 | Polysorbate 20 |
| | 2.00 | Dry Flo Pure | Aluminum starch octenyl succinate |
| B | 5.00 | Z-COTE MAX | Zinc oxide (and) diphenylcapryl-methicone |
| | 0.03 | Sicomet Blue P 77 007 | C.I. 77 007, Ultramarine |
| C | 4.00 | 1,2-Propylene glycol Care | Propylene glycol |
| | 2.00 | D-Panthenol 50 P | Panthenol, propylene glycol |
| | 0.20 | Keltrol | Xanthan gum |
| | 0.50 | Simulgel 600 | Acrylamide/sodium acryloyl-dimethyltaurate copolymer, isohexadecane, polysorbate 80 |
| | 0.5% | P18 | |
| | 65.27 | Water dem. | Aqua dem. |
| | q.s. | Preservative | |
| | 0.50 | Vitamin E acetate | Tocopheryl acetate |

(94)

| | | | |
|---|---|---|---|
| A | 6.00 | Gilugel SIL 5 | Cyclomethicone (and) aluminum/magnesium hydroxide stearate |
| | 5.00 | Uvinul N 539 T | Octocrylene |
| | 2.00 | Mexoryl XL | Drometrizole trisiloxane |
| | 1.00 | Uvinul T 150 | Ethylhexyltriazone |
| | 3.00 | T-Lite SF-S | Titanium dioxide, silicon hydrate, aluminum hydrate, methicone/dimethicone copolymer |
| | 5.00 | Finsolv TN | $C_{12-15}$-Alkyl benzoate |
| | 4.00 | Abil WE 09 | Polyglyceryl-4 isostearate, cetyl-PEG-/PPG-10-/1-dimethicone, hexyl laurate |
| | 2.00 | Cosmacol EMI | Di-$C_{12-13}$-alkyl malate |
| | 3.00 | Isopropyl palmitate | Isopropyl palmitate |
| | 5.00 | Abil B 8839 | Cyclopentasiloxane, cyclohexasiloxane |
| | 0.50 | Abil 350 | Dimethicone |
| B | 0.50 | Sodium chloride | Sodium chloride |
| | 0.20 | Edeta BD | Disodium EDTA |
| | 1.0% | P18 | |
| | 61.30 | Water dem. | Aqua dem. |
| C | 1.00 | Vitamin E acetate | Tocopheryl acetate |
| | 0.50 | Phenonip | |

(95)

| | | | |
|---|---|---|---|
| A | 1.00 | Abil Care 85 | Bis-PEG-/PPG-16-/16-PEG-/PPG-16-/16-dimethicone, caprylic/capric triglyceride |
| | 3.00 | Cremophor CO 40 | PEG-40 hydrogenated castor oil |
| | 0.30 | Cremophor WO 7 | PEG-7 hydrogenated castor oil |
| | 5.00 | Uvinul N 539 T | Octocrylene |
| | 10.00 | Witconol APM | PPG-3 myristyl ether |
| | 2.00 | Uvinul T 150 | Ethylhexyltriazone |
| | 1.00 | Dow Corning 345 Fluid | Cyclopentasiloxane, cyclohexasiloxane |
| | 2.00 | Uvinul A Plus | Diethylaminohydroxybenzoylhexyl benzoate |
| B | 5.00 | Z-COTE MAX | Zinc oxide (and) diphenylcaprylsilane |
| C | 5.00 | 1,2-Propylene glycol | Propylene glycol |
| | 0.20 | Keltrol | Xanthan gum |
| | 0.10 | Edeta BD | Disodium EDTA |
| | 1.0% | P18 | |
| | 1.50 | Simulgel 600 | Acrylamide/sodium acryloyldimethyl-taurate copolymer, isohexadecane, polysorbate 80 |
| | 59.40 | Water dem. | Aqua dem. |
| D | q.s. | Perfume oil | |
| | 0.50 | Glydant | DMDM hydantoin |

(96)

| | | | |
|---|---|---|---|
| A | 7.00 | Uvinul A Plus B | Ethylhexyl methoxycinnamate, diethylaminohydroxybenzoylhexyl benzoate |
| | 1.00 | Tinosorb S | Bisethylhexyloxyphenol methoxyphenyltriazine |
| | 1.00 | Uvinul T 150 | Ethylhexyltriazone |
| | 7.00 | Uvinul N 539 T | Octocrylene |
| | 4.00 | Eumulgin VL 75 | Lauryl glucoside, polyglyceryl-2 dipolyhydroxystearate, glycerol |
| | 8.00 | Cetiol B | Dibutyl adipate |
| | 8.00 | Finsolv TN | $C_{12-15}$-Alkyl benzoate |
| | 12.00 | Myritol 331 | Cocoglycerides |
| | 1.00 | Lanette E | Sodium cetearyl sulfate |
| | 2.00 | Lanette O | Cetearyl alcohol |
| B | 5.00 | Z-COTE MAX | Zinc oxide (and) diphenylcapryl-methicone |
| C | 35.35 | Water dem. | Aqua dem. |
| | 3.00 | Glycerol 87% | Glycerol |
| | 0.05 | Edeta BD | Disodium EDTA |
| | 0.20 | Allantoin | Allantoin |
| | 0.30 | Keltrol | Xanthan gum |
| | 0.1% | P18 | |
| | 1.50 | Veegum Ultra | Magnesium aluminum silicate |
| D | 0.50 | Phenonip | |
| | 1.00 | Vitamin E acetate | Tocopheryl acetate |

(97)

| | | | |
|---|---|---|---|
| A | 7.00 | Uvinul A Plus B | Ethylhexyl methoxycinnamate, diethylaminohydroxybenzoylhexyl benzoate |
| | 1.00 | Tinosorb S | Bisethylhexyloxyphenol methoxyphenyltriazine |
| | 1.00 | Uvinul T 150 | Ethylhexyltriazone |
| | 7.00 | Uvinul N 539 T | Octocrylene |
| | 4.00 | Eumulgin VL 75 | Lauryl glucoside, polyglyceryl-2 dipolyhydroxystearate, glycerol |
| | 8.00 | Cetiol B | Dibutyl adipate |
| | 8.00 | Finsolv TN | $C_{12-15}$-Alkyl benzoate |
| | 12.00 | Myritol 331 | Cocoglycerides |
| | 1.00 | Lanette E | Sodium cetearyl sulfate |
| | 2.00 | Lanette O | Cetearyl alcohol |
| B | 5.00 | T-Lite SF | Titanium dioxide, aluminum hydrate, dimethicone/methicone copolymer |
| C | 30.45 | Water dem. | Aqua dem. |
| | 3.00 | Glycerol 87% | Glycerol |
| | 0.05 | Edeta BD | Disodium EDTA |
| | 0.20 | Allantoin | Allantoin |
| | 0.30 | Keltrol | Xanthan gum |
| | 5.0% | P18 | |
| | 1.50 | Veegum Ultra | Magnesium aluminum silicate |
| D | 0.50 | Phenonip | |
| | 1.00 | Vitamin E acetate | Tocopheryl acetate |

(98)

| | | |
|---|---|---|
| 5.00 | Z-COTE MAX | Zinc oxide (and) diphenylcapryl-methicone |
| 2.00 | Uvinul A Plus | Diethylaminohydroxybenzoylhexyl benzoate |
| 2.00 | Mexoryl XL | Drometrizole trisiloxane |
| 3.00 | Uvinul MC 80 | Ethylhexyl methoxycinnamate |
| 0.50 | Abil 350 | Dimethicone |
| 2.75 | Carnico wax LT 20 | Carnauba (*Copernica cerifera*) wax, paraffin |
| 3.70 | Candelilla wax LT 281 LJ | Candelilla (*Euphorbia cerifera*) wax |

-continued

| | | | |
|---|---|---|---|
| | 1.80 | Beeswax 3050 PH | Beeswax |
| | 3.20 | TeCero-wax 30445 | Microcrystalline wax |
| | 3.20 | TeCero-wax 1030 K | Microcrystalline wax |
| | 1.34 | Cutina CP | Cetyl palmitate |
| | 6.40 | Vaseline | Petrolatum |
| | 7.30 | Softisan 100 | Hydrogenated cocoglycerides |
| | 10.00 | Luvitol EHO | Cetearyl ethylhexanoate |
| | 0.17 | Bisabolol nat. | Bisabolol |
| | 1.84 | Vitamin E acetate | Tocopheryl acetate |
| | 1.0% | P18 | |
| | 0.42 | D,L-Alpha-tocopherol | Tocopherol |
| | 40.38 | Castor oil | Castor (*Ricinus communis*) oil |

(99)

| | | | |
|---|---|---|---|
| A | 1.00 | Abil Care 85 | Bis-PEG-/PPG-16-/16-PEG-/PPG-16-/16-dimethicone, caprylic/capric triglyceride |
| | 3.00 | Cremophor CO 40 | PEG-40 hydrogenated castor oil |
| | 0.30 | Cremophor WO 7 | PEG-7 hydrogenated castor oil |
| | 2.00 | Mexoryl XL | Drometrizole trisiloxane |
| | 10.00 | Witconol APM | PPG-3 myristyl ether |
| | 1.00 | Uvinul T 150 | Ethylhexyltriazone |
| | 1.00 | Dow Corning 345 Fluid | Cyclopentasiloxane, cyclohexasiloxane |
| | 5.00 | Uvinul N 539 T | Octocrylene |
| B | 3.00 | T-Lite SF-S | Titanium dioxide, silicon hydrate, aluminum hydrate, methicone/dimethicone copolymer |
| C | 5.00 | 1,2-Propylene glycol | Propylene glycol |
| | 1.00 | Mexoryl SX | Terephthalidenedicamphorsulfonic acid |
| | 0.20 | Keltrol | Xanthan gum |
| | 0.10 | Edeta BD | Disodium EDTA |
| | 1.0% | P18 | |
| | 1.50 | Simulgel 600 | Acrylamide/sodium acryloyldimethyltaurate copolymer, isohexadecane, polysorbate 80 |
| | 69.50 | Water dem. | Aqua dem. |
| D | q.s. | Perfume oil | |
| | 0.50 | Glydant | DMDM hydantoin |

(100)

| | | | |
|---|---|---|---|
| A | 1.00 | Abil Care 85 | Bis-PEG-/PPG-16-/16-PEG-/PPG-16-/16-dimethicone, caprylic/capric triglyceride |
| | 3.00 | Cremophor CO 40 | PEG-40 hydrogenated castor oil |
| | 0.30 | Cremophor WO 7 | PEG-7 hydrogenated castor oil |
| | 2.00 | Parsol 1789 | Butylmethoxydibenzoylmethane |
| | 2.00 | Mexoryl XL | Drometrizole trisiloxane |
| | 10.00 | Witconol APM | PPG-3 myristyl ether |
| | 1.00 | Uvinul T 150 | Ethylhexyltriazone |
| | 1.00 | Dow Corning 345 Fluid | Cyclopentasiloxane, cyclohexasiloxane |
| | 5.00 | Uvinul N 539 T | Octocrylene |
| B | 3.00 | T-Lite SF-S | Titanium dioxide, silicon hydrate, aluminum hydrate, methicone/dimethicone copolymer |
| C | 5.00 | 1,2-Propylene glycol | Propylene glycol |
| | 1.00 | Mexoryl SX | Terephthalidenedicamphorsulfonic acid |
| | 0.20 | Keltrol | Xanthan gum |
| | 0.10 | Edeta BD | Disodium EDTA |
| | 0.2% | P18 | |
| | 1.50 | Simulgel 600 | Acrylamide/sodium acryloyldimethyltaurate copolymer, isohexadecane, polysorbate 80 |
| | 68.30 | Water dem. | Aqua dem. |
| D | q.s. | Perfume oil | |
| | 0.50 | Glydant | DMDM hydantoin |

(101)

| | | | |
|---|---|---|---|
| A | 0.70 | Cremophor A 25 | Ceteareth-25 |
| | 1.70 | Cremophor A 6 | Ceteareth-6, stearyl alcohol |
| | 2.00 | Parsol 1789 | Butylmethoxydibenzoylmethane |
| | 5.00 | Uvinul N 539 T | Octocrylene |
| | 4.00 | Z-COTE MAX | Zinc oxide (and) diphenylcaprylmethicone |
| | 2.00 | Abil B 8843 | PEG-14 dimethicone |
| | 3.60 | Lanette O | Cetearyl alcohol |
| | 1.00 | Uvinul T150 | Ethylhexyltriazone |
| | 2.00 | Cetiol B | Dibutyl adipate |
| B | 4.00 | Glycerol 87% | Glycerol |
| | 0.20 | Edeta BD | Disodium EDTA |
| | 71.00 | Water dem. | Panthenol |
| C | 4.00 | Luvigel EM | Caprylic/capric triglyceride, sodium acrylate copolymer |
| | 1.0% | P18 | |
| D | 1.00 | Vitamin E acetate | Tocopheryl acetate |
| | 0.20 | Bisabolol rac. | Bisabolol |
| | q.s. | Preservative | |

Example 39

Use of P18 in a Hair Tonic

AI 5%:

| | % | Ingredient (INCI) |
|---|---|---|
| A | q.s. | Perfume oil |
| | 1.00 | PEG-40 Hydrogenated Castor Oil |
| B | 65.0 | Alcohol |
| | 1.0 | Panthenol |
| | 0.5 | Polyquarternium-16 |
| | 0.1 | Menthol |
| | 27.4 | Aqua dem. |
| | 5.00 | Aqueous solution with about 7% P18 |

Preparation: Mix phase A. Add phase B and stir until everything has dissolved. Adjust pH to pH 7.0.

Example 40

Use of P18 in a Hair Gel

AI 5%:

| | % | Ingredient (INCI) |
|---|---|---|
| A | 45.00 | Carbopol 940 1% in water |
| | 0.70 | Aminomethyl Propanol |
| B | 7.50 | VP/Methacrylamide/Vinyl Imidazole Copolymer |
| | 0.10 | Perfume oil |
| | 0.30 | PEG-40 Hydrogenated Castor Oil |
| | 0.30 | Preservative |
| | 0.05 | Disodium EDTA |
| | 0.30 | Panthenol |
| | 8.00 | Alcohol |
| | 5.00 | Aqueous solution with about 7% P18 |
| | 32.75 | Aqua dem. |

Preparation: Weigh in the components of phase A and homogenize. Dissolve phase B and stir into phase A. Adjust pH to pH 6.9.

3. Test Examples B

Example 41

Long-Term Stability of P18 Tested on *Malassezia furfur*

Since storage over longer time periods may be necessary, in the following a 1 mM P18 peptide solution (P18 sequence H-KWKLFKKIPKFLHLAKKF-NH$_2$; SEQ ID NO: 3) was stored for 12 weeks at 37° C. and the antifungal activity of the stored solution on *Malassezia furfur* was compared to the activity of a freshly prepared 1 mM P18 peptide solution. This was done through a growth test, which was carried out as follows:

Growth medium: M472-Pityrosporum medium according to DSMZ 40 g/L malt extract 20 g/L ox bile 10 g/L Tween 40

The components were sterilized at 121° C., 1 bar superatmospheric pressure for 20 minutes.

2 g/L of olive oil (sterilized by filtration and, after autoclaving, added to the other components)

Since it was a two-phase medium, the complete medium was treated with sonication in order to enlarge the phase boundary.

For agar plates, if appropriate, 150 g/L of agar agar were added to the medium.

The growth test was carried out as follows: A shake flask with M472-Pityrosporum medium was inoculated with *M. furfur* and incubated with shaking overnight at 30° C. and 200 rpm.

A 96-well microtiter plate was filled with in each case 100 μl of M472-Pityrosporum medium and inoculated with *M. furfur* suspension of the overnight culture. The *M. furfur* suspension was adjusted at the start of the experiment to an optical density, measured at 600 nm, of 0.02. The concentrates of the inhibitor solutions were 1 mM in water.

The growth of the following batches was compared:

*M. furfur* suspension without the addition of an inhibitor.

*M. furfur* suspension and addition of a fresh aqueous P18 solution with a final concentration of 50 μM.

*M. furfur* suspension and addition of a fresh aqueous P18 solution with a final concentration of 25 μM.

*M. furfur* suspension and addition of a P18 solution that had been stored at 37° C. for 12 weeks, with a final concentration of 50 μM.

*M. furfur* suspension and addition of a P18 solution that had been stored at 37° C. for 12 weeks, with a final concentration of 25 μM.

The microtiter plate was incubated with shaking at 30° C.

The growth was observed over 24 hours by measuring the optical density. The colony-forming units (CFU) were then determined by plating out 1 μl and 5 μl from each of the suspensions and, after incubation for 6 days, counting the colonies. The CFU was determined in order to exclude an influence of the two-phase medium and also the growth form of *M. furfur* on the optical density. The experiments were carried out at least in triple determinations.

TABLE 7

Counting the colony-forming units (the values given are mean values with standard deviation)

| Incubation time [h] | without inhib. | addition of aqueous P18 solution [50 μM final conc.] | addition of stored aqueous P18 solution [50 μM final conc.] | addition of aqueous P18 solution [25 μM final conc.] | addition of stored aqueous P18 solution [25 μM final conc.] |
|---|---|---|---|---|---|
| 16-18 | >1000 | 0 ± 0 | 0 ± 0 | 5 ± 8 | 6 ± 7 |
| 24 | >1000 | 1 ± 1 | 1 ± 1 | 1 ± 2 | 5 ± 5 |

The results of the growth test show that the growth of *M. furfur*, measured as colony forming unit, was effectively inhibited by the P18 peptide solution that had been stored for 12 weeks as well as by the fresh P18 peptide solution. This means that the storage of the P18 peptide solution has not influenced the activity of the solution and, consequently, that the solution was storable over this time period.

Example 42

Formulability of P18

The formulability of the peptide P18 was tested in three shampoo basic formulations. For this, in a first step the formulations with the following compositions were prepared:

TABLE 8 composition of the basic formulations

| Trade name (INCI) | formulation 31-1 | formulation 31-2 | formulation 31-3 |
|---|---|---|---|
| Texapon NSO (Sodium Laureth Sulfate) | 40% | 30% | 20% |
| Tego Betain L7 (Cocamidopropyl Betaine) | 10% | 10% | 20% |

The components were mixed and dissolved. The pH was adjusted to pH 6-7 with NaOH. In the following, two 100 mM solutions of the peptide P18 (P18 sequence H-KWKLFK-KIPKFLHLAKKF-NH$_2$; SEQ ID NO: 3) were prepared. One solution was prepared using DMSO as solvent, the other solution was prepared using water. A corresponding volume of 100 mM peptide solution was added to each of the formulations, so that the final concentration in formulations 31-1 and 31-2 was 10 mM, the final concentration of the peptide P18 in formulation 31-3 was 5 mM. The formulations thus obtained were clear and homogenic.

Example 43

Effect of Shampoo Basic Formulations Containing P18 as Ingredient

The aim of the experiment was to analyze the effect of a shampoo basic formulation containing the peptide P18 as ingredient (P18 sequence H-KWKLFKKIPKFLHLAKKF-NH$_2$). For this, in this experiment the peptide P18 was directly added to the formulation. In a first step, formulations with the following compositions were prepared:

TABLE 9

Composition of the shampoo basic formulation and the shampoo basic formulation containing P18 as ingredient.

| Trade name (INCI) | shampoo basic formulation 31-3 | shampoo basic formulation 31-3 containing P18 as ingredient |
|---|---|---|
| Texapon NSO (Sodium Laureth Sulfate) | 20% | 20% |
| Tego Betain L7 (Cocamidopropyl Betaine) | 20% | 20% |
| peptide P18 (H-KWKLFKKIPKFLHLAKKF-NH$_2$) | — | 5 mM (~1%) |

The components Texapon NSO and Tego Betain L7 were mixed and dissolved. The pH was adjusted to pH 6-7 with NaOH. In the following, a 100 mM aqueous solution of the peptide P18 (P18 sequence H-KWKLFKKIPKFLHLAKKF-NH$_2$; SEQ ID NO: 3) was prepared. A corresponding volume of the 100 mM P18 peptide solution was added to the formulation, so that the final concentration of the peptide P18 in formulation 31-3 was 5 mM. As described above, the formulation thus obtained was clear and homogenic. The effectiveness of the formulations against the fungus *Malassezia furfur* was then compared to the shampoo basic formulation containing no peptide P18.

In summary, the test was carried out as follows:
Growth medium: M472-Pityrosporum medium according to DSMZ
40 g/L malt extract
20 g/L ox bile
10 g/L Tween 40
The components were sterilized at 121° C., 1 bar superatmospheric pressure for 20 minutes.
2 g/L of olive oil (sterilized by filtration and, after autoclaving, added to the other components)
Since it was a two-phase medium, the complete medium was treated with sonication in order to enlarge the phase boundary.
For agar plates, if appropriate, 150 g/L of agar agar were added to the medium.
The growth test was carried out as follows: A shake flask with M472-Pityrosporum medium was inoculated with *M. furfur* and incubated with shaking overnight at 30° C. and 200 rpm.
A 96-well microtiter plate was filled with in each case 170 μl of M472-Pityrosporum medium and inoculated with 10 μl of *M. furfur* suspension of the overnight culture. This corresponded to an optical density, measured at 620 nm, of 0.02-0.1. 20 μl of shampoo basic formulation and 20 μl of shampoo basic formulation 31-3 containing P18 as ingredient, respectively, were added to this mixture.
Thus, in summary, the following mixtures were compared in this experiment:
*M. furfur* suspension
*M. furfur* suspension and addition of 20 μl of shampoo basic formulation 31-3
*M. furfur* suspension and addition of 20 μl of shampoo basic formulation 31-3 containing P18 as ingredient.
The microtiter plate was incubated with shaking at 30° C. After 24 hours of incubation, the colony-forming units (CFU) were determined by resuspending 1 μl of each suspension in 10 μl of medium and then plating out the obtained suspension. After incubation for 6 days, the colonies on the plate were counted. The CFU was determined in order to exclude an influence of the two-phase medium and also the growth form of *M. furfur* on the optical density. The experiments were carried out in at least two independent experiments, each with double determination.

TABLE 10

Counting the colony-forming units after incubation for 24 hours

| | *M. furfur* suspension | *M. furfur* suspension and addition of shampoo basic formulation 31-3 | *M. furfur* suspension and addition of shampoo basic formulation 31-3 containing P18 as ingredient |
|---|---|---|---|
| 24 h | >2000 | 300 ± 199 | 0 ± 0 |

The results show that shampoo basic formulation 31-3 per se already has a measurable growth inhibiting effect against *Malassezia furfur*. However, with shampoo basic formulation 31-3 containing P18 as ingredient there is no measurable growth at all. This shows that the antifungal effect of the peptide P18 is maintained in this formulation. Since no growth of *M. furfur* could be measured, it can actually be assumed that even lower concentrations of the ingredient P18 or comparable peptides or other comparable formulations can be used to inhibit the growth of *Malassezia furfur* and other *Malassezia* ssp.

Example 44

Growth Inhibition of *Malassezia furfur* with Equal Concentrations of the Peptide P18, Zincpyrithione, Climbazole and Ketoconazole, Based on % by Weight (%(Weight/Weight)

The molar masses of the peptide P18 (P18 peptide sequence H-KWKLFKKIPKFLHLAKKF-NH$_2$) and the current commercial ingredients of antidandruff shampoos inhibiting the growth of the fungus *Malassezia furfur* differ considerably. The peptide P18 has a molar mass of 2300 g/mol, Zincpyrithione has 317 g/mol, Ketokonazol has 531 g/mol and Climbazole has a molar mass of 292 g/mol. Since the experiments analyzing growth inhibition of *M. furfur* had been carried out with comparable molarities in the preceding examples, in this example growth inhibition of *Malassezia furfur* was analyzed using equal concentrations of the peptide P18, Zincpyrithione, Climbazole and Cetoconazol, based on % by weight (% (weigth/weight). For this, the procedure was as follows:
Growth medium: M472-Pityrosporum medium according to DSMZ
40 g/L malt extract
20 g/L ox bile
10 g/L Tween 40
The components were sterilized at 121° C., 1 bar superatmospheric pressure for 20 minutes.
2 g/L of olive oil (sterilized by filtration and, after autoclaving, added to the other components)
Since it was a two-phase medium, the complete medium was treated with sonication in order to enlarge the phase boundary.
For agar plates, if appropriate, 150 g/L of agar agar were added to the medium.
The growth test was carried out as follows: A shake flask with M472-Pityrosporum medium was inoculated with *M. furfur* and incubated with shaking overnight at 30° C. and 200 rpm.

A 96-well microtiter plate was filled with in each case 100 µl of M472-Pityrosporum medium and inoculated with *M. furfur* suspension of the overnight culture. The *M. furfur* suspension was adjusted at the start of the experiment to an optical density, measured at 600 nm, of 0.02. The concentrates of the inhibitor solutions were 1 mM in DMSO for the peptide P18 and 10 mM in DMSO for Zincpyrithione, Ketoconazole and Climbazole. The DMSO final concentrations were maintained the same in all experiments. This means that a corresponding volume of DMSO was added to the mixture in the case of a higher concentration of Zincpyrithione, Ketoconazole or Climbazole concentrate in order to ensure comparability to the mixtures containing P18.

The growth of the following batches was compared by measuring the optical density:

*M. furfur* suspension and addition of P18 solution with a final concentration of 50 µM (equal to 0.0115% (w/w))

*M furfur* suspension and addition of Zincpyrithione (ZPT) solution with a final concentration of 362 µM (comparison to the mixture containing 50 µM of the peptide P18)

*M furfur* suspension and addition of Ketoconazole solution with a final concentration of 216 µM (comparison to the mixture containing 50 µM of the peptide P18)

*M furfur* suspension and addition of Climbazole solution with a final concentration of 390 µM (comparison to the mixture containing 50 µM of the peptide P18)

The microtiter plate was incubated with shaking at 30° C.

After 24 hours of incubation, the colony-forming units (CFU) were determined by plating out 10 µl of medium from each of the suspensions on agar plates. After incubation for 6 days, the colonies on the plates were counted. The CFU was determined in order to exclude an influence of the two-phase medium and also the growth form of *M. furfur* on the optical density. The experiments were carried out in at least two independent experiments, each with double determination.

TABLE 11

Counting the colony-forming units (the values given are mean values from the experiments with standard deviation)

| Incubation time [h] | addition of P18 peptide solution [50 µM final conc.] | addition of Zincpyrithione solution [362 µM final conc.] | addition of Climbazole solution [390 µM final conc.] | addition of Ketoconazole solution [216 µM final conc.] |
|---|---|---|---|---|
| 24 | 1 ± 1 | 60 ± 40 | 137 ± 33 | 84 ± 76 |
| 40 | 0 ± 0 | 26 ± 7 | 35 ± 15 | 9 ± 5 |

It was observed that within the experimental period the addition of the peptide P18 reduced the CFU and, consequently, the growth of *Malassezia furfur* more effectively than the reference substances Zincpyrithione, Climbazole and Ketoconazole.

These results show effective, at least comparable growth inhibition of *Malassezia furfur* by the peptide P18 compared to Zincpyrithione, Climbazole and Ketoconazole with equal concentrations, based on % by weight (% (w/w)).

Example 45

Incubation Times with the Peptide P18 from 5 Minutes to 1 Hour

Since growth inhibition of *M. furfur* by the peptide P18 (P18 peptide sequence H-KWKLFKKIPKFLHLAKKF-NH$_2$; SEQ ID NO: 3) had so far only been analyzed over incubation times of more than one hour, now the effect of the peptide P18 within the first minutes of incubation (5 minutes, 10 minutes and 20 minutes) up to the first hour after adding to the *M. furfur* overnight culture was tested and compared to the reference substance Zincpyrithione (Sigma Aldrich). For this, the peptide P18 and the reference substance Zincpyrithione were used in concentrations of 100 µM, 200 µM and 500 µM. The experiments were carried out as follows:

Growth medium: M472-Pityrosporum medium according to DSMZ 40 g/L malt extract 20 g/L ox bile 10 g/L Tween 40

The components were sterilized at 121° C., 1 bar superatmospheric pressure for 20 minutes.

2 g/L of olive oil (sterilized by filtration and, after autoclaving, added to the other components)

Since it was a two-phase medium, the complete medium was treated with sonication in order to enlarge the phase boundary.

For agar plates, if appropriate, 150 g/L of agar agar were added to the medium.

The growth test was carried out as follows: A shake flask with M472-Pityrosporum medium was inoculated with *M. furfur* and incubated with shaking overnight at 30° C. and 200 rpm.

A 96-well microtiter plate was filled with in each case 100 µl of M472-Pityrosporum medium and inoculated with *M. furfur* suspension of the overnight culture. The *M. furfur* suspension was adjusted at the start of the experiment to an optical density, measured at 600 nm, of 0.1.

The growth of the following batches was compared:

*M. furfur* suspension and addition of the peptide P18 with a final concentration of 100 µM, plating out after 5 minutes, 10 minutes, 20 minutes and 60 minutes

*M. furfur* suspension and addition of the peptide P18 with a final concentration of 200 µM plating out after 5 minutes, 10 minutes, 20 minutes and 60 minutes

*M. furfur* suspension and addition of the peptide P18 with a final concentration of 500 µM plating out after 5 minutes, 10 minutes, 20 minutes and 60 minutes

*M. furfur* suspension and addition of Zincpyrithione with a final concentration of 100 µM plating out after 5 minutes, 10 minutes, 20 minutes and 60 minutes

*M. furfur* suspension and addition of Zincpyrithione with a final concentration of 200 µM plating out after 5 minutes, 10 minutes, 20 minutes and 60 minutes

*M. furfur* suspension and addition of Zincpyrithione with a final concentration of 500 µM plating out after 5 minutes, 10 minutes, 20 minutes and 60 minutes The microtiter plate was incubated with shaking at 30° C.

After the incubation times indicated above, the colony-forming units (CFU) were determined by plating out 50 µl from each of the suspensions and, after incubation for 6 days, counting the colonies. The CFU was determined in order to exclude an influence of the two-phase medium and also the growth form of *M. furfur* on the optical density. The experiments were independently repeated. Below, those colony-forming units are indicated which showed less than 1000 colonies and thus a significant growth inhibition.

TABLE 12

Counting the colony-forming units after the indicated incubation time

| Substance | final concentration in the experiment [μM] | colony-forming units after the indicated incubation time | | | |
|---|---|---|---|---|---|
| | | 5 minutes | 10 minutes | 20 minutes | 60 minutes |
| P18 | 100 | >1000 | >1000 | 604 | 149 ± 60 |
| | 200 | >1000 | >1000 | >1000 | 52 ± 16 |
| | 500 | >1000 | 398 ± 290 | 26 ± 6 | 1 ± 1 |
| ZPT (Zincpyrithione) | 100 | >1000 | >1000 | >1000 | >1000 |
| | 200 | >1000 | >1000 | >1000 | >1000 |
| | 500 | >1000 | >1000 | >1000 | >1000 |

The results show that after the first 10 minutes of incubation with the peptide P18 the number of living *Malassezia furfur* cells was already considerably reduced as compared to incubation with Zincpyrithione. After 60 minutes of incubation with even lower peptide P18 concentrations the colony-forming units were considerably reduced as compared to shorter incubation times. This means that the mechanism of action of the peptide P18 clearly differs from the mechanism of action of Zincpyrithione and that the peptide P18 is effective against *M. furfur* even after short incubation times.

Example 46

Effect of P18 Variants

The inhibitory effect of the following P18 variants against *M. furfur* was analyzed:

```
H-KWKLFKKIPKFLHLAKKF-NH2    (P18; carboxy-terminal end amidated;
                             SEQ ID NO: 3)

H-KWKLFKKIPKFLHLAKKF-OH     (P18-OH; carboxy-terminal end not modified;
                             SEQ ID NO: 3)

H-PKWKLFKKIPKFLHLAKKFD-OH   (P18AC-OH; carboxy-terminal end not modified;
                             SEQ ID NO: 4734)

H-PKWKLFKKIPKFLHLAKKFN-NH2  (P18AC-NH2; carboxy-terminal end amidated;
                             SEQ ID NO: 4738)
```

The experiments were carried out as follows:
Growth medium: M472-Pityrosporum medium according to DSMZ
40 g/L malt extract
20 g/L ox bile
10 g/L Tween 40

The components were sterilized at 121° C., 1 bar superatmospheric pressure for 20 minutes.

2 g/L of olive oil (sterilized by filtration and, after autoclaving, added to the other components)

Since it was a two-phase medium, the complete medium was treated with sonication in order to enlarge the phase boundary.

For agar plates, if appropriate, 150 g/L of agar agar were added to the medium.

The growth test was carried out as follows: A shake flask with M472-Pityrosporum medium was inoculated with *M. furfur* and incubated with shaking overnight at 30° C. and 200 rpm.

A 96-well microtiter plate was filled with in each case 100 μl of M472-Pityrosporum medium and inoculated with *M. furfur* suspension of the overnight culture. The *M. furfur* suspension was adjusted at the start of the experiment to an optical density, measured at 600 nm, of 0.1.

The peptide variants were dissolved in Dimethylsulfoxide (DMSO) with a final concentration of 1 mM. Optionally, DMSO can be omitted and a pure aqueous peptide solution can be used instead. 5 μl of said solution were added to 100 μl of *M. furfur* suspension (peptide P18 having a final concentration of 50 μM). In a reference mixture the same amount of DMSO containing no peptide P18 was added.

The microtiter plate was incubated with shaking at 30° C.

After 24 hours, the colony-forming units (CFU were determined by plating out 10 μl from each of the suspensions and, after incubation for 6 days, counting the colonies. Two independent experiments with in each case three identical mixtures were carried out and the number of colony-forming units was averaged.

TABLE 13

Averaged number of colony-forming units (CFU) after incubation of *M. furfur* with 50 μM of different P18 variants

| mixtures | CFU |
|---|---|
| *M. furfur* suspension without additives | 1377 |
| suspension + DMSO | 150 |
| suspension + DMSO + P18 | 0 |
| suspension + DMSO + P18-OH | 3 |
| suspension + DMSO + P18AC-OH | 37 |

The experiment shows that the solvent DMSO per se already reduces the CFU. However, all P18 variants show an increased inhibitory effect against *M. furfur* as compared to DMSO, with effectiveness increasing in the order P18AC-OH; P18-OH; P18. Following the same order, the number of negatively charged carboxylic groups decreases in the peptide molecule. It can therefore be concluded that peptide variants carrying a weak negative charge are most effective.

Example 47

Kinetics of the Effect of the Peptide P18 on *M. furfur* in the Presence of a Shampoo Basic Formulation The effect of the peptide P18 (H-KWKLFKKIPK-FLHLAKKF-NH$_2$; carboxy-terminal end amidated; SEQ ID NO: 3) as compared to Zincpyrithione and Climbazole was tested in the presence of the shampoo basic formulation and at different incubation times (table 14). The experiments were carried out as follows:

The following shampoo basic formulation was prepared:

TABLE 14 composition of the shampoo basic formulation

| Trade name (INCI) | Shampoo basic fomulation 31-3 |
|---|---|
| Texapon NSO (Sodium Laureth Sulfate) | 20% |
| Tego Betain L7 (Cocamidopropyl Betaine) | 20% |

The components Texapon NSO and Tego Betain L7 were mixed and dissolved. The pH was adjusted to pH 6-7 with NaOH.

The effect of P18, ZPT and Climbazole against *M. furfur* was analyzed as follows:

Growth medium: M472-Pityrosporum medium according to DSMZ
40 g/L malt extract
20 g/L ox bile
10 g/L Tween 40

The components were sterilized at 121° C., 1 bar superatmospheric pressure for 20 minutes.

2 g/L of olive oil (sterilized by filtration and, after autoclaving, added to the other components)

Since it was a two-phase medium, the complete medium was treated with sonication in order to enlarge the phase boundary.

For agar plates, if appropriate, 150 g/L of agar agar were added to the medium.

The growth test was carried out as follows: A shake flask with M472-Pityrosporum medium was inoculated with *M. furfur* and incubated with shaking overnight at 30° C. and 200 rpm.

A 96-well microtiter plate was filled with in each case 100 μl of M472-Pityrosporum medium and inoculated with *M. furfur* suspension of the overnight culture. The *M. furfur* suspension was adjusted at the start of the experiment to an optical density, measured at 600 nm, of 0.1. 10% (v/v) of shampoo basic formulation 31-3 were added to the *M. furfur* suspension (see table 14).

The peptide P18 was dissolved in water with a concentration of 230 g/l. The active ingredients Zincpyrithione and Climbazole were dissolved in DMSO with a concentration of 230 g/l, with the active ingredients partially remaining insolubly suspended. The peptide solution and the active ingredient solutions, respectively, were added to the *M. furfur* suspension containing shampoo basic formulation, with a final concentration of 2.3 g/l; 1.15 g/l; 0.46 g/l and 0.23 g/l.

The microtiter plate was incubated with shaking at 30° C. After incubation of the mixtures for 5 min; 10 min; 20 min; 60 min and 24 hours, the colony-forming units were determined by plating out 1 μl from each of the suspensions and, after incubation for 6 days, counting the colonies.

It was observed that in this test P18 shows superior characteristics as compared to Zincpyrithione or Climbazole.

Example 48

Long-Term Stability of the Peptide P18 in Shampoo Basic Formulations Tested on *M. furfur*

Long-term stability of the peptide P18 (H-KWKLFKKIPKFLHLAKKF-NH$_2$; carboxy-terminal end amidated) in shampoo basic formulations was tested.

The following shampoo basic formulations were prepared:

TABLE 15

| | Composition of the formulations | | |
|---|---|---|---|
| Trade name (INCI) | formulation 31-1-10 | formulation 31-3-5 | formulation 31-3-2 |
| Texapon NSO (Sodium Laureth Sulfate) | 40% | 20% | 20% |
| Tego Betain L7 (Cocamidopropyl Betaine) | 10% | 20% | 20% |
| peptide P18 | 10 mM | 5 mM | 2 mM |

The components Texapon NSO and Tego Betain L7 were mixed and dissolved. The pH was adjusted to pH 6-7 with NaOH. In the following, 100 mM of aqueous P18 peptide solution were prepared. A corresponding volume of 100 mM P18 peptide solution was added to each formulation in order to obtain peptide P18 final concentrations as indicated in table 15.

The formulations were stored at 40° C.

After 0; 12 and 22 days, the effect of the formulations against *M. furfur* was analyzed.

Growth medium: M472-Pityrosporum medium according to DSMZ
40 g/L malt extract
20 g/L ox bile
10 g/L Tween 40

The components were sterilized at 121° C., 1 bar superatmospheric pressure for 20 minutes.

2 g/L of olive oil (sterilized by filtration and, after autoclaving, added to the other components)

Since it was a two-phase medium, the complete medium was treated with sonication in order to enlarge the phase boundary.

For agar plates, if appropriate, 150 g/L of agar agar were added to the medium.

The growth test was carried out as follows: A shake flask with M472-Pityrosporum medium was inoculated with *M. furfur* and incubated with shaking overnight at 30° C. and 200 rpm.

A 96-well microtiter plate was filled with in each case 100 μl of M472-Pityrosporum medium and inoculated with *M. furfur* suspension of the overnight culture. The *M. furfur* suspension was adjusted at the start of the experiment to an optical density, measured at 600 nm, of 0.1.

10% (v/v) of the stored formulations 31-1-10; 31-3-5; 31-3-2 (table 15) were added to the *M. furfur* suspension.

The microtiter plate was incubated with shaking at 30° C. After 24 hours, the colony-forming units (CFU) were determined. For this, 1 μl and 10 μl were plated out from each of the suspensions and, after incubation for 6 days, the colonies were counted.

It was observed that P18 shows stable characteristics at the tested conditions.

Example 49

Determining the Minimum Inhibitory Concentration (MIC) of P18 Peptide in the Presence of a Shampoo Basic Formulation The minimum inhibitory concentration (MIC) of the peptide P18 (H-KWKLFKKIPKFLHLAKKF-NH$_2$; carboxy-terminal end amidated; SEQ ID NO: 3) in the presence of the shampoo basic formulation 31-3 (table 16) was tested as follows:

The following shampoo basic formulation was prepared:

TABLE 16 composition of the shampoo basic formulation

| Trade name (INCI) | shampoo basic formulation 31-3 containing P18 as ingredient |
| --- | --- |
| Texapon NSO (Sodium Laureth Sulfate) | 20% |
| Tego Betain L7 (Cocamidopropyl Betaine) | 20% |

The shampoo basic formulation was prepared by mixing and dissolving the components Texapon NSO and Tego Betain L7. The pH was adjusted to pH 6-7 with NaOH.

The effect of the peptide against *M. furfur* was analyzed as follows:

Growth medium: M472-Pityrosporum medium according to DSMZ
40 g/L malt extract
20 g/L ox bile
10 g/L Tween 40

The components were sterilized at 121° C., 1 bar superatmospheric pressure for 20 minutes.

2 g/L of olive oil (sterilized by filtration and, after autoclaving, added to the other components)

Since it was a two-phase medium, the complete medium was treated with sonication in order to enlarge the phase boundary.

For agar plates, if appropriate, 150 g/L of agar agar were added to the medium.

The growth test was carried out as follows: A shake flask with M472-Pityrosporum medium was inoculated with *M. furfur* and incubated with shaking overnight at 30° C. and 200 rpm.

A 96-well microtiter plate was filled with in each case 170 µl of M472-Pityrosporum medium and inoculated with 10 µl of *M. furfur* suspension of the overnight culture. This corresponded to an optical density of 0.02-0.1, measured at 620 nm. 20 µl of shampoo basic formulation 31-3 were added to this mixture. Peptide P18 was dissolved in DMSO with a concentration of 10 mM. Corresponding amounts of P18 solution were added in order to obtain final concentrations as indicated in table 17.

The microtiter plate was incubated with shaking at 30° C. After incubation for 24 hours, the colony-forming units (CFU) were determined by resuspending 1 µl of each of the suspensions in 10 µl of medium and then plating out the obtained suspensions. After incubation for 6 days, the colonies on the plate were counted. The experiment was carried out in double determination.

TABLE 17

Counting the colony-forming units (CFU) after 24 hours of incubation

| P18 concentration | CFU |
| --- | --- |
| 0 µM | 538 |
| 25 µM | 80 |
| 50 µM | 32 |
| 100 µM | 0 |
| 200 µM | 0 |
| 300 µM | 0 |
| 400 µM | 0 |
| 500 µM | 0 |

The results show that growth of *M. furfur* is completely inhibited by P18 concentrations above 100 µM. The minimum inhibitory concentration in the presence of shampoo basic formulation 31-3 is therefore between 50 µM and 100 µM. This shows that the antifungal effect of the peptide P18 is maintained in this formulation, even though, as compared to mixtures containing no shampoo formulation (see example 41), the activity is slightly reduced by the shampoo basic formulation used.

Example 50

Combination of the Peptide P18 with Conventional Fungicidal Active Ingredients

The effect of combinations of active ingredients comprising proportions of the conventional fungicidal active ingredient Zincpyrithion, Ketoconazole or Climbazole and of the peptide P18 (H-KWKLFKKIPKFLHLAKKF-NH$_2$; carboxy-terminal end amidated; SEQ ID NO: 3) was tested in aqueous solution and in the presence of shampoo formulation 31-3 as follows:

The following shampoo basic formulation was prepared:

TABLE 18

Composition of the shampoo basic formulation:

| Trade name (INCI) | shampoo basic formulation 31-3 |
| --- | --- |
| Texapon NSO (Sodium Laureth Sulfate) | 20% |
| Tego Betain L7 (Cocamidopropyl Betaine) | 20% |

The shampoo basic formulation was prepared by mixing and dissolving the components Texapon NSO and Tego Betain L7. The pH was adjusted to pH 6-7 with NaOH.

The effect of the peptide P18 and of said conventional agents against *M. furfur* was analyzed as follows:

Growth medium: M472-Pityrosporum medium according to DSMZ
40 g/L malt extract
20 g/L ox bile
10 g/L Tween 40

The components were sterilized at 121° C., 1 bar superatmospheric pressure for 20 minutes.

2 g/L of olive oil (sterilized by filtration and, after autoclaving, added to the other components)

Since it was a two-phase medium, the complete medium was treated with sonication in order to enlarge the phase boundary.

For agar plates, if appropriate, 150 g/L of agar agar were added to the medium.

The growth test was carried out as follows: A shake flask with M472-Pityrosporum medium was inoculated with *M. furfur* and incubated with shaking overnight at 30° C. and 200 rpm.

A 96-well microtiter plate was filled with in each case 170 µl of M472-Pityrosporum medium and inoculated with 10 µl of *M. furfur* suspension of the overnight culture. This corresponded to an optical density of 0.02-0.1, measured at 620 nm. 20 µl of shampoo basic formulation 31-3 or alternatively water were added to this mixture. The peptide P18 was dissolved in water with a concentration of 10 mM. The conventional fungicidal active ingredient was dissolved in DMSO with a concentration of 10 mM. Corresponding amounts of P18 solution and conventional fungicidal active ingredient solution were added to the mixtures in order to obtain final concentrations as indicated in table 19.

TABLE 19

Concentrations of conventional fungicidal active ingredients and P18

| Mixture no. | conventional fungicidal active ingredient concentration | P18 concentration [µM] |
|---|---|---|
| 1 | 500 µM Zincpyrithione | 1000 |
| 2 | 500 µM Zincpyrithione | 200 |
| 3 | 500 µM Zincpyrithione | 50 |
| 4 | 500 µM Zincpyrithione | 0 |
| 5 | 100 µM Zincpyrithione | 1000 |
| 6 | 100 µM Zincpyrithione | 200 |
| 7 | 100 µM Zincpyrithione | 50 |
| 8 | 100 µM Zincpyrithione | 0 |
| 9 | 20 µM Zincpyrithione | 1000 |
| 10 | 20 µM Zincpyrithione | 200 |
| 11 | 20 µM Zincpyrithione | 50 |
| 12 | 20 µM Zincpyrithione | 0 |
| 13 | 0 µM Zincpyrithione | 1000 |
| 14 | 0 µM Zincpyrithione | 200 |
| 15 | 0 µM Zincpyrithione | 50 |
| 16 | 0 µM Zincpyrithione | 0 |
| 17 | 500 µM Ketoconazole | 1000 |
| 18 | 500 µM Ketoconazole | 200 |
| 19 | 500 µM Ketoconazole | 50 |
| 20 | 500 µM Ketoconazole | 0 |
| 21 | 100 µM Ketoconazole | 1000 |
| 22 | 100 µM Ketoconazole | 200 |
| 23 | 100 µM Ketoconazole | 50 |
| 24 | 100 µM Ketoconazole | 0 |
| 25 | 20 µM Ketoconazole | 1000 |
| 26 | 20 µM Ketoconazole | 200 |
| 27 | 20 µM Ketoconazole | 50 |
| 28 | 20 µM Ketoconazole | 0 |
| 29 | 0 µM Ketoconazole | 1000 |
| 30 | 0 µM Ketoconazole | 200 |
| 31 | 0 µM Ketoconazole | 50 |
| 32 | 0 µM Ketoconazole | 0 |
| 33 | 500 µM Climbazole | 1000 |
| 34 | 500 µM Climbazole | 200 |
| 35 | 500 µM Climbazole | 50 |
| 36 | 500 µM Climbazole | 0 |
| 37 | 100 µM Climbazole | 1000 |
| 38 | 100 µM Climbazole | 200 |
| 39 | 100 µM Climbazole | 50 |
| 40 | 100 µM Climbazole | 0 |
| 41 | 20 µM Climbazole | 1000 |
| 42 | 20 µM Climbazole | 200 |
| 43 | 20 µM Climbazole | 50 |
| 44 | 20 µM Climbazole | 0 |
| 45 | 0 µM Climbazole | 1000 |
| 46 | 0 µM Climbazole | 200 |
| 47 | 0 µM Climbazole | 50 |
| 48 | 0 µM Climbazole | 0 |

The microtiter plate was incubated with shaking at 30° C.

After incubation for 24 hours, the colony-forming units (CFU) were determined by resuspending 1 µl of each of the suspensions in 10 µl of medium and then plating out the obtained suspensions. After incubation for 6 days, the colonies on the plate were counted. It turns out that combinations of P18 with conventional fungicidal active ingredients show superior characteristics as compared to conventional fungicidal active ingredients taken alone.

4. Formulation Examples B

Cosmetic antidandruff shampoo preparations comprising the peptide P18 are described below. The peptide P18 is specified in the examples below by way of representation of all of the other peptides described above. It will be appreciated by the person skilled in the art that all of the other specified peptides according to the invention can also be used in the preparations given below.

The peptide P18 can be the sole active ingredient contained in the preparations or it can be used in combination with other antidandruff active ingredients (see description).

Example 51

| Ingredients (INCI) | 1 % | 2 % | 3 % | 4 % |
|---|---|---|---|---|
| A Ammonium Laureth Sulfate | 8.7 | 8.7 | 8.7 | 8.7 |
| Ammonium Lauryl Sulfate | 7.2 | 7.2 | 7.2 | 7.2 |
| Glycol Distearate | 1.5 | 1.5 | 1.5 | 1.5 |
| Dimethicone | 1.2 | 1.2 | 1.2 | 1.2 |
| Peptide P18 | 0.05 | 0.3 | 0.05 | 0.3 |
| Zinc Pyrithione | 0 | 0 | 1 | 0.7 |
| Ammonium Xylenesulfonate | 0.8 | 0.8 | 0.8 | 0.8 |
| Cetyl Alcohol | 0.7 | 0.7 | 0.7 | 0.7 |
| Cocamide MEA | 0.6 | 0.6 | 0.6 | 0.6 |
| Hydrogenated Polydecene | 0.5 | 0.5 | 0.5 | 0.5 |
| Polyquaternium-10 | 0.4 | 0.4 | 0.4 | 0.4 |
| PEG-7M | 0.3 | 0.3 | 0.3 | 0.3 |
| Panthenol | 0.3 | 0.3 | 0.3 | 0.3 |
| Panthenyl Ethyl Ether | 0.3 | 0.3 | 0.3 | 0.3 |
| Methyl Tyrosinate HCl | 0.2 | 0.2 | 0.2 | 0.2 |
| Histidine | 0.15 | 0.15 | 0.15 | 0.15 |
| Trimethylolpropane Tricaprylate/Tricaprate | 0.15 | 0.15 | 0.15 | 0.15 |
| Lysine HCl | 0.1 | 0.1 | 0.1 | 0.1 |
| Sodium Polynaphthalenesulfonate | 0.1 | 0.1 | 0.1 | 0.1 |
| Tocopherol | 0.1 | 0.1 | 0.1 | 0.1 |
| Aqua | ad 100 | ad 100 | ad 100 | ad 100 |
| Preservative | q.s. | q.s. | q.s. | q.s. |
| Parfum | q.s. | q.s. | q.s. | q.s. |
| Tetrasodium EDTA | q.s. | q.s. | q.s. | q.s. |
| Sodium Chloride | q.s. | q.s. | q.s. | q.s. |
| B Citric Acid | q.s. | q.s. | q.s. | q.s. |
| Sodium Citrate | q.s. | q.s. | q.s. | q.s. |

Preparation: Mix and dissolve the components of phase A. Adjust the pH to pH 5-7 with phase B. Viscosity can be adjusted through Tetrasodium EDTA and/or Sodium Chloride. Preferred viscosity is between 5000-15000 mPas.

Example 52

| | Ingredients (INCI) | 1 % | 2 % | 3 % | 4 % |
|---|---|---|---|---|---|
| A | Sodium Laureth Sulfate | 9 | 9 | 9 | 9 |
| | Cocamidopropyl Betaine | 6 | 6 | 6 | 6 |
| | Sodium Chloride | 3 | 3 | 3 | 3 |
| | PEG-3 Distearate | 1.5 | 1.5 | 1.5 | 1.5 |
| | Propylene Glycol | 1.5 | 1.5 | 1.5 | 1.5 |
| | Zinc Pyrithione | 0 | 0 | 1 | 0.7 |
| | Piroctone Olamine | 0 | 0 | 0.8 | 0.6 |
| | Climbazolee | 0 | 0 | 0.5 | 0.3 |
| | Peptid P18 | 0.05 | 0.3 | 0.05 | 0.3 |
| | Guar Hydroxypropyltrimonium Chloride | 0.2 | 0.2 | 0.2 | 0.2 |
| | Panthenol | 0.3 | 0.3 | 0.3 | 0.3 |
| | Sodium Polynaphthalenesulfonate | 0.2 | 0.2 | 0.2 | 0.2 |
| | Glucose | 0.2 | 0.2 | 0.2 | 0.2 |
| | Tocopherol | 0.1 | 0.1 | 0.1 | 0.1 |
| | Aqua | ad 100 | ad 100 | ad 100 | ad 100 |
| | Acrylates/Beheneth-25 Methacrylate Copolymer | q.s. | q.s. | q.s. | q.s. |
| | Cellulose Gum | q.s. | q.s. | q.s. | q.s. |
| | Parfum | q.s. | q.s. | q.s. | q.s. |
| | Preservative | q.s. | q.s. | q.s. | q.s. |
| B | Sodium Citrate | q.s. | q.s. | q.s. | q.s. |
| | Lactic Acid | q.s. | q.s. | q.s. | q.s. |

Preparation: Mix and dissolve components of phase A. Adjust the pH to pH 5-7 with phase B. Viscosity can be adjusted through Cellulose Gum and/or Acrylates/Beheneth-25 Methacrylate Copolymer. Preferred viscosity is between 5000-15000 mPas.

Example 53

| | Ingredients (INCI) | 1 % | 2 % | 3 % | 4 % |
|---|---|---|---|---|---|
| A | Sodium Laureth Sulfate | 7 | 7 | 7 | 7 |
| | Disodium Laureth Sulfosuccinate | 5.5 | 5.5 | 5.5 | 5.5 |
| | Cocamidopropyl Betaine | 3 | 3 | 3 | 3 |
| | Glycerin | 1.5 | 1.5 | 1.5 | 1.5 |
| | Zinc Pyrithione | 0 | 0 | 1 | 0.7 |
| | Zinc Sulfate | 0 | 0 | 0.7 | 0.5 |
| | Peptid P18 | 0.05 | 0.3 | 0.05 | 0.3 |
| | Sodium Chloride | 0.8 | 0.8 | 0.8 | 0.8 |
| | Dimethiconol | 0.8 | 0.8 | 0.8 | 0.8 |
| | PPG-12 | 0.8 | 0.8 | 0.8 | 0.8 |
| | Guar Hydroxypropyltrimonium Chloride | 0.3 | 0.3 | 0.3 | 0.3 |
| | TEA-Dodecylbenzenesulfonate | 0.4 | 0.4 | 0.4 | 0.4 |
| | Sodium Polynaphthalenesulfonate | 0.1 | 0.1 | 0.1 | 0.1 |
| | Ascorbyl Palmitate | 0.15 | 0.15 | 0.15 | 0.15 |
| | Tocopherol | 0.1 | 0.1 | 0.1 | 0.1 |
| | Lysine HCl | 0.15 | 0.15 | 0.15 | 0.15 |
| | Aqua | ad 100 | ad 100 | ad 100 | ad 100 |
| | Parfum | q.s. | q.s. | q.s. | q.s. |
| | Carbomer | q.s. | q.s. | q.s. | q.s. |
| | Preservative | q.s. | q.s. | q.s. | q.s. |
| B | Sodium Hydroxide | q.s. | q.s. | q.s. | q.s. |
| | Citric Acid | q.s. | q.s. | q.s. | q.s. |

Preparation: Mix and dissolve components of phase A. Adjust the pH to pH 5-7 with phase B. Viscosity can be adjusted through Carbomer and/or Sodium Hydroxide. Preferred viscosity is between 5000-15000 mPas.

Example 54

| | Ingredients (INCI) | 1 % | 2 % | 3 % | 4 % |
|---|---|---|---|---|---|
| A | Ammonium Lauryl Sulfate | 8.1 | 8.1 | 8.1 | 8.1 |
| | Ammonium Laureth Sulfate | 5.8 | 5.8 | 5.8 | 5.8 |
| | Cocamide MEA | 4 | 4 | 4 | 4 |
| | Cocamidopropyl Betaine | 2.3 | 2.3 | 2.3 | 2.3 |
| | Dimethiconol | 1 | 1 | 1 | 1 |
| | PEG-5 Cocamide | 0.95 | 0.95 | 0.95 | 0.95 |
| | Zinc Pyrithione | 0 | 0 | 0.5 | 0.3 |
| | Peptid P18 | 0.05 | 0.3 | 0.05 | 0.3 |
| | Glycol Distearate | 0.5 | 0.5 | 0.5 | 0.5 |
| | PPG-9 | 0.7 | 0.7 | 0.7 | 0.7 |
| | Guar Hydroxypropyltrimonium Chloride | 0.25 | 0.25 | 0.25 | 0.25 |
| | TEA-Dodecylbenzenesulfonate | 0.3 | 0.3 | 0.3 | 0.3 |
| | Ammonium Chloride | 0.2 | 0.2 | 0.2 | 0.2 |
| | Ammonium Xylenesulfonate | 0.1 | 0.1 | 0.1 | 0.1 |
| | Aqua | ad 100 | ad 100 | ad 100 | ad 100 |
| | Carbomer | q.s. | q.s. | q.s. | q.s. |
| | Preservative | q.s. | q.s. | q.s. | q.s. |
| | Parfum | q.s. | q.s. | q.s. | q.s. |

Preparation: Mix and dissolve components of phase A. Adjust the pH to pH 5-7 with phase B. Viscosity can be adjusted through Carbomer. Preferred viscosity is between 5000-15000 mPas.

Example 55

| | Ingredients (INCI) | 1 % | 2 % | 3 % | 4 % |
|---|---|---|---|---|---|
| A | Sodium Myreth Sulfate | 7.4 | 7.4 | 7.4 | 7.4 |
| | Sodium Laureth Sulfate | 6.1 | 6.1 | 6.1 | 6.1 |
| | Cocamidopropyl Betaine | 4.3 | 4.3 | 4.3 | 4.3 |
| | Disodium PEG-5 Laurylcitrate Sulfosuccinate | 3.4 | 3.4 | 3.4 | 3.4 |
| | PEG-3 Distearate | 1.5 | 1.5 | 1.5 | 1.5 |
| | PEG-40 Hydrogenated Castor Oil | 0.1 | 0.1 | 0.1 | 0.1 |
| | Tetrasodium Iminodisuccinate | 0.6 | 0.6 | 0.6 | 0.6 |
| | Peptid P18 | 0.05 | 0.3 | 0.05 | 0.3 |
| | Piroctone Olamine | 0 | 0 | 1 | 0.7 |
| | Polyquaternium-10 | 0.2 | 0.2 | 0.2 | 0.2 |
| | Sodium Chloride | 0.8 | 0.8 | 0.8 | 0.8 |
| | Panthenol | 0.4 | 0.4 | 0.4 | 0.4 |
| | Guar Hydroxypropyltrimonium Chloride | 0.7 | 0.7 | 0.7 | 0.7 |
| | Oryzanol | 0.3 | 0.3 | 0.3 | 0.3 |
| | Aqua | ad 100 | ad 100 | ad 100 | ad 100 |
| | Parfum | q.s. | q.s. | q.s. | q.s. |
| | Preservatives | q.s. | q.s. | q.s. | q.s. |
| B | Citric Acid | q.s. | q.s. | q.s. | q.s. |

Preparation: Mix and dissolve components of phase A. Adjust the pH to pH 5-7 with phase B. Preferred viscosity is between 5000-15000 mPas.

Example 56

| | Ingredients (INCI) | 1 % | 2 % | 3 % | 4 % |
|---|---|---|---|---|---|
| A | Sodium Laureth Sulfate | 11 | 11 | 11 | 11 |
| | Cocamidopropyl Betaine | 6 | 6 | 6 | 6 |
| | PEG-3 Distearate | 2 | 2 | 2 | 2 |
| | Peptid P18 | 0.05 | 0.3 | 0.05 | 0.3 |
| | Piroctone Olamine | 0 | 0 | 1 | 0.7 |
| | Polyquaternium-10 | 0.2 | 0.2 | 0.2 | 0.2 |
| | PEG-40 Hydrogenated Castor Oil | 0.2 | 0.2 | 0.2 | 0.2 |
| | Sodium Chloride | 0.8 | 0.8 | 0.8 | 0.8 |
| | Propylene Glycol | 0.4 | 0.4 | 0.4 | 0.4 |
| | Trideceth-9 | 0.6 | 0.6 | 0.6 | 0.6 |
| | Aqua | ad 100 | ad 100 | ad 100 | ad 100 |
| | Parfum | q.s. | q.s. | q.s. | q.s. |
| | Preservatives | q.s. | q.s. | q.s. | q.s. |
| B | Citric Acid | q.s. | q.s. | q.s. | q.s. |

Preparation: Mix and dissolve components of phase A. Adjust the pH to pH 5-7 with phase B. Preferred viscosity is between 5000-15000 mPas.

Example 57

| | Ingredients (INCI) | 1 % | 2 % | 3 % | 4 % |
|---|---|---|---|---|---|
| A | Alcohol denat. | 3 | 3 | 3 | 3 |
| | VP/VA Copolymer | 2.9 | 2.9 | 2.9 | 2.9 |
| | PEG 32 | 1.5 | 1.5 | 1.5 | 1.5 |
| | PEG-40 Hydrogenated Castor Oil | 0.1 | 0.1 | 0.1 | 0.1 |
| | Amino Methyl Propanol | 0.4 | 0.4 | 0.4 | 0.4 |
| | PEG-12 Dimethicone | 0.2 | 0.2 | 0.2 | 0.2 |
| | Panthenol | 0.3 | 0.3 | 0.3 | 0.3 |
| | Peptid P18 | 0.05 | 0.3 | 0.05 | 0.3 |
| | Piroctone Olamine | 0 | 0 | 1 | 0.7 |
| | Benzophenone-4 | 0.05 | 0.05 | 0.05 | 0.05 |
| | VP/Methacrylamide/Vinyl Imidazole Copolymer | 0.9 | 0.9 | 0.9 | 0.9 |
| | Aqua | ad 100 | ad 100 | ad 100 | ad 100 |
| | Preservatives | q.s. | q.s. | q.s. | q.s. |
| | Parfum | q.s. | q.s. | q.s. | q.s. |
| | Carbomer | q.s. | q.s. | q.s. | q.s. |

Preparation: Mix and dissolve components of phase A. Adjust the pH to pH 5-7 with phase B. Viscosity can be adjusted through Carbomer. Preferred viscosity is between 5000-15000 mPas.

Example 58

| | Ingredients (INCI) | 1 % | 2 % | 3 % | 4 % |
|---|---|---|---|---|---|
| A | Sodium Laureth Sulfate | 13 | 13 | 13 | 13 |
| | Disodium Cocoamphodiacetate | 3.3 | 3.3 | 3.3 | 3.3 |
| | Sodium Chloride | 1.2 | 1.2 | 1.2 | 1.2 |
| | Glycol Distearate | 0.7 | 0.7 | 0.7 | 0.7 |
| | Peptid P18 | 0.05 | 0.3 | 0.05 | 0.3 |
| | Climbazole | 0 | 0 | 0.5 | 0.3 |
| | PEG-7 Glyceryl Cocoate | 0.2 | 0.2 | 0.2 | 0.2 |
| | Salicylic Acid | 0.4 | 0.4 | 0.4 | 0.4 |
| | Styrene/Acrylates Copolymer | 0.36 | 0.36 | 0.36 | 0.36 |
| | Laureth-4 | 0.2 | 0.2 | 0.2 | 0.2 |
| | Panthenol | 0.3 | 0.3 | 0.3 | 0.3 |
| | PEG-40 Hydrogenated Castor Oil | 0.3 | 0.3 | 0.3 | 0.3 |
| | Hydrogenated Castor Oil | 0.6 | 0.6 | 0.6 | 0.6 |
| | Cocamidopropyl Betaine | 0.9 | 0.9 | 0.9 | 0.9 |
| | Polyquaternium-10 | 0.3 | 0.3 | 0.3 | 0.3 |
| | Glycerin | 0.8 | 0.8 | 0.8 | 0.8 |
| | Aqua | ad 100 | ad 100 | ad 100 | ad 100 |
| | Preservatives | q.s. | q.s. | q.s. | q.s. |
| | Parfum | q.s. | q.s. | q.s. | q.s. |
| B | Citric Acid | q.s. | q.s. | q.s. | q.s. |

Preparation: Mix and dissolve components of phase A. Adjust the pH to pH 5-7 with phase B. Preferred viscosity is between 5000-15000 mPas.

Example 59

| | Ingredients (INCI) | 1 % | 2 % | 3 % | 4 % |
|---|---|---|---|---|---|
| A | Sodium Laureth Sulfate | 11 | 11 | 11 | 11 |
| | Coco-Betaine | 5 | 5 | 5 | 5 |
| | Dimethicone | 0.9 | 0.9 | 0.9 | 0.9 |
| | Cetyl Alcohol | 0.4 | 0.4 | 0.4 | 0.4 |
| | Hydroxystearyl Cetyl Ether | 0.4 | 0.4 | 0.4 | 0.4 |
| | Sodium Chloride | 0.3 | 0.3 | 0.3 | 0.3 |
| | Cocamide MIPA | 0.4 | 0.4 | 0.4 | 0.4 |
| | Polyquaternium 10 | 0.3 | 0.3 | 0.3 | 0.3 |
| | Propylene Glycol | 0.3 | 0.3 | 0.3 | 0.3 |
| | Pyridoxine HCL | 0.1 | 0.1 | 0.1 | 0.1 |
| | Peptid P18 | 0.05 | 0.3 | 0.05 | 0.3 |
| | Zinc Pyrithione | 0 | 0 | 1 | 0.7 |
| | Aqua | ad 100 | ad 100 | ad 100 | ad 100 |
| | Preservatives | q.s. | q.s. | q.s. | q.s. |
| | Carbomer | q.s. | q.s. | q.s. | q.s. |
| | Parfum | q.s. | q.s. | q.s. | q.s. |

Preparation: Mix and dissolve components of phase A. Adjust the pH to pH 5-7 with phase B. Viscosity can be adjusted through Carbomer. Preferred viscosity is between 5000-15000 mPas.

Example 60

| | Ingredients (INCI) | 1 % | 2 % | 3 % | 4 % |
|---|---|---|---|---|---|
| A | Sodium Laureth Sulfate | 13 | 13 | 13 | 13 |
| | Polysorbate (21) | 5 | 5 | 5 | 5 |
| | Dimethicone | 0.8 | 0.8 | 0.8 | 0.8 |
| | Cocamidopropyl Betaine | 0.9 | 0.9 | 0.9 | 0.9 |
| | Cetyl Alcohol | 0.4 | 0.4 | 0.4 | 0.4 |
| | Hexylene Glycol | 0.3 | 0.3 | 0.3 | 0.3 |
| | Guar Hydroxypropyltrimonium Chloride | 0.2 | 0.2 | 0.2 | 0.2 |
| | Cocamide MIPA | 0.5 | 0.5 | 0.5 | 0.5 |
| | Hydroxystearyl Cetyl Ether | 0.6 | 0.6 | 0.6 | 0.6 |
| | Sodium Chloride | 0.3 | 0.3 | 0.3 | 0.3 |
| | Propylene Glycol | 0.3 | 0.3 | 0.3 | 0.3 |
| | Peptid P18 | 0.05 | 0.3 | 0.05 | 0.3 |
| | Pyroctone Olamine | 0 | 0 | 1 | 0.7 |

| Ingredients (INCI) | 1 % | 2 % | 3 % | 4 % |
|---|---|---|---|---|
| Aqua | ad 100 | ad 100 | ad 100 | ad 100 |
| Preservatives | q.s. | q.s. | q.s. | q.s. |
| Carbomer | q.s. | q.s. | q.s. | q.s. |
| Parfum | q.s. | q.s. | q.s. | q.s. |

Preparation: Mix and dissolve components of phase A. Adjust the pH to pH 5-7 with phase B. Viscosity can be adjusted through Carbomer. Preferred viscosity is between 5000-15000 mPas.

Example 61

| | Ingredients (INCI) | 1 % | 2 % | 3 % | 4 % |
|---|---|---|---|---|---|
| A | Sodium Laureth Sulfate | 9 | 9 | 9 | 9 |
| | Disodium Cocoamphodiacetate | 6 | 6 | 6 | 6 |
| | Glycerin | 2.1 | 2.1 | 2.1 | 2.1 |
| | Glycol Distearate | 1.2 | 1.2 | 1.2 | 1.2 |
| | Sodium Chloride | 0.9 | 0.9 | 0.9 | 0.9 |
| | Sodium Laureth-8 Sulfate | 0.9 | 0.9 | 0.9 | 0.9 |
| | Hexylene Glycol | 0.3 | 0.3 | 0.3 | 0.3 |
| | Polyquaternium-10 | 0.1 | 0.1 | 0.1 | 0.1 |
| | Magnesium Laureth-8 Sulfate | 0.3 | 0.3 | 0.3 | 0.3 |
| | Propylene Glycol | 0.8 | 0.8 | 0.8 | 0.8 |
| | Magnesium Laureth Sulfate | 0.6 | 0.6 | 0.6 | 0.6 |
| | Sodium Oleth Laureth | 0.7 | 0.7 | 0.7 | 0.7 |
| | PEG-55 Propylene Glycol Oleate | 0.7 | 0.7 | 0.7 | 0.7 |
| | Peptid P18 | 0.05 | 0.3 | 0.05 | 0.3 |
| | Salicylic Acid | 0 | 0 | 0.5 | 0.3 |
| | Polyquaternium-30 | 0.35 | 0.35 | 0.35 | 0.35 |
| | Magnesium Oleth Sulfate | 0.65 | 0.65 | 0.65 | 0.65 |
| | 2-Oleamido-1,3-Octadecanediol | 0.4 | 0.4 | 0.4 | 0.4 |
| | Aqua | ad 100 | ad 100 | ad 100 | ad 100 |
| | Preservatives | q.s. | q.s. | q.s. | q.s. |
| | Carbomer | q.s. | q.s. | q.s. | q.s. |
| | Parfum | q.s. | q.s. | q.s. | q.s. |

Preparation: Mix and dissolve components of phase A. Adjust the pH to pH 5-7 with phase B. Viscosity can be adjusted through Carbomer. Preferred viscosity is between 5000-15000 mPas.

Example 62

| | Ingredients (INCI) | 1 % | 2 % | 3 % | 4 % |
|---|---|---|---|---|---|
| A | Sodium Laureth Sulfate | 10.5 | 10.5 | 10.5 | 10.5 |
| | Cocamidopropyl Betaine | 8 | 8 | 8 | 8 |
| | Glycerin | 3 | 3 | 3 | 3 |
| | Peptid P18 | 0.05 | 0.3 | 0.05 | 0.3 |
| | Zinc pyrithone | 0 | 0 | 1 | 0.7 |
| | PEG-55 Propylene Glycol Oleate | 0.7 | 0.7 | 0.7 | 0.7 |
| | Disodium ricinoleamido MEA-sulfosuccinate | 0.6 | 0.6 | 0.6 | 0.6 |
| | Propylene Glycol | 0.7 | 0.7 | 0.7 | 0.7 |
| | Glyceryl Laurate | 0.4 | 0.4 | 0.4 | 0.4 |
| | PPG-5-Ceteth-20 | 0.32 | 0.32 | 0.32 | 0.32 |
| | Acrylates Copolymer | 0.2 | 0.2 | 0.2 | 0.2 |
| | Disodium Cocoamphodipropionate | 0.54 | 0.54 | 0.54 | 0.54 |
| | Lecithin | 0.4 | 0.4 | 0.4 | 0.4 |

| | Ingredients (INCI) | 1 % | 2 % | 3 % | 4 % |
|---|---|---|---|---|---|
| | Aqua | ad 100 | ad 100 | ad 100 | ad 100 |
| | Preservatives | q.s. | q.s. | q.s. | q.s. |
| | Parfum | q.s. | q.s. | q.s. | q.s. |
| B | Phosphoric Acid | q.s. | q.s. | q.s. | q.s. |

Preparation: Mix and dissolve components of phase A. Adjust the pH to pH 5-7 with phase B. Preferred viscosity is between 5000-15000 mPas.

Example 63

| | Ingredients (INCI) | 1 % | 2 % | 3 % | 4 % |
|---|---|---|---|---|---|
| A | Sodium Laureth Sulfate | 9.3 | 9.3 | 9.3 | 9.3 |
| | Sodium Lauryl Sulfate | 7.6 | 7.6 | 7.6 | 7.6 |
| | Cocamide MEA | 1 | 1 | 1 | 1 |
| | Zinc Carbonate | 0.6 | 0.6 | 0.6 | 0.6 |
| | Glycol Distearate | 0.8 | 0.8 | 0.8 | 0.8 |
| | Peptid P18 | 0.05 | 0.3 | 0.05 | 0.3 |
| | Zinc Pyrithione | 0 | 0 | 1 | 0.7 |
| | Cetyl Alcohol | 0.36 | 0.36 | 0.36 | 0.36 |
| | Dimethicone | 0.42 | 0.42 | 0.42 | 0.42 |
| | Sodium Xylenesulfonate | 0.23 | 0.23 | 0.23 | 0.23 |
| | Magnesium Sulfate | 0.37 | 0.37 | 0.37 | 0.37 |
| | Ammonium Laureth Sulfate | 0.9 | 0.9 | 0.9 | 0.9 |
| | Sodium Diethylenetriamine Pentamethylene Phosphonate | 0.6 | 0.6 | 0.6 | 0.6 |
| | Etidronic Acid | 0.2 | 0.2 | 0.2 | 0.2 |
| | Sodium Polynaphthalenesulfonate | 0.35 | 0.35 | 0.35 | 0.35 |
| | Aqua | ad 100 | ad 100 | ad 100 | ad 100 |
| | Preservatives | q.s. | q.s. | q.s. | q.s. |
| | Sodium Chloride | q.s. | q.s. | q.s. | q.s. |
| | Magnesium Carbonate Hydroxide | q.s. | q.s. | q.s. | q.s. |
| | Tetrasodium EDTA | q.s. | q.s. | q.s. | q.s. |
| | Parfum | q.s. | q.s. | q.s. | q.s. |

Preparation: Mix and dissolve components of phase A. Adjust the pH to pH 5-7 with phase B. Viscosity can be adjusted through Tetrasodium EDTA and/or Sodium Chloride. Preferred viscosity is between 5000-15000 mPas.

Example 64

| | Ingredients (INCI) | 1 % | 2 % | 3 % | 4 % |
|---|---|---|---|---|---|
| A | Sodium Laureth Sulfate | 9.3 | 9.3 | 9.3 | 9.3 |
| | Sodium Lauryl Sulfate | 7.6 | 7.6 | 7.6 | 7.6 |
| | Cocamide MEA | 1 | 1 | 1 | 1 |
| | Zinc Carbonate | 0.6 | 0.6 | 0.6 | 0.6 |
| | Glycol Distearate | 0.8 | 0.8 | 0.8 | 0.8 |
| | Sodium Chloride | 0.7 | 0.7 | 0.7 | 0.7 |
| | Peptid P18 | 0.05 | 0.3 | 0.05 | 0.3 |
| | Zinc Pyrithione | 0 | 0 | 1 | 0.7 |
| | Dimethicone | 0.42 | 0.42 | 0.42 | 0.42 |
| | Cetyl Alcohol | 0.36 | 0.36 | 0.36 | 0.36 |
| | Sodium Xylenesulfonate | 0.23 | 0.23 | 0.23 | 0.23 |
| | Magnesium Sulfate | 0.37 | 0.37 | 0.37 | 0.37 |
| | Guar Hydroxypropyltrimonium Chloride | 0.3 | 0.3 | 0.3 | 0.3 |
| | Ammonium Laureth Sulfate | 0.9 | 0.9 | 0.9 | 0.9 |
| | Sodium Diethylenetriamine Pentamethylene Phosphonate | 0.6 | 0.6 | 0.6 | 0.6 |

-continued

| Ingredients (INCI) | 1 % | 2 % | 3 % | 4 % |
|---|---|---|---|---|
| Etidronic Acid | 0.2 | 0.2 | 0.2 | 0.2 |
| Paraffinum Liquidum | 0.3 | 0.3 | 0.3 | 0.3 |
| Tocopheryl Acetate | 0.3 | 0.3 | 0.3 | 0.3 |
| Aqua | ad 100 | ad 100 | ad 100 | ad 100 |
| Preservatives | q.s. | q.s. | q.s. | q.s. |
| Parfum | q.s. | q.s. | q.s. | q.s. |
| Magnesium Carbonate Hydroxide | q.s. | q.s. | q.s. | q.s. |
| Sodium Polynaphthalenesulfonate | q.s. | q.s. | q.s. | q.s. |

Preparation: Mix and dissolve components of phase A. Adjust the pH to pH 5-7 with phase B. Viscosity can be adjusted through Magnesium Carbonate Hydroxide and/or Sodium Polynaphthalenesulfonate. Preferred viscosity is between 5000-15000 mPas.

Example 65

| | Ingredients (INCI) | 1 % | 2 % | 3 % | 4 % |
|---|---|---|---|---|---|
| A | Ammonium Laureth Sulfate | 11.2 | 11.2 | 11.2 | 11.2 |
| | Ammonium Lauryl Sulfate | 8.6 | 8.6 | 8.6 | 8.6 |
| | Glycol Distearate | 0.8 | 0.8 | 0.8 | 0.8 |
| | Dimethicone | 0.9 | 0.9 | 0.9 | 0.9 |
| | Peptid P18 | 0.05 | 0.3 | 0.05 | 0.3 |
| | Zinc Pyrithione | 0 | 0 | 1 | 0.7 |
| | Cetyl Alcohol | 0.3 | 0.3 | 0.3 | 0.3 |
| | Ammonium Xylenesulphonate | 0.23 | 0.23 | 0.23 | 0.23 |
| | Cocamide MEA | 0.8 | 0.8 | 0.8 | 0.8 |
| | Hydrogenated Polydecene | 0.3 | 0.3 | 0.3 | 0.3 |
| | PEG-7M | 0.1 | 0.1 | 0.1 | 0.1 |
| | Trimethylolpropane Tricaprylate/Tricaprate | 0.2 | 0.2 | 0.2 | 0.2 |
| | Sodium Polynaphthalenesulphonate | 0.35 | 0.35 | 0.35 | 0.35 |
| | Tocopherol | 0.8 | 0.8 | 0.8 | 0.8 |
| | Aqua | ad 100 | ad 100 | ad 100 | ad 100 |
| | Preservatives | q.s. | q.s. | q.s. | q.s. |
| | Parfum | q.s. | q.s. | q.s. | q.s. |
| | Sodium Chloride | q.s. | q.s. | q.s. | q.s. |
| | Tetrasodium EDTA | q.s. | q.s. | q.s. | q.s. |
| B | Citric Acid | q.s. | q.s. | q.s. | q.s. |
| | Sodium citrate | q.s. | q.s. | q.s. | q.s. |

Preparation: Mix and dissolve components of phase A. Adjust the pH to pH 5-7 with phase B. Viscosity can be adjusted through Tetrasodium EDTA and/or Sodium Chloride. Preferred viscosity is between 5000-15000 mPas.

Example 66

| | Ingredients (INCI) | 1 % | 2 % | 3 % | 4 % |
|---|---|---|---|---|---|
| A | Ammonium Laureth Sulfate | 11.2 | 11.2 | 11.2 | 11.2 |
| | Ammonium Lauryl Sulfate | 8.6 | 8.6 | 8.6 | 8.6 |
| | Dimethicone | 1 | 1 | 1 | 1 |
| | Glycol Distearate | 0.8 | 0.8 | 0.8 | 0.8 |
| | Peptid P18 | 0.05 | 0.3 | 0.05 | 0.3 |
| | Zinc Pyrithione | 0 | 0 | 1 | 0.7 |
| | Cetyl Alcohol | 0.3 | 0.3 | 0.3 | 0.3 |
| | Cocamide MEA | 0.8 | 0.8 | 0.8 | 0.8 |
| | Hydrogenated Polydecene | 0.3 | 0.3 | 0.3 | 0.3 |
| | Trimethylolpropane Tricaprylate/tricaprate | 0.2 | 0.2 | 0.2 | 0.2 |
| | Ammonium Xylenesulfonate | 0.23 | 0.23 | 0.23 | 0.23 |
| | Sodium Polynapthalenesulfonate | 0.35 | 0.35 | 0.35 | 0.35 |
| | Aqua | ad 100 | ad 100 | ad 100 | ad 100 |
| | Preservatives | q.s. | q.s. | q.s. | q.s. |
| | Sodium Chloride | q.s. | q.s. | q.s. | q.s. |
| | Tetrasodium EDTA | q.s. | q.s. | q.s. | q.s. |
| | Parfum | q.s. | q.s. | q.s. | q.s. |
| B | Citric Acid | q.s. | q.s. | q.s. | q.s. |
| | Sodium citrate | q.s. | q.s. | q.s. | q.s. |

Preparation: Mix and dissolve components of phase A. Adjust the pH to pH 5-7 with phase B. Viscosity can be adjusted through Tetrasodium EDTA and/or Sodium Chloride. Preferred viscosity is between 5000-15000 mPas.

Unless otherwise stated the term P18 refers to a peptide of SEQ ID NO:3.

The disclosure of documents cited herein is incorporated by reference.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08765688B2). An electronic copy of the "Sequence Listing" will also be available from the USPTO upon request and payment of the fee set forth in 37 CFR 1.19(b)(3).

The invention claimed is:

1. A method for treatment of dandruff, comprising topical application to a person in need of treatment of dandruff of a composition comprising a cosmetic carrier and a *Malassezia furfur*-inhibiting amount of at least one peptide with a sequence or a repetitive sequence motif according to SEQ ID NO: 2:

(SEQ ID NO: 2)
$X_1$ $X_2$K $X_3$ $X_4$ $X_5$KIP $X_{11}$ $X_{12}$ KF$X_6$$X_7$ $X_8$ A$X_9$KF in which
$X_1$ is lysine, arginine or phenylalanine,
$X_2$ is lysine or tryptophan,
$X_3$ is leucine or lysine,
$X_4$ is phenylalanine or leucine, $X_5$ is leucine or lysine,
$X_6$ is leucine or lysine,
$X_7$ is histidine or lysine,
$X_8$ is alanine, leucine, valine or serine,
$X_9$ is leucine or lysine,
$X_{11}$ is proline or a chemical bond, and
$X_{12}$ is proline or a chemical bond,
where the repetitive sequence motifs are identical or different; or peptide derivatives thereof selected from the group consisting of aliphatic esters, amides, N-acyl peptides, O-acyl peptides, and peptides wherein between 1 to 5 arbitrary amino acid residues are N- and/or C-terminally added or deleted.

2. The method of claim 1, wherein the composition comprises a peptide with a sequence or a repetitive sequence motif according to SEQ ID NO: 3

```
KWKLFKKIPKFLHLAKKF      (SEQ ID NO: 3)
``` or peptide derivatives thereof selected from the group consisting of aliphatic esters, amides, N-acyl peptides, O-acyl peptides, and peptides wherein between 1 to 5 arbitrary amino acid residues are N- and/or C-terminally added or deleted.

3. The method of claim 2, wherein the composition comprises a peptide with a repetitive sequence motif, where a plurality of peptides according to SEQ ID NO: 3 or said peptide derivatives thereof are peptidically linked together via linker groups.

4. The method of claim 1, wherein the composition comprises a peptide with a repetitive sequence motif, where a plurality of peptides according to SEQ ID NO: 2 or said peptide derivatives thereof are peptidically linked together via linker groups.

5. The method according to of claim 4, where the linkers comprise 1 to 10 continuous identical or different amino acid residues selected from alanine, glycine, threonine and serine.

6. The method of claim 1, where the C-terminal carboxyl group of the peptide is amidated.

7. The method of claim 1, wherein the composition inhibits *Malassezia furfur* under standard conditions at a minimum inhibitory concentration of about 0.1 µM-1500 µM.

8. The method of claim 1, wherein the composition additionally comprises at least one further cosmetic or pharmaceutical active ingredient.

9. The method of claim 1, wherein the composition additionally comprises at least one anti-inflammatory active ingredient.

10. The method of claim 1, wherein the composition additionally comprises an antimicrobial active ingredient for inhibiting the growth and/or the activity of undesired germs.

11. The method of claim 1, wherein the composition additionally comprises a sebum-regulating active ingredient.

12. The method of claim 1, where the peptide is present in the composition in a fraction of from 0.0001 to 50% by weight, based on the total weight of the finished composition.

* * * * *